US011897882B2

(12) United States Patent
Ji et al.

(10) Patent No.: US 11,897,882 B2
(45) Date of Patent: Feb. 13, 2024

(54) TRICYCLIC CRBN LIGANDS AND USES THEREOF

(71) Applicant: Kymera Therapeutics, Inc., Watertown, MA (US)

(72) Inventors: Nan Ji, Arlington, MA (US); Arthur F. Kluge, Gainesville, FL (US); Matthew M. Weiss, Boston, MA (US); Yi Zhang, Belmont, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/679,496

(22) Filed: Feb. 24, 2022

(65) Prior Publication Data
US 2022/0306631 A1    Sep. 29, 2022

Related U.S. Application Data

(62) Division of application No. 16/502,529, filed on Jul. 3, 2019, now Pat. No. 11,292,792.

(60) Provisional application No. 62/863,949, filed on Jun. 20, 2019, provisional application No. 62/820,634, filed on Mar. 19, 2019, provisional application No. 62/694,924, filed on Jul. 6, 2018.

(51) Int. Cl.
    C07D 401/04    (2006.01)
    C07D 471/14    (2006.01)
    C07D 495/04    (2006.01)
    C07D 471/04    (2006.01)

(52) U.S. Cl.
    CPC ......... *C07D 471/14* (2013.01); *C07D 401/04* (2013.01); *C07D 471/04* (2013.01); *C07D 495/04* (2013.01)

(58) Field of Classification Search
    CPC .............................. C07D 401/04; A61K 31/45
    See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,217,866 A | 6/1993 | Summerton et al. |
| 5,360,811 A | 11/1994 | Tegeler et al. |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,721,246 A | 2/1998 | Yoshino et al. |
| 6,306,663 B1 | 10/2001 | Kenten et al. |
| 6,552,065 B2 | 4/2003 | Remiszewski et al. |
| 6,559,280 B2 | 5/2003 | Kenten et al. |
| 6,627,754 B2 | 9/2003 | Blumenkopf et al. |
| 6,949,537 B2 | 9/2005 | Garlich et al. |
| 7,041,298 B2 | 5/2006 | Deshaies et al. |
| 7,071,189 B2 | 7/2006 | Kawashima et al. |
| 7,074,620 B2 | 7/2006 | Kenten et al. |
| 7,173,015 B2 | 2/2007 | Schreiber et al. |
| 7,208,157 B2 | 4/2007 | Dashaies et al. |
| 7,273,920 B2 | 9/2007 | Kenten et al. |
| 7,307,077 B2 | 12/2007 | Kawashima et al. |
| 7,390,799 B2 | 6/2008 | Bruncko et al. |
| 7,402,325 B2 | 7/2008 | Addington |
| 7,449,458 B2 | 11/2008 | Bhamidipati et al. |
| 7,501,496 B1 | 3/2009 | Endl et al. |
| 7,514,444 B2 | 4/2009 | Honigberg et al. |
| 7,528,143 B2 | 5/2009 | Noronha et al. |
| 7,557,210 B2 | 7/2009 | Singh et al. |
| 7,598,257 B2 | 10/2009 | Rodgers et al. |
| 7,622,496 B2 | 11/2009 | Larsen et al. |
| 7,667,039 B2 | 2/2010 | Garcia-Echeverria et al. |
| 7,713,943 B2 | 5/2010 | Klippel-Giese et al. |
| 7,781,433 B2 | 8/2010 | Chuckowree et al. |
| 7,932,260 B2 | 4/2011 | Fowler et al. |
| 7,989,622 B2 | 8/2011 | Bajjalieh et al. |
| 8,138,347 B2 | 3/2012 | Knight et al. |
| 8,185,616 B2 | 5/2012 | Nagata et al. |
| 8,217,035 B2 | 7/2012 | Burger et al. |
| 8,338,439 B2 | 12/2012 | Singh et al. |
| 8,486,941 B2 | 7/2013 | Burns et al. |
| 8,906,682 B2 | 12/2014 | June et al. |
| 9,500,653 B2 | 11/2016 | Crews et al. |
| 9,632,089 B2 | 4/2017 | Crews et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |

(Continued)

FOREIGN PATENT DOCUMENTS

| | | |
|---|---|---|
| CN | 105085620 B | 5/2018 |
| WO | WO-1996007655 A1 | 3/1996 |
| WO | WO-2001042246 A2 | 6/2001 |
| WO | WO-2002020740 A2 | 3/2002 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |

(Continued)

OTHER PUBLICATIONS

Acute Leukemia, Merck Manual (Online Edition) 6 pages, pp. 1-6 (2013).*

(Continued)

*Primary Examiner* — Deepak R Rao
(74) *Attorney, Agent, or Firm* — Dechert LLP; Andrea L. C. Reid; Aaron Pearson

(57) ABSTRACT

The present invention provides compounds, compositions thereof, and methods of using the same for the inhibition of CRBN, and the treatment of CRBN-mediated disorders.

19 Claims, No Drawings

(56) References Cited

U.S. PATENT DOCUMENTS

| | | |
|---|---|---|
| 9,969,710 B2 | 5/2018 | Jorand-Lebrun et al. |
| 10,125,114 B2 | 11/2018 | Bradner et al. |
| 10,336,744 B2 | 7/2019 | Harling et al. |
| 10,874,743 B2 | 12/2020 | Mainolfi et al. |
| 11,292,792 B2 * | 4/2022 | Ji .................... C07D 495/04 |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | McElroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Kelley et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0152263 A1 | 6/2017 | Gummadi et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 5/2018 | Harling et al. |
| 2018/0134684 A1 | 5/2018 | Bradner et al. |
| 2018/0147202 A1 | 5/2018 | Crew et al. |
| 2018/0186799 A1 | 7/2018 | Gardner et al. |
| 2018/0194724 A1 | 7/2018 | Kemp et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0151457 A1 | 5/2019 | Bradner et al. |
| 2019/0192668 A1 | 6/2019 | Mainolfi et al. |
| 2019/0276474 A1 | 9/2019 | Chan et al. |
| 2020/0010468 A1 | 1/2020 | Ji et al. |
| 2020/0347045 A1 | 11/2020 | Mainolfi et al. |
| 2020/0377469 A1 | 12/2020 | Mainolfi et al. |
| 2021/0002296 A1 | 1/2021 | Mainolfi et al. |

FOREIGN PATENT DOCUMENTS

| | | |
|---|---|---|
| WO | WO-2004106328 A1 | 12/2004 |
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |
| WO | WO-2006105021 A2 | 10/2006 |
| WO | WO-2006122806 A2 | 11/2006 |
| WO | WO-2007005874 A2 | 1/2007 |

(56) References Cited

FOREIGN PATENT DOCUMENTS

| | | |
|---|---|---|
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2008132601 A1 | 11/2008 |
| WO | WO-2009009116 A2 | 1/2009 |
| WO | WO-2009044273 A2 | 4/2009 |
| WO | WO-2009073620 A2 | 6/2009 |
| WO | WO-2009114512 A1 | 9/2009 |
| WO | WO-2009132238 A3 | 10/2009 |
| WO | WO-2010019570 A2 | 2/2010 |
| WO | WO-2010077634 A1 | 7/2010 |
| WO | WO-2011028683 A1 | 3/2011 |
| WO | WO-2011043371 A1 | 4/2011 |
| WO | WO-2011056652 A1 | 5/2011 |
| WO | WO-2011070024 A1 | 6/2011 |
| WO | WO-2011090760 A1 | 7/2011 |
| WO | WO-2011107553 A1 | 9/2011 |
| WO | WO-2011109400 A2 | 9/2011 |
| WO | WO-2011131407 A1 | 10/2011 |
| WO | WO-2011140249 A2 | 11/2011 |
| WO | WO-2012003281 A3 | 1/2012 |
| WO | WO-2012007375 A1 | 1/2012 |
| WO | WO-2012032433 A1 | 3/2012 |
| WO | WO-2012068546 A1 | 5/2012 |
| WO | WO-2012078559 A2 | 6/2012 |
| WO | WO-2012084704 A1 | 6/2012 |
| WO | WO-2012097013 A1 | 7/2012 |
| WO | WO-2012129258 | 9/2012 |
| WO | WO-2012142237 A1 | 10/2012 |
| WO | WO-2012145493 A1 | 10/2012 |
| WO | WO-2013042137 A1 | 3/2013 |
| WO | WO-2013066729 A1 | 5/2013 |
| WO | WO-2013079174 A1 | 6/2013 |
| WO | WO-2013087699 A1 | 6/2013 |
| WO | WO-2013106535 A1 | 7/2013 |
| WO | WO-2013106612 A1 | 7/2013 |
| WO | WO-2013106614 A1 | 7/2013 |
| WO | WO-2013106641 A1 | 7/2013 |
| WO | WO-2013106643 A2 | 7/2013 |
| WO | WO-2013106646 A2 | 7/2013 |
| WO | WO-2013119716 A1 | 8/2013 |
| WO | WO-2013132044 A1 | 9/2013 |
| WO | WO-2013169264 A1 | 11/2013 |
| WO | WO-2014008218 A1 | 1/2014 |
| WO | WO-2014008992 A1 | 1/2014 |
| WO | WO-2014011902 A1 | 1/2014 |
| WO | WO-2014011906 A2 | 1/2014 |
| WO | WO-2014011911 A2 | 1/2014 |
| WO | WO-2014036357 A1 | 3/2014 |
| WO | WO-2014044622 A1 | 3/2014 |
| WO | WO-2014058685 A1 | 4/2014 |
| WO | WO-2014058691 A1 | 4/2014 |
| WO | WO-2014063061 A1 | 4/2014 |
| WO | WO-2014074675 A1 | 5/2014 |
| WO | WO-2014108452 A1 | 7/2014 |
| WO | WO-2014121931 A1 | 8/2014 |
| WO | WO-2014121942 A1 | 8/2014 |
| WO | WO-2014143672 A1 | 9/2014 |
| WO | WO-2015048281 A1 | 4/2015 |
| WO | WO-2015068856 A1 | 5/2015 |
| WO | WO-2015071393 A1 | 5/2015 |
| WO | WO-2015091426 A1 | 6/2015 |
| WO | WO-2015103453 A1 | 7/2015 |
| WO | WO-2015104662 A1 | 7/2015 |
| WO | WO-2015104688 A1 | 7/2015 |
| WO | WO-2015116904 A1 | 8/2015 |
| WO | WO-2015150995 A1 | 10/2015 |
| WO | WO-2015160845 A3 | 10/2015 |
| WO | WO-2015164374 A1 | 10/2015 |
| WO | WO-2015193846 A1 | 12/2015 |
| WO | WO-2016011390 A1 | 1/2016 |
| WO | WO-2016053769 A1 | 4/2016 |
| WO | WO-2016053770 A1 | 4/2016 |
| WO | WO-2016053771 A1 | 4/2016 |
| WO | WO-2016053772 A1 | 4/2016 |
| WO | WO-2016081679 A1 | 5/2016 |
| WO | WO-2016105518 A1 | 6/2016 |
| WO | WO-2016118666 A1 | 7/2016 |
| WO | WO-2016144844 A1 | 9/2016 |
| WO | WO-2016144846 A1 | 9/2016 |
| WO | WO-2016144847 A1 | 9/2016 |
| WO | WO-2016144848 A1 | 9/2016 |
| WO | WO-2016144849 A1 | 9/2016 |
| WO | WO-2016149668 A1 | 9/2016 |
| WO | WO-2016169989 A1 | 10/2016 |
| WO | WO-2016172560 A1 | 10/2016 |
| WO | WO-2016174183 A1 | 11/2016 |
| WO | WO-2016197032 A1 | 12/2016 |
| WO | WO-2016197114 A1 | 12/2016 |
| WO | WO-2016210034 A1 | 12/2016 |
| WO | WO-2017004133 A1 | 1/2017 |
| WO | WO-2017004134 | 1/2017 |
| WO | WO-2017007612 A1 | 1/2017 |
| WO | WO-2017009798 A1 | 1/2017 |
| WO | WO-2017009806 A1 | 1/2017 |
| WO | WO-2017011371 A1 | 1/2017 |
| WO | WO-2017011590 A1 | 1/2017 |
| WO | WO-2017030814 A1 | 2/2017 |
| WO | WO-2017033093 A1 | 3/2017 |
| WO | WO-2017049068 A1 | 3/2017 |
| WO | WO-2017059280 A1 | 4/2017 |
| WO | WO-2017079267 A1 | 5/2017 |
| WO | WO-2017108723 A2 | 6/2017 |
| WO | WO-2017117473 A1 | 7/2017 |
| WO | WO-2017117474 A1 | 7/2017 |
| WO | WO-2017127430 A1 | 7/2017 |
| WO | WO-2017161119 A1 | 9/2017 |
| WO | WO-2017176708 A1 | 10/2017 |
| WO | WO-2017176957 A1 | 10/2017 |
| WO | WO-2017176958 A1 | 10/2017 |
| WO | WO-2017197036 A1 | 11/2017 |
| WO | WO-2017197046 A1 | 11/2017 |
| WO | WO-2017197051 A1 | 11/2017 |
| WO | WO-2017197055 A1 | 11/2017 |
| WO | WO-2017197056 A1 | 11/2017 |
| WO | WO-2017201449 A1 | 11/2017 |
| WO | WO-2017205762 A1 | 11/2017 |
| WO | WO-2017205766 A1 | 11/2017 |
| WO | WO-2017207385 A1 | 12/2017 |
| WO | WO-2017211924 A1 | 12/2017 |
| WO | WO-2018052058 A1 | 3/2018 |
| WO | WO-2018089736 A1 | 5/2018 |
| WO | WO-2018098367 A1 | 5/2018 |
| WO | WO-2018144649 A1 | 8/2018 |
| WO | WO-2018209012 A1 | 11/2018 |
| WO | WO-2018237026 A1 | 12/2018 |
| WO | WO-2019043214 A1 | 3/2019 |
| WO | WO-2019060693 A1 | 3/2019 |
| WO | WO-2019060742 A1 | 3/2019 |
| WO | WO-2019084026 A1 | 5/2019 |
| WO | WO-2019084030 A1 | 5/2019 |
| WO | WO-2019099868 A1 | 5/2019 |
| WO | WO-2019099926 A1 | 5/2019 |
| WO | WO-2019133531 A1 | 7/2019 |
| WO | WO-2019140380 A1 | 7/2019 |
| WO | WO-2019140387 A1 | 7/2019 |
| WO | WO-2019165229 A1 | 8/2019 |
| WO | WO-2020010177 A1 | 1/2020 |
| WO | WO-2020010210 A1 | 1/2020 |
| WO | WO-2020010227 A1 | 1/2020 |
| WO | WO-2021011631 A1 | 1/2021 |

OTHER PUBLICATIONS

Damasio, Alzheimer's Disease and related dementias, Cecil Textbook of Medicine, 20th Edition, vol. 2, pp. 1992-1996, 1996.*

(56) References Cited

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Layzer, Degenerative diseases of the nervous system, Cecil Textbook of Medicine, 20th Edition, vol. 2, pp. 2050-2057, 1996.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Adams et al., "Big opportunities for small molecules in immuno-oncology," Nat Rev Drug Discov. 2015;14(9):603-22.
Aruri et al., "Metal-free Cross-Dehydrogenative Coupling of HN-azoles with a-C(sp3)-H Amides via C-H Activation and Its Mechanistic and Application Studies," J Org Chem. 2017;82(2):1000-1012.
Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.
Berge et al., "Pharmaceutical Salts," J Pharm Sci. 1977; 66(1):1-19.
Berndsen et al., "New insights into ubiquitin E3 ligase mechanism," Nat Struct Mol Biol. 2014;21(4):301-7.
Boichenko et al., "A FRET-Based Assay for the Identification and Characterization of Cereblon Ligands," J Med Chem. 2016;59(2):770-4.
Buckley et al., "IRAK-4 inhibitors. Part 1: a series of amides," Bioorg Med Chem Lett. 2008;18(11):3211-4.
Buckley et al., "IRAK-4 inhibitors. Part II: a structure-based assessment of imidazo[1,2-a]pyridine binding," Bioorg Med Chem Lett. 2008;18(11):3291-5.
Buckley et al., "IRAK-4 inhibitors. Part III: A series of imidazo[1,2-a]pyridines," Bioorg Med Chem Lett. 2008;18(12):3656-60.
Cameron et al., "Loss of Interleukin Receptor-Associated Kinase 4 Signaling Suppresses Amyloid Pathology and Alters Microglial Phenotype in a Mouse Model of Alzheimer's Disease," J Neurosci. 2012;32(43):15112-23.
Cario, "Therapeutic Impact of Toll-like Receptors on Inflammatory Bowel Diseases: A Multiple-edged Sword," Inflamm Bowel Dis. 2008;14(3):411-21.
CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).
Chang et al., "What is the functional role of the thalidomide binding protein cereblon?" Int J Biochem Mol Biol. 2011;2(3):287-94.
Charrier et al., "Desulfonylative radical ring closure onto aromatics. A modular route to benzazepin-2-ones and 5-arylpiperidin-2-ones," Org Lett. 2012;14(8):2018-21.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem. 2015;58(1):96-110.
Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol. 2011;186(2):1279-88.
Cohen, "Targeting protein kinases for the development of anti-inflammatory drugs," Curr Opin Cell Biol. 2009;21(2):17-24.
Connolly et al., "Complexities of TGF-beta Targeted Cancer Therapy," Int J Biol Sci. 2012;8(7):964-978.

Contino-Pepin et al., "Preliminary biological evaluations of new thalidomide analogues for multiple sclerosis application," Bioorg Med Chem Lett. 2009;19(3):878-81.
Crews, "Targeting the Undruggable Proteome: The Small Molecules of My Dreams," Chem Biol. 2010;17(6):551-5.
Cushing et al., "IRAK4 kinase controls Toll-like receptor induced inflammation through the transcription factor IRF5 in primary human monocytes," J Biol Chem. 2017;292(45):18689-18698.
Dalbeth et al., "Hyperuricaemia and gout: state of the art and future perspectives," Ann Rheum Dis. 2014;73(9):1598-600.
Degorce et al.,"Optimization of permeability in a series of pyrrolotriazine inhibitors of IRAK4," Bioorg Med Chem. 2018;26(4):913-924.
Deshaies and Joazeiro, "RING domain E3 ubiquitin ligases," Annu Rev Biochem. 2009;78:399-434.
Dinarello, "IL-1: Discoveries, controversies and future directions," Eur J Immunol. 2010;40(3):599-606.
Dinarello, "Interleukin 1 and interleukin 18 as mediators of inflammation and the aging process," Am J Clin Nutr. 2006;83(suppl):447S-55S.
Dinarello, "Interleukin-18 and the Pathogenesis of Inflammatory Diseases," Semin Nephrol. 2007;27(1):98-114.
Dudhgaonkar et al., "Selective IRAK4 Inhibition Attenuates Disease in Murine Lupus Models and Demonstrates Steroid Sparing Activity," J Immunol. 2017;198(3):1308-1319.
Dunne et al., "IRAK1 and IRAK4 Promote Phosphorylation, Ubiquitation, and Degradation of MyD88 Adaptor-like (Mal)," J Biol Chem. 2010;285(24):18276-82.
Fischer et al., "Structure of the DDB1-CRBN E3 ubiquitin ligase in complex with thalidomide," Nature. 2014;512(7512):49-53.
Flannery et al., "The interleukin-1 receptor-associated kinases: Critical regulators of innate immune signaling," Biochem Pharmacol. 2010;80(12):1981-91.
Gearing, "Targeting toll-like receptors for drug development: a summary of commercial approaches," Immunol Cell Biol. 2007;85(6):490-4.
Geyer and Müller-Ladner, "Actual status of antiinterleukin-1 therapies in rheumatic diseases," Curr Opin Rheumatol. 2010;22(3):246-51.
Gottipati et al., "IRAK1: A critical signaling mediator of innate immunity," Cell Signal. 2008;20(2):269-76.
Hagner et al., "CC-122, a pleiotropic pathway modifier, mimics an interferon response and has antitumor activity in DLBCL," Blood. 2015;126(6):779-89.
Hennessy et al., "Targeting Toll-like receptors: emerging therapeutics?" Nat Rev Drug Discov. 2010;9(4):293-307.
Hines et al., "MDM2-Recruiting PROTAC Offers Superior, Synergistic Antiproliferative Activity via Simultaneous Degradation of BRD4 and Stabilization of p53," Cancer Res. 2019;79(1):251-262.
Hoffman et al., "Efficacy and Safety of Rilonacept (Interleukin-1 Trap) in Patients with Cryopyrin-Associated Periodic Syndromes," Arthritis Rheum. 2008;58(8):2443-5.
Iannello et al., "Role of Interleukin-18 in the Development and Pathogenesis of AIDS," AIDS Rev. 2009;11(3):115-25.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science. 2010;327(5971):1345-50.
Kelly et al., "Selective interleukin-1 receptor-associated kinase 4 inhibitors for the treatment of autoimmune disorders and lymphoid malignancy," J Exp Med. 2015;212(13):2189-201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Kim et al., "A critical role for IRAK4 kinase activity in Toll-like receptor-mediated innate immunity," J Exp Med. 2007;204(5):1025-36.

(56) References Cited

OTHER PUBLICATIONS

Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol. 2014;387(10):909-19.
Kou et al., "Effects of RuPeng15 Powder (RPP15) on Monosodium Urate Crystal-Induced Gouty Arthritis in Rats," Evid Based Complement Alternat Med. 2015;2015:527019.
Koziczak-Holbro et al., "IRAK-4 Kinase Activity Is Required for Interleukin-1 (IL-1) Receptor-and Toll-like Receptor 7-mediated Signaling and Gene Expression," J Biol Chem. 2007;282(18):13552-60.
Krönke et al., "Lenalidomide causes selective degradation of IKZF1 and IKZF3 in multiple myeloma cells" Science. 2014;343(6168):301-305.
Ku et al., "Selective predisposition to bacterial infections in IRAK-4-deficient children: IRAK-4-dependent TLRs are otherwise redundant in protective immunity," J Exp Med. 2007;204(10):2407-2422.
Kubo-Murai et al., "IRAK-4-dependent Degradation of IRAK-1 is a Negative Feedback Signal for TLR-mediated NF-kB Activation," J Biochem. 2008;143(3):295-302.
Küppers, "IRAK inhibition to shut down TLR signaling in autoimmunity and MyD88-dependent lymphomas," J Exp Med. 2015;212(13):2184.
Lebakken et al., "A Fluorescence Lifetime Based Binding Assay to Characterize Kinase Inhibitors," J Biomol Screen. 2007;12(6):828-41.
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," J Med Chem. 2017;60(13):5521-5542.
Li et al., "Genome-wide and functional annotation of human E3 ubiquitin ligases identifies MULAN, a mitochondrial E3 that regulates the organelle's dynamics and signaling," PLoS One. 2008;3(1):e1487.
Li et al., "IRAK-4: A novel member of the IRAK family with the properties of an IRAK-kinase," Proc Natl Acad Sci USA. 2002;99(8):5567-72.
Li et al., "Targeting interleukin-1 receptor-associated kinase for human hepatocellular carcinoma," J Exp Clin Cancer Res. 2016;35(1):140.
Li, "IRAK4 in TLR/IL-1R signaling: Possible clinical applications," Eur J Immunol. 2008;38(3):614-8.
Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015;6(6):683-688.
Lin et al., "Helical assembly in the MyD88-IRAK4-IRAK2 complex in TLR /IL-1R signalling," Nature. 2010:465(7300):885-90.
Lu et al., "Hijacking the E3 Ubiquitin Ligase Cereblon to Efficiently Target BRD4," Chem Biol. 2015;2(6):755-63.
Lu et al., "The myeloma drug lenalidomide promotes the cereblon-dependent destruction of Ikaros proteins," Science. 2014;343(6168):305-309.
Lust et al., "Induction of a Chronic Disease State in patients With Smoldering of Indolent Multiple Myeloma by Targeting Interleukin 1ß-Induced Interleukin 6 Production and the Myeloma Proliferative Component," Mayo Clin Proc. 2009;84(2):114-22.
Martinon et al., "Gout-associated uric acid crystals activate the NALP3 inflammasome," Nature. 2006;440(7081):237-41.
Maschera et al., "Overexpression of an enzymatically inactive interleukin-1-receptor-associated kinase activates nuclear factor-kB," Biochem J. 1999;339(Pt2):227-31.
Matyskiela et al., "A Cereblon Modulator (CC-220) with Improved Degradation of Ikaros and Aiolos," J Med Chem. 2018;61(2):535-542.
McElroy et al., "Discovery and hit-to-lead optimization of 2,6-diaminopyrimidine Inhibitors of interleukin-1 receptor-associated kinase 4," Bioorg Med Chem Lett. 2015;25(9):1836-41.

McElroy et al., "Potent and Selective Amidopyrazole Inhibitors of IRAK4 That Are Efficacious in a Rodent Model of Inflammation," ACS Med Chem Lett. 2015;6(6):677-682.
Muller et al., "Amino-Substituted Thalidomide Analogs: Potent Inhibitors of TNF-? Production," Bioorg Med Chem Lett. 1999;9(11):1625-30.
Ngo et al., "Oncogenically active MYD88 mutations in human lymphoma," Nature. 2011;470(7332):115-9.
Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556- 4570.
Okazaki et al., "A rheostat for immune responses: the unique properties of PD-1 and their advantages for clinical application," Nat. Immunol. 2013; 14(12): 1212-1218.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/042105, dated Nov. 20, 2020.
Picard et al., "Clinical features and outcome of patients with IRAK-4 and MyD88 deficiency," Medicine (Baltimore). 2010;89(6):403-425.
Picard et al., "Inherited human IRAK-4 deficiency: an update," Immunol Res. 2007;38(1-3):347-52.
Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood. 2016;126(23): 675-676.
Powers et al., "Discovery and initial SAR of inhibitors of interleukin-1 receptor-associated kinase-4," Bioorg Med Chem Lett. 2006;16(11):2842-5.
Priyadarshini et al., "Copper catalyzed oxidative cross-coupling of aromatic amines with 2-pyrrolidinone: a facile synthesis of N-aryl-r-amino-r-lactams," Tetrahedron. 2014;70(36):6068-6074.
Pubmed Compound Summary for CID 101524675, "(2R)-3-Fluoro-2-(2-methylpropyl)-3-phenyl-1,3-azasilinan-6-one," *U.S. National Library of Medicine*, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, '3-(5-Amino-2-oxo-3H-benzimidazol-1-yl)piperidine-2,6-dione, *U.S. Library of Medicine*, created Jan. 18, 2016, https://pubchem.ncbi.nlm.nih.gov/compound/110491408. Date Accessed: Feb. 25, 2020 (7 pages).
Pubmed Compound Summary for CID 110491555, '3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).

(56) References Cited

OTHER PUBLICATIONS

Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).

Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).

Pubmed Compound Summary for CID 63661260,"5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).

Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).

Pubmed Compound Summary for CID 65967733, "3-(2,5-Dioxo-3-phenylpyrrolidin-1-yl)piperidine-2,6-dione," *U.S. National Library of Medicine*, created Dec. 24, 2015, https://pubchem.ncbi.nlm.nih.gov/compound/65967733. Date Accessed: Feb. 25, 2020 (7 pages).

Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).

Pubmed Compound Summary for CID 67258040, "[1-(9H-Fluoren-9-yl)-1-(6-oxopiperidin-3-yl)ethyl] hydrogen carbonate," *U.S. National Library of Medicine*, Nov. 30, 2012, https://pubchem.ncbi.nlm.nih.gov/compound/67258040. Date Accessed: Feb. 25, 2020 (9 pages).

Pubmed Compound Summary for CID 83543479, "5(Aminomethyl)-5-(1H-indol-3-yl)piperidin-2-one," *U.S. National Library of Medicine*, created Oct. 20, 2014, https://pubchem.ncbi.nlm.nih.gov/compound/83543479. Date Accessed: Feb. 25, 2020 (6 pages).

Pubmed Compound Summary for CID 84036945, '1-Piperidin-3-yl-3H-indol-2-one, *U.S. Library of Medicine*, created Oct. 20, 2014, https://pubchem.ncbi.nlm.nih.gov/compound/84036945. Date Accessed: Feb. 25, 2020 (7 pages).

Pubmed Compound Summary for CID 86793742, '3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.

Pubmed Compound Summary for CID 91648396, '3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.

Pubmed Compound Summary for CID 99784232, '(3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.

Raina et al., "Chemical Inducers of Targeted Protein Degradation," J Biol Chem. 2010;285(15):11057-60.

Ramirez et al., "Defining causative factors contributing in the activiation of hedgehog signaling in diffuse large B-cell lymphoma," Leuk Res. 2012;36(10):1267-73.

Rokosz et al., 2008, "Kinase inhibitors as drugs for chronic inflammatory and immunological diseases: progress and challenges," Expert Opinions on Therapeutic Targets 12(7): 883-903.

Ronnebaum et al., "Synthesis of 1, 2, 3-triazole 'click' analogues of thalidomide," Tetrahedron. 2016;72(40): 6136-6141.

Ross et al., "Bispecific T cell engager (BITE®) antibody constructs can mediate bystander tumor cell killing," PLoS ONE. 2017; 12(8): e0183390.

Rostovtsev et al., "A stepwise huisgen cycloaddition process: copper(I)-catalyzed regioselective "ligation" of azides and terminal alkynes," Angew. Chem. Int. Ed. Engl. 2002;41(14):2596-9.

Schnnekloth et al., "Chemical approaches to controlling intracellular protein degradation," Chembiochem. 2005;6(1):40-46.

Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017;60(24):10071-10091.

Seganish et al., "Discovery and Structure Enabled Synthesis of 2,6-diaminopyrimidine-4-one IRAK4 Inhibitors," ACS Med Chem Lett. 2015;6(8):942-947.

Seganish et al., "Initial optimization and series evolution of diaminopyrimidine inhibitors of interleukin-1 receptor associated kinase 4," Bioorg Med Chem Lett. 2015;25(16):3203-3207.

Seitz et al., "Sulfenylation and Halogenation of Di-and Trianions Derived from Substituted Glutarimides," Synthetic Communications. 1977;7(6):367-374.

Sen et al., "Transcriptional signaling by double-stranded RNA: role of TLR3," Cytokine Growth Factor Rev. 2005;16(1):1-14.

Shanmugasundaram et al., "A modular PROTAC design for target destruction using a degradation signal based on a single amino acid," J Biol Chem. 2019;294(41):15172-15175.

Smith et al., "Identification of quinazoline based inhibitors of IRAK4 for the treatment of inflammation," Bioorg Med Chem Lett. 2017;27(12):2721-2726.

So et al., "A pilot study of IL-1 inhibition by anakinra in acute gout," Arthritis Res Ther. 2007;9(2):R28.

Song et al., "The kinase activities of interleukin-e receptor associated kinase (IRAK)-1 and 4 are redundant in the control of inflammatory cytokine expression in human cells," Mol Immunol. 2009;46(7):1458-66.

Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.

Spratt et al., "RBR E3 ubiquitin ligases: new structures, new insights, new question," Biochem J. 2014;458(3);421-37.

Stewart et al., "Efforts toward elucidating Thalidomide's molecular target: an expedient synthesis of the first Thalidomide biotin analogue," Organic & Biomolecular Chemistry. 2010;8(18): 4059-4062.

Sun et al., "Carbohydrate and protein immobilization onto solid surfaces by sequential Diels-Alder and azide-alkyne cycloadditions," Bioconjug. Chem. 2006;17(1):52-7.

Suzuki et al., "IRAK-4 as the central TIR signaling mediator in innate immunity," Trends Immunol. 2002;23(10):503-6.

Suzuki et al., "Severe impairment of interleukin-1 and Toll-like receptor signalling in mice lacking IRAK-4," Nature. 2002;416(6882):750-6.

Swantek et al., "IL-1 Receptor-Associated Kinase Modulates Host Responsiveness to Endotoxin," Journal of Immunology 164: 4301-4306, J Immunol. 2000;164(8):4301-6.

Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009;68(10):1613-7.

Terkeltaub, "Update on gout: new therapeutic strategies and options," Nat Rev Rheumatol. 2010;6(1):30-8.

Toogood, "Small molecule immuno-oncology therapeutic agents," Bioorg. Med. Chem. Lett. 2018;28(3):319-329.

Torres et al., "Hyperalgesia, synovitis and multiple biomarkers of inflammation are suppressed by interleukin 1 inhibition in a novel animal model of gouty arthritis," Ann Rheum Dis. 2009;68(10):1602-8.

Toure and Crews, "Small-Molecule PROTACS: New Approaches to Protein Degradation," Angew Chem Int Ed Engl. 2016;55(6):1966-73.

Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].

Trøseid et al., "The role of interleukin-18 in the metabolic syndrome," Cardiovasc Diabetol. 2010;9:11.

Tumey et al., "Identification and optimization of indolo[2,3-c]quinoline inhibitors of IRAK4," Bioorg Med Chem Lett. 2014;24(9):2066-72.

(56) References Cited

OTHER PUBLICATIONS

Uehara et al., "Selective degradation of splicing factor CAPER? by anticancer sulfonamides," Nat Chem Biol. 2017;13(6):675-680.
Varfolomeev et al., "IAP antagonists induce autoubiquitination of c-IAPs, NF-kappaB activation, and TNFalpha-dependent apoptosis," Cell. 2007;131(4):669-81.
Vollmer et al., "The mechanism of activation of IRAK1 and IRAK4 by interleukin-1 and Toll-like receptor agonists," Biochem J. 2017;474(12):2027-2038.
Wang et al., "Crystal Structure of IRAK-4 Kinase in Complex with Inhibitors: Serine/Threonine Kinase with Tyrosine as a Gatekeeper," Structure. 2006;14(12):1835-44.
Wang et al., "Discovery of potent, selective, and orally bioavailable inhibitors of interleukin-1 receptor-associated kinase 4," Bioorg Med Chem Lett. 2015;25(23):5546-5550.
Wang et al., "IRAK-4 Inhibitors for Inflammation," Curr Top Med Chem. 2009;9(8):724-37.
Wang et al., "Roles of F-box proteins in cancer," Nat Rev Cancer. 2014;14(4):233-47.
Ward et al., "Covalent Ligand Screening Uncovers a RNF4 E3 Ligase Recruiter for Targeted Protein Degradation Applications," *bioRxiv.org*, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med. 2008;75 Suppl 5:S9-12.
Winter et al., "Selective Target Protein Degradation via Phthalimide Conjugation," Science. 2015;348(6241):1376-1381.
Xia and Chen, "Iron-catalyzed N-alkylation of azoles via cleavage of an sp3 C-H bond adjacent to a nitrogen atom," J Org Chem. 2012;77(20):9366-73.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, NK-kb and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Yang et al., "Exploiting synthetic lethality for the therapy of ABC diffuse large B cell lymphoma," Cancer Cell. 2012;21(6):723-37.
Zhang et al., "Constitutive IRAK4 Activation Underlies Poor Prognosis and Chemoresistance in Pancreatic Ductal Adenocarcinoma," Clin Cancer Res. 2017;23(7):1748-1759.
Zhang et al., "Electrophilic PROTACs that degrade nuclear proteins by engaging DCAF16," *bioRxiv.org*, https://www.biorxiv.org/content/biorxiv/early/2018/10/15/443804.full.pdf. Date Accessed, Oct. 3, 2019.
Zhou et al., "Targets of curcumin," Curr Drug Targets. 2011;12(3):332-347.
Zinc 170596280, Date Added Aug. 8, 2015, https://zinc.docking.org/substances/ZINC000170596280/. Date Accessed: Jan. 10, 2022.
Zou et al., "PD-L1 (B7-H1) and PD-1 pathway blockade for cancer therapy: Mechanisms, response biomarkers, and combinations," Sci. Transl. Med. 2016;8(328):328rv4.

\* cited by examiner

TRICYCLIC CRBN LIGANDS AND USES THEREOF

CROSS-REFERENCE TO RELATED APPLICATIONS

This application is a division of U.S. patent application Ser. No. 16/502,529, filed Jul. 3, 2019, which claims the benefit under 35 U.S.C. § 119(e) of U.S. Provisional Application No. 62/694,924, filed Jul. 6, 2018, U.S. Provisional Application No. 62/820,634, filed Mar. 19, 2019, and U.S. Provisional Application No. 62/863,949, filed Jun. 20, 2019, the content of each of which is incorporated herein in its entirety by reference.

TECHNICAL FIELD OF THE INVENTION

The present invention relates to compounds and methods useful for binding and modulating the activity of cereblon (CRBN). The invention also provides pharmaceutically acceptable compositions comprising compounds of the present invention and methods of using said compositions in the treatment of various disorders.

BACKGROUND OF THE INVENTION

The Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity.

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

Cereblon (CRBN) interacts with damaged DNA binding protein 1 and forms an E3 ubiquitin ligase complex with Cullin 4 where it functions as a substrate receptor in which the proteins recognized by CRBN might be ubiquitinated and degraded by proteasomes.

A new role for CRBN has been identified; i.e., the binding of immunomodulatory drugs (IMiDs), e.g. thalidomide, to CRBN has now been associated with teratogenicity and also the cytotoxicity of IMiDs, including lenalidomide, which are widely used to treat multiple myeloma patients. CRBN is likely a key player in the binding, ubiquitination and degradation of factors involved in maintaining function of myeloma cells. These new findings regarding the role of CRBN in IMiD action stimulated intense investigation of CRBN's downstream factors involved in maintaining regular function of a cell (Chang and Stewart Int J Biochem Mol Biol. 2011; 2(3): 287-294).

Accordingly, there remains a need to find CRBN ligands useful as therapeutic agents.

SUMMARY OF THE INVENTION

It has now been found that compounds of this invention, and pharmaceutically acceptable compositions thereof, are effective as CRBN ligands. Such compounds have the general formula I:

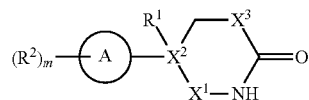

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with CRBN. Such diseases, disorders, or conditions include those described herein.

Compounds provided by this invention are also useful for the study of CRBN and associated proteins in biological and pathological phenomena; the study of CRBN occurring in bodily tissues; and the comparative evaluation of new CRBN ligands or other regulators of CRBN in vitro or in vivo.

DETAILED DESCRIPTION OF CERTAIN EMBODIMENTS

1. General Description of Certain Embodiments of the Invention

Compounds of the present invention, and compositions thereof, are useful as CRBN ligands. As defined herein, the terms "binder," "modulator," and "ligand" are used interchangeably and describe a compound that binds to, modulates or is a ligand for CRBN.

In certain embodiments, the present invention provides a compound of formula I-a:

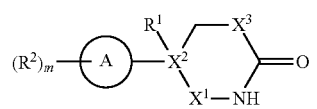

I-a or a pharmaceutically acceptable salt thereof, wherein:

$X^1$ is a bivalent moiety selected from a covalent bond, —$CH_2$—, —C(O)—, —C(S)—, or

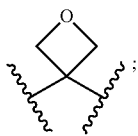 [SMILES: *C1(*)COC1]

X² is a carbon atom or silicon atom;
X³ is a bivalent moiety selected from —CH₂— or —Si(R₂)—;
R¹ is hydrogen, deuterium, halogen, —CN, —OR, —SR, —S(O)R, —S(O)₂R, —N(R)₂, —Si(R)₃, or an optionally substituted $C_{1-4}$ aliphatic;
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each R² is independently hydrogen, deuterium, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;
each R³ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
Ring A is a tricyclic ring selected from

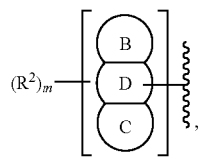

wherein
  each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and
  m is 0, 1, 2, 3, 4, 5, 6, 7, 8, 9, 10, 11, 12, 13, 14, 15, or 16.
Where a point of attachment of —(R²)$_m$ is depicted on Ring B, Ring C, and Ring D, it is intended, and one of ordinary skill in the art would appreciate, that the point of attachment of —(R²)$_m$ may be on Ring A and may also be at any available carbon or nitrogen atom on Ring A including the carbon atom to which Ring B or Ring C are fused to Ring D.
Where a point of attachment of

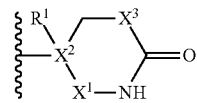

is depicted on Ring D, it is intended, and one of ordinary skill in the art would appreciate, that the point of attachment of

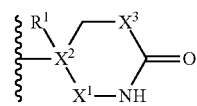

may be on any available carbon or nitrogen atom on Ring D including the carbon atom to which Ring B or Ring C are fused to Ring D.
In certain embodiments, the present invention provides a compound of formula I-a':

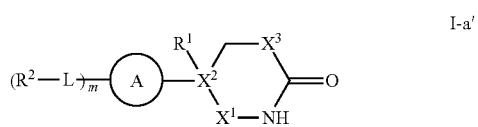

I-a' or a pharmaceutically acceptable salt thereof, wherein:
X¹ is a bivalent moiety selected from a covalent bond, —CH₂—, —CHCF₃—, —SO₂—, —S(O)—, —P(O)R—, —P(O)OR—, —P(O)NR₂—, —C(O)—, —C(S)—, or

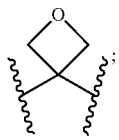

X² is a carbon atom or silicon atom;
X³ is a bivalent moiety selected from —CR₂—, —NR—, —O—, —S—, or —Si(R₂)—;
R¹ is hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)(R)₂, —Si(R)₃, or an optionally substituted $C_{1-4}$ aliphatic;
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —Si(R)$_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —OP(O)(OR)(NR$_2$), —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —N(R)P(O)(OR)(NR$_2$), —$N(R)P(O)(NR_2)_2$, or —$N(R)S(O)_2R$;

each L is independently a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

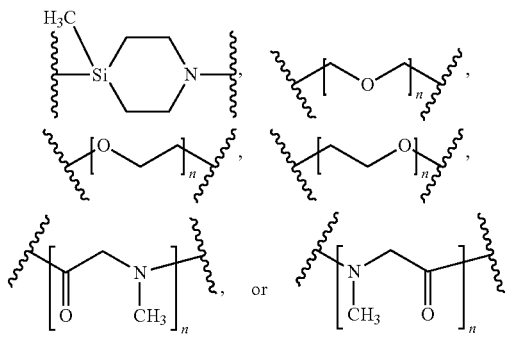

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

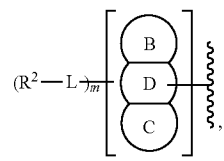

wherein each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

Where a point of attachment of —(R$^2$)$_m$ is depicted on Ring B, Ring C, and Ring D, it is intended, and one of ordinary skill in the art would appreciate, that the point of attachment of —(R$^2$)$_m$ may be on Ring A and may also be at any available carbon or nitrogen atom on Ring A including the carbon atom to which Ring B or Ring C are fused to Ring D.

Where a point of attachment of

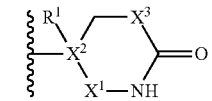

is depicted on Ring B, Ring C, and Ring D, it is intended, and one of ordinary skill in the art would appreciate, that the point of attachment of

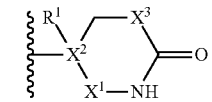

may be on Ring A and may also be at any available carbon or nitrogen atom on Ring A including the carbon atom to which Ring B or Ring C are fused to Ring D.

In certain embodiments, the present invention provides a compound of formula I-b:

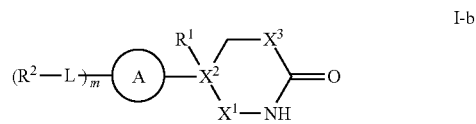

I-b or a pharmaceutically acceptable salt thereof, wherein:
$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

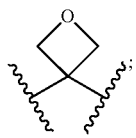 [SMILES: *C1(*)COC1]

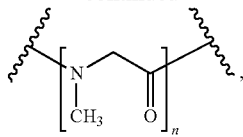

X² is a carbon atom or silicon atom;
X³ is a bivalent moiety selected from —CR₂—, —NR—, —O—, —S—, or —Si(R₂)—;
R¹ is hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)(R)₂, —Si(R)₃, or an optionally substituted C₁₋₄ aliphatic;
each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or.
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each R² is independently hydrogen, deuterium, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —OP(O)R₂, —OP(O)(OR)₂, —OP(O)(OR)(NR₂), —OP(O)(NR₂)₂—, —N(R)C(O)OR, —N(R)C(O)R, —N(R)C(O)N(R)₂, —N(R)S(O)₂R, —NP(O)R₂, —N(R)P(O)(OR)₂, —N(R)P(O)(OR)(NR₂), —N(R)P(O)(NR₂)₂, or —N(R)S(O)₂R;
each L is independently a covalent bond or a bivalent, saturated or unsaturated, straight or branched C₁₋₅₀ hydrocarbon chain, wherein 0-6 methylene units of L are independently replaced by —C(D)(H)—, —C(D)₂-, -Cy-, —O—, —N(R)—, —Si(R)₂—, —Si(OH)(R)—, —Si(OH)₂—, —P(O)(OR)—, —P(O)(R)—, —P(O)(NR₂)—, —S—, —OC(O)—, —C(O)O—, —C(O)—, —S(O)—, —S(O)₂—, —N(R)S(O)₂—, —S(O)₂N(R)—, —N(R)C(O)—, —C(O)N(R)—, —OC(O)N(R)—, —N(R)C(O)O—,

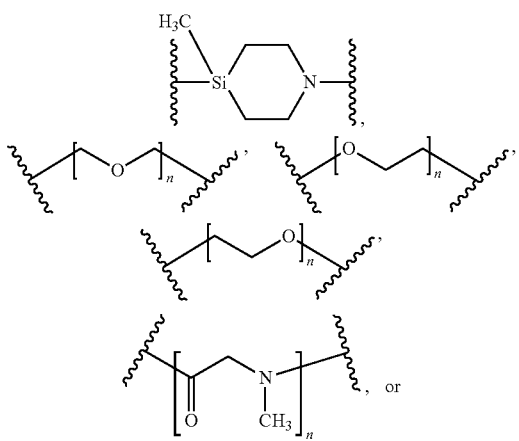

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
each R³ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
Ring A is a bicyclic ring system selected from

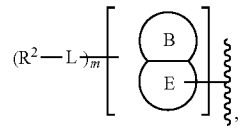

wherein
Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;
Ring E is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;
each of n is independently 1, 2, 3, 4, 5, 6, 7, 8, 9, or 10; and
m is 0, 1, 2, 3, 4, 5, 6, 7, 8, 9, 10, 11, 12, 13, 14, 15, or 16.

Where a point of attachment of —(R²)ₘ is depicted on Ring B and Ring E, it is intended, and one of ordinary skill in the art would appreciate, that the point of attachment of —(R²)ₘ may be on Ring A and may also be at any available carbon or nitrogen atom on Ring A including the carbon atom to which Ring B and Ring E are fused.

Where a point of attachment of

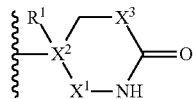

is depicted on Ring B and Ring E, it is intended, and one of ordinary skill in the art would appreciate, that the point of attachment of

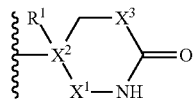

may be on Ring A and may also be at any available carbon or nitrogen atom on Ring A including the carbon atom to which Ring B and Ring E are fused.

In certain embodiments, the present invention provides a compound of formula I-c:

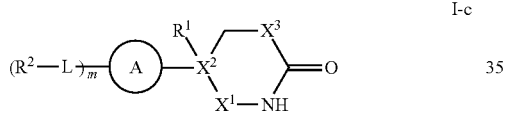

I-c or a pharmaceutically acceptable salt thereof, wherein:
X¹ is a bivalent moiety selected from a covalent bond, —CH₂—, —CHCF₃—, —SO₂—, —S(O)—, —P(O)R—, —P(O)OR—, —P(O)NR₂—, —C(O)—, —C(S)—, or

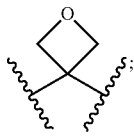 [SMILES: *C1(*)COC1]

X² is a carbon atom or silicon atom;
X³ is a bivalent moiety selected from —CR₂—, —NR—, —O—, —S—, or —Si(R₂)—;
R¹ is hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)(R)₂, —Si(R)₃, or an optionally substituted C₁₋₄ aliphatic;
each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each R² is independently hydrogen, deuterium, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —OP(O)R₂, —OP(O)(OR)₂, —OP(O)(OR)(NR₂), —OP(O)(NR₂)₂—, —N(R)C(O)OR, —N(R)C(O)R, —N(R)C(O)N(R)₂, —N(R)S(O)₂R, —NP(O)R₂, —N(R)P(O)(OR)₂, —N(R)P(O)(OR)(NR₂), —N(R)P(O)(NR₂)₂, or —N(R)S(O)₂R;
each L is independently a covalent bond or a bivalent, saturated or unsaturated, straight or branched C₁₋₅₀ hydrocarbon chain, wherein 0-6 methylene units of L are independently replaced by —C(D)(H)—, —C(D)₂-, -Cy-, —O—, —N(R)—, —Si(R)₂—, —Si(OH)(R)—, —Si(OH)₂—, —P(O)(OR)—, —P(O)(R)—, —P(O)(NR₂)—, —S—, —OC(O)—, —C(O)O—, —C(O)—, —S(O)—, —S(O)₂—, —N(R)S(O)₂—, —S(O)₂N(R)—, —N(R)C(O)—, —C(O)N(R)—, —OC(O)N(R)—, —N(R)C(O)O—,

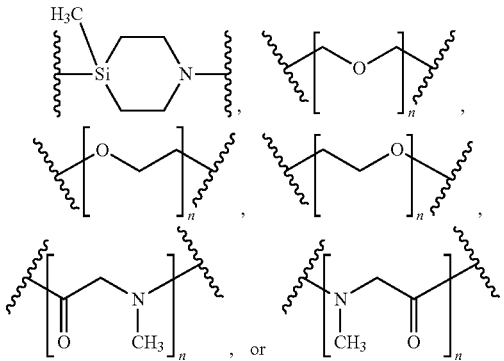

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
each R³ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring system selected from

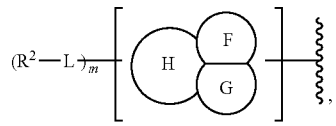

wherein
each of Ring F and G is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

Where a point of attachment of $-(R^2)_m$ is depicted on Ring F, Ring G, and Ring H, it is intended, and one of ordinary skill in the art would appreciate, that the point of attachment of $-(R^2)_m$ may be on Ring A and may also be at any available carbon or nitrogen atom on Ring A including the carbon atom to which Ring F, Ring G, and Ring H are fused.

Where a point of attachment of

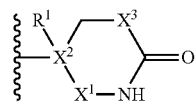

is depicted on Ring F, Ring G, and Ring H, it is intended, and one of ordinary skill in the art would appreciate, that the point of attachment of

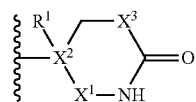

may be on Ring A and may also be at any available carbon or nitrogen atom on Ring A including the carbon atom to which Ring F, Ring G, and Ring H are fused.

In certain embodiments, the present invention provides a compound of formula I-d:

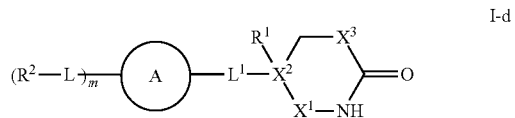

or a pharmaceutically acceptable salt thereof, wherein:

$X^1$ is a bivalent moiety selected from a covalent bond, $-CH_2-$, $-CHCF_3-$, $-SO_2-$, $-S(O)-$, $-P(O)R-$, $-P(O)OR-$, $-P(O)NR_2-$, $-C(O)-$, $-C(S)-$, or

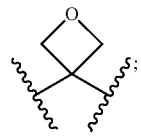 [SMILES: *C1(*)COC1]

$X^2$ is a carbon atom or silicon atom;

$X^3$ is a bivalent moiety selected from $-CR_2-$, $-NR-$, $-O-$, $-S-$, or $-Si(R_2)-$;

$R^1$ is hydrogen, deuterium, halogen, $-CN$, $-OR$, $-SR$, $-S(O)R$, $-S(O)_2R$, $-N(R)_2$, $-P(O)(OR)_2$, $-P(O)(NR_2)OR$, $-P(O)(NR_2)_2$, $-Si(OH)_2R$, $-Si(OH)(R)_2$, $-Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $-R^3$, halogen, $-CN$, $-NO_2$, $-OR$, $-SR$, $-N(R)_2$, $-Si(R)_3$, $-S(O)_2R$, $-S(O)_2N(R)_2$, $-S(O)R$, $-C(O)R$, $-C(O)OR$, $-C(O)N(R)_2$, $-C(O)N(R)OR$, $-C(R)_2N(R)C(O)R$, $-C(R)_2N(R)C(O)N(R)_2$, $-OC(O)R$, $-OC(O)N(R)_2$, $-OP(O)R_2$, $-OP(O)(OR)_2$, $-OP(O)(OR)(NR_2)$, $-OP(O)(NR_2)_2-$, $-N(R)C(O)OR$, $-N(R)C(O)R$, $-N(R)C(O)N(R)_2$, $-N(R)S(O)_2R$, $-NP(O)R_2$, $-N(R)P(O)(OR)_2$, $-N(R)P(O)(OR)(NR_2)$, $-N(R)P(O)(NR_2)_2$, or $-N(R)S(O)_2R$;

each L is independently a covalent bond or a bivalent, saturated or unsaturated, straight or branched $C_{1-50}$ hydrocarbon chain, wherein 0-6 methylene units of L are independently replaced by $-C(D)(H)-$, $-C(D)_2-$, -Cy-, $-O-$, $-N(R)-$, $-Si(R)_2-$, $-Si(OH)(R)-$, $-Si(OH)_2-$, $-P(O)(OR)-$, $-P(O)(R)-$, $-P(O)(NR_2)-$, $-S-$, $-OC(O)-$, $-C(O)O-$, $-C(O)-$, $-S(O)-$, $-S(O)_2-$, $-N(R)S(O)_2-$, $-S(O)_2N(R)-$, $-N(R)C(O)-$, $-C(O)N(R)-$, $-OC(O)N(R)-$, $-N(R)C(O)O-$,

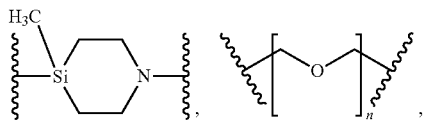

-continued

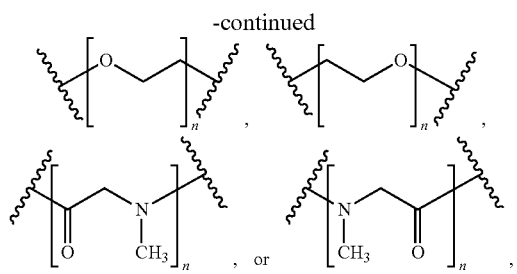

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

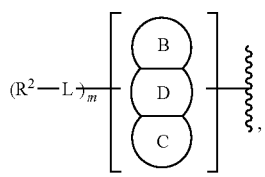

wherein
each of Ring B, Ring D, and Ring C is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —CR$_2$—, —CFR—, —CF$_2$—, —NR—, —S—, —S(O)$_2$— or —CR═CR—;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

Where a point of attachment of —(R$^2$)$_m$ is depicted on Ring B, Ring D, or Ring C, it is intended, and one of ordinary skill in the art would appreciate, that the point of attachment of —(R$^2$)$_m$ may be at any available carbon or nitrogen atom on Ring B, Ring D, or Ring C including the carbon atom to which Ring B or Ring C are fused to Ring D.

Where a point of attachment of

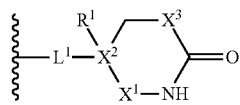

is depicted on Ring B, Ring D, or Ring C, it is intended, and one of ordinary skill in the art would appreciate, that the point of attachment of

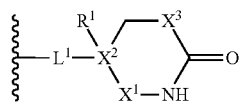

may be on any available carbon or nitrogen atom on Ring B, Ring D, or Ring C, including the carbon atom to which Ring B or Ring C are fused to Ring D.

In certain embodiments, the present invention provides a compound of formula II:

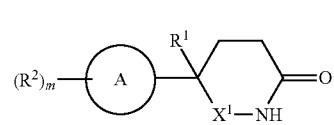

II or a pharmaceutically acceptable salt thereof, wherein:
$X^1$ is a bivalent moiety selected from a covalent bond, —CH$_2$—, —C(O)—, —C(S)—, or

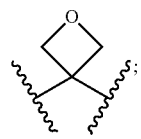 [SMILES: *C1(*)COC1]

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, deuterium, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;

each R³ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

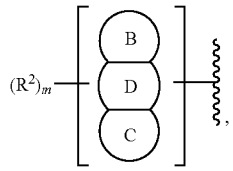

wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

Where a point of attachment of —(R²)ₘ is depicted on Ring B, Ring C, and Ring D, it is intended, and one of ordinary skill in the art would appreciate, that the point of attachment of —(R²)ₘ may be on Ring A and may also be at any available carbon or nitrogen atom on Ring A including the carbon atom to which Ring B or Ring C are fused to Ring D.

Where a point of attachment of

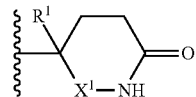

is depicted on Ring D, it is intended, and one of ordinary skill in the art would appreciate, that the point of attachment of

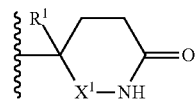

may be on any available carbon or nitrogen atom on Ring D including the carbon atom to which Ring B or Ring C are fused to Ring D.

In certain embodiments, the present invention provides a compound of formula II':

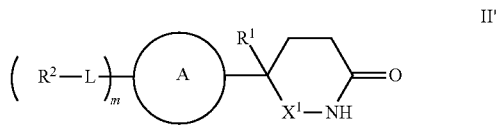

II' or a pharmaceutically acceptable salt thereof, wherein:

X¹ is a bivalent moiety selected from a covalent bond, —CH₂—, —CHCF₃—, —SO₂—, —S(O)—, —P(O)R—, —P(O)OR—, —P(O)NR₂—, —C(O)—, —C(S)—, or

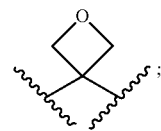

R¹ is hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)(R)₂, —Si(R)₃, or an optionally substituted C₁₋₄ aliphatic;

each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, deuterium, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —OP(O)R₂, —OP(O)(OR)₂, —OP(O)(OR)(NR₂), —OP(O)(NR₂)₂—, —N(R)C(O)OR, —N(R)C(O)R, —N(R)C(O)N(R)₂, —N(R)S(O)₂R, —NP(O)R₂, —N(R)P(O)(OR)₂, —N(R)P(O)(OR)(NR₂), —N(R)P(O)(NR₂)₂, or —N(R)S(O)₂R;

each L is independently a covalent bond or a bivalent, saturated or unsaturated, straight or branched C₁₋₅₀ hydrocarbon chain, wherein 0-6 methylene units of L are independently replaced by —C(D)(H)—, —C(D)₂-, -Cy-, —O—, —N(R)—, —Si(R)₂—, —Si(OH)(R)—, —Si(OH)₂—, —P(O)(OR)—, —P(O)(R)—, —P(O)

(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

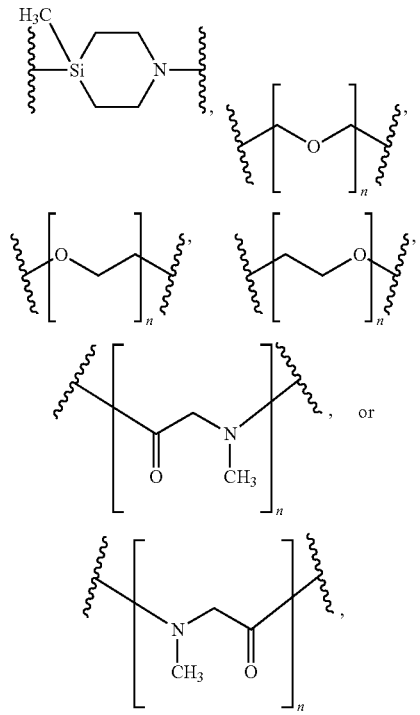

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each R$^3$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

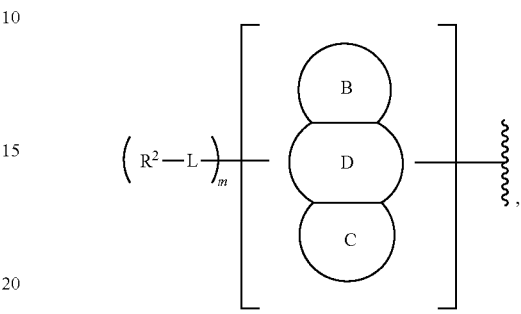

wherein
each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

Where a point of attachment of —(R$^2$)$_m$ is depicted on Ring B, Ring C, and Ring D, it is intended, and one of ordinary skill in the art would appreciate, that the point of attachment of —(R$^2$)$_m$ may be on Ring A and may also be at any available carbon or nitrogen atom on Ring A including the carbon atom to which Ring B or Ring C are fused to Ring D.

Where a point of attachment of

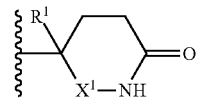

is depicted on Ring B, Ring C, and Ring D, it is intended, and one of ordinary skill in the art would appreciate, that the point of attachment of

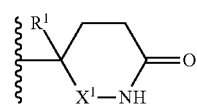

may be on any available carbon or nitrogen atom on Ring A including the carbon atom to which Ring B or Ring C are fused to Ring D.

In certain embodiments, the present invention provides a compound of formula II-a:

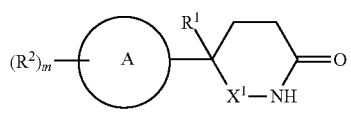

II-a or a pharmaceutically acceptable salt thereof, wherein:

$X^1$ is a bivalent moiety selected from a covalent bond, —$CH_2$—, —C(O)—, —C(S)—, or

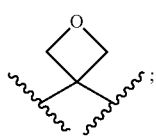 [SMILES: *C1(*)COC1]

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

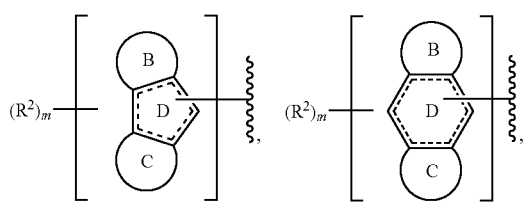

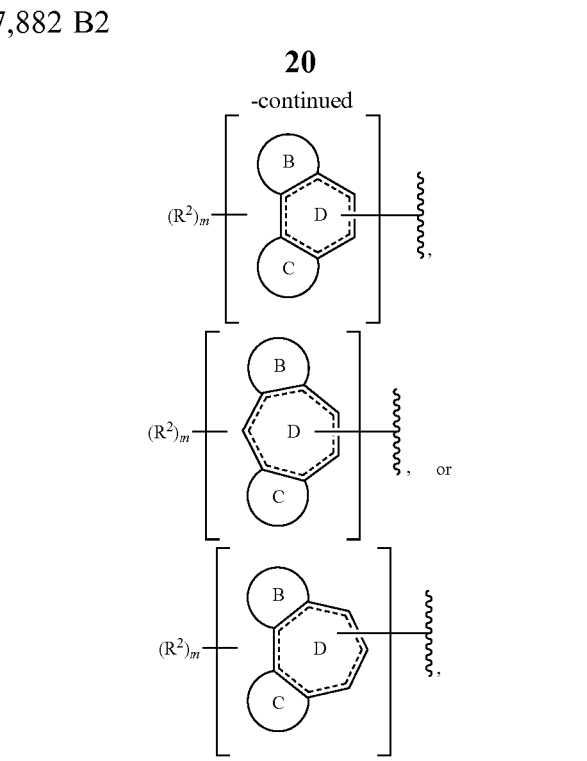

wherein each of Ring B and Ring C is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen or sulfur, or 5-membered heteroaryl with 1-3 heteroatoms independently selected from nitrogen, oxygen or sulfur;

Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur;

═══ is a single or double bond; and m is 0, 1, 2, 3, 4, 5, 6, 7, 8, 9, 10, 11, 12, 13, 14, 15, or 16.

Where a point of attachment of —(R$^2$)$_m$ is depicted on Ring B, Ring C, and Ring D, it is intended, and one of ordinary skill in the art would appreciate, that the point of attachment of —(R$^2$)$_m$ may be on Ring A and may also be at any available carbon or nitrogen atom on Ring A including the carbon atom to which Ring B or Ring C are fused to Ring D.

Where a point of attachment of

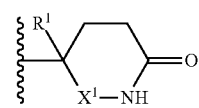

is depicted on Ring D, it is intended, and one of ordinary skill in the art would appreciate, that the point of attachment of

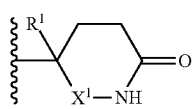

may be on any available carbon or nitrogen atom on Ring D including the carbon atom to which Ring B or Ring C are fused to Ring D.

In certain embodiments, the present invention provides a compound of formula II-b:

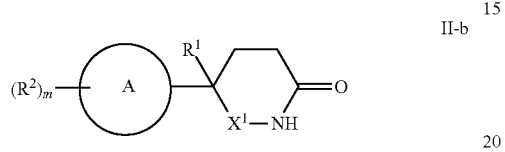

II-b or a pharmaceutically acceptable salt thereof, wherein:

$X^1$ is a bivalent moiety selected from a covalent bond, —$CH_2$—, —C(O)—, —C(S)—, or

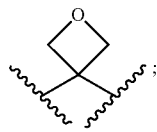 [SMILES: *C1(*)COC1]

;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

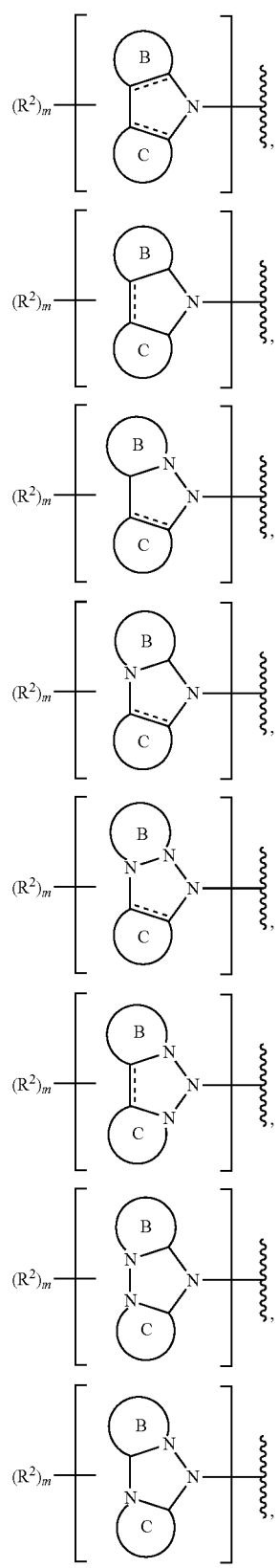

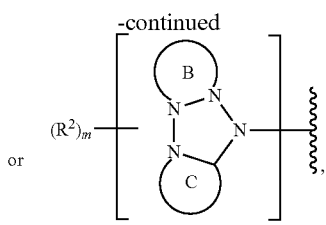

wherein
each of Ring B and Ring C is independently a fused ring selected from 6-membered aryl containing 0-2 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur;

--- is a single or double bond; and m is 0, 1, 2, 3, 4, 5, 6, 7, or 8.

Where a point of attachment of —(R$^2$)$_m$ is depicted on Ring B or Ring C, it is intended, and one of ordinary skill in the art would appreciate, that the point of attachment of —(R$^2$)$_m$ may be on Ring A and may also be at any available carbon or nitrogen atom on Ring A including the carbon atom ring to which Ring B or Ring C is fused.

In certain embodiments, the present invention provides a compound of formula II-c:

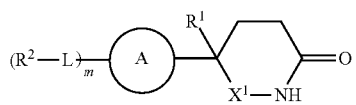

II-c or a pharmaceutically acceptable salt thereof, wherein:
X$^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

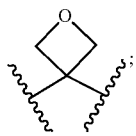 [SMILES: *C1(*)COC1]

R$^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R$^2$ is independently hydrogen, deuterium, —R$^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each L is independently a covalent bond or a bivalent, saturated or unsaturated, straight or branched C$_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

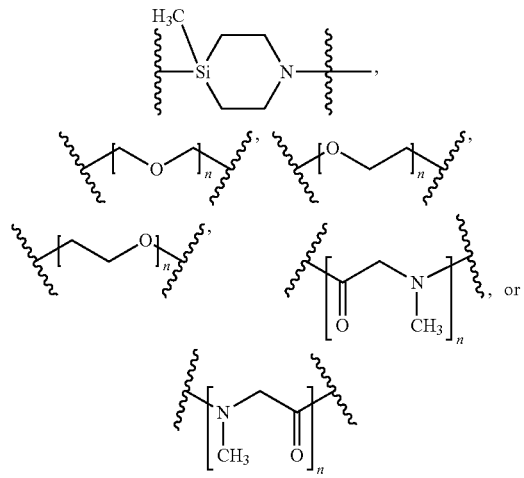

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each R³ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a bicyclic ring system selected from

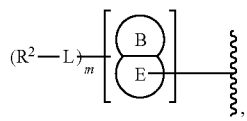

wherein
Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring E is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

Where a point of attachment of —(R²)ₘ is depicted on Ring B and Ring E, it is intended, and one of ordinary skill in the art would appreciate, that the point of attachment of —(R²)ₘ may be on Ring A and may also be at any available carbon or nitrogen atom on Ring A including the carbon atom to which Ring B and Ring E are fused.

Where a point of attachment of

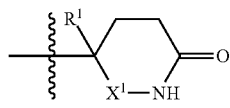

is depicted on Ring B and Ring E, it is intended, and one of ordinary skill in the art would appreciate, that the point of attachment of

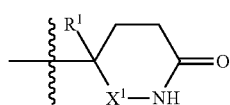

may be on Ring A and may also be at any available carbon or nitrogen atom on Ring A including the carbon atom to which Ring B and Ring E are fused.

In certain embodiments, the present invention provides a compound of formula II-d:

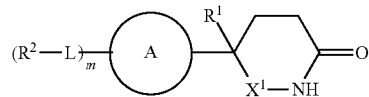

or a pharmaceutically acceptable salt thereof, wherein:
X¹ is a bivalent moiety selected from a covalent bond, —CH₂—, —CHCF₃—, —SO₂—, —S(O)—, —P(O)R—, —P(O)OR—, —P(O)NR₂—, —C(O)—, —C(S)—, or

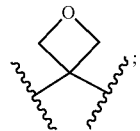 [SMILES: *C1(*)COC1]

R¹ is hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)(R)₂, —Si(R)₃, or an optionally substituted C₁₋₄ aliphatic;

each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, deuterium, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —OP(O)R₂, —OP(O)(OR)₂, —OP(O)(OR)(NR₂), —OP(O)(NR₂)₂—, —N(R)C(O)OR, —N(R)C(O)R, —N(R)C(O)N(R)₂, —N(R)S(O)₂R, —NP(O)R₂, —N(R)P(O)(OR)₂, —N(R)P(O)(OR)(NR₂), —N(R)P(O)(NR₂)₂, or —N(R)S(O)₂R;

each L is independently a covalent bond or a bivalent, saturated or unsaturated, straight or branched C₁₋₅₀ hydrocarbon chain, wherein 0-6 methylene units of L are independently replaced by —C(D)(H)—, —C(D)₂-, -Cy-, —O—, —N(R)—, —Si(R)₂—, —Si(OH)(R)—, —Si(OH)₂—, —P(O)(OR)—, —P(O)(R)—, —P(O)(NR₂)—, —S—, —OC(O)—, —C(O)O—, —C(O)—, —S(O)—, —S(O)₂—, —N(R)S(O)₂—, —S(O)₂N(R)—, —N(R)C(O)—, —C(O)N(R)—, —OC(O)N(R)—, —N(R)C(O)O—,

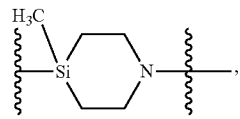

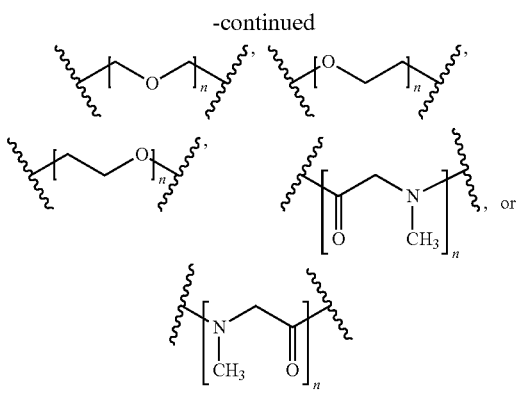

wherein:
  each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
  each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
  Ring A is a tricyclic ring system selected from

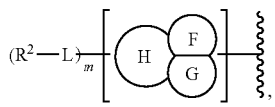

wherein
    each of Ring F and G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;
    Ring H is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;
    each of n is independently 1, 2, 3, 4, 5, 6, 7, 8, 9, or 10; and
    m is 0, 1, 2, 3, 4, 5, 6, 7, 8, 9, 10, 11, 12, 13, 14, 15, or 16.

Where a point of attachment of $-(R^2)_m$ is depicted on Ring F, Ring G, and Ring H, it is intended, and one of ordinary skill in the art would appreciate, that the point of attachment of $-(R^2)_m$ may be on Ring A and may also be at any available carbon or nitrogen atom on Ring A including the carbon atom to which Ring F, Ring G, and Ring H are fused.

Where a point of attachment of

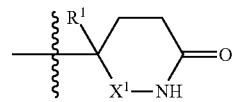

is depicted on Ring F, Ring G, and Ring H, it is intended, and one of ordinary skill in the art would appreciate, that the point of attachment of

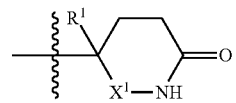

may be on Ring A and may also be at any available carbon or nitrogen atom on Ring A including the carbon atom to which Ring F, Ring G, and Ring H are fused.

In certain embodiments, the present invention provides a compound of formula III or IV:

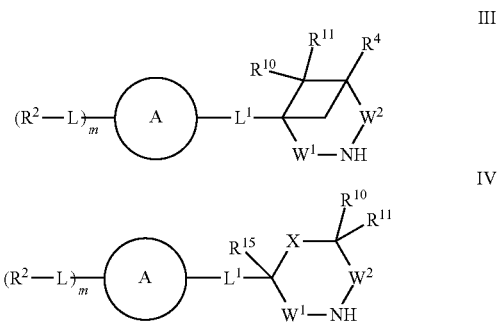

or a pharmaceutically acceptable salt thereof, wherein:
  each $R^2$ is independently hydrogen, deuterium, $-R^3$, halogen, $-CN$, $-NO_2$, $-OR$, $-SR$, $-N(R)_2$, $-Si(R)_3$, $-S(O)_2R$, $-S(O)_2N(R)_2$, $-S(O)R$, $-C(O)R$, $-C(O)OR$, $-C(O)N(R)_2$, $-C(O)N(R)OR$, $-C(R)_2N(R)C(O)R$, $-C(R)_2N(R)C(O)N(R)_2$, $-OC(O)R$, $-OC(O)N(R)_2$, $-OP(O)R_2$, $-OP(O)(OR)_2$, $-OP(O)(OR)(NR_2)$, $-OP(O)(NR_2)_2-$, $-N(R)C(O)OR$, $-N(R)C(O)R$, $-N(R)C(O)N(R)_2$, $-N(R)S(O)_2R$, $-NP(O)R_2$, $-N(R)P(O)(OR)_2$, $-N(R)P(O)(OR)(NR_2)$, $-N(R)P(O)(NR_2)_2$, or $-N(R)S(O)_2R$;
  each L is independently a covalent bond or a bivalent, saturated or unsaturated, straight or branched $C_{1-50}$ hydrocarbon chain, wherein 0-6 methylene units of L are independently replaced by —C(D)(H)—, —C(D)₂-, -Cy-, —O—, —N(R)—, —Si(R)₂—, —Si(OH)(R)—, —Si(OH)₂—, —P(O)(OR)—, —P(O)(R)—, —P(O)(NR₂)—, —S—, —OC(O)—, —C(O)O—, —C(O)—, —S(O)—, —S(O)₂—, —N(R)S(O)₂—, —S(O)₂N(R)—, —N(R)C(O)—, —C(O)N(R)—, —OC(O)N(R)—, —N(R)C(O)O—,

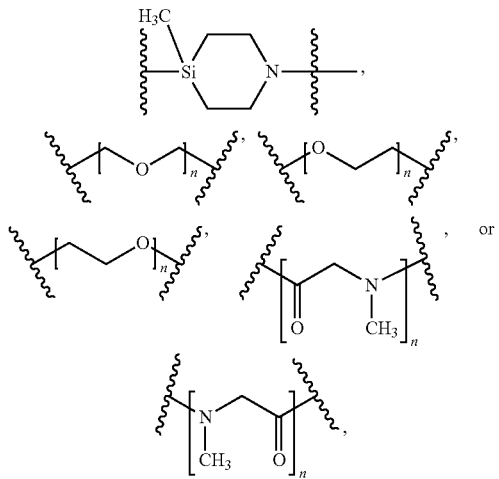

wherein:
  each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
  each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
  Ring A is a tricyclic ring selected from

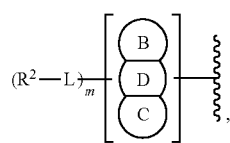

wherein
  each of Ring B, Ring D, and Ring C is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;
  each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
    two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
  $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —CR₂—, —CFR—, —CF₂—, —NR—, —S—, —S(O)₂— or —CR=CR—;
  each of n is independently 1, 2, 3, 4, 5, 6, 7, 8, 9, or 10;
  m is 0, 1, 2, 3, 4, 5, 6, 7, 8, 9, 10, 11, 12, 13, 14, 15, or 16; and
  $R^4$, $R^{10}$, $R^{11}$, $R^{15}$, $W^1$, $W^2$, and X is as defined in WO 2019/099868, the entirety of each of which is herein incorporated by reference.

Where a point of attachment of —(R²)ₘ is depicted on Ring B, Ring D, or Ring C, it is intended, and one of ordinary skill in the art would appreciate, that the point of attachment of —(R²)ₘ may be at any available carbon or nitrogen atom on Ring B, Ring D, or Ring C including the carbon atom to which Ring B or Ring C are fused to Ring D.

Where a point of attachment of

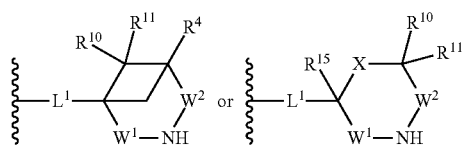

is depicted on Ring B, Ring D, or Ring C, it is intended, and one of ordinary skill in the art would appreciate, that the point of attachment of

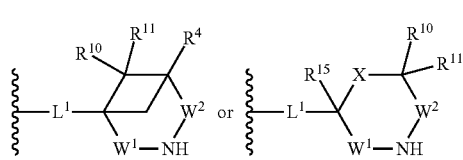

may be on any available carbon or nitrogen atom on Ring B, Ring D, or Ring C, including the carbon atom to which Ring B or Ring C are fused to Ring D.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

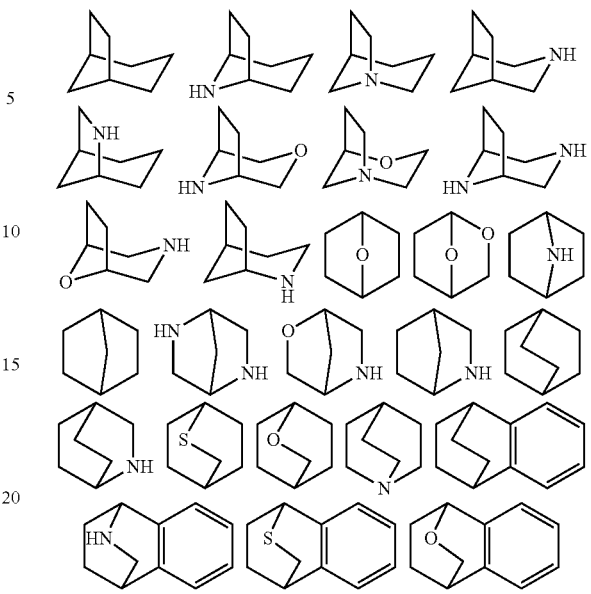

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

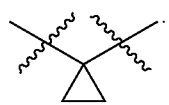 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 9-membered monocyclic or 7- to 11-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)$C(O)OR^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a provided compound may be substituted with one or more deuterium atoms.

As used herein, the term "provided compound" refers to any genus, subgenus, and/or species set forth herein.

As used herein, the term "binder" or "ligand" is defined as a compound that binds to CRBN with measurable affinity. In certain embodiments, a compound has a binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxy-rhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably modulate," as used herein, means a measurable change in a CRBN activity between a sample comprising a compound of the present invention, or composition thereof, and CRBN, and an equivalent sample comprising CRBN, in the absence of said compound, or composition thereof.

3. Description of Exemplary Embodiments

As described above, in certain embodiments, the present invention provides a compound of formula I-a:

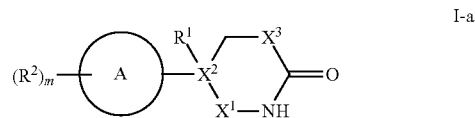

I-a or a pharmaceutically acceptable salt thereof, wherein:
$X^1$ is a bivalent moiety selected from a covalent bond, —CH$_2$—, —C(O)—, —C(S)—, or

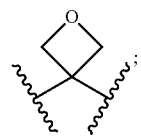 [SMILES: *C1(*)COC1]

$X^2$ is a carbon atom or silicon atom;
$X^3$ is a bivalent moiety selected from —CH$_2$— or —Si(R$_2$)—;
$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

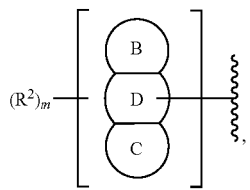

wherein
each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-2 heteroatoms independently selected from nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16.

As described above, in certain embodiments, the present invention provides a compound of formula I-a':

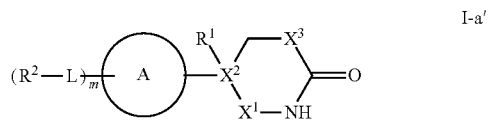

or a pharmaceutically acceptable salt thereof, wherein:
$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

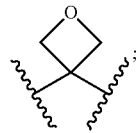

$X^2$ is a carbon atom or silicon atom;
$X^3$ is a bivalent moiety selected from —CR$_2$—, —NR—, —O—, —S—, or —Si(R$_2$)—;
$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each L is independently a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

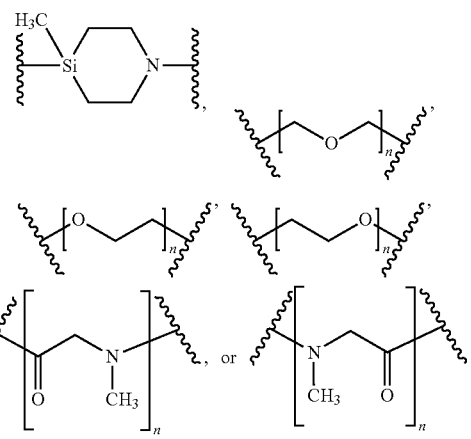

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

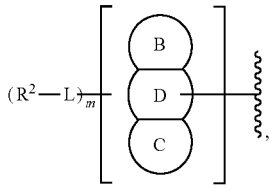

wherein
each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;
each of n is independently 1, 2, 3, 4, 5, 6, 7, 8, 9, or 10; and
m is 0, 1, 2, 3, 4, 5, 6, 7, 8, 9, 10, 11, 12, 13, 14, 15, or 16.

In some embodiments, a compound of formula I-a' above is provided as a compound of formula I-a" or formula I-a''':

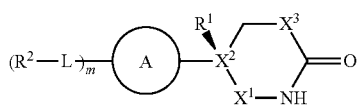

I-a"

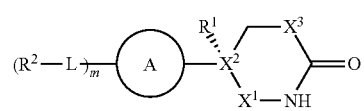

I-a''' or a pharmaceutically acceptable salt thereof, wherein:
each of Ring A, L, $X^1$, $X^2$, $X^3$, $R^1$, $R^2$, and m is as defined above.

As described above, in certain embodiments, the present invention provides a compound of formula I-b:

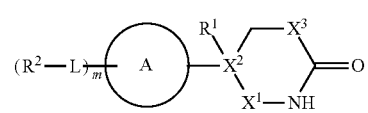

I-b or a pharmaceutically acceptable salt thereof, wherein:
$X^1$ is a bivalent moiety selected from a covalent bond, —$CH_2$—, —$CHCF_3$—, —$SO_2$—, —$S(O)$—, —$P(O)R$—, —$P(O)OR$—, —$P(O)NR_2$—, —$C(O)$—, —$C(S)$—, or

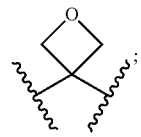

$X^2$ is a carbon atom or silicon atom;
$X^3$ is a bivalent moiety selected from —$CR_2$—, —NR—, —O—, —S—, or —$Si(R_2)$—;
$R^1$ is hydrogen, deuterium, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)(R)_2$, —$Si(R)_3$, or an optionally substituted $C_{1-4}$ aliphatic;
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each $R^2$ is independently hydrogen, deuterium, —$R^3$, halogen, —CN, —$NO_2$, —OR, —SR, —$N(R)_2$, —$Si(R)_3$, —$S(O)_2R$, —$S(O)_2N(R)_2$, —$S(O)R$, —$C(O)R$, —$C(O)OR$, —$C(O)N(R)_2$, —$C(O)N(R)OR$, —$C(R)_2N(R)C(O)R$, —$C(R)_2N(R)C(O)N(R)_2$, —$OC(O)R$, —$OC(O)N(R)_2$, —$OP(O)R_2$, —$OP(O)(OR)_2$, —$OP(O)(OR)(NR_2)$, —$OP(O)(NR_2)_2$—, —$N(R)C(O)OR$, —$N(R)C(O)R$, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;
each L is independently a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

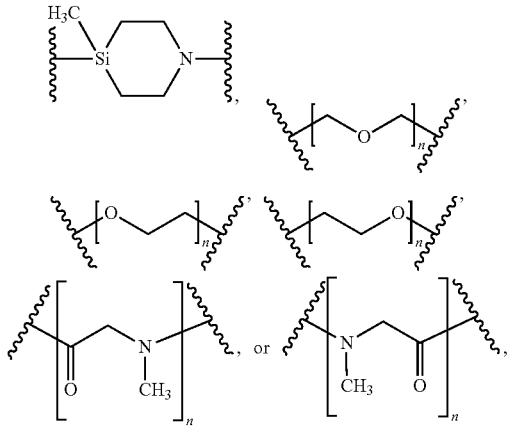

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
Ring A is a bicyclic ring system selected from

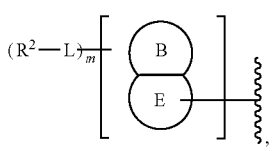

wherein
Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;
Ring E is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;
each of n is independently 1, 2, 3, 4, 5, 6, 7, 8, 9, or 10; and
m is 0, 1, 2, 3, 4, 5, 6, 7, 8, 9, 10, 11, 12, 13, 14, 15, or 16.

In some embodiments, a compound of formula I-b above is provided as a compound of formula I-b' or formula I-b":

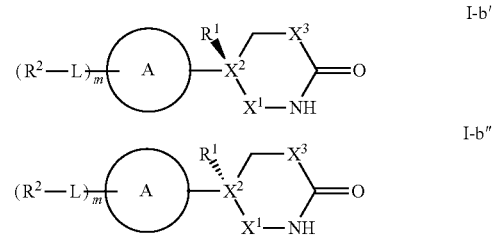

or a pharmaceutically acceptable salt thereof, wherein:
each of Ring A, L, $X^1$, $X^2$, $X^3$, $R^1$, $R^2$, and m is as defined above.

As described above, in certain embodiments, the present invention provides a compound of formula I-c:

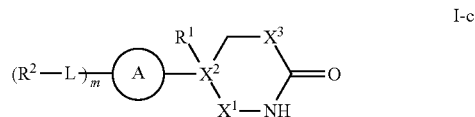

or a pharmaceutically acceptable salt thereof, wherein:
$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

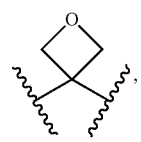 [SMILES: *C1(*)COC1]

$X^2$ is a carbon atom or silicon atom;
$X^3$ is a bivalent moiety selected from —CR$_2$—, —NR—, —O—, —S—, or —Si(R$_2$)—;
$R^1$ is hydrogen, deuterium, halogen, —CN, —OR, —SR, —S(O)R, —S(O)$_2$R, —NR$_2$, —P(O)(OR)$_2$, —P(O)

(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R$^2$ is independently hydrogen, deuterium, —R$^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each L is independently a covalent bond or a bivalent, saturated or unsaturated, straight or branched C$_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

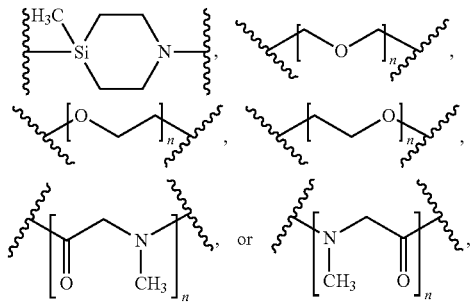

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each R$^3$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring system selected from

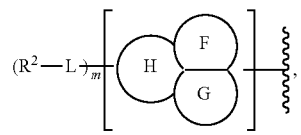

wherein each of Ring F and G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

In some embodiments, a compound of formula I-c above is provided as a compound of formula I-c' or formula I-c'':

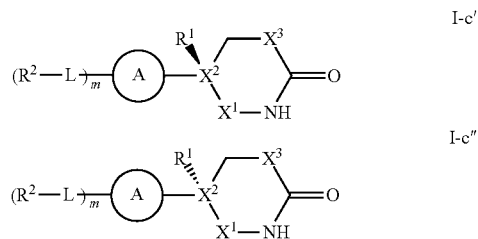

or a pharmaceutically acceptable salt thereof, wherein:
each of Ring A, L, X$^1$, X$^2$, X$^3$, R$^1$, R$^2$, and m is as defined above.

In certain embodiments, the present invention provides a compound of formula I-d:

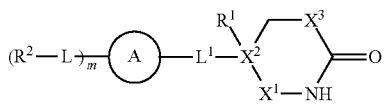

I-d or a pharmaceutically acceptable salt thereof, wherein:

X$^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

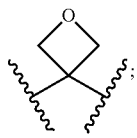

X$^2$ is a carbon atom or silicon atom;
X$^3$ is a bivalent moiety selected from —CR$_2$—, —NR—, —O—, —S—, or —Si(R$_2$)—;
R$^1$ is hydrogen, deuterium, halogen, —CN, —OR, —SR, —S(O)R, —S(O)$_2$R, —N(R)$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each R$^2$ is independently hydrogen, deuterium, —R$^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;
each L is independently a covalent bond or a bivalent, saturated or unsaturated, straight or branched C$_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

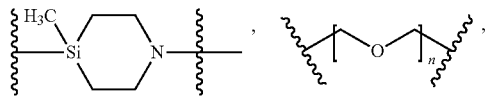

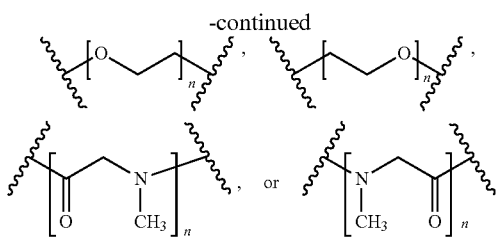

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
each R$^3$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
Ring A is a tricyclic ring selected from

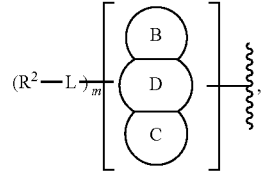

wherein
each of Ring B, Ring D, and Ring C is independently a use ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;
L$^1$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —CR$_2$—, —CFR—, —CF$_2$—, —NR—, —S—, —S(O)$_2$— or —CR=CR—;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

In some embodiments, a compound of formula I-d above is provided as a compound of formula I-d' or formula I-d":

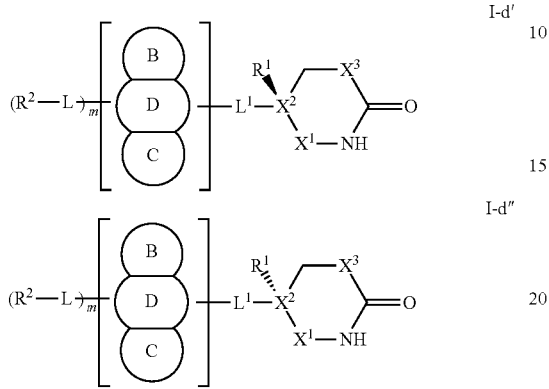

or a pharmaceutically acceptable salt thereof, wherein:
each of Ring B, Ring C, Ring D, L, $L^1$, $R^1$, $R^2$, $X^1$, $X^2$, $X^3$, and m is as defined above.

As described above, in certain embodiments, the present invention provides a compound of formula II:

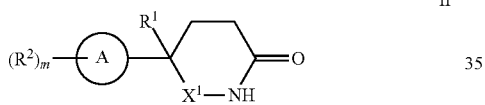

or a pharmaceutically acceptable salt thereof, wherein:
$X^1$ is a bivalent moiety selected from a covalent bond, —CH$_2$—, —C(O)—, —C(S)—, or

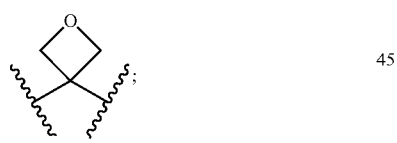

$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^3$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

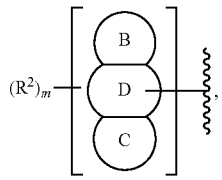

wherein
each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-2 heteroatoms independently selected from nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16.

As described above, in certain embodiments, the present invention provides a compound of formula II':

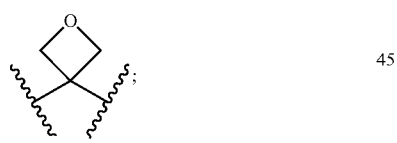

or a pharmaceutically acceptable salt thereof, wherein:
$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

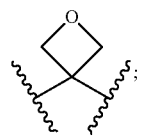 [SMILES: *C1(*)COC1]

$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each L is independently a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

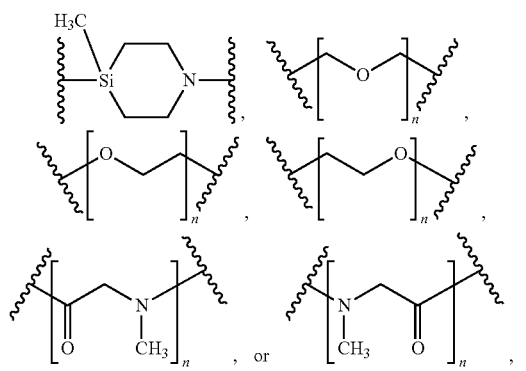

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

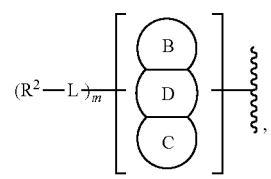

wherein
each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each of n is independently 1, 2, 3, 4, 5, 6, 7, 8, 9, or 10; and
m is 0, 1, 2, 3, 4, 5, 6, 7, 8, 9, 10, 11, 12, 13, 14, 15, or 16.

In some embodiments, a compound of formula II' above is provided as a compound of formula II" or formula II''':

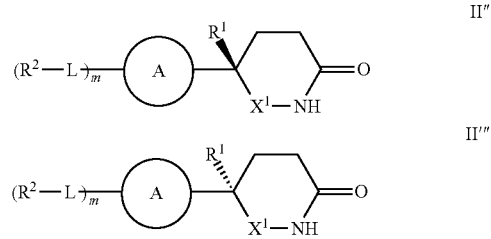

or a pharmaceutically acceptable salt thereof, wherein:
each of Ring A, L, $X^1$, $R^1$, $R^2$, and m is as defined above.

As described above, in certain embodiments, the present invention provides a compound of formula II-a:

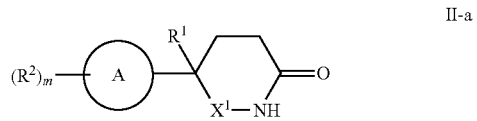

or a pharmaceutically acceptable salt thereof, wherein:
$X^1$ is a bivalent moiety selected from a covalent bond, —$CH_2$—, —C(O)—, —C(S)—, or

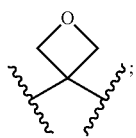 [SMILES: *C1(*)COC1]

R¹ is hydrogen, deuterium, halogen, —CN, —OR, —SR, —S(O)R, —S(O)₂R, —N(R)₂, —Si(R)₃, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;

each R³ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

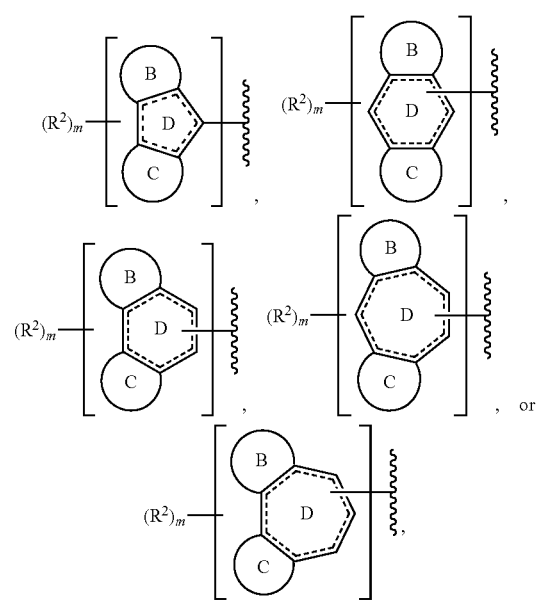

wherein
each of Ring B and Ring C is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-2 heteroatoms independently selected from nitrogen, oxygen or sulfur, or 5-membered heteroaryl with 1-3 heteroatoms independently selected from nitrogen, oxygen or sulfur;

Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen or sulfur, or heteroaryl with 1-3 heteroatoms independently selected from nitrogen, oxygen or sulfur;

--- is a single or double bond; and m is 0, 1, 2, 3, 4, 5, 6, 7, 8, 9, 10, 11, 12, 13, 14, 15, or 16.

As described above, in certain embodiments, the present invention provides a compound of formula II-b:

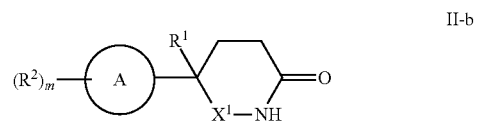

II-b or a pharmaceutically acceptable salt thereof, wherein:
X¹ is a bivalent moiety selected from a covalent bond, —CH₂—, —C(O)—, —C(S)—, or

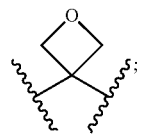 [SMILES: *C1(*)COC1]

R¹ is hydrogen, deuterium, halogen, —CN, —OR, —SR, —S(O)R, —S(O)₂R, —N(R)₂, —Si(R)₃, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;

each R³ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

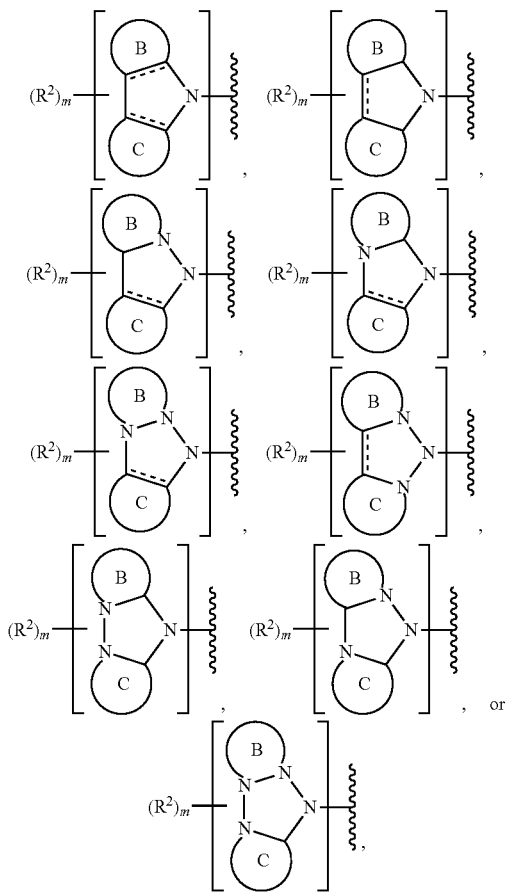

wherein
each of Ring B and Ring C is independently a fused ring selected from 6-membered aryl containing 0-2 nitrogens, 5 to 7-membered saturated or partially unsaturated carbocyclyl, 5 to 7-membered saturated or partially unsaturated heterocyclyl ring with 1-2 heteroatoms independently selected from nitrogen, oxygen or sulfur, or 5-membered heteroaryl with 1-3 heteroatoms independently selected from nitrogen, oxygen or sulfur;

═══ is a single or double bond; and m is 0, 1, 2, 3, 4, 5, 6, 7, or 8.

As defined above and described herein, in certain embodiments, the present invention provides a compound of formula II-c:

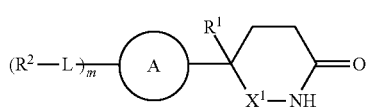

II-c or a pharmaceutically acceptable salt thereof, wherein:
$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

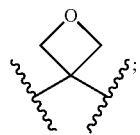

$R^1$ is hydrogen, deuterium, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or.

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each L is independently a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

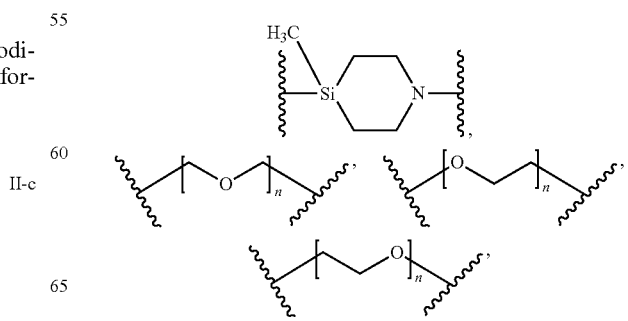

-continued

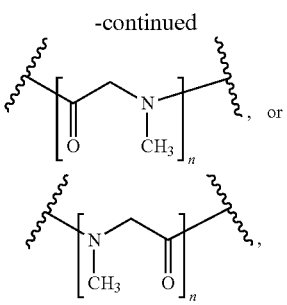, or wherein:
  each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;
  each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
  Ring A is a bicyclic ring system selected from

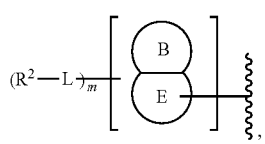

wherein
  Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;
  Ring E is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

each of n is independently 1, 2, 3, 4, 5, 6, 7, 8, 9, or 10; and
m is 0, 1, 2, 3, 4, 5, 6, 7, 8, 9, 10, 11, 12, 13, 14, 15, or 16.

In some embodiments, a compound of formula II-c above is provided as a compound of formula II-c' or formula II-c":

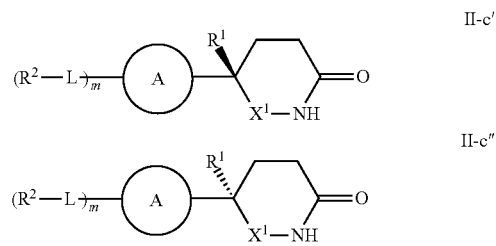

or a pharmaceutically acceptable salt thereof, wherein:
  each of Ring A, L, $X^1$, $R^1$, $R^2$, and m is as defined above.

In some embodiments, a compound of formula II-c above is provided as a compound of formula II-c-1:

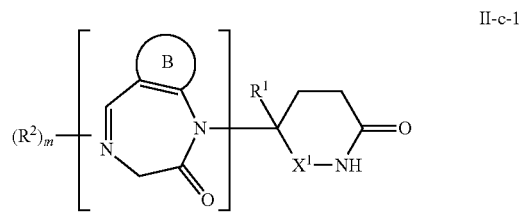

or a pharmaceutically acceptable salt thereof, wherein:
  each of Ring B, $X^1$, $R^1$, $R^2$, and m is as defined above.

As described above, in certain embodiments, the present invention provides a compound of formula II-d:

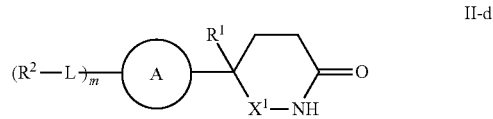

or a pharmaceutically acceptable salt thereof, wherein:
  $X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

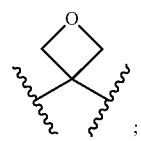 [SMILES: *C1(*)COC1];

$R^1$ is hydrogen, deuterium, halogen, —CN, —OR, —SR, —S(O)R, —S(O)$_2$R, —$NR_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted $C_{1-4}$ aliphatic;
  each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^3$, halogen, —CN, —$NO_2$, —OR, —SR, —$N(R)_2$, —Si$(R)_3$, —$S(O)_2R$, —$S(O)_2N(R)_2$, —S(O)R, —C(O)R, —C(O)OR, —C(O)$N(R)_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each L is independently a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

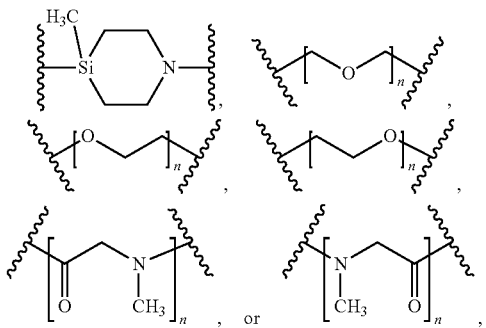

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring system selected from

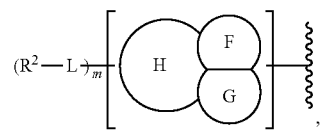

wherein
each of Ring F and G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

each of n is independently 1, 2, 3, 4, 5, 6, 7, 8, 9, or 10; and m is 0, 1, 2, 3, 4, 5, 6, 7, 8, 9, 10, 11, 12, 13, 14, 15, or 16.

In some embodiments, a compound of formula II-d above is provided as a compound of formula II-d' or formula II-d":

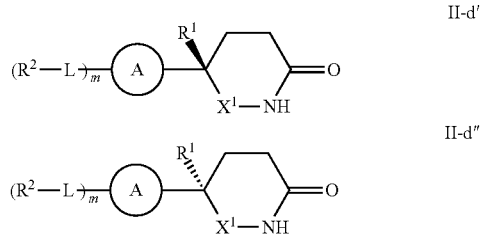

or a pharmaceutically acceptable salt thereof, wherein:
each of Ring A, L, $X^1$, $R^1$, $R^2$, and m is as defined above.

In some embodiments, a compound of formula II-d above is provided as a compound of formula II-d-1:

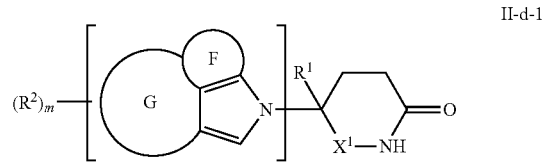

or a pharmaceutically acceptable salt thereof, wherein:
each of Ring F, Ring G, $X^1$, $R^1$, $R^2$, and m is as defined above.

In certain embodiments, the present invention provides a compound of formula III or IV:

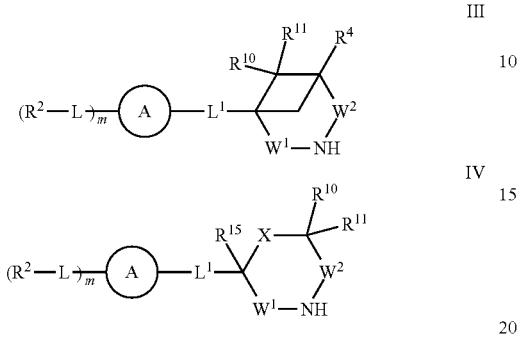

or a pharmaceutically acceptable salt thereof, wherein:
each $R^2$ is independently hydrogen, deuterium, —$R^3$, halogen, —CN, —$NO_2$, —OR, —SR, —$N(R)_2$, —Si$(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —OP(O)(OR)($NR_2$), —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —N(R)P(O)(OR)($NR_2$), —$N(R)P(O)(NR_2)_2$, or —$N(R)S(O)_2R$;

each L is independently a covalent bond or a bivalent, saturated or unsaturated, straight or branched $C_{1-50}$ hydrocarbon chain, wherein 0-6 methylene units of L are independently replaced by —C(D)(H)—, —$C(D)_2$-, -Cy-, —O—, —N(R)—, —$Si(R)_2$—, —Si(OH)(R)—, —$Si(OH)_2$—, —P(O)(OR)—, —P(O)(R)—, —P(O)($NR_2$)—, —S—, —OC(O)—, —C(O)O—, —C(O)—, —S(O)—, —$S(O)_2$—, —$N(R)S(O)_2$—, —$S(O)_2N(R)$—, —N(R)C(O)—, —C(O)N(R)—, —OC(O)N(R)—, —N(R)C(O)O—,

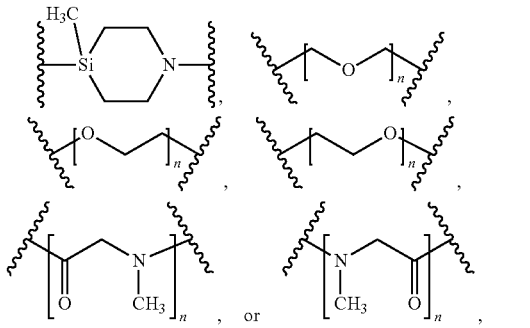

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

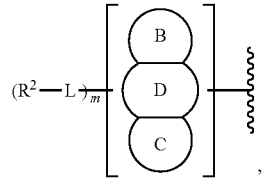

wherein
each of Ring B, Ring D, and Ring C is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$CR_2$—, —CFR—, —$CF_2$—, —NR—, —S—, —$S(O)_2$— or —CR=CR—;

each of n is independently 1, 2, 3, 4, 5, 6, 7, 8, 9, or 10;
m is 0, 1, 2, 3, 4, 5, 6, 7, 8, 9, 10, 11, 12, 13, 14, 15, or 16; and
$R^4$, $R^{10}$, $R^{11}$, $R^{15}$, $W^1$, $W^2$, and X is as defined in WO 2019/099868, the entirety of each of which is herein incorporated by reference.

As defined above and described herein, X¹ is a bivalent moiety selected from a cova covalent bond, —CH₂—, —CHCF₃—, —SO₂—, —S(O)—, —P(O)R—, —P(O)OR—, —P(O)NR₂—, —C(O)—, —C(S)—, or

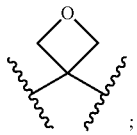 [SMILES: *C1(*)COC1]

lent bond, —CH₂—, —C(O)—, —C(S)—, or

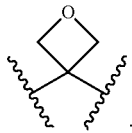

In some embodiments, X¹ is a covalent bond. In some embodiments, X¹ is —CH₂—. In some embodiments, X¹ is —CHCF₃—. In some embodiments, X¹ is —SO₂—. In some embodiments, X¹ is —S(O)—. In some embodiments, X¹ is —P(O)R—. In some embodiments, X¹ is —P(O)OR—. In some embodiments, X¹ is —P(O)NR₂—. In some embodiments, X¹ is —C(O)—. In some embodiments, X¹ is —C(S)—. In some embodiments, X¹ is

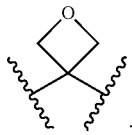

In some embodiments, X¹ is selected from those depicted in Table 1, below.

As defined above and described herein, X² is a carbon atom or silicon atom.

In some embodiments, X² is a carbon atom. In some embodiments, X² is a silicon atom.

In some embodiments, X² is selected from those depicted in Table 1, below.

As defined above and described herein, X³ is a bivalent moiety selected from —CH₂—, —NR—, —O—, —S—, or —Si(R₂)—.

In some embodiments, X³ is —CH₂—. In some embodiments, X³ is —NR—. In some embodiments, X³ is —O—. In some embodiments, X³ is —S—. In some embodiments, X² is —Si(R₂)—.

In some embodiments, X³ is selected from those depicted in Table 1, below.

As defined above and described herein, R¹ is hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)(R)₂, —Si(R)₃, or an optionally substituted C₁₋₄ aliphatic.

In some embodiments, R¹ is hydrogen. In some embodiments, R¹ is deuterium. In some embodiments, R¹ is halogen. In some embodiments, R¹ is —CN. In some embodiments, R¹ is —OR. In some embodiments, R¹ is —SR. In some embodiments, R¹ is —S(O)R. In some embodiments, R¹ is —S(O)₂R. In some embodiments, R¹ is —NR₂. In some embodiments, R¹ is —P(O)(OR)₂. In some embodiments, R¹ is —P(O)(NR₂)OR. In some embodiments, R¹ is —P(O)(NR₂)₂. In some embodiments, R¹ is —Si(OH)₂R. In some embodiments, R¹ is —Si(OH)(R)₂. In some embodiments, R¹ is —Si(R₃). In some embodiments, R¹ is an optionally substituted C₁₋₄ aliphatic.

In some embodiments, R¹ is selected from those depicted in Table 1, below.

As defined above and described herein, each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is optionally substituted C₁₋₆ aliphatic. In some embodiments, R is optionally substituted phenyl. In some embodiments, R is optionally substituted 4-7 membered saturated or partially unsaturated heterocyclic having 1-2 heteroatoms independently selected from nitrogen, oxygen, and sulfur. In some embodiments, R is optionally substituted 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As defined above and described herein, each R² is independently hydrogen, deuterium, —R³, halogen, —CN, —NO₂, —OR, —SR, —N(R)₂, —P(O)(OR)₂, —P(O)(NR₂)OR, —P(O)(NR₂)₂, —Si(OH)₂R, —Si(OH)(R)₂, —Si(R₃), —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R.

In some embodiments, R² is hydrogen. In some embodiments, R² is deuterium. In some embodiments, R² is —R³. In some embodiments, R² is halogen. In some embodiments, R² is —CN. In some embodiments, R² is —NO₂. In some embodiments, R² is —OR. In some embodiments, R² is —SR. In some embodiments, R² is —NR₂. In some embodiments, R² is —P(O)(OR)₂. In some embodiments, R² is —P(O)(NR₂)OR. In some embodiments, R² is —P(O)(NR₂)₂. In some embodiments, R² is —Si(OH)₂R. In some embodiments, R² is —Si(OH)(R)₂. In some embodiments, R² is —Si(R₃). In some embodiments, R² is —S(O)₂R. In some embodiments, R² is —S(O)₂NR₂. In some embodiments, R² is —S(O)R. In some embodiments, R² is —C(O)R. In some embodiments, R² is —C(O)OR. In some embodiments, R² is —C(O)NR₂. In some embodiments, R² is —C(O)N(R)OR. In some embodiments, R² is —C(R)₂N(R)C(O)R. In some embodiments, R² is —C(R)₂N(R)C(O)N(R)₂. In some embodiments, R² is —OC(O)R. In some embodiments, R² is —OC(O)NR₂. In some embodiments, R² is —N(R)C(O)OR. In some embodiments, R² is —N(R)C(O)R. In some embodiments, R² is —N(R)C(O)NR₂. In some embodiments, R² is —N(R)S(O)₂R.

In some embodiments, $R^2$ is —OH. In some embodiments, $R^2$ is —NH$_2$. In some embodiments, $R^2$ is —CH$_2$NH$_2$. In some embodiments, $R^2$ is —CH$_2$NHCOMe. In some embodiments, $R^2$ is —CH$_2$NHCONHMe. In some embodiments, $R^2$ is —NHCOMe. In some embodiments, $R^2$ is —NHCONHEt. In some embodiments, $R^2$ is —SiMe$_3$. In some embodiments, $R^2$ is Br. In some embodiments, $R^2$ is —SiMe(OH)$_2$. In some embodiments, $R^2$ is

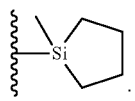

In some embodiments, $R^2$ is Br. In some embodiments, $R^2$ is Cl. In some embodiments, $R_2$ is F. In some embodiments, $R_2$ is Me. In some embodiments, $R_2$ is —NHMe. In some embodiments, $R^2$ is —NMe$_2$. In some embodiments, $R^2$ is —NHCO$_2$Et. In some embodiments, $R^2$ is —CN. In some embodiments, $R^2$ is —CH$_2$Ph. In some embodiments, $R^2$ is —NHCO$_2$tBu. In some embodiments, $R^2$ is —CO$_2$tBu. In some embodiments, $R^2$ is —OMe. In some embodiments, $R^2$ is —CF$_3$.

In some embodiments, $R^2$ is selected from those depicted in Table 1, below.

As defined above and described herein, L is independently a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

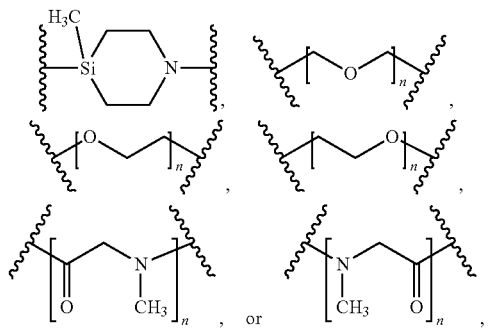

wherein each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur.

In some embodiments, L is independently a covalent bond. In some embodiments, L is independently a bivalent, saturated or unsaturated, straight or branched $C_{1-50}$ hydrocarbon chain, wherein 0-6 methylene units of L are independently replaced by —C(D)(H)—, —C(D)$_2$-, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

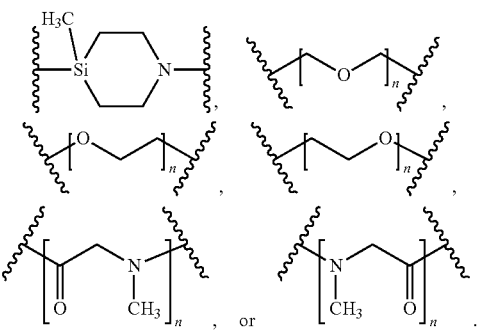

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-7 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy- is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-7 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

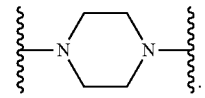

In some embodiments, -Cy- is selected from those depicted in Table 1, below.

In some embodiments, L is

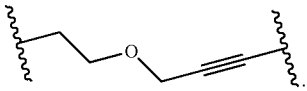 [SMILES: *C#CCOCC*]

In some embodiments, L is

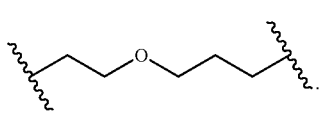 [SMILES: *CCCOCC*]

In some embodiments, L is

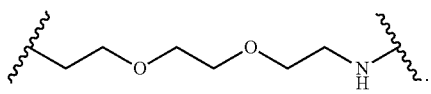 [SMILES: *CCOCCOCCN*]

In some embodiments L is

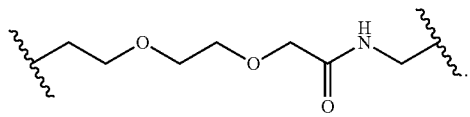 [SMILES: *CCOCCOCC(=O)NC*]

In some embodiments, L is

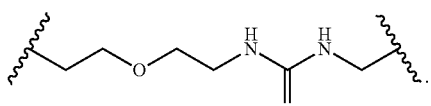

In some embodiments, L is

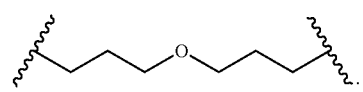 [SMILES: *CCCOCCC*]

In some embodiments L is

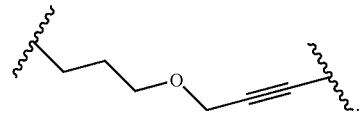 [SMILES: *C#CCOCCC*]

In some embodiments, L is

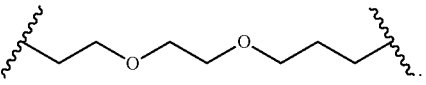 [SMILES: *CCCOCCOCC*]

In some embodiments, L is

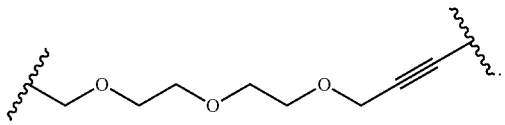 [SMILES: *C#CCOCCOCCOC*]

In some embodiments, L is

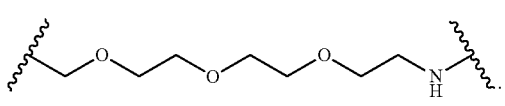 [SMILES: *COCCOCCOCCN*]

In some embodiments, L is

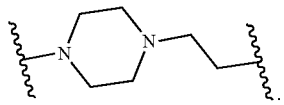 [SMILES: *CCN1CCN(*)CC1]

In some embodiments, L is

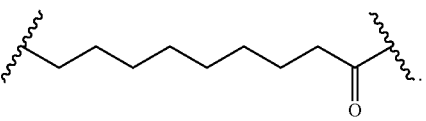 [SMILES: *CCCCCCCCC(*)=O]

In some embodiments, L is

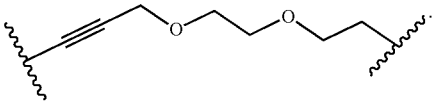 [SMILES: *C#CCOCCOCC*]

In some embodiments, L is selected from those depicted in Table 1, below.

As defined above and described herein, each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^3$ is an optionally substituted $C_{1-6}$ aliphatic. In some embodiments, $R^3$ is an optionally substituted phenyl. In some embodiments, $R^3$ is an optionally substituted 4-7 membered saturated or partially unsaturated heterocyclic ring having 1-2 heteroatoms independently selected from nitrogen, oxygen, and sulfur. In some embodiments, $R^3$ is an optionally substituted 5-6 membered heteroaryl ring having 1-4 heteroatoms independently selected from nitrogen, oxygen, and sulfur.

In some embodiments, R³ is selected from those depicted in Table 1, below.

As defined above and described herein, Ring A is a tricyclic ring selected from

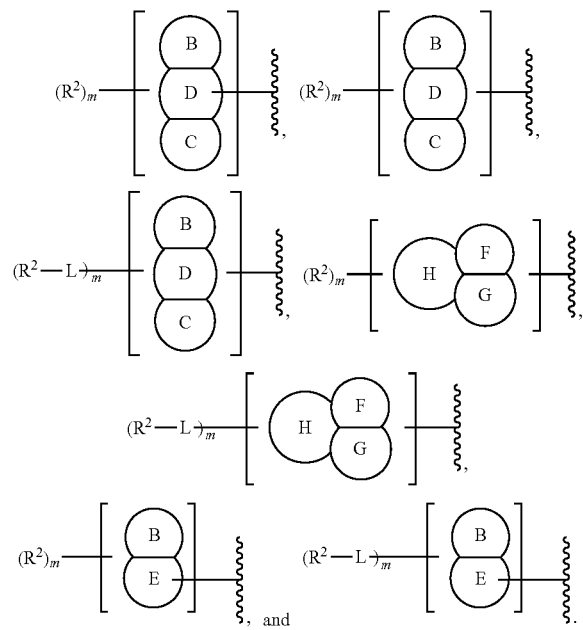

In some embodiments, Ring A is

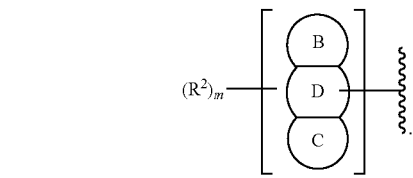

In some embodiments, Ring A is

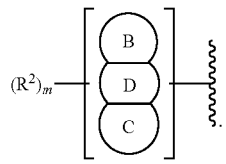

In some embodiments, Ring A is

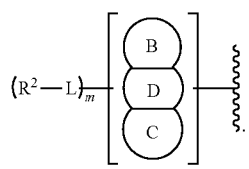

In some embodiments, Ring A is

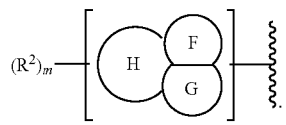

In some embodiments, Ring A is

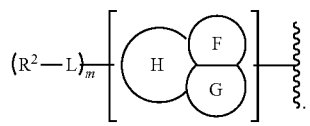

In some embodiments, Ring A is

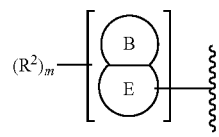

In some embodiments, Ring A is

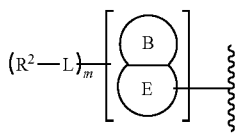

In some embodiments, Ring A is selected from those depicted in Table 1, below.

As defined above and described herein, each of Ring B, Ring C, and Ring D is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur.

In some embodiments, each Ring B, Ring C, and Ring D is independently a 6-membered aryl. In some embodiments, each Ring B, Ring C, and Ring D is independently a 6-membered heteroaryl containing 1-4 heteroatoms independently selected from nitrogen, oxygen, or sulfur. In some embodiments, each Ring B, Ring C, and Ring D is independently a 5 to 7-membered saturated or partially unsaturated carbocyclyl. In some embodiments, each Ring B, Ring C, and Ring D is independently a 5 to 7-membered saturated or partially unsaturated heterocyclyl with 1-3 heteroatoms independently selected from boron, nitrogen, oxygen, silicon, or sulfur. In some embodiments, each Ring B, Ring C, and Ring D is independently a 5-membered heteroaryl with 1-4 heteroatoms independently selected from nitrogen, oxygen or sulfur.

In some embodiments, each Ring B, Ring C, and Ring D is independently selected from those depicted in Table 1, below.

As defined above and described herein, Ring E is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring E is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring E is

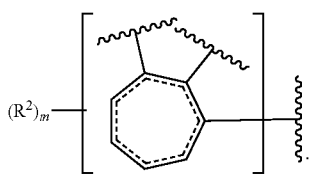

In some embodiments, Ring E is

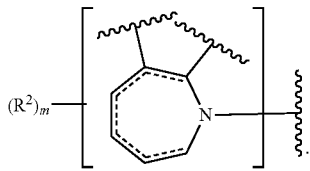

In some embodiments, Ring E is

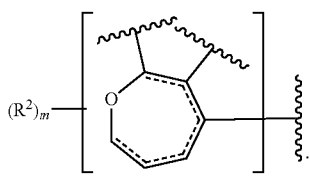

In some embodiments, Ring E is

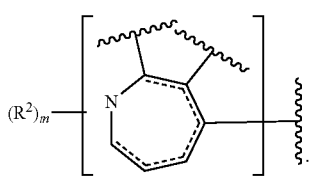

In some embodiments, Ring E is

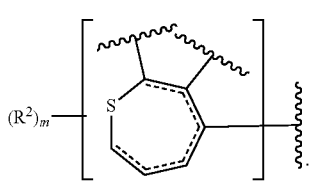

In some embodiments, Ring E is

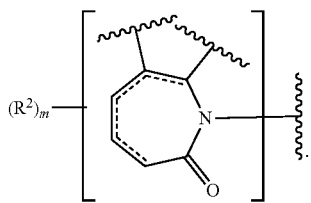

In some embodiments, Ring E is

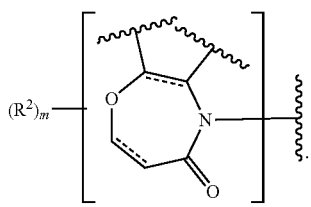

In some embodiments, Ring E is

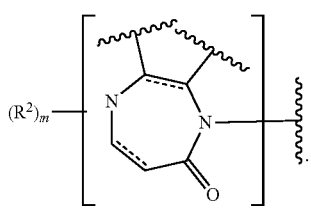

In some embodiments, Ring E is

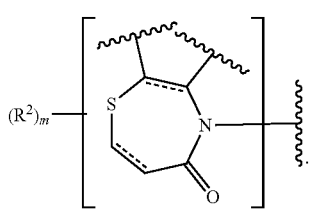

some embodiments, Ring E is

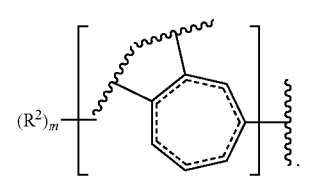

In some embodiments, Ring E is

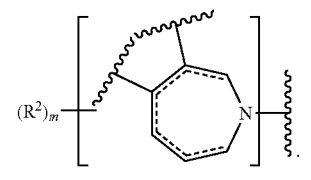

In some embodiments, Ring E is

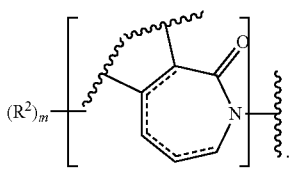

In some embodiments, Ring E is

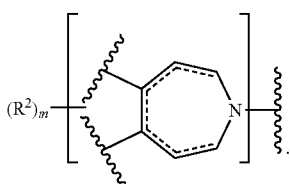

In some embodiments, Ring E is

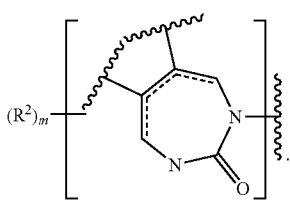

In some embodiments, Ring E is

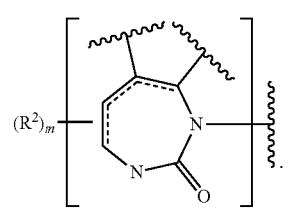

In some embodiments, Ring E is

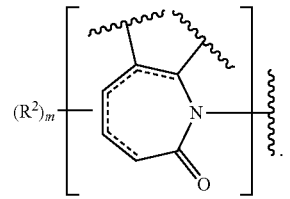

In some embodiments, Ring E is

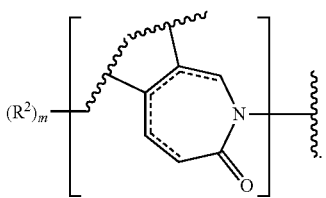

In some embodiments, Ring E is

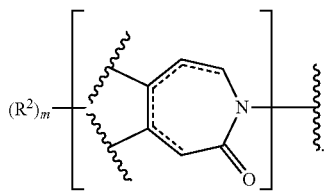

In some embodiments, Ring E is

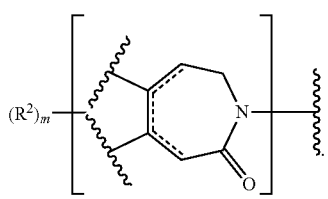

In some embodiments, Ring E is

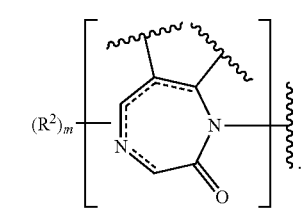

In some embodiments, Ring E is

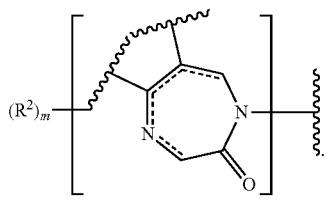

In some embodiments, Ring E is selected from those depicted in Table 1, below.

As defined above and described herein, each of Ring F and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring F and Ring G is independently a 6-membered aryl. In some embodiments, each of Ring F and Ring G is independently a 6-membered heteroaryl containing 1-4 heteroatoms independently selected from nitrogen, oxygen, or sulfur. In some embodiments, each of Ring F and Ring G is independently a 5 to 7-membered saturated or partially unsaturated carbocyclyl. In some embodiments, each of Ring F and Ring G is independently a 5 to 7-membered saturated or partially unsaturated heterocyclyl ring with 1-3 heteroatoms independently selected from boron, nitrogen, oxygen, silicon, or sulfur. In some embodiments, each of Ring F and Ring G is independently a 5-membered heteroaryl with 1-3 heteroatoms independently selected from nitrogen, oxygen or sulfur.

In some embodiments, each Ring F and Ring G is independently

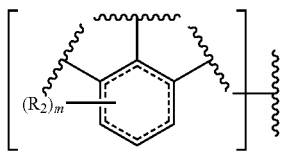

In some embodiments, each Ring F and Ring G is independently

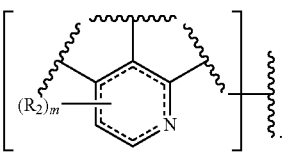

In some embodiments, each Ring F and Ring G is independently

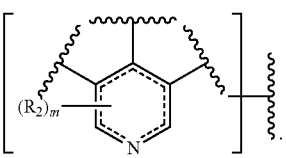

In some embodiments, each Ring F and Ring G is independently

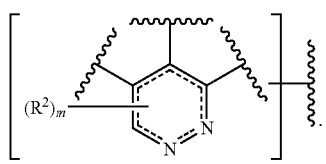

In some embodiments, Ring F and Ring G is independently

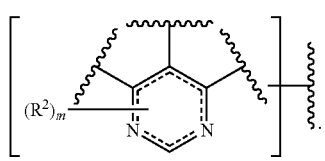

In some embodiments, Ring F and Ring G is independently

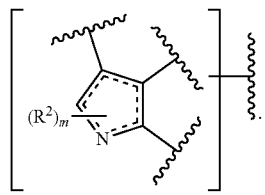

In some embodiments, Ring F and Ring G is independently

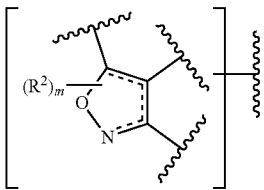

In some embodiments, Ring F and Ring G is independently

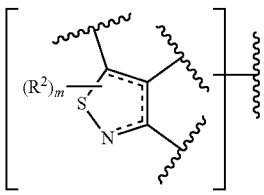

In some embodiments, each of Ring F and G is independently selected from those depicted in Table 1, below.

As defined above and described herein, Ring H is a fused ring selected from a 7-12 membered saturated or partially unsaturated carbocyclyl or heterocyclyl with 1-3 heteroatoms independently selected from boron, nitrogen, oxygen, silicon, or sulfur, wherein Ring H is optionally further substituted with 1-2 oxo groups.

In some embodiments, Ring H is a 7-12 membered saturated or partially unsaturated carbocyclyl. In some embodiments, Ring H is a 7-12 membered saturated or partially unsaturated heterocyclyl with 1-3 heteroatoms independently selected from boron, nitrogen, oxygen, silicon, or sulfur. In some embodiments, Ring H is optionally further substituted with 1-2 oxo groups.

In some embodiments, Ring H is

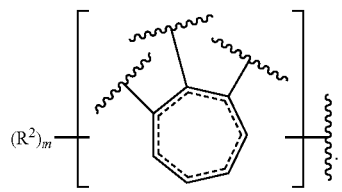

In some embodiments, Ring H is
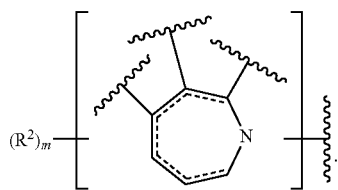
In some embodiments, Ring H is
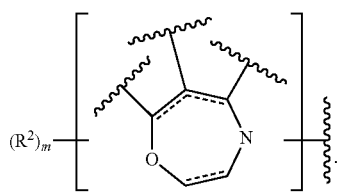
In some embodiments, Ring H is
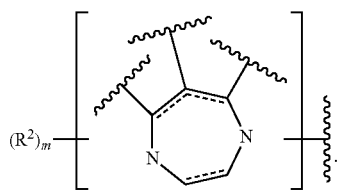
In some embodiments, Ring H is
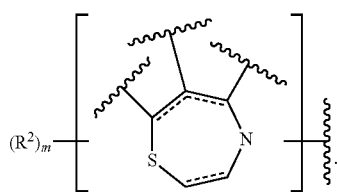
In some embodiments, Ring H is
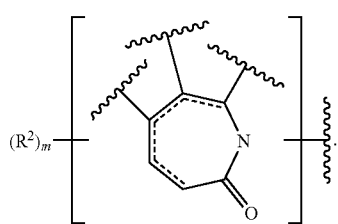
In some embodiments, Ring H is
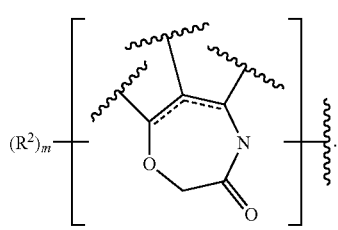
In some embodiments, Ring H is
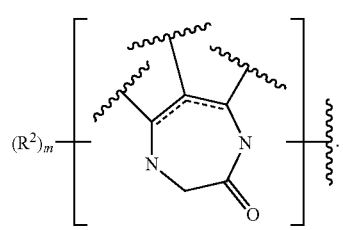
In some embodiments, Ring H is
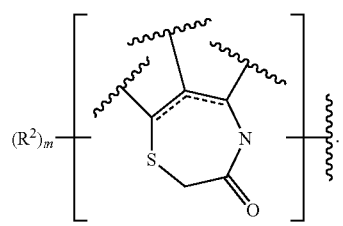
some embodiments, Ring H is
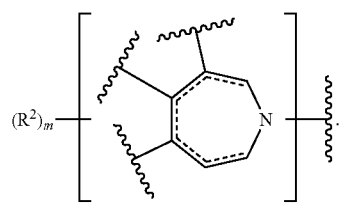
In some embodiments, Ring H is
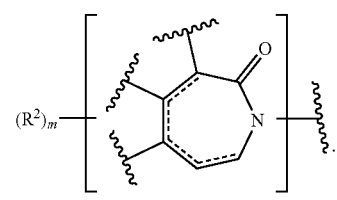
In some embodiments, Ring H is
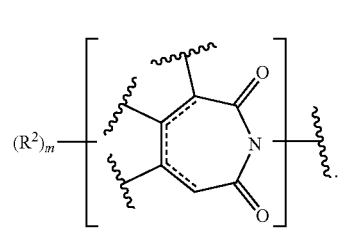

In some embodiments, Ring H is
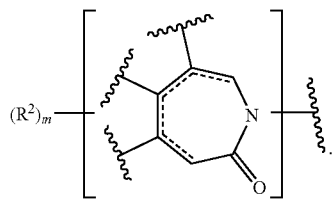
In some embodiments, Ring H is
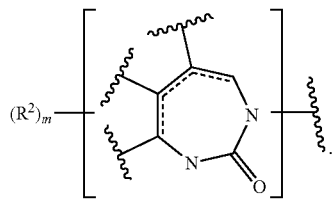
In some embodiments, Ring H is
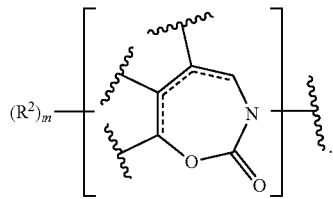
In some embodiments, Ring H is selected from those depicted in Table 1, below.
As defined above and described herein, Ring A is a tricyclic ring selected from
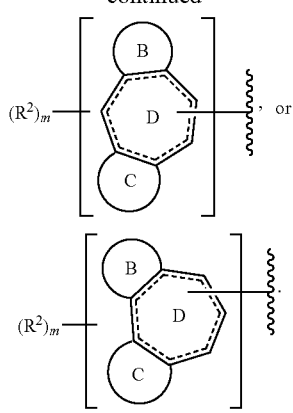
-continued
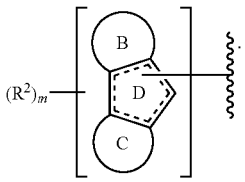, or
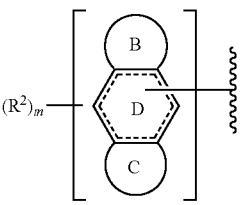
In some embodiments, Ring A is
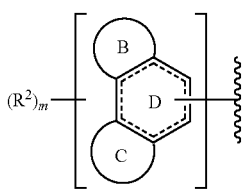
In some embodiments, Ring A is
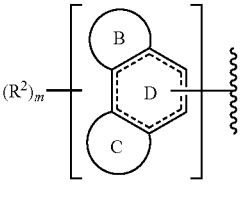
In some embodiment, Ring A is
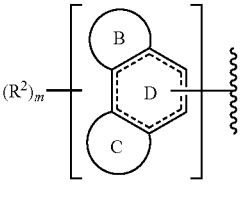

In some embodiments, Ring A is

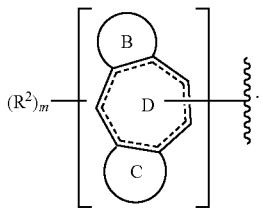

In some embodiments, Ring A is

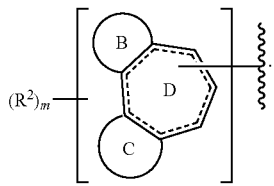

In some embodiments, Ring A is selected from those depicted in Table 1, below.

As defined above and described herein, Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen or sulfur, or heteroaryl with 1-3 heteroatoms independently selected from nitrogen, oxygen or sulfur.

In some embodiments, Ring D is an aryl containing 0-2 nitrogen atoms. In some embodiments, Ring D is a saturated or partially unsaturated carbocyclyl. In some embodiments, each Ring D is a saturated or partially unsaturated heterocyclyl with 1-3 heteroatoms independently selected from nitrogen, oxygen, silicon, or sulfur. In some embodiments, Ring D is a heteroaryl with 1-3 heteroatoms independently selected from nitrogen, oxygen or sulfur.

In some embodiments, Ring D is

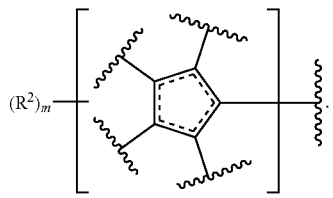

In some embodiments, Ring D is

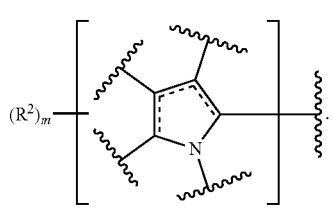

In some embodiments, Ring D is

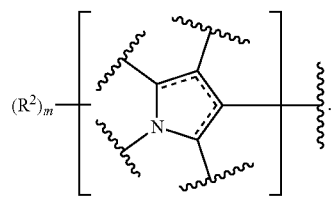

In some embodiments, Ring D is

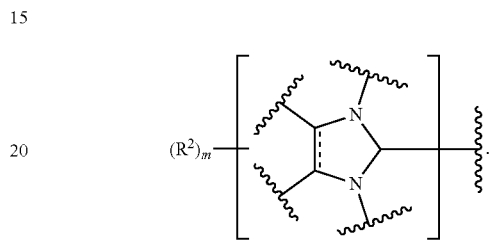

In some embodiments, Ring D is

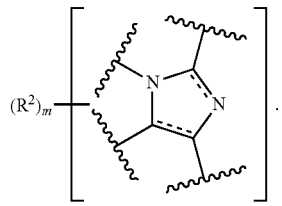

In some embodiments, Ring D is

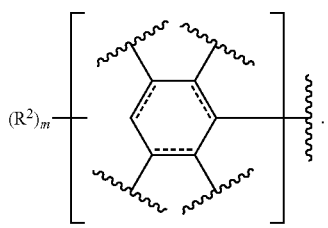

In some embodiments, Ring D is

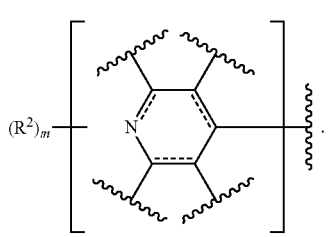

In some embodiments, Ring D is
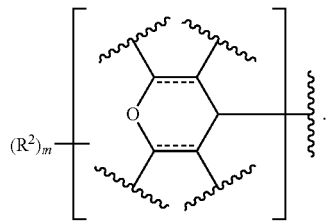
In some embodiments, Ring D is
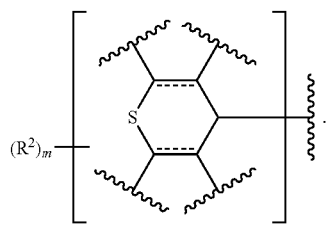
In some embodiments, Ring D is
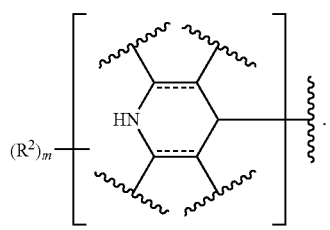
In some embodiments, Ring D is
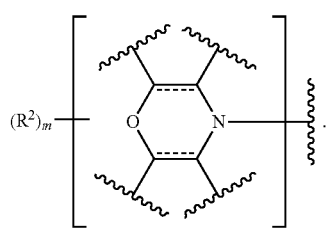
In some embodiments, Ring D is
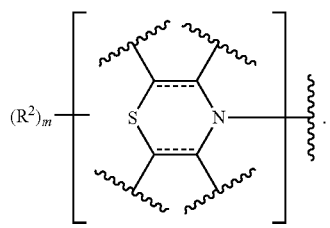
In some embodiments, Ring D is
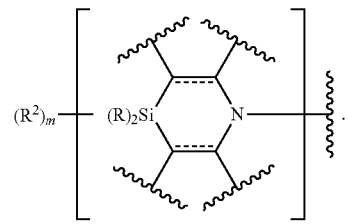
In some embodiments, Ring D is
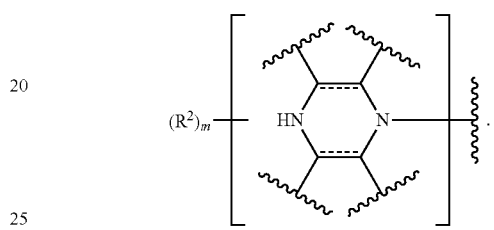
In some embodiments, Ring D is
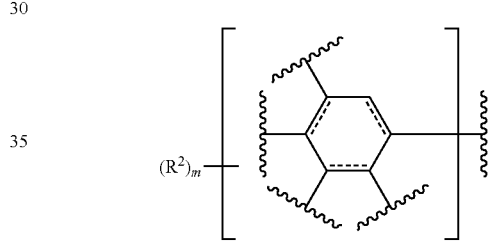
In some embodiments, Ring D is
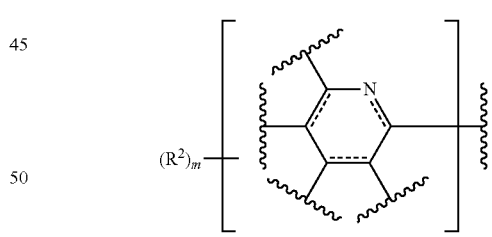
In some embodiments, Ring D is
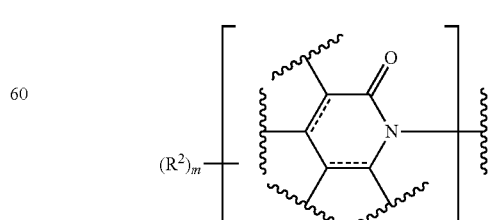

In some embodiments, Ring D is
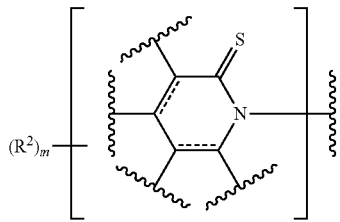
In some embodiments, Ring D is
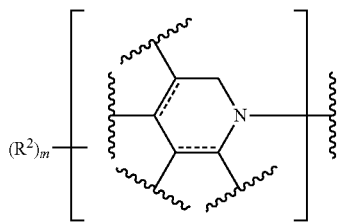
In some embodiments, Ring D is
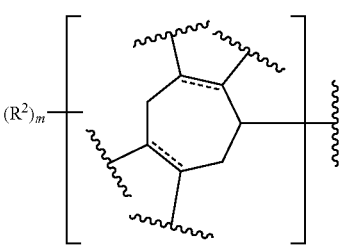
In some embodiments, Ring D is
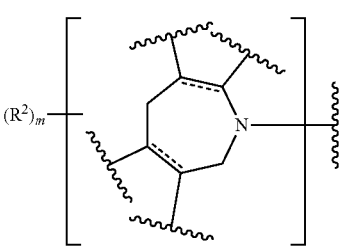
In some embodiments, Ring D is
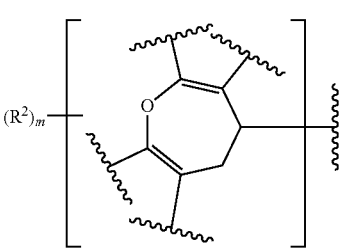
In some embodiments, Ring D is
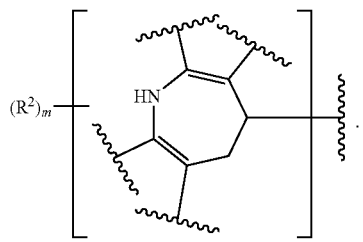
In some embodiments, Ring D is
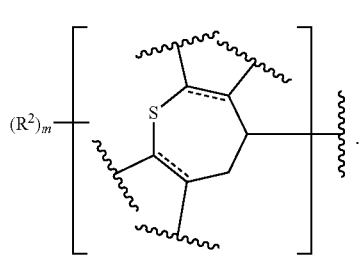
In some embodiments, Ring D is
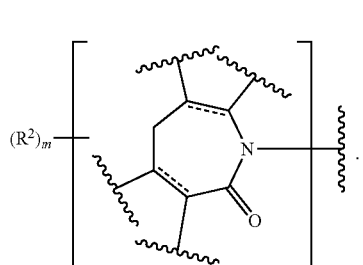
In some embodiments, Ring D is
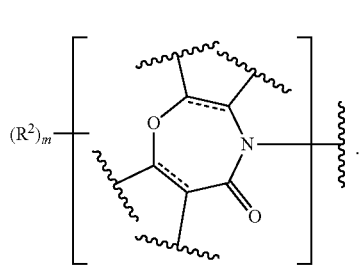
In some embodiments, Ring D is
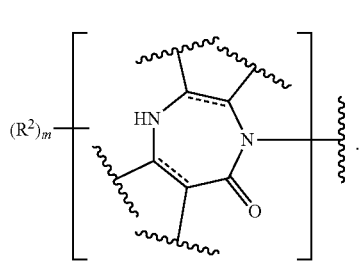

In some embodiments, Ring D is

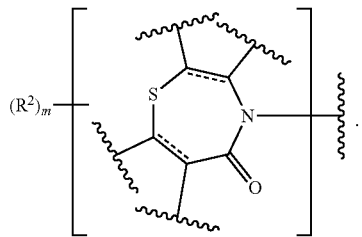

In some embodiments, Ring D is

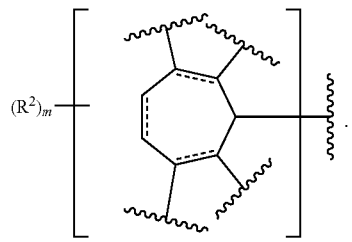

In some embodiments, Ring D is

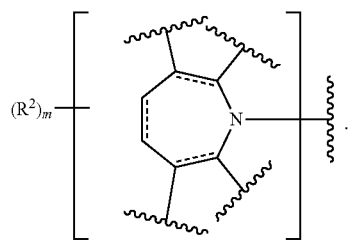

In some embodiments, Ring D is

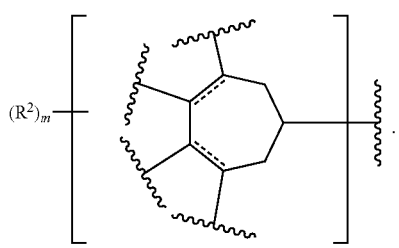

In some embodiments, Ring D is

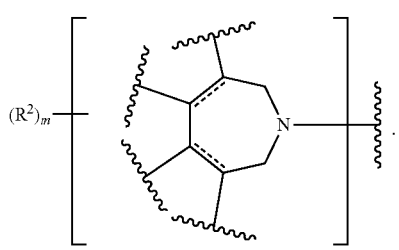

In some embodiments, Ring D is

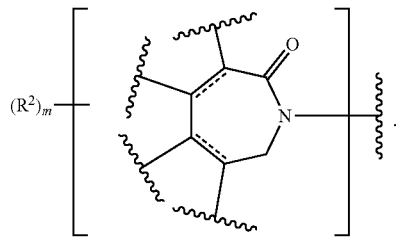

In some embodiments, Ring D is

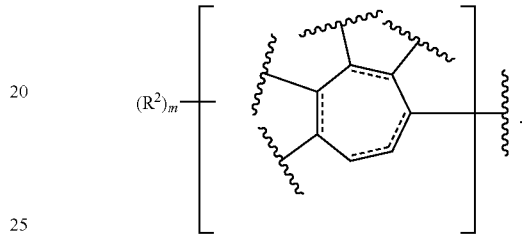

In some embodiments, Ring D is

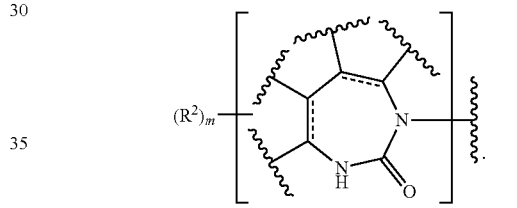

In some embodiments, Ring D is

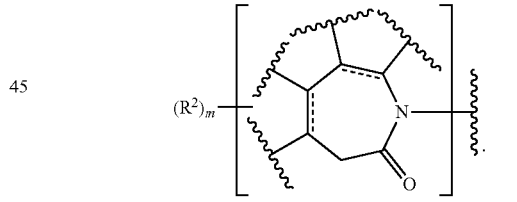

In some embodiments, Ring D is selected from those depicted in Table 1, below.

As defined above and described herein, ═══ is a single or double bond.

In some embodiments, ═══ is a single bond. In some embodiments, ═══ is a double bond.

In some embodiments, ═══ is selected from those depicted in Table 1, below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1, below.

As defined above and described herein, Ring A is a tricyclic ring selected from

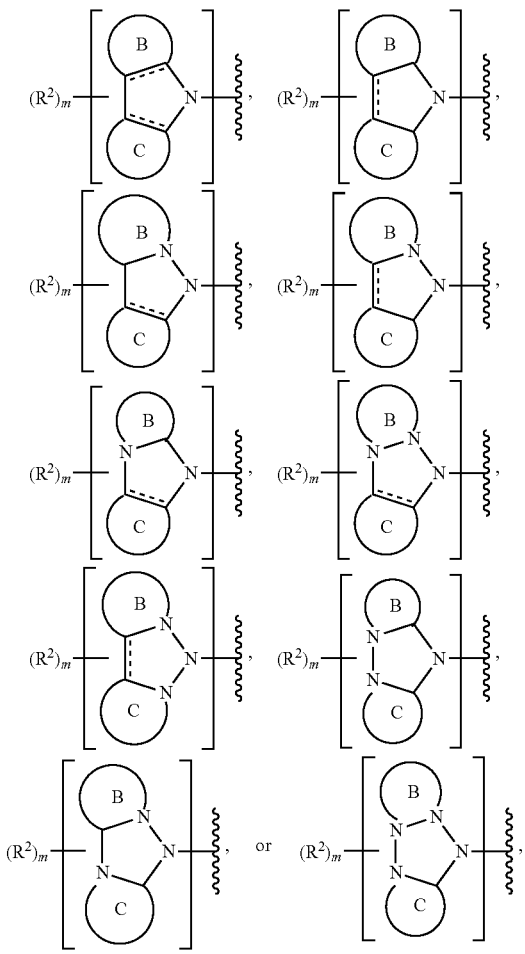

In some embodiments, Ring A is

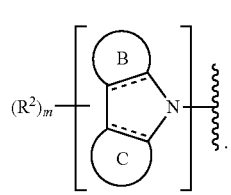

In some embodiments, Ring A is

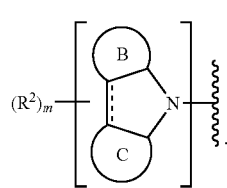

In some embodiment, Ring A is

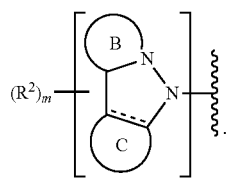

In some embodiments, Ring A is

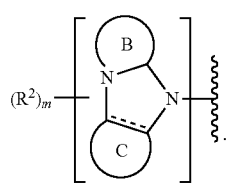

In some embodiments, Ring A is

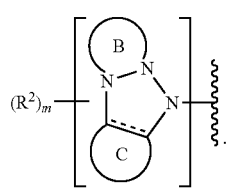

In some embodiments, Ring A is

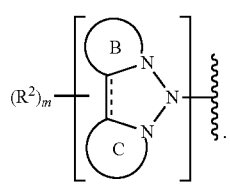

In some embodiments, Ring A is

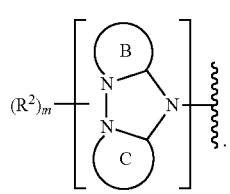

In some embodiments, Ring A is

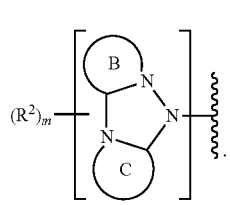

In some embodiments, Ring A is

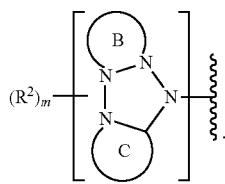

In some embodiments, Ring A is

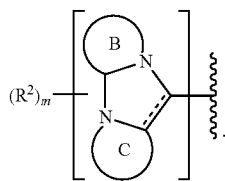

In some embodiments, Ring A is

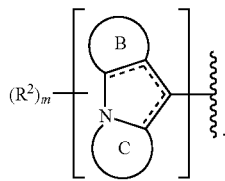

In some embodiments, Ring A is

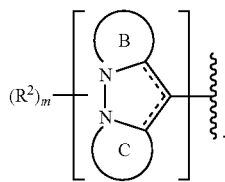

In some embodiments, Ring A is

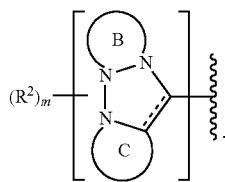

In some embodiments, Ring A is selected from those depicted in Table 1, below.

As defined above and described herein, each Ring B and Ring C is independently a fused ring selected from 6-membered aryl containing 0-2 nitrogen atoms, 5 to 7-membered saturated or partially unsaturated carbocyclyl, 5 to 7-membered saturated or partially unsaturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments, each Ring B and Ring C is independently a 6-membered aryl containing 0-2 nitrogen atoms. In some embodiments, each Ring B and Ring C is independently a 5 to 7-membered saturated or partially unsaturated carbocyclyl. In some embodiments, each Ring B and Ring C is independently a 5 to 7-membered saturated or partially unsaturated heterocyclyl with 1-2 heteroatoms independently selected from nitrogen, oxygen or sulfur. In some embodiments, each Ring B and Ring C is independently a 5-membered heteroaryl with 1-3 heteroatoms independently selected from nitrogen, oxygen or sulfur.

In some embodiments, each Ring B and Ring C is independently

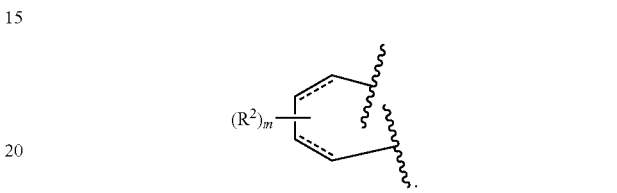

In some embodiments, each Ring B and Ring C is independently

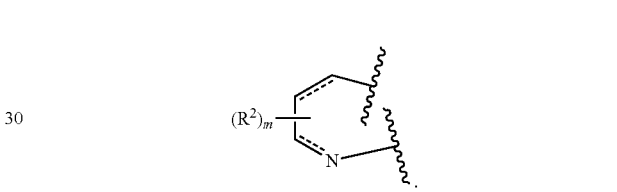

In some embodiments, each Ring B and Ring C is independently

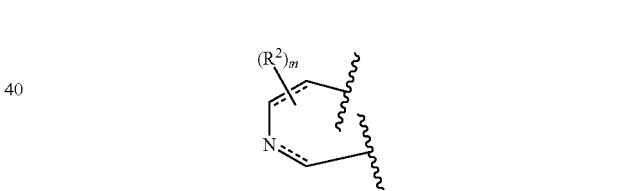

In some embodiments, each Ring B and Ring C is independently

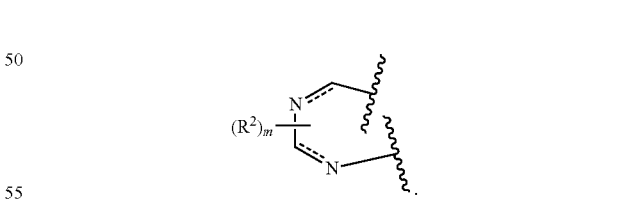

In some embodiments, Ring B and Ring C is independently

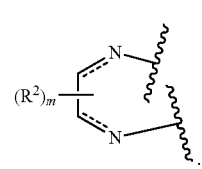

In some embodiments, Ring B and Ring C is independently is

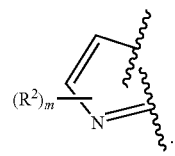

In some embodiments, Ring B and Ring C is independently

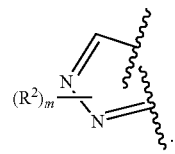

In some embodiments, Ring B and Ring C is independently

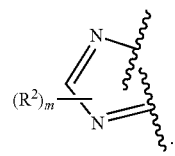

In some embodiments, Ring B and Ring C is independently

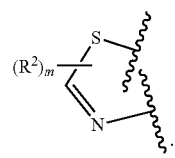

In some embodiments, Ring B and Ring C is independently

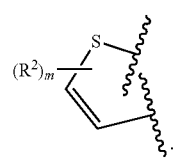

In some embodiments, Ring B and Ring C is independently

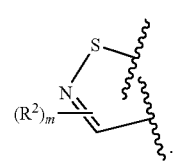

In some embodiments, Ring B and Ring C is independently

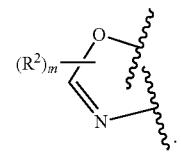

In some embodiments, Ring B and Ring C is independently

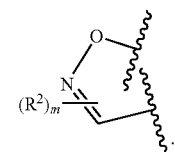

In some embodiments, Ring B and Ring C is independently

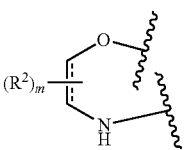

In some embodiments, Ring B and Ring C is independently

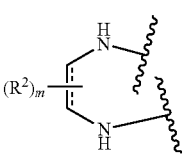

In some embodiments, B and Ring C is independently

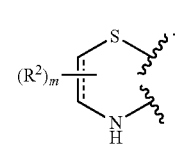

In some embodiments, Ring B and Ring C is independently

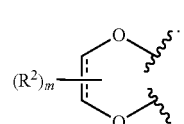

In some embodiments, Ring B and Ring C is independently

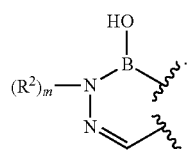

In some embodiments, Ring B and Ring C is independently selected from those depicted in Table 1, below.

In some embodiments, Ring A is

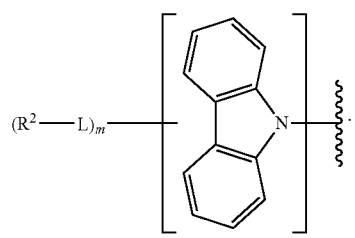

In some embodiments, Ring A is

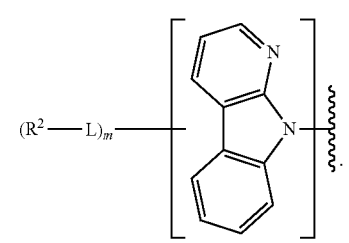

In some embodiments, Ring A is

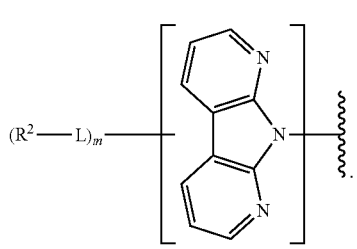

In some embodiments, Ring A is

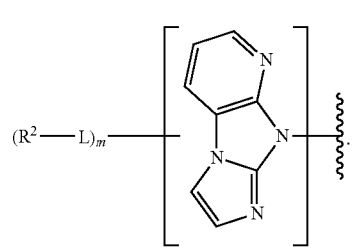

In some embodiments, Ring A is

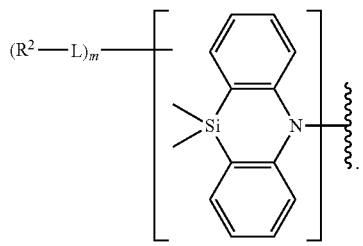

In some embodiments, Ring A is

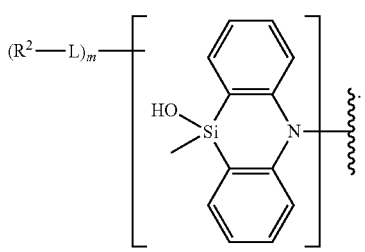

In some embodiments, Ring A is

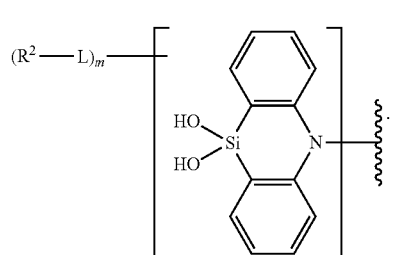

In some embodiments, Ring A is

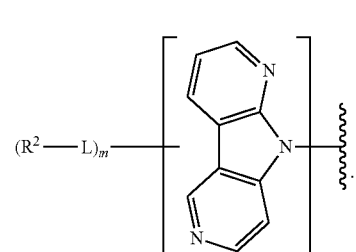

In some embodiments, Ring A is

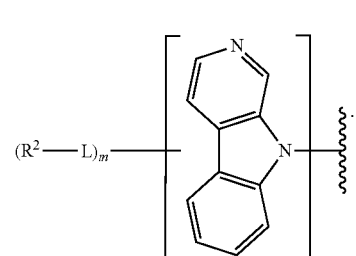

In some embodiments Ring A is
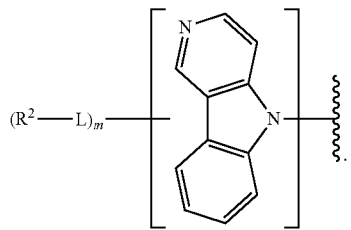
In some embodiments, Ring A is
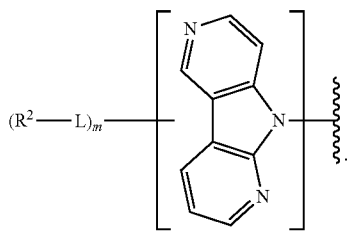
In some embodiments, Ring A is
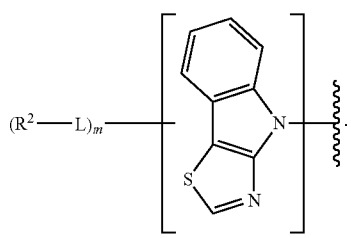
In some embodiments, Ring A is
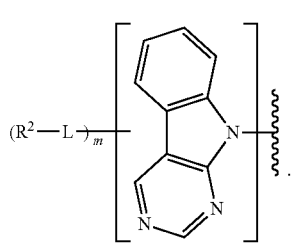
In some embodiments, Ring A is
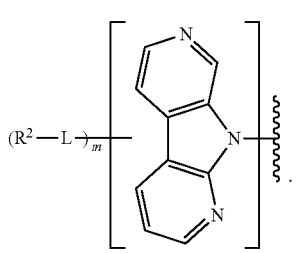
In some embodiments, Ring A is
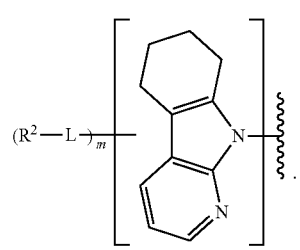
In some embodiments Ring A is
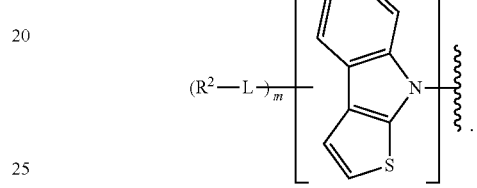
In some embodiments, Ring A is
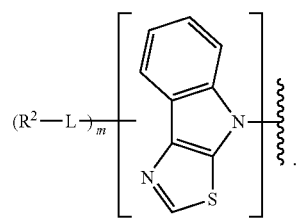
In some embodiments, Ring A is
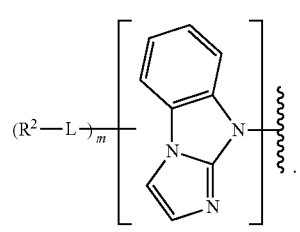
In some embodiments, Ring A is
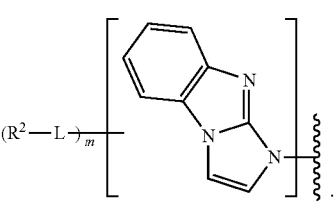

In some embodiments, Ring A is

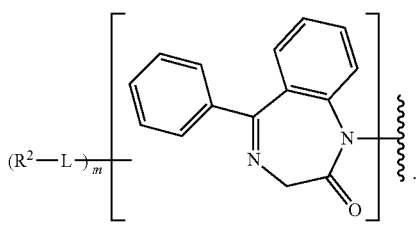

In some embodiments, Ring A is

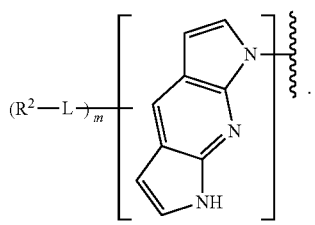

In some embodiments, Ring A is

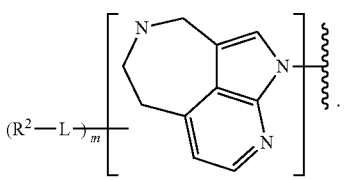

In some embodiments, Ring A is

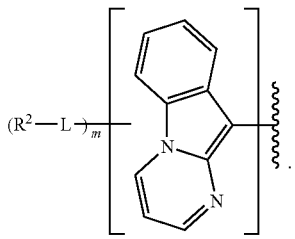

In some embodiments, Ring A is

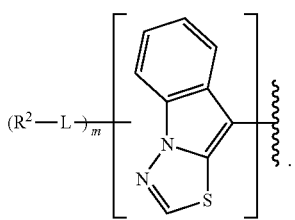

In some embodiments, Ring A is selected from those depicted in Table 1, below.

As defined above and described herein, ═ is a single or double bond

In some embodiments, ═ is a single bond. In some embodiments, is a double bond.

In some embodiments, ═ is selected from those depicted in Table 1, below.

As defined above and described herein, m is 0, 1, 2, 3, 4, 5, 6, 7, or 8.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8.

In some embodiments, m is selected from those depicted in Table 1, below.

Exemplary compounds of the invention are set forth in Table 1, below.

TABLE 1

| Exemplary Compounds | |
|---|---|
| I-# | Structure |
| I-1 | (structure shown) |

TABLE 1-continued

Exemplary Compounds

| I-# | Structure |
|---|---|
| I-2 | 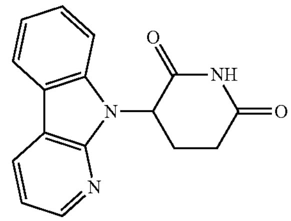 [SMILES: O=C1CCC(n2c3ccccc3c3cccnc32)C(=O)N1] |
| I-3 | 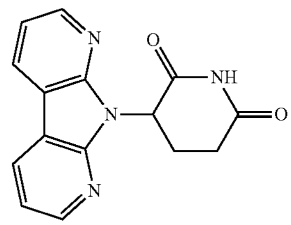 [SMILES: O=C1CCC(n2c3ncccc3c3cccnc32)C(=O)N1] |
| I-4 | 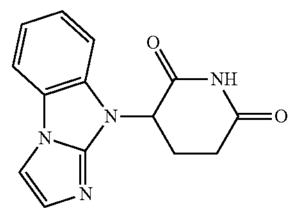 [SMILES: O=C1CCC(n2c3ccccc3n3ccnc23)C(=O)N1] |
| I-5 | 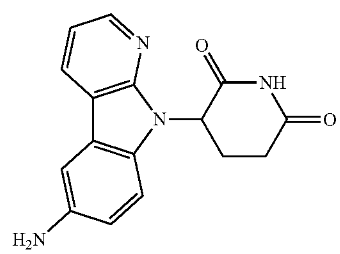 [SMILES: Nc1ccc2c(c1)c1cccnc1n2C1CCC(=O)NC1=O] |
| I-6 | 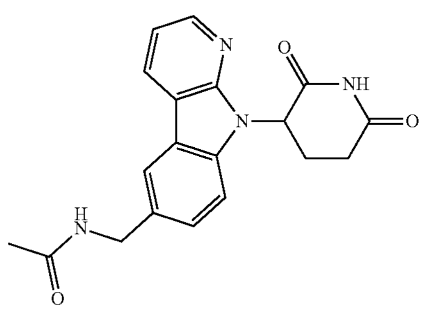 [SMILES: CC(=O)NCc1ccc2c(c1)c1cccnc1n2C1CCC(=O)NC1=O] |
| I-7 | 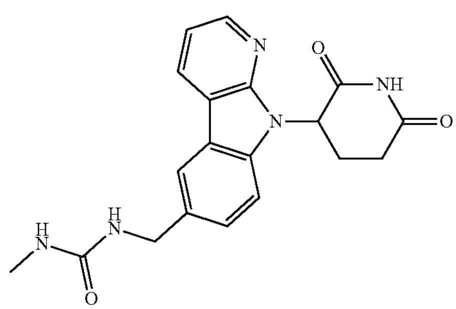 [SMILES: CNC(=O)NCc1ccc2c(c1)c1cccnc1n2C1CCC(=O)NC1=O] |

TABLE 1-continued

Exemplary Compounds

| I-# | Structure |
|---|---|
| I-8 | 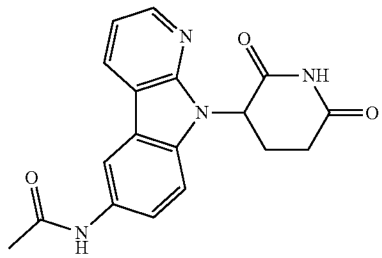 [SMILES: CC(=O)Nc1ccc2c(c1)c1cccnc1n2C1CCC(=O)NC1=O] |
| I-9 | 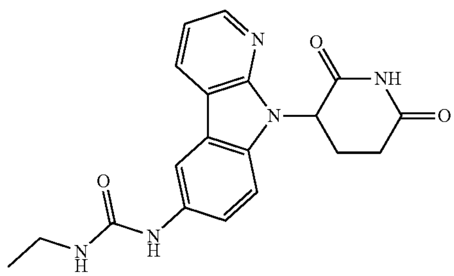 [SMILES: CCNC(=O)Nc1ccc2c(c1)c1cccnc1n2C1CCC(=O)NC1=O] |
| I-10 | 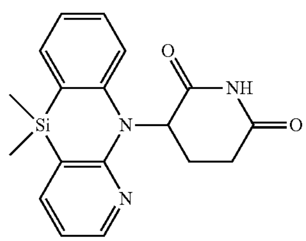 [SMILES: C[Si]1(C)c2ccccc2N(C2CCC(=O)NC2=O)c2ncccc21] |
| I-11 | 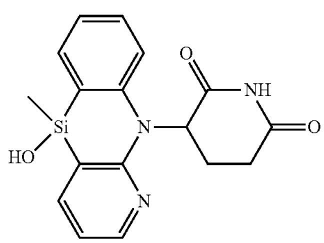 [SMILES: C[Si]1(O)c2ccccc2N(C2CCC(=O)NC2=O)c2ncccc21] |
| I-12 | 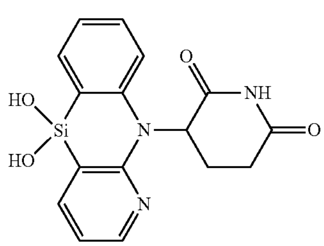 [SMILES: O=C1CCC(N2c3ccccc3[Si](O)(O)c3cccnc32)C(=O)N1] |
| I-13 | 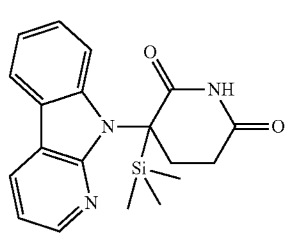 [SMILES: C[Si](C)(C)C1(n2c3ccccc3c3cccnc32)CCC(=O)NC1=O] |

TABLE 1-continued

Exemplary Compounds

| I-# | Structure |
|---|---|
| I-14 | 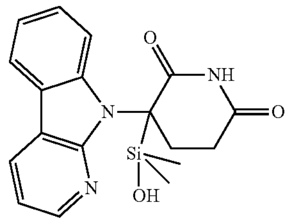 [SMILES: C[Si](C)(O)C1(n2c3ccccc3c3cccnc32)CCC(=O)NC1=O] |
| I-15 | 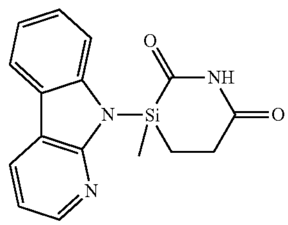 [SMILES: C[Si]1(n2c3ccccc3c3cccnc32)CCC(=O)NC1=O] |
| I-16 | 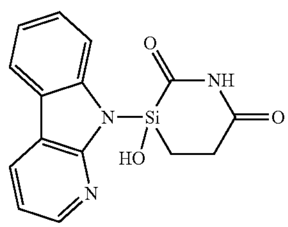 [SMILES: O=C1CC[Si](O)(n2c3ccccc3c3cccnc32)C(=O)N1] |
| I-17 | 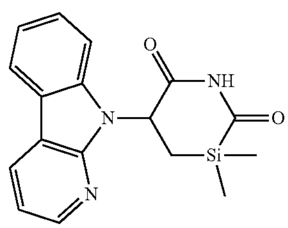 [SMILES: C[Si]1(C)CC(n2c3ccccc3c3cccnc32)C(=O)NC1=O] |
| I-18 | 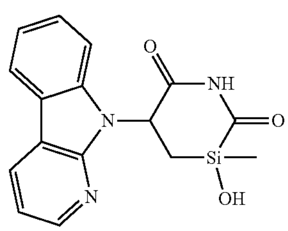 [SMILES: C[Si]1(O)CC(n2c3ccccc3c3cccnc32)C(=O)NC1=O] |
| I-19 | 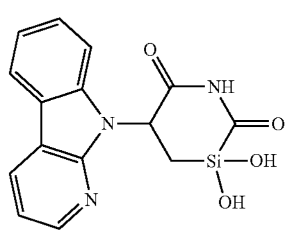 [SMILES: O=C1NC(=O)[Si](O)(O)CC1n1c2ccccc2c2cccnc21] |

TABLE 1-continued
Exemplary Compounds
| I-# | Structure |
|---|---|
| I-20 | 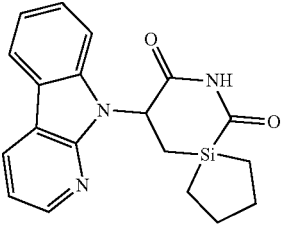 [SMILES: O=C1NC(=O)[Si]2(CCCC2)CC1n1c2ccccc2c2cccnc21] |
| I-21 | 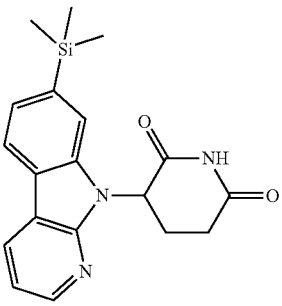 [SMILES: C[Si](C)(C)c1ccc2c3cccnc3n(C3CCC(=O)NC3=O)c2c1] |
| I-22 | 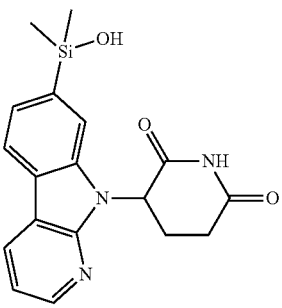 [SMILES: C[Si](C)(O)c1ccc2c3cccnc3n(C3CCC(=O)NC3=O)c2c1] |
| I-23 | 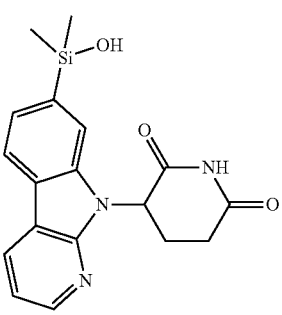 [SMILES: C[Si](C)(O)c1ccc2c3cccnc3n(C3CCC(=O)NC3=O)c2c1] |
| I-24 | 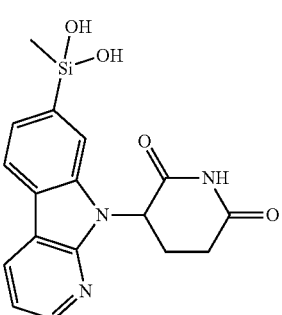 |

TABLE 1-continued

Exemplary Compounds

| I-# | Structure |
|---|---|
| I-25 | 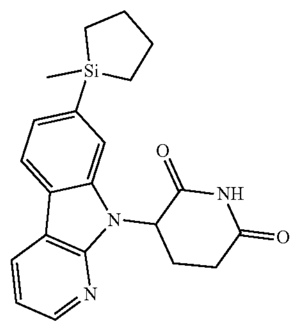 [SMILES: C[Si]1(c2ccc3c4cccnc4n(C4CCC(=O)NC4=O)c3c2)CCCC1] |
| I-26 | 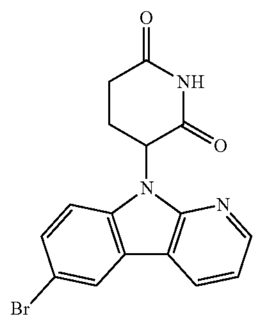 [SMILES: O=C1CCC(n2c3ccc(Br)cc3c3cccnc32)C(=O)N1] |
| I-27 | 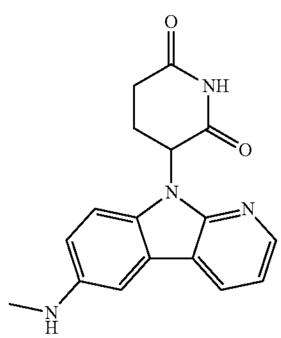 [SMILES: CNc1ccc2c(c1)c1cccnc1n2C1CCC(=O)NC1=O] |
| I-28 | 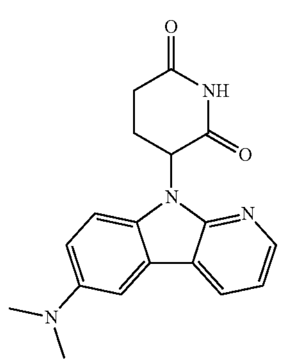 [SMILES: CN(C)c1ccc2c(c1)c1cccnc1n2C1CCC(=O)NC1=O] |

TABLE 1-continued
Exemplary Compounds
| I-# | Structure |
|---|---|
| I-29 | 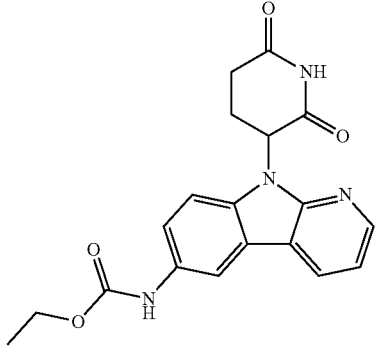 [SMILES: CCOC(=O)Nc1ccc2c(c1)c1cccnc1n2C1CCC(=O)NC1=O] |
| I-30 | 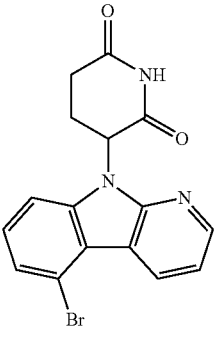 [SMILES: O=C1CCC(n2c3cccc(Br)c3c3cccnc32)C(=O)N1] |
| I-31 | 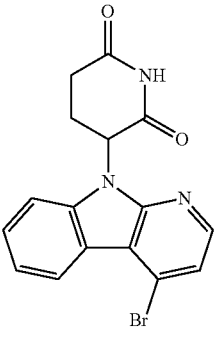 [SMILES: O=C1CCC(n2c3ccccc3c3c(Br)ccnc32)C(=O)N1] |
| I-32 | 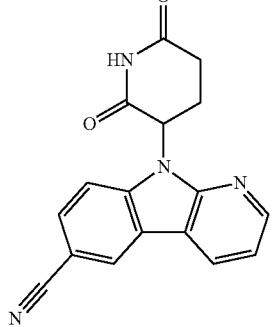 |

TABLE 1-continued
Exemplary Compounds
| I-# | Structure |
|---|---|
| I-33 | 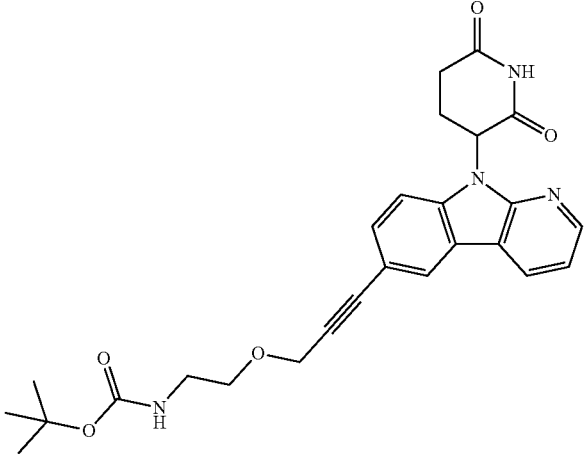 [SMILES: CC(C)(C)OC(=O)NCCOCC#Cc1ccc2c(c1)c1cccnc1n2C1CCC(=O)NC1=O] |
| I-34 | 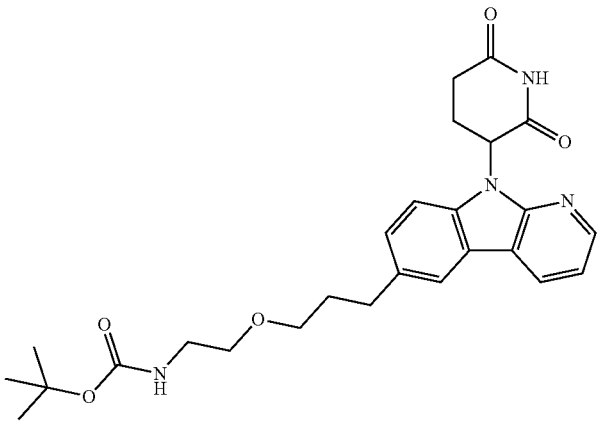 [SMILES: CC(C)(C)OC(=O)NCCOCCCc1ccc2c(c1)c1cccnc1n2C1CCC(=O)NC1=O] |
| I-35 | 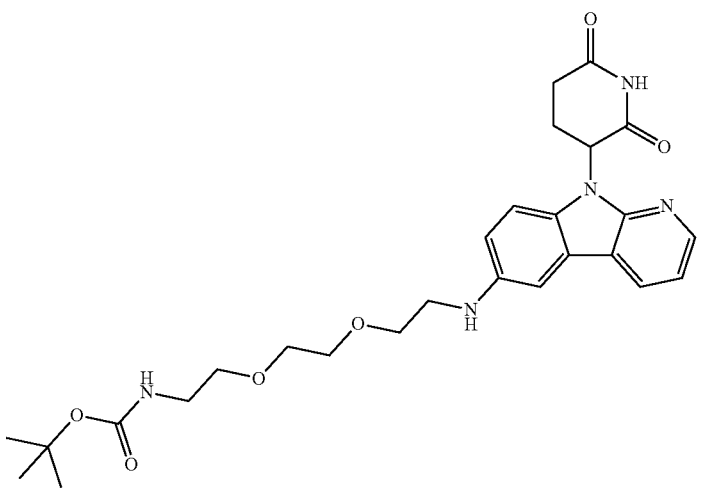 [SMILES: CC(C)(C)OC(=O)NCCOCCOCCNc1ccc2c(c1)c1cccnc1n2C1CCC(=O)NC1=O] |

TABLE 1-continued
| Exemplary Compounds | |
|---|---|
| I-# | Structure |
I-36
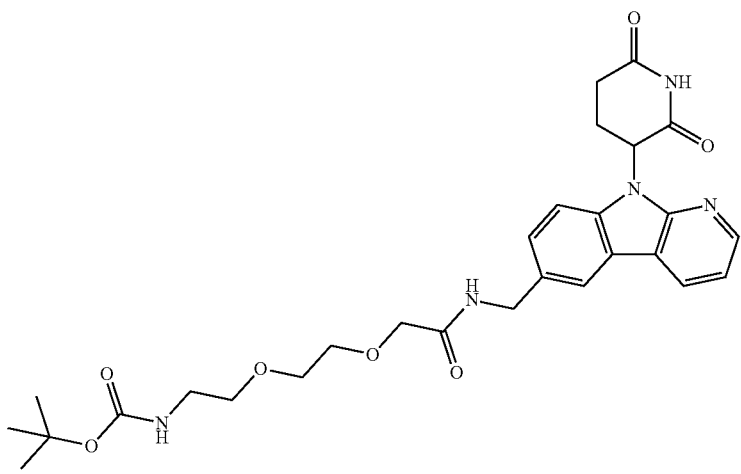 [SMILES: CC(C)(C)OC(=O)NCCOCCOCC(=O)NCc1ccc2c(c1)c1cccnc1n2C1CCC(=O)NC1=O]
I-37
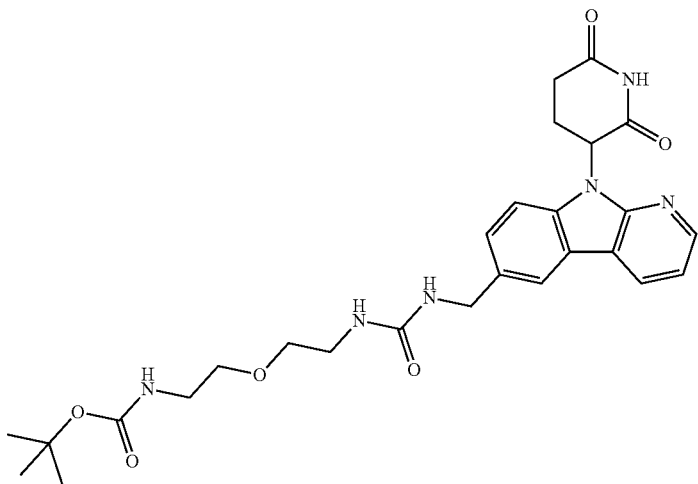 [SMILES: CC(C)(C)OC(=O)NCCOCCNC(=O)NCc1ccc2c(c1)c1cccnc1n2C1CCC(=O)NC1=O]
I-38
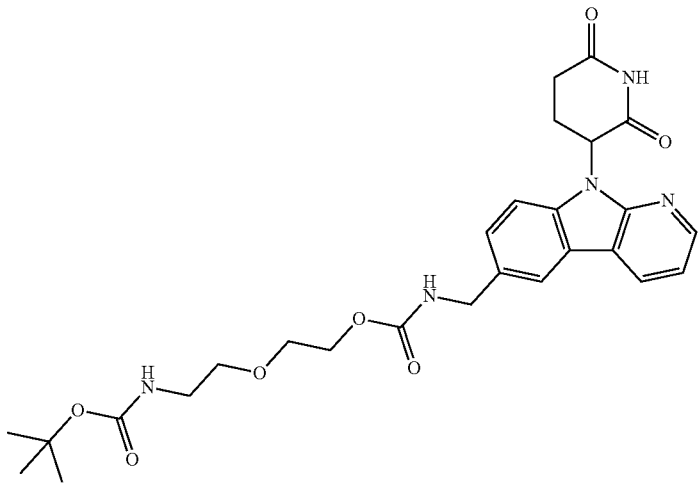 [SMILES: CC(C)(C)OC(=O)NCCOCCOC(=O)NCc1ccc2c(c1)c1cccnc1n2C1CCC(=O)NC1=O]

US 11,897,882 B2
TABLE 1-continued
Exemplary Compounds
| I-# | Structure |
|---|---|
| I-39 | 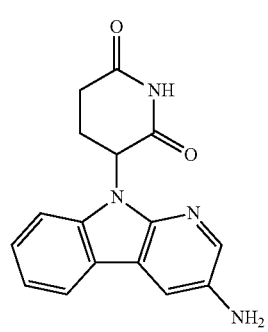 [SMILES: Nc1cnc2c(c1)c1ccccc1n2C1CCC(=O)NC1=O] |
| I-40 | 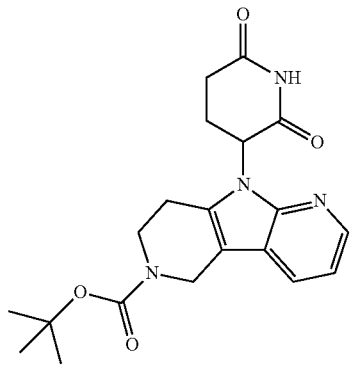 [SMILES: CC(C)(C)OC(=O)N1CCc2c(c3cccnc3n2C2CCC(=O)NC2=O)C1] |
| I-41 | 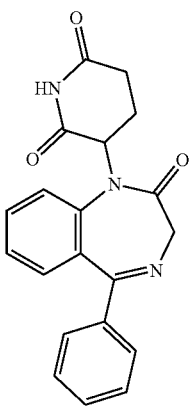 [SMILES: O=C1CCC(N2C(=O)CN=C(c3ccccc3)c3ccccc32)C(=O)N1] |
| I-42 | 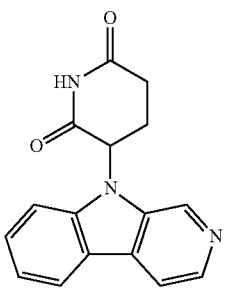 [SMILES: O=C1CCC(n2c3ccccc3c3ccncc32)C(=O)N1] |

TABLE 1-continued
Exemplary Compounds
| I-# | Structure |
|---|---|
| I-43 | 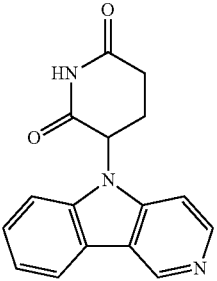 [SMILES: O=C1CCC(n2c3ccccc3c3cnccc32)C(=O)N1] |
| I-44 | 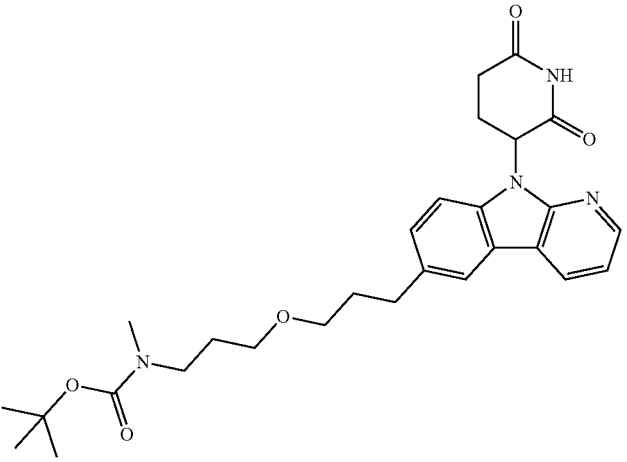 [SMILES: CN(CCCOCCCc1ccc2c(c1)c1cccnc1n2C1CCC(=O)NC1=O)C(=O)OC(C)(C)C] |
| I-45 | 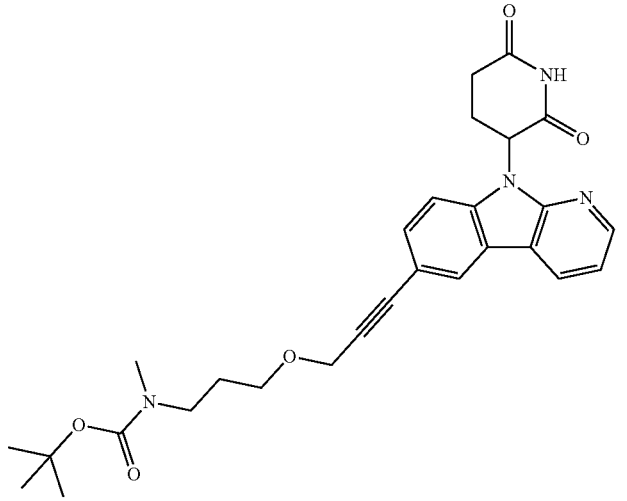 [SMILES: CN(CCCOCC#Cc1ccc2c(c1)c1cccnc1n2C1CCC(=O)NC1=O)C(=O)OC(C)(C)C] |

TABLE 1-continued
Exemplary Compounds
| I-# | Structure |
|---|---|
| I-46 | 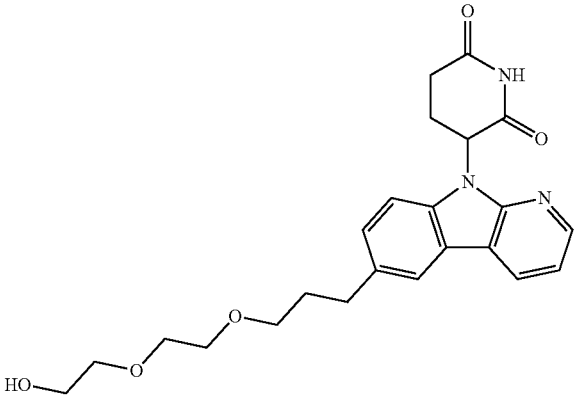 [SMILES: O=C1CCC(n2c3ccc(CCCOCCOCCO)cc3c3cccnc32)C(=O)N1] |
| I-47 | 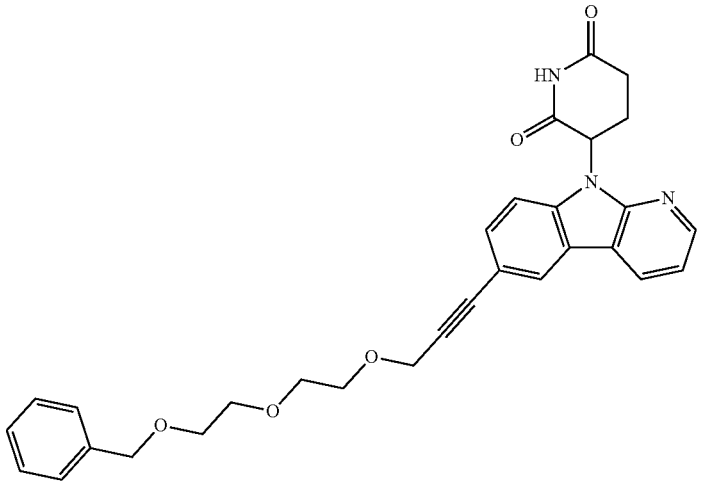 [SMILES: O=C1CCC(n2c3ccc(C#CCOCCOCCOCc4ccccc4)cc3c3cccnc32)C(=O)N1] |
| I-48 | 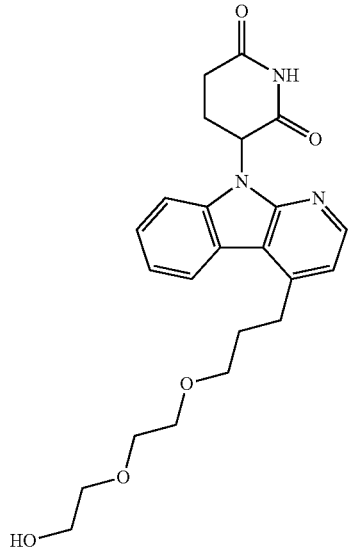 [SMILES: O=C1CCC(n2c3ccccc3c3c(CCCOCCOCCO)ccnc32)C(=O)N1] |

TABLE 1-continued
Exemplary Compounds
| I-# | Structure |
|---|---|
| I-49 | 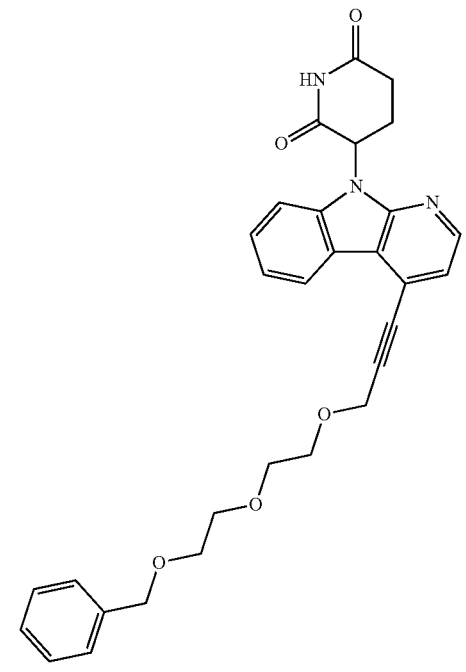 [SMILES: O=C1CCC(n2c3ccccc3c3c(C#CCOCCOCCOCc4ccccc4)ccnc32)C(=O)N1] |
| I-50 | 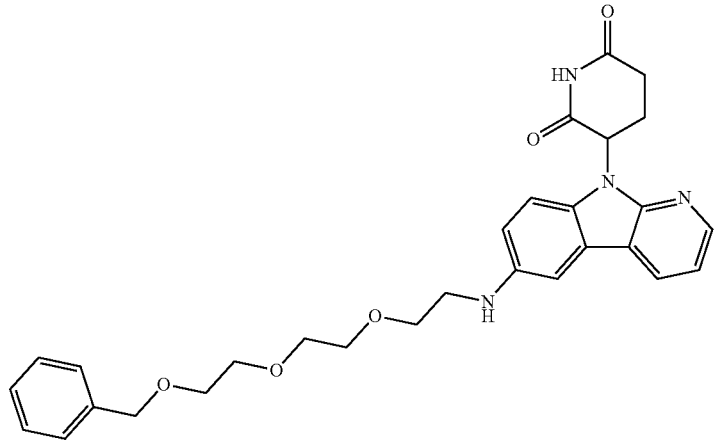 [SMILES: O=C1CCC(n2c3ccc(NCCOCCOCCOCc4ccccc4)cc3c3cccnc32)C(=O)N1] |

TABLE 1-continued
Exemplary Compounds
| I-# | Structure |
|---|---|
| I-51 | 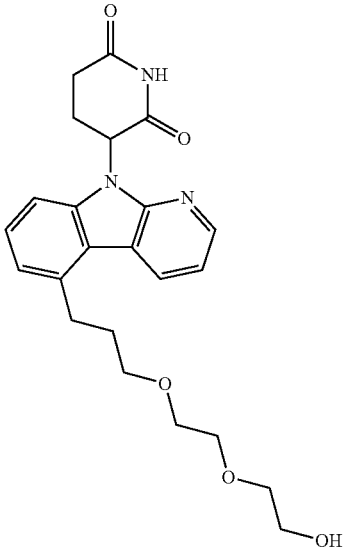 [SMILES: O=C1CCC(n2c3cccc(CCCOCCOCCO)c3c3cccnc32)C(=O)N1] |
| I-52 | 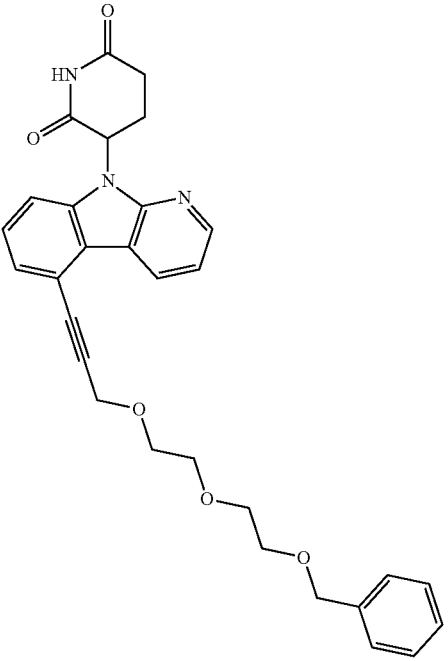 [SMILES: O=C1CCC(n2c3cccc(C#CCOCCOCCOCc4ccccc4)c3c3cccnc32)C(=O)N1] |
| I-53 | 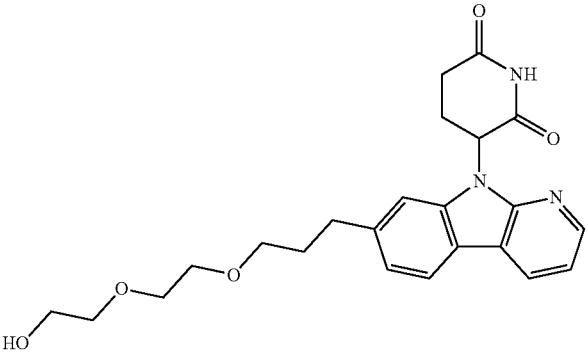 [SMILES: O=C1CCC(n2c3cc(CCCOCCOCCO)ccc3c3cccnc32)C(=O)N1] |

TABLE 1-continued
Exemplary Compounds
| I-# | Structure |
|---|---|
| I-54 | 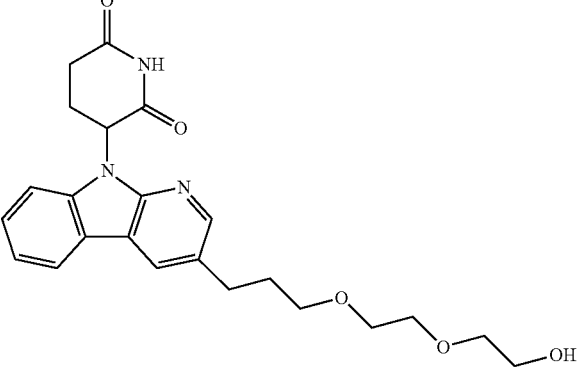 |
| I-55 | 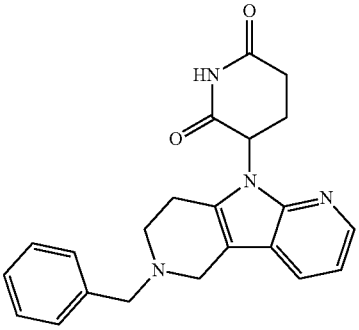 [SMILES: O=C1CCC(n2c3c(c4cccnc42)CN(Cc2ccccc2)CC3)C(=O)N1] |
| I-56 | 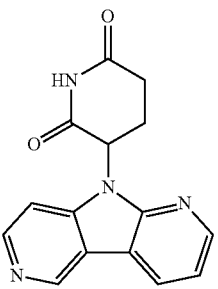 [SMILES: O=C1CCC(n2c3ccncc3c3cccnc32)C(=O)N1] |

TABLE 1-continued
Exemplary Compounds
| I-# | Structure |
|---|---|
| I-57 | 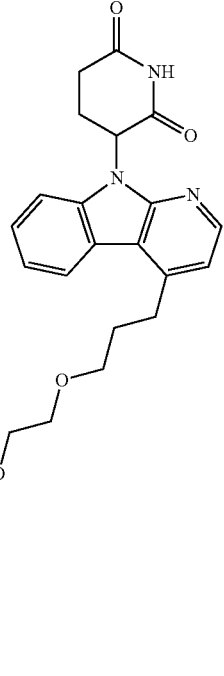 |
| I-58 | 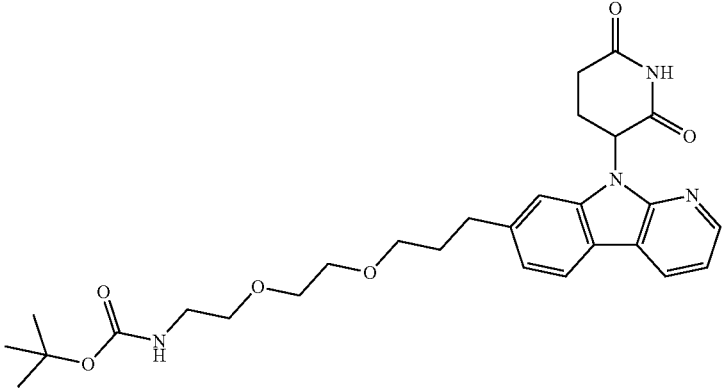 [SMILES: CC(C)(C)OC(=O)NCCOCCOCCCc1ccc2c3cccnc3n(C3CCC(=O)NC3=O)c2c1] |
| I-59 | 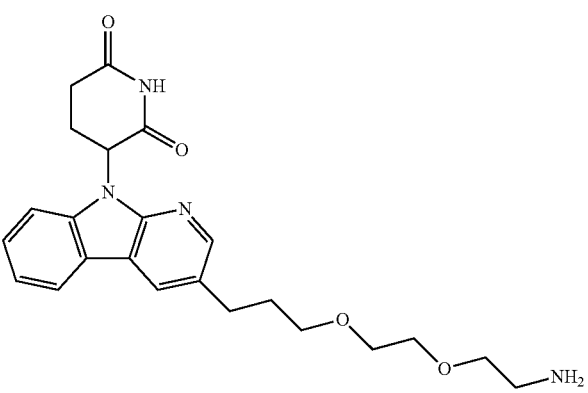 [SMILES: NCCOCCOCCCc1cnc2c(c1)c1ccccc1n2C1CCC(=O)NC1=O] |

TABLE 1-continued
Exemplary Compounds
| I-# | Structure |
|---|---|
| I-60 | 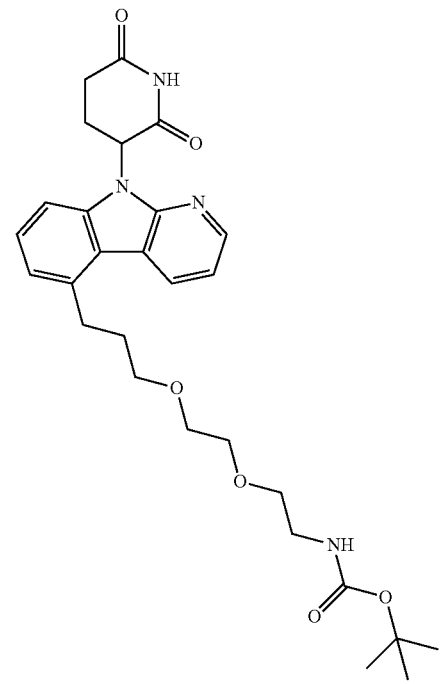 [SMILES: CC(C)(C)OC(=O)NCCOCCOCCCc1cccc2c1c1cccnc1n2C1CCC(=O)NC1=O] |
| I-61 | 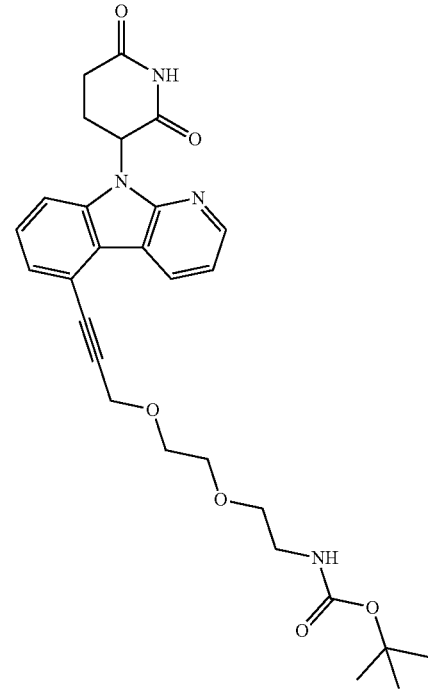 [SMILES: CC(C)(C)OC(=O)NCCOCCOCC#Cc1cccc2c1c1cccnc1n2C1CCC(=O)NC1=O] |

TABLE 1-continued
Exemplary Compounds
| I-# | Structure |
|---|---|
| I-62 | 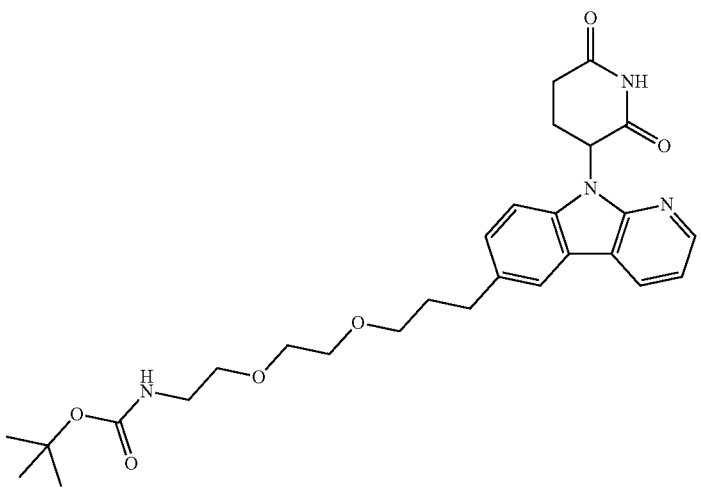 [SMILES: CC(C)(C)OC(=O)NCCOCCOCCCc1ccc2c(c1)c1cccnc1n2C1CCC(=O)NC1=O] |
| I-63 | 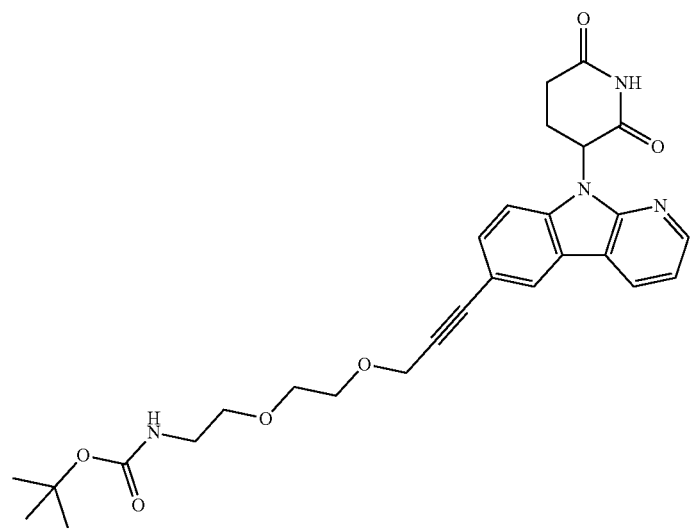 [SMILES: CC(C)(C)OC(=O)NCCOCCOCC#Cc1ccc2c(c1)c1cccnc1n2C1CCC(=O)NC1=O] |
| I-64 | 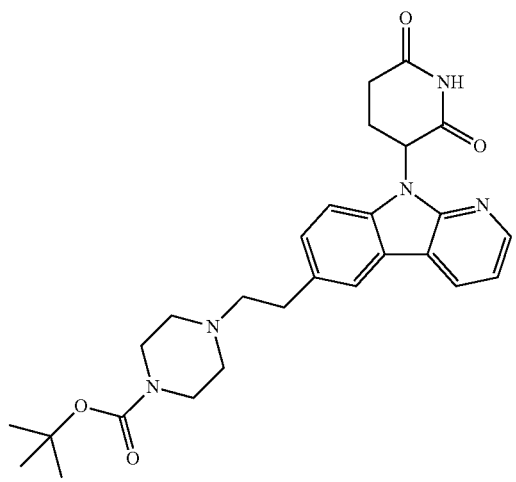 [SMILES: CC(C)(C)OC(=O)N1CCN(CCc2ccc3c(c2)c2cccnc2n3C2CCC(=O)NC2=O)CC1] |

TABLE 1-continued

Exemplary Compounds

| I-# | Structure |
|---|---|
| I-65 | 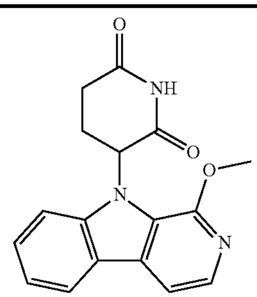 |
| I-66 | 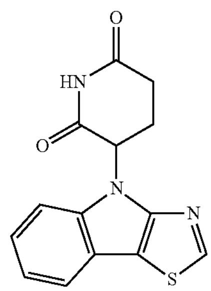 [SMILES: O=C1CCC(n2c3ccccc3c3scnc32)C(=O)N1] |
| I-67 | 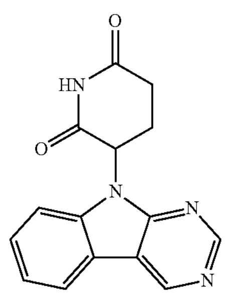 [SMILES: O=C1CCC(n2c3ccccc3c3cncnc32)C(=O)N1] |
| I-68 | 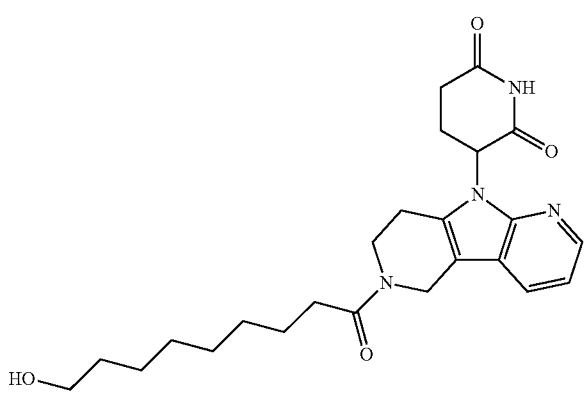 [SMILES: O=C1CCC(n2c3c(c4cccnc42)CN(C(=O)CCCCCCCCO)CC3)C(=O)N1] |
| I-69 | 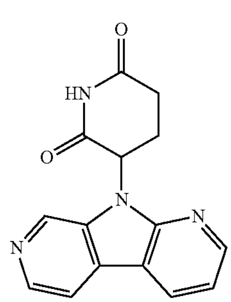 [SMILES: O=C1CCC(n2c3cnccc3c3cccnc32)C(=O)N1] |

TABLE 1-continued

Exemplary Compounds

| I-# | Structure |
|---|---|
| I-70 | 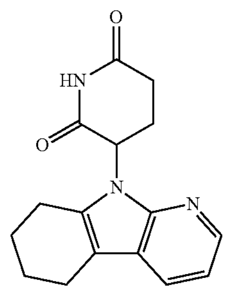 [SMILES: O=C1CCC(n2c3c(c4cccnc42)CCCC3)C(=O)N1] |
| I-71 | 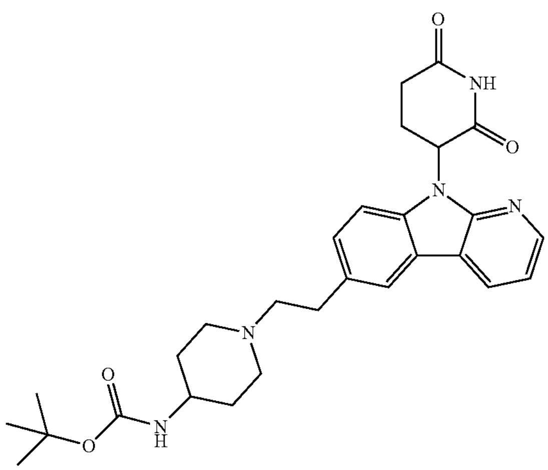 [SMILES: CC(C)(C)OC(=O)NC1CCN(CCc2ccc3c(c2)c2cccnc2n3C2CCC(=O)NC2=O)CC1] |
| I-72 | 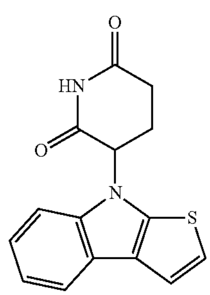 [SMILES: O=C1CCC(n2c3ccccc3c3ccsc32)C(=O)N1] |
| I-73 | 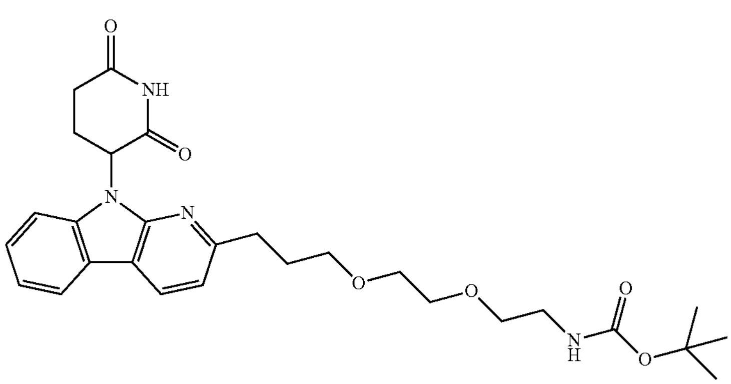 [SMILES: CC(C)(C)OC(=O)NCCOCCOCCCc1ccc2c3ccccc3n(C3CCC(=O)NC3=O)c2n1] |

TABLE 1-continued
Exemplary Compounds
| I-# | Structure |
|---|---|
| I-74 | 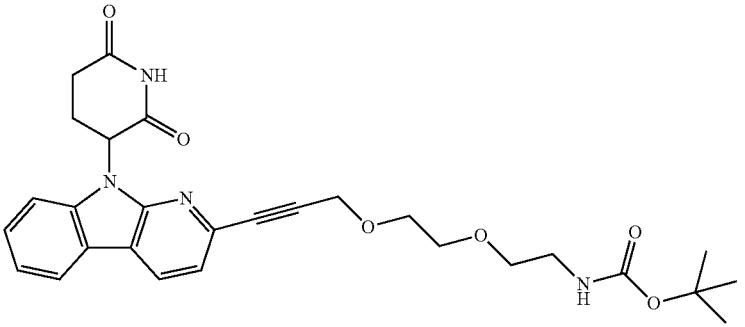 [SMILES: CC(C)(C)OC(=O)NCCOCCOCC#Cc1ccc2c3ccccc3n(C3CCC(=O)NC3=O)c2n1] |
| I-75 | 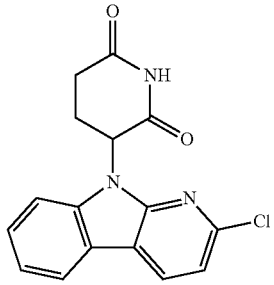 [SMILES: O=C1CCC(n2c3ccccc3c3ccc(Cl)nc32)C(=O)N1] |
| I-76 | 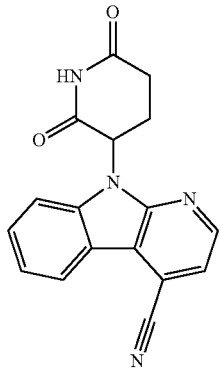 [SMILES: N#Cc1ccnc2c1c1ccccc1n2C1CCC(=O)NC1=O] |
| I-77 | 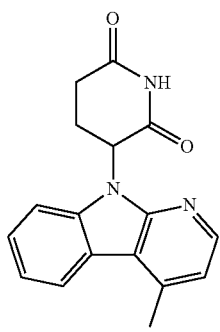 [SMILES: Cc1ccnc2c1c1ccccc1n2C1CCC(=O)NC1=O] |

TABLE 1-continued
Exemplary Compounds
| I-# | Structure |
|---|---|
| I-78 | 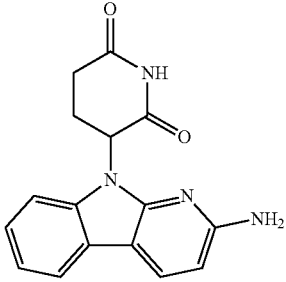 [SMILES: Nc1ccc2c3ccccc3n(C3CCC(=O)NC3=O)c2n1] |
| I-79 | 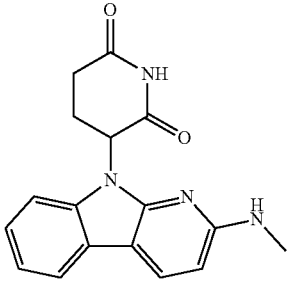 [SMILES: CNc1ccc2c3ccccc3n(C3CCC(=O)NC3=O)c2n1] |
| I-80 | 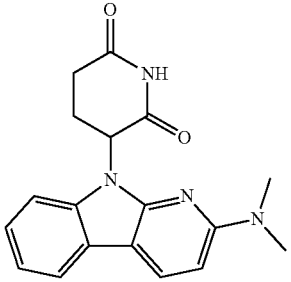 [SMILES: CN(C)c1ccc2c3ccccc3n(C3CCC(=O)NC3=O)c2n1] |
| I-81 | 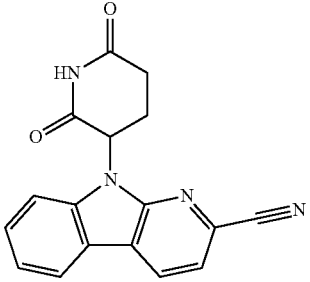 [SMILES: N#Cc1ccc2c3ccccc3n(C3CCC(=O)NC3=O)c2n1] |
| I-82 | 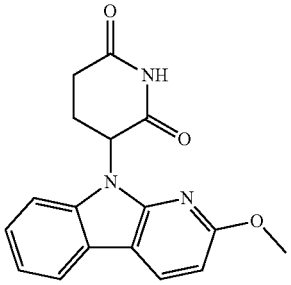 [SMILES: COc1ccc2c3ccccc3n(C3CCC(=O)NC3=O)c2n1] |

TABLE 1-continued
| Exemplary Compounds | |
|---|---|
| I-# | Structure |
I-83 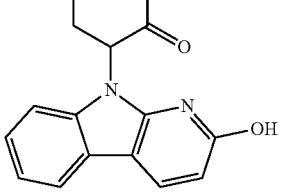
I-84 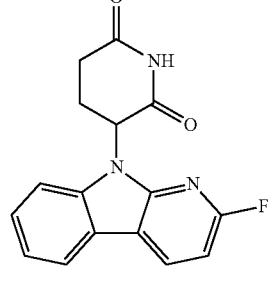
I-85 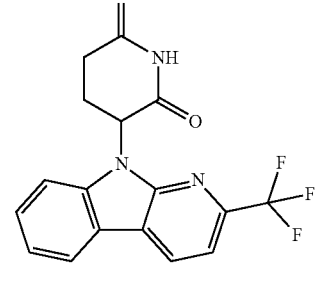
I-86 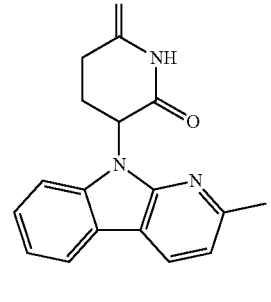
I-87 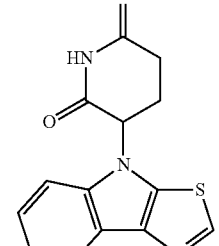

TABLE 1-continued
Exemplary Compounds
| I-# | Structure |
|---|---|
| I-88 | 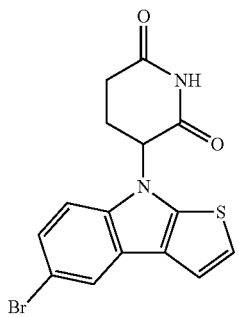 [SMILES: O=C1CCC(n2c3ccc(Br)cc3c3ccsc32)C(=O)N1] |
| I-89 | 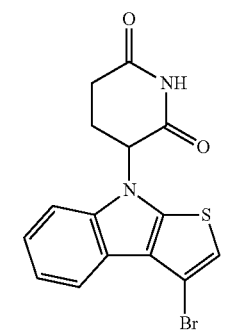 [SMILES: O=C1CCC(n2c3ccccc3c3c(Br)csc32)C(=O)N1] |
| I-90 | 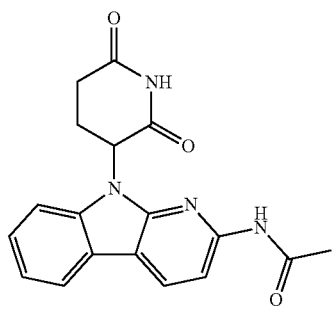 [SMILES: CC(=O)Nc1ccc2c3ccccc3n(C3CCC(=O)NC3=O)c2n1] |
| I-91 | 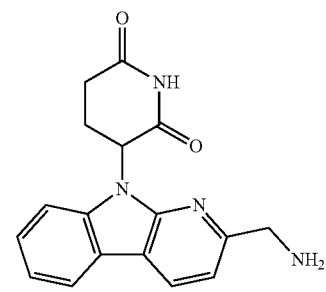 [SMILES: NCc1ccc2c3ccccc3n(C3CCC(=O)NC3=O)c2n1] |
| I-92 | 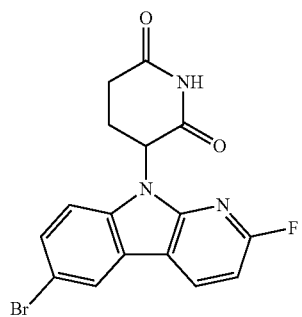 [SMILES: O=C1CCC(n2c3ccc(Br)cc3c3ccc(F)nc32)C(=O)N1] |

TABLE 1-continued

| Exemplary Compounds | |
|---|---|
| I-# | Structure |

I-93

I-94

I-95

I-96

I-97

TABLE 1-continued
Exemplary Compounds
| I-# | Structure |
|---|---|
| I-98 | 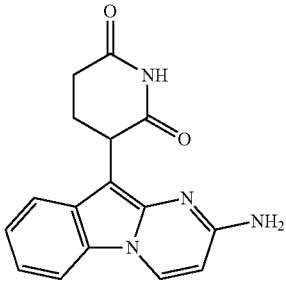 [SMILES: Nc1ccn2c(n1)c(C1CCC(=O)NC1=O)c1ccccc12] |
| I-99 | 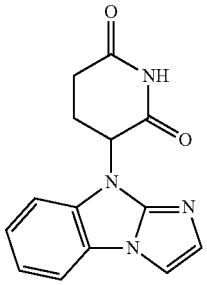 [SMILES: O=C1CCC(n2c3ccccc3n3ccnc23)C(=O)N1] |
| I-100 | 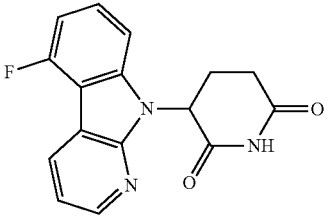 [SMILES: O=C1CCC(n2c3cccc(F)c3c3cccnc32)C(=O)N1] |
| I-101 | 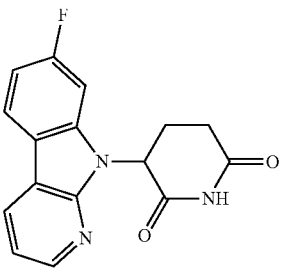 [SMILES: O=C1CCC(n2c3cc(F)ccc3c3cccnc32)C(=O)N1] |
| I-102 | 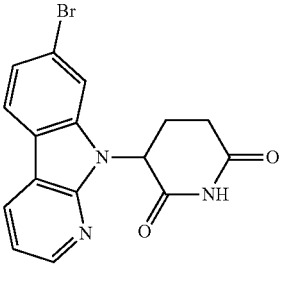 [SMILES: O=C1CCC(n2c3cc(Br)ccc3c3cccnc32)C(=O)N1] |
| I-103 | 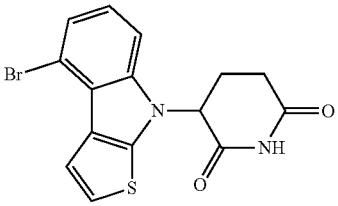 [SMILES: O=C1CCC(n2c3cccc(Br)c3c3ccsc32)C(=O)N1] |

TABLE 1-continued

Exemplary Compounds

| I-# | Structure |
|---|---|
| I-104 | 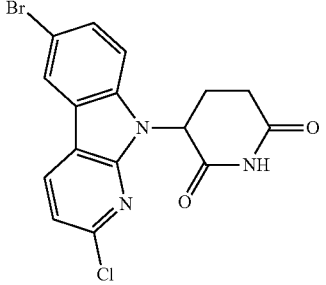 [SMILES: O=C1CCC(n2c3ccc(Br)cc3c3ccc(Cl)nc32)C(=O)N1] |
| I-105 | 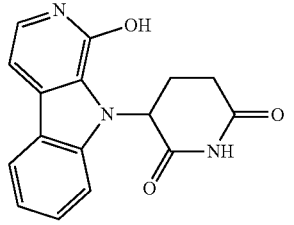 [SMILES: O=C1CCC(n2c3ccccc3c3ccnc(O)c32)C(=O)N1] |
| I-106 | 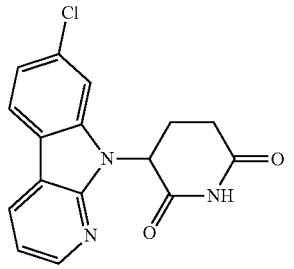 [SMILES: O=C1CCC(n2c3cc(Cl)ccc3c3cccnc32)C(=O)N1] |

In some embodiments, the present invention provides a compound set forth in Table 1, above, or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably bind CRBN, or a mutant thereof, in a biological sample or in a patient. In certain embodiments, the amount of compound in compositions of this invention is such that is effective to measurably bind CRBN, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

As used herein, the term "active metabolite or residue thereof" means that a metabolite or residue thereof is also a binder of CRBN, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulation of CRBN. In some embodiments the protein complex bound by the compounds and methods of the invention comprises CRBN.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Accordingly, compounds that bind CRBN are beneficial, especially those with selectivity over other E3 ligases. Such compounds should deliver a pharmacological response that favorably treats one or more of the conditions described herein without the side-effects associated with the binding of other E3 ligases.

Even though CRBN ligands are known in the art, there is a continuing need to provide novel ligands having more effective or advantageous pharmaceutically relevant properties. For example, compounds with increased activity, selectivity over other E3 ligases, and ADMET (absorption, distribution, metabolism, excretion, and/or toxicity) properties. Thus, in some embodiments, the present invention provides binders of CRBN which show selectivity over other E3 ligases.

The activity of a compound utilized in this invention as an binder of CRBN, or a mutant thereof, may be assayed in vitro, in vivo or in a cell line. In vitro assays include assays that determine the subsequent functional consequences, or activity of activated CRBN, or a mutant thereof. Alternate in vitro assays quantitate the ability of the compound to bind to CRBN. Compound binding may be measured by radiolabeling the compound prior to binding, isolating the compound/CRBN complex and determining the amount of radiolabel bound. Alternatively, compound binding may be determined by running a competition experiment where new compounds are incubated with CRBN bound to known radioligands. Representative in vitro and in vivo assays useful in assaying a CRBN binder include those described and disclosed in, Boichenko et al. J. Med. Chem. (2016) 59, 770-774 and Iconomou and Saunders Biochemical Journal (2016) 473, 4083-4101, each of which is herein incorporated by reference in its entirety. Detailed conditions for assaying a compound utilized in this invention as a binder of CRBN, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are binders of CRBN and are therefore useful for treating one or more disorders associated with activity of CRBN or mutants thereof. Thus, in certain embodiments, the present invention provides a method for treating a CRBN-mediated disorder comprising the step of administering to a patient in need thereof a compound of the present invention, or pharmaceutically acceptable composition thereof.

As used herein, the term "CRBN-mediated" disorders, diseases, and/or conditions as used herein means any disease or other deleterious condition in which CRBN or a mutant thereof is known to play a role. Accordingly, another embodiment of the present invention relates to treating or lessening the severity of one or more diseases in which CRBN, or a mutant thereof, is known to play a role. Such CRBN-mediated disorders include but are not limited to proliferative disorders, neurological disorders and disorders associated with transplantation.

In some embodiments, the present invention provides a method for treating one or more disorders, wherein the disorders are selected from proliferative disorders, neurological disorders and disorders associated with transplantation, said method comprising administering to a patient in need thereof, a pharmaceutical composition comprising an effective amount of a compound of the present invention, or a pharmaceutically acceptable salt thereof.

In some embodiments, the disorder is a proliferative disorder. In some embodiments, the proliferative disorder is a hematological cancer. In some embodiments, the proliferative disorder is a leukemia. In some embodiments, the proliferative disorder is a leukemia selected from the group consisting of anemia, acute leukemia, acute lymphoblastic leukemia (ALL), chronic lymphocytic leukemia (CLL), acute myelogenous leukemia, acute myeloid leukemia (AML), myelodysplastic syndromes (MDS), adult acute basophilic leukemia, adult acute eosinophilic leukemia, adult acute megakaryoblastic leukemia, adult acute minimally differentiated myeloid leukemia, adult acute monoblastic leukemia, adult acute monocytic leukemia, adult acute myeloblastic leukemia with maturation, adult acute myeloblastic leukemia without maturation, adult acute myeloid leukemia with abnormalities, adult acute myelomonocytic leukemia, adult erythroleukemia, adult pure erythroid leukemia, secondary acute myeloid leukemia, untreated adult acute myeloid leukemia, adult acute myeloid leukemia in remission, adult acute promyelocytic leukemia with PML-RARA, alkylating agent-related acute myeloid leukemia, prolymphocytic leukemia, and chronic myelomonocytic leukemia.

In some embodiments, the proliferative disorder is a lymphoma. In some embodiments, the proliferative disorder is a lymphoma selected from the group consisting of adult grade III lymphomatoid granulomatosis, adult nasal type extranodal NK/T-cell lymphoma, anaplastic large cell lymphoma, angioimmunoblastic T-cell lymphoma, cutaneous B-Cell non-Hodgkin lymphoma, extranodal marginal zone lymphoma of mucosa-associated lymphoid tissue, hepatosplenic T-cell lymphoma, intraocular lymphoma, lymphomatous involvement of non-cutaneous extranodal site, mature T-cell and NK-cell non-Hodgkin lymphoma, nodal marginal zone lymphoma, post-transplant lymphoproliferative disorder, recurrent adult Burkitt lymphoma, recurrent adult diffuse large cell lymphoma, recurrent adult diffuse mixed cell lymphoma, recurrent adult diffuse small cleaved cell lymphoma, recurrent adult grade III lymphomatoid granulomatosis, recurrent adult immunoblastic lymphoma, recurrent adult lymphoblastic lymphoma, recurrent adult T-cell leukemia/lymphoma, recurrent cutaneous T-cell non-Hodgkin lymphoma, recurrent grade 1 follicular lymphoma, recurrent grade 2 follicular lymphoma, recurrent grade 3 follicular lymphoma, recurrent mantle cell lymphoma, recurrent marginal zone lymphoma, recurrent mycosis fungoides and Sezary syndrome, recurrent small lymphocytic lymphoma, refractory chronic lymphocytic leukemia, refractory hairy cell leukemia, Richter syndrome, small intestinal lymphoma, splenic marginal zone lymphoma, T-cell large granular lymphocyte leukemia, testicular lymphoma, Waldenstrom macroglobulinemia, adult T-cell leukemia-lymphoma, peripheral T-cell lymphoma, B-cell lymphoma, Hodgkin's disease, cutaneous T-cell lymphoma, diffuse large B-cell lymphoma, MALT lymphoma, mantle cell lymphoma, non-Hodgkins lymphoma, central nervous system lymphoma, refractory primary-cutaneous large B-cell lymphoma (Leg-type), relapsed or refractory chronic lymphocytic leukemia, refractory anemia, refractory anemia with excess blasts, refractory anemia with ringed sideroblasts, refractory cytopenia with multilineage dysplasia, and secondary myelodysplastic syndromes.

In some embodiments, the disorder is a neurological disorder. In some embodiments, the neurological disorder is Alzheimer's disease.

In some embodiments, the disorder is associated with transplantation. In some embodiments the disorder associated with transplantation is transplant rejection, or graft versus host disease.

In some embodiments, the proliferative disorder is a cancer or tumor. In some embodiments, the proliferative disorder is a cancer or tumor selected from the group consisting of head and neck cancer, liver cancer, hormone-refractory prostate cancer, kidney cancer, small intestine cancer, glioblastoma, non-small cell lung cancer, ovarian cancer, endometrial cancer, esophageal cancer, colon cancer, lung cancer, brain and central nervous system tumors, gastrointestinal carcinoid tumor, islet cell tumor, and childhood solid tumor.

In some embodiments, the proliferative disorder is a myeloma. In some embodiments, the proliferative disorder is a multiple myeloma.

In some embodiments, the proliferative disorder is a myeloma selected from the group consisting of refractory multiple myeloma, stage I multiple myeloma, stage II multiple myeloma, stage III multiple myeloma, smoldering plasma cell myeloma, and plasma cell myeloma.

In some embodiments, the proliferative disorder is selected from the group consisting of hepatocellular carcinoma, melanoma, malignant melanoma, thyroid neoplasms, urinary bladder neoplasms, amyotrophic lateral sclerosis (ALS), sickle cell anemia, ankylosing spondylitis, arachnoiditis, arterivenous malformation, and hereditary hemorrhagic telangiectasia.

In some embodiments, the disorder is selected from the group consisting of AIDS-related Kaposi sarcoma, amyloidosis, hematochezia, melena, autism, burning mouth syndrome associated with HIV infection, hepatocellular carcinoma, non-small-cell lung carcinoma, central nervous system neoplasms, medulloblastoma, chronic myeloproliferative disorders, secondary myelofibrosis, chronic pancreatitis, chronic prostatitis, complex regional pain syndrome (RSD), Type 1 complex regional pain syndrome, Crohn's disease, cutaneous lupus erythematosus (CLE), discoid lupus erythematosus, endometriosis, neoplastic syndrome, gastrointestinal hemorrhage, gastrointestinal vascular malformation, hepatitis C, high grade squamous intra-epithelial lesion (HSIL), HIV wasting syndrome, HIV-associated mycobacterium infections, HIV-associated tuberculosis, HIV-associated aphthous stomatitis, HIV-associated avium-intracellulare infection, idiopathic pulmonary fibrosis (IPF), Langerhans cell histiocytosis (LCH), histiocytosis, Erdheim-Chester disease, histiocytic light chain deposition disease, myelofibrosis, myeloproliferative neoplasms, neurofibromatosis type 1, recurrent central nervous system neoplasm, recurrent childhood brain stem glioma, recurrent childhood visual pathway glioma, refractory central nervous system neoplasm, nonmalignant monoclonal gammopathy of undetermined significance (MGUS), primary amyloidosis, primary myelofibrosis, primary sclerosing cholangitis, plaque-type psoriasis, pulmonary fibrosis, radiation injuries, radiculopathy, recurrent uterine corpus sarcoma, uterine carcinosarcoma, refractory epilepsy, sarcoidosis, systemic scleroderma, systemic sclerosis, Sjogren's Syndrome, xerostomia, soft tissue sarcoma, thalassemia, and uveitis.

In some embodiments, compounds of the present invention bind to CRBN, altering the specificity of the complex to induce the ubiquitination and degradation of Ikaros (IKZF1) and Aiolos (IKZF3), transcription factors essential for multiple myeloma growth.

In some embodiments, compounds of the present invention bind to CRBN, altering the specificity of the complex to induce the ubiquitination and degradation of a complex-associated protein selected from the group consisting of A1BG, A1CF, A2M, A2ML1, A3GALT2, A4GALT, A4GNT, AAAS, AACS, AADAC, AADACL2, AADACL3, AADACL4, AADAT, AAED1, AAGAB, AAK1, AAMDC, AAMP, AANAT, AAR2, AARD, AARS, AARS2, AARSD1, AASDH, AASDHPPT, AASS, AATF, AATK, AATK-AS1, ABAT, ABCA1, ABCA10, ABCA12, ABCA13, ABCA2, ABCA3, ABCA4, ABCA5, ABCA6, ABCA7, ABCA8, ABCA9, ABCB1, ABCB10, ABCB11, ABCB4, ABCB5, ABCB6, ABCB7, ABCB8, ABCB9, ABCC1, ABCC10, ABCC11, ABCC12, ABCC2, ABCC3, ABCC4, ABCC5, ABCC6, ABCC8, ABCC9, ABCD1, ABCD2, ABCD3, ABCD4, ABCE1, ABCF1, ABCF2, ABCF3, ABCG1, ABCG2, ABCG4, ABCG5, ABCG8, ABHD1, ABHD10, ABHD11, ABHD12, ABHD12B, ABHD13, ABHD14A, ABHD14A-ACY1, ABHD14B, ABHD15, ABHD16A, ABHD16B, ABHD17A, ABHD17B, ABHD17C, ABHD18, ABHD2, ABHD3, ABHD4, ABHD5, ABHD6, ABHD8, ABI1, ABI2, ABI3, ABI3BP, ABL1, ABL2, ABLIM1, ABLIM2, ABLIM3, ABO, ABR, ABRA, ABRACL, ABRAXAS1, ABRAXAS2, ABT1, ABTB1, ABTB2, AC001226.2, AC002094.3, ACO002115.2, AC002310.4, AC002310.5, AC002429.2, AC002985.1, AC002996.1, ACO003002.1, AC003002.2, AC003002.3, AC003002.4, AC003005.1, AC003006.1, AC003688.1, AC004076.1, AC004080.3, AC004223.3, AC004233.2, AC004556.1, AC004691.2, AC004706.4, AC004754.1, AC004805.1, AC004832.3, AC004922.1, AC004997.1, AC005020.2, AC005041.1, ACO005154.6, AC005258.1, AC005324.3, AC005324.4, AC005520.1, AC005551.1, AC005670.2, AC005697.1, AC005702.2, AC005726.2, AC005779.2, AC005832.4, AC005833.1, AC005833.3, AC005837.2, AC005841.2, AC005885.1, AC005943.1, AC006030.1, AC006254.1, AC006269.1, AC006449.4, AC006486.1, AC006538.2, AC006978.2, AC007040.2, AC007192.1, AC007240.1, AC007325.1, AC007325.2, AC007325.4, AC007326.4, AC007375.2, AC007383.6, AC007537.5, AC007731.5, AC007906.2, AC007998.2, AC008073.3, AC008162.2, AC008393.2, AC008403.1, AC008481.3, AC008537.1, AC008560.1, AC008575.1, AC008575.2, AC008687.1, AC008687.4, AC008687.8, AC008695.1, AC008735.6, AC008750.8, AC008758.1, AC008758.4, AC008758.5, AC008758.6, AC008763.2, AC008763.3, AC008764.1, AC008764.4, AC008770.2, AC008770.3, AC008878.1, AC008878.2, AC008878.3, AC008982.1, AC008982.3, AC009014.1, AC009086.2, AC009119.2, AC009122.1, AC009133.6, AC009163.2, AC009163.4, AC009286.3, AC009336.2, AC009477.2, AC009690.1, AC009690.3, AC009779.3, AC010132.3, AC010255.3, AC010319.2, AC010323.1, AC010325.1, AC010326.2, AC010327.1, AC010422.3, AC010422.5, AC010422.6, AC010463.1, AC010487.3, AC010522.1, AC010531.1, AC010542.3, AC010547.4, AC010547.5, AC010615.4, AC010616.1, AC010619.1, AC010646.1, AC010724.2, AC011005.1, AC011043.1, AC011043.2, AC011195.2,
AC011295.1, AC011346.1, AC011448.1, AC011452.1,
AC011455.3, AC011455.4, AC011462.1, AC011473.4,
AC011479.1, AC011498.4, AC011499.1, AC011511.1,
AC011511.4, AC011530.1, AC011604.2, AC011841.1,
AC012184.2, AC012254.2, AC012309.1, AC012314.1,
AC012314.10, AC012314.11, AC012314.12, AC012314.4,
AC012314.5, AC012314.6, AC012314.8, AC012531.3,
AC012651.1, AC013269.1, AC013271.1, AC013394.1,
AC013470.2, AC015688.5, AC015802.6, AC015813.2,
AC017081.3, AC017081.4, AC017081.5, AC017083.4,
AC018512.1, AC018523.2, AC018554.3, AC018630.6,
AC018709.1, AC018755.2, AC018793.1, AC018793.2,
AC018793.3, AC018793.4, AC018793.5, AC019117.3,
AC020636.2, AC020909.1, AC020914.1, AC020915.1,
AC020915.2, AC020915.6, AC020922.1, AC020934.3,
AC021072.1, AC022016.2, AC022167.5, AC022335.1,
AC022384.1, AC022400.6, AC022826.2, AC023055.1,
AC023491.2, AC023509.3, AC024592.3, AC024940.1,
AC024940.6, AC025165.3, AC025263.2, AC025283.2,
AC025287.4, AC025594.2, AC026369.8, AC026398.1,
AC026461.4, AC026464.1, AC026464.3, AC026464.4,
AC026786.1, AC026954.2, AC027796.3, AC034102.2,
AC036214.3, AC037459.1, AC037482.2, AC037483.2,
AC040162.1, AC040162.4, AC044810.8, AC046185.1,
AC048338.1, AC051649.2, AC053481.5, AC055811.2,
AC058822.1, AC064853.2, AC064853.3, AC064853.4,
AC064853.5, AC064853.6, AC067968.1, AC068234.1,
AC068533.4, AC068547.1, AC068580.4, AC068631.2,
AC068775.1, AC068775.2, AC068790.8, AC068896.1,
AC068946.1, AC068987.5, AC069257.3, AC069368.1,
AC069503.2, AC069544.2, AC072022.1, AC073082.1,
AC073111.3, AC073111.5, AC073264.3, AC073508.2,
AC073610.2, AC073610.3, AC073612.1, AC073896.1,
AC074143.1, AC078927.1, AC079325.2, AC079447.1,
AC079594.2, AC083800.1, AC083902.2, AC084337.2,
AC087289.3, AC087498.1, AC087632.1, AC090004.1,
AC090227.1, AC090360.1, AC090527.2, AC090958.3,
AC091167.3, AC091167.7, AC091167.8, AC091304.7,
AC091491.1, AC091551.1, AC091959.3, AC091980.2,
AC092017.3, AC092042.3, AC092073.1, AC092111.3,
AC092143.1, AC092329.3, AC092442.1, AC092587.1,
AC092647.5, AC092718.3, AC092718.8, AC092821.1,
AC092824.3, AC092835.1, AC093155.3, AC093227.3,
AC093423.3, AC093525.1, AC093525.2, AC093668.1,
AC093762.1, AC093762.2, AC093762.3, AC093899.2,
AC096582.3, AC096887.1, AC097372.1, AC097495.1,
AC097637.1, AC097662.2, AC098484.3, AC098650.1,
AC098850.4, AC099329.3, AC099489.1, AC099518.3,
AC099811.2, AC099850.2, AC100868.1, AC104109.3,
AC104151.1, AC104304.1, AC104452.1, AC104532.1,
AC104534.3, AC104581.1, AC104581.3, AC104662.2,
AC104836.1, AC105001.2, AC105052.1, AC106774.10,
AC106774.5, AC106774.6, AC106774.7, AC106774.8,
AC106774.9, AC106782.1, AC106886.5, AC107871.1,
AC108488.2, AC108750.1, AC108941.2, AC109583.3,
AC110275.1, AC112229.3, AC112484.1, AC113189.6,
AC113189.9, AC113331.2, AC113554.2, AC114296.1,
AC114490.2, AC115220.1, AC116366.3, AC116565.1,
AC117457.1, AC118470.1, AC118553.2, AC119396.1,
AC119674.2, AC120057.3, AC120114.5, AC124312.1,
AC126755.2, AC127537.5, AC127537.6, AC127537.8,
AC129492.3, AC131097.2, AC131160.1, AC133551.1,
AC133555.3, AC134669.2, AC134772.2, AC135050.2,
AC135068.1, AC135068.2, AC135068.3, AC135068.8,
AC135178.2, AC135586.2, AC136352.3, AC136352.4,
AC136428.1, AC136612.1, AC136616.1, AC136616.2,
AC136616.3, AC137834.1, AC138517.2, AC138647.1,
AC138696.1, AC138811.2, AC138894.1, AC138969.1,
AC139530.2, AC139677.1, AC139677.2, AC140504.1,
AC141272.1, AC142391.1, AC142525.4, AC145029.2,
AC145212.1, AC145212.2, AC171558.1, AC171558.3,
AC171558.5, AC171558.6, AC187653.1, AC207056.1,
AC209232.1, AC209539.2, AC210544.1, AC213203.1,
AC229888.1, AC229888.10, AC229888.2, AC229888.3,
AC229888.4, AC229888.5, AC229888.6, AC229888.7,
AC229888.8, AC229888.9, AC233282.1, AC233282.2,
AC233723.1, AC233724.12, AC233724.16, AC233724.17,
AC233724.18, AC233724.19, AC233724.20, AC233724.21,
AC233724.6, AC233755.1, AC233755.2, AC233992.2,
AC234301.1, AC234301.3, AC234635.1, AC234635.3,
AC234635.4, AC234635.5, AC236040.1, AC239612.1,
AC239618.1, AC239618.2, AC239618.3, AC239618.4,
AC239618.5, AC239618.6, AC239618.7, AC239618.9,
AC239799.1, AC240274.1, AC241401.1, AC241409.2,
AC241410.1, AC241556.3, AC241556.4, AC241640.1,
AC241640.2, AC241640.4, AC242528.1, AC242528.2,
AC243547.3, AC243733.1, AC243734.1, AC243756.1,
AC243790.1, AC243967.1, AC244196.1, AC244196.2,
AC244196.3, AC244196.4, AC244196.5, AC244197.3,
AC244216.4, AC244216.5, AC244226.1, AC244226.2,
AC244472.1, AC244472.2, AC244472.3, AC244472.4,
AC244472.5, AC244489.1, AC244489.2, AC244517.10,
AC244517.6, AC245033.1, AC245034.2, AC245078.1,
AC245088.2, AC245088.3, AC245369.1, AC245369.2,
AC245369.3, AC245369.4, AC245369.6, AC245427.1,
AC245427.3, AC245427.4, AC245427.5, AC245427.6,
AC245427.7, AC245427.8, AC245427.9, AC245748.1,
AC247036.3, AC247036.4, AC247036.5, AC247036.6,
AC254560.1, AC254788.1, AC254788.2, AC254952.1,
AC255093.3, AC255093.5, AC256236.1, AC256236.2,
AC256236.3, AC256300.2, AC256309.2, AC270107.1,
AC270107.10, AC270107.12, AC270107.2, AC270107.3,
AC270107.4, AC270107.5, AC270107.7, AC270107.8,
AC270107.9, AC270227.1, AC270306.4, AC275455.2,
ACAA1, ACAA2, ACACA, ACACB, ACAD10, ACAD11,
ACAD8, ACAD9, ACADL, ACADM, ACADS, ACADSB,
ACADVL, ACAN, ACAP1, ACAP2, ACAP3, ACAT1,
ACAT2, ACBD3, ACBD4, ACBD5, ACBD6, ACBD7,
ACCS, ACCSL, ACD, ACE, ACE2, ACER1, ACER2,
ACER3, ACHE, ACIN1, ACKR1, ACKR2, ACKR3,
ACKR4, ACLY, ACMSD, ACO1, ACO2, ACOD1, ACOT1,
ACOT11, ACOT12, ACOT13, ACOT2, ACOT4, ACOT6,
ACOT7, ACOT8, ACOT9, ACOX1, ACOX2, ACOX3,
ACOXL, ACP1, ACP2, ACP4, ACP5, ACP6, ACP7, ACPP,
ACR, ACRBP, ACRV1, ACSBG1, ACSBG2, ACSF2,
ACSF3, ACSL1, ACSL3, ACSL4, ACSL5, ACSL6,
ACSM1, ACSM2A, ACSM2B, ACSM3, ACSM4, ACSM5,
ACSM6, ACSS1, ACSS2, ACSS3, ACTA1, ACTA2, ACTB,
ACTBL2, ACTC1, ACTG1, ACTG2, ACTL10, ACTL6A,
ACTL6B, ACTL7A, ACTL7B, ACTL8, ACTL9, ACTN1,
ACTN2, ACTN3, ACTN4, ACTR10, ACTRIA, ACTRIB,
ACTR2, ACTR3, ACTR3B, ACTR3C, ACTR5, ACTR6,
ACTR8, ACTRT1, ACTRT2, ACTRT3, ACVR1, ACVR1B,
ACVR1C, ACVR2A, ACVR2B, ACVRL1, ACY1, ACY3,
ACYP1, ACYP2, AD000671.1, AD000671.2, ADA, ADA2,
ADAD1, ADAD2, ADAL, ADAM10, ADAM11, ADAM12,
ADAM15, ADAM17, ADAM18, ADAM19, ADAM2,
ADAM20, ADAM21, ADAM22, ADAM23, ADAM28,
ADAM29, ADAM30, ADAM32, ADAM33, ADAM7,
ADAM8, ADAM9, ADAMDEC1, ADAMTS1,
ADAMTS10, ADAMTS12, ADAMTS13, ADAMTS14,
ADAMTS15, ADAMTS16, ADAMTS17, ADAMTS18,
ADAMTS19, ADAMTS2, ADAMTS20, ADAMTS3, ADAMTS4, ADAMTS5, ADAMTS6, ADAMTS7, ADAMTS8, ADAMTS9, ADAMTSL1, ADAMTSL2, ADAMTSL3, ADAMTSL4, ADAMTSL5, ADAP1, ADAP2, ADAR, ADARB1, ADARB2, ADAT1, ADAT2, ADAT3, ADCK1, ADCK2, ADCK5, ADCY1, ADCY10, ADCY2, ADCY3, ADCY4, ADCY5, ADCY6, ADCY7, ADCY8, ADCY9, ADCYAP1, ADCYAP1R1, ADD1, ADD2, ADD3, ADGB, ADGRA1, ADGRA2, ADGRA3, ADGRB1, ADGRB2, ADGRB3, ADGRD1, ADGRD2, ADGRE1, ADGRE2, ADGRE3, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADH1A, ADH1B, ADH1C, ADH4, ADH5, ADH6, ADH7, ADHFE1, ADI1, ADIG, ADIPOQ, ADIPOR1, ADIPOR2, ADIRF, ADK, ADM, ADM2, ADM5, ADNP, ADNP2, ADO, ADORA1, ADORA2A, ADORA2B, ADORA3, ADPGK, ADPRH, ADPRHL1, ADPRHL2, ADPRM, ADRA1A, ADRA1B, ADRA1D, ADRA2A, ADRA2B, ADRA2C, ADRB1, ADRB2, ADRB3, ADRM1, ADSL, ADSS, ADSSL1, ADTRP, AEBP1, AEBP2, AEN, AES, AF130351.1, AF241726.2, AFAP1, AFAP1L1, AFAP1L2, AFDN, AFF1, AFF2, AFF3, AFF4, AFG1L, AFG3L2, AFM, AFMID, AFP, AFTPH, AGA, AGAP1, AGAP2, AGAP3, AGAP4, AGAP5, AGAP6, AGAP9, AGBL1, AGBL2, AGBL3, AGBL4, AGBL5, AGER, AGFG1, AGFG2, AGGF1, AGK, AGL, AGMAT, AGMO, AGO1, AGO2, AGO3, AGO4, AGPAT1, AGPAT2, AGPAT3, AGPAT4, AGPAT5, AGPS, AGR2, AGR3, AGRN, AGRP, AGT, AGTPBP1, AGTR1, AGTR2, AGTRAP, AGXT, AGXT2, AHCTF1, AHCY, AHCYL1, AHCYL2, AHDC1, AHI1, AHNAK, AHNAK2, AHR, AHRR, AHSA1, AHSA2, AHSG, AHSP, AICDA, AIDA, AIF1, AIF1L, AIFM1, AIFM2, AIFM3, AIG1, AIM2, AIMP1, AIMP2, AIP, AIPL1, AIRE, AJAP1, AJUBA, AK1, AK2, AK3, AK4, AK5, AK6, AK7, AK8, AK9, AKAIN1, AKAP1, AKAP10, AKAP11, AKAP12, AKAP13, AKAP14, AKAP17A, AKAP2, AKAP3, AKAP4, AKAP5, AKAP6, AKAP7, AKAP8, AKAP8L, AKAP9, AKIP1, AKIRIN1, AKIRIN2, AKNA, AKNAD1, AKR1A1, AKR1B1, AKR1B10, AKR1B15, AKR1C1, AKR1C2, AKR1C3, AKR1C4, AKR1D1, AKR1E2, AKR7A2, AKR7A3, AKR7L, AKT1, AKT1S1, AKT2, AKT3, AKTIP, AL020996.2, AL021154.3, AL021546.1, AL021997.3, AL022238.4, AL022318.4, AL024498.2, ALO31708.1, AL032819.3, AL033529.1, AL035425.2, ALO35460.1, AL049634.2, AL049650.1, AL049697.1, AL049779.1, AL049839.2, AL049844.1, AL049844.3, AL080251.1, AL096814.1, AL096870.1, AL109810.2, AL109811.4, AL109827.1, AL109936.3, AL109936.4, AL110118.2, AL110118.4, AL117258.1, AL117339.5, AL117348.2, AL121581.1, AL121594.3, AL121722.1, AL121753.1, AL121758.1, AL121845.2, AL121845.3, AL132671.2, AL132780.3, AL133352.1, AL133414.1, AL133414.2, AL136295.1, AL136295.3, AL136295.4, AL136295.5, AL136373.1, AL136531.2, AL138694.1, AL138752.2, AL138826.1, AL139011.2, AL139260.3, AL139300.1, AL139353.1, AL157392.5, AL159163.1, AL160275.1, AL160276.1, AL160396.2, AL161669.4, AL161911.1, AL162231.1, AL162231.3, AL163195.3, AL163636.2, AL353572.3, AL353588.1, AL354761.2, AL354822.1, AL355102.2, AL355315.1, AL355860.1, AL355916.3, AL355987.1, AL355987.3, AL356585.9, AL357673.1, AL358075.4, AL359736.1, AL359736.3, AL359922.1, AL360181.5, AL360181.5, AL365205.1, AL365214.3, AL365232.1, AL365273.2, AL391650.1, AL449266.1, AL451007.3, AL512428.1, AL512506.3, AL512785.2, AL513165.2, AL513523.10, AL513523.9, AL583836.1, AL589666.1, AL590132.1, AL590560.1, AL591806.3, AL592183.1, AL592490.1, AL593848.2, AL603832.3, AL645922.1, AL645941.2, AL662828.1, AL662852.6, AL662899.1, AL662899.2, AL662899.3, AL669918.1, AL672043.1, AL672142.1, AL691442.1, AL713999.1, AL772284.2, AL807752.6, AL807752.7, AL844853.2, AL845331.2, AL845464.1, AL928654.4, AL929554.1, AL929561.7, ALAD, ALAS1, ALAS2, ALB, ALCAM, ALDH16A1, ALDH18A1, ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDOA, ALDOB, ALDOC, ALG1, ALG10, ALG10B, ALG11, ALG12, ALG13, ALG14, ALG1L, ALG1L2, ALG2, ALG3, ALG5, ALG6, ALG8, ALG9, ALK, ALKAL1, ALKAL2, ALKBH1, ALKBH2, ALKBH3, ALKBH4, ALKBH5, ALKBH6, ALKBH7, ALKBH8, ALLC, ALMS1, ALOX12, ALOX12B, ALOX15, ALOX15B, ALOX5, ALOX5AP, ALOXE3, ALPI, ALPK1, ALPK2, ALPK3, ALPL, ALPP, ALPPL2, ALS2, ALS2CL, ALS2CR12, ALX1, ALX3, ALX4, ALYREF, AMACR, AMBN, AMBP, AMBRA1, AMD1, AMDHD1, AMDHD2, AMELX, AMELY, AMER1, AMER2, AMER3, AMFR, AMH, AMHR2, AMIGO1, AMIGO2, AMIGO3, AMMECR1, AMMECR1L, AMN, AMN1, AMOT, AMOTL1, AMOTL2, AMPD1, AMPD2, AMPD3, AMPH, AMT, AMTN, AMY1A, AMY1B, AMY1C, AMY2A, AMY2B, AMZ1, AMZ2, ANAPC1, ANAPC10, ANAPC11, ANAPC13, ANAPC15, ANAPC16, ANAPC2, ANAPC4, ANAPC5, ANAPC7, ANG, ANGEL1, ANGEL2, ANGPT1, ANGPT2, ANGPT4, ANGPTL1, ANGPTL2, ANGPTL3, ANGPTL4, ANGPTL5, ANGPTL6, ANGPTL7, ANGPTL8, ANHX, ANK1, ANK2, ANK3, ANKAR, ANKDD1A, ANKDD1B, ANKEF1, ANKFN1, ANKFY1, ANKH, ANKHD1, ANKHD1-EIF4EBP3, ANKIB1, ANKK1, ANKLE1, ANKLE2, ANKMY1, ANKMY2, ANKRA2, ANKRD1, ANKRD10, ANKRD11, ANKRD12, ANKRD13A, ANKRD13B, ANKRD13C, ANKRD13D, ANKRD16, ANKRD17, ANKRD18A, ANKRD18B, ANKRD2, ANKRD20A1, ANKRD20A2, ANKRD20A3, ANKRD20A4, ANKRD20A8P, ANKRD22, ANKRD23, ANKRD24, ANKRD26, ANKRD27, ANKRD28, ANKRD29, ANKRD30A, ANKRD30B, ANKRD30BL, ANKRD31, ANKRD33, ANKRD33B, ANKRD34A, ANKRD34B, ANKRD34C, ANKRD35, ANKRD36, ANKRD36B, ANKRD36C, ANKRD37, ANKRD39, ANKRD40, ANKRD42, ANKRD44, ANKRD45, ANKRD46, ANKRD49, ANKRD50, ANKRD52, ANKRD53, ANKRD54, ANKRD55, ANKRD6, ANKRD60, ANKRD61, ANKRD62, ANKRD63, ANKRD65, ANKRD66, ANKRD7, ANKRD9, ANKS1A, ANKS1B, ANKS3, ANKS4B, ANKS6, ANKUB1, ANKZF1, ANLN, ANO1, ANO10, ANO2, ANO3, ANO4, ANO5, ANO6, ANO7, ANO8, ANO9, ANOS1, ANP32A, ANP32B, ANP32D, ANP32E, ANPEP, ANTXR1, ANTXR2, ANTXRL, ANXA1, ANXA10, ANXA11, ANXA13, ANXA2, ANXA2R, ANXA3, ANXA4, ANXA5, ANXA6, ANXA7, ANXA8, ANXA8L1, ANXA9, AOAH, AOC1, AOC2, AOC3, AOX1, AP000275.2, AP000295.1, AP000311.1, AP000322.1, AP000349.1, AP000350.12, AP000350.4, AP000351.1, AP000351.7, AP000721.1, AP000781.2, AP001160.5, AP001273.2, AP001458.2, AP001781.3, AP001931.1, AP002360.1, AP002373.1, AP002495.1, AP002512.3, AP002512.4, AP002748.4, AP002990.1, AP003071.5, AP003108.2, AP003419.2, AP004243.1, AP006285.3, AP1AR, AP1B1, AP1G1, AP1G2, AP1M1, AP1M2, AP1S1, AP1S2, AP1S3, AP2A1, AP2A2, AP2B1, AP2M1, AP2S1, AP3B1, AP3B2, AP3D1, AP3M1, AP3M2, AP3S1, AP3S2, AP4B1, AP4E1, AP4M1, AP4S1, AP5B1, AP5M1, AP5S1, AP5Z1, APAF1, APBA1, APBA2, APBA3, APBB1, APBB1IP, APBB2, APBB3, APC, APC2, APCDD1, APCDD1L, APCS, APEH, APELA, APEX1, APEX2, APH1A, APH1B, API5, APIP, APLF, APLN, APLNR, APLP1, APLP2, APMAP, APOA1, APOA2, APOA4, APOA5, APOB, APOBEC1, APOBEC2, APOBEC3A, APOBEC3B, APOBEC3C, APOBEC3D, APOBEC3F, APOBEC3G, APOBEC3H, APOBEC4, APOBR, APOC1, APOC2, APOC3, APOC4, APOC4-APOC2, APOD, APOE, APOF, APOH, APOL1, APOL2, APOL3, APOL4, APOL5, APOL6, APOLD1, APOM, APOO, APOOL, APOPT1, APP, APPBP2, APPL1, APPL2, APRT, APTX, AQP1, AQP10, AQP11, AQP12A, AQP12B, AQP2, AQP3, AQP4, AQP5, AQP6, AQP7, AQP8, AQP9, AQR, AR, ARAF, ARAP1, ARAP2, ARAP3, ARC, ARCN1, AREG, AREL1, ARF1, ARF3, ARF4, ARF5, ARF6, ARFGAP1, ARFGAP2, ARFGAP3, ARFGEF1, ARFGEF2, ARFGEF3, ARFIP1, ARFIP2, ARFRP1, ARG1, ARG2, ARGFX, ARGLU1, ARHGAP1, ARHGAP10, ARHGAP11A, ARHGAP11B, ARHGAP12, ARHGAP15, ARHGAP17, ARHGAP18, ARHGAP19, ARHGAP19-SLIT1, ARHGAP20, ARHGAP21, ARHGAP22, ARHGAP23, ARHGAP24, ARHGAP25, ARHGAP26, ARHGAP27, ARHGAP28, ARHGAP29, ARHGAP30, ARHGAP31, ARHGAP32, ARHGAP33, ARHGAP35, ARHGAP36, ARHGAP39, ARHGAP4, ARHGAP40, ARHGAP42, ARHGAP44, ARHGAP45, ARHGAP5, ARHGAP6, ARHGAP8, ARHGAP9, ARHGDIA, ARHGDIB, ARHGDIG, ARHGEF1, ARHGEF10, ARHGEF10L, ARHGEF11, ARHGEF12, ARHGEF15, ARHGEF16, ARHGEF17, ARHGEF18, ARHGEF19, ARHGEF2, ARHGEF25, ARHGEF26, ARHGEF28, ARHGEF3, ARHGEF33, ARHGEF35, ARHGEF37, ARHGEF38, ARHGEF39, ARHGEF4, ARHGEF40, ARHGEF5, ARHGEF6, ARHGEF7, ARHGEF9, ARID1A, ARID1B, ARID2, ARID3A, ARID3B, ARID3C, ARID4A, ARID4B, ARID5A, ARID5B, ARIH1, ARIH2, ARIH2OS, ARL1, ARL10, ARL11, ARL13A, ARL13B, ARL14, ARL14EP, ARL14EPL, ARL15, ARL16, ARL17A, ARL17B, ARL2, ARL2BP, ARL2-SNX15, ARL3, ARL4A, ARL4C, ARL4D, ARL5A, ARL5B, ARL5C, ARL6, ARL6IP1, ARL6IP4, ARL6IP5, ARL6IP6, ARL8A, ARL8B, ARL9, ARMC1, ARMC10, ARMC12, ARMC2, ARMC3, ARMC4, ARMC5, ARMC6, ARMC7, ARMC8, ARMC9, ARMCX1, ARMCX2, ARMCX3, ARMCX4, ARMCX5, ARMCX6, ARMS2, ARMT1, ARNT, ARNT2, ARNTL, ARNTL2, ARPC1A, ARPC1B, ARPC2, ARPC3, ARPC4, ARPC4-TTLL3, ARPC5, ARPC5L, ARPIN, ARPP19, ARPP21, ARR3, ARRB1, ARRB2, ARRDC1, ARRDC2, ARRDC3, ARRDC4, ARRDC5, ARSA, ARSB, ARSD, ARSE, ARSF, ARSG, ARSH, ARSI, ARSJ, ARSK, ART1, ART3, ART4, ART5, ARTN, ARV1, ARVCF, ARX, AS3MT, ASAH1, ASAH2, ASAH2B, ASAP1, ASAP2, ASAP3, ASB1, ASB10, ASB11, ASB12, ASB13, ASB14, ASB15, ASB16, ASB17, ASB18, ASB2, ASB3, ASB4, ASB5, ASB6, ASB7, ASB8, ASB9, ASCC1, ASCC2, ASCC3, ASCL1, ASCL2, ASCL3, ASCL4, ASCL5, ASF1A, ASF1B, ASGR1, ASGR2, ASH1L, ASH2L, ASIC1, ASIC2, ASIC3, ASIC4, ASIC5, ASIP, ASL, ASMT, ASMTL, ASNA1, ASNS, ASNSD1, ASPA, ASPDH, ASPG, ASPH, ASPHD1, ASPHD2, ASPM, ASPN, ASPRV1, ASP-SCR1, ASRGL1, ASS1, ASTE1, ASTL, ASTN1, ASTN2, ASXL1, ASXL2, ASXL3, ASZ1, ATAD1, ATAD2, ATAD2B, ATAD3A, ATAD3B, ATAD3C, ATAD5, ATAT1, ATCAY, ATE1, ATF1, ATF2, ATF3, ATF4, ATF5, ATF6, ATF6B, ATF7, ATF7IP, ATF7IP2, ATG10, ATG101, ATG12, ATG13, ATG14, ATG16L1, ATG16L2, ATG2A, ATG2B, ATG3, ATG4A, ATG4B, ATG4C, ATG4D, ATG5, ATG7, ATG9A, ATG9B, ATIC, ATL1, ATL2, ATL3, ATM, ATMIN, ATN1, ATOH1, ATOH7, ATOH8, ATOX1, ATP10A, ATP10B, ATP10D, ATP11A, ATP11B, ATP11C, ATP12A, ATP13A1, ATP13A2, ATP13A3, ATP13A4, ATP13A5, ATP1A1, ATP1A2, ATP1A3, ATP1A4, ATP1B1, ATP1B2, ATP1B3, ATP1B4, ATP23, ATP2A1, ATP2A2, ATP2A3, ATP2B1, ATP2B2, ATP2B3, ATP2B4, ATP2C1, ATP2C2, ATP4A, ATP4B, ATP5A1, ATP5B, ATP5C1, ATP5D, ATP5E, ATP5EP2, ATP5F1, ATP5G1, ATP5G2, ATP5G3, ATP5H, ATP5I, ATP5J, ATP5J2, ATP5J2-PTCD1, ATP5L, ATP5L2, ATP5O, ATP5S, ATP6AP1, ATP6AP1L, ATP6AP2, ATP6V0A1, ATP6V0A2, ATP6V0A4, ATP6V0B, ATP6V0C, ATP6V0D1, ATP6V0D2, ATP6V0E1, ATP6V0E2, ATP6V1A, ATP6V1B1, ATP6V1B2, ATP6V1C1, ATP6V1C2, ATP6V1D, ATP6V1E1, ATP6V1E2, ATP6V1F, ATP6V1G1, ATP6V1G2, ATP6V1G2-DDX39B, ATP6V1G3, ATP6V1H, ATP7A, ATP7B, ATP8A1, ATP8A2, ATP8B1, ATP8B2, ATP8B3, ATP8B4, ATP9A, ATP9B, ATPAF1, ATPAF2, ATPIF1, ATR, ATRAID, ATRIP, ATRN, ATRNL1, ATRX, ATXN1, ATXN10, ATXN1L, ATXN2, ATXN2L, ATXN3, ATXN3L, ATXN7, ATXN7L1, ATXN7L2, ATXN7L3, ATXN7L3B, AUH, AUNIP, AUP1, AURKA, AURKAIP1, AURKB, AURKC, AUTS2, AVEN, AVIL, AVL9, AVP, AVPI1, AVPR1A, AVPR1B, AVPR2, AWAT1, AWAT2, AXDND1, AXIN1, AXIN2, AXL, AZGP1, AZI2, AZIN1, AZIN2, AZU1, B2M, B3GALNT1, B3GALNT2, B3GALT1, B3GALT2, B3GALT4, B3GALT5, B3GALT6, B3GAT1, B3GAT2, B3GAT3, B3GLCT, B3GNT2, B3GNT3, B3GNT4, B3GNT5, B3GNT6, B3GNT7, B3GNT8, B3GNT9, B3GNTL1, B4GALNT1, B4GALNT2, B4GALNT3, B4GALNT4, B4GALT1, B4GALT2, B4GALT3, B4GALT4, B4GALT5, B4GALT6, B4GALT7, B4GAT1, B9D1, B9D2, BAALC, BAAT, BABAM1, BABAM2, BACE1, BACE2, BACH1, BACH2, BAD, BAG1, BAG2, BAG3, BAG4, BAG5, BAG6, BAGE3, BAHCC1, BAHD1, BAIAP2, BAIAP2L1, BAIAP2L2, BAIAP3, BAK1, BAMBI, BANF1, BANF2, BANK1, BANP, BAP1, BARD1, BARHL1, BARHL2, BARX1, BARX2, BASP1, BATF, BATF2, BATF3, BAX, BAZ1A, BAZ1B, BAZ2A, BAZ2B, BBC3, BBIP1, BBOF1, BBOX1, BBS1, BBS10, BBS12, BBS2, BBS4, BBS5, BBS7, BBS9, BBX, BCAM, BCAN, BCAP29, BCAP31, BCAR1, BCAR3, BCAS1, BCAS2, BCAS3, BCAS4, BCAT1, BCAT2, BCCIP, BCDIN3D, BCHE, BCKDHA, BCKDHB, BCKDK, BCL10, BCL11A, BCL11B, BCL2, BCL2A1, BCL2L1, BCL2L10, BCL2L11, BCL2L12, BCL2L13, BCL2L14, BCL2L15, BCL2L2, BCL2L2-PABPN1, BCL3, BCL6, BCL6B, BCL7A, BCL7B, BCL7C, BCL9, BCL9L, BCLAF1, BCLAF3, BCO1, BCO2, BCOR, BCORL1, BCR, BCS1L, BDH1, BDH2, BDKRB1, BDKRB2, BDNF, BDP1, BEAN1, BECN1, BECN2, BEGAIN, BEND2, BEND3, BEND4, BEND5, BEND6, BEND7, BEST1, BEST2, BEST3, BEST4, BET1, BET1L, BEX1, BEX2, BEX3, BEX4, BEX5, BFAR, BFSP1, BFSP2, BGLAP, BGN, BHLHA15, BHLHA9, BHLHB9, BHLHE22, BHLHE23, BHLHE40, BHLHE41, BHMG1, BHMT, BHMT2, BICC1, BICD1, BICD2, BICDL1, BICDL2, BICRA, BICRAL, BID, BIK, BIN1, BIN2, BIN3, BIRC2, BIRC3, BIRC5, BIRC6, BIRC7, BIRC8, BIVM, BIVM-ERCC5, BLACE, BLCAP, BLID, BLK, BLM, BLMH, BLNK, BLOC1S1, BLOC1S2, BLOC1S3, BLOC1S4, BLOC1S5, BLOC1S5-TXNDC5, BLOC1S6, BLVRA, BLVRB, BLZF1, BMF, BMI1, BMP1, BMP10, BMP15, BMP2, BMP2K, BMP3, BMP4, BMP5, BMP6, BMP7, BMP8A, BMP8B, BMPER, BMPR1A, BMPR1B, BMPR2, BMS1, BMT2, BMX, BNC1, BNC2, BNIP1, BNIP2, BNIP3, BNIP3L, BNIPL, BOC, BOD1, BOD1L1, BOD1L2, BOK, BOLA1, BOLA2, BOLA2B, BOLA2-SMG1P6, BOLA3, BOLL, BOP1, BORA, BORCS5, BORCS6, BORCS7, BORCS7-ASMT, BORCS8, BORCS8-MEF2B, BPGM, BPHL, BPI, BPIFA1, BPIFA2, BPIFA3, BPIFB1, BPIFB2, BPIFB3, BPIFB4, BPIFB6, BPIFC, BPNT1, BPTF, BPY2, BPY2B, BPY2C, BRAF, BRAP, BRAT1, BRCA1, BRCA2, BRCC3, BRD1, BRD2, BRD3, BRD4, BRD7, BRD8, BRD9, BRDT, BRF1, BRF2, BRI3, BRI3BP, BRICD5, BRINP1, BRINP2, BRINP3, BRIP1, BRIX1, BRK1, BRMS1, BRMS1L, BROX, BRPF1, BRPF3, BRS3, BRSK1, BRSK2, BRWD1, BRWD3, BSCL2, BSDC1, BSG, BSN, BSND, BSPH1, BSPRY, BST1, BST2, BSX, BTAF1, BTBD1, BTBD10, BTBD11, BTBD16, BTBD17, BTBD18, BTBD19, BTBD2, BTBD3, BTBD6, BTBD7, BTBD8, BTBD9, BTC, BTD, BTF3, BTF3L4, BTG1, BTG2, BTG3, BTG4, BTK, BTLA, BTN1A1, BTN2A1, BTN2A2, BTN3A1, BTN3A2, BTN3A3, BTNL2, BTNL3, BTNL8, BTNL9, BTRC, BUB1, BUB1B, BUB1B-PAK6, BUB3, BUD13, BUD23, BUD31, B VES, BX004987.1, BX072566.1, BX088645.1, BX248244.1, BX248413.4, BX248415.1, BX248516.1, BX276092.9, BYSL, BZW1, BZW2, C10orf10, C10orf105, C10orf107, C10orf113, C10orf120, C10orf126, C10orf128, C10orf142, C10orf35, C10orf53, C10orf55, C10orf62, C10orf67, C10orf71, C10orf76, C10orf82, C10orf88, C10orf90, C10orf95, C10orf99, C11orf1, C11orf16, C11orf21, C11orf24, C11orf40, C11orf42, C11orf45, C11orf49, C11orf52, C11orf53, C11orf54, C11orf57, C11orf58, C11orf63, C11orf65, C11orf68, C11orf70, C11orf71, C11orf74, C11orf80, C11orf84, C11orf86, C11orf87, C11orf88, C11orf91, C11orf94, C11orf95, C11orf96, C11orf97, C11orf98, C12orf10, C12orf29, C12orf4, C12orf40, C12orf42, C12orf43, C12orf45, C12orf49, C12orf50, C12orf54, C12orf56, C12orf57, C12orf60, C12orf65, C12orf66, C12orf71, C12orf73, C12orf74, C12orf75, C12orf76, C13orf42, C14orf105, C14orf119, C14orf132, C14orf159, C14orf166, C14orf177, C14orf178, C14orf180, C14orf2, C14orf28, C14orf37, C14orf39, C14orf79, C14orf80, C14orf93, C15orf38-AP3S2, C15orf39, C15orf40, C15orf41, C15orf48, C15orf52, C15orf53, C15orf59, C15orf61, C15orf62, C15orf65, C16orf45, C16orf46, C16orf52, C16orf54, C16orf58, C16orf59, C16orf62, C16orf70, C16orf71, C16orf72, C16orf74, C16orf78, C16orf82, C16orf86, C16orf87, C16orf89, C16orf90, C16orf91, C16orf92, C16orf95, C16orf96, C17orf100, C17orf105, C17orf107, C17orf113, C17orf47, C17orf49, C17orf50, C17orf51, C17orf53, C17orf58, C17orf62, C17orf64, C17orf67, C17orf74, C17orf75, C17orf78, C17orf80, C17orf97, C17orf98, C17orf99, C18orf21, C18orf25, C18orf32, C18orf54, C18orf63, C18orf8, C19orf12, C19orf18, C19orf24, C19orf25, C19orf33, C19orf35, C19orf38, C19orf44, C19orf47, C19orf48, C19orf53, C19orf54, C19orf57, C19orf60, C19orf66, C19orf67, C19orf68, C19orf70, C19orf71, C19orf73, C19orf81, C19orf84, C1D, C1GALT1, C1GALT1C1, C1GALT1C1L, C1orf100, C1orf105, C1orf109, C1orf112, C1orf115, C1orf116, C1orf122, C1orf123, C1orf127, C1orf131, C1orf141, C1orf146, C1orf158, C1orf159, C1orf162, C1orf167, C1orf174, C1orf185, C1orf186, C1orf189, C1orf194, C1orf198, C1orf21, C1orf210, C1orf216, C1orf226, C1orf228, C1orf232, C1orf27, C1orf35, C1orf43, C1orf50, C1orf52, C1orf53, C1orf54, C1orf56, C1orf61, C1orf64, C1orf68, C1orf74, C1orf87, C1orf94, C1QA, C1QB, C1QBP, C1QC, C1QL1, C1QL2, C1QL3, C1QL4, C1QTNF1, C1QTNF2, C1QTNF12, C1QTNF3, C1QTNF3-AMACR, C1QTNF4, C1QTNF5, C1QTNF6, C1QTNF7, C1QTNF8, C1QTNF9, C1QTNF9B, C1R, C1RL, C1S, C2, C20orf141, C20orf144, C20orf173, C20orf194, C20orf196, C20orf202, C20orf204, C20orf24, C20orf27, C20orf85, C20orf96, C21orf140, C21orf2, C21orf33, C21orf58, C21orf59, C21orf62, C21orf91, C22orf15, C22orf23, C22orf31, C22orf39, C22orf42, C22orf46, C2CD2, C2CD2L, C2CD3, C2CD4A, C2CD4B, C2CD4C, C2CD4D, C2CD5, C2CD6, C2orf15, C2orf16, C2orf40, C2orf42, C2orf49, C2orf50, C2orf54, C2orf66, C2orf68, C2orf69, C2orf70, C2orf71, C2orf72, C2orf73, C2orf74, C2orf76, C2orf78, C2orf80, C2orf81, C2orf82, C2orf83, C2orf88, C2orf91, C3, C3AR1, C3orf14, C3orf18, C3orf20, C3orf22, C3orf30, C3orf33, C3orf35, C3orf36, C3orf38, C3orf49, C3orf52, C3orf56, C3orf58, C3orf62, C3orf67, C3orf70, C3orf80, C3orf84, C3orf85, C4A, C4B, C4B2, C4BPA, C4BPB, C4orf17, C4orf19, C4orf22, C4orf26, C4orf3, C4orf32, C4orf33, C4orf36, C4orf45, C4orf46, C4orf47, C4orf48, C4orf50, C4orf51, C5, C5AR1, C5AR2, C5orf15, C5orf22, C5orf24, C5orf30, C5orf34, C5orf38, C5orf42, C5orf46, C5orf47, C5orf49, C5orf51, C5orf52, C5orf56, C5orf58, C5orf60, C5orf63, C5orf67, C6, C6orf10, C6orf106, C6orf118, C6orf120, C6orf132, C6orf136, C6orf141, C6orf15, C6orf163, C6orf201, C6orf203, C6orf222, C6orf223, C6orf226, C6orf229, C6orf47, C6orf48, C6orf52, C6orf58, C6orf62, C6orf89, C7, C7orf25, C7orf26, C7orf31, C7orf33, C7orf34, C7orf43, C7orf49, C7orf50, C7orf55-LUC7L2, C7orf57, C7orf61, C7orf72, C7orf73, C7orf77, C8A, C8B, C8G, C8orf22, C8orf33, C8orf34, C8orf37, C8orf4, C8orf44, C8orf44-SGK3, C8orf46, C8orf48, C8orf58, C8orf59, C8orf74, C8orf76, C8orf82, C8orf86, C8orf88, C8orf89, C9, C9orf116, C9orf129, C9orf131, C9orf135, C9orf152, C9orf153, C9orf16, C9orf172, C9orf24, C9orf3, C9orf40, C9orf43, C9orf47, C9orf50, C9orf57, C9orf64, C9orf66, C9orf72, C9orf78, C9orf84, C9orf85, C9orf92, CA1, CA10, CA11, CA12, CA13, CA14, CA2, CA3, CA4, CA5A, CA5B, CA6, CA7, CA8, CA9, CAAP1, CAB39, CAB39L, CABIN1, CABLES1, CABLES2, CABP1, CABP2, CABP4, CABP5, CABP7, CABS1, CABYR, CACFD1, CACHD1, CACNA1A, CACNA1B, CACNA1C, CACNA1D, CACNA1E, CACNA1F, CACNA1G, CACNA1H, CACNA1I, CACNA1S, CACNA2D1, CACNA2D2, CACNA2D3, CACNA2D4, CACNB1, CACNB2, CACNB3, CACNB4, CACNG1, CACNG2, CACNG3, CACNG4, CACNG5, CACNG6, CACNG7, CACNG8, CACTIN, CACUL1, CACYBP, CAD, CADM1, CADM2, CADM3, CADM4, CADPS, CADPS2, CAGE1, CALB1, CALB2, CALCA, CALCB, CALCOCO1, CALCOCO2, CALCR, CALCRL, CALD1, CALHM1, CALHM2, CALHM3, CALM1, CALM2, CALM3, CALML3, CALML4, CALML5, CALML6, CALN1, CALR, CALR3, CALU, CALY, CAMK1, CAMK1D, CAMK1G, CAMK2A, CAMK2B, CAMK2D, CAMK2G, CAMK2N1, CAMK2N2, CAMK4, CAMKK1, CAMKK2, CAMKMT, CAMKV, CAMLG, CAMP, CAMSAP1, CAMSAP2, CAMSAP3, CAMTA1, CAMTA2, CAND1, CAND2, CANT1, CANX, CAP1, CAP2, CAPG, CAPN1, CAPN10, CAPN11, CAPN12, CAPN13, CAPN14, CAPN15, CAPN2, CAPN3, CAPN5, CAPN6, CAPN7, CAPN8, CAPN9, CAPNS1, CAPNS2, CAPRIN1, CAPRIN2, CAPS, CAPS2, CAPSL, CAPZA1, CAPZA2, CAPZA3, CAPZB, CARD10, CARD11, CARD14, CARD16, CARD17, CARD18, CARD19, CARD6, CARD8, CARD9, CARF, CARHSP1, CARM1, CARMIL1, CARMIL2, CARMIL3, CARNMT1, CARNS1, CARS, CARS2, CARTPT, CASC1, CASC10, CASC3, CASC4, CASD1, CASK, CASKIN1, CASKIN2, CASP1, CASP10, CASP12, CASP14, CASP2, CASP3, CASP4, CASP5, CASP6, CASP7, CASP8, CASP8AP2, CASP9, CASQ1, CASQ2, CASR, CASS4, CAST, CASTOR1, CASTOR2, CASZ1, CAT, CATIP, CATSPER1, CATSPER2, CATSPER3, CATSPER4, CATSPERB, CATSPERD, CATSPERE, CATSPERG, CATSPERZ, CAV1, CAV2, CAV3, CAVIN1, CAVIN2, CAVIN3, CAVIN4, CBARP, CBFA2T2, CBFA2T3, CBFB, CBL, CBLB, CBLC, CBLL1, CBLN1, CBLN2, CBLN3, CBLN4, CBR1, CBR3, CBR4, CBS, CBSL, CBWD1, CBWD2, CBWD3, CBWD5, CBWD6, CBX1, CBX2, CBX3, CBX4, CBX5, CBX6, CBX7, CBX8, CBY1, CBY3, CC2D1A, CC2D1B, CC2D2A, CC2D2B, CCAR1, CCAR2, CCBE1, CCDC102A, CCDC102B, CCDC103, CCDC105, CCDC106, CCDC107, CCDC110, CCDC112, CCDC113, CCDC114, CCDC115, CCDC116, CCDC117, CCDC12, CCDC120, CCDC121, CCDC122, CCDC124, CCDC125, CCDC126, CCDC127, CCDC129, CCDC13, CCDC130, CCDC134, CCDC136, CCDC137, CCDC138, CCDC14, CCDC140, CCDC141, CCDC142, CCDC144A, CCDC144NL, CCDC146, CCDC148, CCDC149, CCDC15, CCDC150, CCDC151, CCDC152, CCDC153, CCDC154, CCDC155, CCDC157, CCDC158, CCDC159, CCDC160, CCDC163, CCDC166, CCDC167, CCDC168, CCDC169, CCDC169-SOHLH2, CCDC17, CCDC170, CCDC171, CCDC172, CCDC173, CCDC174, CCDC175, CCDC177, CCDC178, CCDC179, CCDC18, CCDC180, CCDC181, CCDC182, CCDC183, CCDC184, CCDC185, CCDC186, CCDC187, CCDC188, CCDC189, CCDC190, CCDC191, CCDC192, CCDC194, CCDC195, CCDC196, CCDC197, CCDC22, CCDC24, CCDC25, CCDC27, CCDC28A, CCDC28B, CCDC3, CCDC30, CCDC32, CCDC33, CCDC34, CCDC36, CCDC38, CCDC39, CCDC40, CCDC42, CCDC43, CCDC47, CCDC50, CCDC51, CCDC54, CCDC57, CCDC58, CCDC59, CCDC6, CCDC60, CCDC61, CCDC62, CCDC63, CCDC65, CCDC66, CCDC68, CCDC69, CCDC7, CCDC70, CCDC71, CCDC71L, CCDC73, CCDC74A, CCDC74B, CCDC77, CCDC78, CCDC8, CCDC80, CCDC81, CCDC82, CCDC83, CCDC84, CCDC85A, CCDC85B, CCDC85C, CCDC86, CCDC87, CCDC88A, CCDC88B, CCDC88C, CCDC89, CCDC9, CCDC90B, CCDC91, CCDC92, CCDC93, CCDC94, CCDC96, CCDC97, CCER1, CCER2, CCHCR1, CCIN, CCK, CCKAR, CCKBR, CCL1, CCL11, CCL13, CCL14, CCL15, CCL15-CCL14, CCL16, CCL17, CCL18, CCL19, CCL2, CCL20, CCL21, CCL22, CCL23, CCL24, CCL25, CCL26, CCL27, CCL28, CCL3, CCL3L1, CCL3L3, CCL4, CCL4L2, CCL5, CCL7, CCL8, CCM2, CCM2L, CCNA1, CCNA2, CCNB1, CCNB1IP1, CCNB2, CCNB3, CCNC, CCND1, CCND2, CCND3, CCNDBP1, CCNE1, CCNE2, CCNF, CCNG1, CCNG2, CCNH, CCNI, CCNI2, CCNJ, CCNJL, CCNK, CCNL1, CCNL2, CCNO, CCNT1, CCNT2, CCNY, CCNYL1, CCP110, CCPG1, CCR1, CCR10, CCR2, CCR3, CCR4, CCR5, CCR6, CCR7, CCR8, CCR9, CCRL2, CCS, CCSAP, CCSER1, CCSER2, CCT2, CCT3, CCT4, CCT5, CCT6A, CCT6B, CCT7, CCT8, CCT8L2, CCZ1, CCZ1B, CD101, CD109, CD14, CD151, CD160, CD163, CD163L1, CD164, CD164L2, CD177, CD180, CD19, CD1A, CD1B, CD1C, CD1D, CD1E, CD2, CD200, CD200R1, CD200R1L, CD207, CD209, CD22, CD226, CD24, CD244, CD247, CD248, CD27, CD274, CD276, CD28, CD2AP, CD2BP2, CD300A, CD300C, CD300E, CD300LB, CD300LD, CD300LF, CD300LG, CD302, CD320, CD33, CD34, CD36, CD37, CD38, CD3D, CD3E, CD3EAP, CD3G, CD4, CD40, CD40LG, CD44, CD46, CD47, CD48, CD5, CD52, CD53, CD55, CD58, CD59, CD5L, CD6, CD63, CD68, CD69, CD7, CD70, CD72, CD74, CD79A, CD79B, CD80, CD81, CD82, CD83, CD84, CD86, CD8A, CD8B, CD9, CD93, CD96, CD99, CD99L2, CDA, CDADC1, CDAN1, CDC123, CDC14A, CDC14B, CDC16, CDC20, CDC20B, CDC23, CDC25A, CDC25B, CDC25C, CDC26, CDC27, CDC34, CDC37, CDC37L1, CDC40, CDC42, CDC42BPA, CDC42BPB, CDC42BPG, CDC42EP1, CDC42EP2, CDC42EP3, CDC42EP4, CDC42EP5, CDC42SE1, CDC42SE2, CDC45, CDC5L, CDC6, CDC7, CDC73, CDCA2, CDCA3, CDCA4, CDCA5, CDCA7, CDCA7L, CDCA8, CDCP1, CDCP2, CDH1, CDH10, CDH11, CDH12, CDH13, CDH15, CDH16, CDH17, CDH18, CDH19, CDH2, CDH20, CDH22, CDH23, CDH24, CDH26, CDH3, CDH4, CDH5, CDH6, CDH7, CDH8, CDH9, CDHR1, CDHR2, CDHR3, CDHR4, CDHR5, CDIP1, CDIPT, CDK1, CDK10, CDK11A, CDK11B, CDK12, CDK13, CDK14, CDK15, CDK16, CDK17, CDK18, CDK19, CDK2, CDK20, CDK2AP1, CDK2AP2, CDK3, CDK4, CDK5, CDK5R1, CDK5R2, CDK5RAP1, CDK5RAP2, CDK5RAP3, CDK6, CDK7, CDK8, CDK9, CDKAL1, CDKL1, CDKL2, CDKL3, CDKL4, CDKL5, CDKN1A, CDKN1B, CDKN1C, CDKN2A, CDKN2AIP, CDKN2AIPNL, CDKN2B, CDKN2C, CDKN2D, CDKN3, CDNF, CDO1, CDON, CDPF1, CDR1, CDR2, CDR2L, CDRT1, CDRT15, CDRT15L2, CDRT4, CDS1, CDS2, CDSN, CDT1, CDV3, CDX1, CDX2, CDX4, CDY1, CDY1B, CDY2A, CDY2B, CDYL, CDYL2, CEACAM1, CEACAM16, CEACAM19, CEACAM20, CEACAM21, CEACAM3, CEACAM4, CEACAM5, CEACAM6, CEACAM7, CEACAM8, CEBPA, CEBPB, CEBPD, CEBPE, CEBPG, CEBPZ, CEBPZOS, CECR2, CEL, CELA1, CELA2A, CELA2B, CELA3A, CELA3B, CELF1, CELF2, CELF3, CELF4, CELF5, CELF6, CELSR1, CELSR2, CELSR3, CEMIP, CEMP1, CEND1, CENPA, CENPB, CENPBD1, CENPC, CENPE, CENPF, CENPH, CENPI, CENPJ, CENPK, CENPL, CENPM, CENPN, CENPO, CENPP, CENPQ, CENPS, CENPS-CORT, CENPT, CENPU, CENPV, CENPVL1, CENPVL2, CENPVL3, CENPW, CENPX, CEP104, CEP112, CEP120, CEP126, CEP128, CEP131, CEP135, CEP152, CEP162, CEP164, CEP170, CEP170B, CEP19, CEP192, CEP250, CEP290, CEP295, CEP295NL, CEP350, CEP41, CEP44, CEP55, CEP57, CEP57L1, CEP63, CEP68, CEP70, CEP72, CEP76, CEP78, CEP83, CEP85, CEP85L, CEP89, CEP95, CEP97, CEPT1, CER1, CERCAM, CERK, CERKL, CERS1, CERS2, CERS3, CERS4, CERS5, CERS6, CES1, CES2, CES3, CES4A, CESSA, CETN1, CETN2, CETN3, CETP, CFAP100, CFAP126, CFAP157, CFAP161, CFAP20, CFAP206, CFAP221, CFAP36, CFAP43, CFAP44, CFAP45, CFAP46, CFAP47, CFAP52, CFAP53, CFAP54, CFAP57, CFAP58, CFAP61, CFAP65, CFAP69, CFAP70, CFAP73, CFAP74, CFAP77, CFAP97, CFAP99, CFB, CFC1, CFC1B, CFD, CFDP1, CFH, CFHR1, CFHR2, CFHR3, CFHR4, CFHR5, CFI, CFL1, CFL2, CFLAR, CFP, CFTR, CGA, CGB1, CGB2, CGB3, CGB5, CGB7, CGB8, CGGBP1, CGN, CGNL1, CGREF1, CGRRF1, CH25H, CHAC1, CHAC2, CHAD, CHADL, CHAF1A, CHAF1B, CHAMP1, CHAT, CHCHD1, CHCHD10, CHCHD2, CHCHD3, CHCHD4, CHCHD5, CHCHD6, CHCHD7, CHD1, CHD1L, CHD2, CHD3, CHD4, CHD5, CHD6, CHD7, CHD8, CHD9, CHDH, CHEK1, CHEK2, CHERP, CHFR, CHGA, CHGB, CHI3L1, CHI3L2, CHIA, CHIC1, CHIC2, CHID1, CHIT1, CHKA, CHKB, CHKB-CPT1B, CHL1, CHM, CHML, CHMP1A, CHMP1B, CHMP2A, CHMP2B, CHMP3, CHMP4A, CHMP4B, CHMP4C, CHMP5, CHMP6, CHMP7, CHN1, CHN2, CHODL, CHORDC1, CHP1, CHP2, CHPF, CHPF2, CHPT1, CHRAC1, CHRD, CHRDL1, CHRDL2, CHRFAM7A, CHRM1, CHRM2, CHRM3, CHRM4, CHRM5, CHRNA1, CHRNA10, CHRNA2, CHRNA3, CHRNA4, CHRNA5, CHRNA6, CHRNA7, CHRNA9, CHRNB1, CHRNB2, CHRNB3, CHRNB4, CHRND, CHRNE, CHRNG, CHST1, CHST10, CHST11, CHST12, CHST13, CHST14, CHST15, CHST2, CHST3, CHST4, CHST5, CHST6, CHST7, CHST8, CHST9, CHSY1, CHSY3, CHTF18, CHTF8, CHTOP, CHUK, CHURC1, CHURC1-FNTB, CIAO1, CIAPIN1, CIART, CIB1, CIB2, CIB3, CIB4, CIC, CIDEA, CIDEB, CIDEC, CIITA, CILP, CILP2, CINP, CIPC, CIR1, CIRBP, CISD1, CISD2, CISD3, CISH, CIT, CITED1, CITED2, CITED4, CIZ1, CKAP2, CKAP2L, CKAP4, CKAP5, CKB, CKLF, CKLF-CMTM1, CKM, CKMT1A, CKMT1B, CKMT2, CKS1B, CKS2, CLASP1, CLASP2, CLASRP, CLC, CLCA1, CLCA2, CLCA4, CLCC1, CLCF1, CLCN1, CLCN2, CLCN3, CLCN4, CLCN5, CLCN6, CLCN7, CLCNKA, CLCNKB, CLDN1, CLDN10, CLDN11, CLDN12, CLDN14, CLDN15, CLDN16, CLDN17, CLDN18, CLDN19, CLDN2, CLDN20, CLDN22, CLDN23, CLDN24, CLDN25, CLDN3, CLDN34, CLDN4, CLDN5, CLDN6, CLDN7, CLDN8, CLDN9, CLDND1, CLDND2, CLEC10A, CLEC11A, CLEC12A, CLEC12B, CLEC14A, CLEC16A, CLEC17A, CLEC18A, CLEC18B, CLEC18C, CLEC19A, CLEC1A, CLEC1B, CLEC20A, CLEC2A, CLEC2B, CLEC2D, CLEC2L, CLEC3A, CLEC3B, CLEC4A, CLEC4C, CLEC4D, CLEC4E, CLEC4F, CLEC4G, CLEC4M, CLEC5A, CLEC6A, CLEC7A, CLEC9A, CLECL1, CLGN, CLHC1, CLIC1, CLIC2, CLIC3, CLIC4, CLIC5, CLIC6, CLINT1, CLIP1, CLIP2, CLIP3, CLIP4, CLK1, CLK2, CLK3, CLK4, CLLU1, CLLU1OS, CLMN, CLMP, CLN3, CLN5, CLN6, CLN8, CLNK, CLNS1A, CLOCK, CLP1, CLPB, CLPP, CLPS, CLPSL1, CLPSL2, CLPTM1, CLPTM1L, CLPX, CLRN1, CLRN2, CLRN3, CLSPN, CLSTN1, CLSTN2, CLSTN3, CLTA, CLTB, CLTC, CLTCL1, CLU, CLUAP1, CLUH, CLUL1, CLVS1, CLVS2, CLYBL, CMA1, CMAS, CMBL, CMC1, CMC2, CMC4, CMIP, CMKLR1, CMPK1, CMPK2, CMSS1, CMTM1, CMTM2, CMTM3, CMTM4, CMTM5, CMTM6, CMTM7, CMTM8, CMTR1, CMTR2, CMYA5, CNBD1, CNBD2, CNBP, CNDP1, CNDP2, CNEP1R1, CNFN, CNGA1, CNGA2, CNGA3, CNGA4, CNGB1, CNGB3, CNIH1, CNIH2, CNIH3, CNIH4, CNKSR1, CNKSR2, CNKSR3, CNMD, CNN1, CNN2, CNN3, CNNM1, CNNM2, CNNM3, CNNM4, CNOT1, CNOT10, CNOT11, CNOT2, CNOT3, CNOT4, CNOT6, CNOT6L, CNOT7, CNOT8, CNOT9, CNP, CNPPD1, CNPY1, CNPY2, CNPY3, CNPY4, CNR1, CNR2, CNRIP1, CNST, CNTD1, CNTD2, CNTF, CNTFR, CNTLN, CNTN1, CNTN2, CNTN3, CNTN4, CNTN5, CNTN6, CNTNAP1, CNTNAP2, CNTNAP3, CNTNAP3B, CNTNAP4, CNTNAP5, CNTRL, CNTROB, COA1, COA3, COA4, COA5, COA6, COA7, COASY, COBL, COBLL1, COCH, COG1, COG2, COG3, COG4, COG5, COG6, COG7, COG8, COIL, COL10A1, COL11A1, COL11A2, COL12A1, COL13A1, COL14A1, COL15A1, COL16A1, COL17A1, COL18A1, COL19A1, COL1A1, COL1A2, COL20A1, COL21A1, COL22A1, COL23A1, COL24A1, COL25A1, COL26A1, COL27A1, COL28A1, COL2A1, COL3A1, COL4A1, COL4A2, COL4A3, COL4A3BP, COL4A4, COL4A5, COL4A6, COL5A1, COL5A2, COL5A3, COL6A1, COL6A2, COL6A3, COL6A5, COL6A6, COL7A1, COL8A1, COL8A2, COL9A1, COL9A2, COL9A3, COLCA2, COLEC10, COLEC11, COLEC12, COLGALT1, COLGALT2, COLQ, COMMD1, COMMD10, COMMD2, COMMD3, COMMD3-BMI1, COMMD4, COMMD5, COMMD6, COMMD7, COMMD8, COMMD9, COMP, COMT, COMTD1, COPA, COPB1, COPB2, COPE, COPG1, COPG2, COPRS, COPS2, COPS3, COPS4, COPS5, COPS6, COPS7A, COPS7B, COPS8, COPS9, COPZ1, COPZ2, COQ10A, COQ10B, COQ2, COQ3, COQ4, COQ5, COQ6, COQ7, COQ8A, COQ8B, COQ9, CORIN, CORO1A, CORO1B, CORO1C, CORO2A, CORO2B, CORO6, CORO7, CORO7-PAM16, CORT, COTL1, COX10, COX11, COX14, COX15, COX16, COX17, COX18, COX19, COX20, COX4I1, COX4I2, COX5A, COX5B, COX6A1, COX6A2, COX6B1, COX6B2, COX6C, COX7A1, COX7A2, COX7A2L, COX7B, COX7B2, COX7C, COX8A, COX8C, CP, CPA1, CPA2, CPA3, CPA4, CPA5, CPA6, CPAMD8, CPB1, CPB2, CPD, CPE, CPEB1, CPEB2, CPEB3, CPEB4, CPED1, CPLX1, CPLX2, CPLX3, CPLX4, CPM, CPN1, CPN2, CPNE1, CPNE2, CPNE3, CPNE4, CPNE5, CPNE6, CPNE7, CPNE8, CPNE9, CPO, CPOX, CPPED1, CPQ, CPS1, CPSF1, CPSF2, CPSF3, CPSF4, CPSF4L, CPSF6, CPSF7, CPT1A, CPT1B, CPT1C, CPT2, CPTP, CPVL, CPXCR1, CPXM1, CPXM2, CPZ, CR1, CR1L, CR2, CR354443.1, CR354443.2, CR388407.3, CR547123.3, CR753842.1, CR753845.2, CR759815.2, CR788250.1, CR847794.2, CR854858.1, CR933783.3, CR936239.1, CRABP1, CRABP2, CRACR2A, CRACR2B, CRADD, CRAMP1, CRAT, CRB1, CRB2, CRB3, CRBN, CRCP, CRCT1, CREB1, CREB3, CREB3L1, CREB3L2, CREB3L3, CREB3L4, CREB5, CREBBP, CREBL2, CREBRF, CREBZF, CREG1, CREG2, CRELD1, CRELD2, CREM, CRH, CRHBP, CRHR1, CRHR2, CRIM1, CRIP1, CRIP2, CRIP3, CRIPT, CRISP1, CRISP2, CRISP3, CRISPLD1, CRISPLD2, CRK, CRKL, CRLF1, CRLF2, CRLF3, CRLS1, CRMP1, CRNKL1, CRNN, CROCC, CROCC2, CROT, CRP, CRTAC1, CRTAM, CRTAP, CRTC1, CRTC2, CRTC3, CRX, CRY1, CRY2, CRYAA, CRYAB, CRYBA1, CRYBA2, CRYBA4, CRYBB1, CRYBB2, CRYBB3, CRYBG1, CRYBG2, CRYBG3, CRYGA, CRYGB, CRYGC, CRYGD, CRYGN, CRYGS, CRYL1, CRYM, CRYZ, CRYZL1, CS, CSAD, CSAG1, CSAG2, CSAG3, CSDC2, CSDE1, CSE1L, CSF1, CSF1R, CSF2, CSF2RA, CSF2RB, CSF3, CSF3R, CSGALNACT1, CSGALNACT2, CSH1, CSH2, CSHL1, CSK, CSMD1, CSMD2, CSMD3, CSN1S1, CSN2, CSN3, CSNK1A1, CSNK1A1L, CSNK1D, CSNK1E, CSNK1G1, CSNK1G2, CSNK1G3, CSNK2A1, CSNK2A2, CSNK2A3, CSNK2B, CSPG4, CSPG5, CSPP1, CSRNP1, CSRNP2, CSRNP3, CSRP1, CSRP2, CSRP3, CST1, CST11, CST2, CST3, CST4, CST5, CST6, CST7, CST8, CST9, CST9L, CSTA, CSTB, CSTF1, CSTF2, CSTF2T, CSTF3, CSTL1, CT45A1, CT45A10, CT45A2, CT45A3, CT45A5, CT45A6, CT45A7, CT45A8, CT45A9, CT476828.1, CT476828.10, CT476828.11, CT476828.12, CT476828.13, CT476828.14, CT476828.15, CT476828.16, CT476828.17, CT476828.18, CT476828.19, CT476828.2, CT476828.20, CT476828.21, CT476828.22, CT476828.3, CT476828.4, CT476828.5, CT476828.6, CT476828.7, CT476828.8, CT476828.9, CT47A1, CT47A10, CT47A11, CT47A12, CT47A2, CT47A3, CT47A4, CT47A5, CT47A6, CT47A7, CT47A8, CT47A9, CT47B1, CT55, CT62, CT83, CTAG1A, CTAG1B, CTAG2, CTAGE1, CTAGE15, CTAGE4, CTAGE5, CTAGE6, CTAGE8, CTAGE9, CTBP1, CTBP2, CTBS, CTC1, CTCF, CTCFL, CTDNEP1, CTDP1, CTDSP1, CTDSP2, CTDSPL, CTDSPL2, CTF1, CTGF, CTH, CTHRC1, CTIF, CTLA4, CTNNA1, CTNNA2, CTNNA3, CTNNAL1, CTNNB1, CTNNBIP1, CTNNBL1, CTNND1, CTNND2, CTNS, CTPS1, CTPS2, CTR9, CTRB1, CTRB2, CTRC, CTRL, CTSA, CTSB, CTSC, CTSD, CTSE, CTSF, CTSG, CTSH, CTSK, CTSL, CTSO, CTSS, CTSV, CTSW, CTSZ, CTTN, CTTNBP2, CTTNBP2NL, CTU1, CTU2, CTXN1, CTXN2, CTXN3, CTXND1, CU464060.1, CU633846.1, CU633980.1, CU633980.2, CU639417.1, CU639417.2, CUBN, CUEDC1, CUEDC2, CUL1, CUL2, CUL3, CUL4A, CUL4B, CUL5, CUL7, CUL9, CUTA, CUTC, CUX1, CUX2, CUZD1, CWC15, CWC22, CWC25, CWC27, CWF19L1, CWF19L2, CWH43, CX3CL1, CX3CR1, CXADR, CXCL1, CXCL10, CXCL11, CXCL12, CXCL13, CXCL14, CXCL16, CXCL17, CXCL2, CXCL3, CXCL5, CXCL6, CXCL8, CXCL9, CXCR1, CXCR2, CXCR3, CXCR4, CXCR5, CXCR6, CXorf21, CXorf36, CXorf38, CXorf40A, CXorf40B, CXorf49, CXorf49B, CXorf51A, CXorf51B, CXorf56, CXorf57, CXorf58, CXorf65, CXorf66, CXorf67, CXXC1, CXXC4, CXXC5, CYB561, CYB561A3, CYB561D1, CYB561D2, CYB5A, CYB5B, CYB5D1, CYB5D2, CYB5R1, CYB5R2, CYB5R3, CYB5R4, CYB5RL, CYBA, CYBB, CYBRD1, CYC1, CYCS, CYFIP1, CYFIP2, CYGB, CYHR1, CYLC1, CYLC2, CYLD, CYP11A1, CYP11B1, CYP11B2, CYP17A1, CYP19A1, CYP1A1, CYP1A2, CYP1B1, CYP20A1, CYP21A2, CYP24A1, CYP26A1, CYP26B1, CYP26C1, CYP27A1, CYP27B1, CYP27C1, CYP2A13, CYP2A6, CYP2A7, CYP2B6, CYP2C18, CYP2C19, CYP2C8, CYP2C9, CYP2D6, CYP2D7, CYP2E1, CYP2F1, CYP2J2, CYP2R1, CYP2S1, CYP2U1, CYP2W1, CYP39A1, CYP3A4, CYP3A43, CYP3A5, CYP3A7, CYP3A7-CYP3A51P, CYP46A1, CYP4A11, CYP4A22, CYP4B1, CYP4F11, CYP4F12, CYP4F2, CYP4F22, CYP4F3, CYP4F8, CYP4V2, CYP4X1, CYP4Z1, CYP51A1, CYP7A1, CYP7B1, CYP8B1, CYR61, CYS1, CYSLTR1, CYSLTR2, CYSRT1, CYSTM1, CYTH1, CYTH2, CYTH3, CYTH4, CYTIP, CYTL1, CYYR1, D2HGDH, DAAM1, DAAM2, DAB1, DAB2, DAB2IP, DACH1, DACH2, DACT1, DACT2, DACT3, DAD1, DAG1, DAGLA, DAGLB, DALRD3, DAND5, DAO, DAOA, DAP, DAP3, DAPK1, DAPK2, DAPK3, DAPL1, DAPP1, DARS, DARS2, DAW1, DAXX, DAZ1, DAZ2, DAZ3, DAZ4, DAZAP1, DAZAP2, DAZL, DBF4, DBF4B, DBH, DBI, DBN1, DBNDD1, DBNDD2, DBNL, DBP, DBR1, DBT, DBX1, DBX2, DCAF1, DCAF10, DCAF11, DCAF12, DCAF12L1, DCAF12L2, DCAF13, DCAF15, DCAF16, DCAF17, DCAF4, DCAF4L1, DCAF4L2, DCAF5, DCAF6, DCAF7, DCAF8, DCAF8L1, DCAF8L2, DCAKD, DCANP1, DCBLD1, DCBLD2, DCC, DCD, DCDC1, DCDC2, DCDC2B, DCDC2C, DCHS1, DCHS2, DCK, DCLK1, DCLK2, DCLK3, DCLRE1A, DCLRE1B, DCLRE1C, DCN, DCP1A, DCP1B, DCP2, DCPS, DCST1, DCST2, DCSTAMP, DCT, DCTD, DCTN1, DCTN2, DCTN3, DCTN4, DCTN5, DCTN6, DCTPP1, DCUN1D1, DCUN1D2, DCUN1D3, DCUN1D4, DCUN1D5, DCX, DCXR, DDA1, DDAH1, DDAH2, DDB1, DDB2, DDC, DDHD1, DDHD2, DDI1, DDI2, DDIAS, DDIT3, DDIT4, DDIT4L, DDN, DDO, DDOST, DDR1, DDR2, DDRGK1, DDT, DDTL, DDX1, DDX10, DDX11, DDX17, DDX18, DDX19A, DDX19B, DDX20, DDX21, DDX23, DDX24, DDX25, DDX27, DDX28, DDX31, DDX39A, DDX39B, DDX3X, DDX3Y, DDX4, DDX41, DDX42, DDX43, DDX46, DDX47, DDX49, DDX5, DDX50, DDX51, DDX52, DDX53, DDX54, DDX55, DDX56, DDX58, DDX59, DDX6, DDX60, DDX60L, DEAF1, DEC 1, DECR1, DECR2, DEDD, DEDD2, DEF6, DEF8, DEFA1, DEFA1B, DEFA3, DEFA4, DEFA5, DEFA6, DEFB1, DEFB103A, DEFB103B, DEFB104A, DEFB104B, DEFB105A, DEFB105B, DEFB106A, DEFB106B, DEFB107A, DEFB107B, DEFB108B, DEFB110, DEFB112, DEFB113, DEFB114, DEFB115, DEFB116, DEFB118, DEFB119, DEFB121, DEFB123, DEFB124, DEFB125, DEFB126, DEFB127, DEFB128, DEFB129, DEFB130A, DEFB130B, DEFB131A, DEFB131B, DEFB132, DEFB133, DEFB134, DEFB135, DEFB136, DEFB4A, DEFB4B, DEGS1, DEGS2, DEK, DENND1A, DENND1B, DENND1C, DENND2A, DENND2C, DENND2D, DENND3, DENND4A, DENND4B, DENND4C, DENND5A, DENND5B, DENND6A, DENND6B, DENR, DEPDC1, DEPDC1B, DEPDC4, DEPDC5, DEPDC7, DEPTOR, DERA, DERL1, DERL2, DERL3, DES, DESI1, DESI2, DET1, DEUP1, DEXI, DFFA, DFFB, DFNA5, DFNB59, DGAT1, DGAT2, DGAT2L6, DGCR2, DGCR6, DGCR6L, DGCR8, DGKA, DGKB, DGKD, DGKE, DGKG, DGKH, DGKI, DGKK, DGKQ, DGKZ, DGUOK, DHCR24, DHCR7, DHDDS, DHDH, DHFR, DHFR2, DHH, DHODH, DHPS, DHRS1, DHRS11, DHRS12, DHRS13, DHRS2, DHRS3, DHRS4, DHRS4L2, DHRS7, DHRS7B, DHRS7C, DHRS9, DHRSX, DHTKD1, DHX15, DHX16, DHX29, DHX30, DHX32, DHX33, DHX34, DHX35, DHX36, DHX37, DHX38, DHX40, DHX57, DHX58, DHX8, DHX9, DIABLO, DIAPH1, DIAPH2, DIAPH3, DICER1, DIDO1, DIEXF, DIMT1, DIO1, DIO2, DIO3, DIP2A, DIP2B, DIP2C, DIRAS1, DIRAS2, DIRAS3, DIRC1, DIRC2, DIRC3, DIS3, DIS3L, DIS3L2, DISC1, DISP1, DISP2, DISP3, DIXDC1, DKC1, DKK1, DKK2, DKK3, DKK4, DKKL1, DLAT, DLC1, DLD, DLEC1, DLEU7, DLG1, DLG2, DLG3, DLG4, DLG5, DLGAP1, DLGAP2, DLGAP3, DLGAP4, DLGAP5, DLK1, DLK2, DLL1, DLL3, DLL4, DLST, DLX1, DLX2, DLX3, DLX4, DLX5, DLX6, DMAC1, DMAC2, DMAP1, DMBT1, DMBX1, DMC1, DMD, DMGDH, DMKN, DMP1, DMPK, DMRT1, DMRT2, DMRT3, DMRTA1, DMRTA2, DMRTB1, DMRTC1, DMRTC1B, DMRTC2, DMTF1, DMTN, DMWD, DMXL1, DMXL2, DNA2, DNAAF1, DNAAF2, DNAAF3, DNAAF4, DNAAF5, DNAH1, DNAH10, DNAH10OS, DNAH11, DNAH12, DNAH14, DNAH17, DNAH2, DNAH3, DNAH5, DNAH6, DNAH7, DNAH8, DNAH9, DNAI1, DNAI2, DNAJA1, DNAJA2, DNAJA3, DNAJA4, DNAJB1, DNAJB11, DNAJB12, DNAJB13, DNAJB14, DNAJB2, DNAJB4, DNAJB5, DNAJB6, DNAJB7, DNAJB8, DNAJB9, DNAJC1, DNAJC10, DNAJC11, DNAJC12, DNAJC13, DNAJC14, DNAJC15, DNAJC16, DNAJC17, DNAJC18, DNAJC19, DNAJC2, DNAJC21, DNAJC22, DNAJC24, DNAJC25, DNAJC25-GNG10, DNAJC27, DNAJC28, DNAJC3, DNAJC30, DNAJC4, DNAJC5, DNAJC5B, DNAJC5G, DNAJC6, DNAJC7, DNAJC8, DNAJC9, DNAL1, DNAL4, DNALI1, DNASE1, DNASE1L1, DNASE1L2, DNASE1L3, DNASE2, DNASE2B, DND1, DNER, DNHD1, DNLZ, DNM1, DNM1L, DNM2, DNM3, DNMBP, DNMT1, DNMT3A, DNMT3B, DNMT3L, DNPEP, DNPH1, DNTT, DNTTIP1, DNTTIP2, DOC2A, DOC2B, DOCK1, DOCK10, DOCK11, DOCK2, DOCK3, DOCK4, DOCK5, DOCK6, DOCK7, DOCK8, DOCK9, DOHH, DOK1, DOK2, DOK3, DOK4, DOK5, DOK6, DOK7, DOLK, DOLPP1, DONSON, DOPEY1, DOPEY2, DOT1L, DPAGT1, DPCD, DPCR1, DPEP1, DPEP2, DPEP3, DPF1, DPF2, DPF3, DPH1, DPH2, DPH3, DPH5, DPH6, DPH7, DPM1, DPM2, DPM3, DPP10, DPP3, DPP4, DPP6, DPP7, DPP8, DPP9, DPPA2, DPPA3, DPPA4, DPPA5, DPRX, DPT, DPY19L1, DPY19L2, DPY19L3, DPY19L4, DPY30, DPYD, DPYS, DPYSL2, DPYSL3, DPYSL4, DPYSL5, DQX1, DR1, DRAM1, DRAM2, DRAP1, DRAXIN, DRC1, DRC3, DRC7, DRD1, DRD2, DRD3, DRD4, DRD5, DRG1, DRG2, DRGX, DRICHI, DROSHA, DRP2, DSC1, DSC2, DSC3, DSCAM, DSCAML1, DSCC1, DSCR3, DSCR4, DSCR8, DSE, DSEL, DSG1, DSG2, DSG3, DSG4, DSN1, DSP, DSPP, DST, DSTN, DSTYK, DTD1, DTD2, DTHD1, DTL, DTNA, DTNB, DTNBP1, DTWD1, DTWD2, DTX1, DTX2, DTX3, DTX3L, DTX4, DTYMK, DUOX1, DUOX2, DUOXA1, DUOXA2, DUPD1, DUS1L, DUS2, DUS3L, DUS4L, DUSP1, DUSP10, DUSP11, DUSP12, DUSP13, DUSP14, DUSP15, DUSP16, DUSP18, DUSP19, DUSP2, DUSP21, DUSP22, DUSP23, DUSP26, DUSP27, DUSP28, DUSP3, DUSP4, DUSP5, DUSP6, DUSP7, DUSP8, DUSP9, DUT, DUX4, DUXA, DUXB, DVL1, DVL2, DVL3, DWORF, DXO, DYDC1, DYDC2, DYM, DYNAP, DYNC1H1, DYNC1I1, DYNC1I2, DYNC1LI1, DYNC1LI2, DYNC2H1, DYNC2LI1, DYNLL1, DYNLL2, DYNLRB1, DYNLRB2, DYNLT1, DYNLT3, DYRKIA, DYRKIB, DYRK2, DYRK3, DYRK4, DYSF, DYTN, DZANK1, DZIP1, DZIP1L, DZIP3, E2F1, E2F2, E2F3, E2F4, E2F5, E2F6, E2F7, E2F8, E4F1, EAF1, EAF2, EAPP, EARS2, EBAG9, EBF1, EBF2, EBF3, EBF4, EBI3, EBLN1, EBLN2, EBNA1BP2, EBP, EBPL, ECD, ECE1, ECE2, ECEL1, ECH1, ECHDC1, ECHDC2, ECHDC3, ECHS1, ECI1, ECI2, ECM1, ECM2, ECSCR, ECSIT, ECT2, ECT2L, EDA, EDA2R, EDAR, EDARADD, EDC3, EDC4, EDDM13, EDDM3A, EDDM3B, EDEM1, EDEM2, EDEM3, EDF1, EDIL3, EDN1, EDN2, EDN3, EDNRA, EDNRB, EDRF1, EEA1, EED, EEF1A1, EEF1A2, EEF1AKMT1, EEF1AKMT2, EEF1AKMT3, EEF1B2, EEF1D, EEF1E1, EEF1E1-BLOC1S5, EEF1G, EEF2, EEF2K, EEF2KMT, EEFSEC, EEPD1, EFCAB1, EFCAB10, EFCAB11, EFCAB12, EFCAB13, EFCAB14, EFCAB2, EFCAB3, EFCAB5, EFCAB6, EFCAB7, EFCAB8, EFCAB9, EFCC1, EFEMP1, EFEMP2, EFHB, EFHC1, EFHC2, EFHD1, EFHD2, EFL1, EFNA1, EFNA2, EFNA3, EFNA4, EFNA5, EFNB1, EFNB2, EFNB3, EFR3A, EFR3B, EFS, EFTUD2, EGF, EGFL6, EGFL7, EGFL8, EGFLAM, EGFR, EGLN1, EGLN2, EGLN3, EGR1, EGR2, EGR3, EGR4, EHBP1, EHBP1L1, EHD1, EHD2, EHD3, EHD4, EHF, EHHADH, EHMT1, EHMT2, E124, EID1, EID2, EID2B, EID3, EIF1, EIF1AD, EIF1AX, EIF1AY, EIF1B, EIF2A, EIF2AK1, EIF2AK2, EIF2AK3, EIF2AK4, EIF2B1, EIF2B2, EIF2B3, EIF2B4, EIF2B5, EIF2D, EIF2S1, EIF2S2, EIF2S3, EIF3A, EIF3B, EIF3C, EIF3CL, EIF3D, EIF3E, EIF3F, EIF3G, EIF3H, EIF3I, EIF3J, EIF3K, EIF3L, EIF3M, EIF4A1, EIF4A2, EIF4A3, EIF4B, EIF4E, EIF4E1B, EIF4E2, EIF4E3, EIF4EBP1, EIF4EBP2, EIF4EBP3, EIF4ENIF1, EIF4G1, EIF4G2, EIF4G3, EIF4H, EIF5, EIF5A, EIF5A2, EIF5AL1, EIF5B, EIF6, EIPR1, ELAC1, ELAC2, ELANE, ELAVL1, ELAVL2, ELAVL3, ELAVL4, ELF1, ELF2, ELF3, ELF4, ELF5, ELFN1, ELFN2, ELK1, ELK3, ELK4, ELL, ELL2, ELL3, ELMO1, ELMO2, ELMO3, ELMOD1, ELMOD2, ELMOD3, ELMSAN1, ELN, ELOA, ELOA2, ELOA3, ELOA3B, ELOA3C, ELOA3D, ELOB, ELOC, ELOF1, ELOVL1, ELOVL2, ELOVL3, ELOVL4, ELOVL5, ELOVL6, ELOVL7, ELP1, ELP2, ELP3, ELP4, ELP5, ELP6, ELSPBP1, EMB, EMC1, EMC10, EMC2, EMC3, EMC4, EMC6, EMC7, EMC8, EMC9, EMCN, EMD, EME1, EME2, EMG1, EMID1, EMILIN1, EMILIN2, EMILIN3, EML1, EML2, EML3, EML4, EML5, EML6, EMP1, EMP2, EMP3, EMSY, EMX1, EMX2, EN1, EN2, ENAH, ENAM, ENC1, ENDOD1, ENDOG, ENDOU, ENDOV, ENG, ENGASE, ENHO, ENKD1, ENKUR, ENO1, ENO2, ENO3, ENO4, ENOPH1, ENOSF1, ENOX1, ENOX2, ENPEP, ENPP1, ENPP2, ENPP3, ENPP4, ENPP5, ENPP6, ENPP7, ENSA, ENTHDI, ENTPD1, ENTPD2, ENTPD3, ENTPD4, ENTPD5, ENTPD6, ENTPD7, ENTPD8, ENY2, EOGT, EOMES, EP300, EP400, EPAS1, EPB41, EPB41L1, EPB41L2, EPB41L3, EPB41L4A, EPB41L4B, EPB41L5, EPB42, EPC1, EPC2, EPCAM, EPDR1, EPG5, EPGN, EPHA1, EPHA10, EPHA2, EPHA3, EPHA4, EPHA5, EPHA6, EPHA7, EPHA8, EPHB1, EPHB2, EPHB3, EPHB4, EPHB6, EPHX1, EPHX2, EPHX3, EPHX4, EPM2A, EPM2AIP1, EPN1, EPN2, EPN3, EPO, EPOP, EPOR, EPPIN, EPPIN-WFDC6, EPPK1, EPRS, EPS15, EPS15L1, EPS8, EPS8L1, EPS8L2, EPS8L3, EPSTII, EPX, EPYC, EQTN, ERAL1, ERAP1, ERAP2, ERAS, ERBB2, ERBB3, ERBB4, ERBIN, ERC1, ERC2, ERCC1, ERCC2, ERCC3, ERCC4, ERCC5, ERCC6, ERCC6L, ERCC6L2, ERCC8, EREG, ERF, ERFE, ERG, ERG28, ERGICI, ERGIC2, ERGIC3, ERH, ERI1, ERI2, ERI3, ERICH1, ERICH2, ERICH3, ERICH4, ERICH5, ERICH6, ERICH6B, ERLEC1, ERLIN1, ERLIN2, ERMAP, ERMARD, ERMN, ERMP1, ERN1, ERN2, ERO1A, ERO1B, ERP27, ERP29, ERP44, ERRFI1, ERV3-1, ERVFRD-1, ERVMER34-1, ERVV-1, ERVV-2, ERVW-1, ESAM, ESCO1, ESCO2, ESD, ESF1, ESM1, ESPL1, ESPN, ESPNL, ESR1, ESR2, ESRP1, ESRP2, ESRRA, ESRRB, ESRRG, ESS2, ESX1, ESYT1, ESYT2, ESYT3, ETAA1, ETDA, ETDB, ETDC, ETF1, ETFA, ETFB, ETFBKMT, ETFDH, ETFRF1, ETHEI, ETNK1, ETNK2, ETNPPL, ETS1, ETS2, ETV1, ETV2, ETV3, ETV3L, ETV4, ETV5, ETV6, ETV7, EVA1A, EVA1B, EVA1C, EVC, EVC2, EVI2A, EVI2B, EVI5, EVI5L, EVL, EVPL, EVPLL, EVX1, EVX2, EWSR1, EXD1, EXD2, EXD3, EXO1, EX05, EXOC1, EXOCIL, EXOC2, EXOC3, EXOC3L1, EXOC3L2, EXOC3L4, EXOC4, EXOC5, EXOC6, EXOC6B, EXOC7, EXOC8, EXOG, EXOSCI, EXOSC10, EXOSC2, EXOSC3, EXOSC4, EXOSC5, EXOSC6, EXOSC7, EXOSC8, EXOSC9, EXPH5, EXT1, EXT2, EXTL1, EXTL2, EXTL3, EYA1, EYA2, EYA3, EYA4, EYS, EZH1, EZH2, EZR, F10, F11, F11R, F12, F13A1, F13B, F2, F2R, F2RL1, F2RL2, F2RL3, F3, F5, F7, F8, F8A1, F8A2, F8A3, F9, FA2H, FAAH, FAAH2, FAAP100, FAAP20, FAAP24, FABP1, FABP12, FABP2, FABP3, FABP4, FABP5, FABP6, FABP7, FABP9, FADD, FADS1, FADS2, FADS3, FADS6, FAF1, FAF2, FAH, FAHD1, FAHD2A, FAHD2B, FAIM, FAIM2, FAM102A, FAM102B, FAM103A1, FAM104A, FAM104B, FAM105A, FAM106A, FAM107A, FAM107B, FAM109A, FAM109B, FAM110A, FAM110B, FAM110C, FAM110D, FAM111A, FAM111B, FAM114A1, FAM114A2, FAM117A, FAM117B, FAM118A, FAM118B, FAM120A, FAM120AOS, FAM120B, FAM120C, FAM122A, FAM122B, FAM122C, FAM124A, FAM124B, FAM126A, FAM126B, FAM129A, FAM129B, FAM129C, FAM131A, FAM131B, FAM131C, FAM133A, FAM133B, FAM135A, FAM135B, FAM136A, FAM13A, FAM13B, FAM13C, FAM149A, FAM149B1, FAM151A, FAM151B, FAM153A, FAM153B, FAM153C, FAM155A, FAM155B, FAM156A, FAM156B, FAM159A, FAM159B, FAM160A1, FAM160A2, FAM160B1, FAM160B2, FAM161A, FAM161B, FAM162A, FAM162B, FAM163A, FAM163B, FAM166A, FAM166B, FAM167A, FAM167B, FAM168A, FAM168B, FAM169A, FAM169B, FAM170A, FAM170B, FAM171A1, FAM171A2, FAM171B, FAM172A, FAM173A, FAM173B, FAM174A, FAM174B, FAM177A1, FAM177B, FAM178B, FAM180A, FAM180B, FAM181A, FAM181B, FAM182B, FAM183A, FAM184A, FAM184B, FAM185A, FAM186A, FAM186B, FAM187A, FAM187B, FAM189A1, FAM189A2, FAM189B, FAM192A, FAM193A, FAM193B, FAM196A, FAM196B, FAM198A, FAM198B, FAM199X, FAM19A1, FAM19A2, FAM19A3, FAM19A4, FAM19A5, FAM200A, FAM200B, FAM204A, FAM205A, FAM205C, FAM206A, FAM207A, FAM208A, FAM208B, FAM209A, FAM209B, FAM20A, FAM20B, FAM20C, FAM210A, FAM210B, FAM212A, FAM212B, FAM213A, FAM213B, FAM214A, FAM214B, FAM216A, FAM216B, FAM217A, FAM217B, FAM218A, FAM219A, FAM219B, FAM220A, FAM221A, FAM221B, FAM222A, FAM222B, FAM227A, FAM227B, FAM228A, FAM228B, FAM229A, FAM229B, FAM230A, FAM231A, FAM231B, FAM231C, FAM231D, FAM234A, FAM234B, FAM236A, FAM236B, FAM236C, FAM236D, FAM237A, FAM237B, FAM240A, FAM240B, FAM24A, FAM24B, FAM25A, FAM25C, FAM25G, FAM26D, FAM26E, FAM26F, FAM32A, FAM35A, FAM3A, FAM3B, FAM3C, FAM3D, FAM43A, FAM43B, FAM45A, FAM46A, FAM46B, FAM46C, FAM46D, FAM47A, FAM47B, FAM47C, FAM47E, FAM47E-STBD1, FAM49A, FAM49B, FAM50A, FAM50B, FAM53A, FAM53B, FAM53C, FAM57A, FAM57B, FAM58A, FAM60A, FAM69A, FAM69B, FAM69C, FAM71A, FAM71B, FAM71C, FAM71D, FAM71E1, FAM71E2, FAM71F1, FAM71F2, FAM72A, FAM72B, FAM72C, FAM72D, FAM76A, FAM76B, FAM78A, FAM78B, FAM81A, FAM81B, FAM83A, FAM83B, FAM83C, FAM83D, FAM83E, FAM83F, FAM83G, FAM83H, FAM84A, FAM84B, FAM86B1, FAM86B2, FAM86C1, FAM89A, FAM89B, FAM8A1, FAM90A1, FAM90A26, FAM91A1, FAM92A, FAM92B, FAM95C, FAM96A, FAM96B, FAM98A, FAM98B, FAM98C, FAM9A, FAM9B, FAM9C, FAN1, FANCA, FANCB, FANCC, FANCD2, FANCD2OS, FANCE, FANCF, FANCG, FANCI, FANCL, FANCM, FANK1, FAP, FAR1, FAR2, FARP1, FARP2, FARS2, FARSA, FARSB, FAS, FASLG, FASN, FASTK, FASTKD1, FASTKD2, FASTKD3, FASTKD5, FAT1, FAT2, FAT3, FAT4, FATE1, FAU, FAXC, FAXDC2, FBF1, FBL, FBLIM1, FBLL1, FBLN1, FBLN2, FBLN5, FBLN7, FBN1, FBN2, FBN3, FBP1, FBP2, FBRS, FBRSL1, FBXL12, FBXL13, FBXL14, FBXL15, FBXL16, FBXL17, FBXL18, FBXL19, FBXL20, FBXL2, FBXL22, FBXL3, FBXL4, FBXL5, FBXL6, FBXL7, FBXL8, FBXO10, FBXO11, FBXO15, FBXO16, FBXO17, FBXO18, FBXO2, FBXO21, FBXO22, FBXO24, FBXO25, FBXO27, FBXO28, FBXO3, FBXO30, FBXO31, FBXO32, FBXO33, FBXO34, FBXO36, FBXO38, FBXO39, FBXO4, FBXO40, FBXO41, FBXO42, FBXO43, FBXO44, FBXO45, FBXO46, FBXO47, FBXO48, FBXO5, FBXO6, FBXO7, FBXO8, FBXO9, FBXW10, FBXW11, FBXW12, FBXW2, FBXW4, FBXW5, FBXW7, FBXW8, FBXW9, FCAMR, FCAR, FCER1A, FCER1G, FCER2, FCF1, FCGBP, FCGR1A, FCGR1B, FCGR2A, FCGR2B, FCGR2C, FCGR3A, FCGR3B, FCGRT, FCHO1, FCHO2, FCHSD1, FCHSD2, FCMR, FCN1, FCN2, FCN3, FCRL1, FCRL2, FCRL3, FCRL4, FCRL5, FCRL6, FCRLA, FCRLB, FDCSP, FDFT1, FDPS, FDX1, FDX2, FDXACB1, FDXR, FECH, FEM1A, FEM1B, FEM1C, FEN1, FER, FER1L5, FER1L6, FERD3L, FERMT1, FERMT2, FERMT3, FES, FETUB, FEV, FEZ1, FEZ2, FEZF1, FEZF2, FFAR1, FFAR2, FFAR3, FGA, FGB, FGD1, FGD2, FGD3, FGD4, FGD5, FGD6, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFBP1, FGFBP2, FGFBP3, FGFR1, FGFR1OP, FGFR1OP2, FGFR2, FGFR3, FGFR4, FGFRL1, FGG, FGGY, FGL1, FGL2, FGR, FH, FHAD1, FHDC1, FHIT, FHL1, FHL2, FHL3, FHL5, FHOD1, FHOD3, FIBCD1, FIBIN, FIBP, FICD, FIG4, FIGLA, FIGN, FIGNL1, FIGNL2, FILTP1, FILIP1L, FIP1L1, FIS1, FITM1, FITM2, FIZ1, FJX1, FKBP10, FKBP11, FKBP14, FKBP15, FKBP1A, FKBP1B, FKBP1C, FKBP2, FKBP3, FKBP4, FKBP5, FKBP6, FKBP7, FKBP8, FKBP9, FKBPL, FKRP, FKTN, FLAD1, FLCN, FLG, FLG2, FLI1, FLII, FLNA, FLNB, FLNC, FLOT1, FLOT2, FLRT1, FLRT2, FLRT3, FLT1, FLT3, FLT3LG, FLT4, FLVCR1, FLVCR2, FLYWCH1, FLYWCH2, FMC1, FMN1, FMN2, FMNL1, FMNL2, FMNL3, FMO1, FMO2, FMO3, FMO4, FMO5, FMOD, FMR1, FMR1NB, FN1, FN3K, FN3KRP, FNBP1, FNBP1L, FNBP4, FNDC1, FNDC10, FNDC11, FNDC3A, FNDC3B, FNDC4, FNDC5, FNDC7, FNDC8, FNDC9, FNIP1, FNIP2, FNTA, FNTB, F0681492.1, F0681542.1, FOCAD, FOLH1, FOLR1, FOLR2, FOLR3, FOPNL, FOS, FOSB, FOSL1, FOSL2, FOXA1, FOXA2, FOXA3, FOXB1, FOXB2, FOXC1, FOXC2, FOXD1, FOXD2, FOXD3, FOXD4, FOXD4L1, FOXD4L3, FOXD4L4, FOXD4L5, FOXD4L6, FOXE1, FOXE3, FOXF1, FOXF2, FOXG1, FOXH1, FOXI1, FOXI2, FOXI3, FOXJ1, FOXJ2, FOXJ3, FOXK1, FOXK2, FOXL1, FOXL2, FOXL2NB, FOXM1, FOXN1, FOXN2, FOXN3, FOXN4, FOXO1, FOXO3, FOXO4, FOXO6, FOXP1, FOXP2, FOXP3, FOXP4, FOXQ1, FOXR1, FOXR2, FOXRED1, FOXRED2, FOXS1, FP236240.1, FP565260.1, FP565260.2, FP565260.3, FP565260.4, FP565260.6, FP565260.7, FP565324.1, FP565324.2, FPGS, FPGT, FPGT-TNNI3K, FPR1, FPR2, FPR3, FRA1OAC1, FRAS1, FRAT1, FRAT2, FREM1, FREM2, FREM3, FRG1, FRG2, FRG2B, FRG2C, FRK, FRMD1, FRMD3, FRMD4A, FRMD4B, FRMD5, FRMD6, FRMD7, FRMD8, FRMPD1, FRMPD2, FRMPD3, FRMPD4, FRRS1, FRRS1L, FRS2, FRS3, FRY, FRYL, FRZB, FSBP, FSCB, FSCN1, FSCN2, FSCN3, FSD1, FSD1L, FSD2, FSHB, FSHR, FSIP1, FSIP2, FST, FSTL1, FSTL3, FSTL4, FSTL5, FTCD, FTCDNL1, FTH1, FTHL17, FTL, FTMT, FTO, FTSJ1, FTSJ3, FUBP1, FUBP3, FUCA1, FUCA2, FUK, FUNDC1, FUNDC2, FUOM, FURIN, FUS, FUT1, FUT10, FUT11, FUT2, FUT3, FUT4, FUT5, FUT6, FUT7, FUT8, FUT9, FUZ, FXN, FXR1, FXR2, FXYD1, FXYD2, FXYD3, FXYD4, FXYD5, FXYD6, FXYD6-FXYD2, FXYD7, FYB1, FYB2, FYCO1, FYN, FYTTD1, FZD1, FZD10, FZD2, FZD3, FZD4, FZD5, FZD6, FZD7, FZD8, FZD9, FZR1, GOS2, G2E3, G3BP1, G3BP2, G6PC, G6PC2, G6PC3, G6PD, GAA, GAB1, GAB2, GAB3, GAB4, GABARAP, GABARAPL1, GABARAPL2, GABBR1, GABBR2, GABPA, GABPB1, GABPB2, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, GAD1, GAD2, GADD45A, GADD45B, GADD45G, GADD45GIP1, GADL1, GAGE1, GAGE10, GAGE12B, GAGE12C, GAGE12D, GAGE12E, GAGE12F, GAGE12G, GAGE12H, GAGE12J, GAGE13, GAGE2A, GAGE2E, GAK, GAL, GAL3ST1, GAL3ST2, GAL3ST3, GAL3ST4, GALC, GALE, GALK1, GALK2, GALM, GALNS, GALNT1, GALNT10, GALNT11, GALNT12, GALNT13, GALNT14, GALNT15, GALNT16, GALNT17, GALNT18, GALNT2, GALNT3, GALNT4, GALNT5, GALNT6, GALNT7, GALNT8, GALNT9, GALNTL5, GALNTL6, GALP, GALR1, GALR2, GALR3, GALT, GAMT, GAN, GANAB, GANC, GAP43, GAPDH, GAPDHS, GAPT, GAPVD1, GAR1, GAREMI, GAREM2, GARNL3, GARS, GART, GAS1, GAS2, GAS2L1, GAS2L2, GAS2L3, GAS6, GAS7, GAS8, GAST, GATA1, GATA2, GATA3, GATA4, GATA5, GATA6, GATAD1, GATAD2A, GATAD2B, GATB, GATC, GATD1, GATM, GATS, GBA, GBA2, GBA3, GBE1, GBF1, GBGT1, GBP1, GBP2, GBP3, GBP4, GBP5, GBP6, GBP7, GBX1, GBX2, GC, GCA, GCAT, GCC1, GCC2, GCDH, GCFC2, GCG, GCGR, GCH1, GCHFR, GCK, GCKR, GCLC, GCLM, GCM1, GCM2, GCN1, GCNA, GCNT1, GCNT2, GCNT3, GCNT4, GCNT7, GCOM1, GCSAM, GCSAML, GCSH, GDA, GDAP1, GDAP1L1, GDAP2, GDE1, GDF1, GDF10, GDF11, GDF15, GDF2, GDF3, GDF5, GDF5OS, GDF6, GDF7, GDF9, GDI1, GDI2, GDNF, GDPD1, GDPD2, GDPD3, GDPD4, GDPD5, GDPGP1, GEM, GEMIN2, GEMIN4, GEMIN5, GEMIN6, GEMIN7, GEMIN8, GEN1, GET4, GFAP, GFER, GFI1, GFI1B, GFM1, GFM2, GFOD1, GFOD2, GFPT1, GFPT2, GFRA1, GFRA2, GFRA3, GFRA4, GFRAL, GFY, GGA1, GGA2, GGA3, GGACT, GGCT, GGCX, GGH, GGN, GGNBP2, GGPS1, GGT1, GGT2, GGT5, GGT6, GGT7, GGTLC1, GGTLC2, GGTLC3, GH1, GH2, GHDC, GHITM, GHR, GHRH, GHRHR, GHRL, GHSR, GID4, GID8, GIF, GIGYF1, GIGYF2, GIMAP1, GIMAP1-GIMAP5, GIMAP2, GIMAP4, GIMAP5, GIMAP6, GIMAP7, GIMAP8, GIMDI1, GIN1, GINM1, GINS1, GINS2, GINS3, GINS4, GIP, GIPC1, GIPC2, GIPC3, GIPR, GIT1, GIT2, GJA1, GJA10, GJA3, GJA4, GJA5, GJA8, GJA9, GJB1, GJB2, GJB3, GJB4, GJB5, GJB6, GJB7, GJC1, GJC2, GJC3, GJD2, GJD3, GJD4, GJE1, GK, GK2, GK3P, GK5, GKAP1, GKN1, GKN2, GLA, GLB1, GLB1L, GLB1L2, GLB1L3, GLCCI1, GLCE, GLDC, GLDN, GLE1, GLG1, GLI1, GLI2, GLI3, GLI4, GLIPR1, GLIPR1L1, GLIPR1L2, GLIPR2, GLIS1, GLIS2, GLIS3, GLMN, GLMP, GLO1, GLOD4, GLOD5, GLP1R, GLP2R, GLRA1, GLRA2, GLRA3, GLRA4, GLRB, GLRX, GLRX2, GLRX3, GLRX5, GLS, GLS2, GLT1D1, GLT6D1, GLT8D1, GLT8D2, GLTP, GLTPD2, GLUD1, GLUD2, GLUL, GLYAT, GLYATL1, GLYATL1P3, GLYATL2, GLYATL3, GLYCTK, GLYR1, GM2A, GMCL1, GMDS, GMEB1, GMEB2, GMFB, GMFG, GMIP, GML, GMNC, GMNN, GMPPA, GMPPB, GMPR, GMPR2, GMPS, GNA11, GNA12, GNA13, GNA14, GNA15, GNAI1, GNAI2, GNAI3, GNAL, GNAO1, GNAQ, GNAS, GNAT1, GNAT2, GNAT3, GNAZ, GNB1, GNB1L, GNB2, GNB3, GNB4, GNB5, GNE, GNG10, GNG11, GNG12, GNG13, GNG14, GNG2, GNG3, GNG4, GNG5, GNG7, GNG8, GNGT1, GNGT2, GNL1, GNL2, GNL3, GNL3L, GNLY, GNMT, GNPAT, GNPDA1, GNPDA2, GNPNAT1, GNPTAB, GNPTG, GNRH1, GNRH2, GNRHR, GNS, GOLGA1, GOLGA2, GOLGA3, GOLGA4, GOLGA5, GOLGA6A, GOLGA6B, GOLGA6C, GOLGA6D, GOLGA6L1, GOLGA6L10, GOLGA6L2, GOLGA6L22, GOLGA6L4, GOLGA6L6, GOLGA6L7P, GOLGA6L9, GOLGA7, GOLGA7B, GOLGA8A, GOLGA8B, GOLGA8F, GOLGA8G, GOLGA8H, GOLGA8J, GOLGA8K, GOLGA8M, GOLGA8N, GOLGA8O, GOLGA8Q, GOLGA8R, GOLGA8S, GOLGA8T, GOLGB1, GOLIM4, GOLM1, GOLPH3, GOLPH3L, GOLT1A, GOLT1B, GON4L, GON7, GOPC, GORAB, GORASP1, GORASP2, GOSR1, GOSR2, GOT1, GOT1L1, GOT2, GP1BA, GP1BB, GP2, GP5, GP6, GP9, GPA33, GPAA1, GPALPP1, GPAM, GPANK1, GPAT2, GPAT3, GPAT4, GPATCH1, GPATCH11, GPATCH2, GPATCH2L, GPATCH3, GPATCH4, GPATCH8, GPBAR1, GPBP1, GPBP1L1, GPC1, GPC2, GPC3, GPC4, GPC5, GPC6, GPCPD1, GPD1, GPD1L, GPD2, GPER1, GPHA2, GPHB5, GPHN, GPI, GPIBP1, GPKOW, GPLD1, GPM6A, GPM6B, GPN1, GPN2, GPN3, GPNMB, GPR1, GPR101, GPR107, GPR108, GPR119, GPR12, GPR132, GPR135, GPR137, GPR137B, GPR137C, GPR139, GPR141, GPR142, GPR143, GPR146, GPR148, GPR149, GPR15, GPR150, GPR151, GPR152, GPR153, GPR155, GPR156, GPR157, GPR158, GPR160, GPR161, GPR162, GPR17, GPR171, GPR173, GPR174, GPR176, GPR179, GPR18, GPR180, GPR182, GPR183, GPR19, GPR20, GPR21, GPR22, GPR25, GPR26, GPR27, GPR3, GPR31, GPR32, GPR33, GPR34, GPR35, GPR37, GPR37L1, GPR39, GPR4, GPR42, GPR45, GPR50, GPR52, GPR55, GPR6, GPR61, GPR62, GPR63, GPR65, GPR68, GPR75, GPR75-ASB3, GPR78, GPR82, GPR83, GPR84, GPR85, GPR87, GPR88, GPR89A, GPR89B, GPRASP1, GPRASP2, GPRC5A, GPRC5B, GPRC5C, GPRC5D, GPRC6A, GPRIN1, GPRIN2, GPRIN3, GPS1, GPS2, GPSM1, GPSM2, GPSM3, GPT, GPT2, GPX1, GPX2, GPX3, GPX4, GPX5, GPX6, GPX7, GPX8, GRAMD1A, GRAMD1B, GRAMD1C, GRAMD2A, GRAMD2B, GRAMD4, GRAP, GRAP2, GRAPL, GRASP, GRB10, GRB14, GRB2, GRB7, GREB1, GREB1L, GREM1, GREM2, GRHL1, GRHL2, GRHL3, GRHPR, GRIA1, GRIA2, GRIA3, GRIA4, GRID1, GRID2, GRID2IP, GRIFIN, GRIK1, GRIK2, GRIK3, GRIK4, GRIK5, GRIN1, GRIN2A, GRIN2B, GRIN2C, GRIN2D, GRIN3A, GRIN3B, GRINA, GRIP1, GRIP2, GRIPAP1, GRK1, GRK2, GRK3, GRK4, GRK5, GRK6, GRK7, GRM1, GRM2, GRM3, GRM4, GRM5, GRM6, GRM7, GRM8, GRN, GRP, GRPEL1, GRPEL2, GRPR, GRSF1, GRTP1, GRWD1, GRXCR1, GRXCR2, GSAP, GSC, GSC2, GSDMA, GSDMB, GSDMC, GSDMD, GSE1, GSG1, GSG1L, GSG1L2, GSK3A, GSK3B, GSKIP, GSN, GSPT1, GSPT2, GSR, GSS, GSTA1, GSTA2, GSTA3, GSTA4, GSTA5, GSTCD, GSTK1, GSTM1, GSTM2, GSTM3, GSTM4, GSTM5, GSTO1, GSTO2, GSTP1, GSTT1, GSTT2, GSTT2B, GSTTP1, GSTZ1, GSX1, GSX2, GTDC1, GTF2A1, GTF2A1L, GTF2A2, GTF2B, GTF2E1, GTF2E2, GTF2F1, GTF2F2, GTF2H1, GTF2H2, GTF2H2C, GTF2H2C_2, GTF2H3, GTF2H4, GTF2H5, GTF2I, GTF2IRD1, GTF2IRD2, GTF2IRD2B, GTF3A, GTF3C1, GTF3C2, GTF3C3, GTF3C4, GTF3C5, GTF3C6, GTPBP1, GTPBP10, GTPBP2, GTPBP3, GTPBP4, GTPBP6, GTPBP8, GTSE1, GTSF1, GTSF1L, GU182339.1, GU182339.3, GU182343.1, GU182343.2, GU182345.1, GU182345.2, GU182347.1, GU182351.2, GU182352.2, GU182353.1, GU182355.1, GU182355.2, GU182355.3, GU182357.1, GU182357.3, GU182359.1, GU182359.2, GUCA1A, GUCA1B, GUCA1C, GUCA2A, GUCA2B, GUCD1, GUCY1A2, GUCY1A3, GUCY1B3, GUCY2C, GUCY2D, GUCY2F, GUF1, GUK1, GULP1, GUSB, GVQW2, GXYLT1, GXYLT2, GYG1, GYG2, GYPA, GYPB, GYPC, GYPE, GYS1, GYS2, GZF1, GZMA, GZMB, GZMH, GZMK, GZMM, H1FO, H1FNT, H1FOO, H1FX, H2AFB1, H2AFB2, H2AFB3, H2AFJ, H2AFV, H2AFX, H2AFY, H2AFY2, H2AFZ, H2BFM, H2BFS, H2BFWT, H3F3A, H3F3B, H3F3C, H6PD, HAAO, HABP2, HABP4, HACD1, HACD2, HACD3, HACD4, HACE1, HACL1, HADH, HADHA, HADHB, HAGH, HAGHL, HAL, HAMP, HAND1, HAND2, HAO1, HAO2, HAP1, HAPLN1, HAPLN2, HAPLN3, HAPLN4, HARBI1, HARS, HARS2, HAS1, HAS2, HAS3, HASPIN, HAT1, HAUS1, HAUS2, HAUS3, HAUS4, HAUS5, HAUS6, HAUS7, HAUS8, HAVCR1, HAVCR2, HAX1, HBA1, HBA2, HBB, HBD, HBE1, HBEGF, HBG1, HBG2, HBM, HBP1, HBQ1, HBS1L, HBZ, HCAR1, HCAR2, HCAR3, HCCS, HCFC1, HCFC1R1, HCFC2, HCK, HCLS1, HCN1, HCN2, HCN3, HCN4, HCRT, HCRTR1, HCRTR2, HCST, HDAC1, HDAC10, HDAC11, HDAC2, HDAC3, HDAC4, HDAC5, HDAC6, HDAC7, HDAC8, HDAC9, HDC, HDDC2, HDDC3, HDGF, HDGFL1, HDGFL2, HDGFL3, HDHD2, HDHD3, HDHD5, HDLBP, HDX, HEATR1, HEATR3, HEATR4, HEATR5A, HEATR5B, HEATR6, HEATR9, HEBP1, HEBP2, HECA, HECTD1, HECTD2, HECTD3, HECTD4, HECW1, HECW2, HEG1, HELB, HELLS, HELQ, HELT, HELZ, HELZ2, HEMGN, HEMK1, HENMT1, HEPACAM, HEPACAM2, HEPH, HEPHL1, HEPN1, HERC1, HERC2, HERC3, HERC4, HERC5, HERC6, HERPUDI, HERPUD2, HES1, HES2, HES3, HES4, HES5, HES6, HES7, HESX1, HEXA, HEXB, HEXDC, HEXIM1, HEXIM2, HEY1, HEY2, HEYL, HFE, HFE2, HFM1, HGD, HGF, HGFAC, HGH1, HGNC:18790, HGNC:24955, HGS, HGSNAT, HHAT, HHATL, HHEX, HHIP, HHIPL1, HHIPL2, HHLA1, HHLA2, HHLA3, HIBADH, HIBCH, HIC1, HIC2, HID1, HIF1A, HIF1AN, HIF3A, HIGD1A, HIGD1B, HIGD1C, HIGD2A, HIGD2B, HIKESHI, HILPDA, HINFP, HINT1, HINT2, HINT3, HIP1, HIP1R, HIPK1, HIPK2, HIPK3, HIPK4, HIRA, HIRIP3, HISTIHIA, HISTIHIB, HISTIHIC, HISTIHID, HISTIHIE, HISTIHIT, HIST1H2AA, HIST1H2AB, HIST1H2AC, HIST1H2AD, HIST1H2AE, HIST1H2AG, HIST1H2AH, HIST1H2AI, HIST1H2AJ, HIST1H2AK, HIST1H2AL, HIST1H2AM, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AA4, HIST2H2AB, HIST2H2AC, HIST2H2BE, HIST2H2BF, HIST2H3A, HIST2H3C, HIST2H3D, HIST2H3PS2, HIST2H4A, HIST2H4B, HIST3H2A, HIST3H2BB, HIST3H3, HIST4H4, HIVEP1, HIVEP2, HIVEP3, HJURP, HK1, HK2, HK3, HKDC1, HKR1, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, HLA-E, HLA-F, HLA-G, HLCS, HLF, HLTF, HLX, HM13, HM190170.1, HMBOX1, HMBS, HMCES, HMCN1, HMCN2, HMG20A, HMG20B, HMGA1, HMGA2, HMGB1, HMGB2, HMGB3, HMGB4, HMGCL, HMGCLL1, HMGCR, HMGCS1, HMGCS2, HMGN1, HMGN2, HMGN3, HMGN4, HMGN5, HMGXB3, HMGXB4, HMHB1, HMMR, HMOX1, HMOX2, HMSD, HMX1, HMX2, HMX3, HNF1A, HNF1B, HNF4A, HNF4G, HNMT, HNRNPA0, HNRNPA1, HNRNPA1L2, HNRNPA2B1, HNRNPA3, HNRNPAB, HNRNPC, HNRNPCL1, HNRNPCL2, HNRNPCL3, HNRNPCL4, HNRNPD, HNRNPDL, HNRNPF, HNRNPH1, HNRNPH2, HNRNPH3, HNRNPK, HNRNPL, HNRNPLL, HNRNPM, HNRNPR, HNRNPU, HNRNPUL1, HNRNPUL2, HNRNPUL2-BSCL2, HOGA1, *HOMERI*, HOMER2, HOMER3, HOMEZ, HOOK1, HOOK2, HOOK3, HOPX, HORMAD1, HORMAD2, HOXA1, HOXA10, HOXA11, HOXA13, HOXA2, HOXA3, HOXA4, HOXA5, HOXA6, HOXA7, HOXA9, HOXB1, HOXB13, HOXB2, HOXB3, HOXB4, HOXB5, HOXB6, HOXB7, HOXB8, HOXB9, HOXC10, HOXC11, HOXC12, HOXC13, HOXC4, HOXC5, HOXC6, HOXC8, HOXC9, HOXD1, HOXD10, HOXD11, HOXD12, HOXD13, HOXD3, HOXD4, HOXD8, HOXD9, HP, HP1BP3, HPCA, HPCAL1, HPCAL4, HPD, HPDL, HPF1, HPGD, HPGDS, HPN, HPR, HPRT1, HPS1, HPS3, HPS4, HPS5, HPS6, HPSE, HPSE2, HPX, HR, HRAS, HRASLS, HRASLS2, HRASLS5, HRC, HRCT1, HRG, HRH1, HRH2, HRH3, HRH4, HRK, HRNR, HS1BP3, HS2ST1, HS3ST1, HS3ST2, HS3ST3A1, HS3ST3B1, HS3ST4, HS3ST5, HS3ST6, HS6ST1, HS6ST2, HS6ST3, HSBP1, HSBP1L1, HSCB, HSD11B1, HSD11B1L, HSD11B2, HSD17B1, HSD17B10, HSD17B11, HSD17B12, HSD17B13, HSD17B14, HSD17B2, HSD17B3, HSD17B4, HSD17B6, HSD17B7, HSD17B8, HSD3B1, HSD3B2, HSD3B7, HSDL1, HSDL2, HSF1, HSF2, HSF2BP, HSF4, HSF5, HSFX1, HSFX2, HSFX3, HSFX4, HSFY1, HSFY2, HSH2D, HSP90AA1, HSP90AB1, HSP90B1, HSPA12A, HSPA12B, HSPA13, HSPA14, HSPA1A, HSPA1B, HSPA1L, HSPA2, HSPA4, HSPA4L, HSPA5, HSPA6, HSPA8, HSPA9, HSPB1, HSPB11, HSPB2, HSPB2-C11orf52, HSPB3, HSPB6, HSPB7, HSPB8, HSPB9, HSPBAP1, HSPBP1, HSPD1, HSPE1, HSPE1-MOB4, HSPG2, HSPH1, HTATIP2, HTATSF1, HTD2, HTN1, HTN3, HTR1A, HTR1B, HTR1D, HTR1E, HTR1F, HTR2A, HTR2B, HTR2C, HTR3A, HTR3B, HTR3C, HTR3D, HTR3E, HTR4, HTR5A, HTR6, HTR7, HTRA1, HTRA2, HTRA3, HTRA4, HTT, HUNK, HUS1, HUS1B, HUWE1, HVCN1, HYAL1, HYAL2, HYAL3, HYAL4, HYDIN, HYI, HYKK, HYLS1, HYOU1, HYPK, HYPM, IAH1, IAPP, IARS, IARS2, I1BA57, IBSP, IBTK, ICA1, ICA1L, ICAM1, ICAM2, ICAM3, ICAM4, ICAM5, ICE1, ICE2, ICK, ICMT, ICOS, ICOSLG, ID1, ID2, ID3, ID4, IDE, IDH1, IDH2, IDH3A, IDH3B, IDH3G, IDI1, IDI2, IDNK, IDO1, IDO2, IDS, IDUA, IER2, IER3, IER3IP1, IER5, IER5L, IFFO1, IFFO2, IFI16, IFI27, IFI27L1, IFI27L2, IFI30, IFI35, IFI44, IFI44L, IFI6, IFIH1, IFIT1, IFIT1B, IFIT2, IFIT3, IFIT5, IFITMI, IFITM1O, IFITM2, IFITM3, IFITM5, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNE, IFNG, IFNGR1, IFNGR2, IFNK, IFNL1, IFNL2, IFNL3, IFNL4, IFNLR1, IFNW1, IFRD1, IFRD2, IFT122, IFT140, IFT172, IFT20, IFT22, IFT27, IFT43, IFT46, IFT52, IFT57, IFT74, IFT80, IFT81, IFT88, IGBP1, IGDCC3, IGDCC4, IGF1, IGF1R, IGF2, IGF2BP1, IGF2BP2, IGF2BP3, IGF2R, IGFALS, IGFBP1, IGFBP2, IGFBP3, IGFBP4, IGFBP5, IGFBP6, IGFBP7, IGFBPL1, IGFL1, IGFL2, IGFL3, IGFL4, IGFLR1, IGFN1, IGHA1, IGHA2, IGHD, IGHD1-1, IGHD1-14, IGHD1-20, IGHD1-26, IGHD1-7, IGHDIOR15-1A, IGHD1OR15-1B, IGHD2-15, IGHD2-2, IGHD2-21, IGHD2-8, IGHD2OR15-2A, IGHD2OR15-2B, IGHD3-10, IGHD3-16, IGHD3-22, IGHD3-3, IGHD3-9, IGHD30R15-3A, IGHD30R15-3B, IGHD4-11, IGHD4-17, IGHD4-23, IGHD4-4, IGHD40R15-4A, IGHD40R15-4B, IGHD5-12, IGHD5-18, IGHD5-24, IGHD5-5, IGHD50R15-5A, IGHD50R15-5B, IGHD6-13, IGHD6-19, IGHD6-25, IGHD6-6, IGHD7-27, IGHE, IGHG1, IGHG2, IGHG3, IGHG4, IGHJ1, IGHJ2, IGHJ3, IGHJ4, IGHJ5, IGHJ6, IGHM, IGHMBP2, IGHV1-18, IGHV1-2, IGHV1-24, IGHV1-3, IGHV1-45, IGHV1-46, IGHV1-58, IGHV1-69, IGHV1OR15-1, IGHV1OR15-9, IGHV1OR21-1, IGHV2-26, IGHV2-5, IGHV2-70, IGHV2OR16-5, IGHV3-11, IGHV3-13, IGHV3-15, IGHV3-16, IGHV3-20, IGHV3-21, IGHV3-23, IGHV3-30, IGHV3-33, IGHV3-35, IGHV3-38, IGHV3-43, IGHV3-48, IGHV3-49, IGHV3-53, IGHV3-64, IGHV3-66, IGHV3-7, IGHV3-72, IGHV3-73, IGHV3-74, IGHV30R15-7, IGHV30R16-10, IGHV30R16-12, IGHV30R16-13, IGHV30R16-8, IGHV30R16-9, IGHV4-28, IGHV4-31, IGHV4-34, IGHV4-39, IGHV4-4, IGHV4-59, IGHV4-61, IGHV4OR15-8, IGHV5-51, IGHV6-1, IGHV7-81, IGIP, IGKC, IGKJ1, IGKJ2, IGKJ3, IGKJ4, IGKJ5, IGKV1-12, IGKV1-16, IGKV1-17, IGKV1-27, IGKV1-33, IGKV1-37, IGKV1-39, IGKV1-5, IGKV1-6, IGKV1-8, IGKV1-9, IGKV1D-12, IGKV1D-13, IGKV1D-16, IGKV1D-17, IGKV1D-33, IGKV1D-37, IGKV1D-39, IGKV1D-42, IGKV1D-43, IGKV1D-8, IGKV1OR2-108, IGKV2-24, IGKV2-28, IGKV2-30, IGKV2-40, IGKV2D-24, IGKV2D-26, IGKV2D-28, IGKV2D-29, IGKV2D-30, IGKV2D-40, IGKV3-11, IGKV3-15, IGKV3-20, IGKV3-7, IGKV3D-11, IGKV3D-15, IGKV3D-20, IGKV3D-7, IGKV3OR2-268, IGKV4-1, IGKV5-2, IGKV6-21, IGKV6D-21, IGKV6D-41, IGLC1, IGLC2, IGLC3, IGLC7, IGLJ1, IGLJ2, IGLJ3, IGLJ4, IGLJ5, IGLJ6, IGLJ7, IGLL1, IGLL5, IGLON5, IGLV10-54, IGLV11-55, IGLV1-36, IGLV1-40, IGLV1-44, IGLV1-47, IGLV1-50, IGLV1-51, IGLV2-11, IGLV2-14, IGLV2-18, IGLV2-23, IGLV2-33, IGLV2-8, IGLV3-1, IGLV3-10, IGLV3-12, IGLV3-16, IGLV3-19, IGLV3-21, IGLV3-22, IGLV3-25, IGLV3-27, IGLV3-32, IGLV3-9, IGLV4-3, IGLV4-60, IGLV4-69, IGLV5-37, IGLV5-45, IGLV5-48, IGLV5-52, IGLV6-57, IGLV7-43, IGLV7-46, IGLV8-61, IGLV9-49, IGSF1, IGSF10, IGSF11, IGSF21, IGSF22, IGSF23, IGSF3, IGSF5, IGSF6, IGSF8, IGSF9, IGSF9B, IHH, IK, IKBIP, IKBKB, IKBKE, IKBKG, IKZF1, IKZF2, IKZF3, IKZF4, IKZF5, IL10, IL10RA, IL10RB, IL11, IL11RA, IL12A, IL12B, IL12RB1, IL12RB2, IL13, IL13RA1, IL13RA2, IL15, IL15RA, IL16, IL17A, IL17B, IL17C, IL17D, IL17F, IL17RA, IL17RB, IL17RC, IL17RD, IL17RE, IL17REL, IL18, IL18BP, IL18R1, IL18RAP, IL19, IL1A, IL1B, IL1F10, IL1R1, IL1R2, IL1RAP, IL1RAPL1, IL1RAPL2, IL1RL1, IL1RL2, IL1RN, IL2, IL20, IL20RA, IL20RB, IL21, IL21R, IL22, IL22RA1, IL22RA2, IL23A, IL23R, IL24, IL25, IL26, IL27, IL27RA, IL2RA, IL2RB, IL2RG, IL3, IL31, IL31RA, IL32, IL33, IL34, IL36A, IL36B, IL36G, IL36RN, IL37, IL3RA, IL4, IL4I1, IL4R, IL5, IL5RA, IL6, IL6R, IL6ST, IL7, IL7R, IL9, IL9R, ILDR1, ILDR2, ILF2, ILF3, ILK, ILKAP, ILVBL, IMMP1L, IMMP2L, IMMT, IVP3, IMP4, IMPA1, IMPA2, IMPACT, IMPAD1, ITMPDH1, IMPDH2, IMPG1, IMPG2, INA, INAFM1, INAFM2, INAVA, *INCA*1, INCENP, INF2, ING1, ING2, ING3, ING4, ING5, INHA, INHBA, INHBB, INHBC, INHBE, INIP, INMT, INMT-MINDY4, INO80, INO80B, INO8OB-WBP1, INO80C, INO80D, INO80E, INPP1, INPP4A, INPP4B, INPP5A, INPP5B, INPP5D, INPP5E, INPP5F, INPP5J, INPP5K, INPPL1, INS, INSC, INSIG1, INSIG2, INS-IGF2, INSL3, INSL4, INSL5, INSL6, INSM1, INSM2, INSR, INSRR, INTS1, INTS10, INTS11, INTS12, INTS13, INTS14, INTS2, INTS3, INTS4, INTS5, INTS6, INTS6L, INTS7, INTS8, INTS9, INTU, INVS, IP6K1, IP6K2, IP6K3, IPCEF1, IPMK, IPO11, IPO13, IPO4, IPO5, IPO7, IPO8, IPO9, IPP, IPPK, IQANKI, IQCA1, IQCA1L, IQCB1, IQCC, IQCD, IQCE, IQCF1, IQCF2, IQCF3, IQCF5, IQCF6, IQCG, IQCH, IQCJ, IQCJ-SCHIP1, IQCK, IQCM, IQGAP1, IQGAP2, IQGAP3, IQSEC1, IQSEC2, IQSEC3, IQUB, IRAK1, IRAKIBPI, IRAK2, IRAK3, IRAK4, IREB2, IRF1, IRF2, IRF2BP1, IRF2BP2, IRF2BPL, IRF3, IRF4, IRF5, IRF6, IRF7, IRF8, IRF9, IRGC, IRGM, IRGQ, IRS1, IRS2, IRS4, IRX1, IRX2, IRX3, IRX4, IRX5, IRX6, ISCA1, ISCA2, ISCU, ISG15, ISG20, ISG20L2, ISL1, ISL2, ISLR, ISLR2, ISM1, ISM2, ISOC1, ISOC2, ISPD, IST1, ISX, ISY1, ISY1-RAB43, ISYNA1, ITCH, ITFG1, ITFG2, ITGA1, ITGA10, ITGA11, ITGA2, ITGA2B, ITGA3, ITGA4, ITGA5, ITGA6, ITGA7, ITGA8, ITGA9, ITGAD, ITGAE, ITGAL, ITGAM, ITGAV, ITGAX, ITGB1, ITGB1BP1, ITGB1BP2, ITGB2, ITGB3, ITGB3BP, ITGB4, ITGB5, ITGB6, ITGB7, ITGB8, ITGBL1, ITIH1, ITIH2, ITIH3, ITIH4, ITIH5, ITIH6, ITK, ITLN1, ITLN2, ITM2A, ITM2B, ITM2C, ITPA, ITPK1, ITPKA, ITPKB, ITPKC, ITPR1, ITPR2, ITPR3, ITPRIP, ITPRIPL1, ITPRIPL2, ITSN1, ITSN2, IVD, IVL, IVNS1ABP, IWS1, IYD, IZUMO1, IZUMOIR, IZUMO2, IZUMO3, IZUMO4, JADE1, JADE2, JADE3, JAG1, JAG2, JAGN1, JAK1, JAK2, JAK3, JAKMIP1, JAKMIP2, JAKMIP3, JAM2, JAM3, JAML, JARID2, JAZF1, JCAD, JCHAIN, JDP2, JKAMP, JMJD1C, JMJD4, JMJD6, JMJD7, JMJD7-PLA2G4B, JMJD8, JMY, JOSD1, JOSD2, JPH1, JPH2, JPH3, JPH4, JPT1, JPT2, JRK, JRKL, JSRP1, JTB, JUN, JUNB, JUND, JUP, KAAG1, KALRN, KANK1, KANK2, KANK3, KANK4, KANSLI, KANSLIL, KANSL2, KANSL3, KANTR, KARS, KAT14, KAT2A, KAT2B, KAT5, KAT6A, KAT6B, KAT7, KAT8, KATNA1, KATNAL1, KATNAL2, KATNB1, KATNBL1, KAZALD1, KAZN, KBTBD11, KBTBD11-OT1, KBTBD12, KBTBD13, KBTBD2, KBTBD3, KBTBD4, KBTBD6, KBTBD7, KBTBD8, KCMF1, KCNA1, KCNA10, KCNA2, KCNA3, KCNA4, KCNA5, KCNA7, KCNAB1, KCNAB2, KCNAB3, KCNB1, KCNB2, KCNC1, KCNC2, KCNC3, KCNC4, KCND1, KCND2, KCND3, KCNE1, KCNE1B, KCNE2, KCNE3, KCNE4, KCNE5, KCNF1, KCNG1, KCNG2, KCNG3, KCNG4, KCNH1, KCNH2, KCNH3, KCNH4, KCNH5, KCNH6, KCNH7, KCNH8, KCNIP1, KCNIP2, KCNIP3, KCNIP4, KCNJ1, KCNJ10, KCNJ11, KCNJ12, KCNJ13, KCNJ14, KCNJ15, KCNJ16, KCNJ18, KCNJ2, KCNJ3, KCNJ4, KCNJ5, KCNJ6, KCNJ8, KCNJ9, KCNK1, KCNK10, KCNK12, KCNK13, KCNK15, KCNK16, KCNK17, KCNK18, KCNK2, KCNK3, KCNK4, KCNK5, KCNK6, KCNK7, KCNK9, KCNMA1, KCNMB1, KCNMB2, KCNMB3, KCNMB4, KCNN1, KCNN2, KCNN3, KCNN4, KCNQ1, KCNQ2, KCNQ3, KCNQ4, KCNQ5, KCNRG, KCNS1, KCNS2, KCNS3, KCNT1, KCNT2, KCNU1, KCNV1, KCNV2, KCP, KCTD1, KCTD10, KCTD11, KCTD12, KCTD13, KCTD14, KCTD15, KCTD16, KCTD17, KCTD18, KCTD19, KCTD2, KCTD20, KCTD21, KCTD3, KCTD4, KCTD5, KCTD6, KCTD7, KCTD8, KCTD9, KDELC1, KDELC2, KDELR1, KDELR2, KDELR3, KDF1, KDM1A, KDM1B, KDM2A, KDM2B, KDM3A, KDM3B, KDM4A, KDM4B, KDM4C, KDM4D, KDM4E, KDM4F, KDM5A, KDM5B, KDM5C, KDM5D, KDM6A, KDM6B, KDM7A, KDM8, KDR, KDSR, KEAP1, KEL, KERA, KF459570.1, KHDC1, KHDC1L, KHDC3L, KHDRBS1, KHDRBS2, KHDRBS3, KHK, KHNYN, KHSRP, KIAA0040, KIAA0100, KIAA0141, KIAA0232, KIAA0319, KIAA0319L, KIAA0355, KIAA0368, KIAA0391, KIAA0408, KIAA0513, KIAA0556, KIAA0586, KIAA0753, KIAA0825, KIAA0895, KIAA0895L, KIAA0907, KIAA0930, KIAA1024, KIAA1024L, KIAA1107, KIAA1109, KIAA1143, KIAA1147, KIAA1161, KIAA1191, KIAA1210, KIAA1211, KIAA1211L, KIAA1217, KIAA1257, KIAA1324, KIAA1324L, KIAA1328, KIAA1456, KIAA1468, KIAA1522, KIAA1524, KIAA1549, KIAA1549L, KIAA1551, KIAA1586, KIAA1614, KIAA1644, KIAA1671, KIAA1683, KIAA1755, KIAA1841, KIAA1958, KIAA2012, KIAA2013, KIAA2026, KIDINS220, KIF11, KIF12, KIF13A, KIF13B, KIF14, KIF15, KIF16B, KIF17, KIF18A, KIF18B, KIF19, KIF1A, KIF1B, KIF1BP, KIF1C, KIF20A, KIF20B, KIF21A, KIF21B, KIF22, KIF23, KIF24, KIF25, KIF26A, KIF26B, KIF27, KIF2A, KIF2B, KIF2C, KIF3A, KIF3B, KIF3C, KIF4A, KIF4B, KIF5A, KIF5B, KIF5C, KIF6, KIF7, KIF9, KIFAP3, KIFC1, KIFC2, KIFC3, KIN, KIR2DL1, KIR2DL2, KIR2DL3, KIR2DL4, KIR2DL5A, KIR2DL5B, KIR2DP1, KIR2DS1, KIR2DS2, KIR2DS3, KIR2DS4, KIR2DS5, KIR3DL1, KIR3DL2, KIR3DL3, KIR3DP1, KIR3DS1, KIR3DX1, KIRREL1, KIRREL2, KIRREL3, KISS1, KISS1R, KIT, KITLG, KIZ, KL, KLB, KLC1, KLC2, KLC3, KLC4, KLF1, KLF10, KLF11, KLF12, KLF13, KLF14, KLF15, KLF16, KLF17, KLF18, KLF2, KLF3, KLF4, KLF5, KLF6, KLF7, KLF8, KLF9, KLHDC1, KLHDC10, KLHDC2, KLHDC3, KLHDC4, KLHDC7A, KLHDC7B, KLHDC8A, KLHDC8B, KLHDC9, KLHL1, KLHL10, KLHL11, KLHL12, KLHL13, KLHL14, KLHL15, KLHL17, KLHL18, KLHL2, KLHL20, KLHL21, KLHL22, KLHL23, KLHL24, KLHL25, KLHL26, KLHL28, KLHL29, KLHL3, KLHL30, KLHL31, KLHL32, KLHL33, KLHL34, KLHL35, KLHL36, KLHL38, KLHL4, KLHL40, KLHL41, KLHL42, KLHL5, KLHL6, KLHL7, KLHL8, KLHL9, KLK1, KLK10, KLK11, KLK12, KLK13, KLK14, KLK15, KLK2, KLK3, KLK4, KLK5, KLK6, KLK7, KLK8, KLK9, KLKB1, KLLN, KLRB1, KLRC1, KLRC2, KLRC3, KLRC4, KLRC4-KLRK1, KLRD1, KLRF1, KLRF2, KLRG1, KLRG2, KLRK1, KMO, KMT2A, KMT2B, KMT2C, KMT2D, KMT2E, KMT5A, KMT5B, KMT5C, KNCN, KNDC1, KNG1, KNL1, KNOP1, KNSTRN, KNTC1, KP420437.1, KP420437.2, KP420437.3, KP420439.1, KP420440.1, KP420440.2, KP420440.3, KP420440.4, KP420440.5, KP420440.6, KP420440.7, KP420440.8, KP420440.9, KP420441.1, KP420441.2, KP420441.3, KP420441.4, KP420441.5, KP420442.2, KP420442.3, KP420443.1, KP420444.1, KP420444.2, KP420444.3, KP420444.4, KP420444.5, KP420444.6, KP420444.7, KP420446.1, KP420446.2, KPNA1, KPNA2, KPNA3, KPNA4, KPNA5, KPNA6, KPNA7, KPNB1, KPRP, KPTN, KRAS, KRBA1, KRBA2, KRBOX1, KRBOX4, KRCC1, KREMEN1, KREMEN2, KRI1, KRIT1, KRR1, KRT1, KRT10, KRT12, KRT13, KRT14, KRT15, KRT16, KRT17, KRT18, KRT19, KRT2, KRT20, KRT222, KRT23, KRT24, KRT25, KRT26, KRT27, KRT28, KRT3, KRT31, KRT32, KRT33A, KRT33B, KRT34, KRT35, KRT36, KRT37, KRT38, KRT39, KRT4, KRT40, KRT5, KRT6A, KRT6B, KRT6C, KRT7, KRT71, KRT72, KRT73, KRT74, KRT75, KRT76, KRT77, KRT78, KRT79, KRT8, KRT80, KRT81, KRT82, KRT83, KRT84, KRT85, KRT86, KRT9, KRTAP10-1, KRTAP10-10, KRTAP10-11, KRTAP10-12, KRTAP10-2, KRTAP10-3, KRTAP10-4, KRTAP10-5, KRTAP10-6, KRTAP10-7, KRTAP10-8, KRTAP10-9, KRTAP1-1, KRTAP11-1, KRTAP12-1, KRTAP12-2, KRTAP12-3, KRTAP12-4, KRTAP1-3, KRTAP13-1, KRTAP13-2, KRTAP13-3, KRTAP13-4, KRTAP1-4, KRTAP1-5, KRTAP15-1, KRTAP16-1, KRTAP17-1, KRTAP19-1, KRTAP19-2, KRTAP19-3, KRTAP19-4, KRTAP19-5, KRTAP19-6, KRTAP19-7, KRTAP19-8, KRTAP20-1, KRTAP20-2, KRTAP20-3, KRTAP20-4, KRTAP2-1, KRTAP21-1, KRTAP21-2, KRTAP21-3, KRTAP2-2, KRTAP22-1, KRTAP22-2, KRTAP2-3, KRTAP23-1, KRTAP2-4, KRTAP24-1, KRTAP25-1, KRTAP26-1, KRTAP27-1, KRTAP29-1, KRTAP3-1, KRTAP3-2, KRTAP3-3, KRTAP4-1, KRTAP4-11, KRTAP4-12, KRTAP4-16, KRTAP4-2, KRTAP4-3, KRTAP4-4, KRTAP4-5, KRTAP4-6, KRTAP4-7, KRTAP4-8, KRTAP4-9, KRTAP5-1, KRTAP5-10, KRTAP5-11, KRTAP5-2, KRTAP5-3, KRTAP5-4, KRTAP5-5, KRTAP5-6, KRTAP5-7, KRTAP5-8, KRTAP5-9, KRTAP6-1, KRTAP6-2, KRTAP6-3, KRTAP7-1, KRTAP8-1, KRTAP9-1, KRTAP9-2, KRTAP9-3, KRTAP9-4, KRTAP9-6, KRTAP9-7, KRTAP9-8, KRTAP9-9, KRTCAP2, KRTCAP3, KRTDAP, KSR1, KSR2, KTI12, KTN1, KU645196.1, KU645196.2, KU645196.3, KU645196.4, KU645196.5, KU645196.6, KU645196.7, KU645196.8, KU645196.9, KU645197.1, KU645197.2, KU645197.3, KU645197.4, KU645197.5, KU645198.1, KXD1, KY, KYAT1, KYAT3, KYNU, L1CAM, L1TD1, L2HGDH, L34079.1, L3HYPDH, L3MBTL1, L3MBTL2, L3MBTL3, L3MBTL4, LACC1, LACRT, LACTB, LACTB2, LACTBL1, LAD1, LAG3, LAGE3, LAIR1, LAIR2, LALBA, *LAMA1*, *LAMA2*, *LAMA3*, *LAMA4*, *LAMA5*, LAMB1, LAMB2, LAMB3, LAMB4, LAMC1, LAMC2, LAMC3, LAMP1, LAMP2, LAMP3, LAMP5, LAMTOR1, LAMTOR2, LAMTOR3, LAMTOR4, LAMTOR5, LANCL1, LANCL2, LANCL3, LAP3, LAPTM4A, LAPTM4B, LAPTM5, LARGE1, LARGE2, LARP1, LARP1B, LARP4, LARP4B, LARP6, LARP7, LARS, LARS2, LAS1L, LASP1, LAT, LAT2, LATS1, LATS2, LAX1, LAYN, LBH, LBHD1, LBP, LBR, LBX1, LBX2, LCA5, LCA5L, LCAT, LCE1A, LCE1B, LCE1C, LCE1D, LCE1E, LCE1F, LCE2A, LCE2B, LCE2C, LCE2D, LCE3A, LCE3B, LCE3C, LCE3D, LCE3E, LCE4A, LCE5A, LCE6A, LCK, LCLAT1, LCMT1, LCMT2, LCN1, LCN10, LCN12, LCN15, LCN2, LCN6, LCN8, LCN9, LCNL1, LCOR, LCORL, LCP1, LCP2, LCT, LCTL, LDAH, LDB1, LDB2, LDB3, LDHA, LDHAL6A, LDHAL6B, LDHB, LDHC, LDHD, LDLR, LDLRAD1, LDLRAD2, LDLRAD3, LDLRAD4, LDL-RAP1, LDOC1, LEAP2, LECT2, LEF1, LEFTY1, LEFTY2, LEKR1, LELP1, LEMD1, LEMD2, LEMD3, LENEP, LENG1, LENG8, LENG9, LEO1, LEP, LEPR, LEPROT, LEPROTL1, LETM1, LETM2, LETMD1, LEUTX, LEXM, LFNG, LGALS1, LGALS12, LGALS13, LGALS14, LGALS16, LGALS2, LGALS3, LGALS3BP, LGALS4, LGALS7, LGALS7B, LGALS8, LGALS9, LGALS9B, LGALS9C, LGALSL, LGI1, LGI2, LGI3, LGI4, LGMN, LGR4, LGR5, LGR6, LGSN, LHB, LHCGR, LHFPL1, LHFPL2, LHFPL3, LHFPL4, LHFPL5, LHFPL6, LHPP, LHX1, LHX2, LHX3, LHX4, LHX5, LHX6, LHX8, LHX9, LIAS, LIF, LIFR, LIG1, LIG3, LIG4, LILRA1, LILRA2, LILRA3, LILRA4, LILRA5, LILRA6, LILRB1, LILRB2, LILRB3, LILRB4, LILRB5, LIM2, LIMA1, LIMCH1, LIMD1, LIMD2, LIME1, LIMK1, LIMK2, LIMS1, LIMS2, LIMS3, LIMS4, LIN28A, LIN28B, LIN37, LIN52, LIN54, LIN7A, LIN7B, LIN7C, LIN9, LINC00094, LINC00116, LINC00282, LINC00672, LINC00675, LINC00694, LINC00854, LINC00890, LINC00959, LINC01125, LINC01556, LINC02210-CRHR1, LINGO1, LINGO2, LINGO3, LINGO4, LINS1, LIPA, LIPC, LIPE, LIPF, LIPG, LIPH, LIPI, LIPJ, LIPK, LIPM, LIPN, LIPT1, LIPT2, LITAF, LIX1, LIX1L, LKAAEAR1, LLGL1, LLGL2, LLPH, LMAN1, LMAN1L, LMAN2, LMAN2L, LMBR1, LMBR1L, LMBRD1, LMBRD2, LMCD1, LMF1, LMF2, LMLN, LMNA, LMNB1, LMNB2, LMNTD1, LMNTD2, LMO1, LMO2, LMO3, LMO4, LMO7, LMO7DN, LMOD1, LMOD2, LMOD3, LMTK2, LMTK3, LMX1A, LMX1B, LNP1, LNPEP, LNPK, LNX1, LNX2, LO000005.1, LONP1, LONP2, LONRF1, LONRF2, LONRF3, LOR, LOX, LOXHD1, LOXL1, LOXL2, LOXL3, LOXL4, LPA, LPAR1, LPAR2, LPAR3, LPAR4, LPAR5, LPAR6, LPCAT1, LPCAT2, LPCAT3, LPCAT4, LPGAT1, LPIN1, LPIN2, LPIN3, LPL, LPO, LPP, LPXN, LRAT, LRBA, LRCH1, LRCH2, LRCH3, LRCH4, LRCOL1, LRFN1, LRFN2, LRFN3, LRFN4, LRFN5, LRG1, LRGUK, LRIF1, LRIG1, LRIG2, LRIG3, LRIT1, LRIT2, LRIT3, LRMDA, LRMP, LRP1, LRP10, LRP11, LRP12, LRP1B, LRP2, LRP2BP, LRP3, LRP4, LRP5, LRP5L, LRP6, LRP8, LRPAP1, LRPPRC, LRR1, LRRC1, LRRC10, LRRC10B, LRRC14, LRRC14B, LRRC15, LRRC17, LRRC18, LRRC19, LRRC2, LRRC20, LRRC23, LRRC24, LRRC25, LRRC26, LRRC27, LRRC28, LRRC29, LRRC3, LRRC30, LRRC31, LRRC32, LRRC34, LRRC36, LRRC37A, LRRC37A2, LRRC37A3, LRRC37B, LRRC38, LRRC39, LRRC3B, LRRC3C, LRRC4, LRRC40, LRRC41, LRRC42, LRRC43, LRRC45, LRRC46, LRRC47, LRRC49, LRRC4B, LRRC4C, LRRC52, LRRC53, LRRC55, LRRC56, LRRC57, LRRC58, LRRC59, LRRC6, LRRC61, LRRC63, LRRC66, LRRC69, LRRC7, LRRC70, LRRC71, LRRC72, LRRC73, LRRC74A, LRRC74B, LRRC75A, LRRC75B, LRRC8A, LRRC8B, LRRC8C, LRRC8D, LRRC8E, LRRC9, LRRCC1, LRRD1, LRRFIP1, LRRFIP2, LRRIQ1, LRRIQ3, LRRIQ4, LRRK1, LRRK2, LRRN1, LRRN2, LRRN3, LRRN4, LRRN4CL, LRRTM1, LRRTM2, LRRTM3, LRRTM4, LRSAM1, LRTM1, LRTM2, LRTOMT, LRWD1, LSAMP, LSG1, LSM1, LSM10, LSM11, LSM12, LSM14A, LSM14B, LSM2, LSM3, LSM4, LSM5, LSM6, LSM7, LSM8, LSMEM1, LSMEM2, LSP1, LSR, LSS, LST1, LTA, LTA4H, LTB, LTB4R, LTB4R2, LTBP1, LTBP2, LTBP3, LTBP4, LTBR, LTC4S, LTF, LTK, LTN1, LTV1, LUC7L, LUC7L2, LUC7L3, LUM, LURAP1, LURAP1L, LUZP1, LUZP2, LUZP4, LUZP6, LVRN, LXN, LY6D, LY6E, LY6G5B, LY6G5C, LY6G6C, LY6G6D, LY6G6E, LY6G6F, LY6H, LY6K, LY6L, LY75, LY75-CD302, LY86, LY9, LY96, LYAR, LYG1, LYG2, LYL1, LYN, LYNX1, LYPD1, LYPD2, LYPD3, LYPD4, LYPD5, LYPD6, LYPD6B, LYPD8, LYPLA1, LYPLA2, LYPLAL1, LYRM1, LYRM2, LYRM4, LYRM7, LYRM9, LYSMD1, LYSMD2, LYSMD3, LYSMD4, LYST, LYVE1, LYZ, LYZL1, LYZL2, LYZL4, LYZL6, LZIC, LZTFL1, LZTR1, LZTS1, LZTS2, LZTS3, M1AP, M6PR, MAATS1, MAB21L1, MAB21L2, MAB21L3, MACC1, MACF1, MACROD1, MACROD2, MAD1L1, MAD2L1, MAD2L1BP, MAD2L2, MADCAM1, MADD, MAEA, MAEL, MAF, MAF1, MAFA, MAFB, MAFF, MAFG, MAFK, MAG, MAGEA1, MAGEA10, MAGEA11, MAGEA12, MAGEA2, MAGEA2B, MAGEA3, MAGEA4, MAGEA6, MAGEA8, MAGEA9, MAGEA9B, MAGEB1, MAGEB10, MAGEB16, MAGEB17, MAGEB18, MAGEB2, MAGEB3, MAGEB4, MAGEB5, MAGEB6, MAGEB6P1, MAGEC1, MAGEC2, MAGEC3, MAGED1, MAGED2, MAGED4, MAGED4B, MAGEE1, MAGEE2, MAGEF1, MAGEH1, MAGEL2, MAGI1, MAGI2, MAGI3, MAGIX, MAGOH, MAGOHB, MAGT1, MAIP1, MAJIN, MAK, MAK16, MAL, MAL2, MALL, MALRD1, MALSU1, MALT1, MAMDC2, MAMDC4, MAML1, MAML2, MAML3, MAMLD1, MAMSTR, MAN1A1, MAN1A2, MAN1B1, MAN1C1, MAN2A1, MAN2A2, MAN2B1, MAN2B2, MAN2C1, MANBA, MANBAL, MANEA, MANEAL, MANF, MANSC1, MANSC4, MAOA, MAOB, MAP10, MAP1A, MAP1B, MAP1LC3A, MAP1LC3B, MAP1LC3B2, MAP1LC3C, MAPIS, MAP2, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K20, MAP3K21, MAP3K3, MAP3K4, MAP3K5, MAP3K6, MAP3K7, MAP3K7CL, MAP3K8, MAP3K9, MAP4, MAP4K1, MAP4K2, MAP4K3, MAP4K4, MAP4K5, MAP6, MAP6D1, MAP7, MAP7D1, MAP7D2, MAP7D3, MAP9, MAPK1, MAPK10, MAPK11, MAPK12, MAPK13, MAPK14, MAPK15, MAPK1IP1L, MAPK3, MAPK4, MAPK6, MAPK7, MAPK8, MAPK8IP1, MAPK8IP2, MAPK8IP3, MAPK9, MAPKAP1, MAPKAPK2, MAPKAPK3, MAPKAPK5, MAPKBP1, MAPRE1, MAPRE2, MAPRE3, MAPT, MARC1, MARC2, MARCHI, MARCH10, MARCH11, MARCH2, MARCH3, MARCH4, MARCH5, MARCH6, MARCH7, MARCH8, MARCH9, MARCKS, MARCKSL1, MARCO, MARF1, MARK1, MARK2, MARK3, MARK4, MARS, MARS2, MARVELD1, MARVELD2, MARVELD3, MAS1, MAS1L, MASP1, MASP2, MAST1, MAST2, MAST3, MAST4, MASTL, MAT1A, MAT2A, MAT2B, MATK, MATN1, MATN2, MATN3, MATN4, MATR3, MAU2, MAVS, MAX, MAZ, MB, MB21D1, MB21D2, MBD1, MBD2, MBD3, MBD3L1, MBD3L2, MBD3L2B, MBD3L3, MBD3L4, MBD3L5, MBD4, MBD5, MBD6, MBIP, MBL2, MBLAC1, MBLAC2, MBNL1, MBNL2, MBNL3, MBOAT1, MBOAT2, MBOAT4, MBOAT7, MBP, MBTD1, MBTPS1, MBTPS2, MC1R, MC2R, MC3R, MC4R, MC5R, MCAM, MCAT, MCC, MCCC1, MCCC2, MCCD1, MCEE, MCEMP1, MCF2, MCF2L, MCF2L2, MCFD2, MCHR1, MCHR2, MCIDAS, MCL1, MCM10, MCM2, MCM3, MCM3AP, MCM4, MCM5, MCM6, MCM7, MCM8, MCM9, MCMBP, MCMDC2, MCOLN1, MCOLN2, MCOLN3, MCPH1, MCRIP1, MCRIP2, MCRS1, MCTP1, MCTP2, MCTS1, MCU, MCUB, MCUR1, MDC1, MDFI, MDFIC, MDFIC2, MDGA1, MDGA2, MDH1, MDH1B, MDH2, MDK, MDM1, MDM2, MDM4, MDN1, MDP1, MDS2, ME1, ME2, ME3, MEA1, MEAF6, MECOM, MECP2, MECR, MED1, MED10, MED11, MED12, MED12L, MED13, MED13L, MED14, MED14OS, MED15, MED16, MED17, MED18, MED19, MED20, MED21, MED22, MED23, MED24, MED25, MED26, MED27, MED28, MED29, MED30, MED31, MED4, MED6, MED7, MED8, MED9, MEDAG, MEF2A, MEF2B, MEF2C, MEF2D, MEFV, MEGF10, MEGF11, MEGF6, MEGF8, MEGF9, MEI1, MEI4, MEIG1, MEIKIN, MEIOB, MEIOC, MEIS1, MEIS2, MEIS3, MELK, MELTF, MEMO1, MEN1, MEOX1, MEOX2, MEPIA, MEP1B, MEPCE, MEPE, MERTK, MESD, MESP1, MESP2, MEST, MET, METAP1, METAP1D, METAP2, METRN, METRNL, METTL1, METTL11B, METTL12, METTL13, METTL14, METTL15, METTL16, METTL17, METTL18, METTL21A, METTL21C, METTL22, METTL23, METTL24, METTL25, METTL26, METTL27, METTL2A, METTL2B, METTL3, METTL4, METTL5, METTL6, METTL7A, METTL7B, METTL8, METTL9, MEX3A, MEX3B, MEX3C, MEX3D, MFAP1, MFAP2, MFAP3, MFAP3L, MFAP4, MFAP5, MFF, MFGE8, MFHAS1, MIFN1, MFN2, MFNG, MFRP, MFSD1, MFSD10, MFSD11, MFSD12, MFSD13A, MFSD14A, MFSD14B, MFSD14C, MFSD2A, MFSD2B, MFSD3, MFSD4A, MFSD4B, MFSD5, MFSD6, MFSD6L, MFSD7, MFSD8, MFSD9, MGA, MGAM, MGAM2, MGARP, MGAT1, MGAT2, MGAT3, MGAT4A, MGAT4B, MGAT4C, MGAT4D, MGAT5, MGAT5B, MGEA5, MGLL, MGME1, MGMT, MGP, MGRN1, MGST1, MGST2, MGST3, MIA, MIA3, MIA-RAB4B, MIB1, MIB2, MICA, MICAL1, MICAL2, MICAL3, MICALCL, MICALL1, MICALL2, MICB, MICU1, MICU2, MICU3, MID1, MID1IP1, MID2, MIDN, MIEF1, MIEF2, MIEN1, MIER1, MIER2, MIER3, MIF, MIF4GD, MIGA1, MIGA2, MIIP, MILR1, MINDY1, MINDY2, MINDY3, MINDY4, MINDY4B, MINK1, MINOS1, MINOS1-NBL1, MINPP1, MIOS, MIOX, MIP, MIPEP, MIPOL1, MIS12, MIS18A, MIS18BP1, MISP, MISP3, MITD1, MITF, MIXL1, MKI67, MKKS, MKL1, MKL2, MKLN1, MKNK1, MKNK2, MKRN1, MKRN2, MKRN2OS, MKRN3, MKS1, MKX, MLANA, MLC1, MLEC, MLF1, MLF2, MLH1, MLH3, MLIP, MLKL, MLLT1, MLLT10, MLLT11, MLLT3, MLLT6, MLN, MLNR, MLPH, MLST8, MLX, MLXIP, MLXIPL, MLYCD, MMAA, MMAB, MMACHC, MMADHC, MMD, MMD2, MME, MMEL1, MMGT1, MMP1, MMP10, MMP11, MMP12, MMPP13, MMP14, MMP15, MMP16, MMP17, MMP19, MMP2, MMP20, MMP21, MMP23B, MMP24, MMP24-AS1, MMP25, MMP26, MMP27, MMP28, MMP3, MMP7, MMP8, MMP9, MMRN1, MMRN2, MMS19, MMS22L, MN1, MNAT 1, MND1, MNDA, MNS1, MNT, MNX1, MOAP1, MOB1A, MOB1B, MOB2, MOB3A, MOB3B, MOB3C, MOB4, MOBP, MOCOS, MOCS1, MOCS2, MOCS3, MOG, MOGAT1, MOGAT2, MOGAT3, MOGS, MOK, MON1A, MON1B, MON2, MORC1, MORC2, MORC3, MORC4, MORF4L1, MORF4L2, MORN1, MORN2, MORN3, MORN4, MORN5, MOS, MOSPD1, MOSPD2, MOSPD3, MOV10, MOV10L1, MOXD1, MPC1, MPC1L, MPC2, MPDU1, MPDZ, MPEG1, MPG, MPHOSPH10, MPHOSPH6, MPHOSPH8, MPHOSPH9, MPI, MPIG6B, MPL, MPLKIP, MPND, MPO, MPP1, MPP2, MPP3, MPP4, MPP5, MPP6, MPP7, MPPE1, MPPED1, MPPED2, MPRIP, MPST, MPV17, MPV17L, MPV17L2, MPZ, MPZL1, MPZL2, MPZL3, MR1, MRAP, MRAP2, MRAS, MRC1, MRC2, MRE11, MREG, MRFAP1, MRFAP1L1, MRGBP, MRGPRD, MRGPRE, MRGPRF, MRGPRG, MRGPRX1, MRGPRX2, MRGPRX3, MRGPRX4, MRII, MRLN, MRM1, MRM2, MRM3, MRNIP, MRO, MROH1, MROH2A, MROH2B, MROH5, MROH6, MROH7, MROH7-TTC4, MROH8, MROH9, MRPL1, MRPL10, MRPL11, MRPL12, MRPL13, MRPL14, MRPL15, MRPL16, MRPL17, MRPL18, MRPL19, MRPL2, MRPL20, MRPL21, MRPL22, MRPL23, MRPL24, MRPL27, MRPL28, MRPL3, MRPL30, MRPL32, MRPL33, MRPL34, MRPL35, MRPL36, MRPL37, MRPL38, MRPL39, MRPL4, MRPL40, MRPL41, MRPL42, MRPL43, MRPL44, MRPL45, MRPL46, MRPL47, MRPL48, MRPL49, MRPL50, MRPL51, MRPL52, MRPL53, MRPL54, MRPL55, MRPL57, MRPL58, MRPL9, MRPS10, MRPS11, MRPS12, MRPS14, MRPS15, MRPS16, MRPS17, MRPS18A, MRPS18B, MRPS18C, MRPS2, MRPS21, MRPS22, MRPS23, MRPS24, MRPS25, MRPS26, MRPS27, MRPS28, MRPS30, MRPS31, MRPS33, MRPS34, MRPS35, MRPS36, MRPS5, MRPS6, MRPS7, MRPS9, MRRF, MRS2, MRTO4, MRVII, MS4A1, MS4A10, MS4A12, MS4A13, MS4A14, MS4A15, MS4A2, MS4A3, MS4A4A, MS4A4E, MS4A5, MS4A6A, MS4A6E, MS4A7, MS4A8, MSANTD1, MSANTD2, MSANTD3, MSANTD3-TMEFF1, MSANTD4, MSC, MSGN1, MSH2, MSH3, MSH4, MSH5, MSH5-SAPCD1, MSH6, MSI1, MSI2, MSL1, MSL2, MSL3, MSLN, MSLNL, MSMB, MSMO1, MSMP, MSN, MSR1, MSRA, MSRB1, MSRB2, MSRB3, MSS51, MST1, MST1R, MSTN, MSTO1, MSX1, MSX2, MT1A, MT1B, MT1E, MT1F, MT1G, MT1H, MT1IL1, MT1M, MT1X, MT2A, MT3, MT4, MTA1, MTA2, MTA3, MTAP, MT-ATP6, MT-ATP8, MTBP, MTCH1, MTCH2, MTCL1, MT-CO1, MT-C02, MT-C03, MTCP1, MT-CYB, MTDH, MTERF1, MTERF2, MTERF3, MTERF4, MTF1, MTF2, MTFMT, MTFP1, MTFR1, MTFR1L, MTFR2, MTG1, MTG2, MTHFD1, MTHFD1L, MTHFD2, MTHFD2L, MTHFR, MTHFS, MTHFSD, MTIF2, MTIF3, MTM1, MTMR1, MTMR10, MTMR11, MTMR12, MTMR14, MTMR2, MTMR3, MTMR4, MTMR6, MTMR7, MTMR8, MTMR9, MT-ND1, MT-ND2, MT-ND3, MT-ND4, MT-ND4L, MT-ND5, MT-ND6, MTNR1A, MTNR1B, MTO1, MTOR, MTPAP, MTPN, MTR, MTRF1, MTRF1L, MTRNR2L1, MTRNR2L10, MTRNR2L11, MTRNR2L12, MTRNR2L13, MTRNR2L3, MTRNR2L4, MTRNR2L5, MTRNR2L6, MTRNR2L7, MTRNR2L8, MTRR, MTSS1, MTSS1L, MTTP, MTURN, MTUS1, MTUS2, MTX1, MTX2, MTX3, MUC1, MUC12, MUC13, MUC15, MUC16, MUC17, MUC2, MUC20, MUC21, MUC22, MUC3A, MUC4, MUC5AC, MUC5B, MUC6, MUC7, MUCL1, MUL1, MUM1, MUM1L1, MUS81, MUSK, MUSTN1, MUT, MUTYH, MVB12A, MVB12B, MVD, MVK, MVP, MX1, MX2, MXD1, MXD3, MXD4, MXII, MXRA5, MXRA7, MXRA8, MYADM, MYADML2, MYB, MYBBP1A, MYBL1, MYBL2, MYBPC1, MYBPC2, MYBPC3, MYBPH, MYBPHL, MYC, MYCBP, MYCBP2, MYCBPAP, MYCL, MYCN, MYCT1, MYD88, MYDGF, MYEF2, MYEOV, MYF5, MYF6, MYH1, MYH10, MYH11, MYH13, MYH14, MYH15, MYH2, MYH3, MYH4, MYH6, MYH7, MYH7B, MYH8, MYH9, MYL1, MYL10, MYL12A, MYL12B, MYL2, MYL3, MYL4, MYL5, MYL6, MYL6B, MYL7, MYL9, MYLIP, MYLK, MYLK2, MYLK3, MYLK4, MYLPF, MYMK, MYMX, MYNN, MYO10, MYO15A, MYO15B, MYO16, MYO18A, MYO18B, MYO19, MYO1A, MYO1B, MYO1C, MYO1D, MYO1E, MYO1F, MYO1G, MYO1H, MYO3A, MYO3B, MYO5A, MYO5B, MYO5C, MYO6, MYO7A, MYO7B, MYO9A, MYO9B, MYOC, MYOCD, MYOCOS, MYOD1, MYOF, MYOG, MYOM1, MYOM2, MYOM3, MYOT, MYOZ1, MYOZ2, MYOZ3, MYPN, MYPOP, MYRF, MYRFL, MYRIP, MYSM1, MYT1, MYT1L, MYZAP, MZB1, MZF1, MZT1, MZT2A, MZT2B, N4BP1, N4BP2, N4BP2L1, N4BP2L2, N4BP3, N6AMT1, NAA10, NAA11, NAA15, NAA16, NAA20, NAA25, NAA30, NAA35, NAA38, NAA40, NAA50, NAA60, NAAA, NAALAD2, NAALADL1, NAALADL2, NAB1, NAB2, NABP1, NABP2, NACA, NACA2, NACAD, NACC1, NACC2, NADK, NADK2, NADSYN1, NAE1, NAF1, NAGA, NAGK, NAGLU, NAGPA, NAGS, NAIF1, NAIP, NALCN, NAMPT, NANOG, NANOGNB, NANOGP8, NANOSI, NANOS2, NANOS3, NANP, NANS, NAP1L1, NAP1L2, NAP1L3, NAP1L4, NAP1L5, NAPA, NAPB, NAPEPLD, NAPG, NAPRT, NAPSA, NARF, NARFL, NARS, NARS2, NASP, NAT1, NAT10, NAT14, NAT16, NAT2, NAT6, NAT8, NAT8B, NAT8L, NAT9, NATD1, NAV1, NAV2, NAV3, NAXD, NAXE, NBAS, NBDY, NBEA, NBEAL1, NBEAL2, NBL1, NBN, NBPF1, NBPF10, NBPF11, NBPF12, NBPF14, NBPF15, NBPF19, NBPF20, NBPF26, NBPF3, NBPF4, NBPF6, NBPF9, NBR1, NCALD, NCAM1, NCAM2, NCAN, NCAPD2, NCAPD3, NCAPG, NCAPG2, NCAPH, NCAPH2, NCBP1, NCBP2, NCBP2-AS2, NCBP2L, NCBP3, NCCRP1, NCDN, NCEH1, NCF1, NCF2, NCF4, NCK1, NCK2, NCKAP1, NCKAP1L, NCKAP5, NCKAP5L, NCKIPSD, NCL, NCLN, NCMAP, NCOA1, NCOA2, NCOA3, NCOA4, NCOA5, NCOA6, NCOA7, NCOR1, NCOR2, NCR1, NCR2, NCR3, NCR3LG1, NCS1, NCSTN, NDC1, NDC80, NDE1, NDEL1, NDFIP1, NDFIP2, NDN, NDNF, NDOR1, NDP, NDRG1, NDRG2, NDRG3, NDRG4, NDST1, NDST2, NDST3, NDST4, NDUFA1, NDUFA10, NDUFA11, NDUFA12, NDUFA13, NDUFA2, NDUFA3, NDUFA4, NDUFA4L2, NDUFA5, NDUFA6, NDUFA7, NDUFA8, NDUFA9, NDUFAB1, NDUFAF1, NDUFAF2, NDUFAF3, NDUFAF4, NDUFAF5, NDUFAF6, NDUFAF7, NDUFAF8, NDUFB1, NDUFB10, NDUFB11, NDUFB2, NDUFB3, NDUFB4, NDUFB5, NDUFB6, NDUFB7, NDUFB8, NDUFB9, NDUFC1, NDUFC2, NDUFC2-KCTD14, NDUFS1, NDUFS2, NDUFS3, NDUFS4, NDUFS5, NDUFS6, NDUFS7, NDUFS8, NDUFV1, NDUFV2, NDUFV3, NEB, NEBL, NECAB1, NECAB2, NECAB3, NECAP1, NECAP2, NECTINI, NECTIN2, NECTIN3, NECTIN4, NEDD1, NEDD4, NEDD4L, NEDD8, NEDD8-MDP1, NEDD9, NEFH, NEFL, NEFM, NEGR1, NEIL1, NEIL2, NEIL3, NEK1, NEK10, NEK11, NEK2, NEK3, NEK4, NEK5, NEK6, NEK7, NEK8, NEK9, NELFA, NELFB, NELFCD, NELFE, NELL1, NELL2, NEMF, NEMP1, NEMP2, NENF, NEO1, NEPRO, NES, NET1, NETO1, NETO2, NEU1, NEU2, NEU3, NEU4, NEURL1, NEURL1B, NEURL2, NEURL3, NEURL4, NEUROD1, NEUROD2, NEUROD4, NEUROD6, NEUROG1, NEUROG2, NEUROG3, NEXMIF, NEXN, NF1, NF2, NFAM1, NFASC, NFAT5, NFATC1, NFATC2, NFATC2IP, NFATC3, NFATC4, NFE2, NFE2L1, NFE2L2, NFE2L3, NFE4, NFIA, NFIB, NFIC, NFIL3, NFIX, NFKB1, NFKB2, NFKBIA, NFKBIB, NFKBID, NFKBIE, NFKBIL1, NFKBIZ, NFRKB, NFS1, NFU1, NFX1, NFXL1, NFYA, NFYB, NFYC, NGB, NGDN, NGEF, NGF, NGFR, NGLY1, NGRN, NHEJ1, NHLH1, NHLH2, NHLRC1, NHLRC2, NHLRC3, NHLRC4, NHP2, NHS, NHSL1, NHSL2, NICN1, NID1, NID2, NIF3L1, NIFK, NIM1K, NIN, NINJ1, NINJ2, NINL, NIP7, NIPA1, NIPA2, NIPAL1, NIPAL2, NIPAL3, NIPAL4, NIPBL, NIPSNAP1, NIPSNAP2, NIPSNAP3A, NIPSNAP3B, NISCH, NIT1, NIT2, NKAIN1, NKAIN2, NKAIN3, NKAIN4, NKAP, NKAPL, NKD1, NKD2, NKG7, NKIRAS1, NKIRAS2, NKPD1, NKRF, NKTR, NKX1-1, NKX1-2, NKX2-1, NKX2-2, NKX2-3, NKX2-4, NKX2-5, NKX2-6, NKX2-8, NKX3-1, NKX3-2, NKX6-1, NKX6-2, NKX6-3, NLE1, NLGN1, NLGN2, NLGN3, NLGN4X, NLGN4Y, NLK, NLN, NLRC3, NLRC4, NLRC5, NLRP1, NLRP10, NLRP11, NLRP12, NLRP13, NLRP14, NLRP2, NLRP2B, NLRP3, NLRP4, NLRP5, NLRP6, NLRP7, NLRP8, NLRP9, NLRX1, NMB, NMBR, NMD3, NME1, NME1-NME2, NME2, NME3, NME4, NME5, NME6, NME7, NME8, NME9, NMI, NMNAT1, NMNAT2, NMNAT3, NMRAL1, NMRK1, NMRK2, NMS, NMT1, NMT2, NMU, NMUR1, NMUR2, NNAT, NNMT, NNT, NOA1, NOB1, NOBOX, NOC2L, NOC3L, NOC4L, NOCT, NOD1, NOD2, NODAL, NOG, NOL10, NOL11, NOL12, NOL3, NOL4, NOL4L, NOL6, NOL7, NOL8, NOL9, NOLC1, NOM1, NOMO1, NOMO2, NOMO3, NONO, NOP10, NOP14, NOP16, NOP2, NOP53, NOP56, NOP58, NOP9, NOS1, NOS1AP, NOS2, NOS3, NOSIP, NOSTRIN, NOTCH1, NOTCH2, NOTCH2NL, NOTCH3, NOTCH4, NOTO, NOTUM, NOV, NOVA1, NOVA2, NOX1, NOX3, NOX4, NOX5, NOXA1, NOXO1, NOXRED1, NPAP1, NPAS1, NPAS2, NPAS3, NPAS4, NPAT, NPB, NPBWR1, NPBWR2, NPC1, NPC1L1, NPC2, NPDC1, NPEPL1, NPEPPS, NPFF, NPFFR1, NPFFR2, NPHP1, NPHP3, NPHP3-ACAD11, NPHP4, NPHS1, NPHS2, NPIPA1, NPIPA2, NPIPA3, NPIPA5, NPIPA7, NPIPA8, NPIPB11, NPIPB12, NPIPB13, NPIPB15, NPIPB2, NPIPB3, NPIPB4, NPIPB5, NPIPB6, NPIPB7, NPIPB8, NPIPB9, NPL, NPLOC4, NPM1, NPM2, NPM3, NPNT, NPPA, NPPB, NPPC, NPR1, NPR2, NPR3, NPRL2, NPRL3, NPS, NPSR1, NPTN, NPTX1, NPTX2, NPTXR, NPVF, NPW, NPY, NPY1R, NPY2R, NPY4R, NPY4R2, NPY5R, NQO1, NQO2, NR0B1, NR0B2, NR1D1, NR1D2, NR1H2, NR1H3, NR1H4, NR1I2, NR1I3, NR2C1, NR2C2, NR2C2AP, NR2E1, NR2E3, NR2F1, NR2F2, NR2F6, NR3C1, NR3C2, NR4A1, NR4A2, NR4A3, NR5A1, NR5A2, NR6A1, NRAP, NRARP, NRAS, NRBF2, NRBP1, NRBP2, NRCAM, NRDC, NRDE2, NREP, NRF1, NRG1, NRG2, NRG3, NRG4, NRGN, NRIP1, NRIP2, NRIP3, NRK, NRL, NRM, NRN1, NRN1L, NRP1, NRP2, NRROS, NRSN1, NRSN2, NRTN, NRXN1, NRXN2, NRXN3, NSA2, NSD1, NSD2, NSD3, NSDHL, NSF, NSFL1C, NSL1, NSMAF, NSMCE1, NSMCE2, NSMCE3, NSMCE4A, NSMF, NSRP1, NSUN2, NSUN3, NSUN4, NSUN5, NSUN6, NSUN7, NT5C, NT5C1A, NT5C1B, NT5C1B-RDH14, NT5C2, NT5C3A, NT5C3B, NT5DC1, NT5DC2, NT5DC3, NT5DC4, NT5E, NT5M, NTAN1, NTF3, NTF4, NTHL1, NTM, NTMT1, NTN1, NTN3, NTN4, NTN5, NTNG1, NTNG2, NTPCR, NTRK1, NTRK2, NTRK3, NTS, NTSR1, NTSR2, NUAK1, NUAK2, NUB1, NUBP1, NUBP2, NUBPL, NUCB1, NUCB2, NUCKS1, NUDC, NUDCD1, NUDCD2, NUDCD3, NUDT1, NUDT10, NUDT11, NUDT12, NUDT13, NUDT14, NUDT15, NUDT16, NUDT16L1, NUDT17, NUDT18, NUDT19, NUDT2, NUDT21, NUDT22, NUDT3, NUDT4, NUDT4P1, NUDT5, NUDT6, NUDT7, NUDT8, NUDT9, NUF2, NUFIP1, NUFIP2, NUGGC, NUMA1, NUMB, NUMBL, NUP107, NUP133, NUP153, NUP155, NUP160, NUP188, NUP205, NUP210, NUP210L, NUP214, NUP35, NUP37, NUP43, NUP50, NUP54, NUP58, NUP62, NUP62CL, NUP85, NUP88, NUP93, NUP98, NUPL2, NUPR1, NUPR2, NUS1, NUSAP1, NUTF2, NUTM1, NUTM2A, NUTM2B, NUTM2D, NUTM2E, NUTM2F, NUTM2G, NVL, NWD1, NWD2, NXF1, NXF2, NXF2B, NXF3, NXF5, NXN, NXNL1, NXNL2, NXPE1, NXPE2, NXPE3, NXPE4, NXPH1, NXPH2, NXPH3, NXPH4, NXT1, NXT2, NYAP1, NYAP2, NYNRIN, NYX, OAF, OARD1, OAS1, OAS2, OAS3, OASL, OAT, OAZ1, OAZ2, OAZ3, OBP2A, OBP2B, OBSCN, OBSCN-AS1, OBSL1, OC90, OCA2, OCEL1, OCIAD1, OCIAD2, OCLM, OCLN, OCM, OCM2, OCRL, OCSTAMP, ODAM, ODC1, ODF1, ODF2, ODF2L, ODF3, ODF3B, ODF3L1, ODF3L2, ODF4, OFCC1, OFD1, OGDH, OGDHL, OGFOD1, OGFOD2, OGFOD3, OGFR, OGFRL1, OGG1, OGN, OGT, OIP5, OIT3, OLA1, OLAH, OLFM1, OLFM2, OLFM3, OLFM4, OLFML1, OLFML2A, OLFML2B, OLFML3, OLIG1, OLIG2, OLIG3, OLR1, OMA1, OMD, OMG, OMP, ONECUT1, ONECUT2, ONECUT3, OOEP, OOSP2, OPA1, OPA3, OPALIN, OPCML, OPHN1, OPLAH, OPN1LW, OPN1MW, OPN1MW2, OPN1MW3, OPN1SW, OPN3, OPN4, OPN5, OPRD1, OPRK1, OPRL1, OPRM1, OPRPN, OPTC, OPTN, OR10A2, OR10A3, OR10A4, OR10A5, OR10A6, OR10A7, OR10AC1, OR10AD1, OR10AG1, OR10C1, OR10D3, OR10G2, OR10G3, OR10G4, OR10G6, OR10G7, OR10G8, OR10G9, OR10H1, OR10H2, OR10H3, OR10H4, OR10H5, OR10J1, OR10J3, OR10J4, OR10J5, OR10K1, OR10K2, OR10P1, OR10Q1, OR10R2, OR10S1, OR10T2, OR10V1, OR10W1, OR10X1, OR10Z1, OR11A1, OR11G2, OR11H1, OR11H12, OR11H2, OR11H4, OR11H6, OR11H7, OR11L1, OR12D1, OR12D2, OR12D3, OR13A1, OR13C2, OR13C3, OR13C4, OR13C5, OR13C7, OR13C8, OR13C9, OR13D1, OR13F1, OR13G1, OR13H1, OR13J1, OR14A16, OR14A2, OR14C36, OR14I1, OR14J1, OR14K1, OR1A1, OR1A2, OR1B1, OR1C1, OR1D2, OR1D5, OR1E1, OR1E2, OR1F1, OR1G1, OR1I1, OR1J1, OR1J2, OR1J4, OR1K1, OR1L1, OR1L3, OR1L4, OR1L6, OR1L8, OR1M1, OR1N1, OR1N2, OR1P1, OR1Q1, OR1S1, OR1S2, OR2A1, OR2A12, OR2A14, OR2A2, OR2A25, OR2A4, OR2A42, OR2A5, OR2A7, OR2AE1, OR2AG1, OR2AG2, OR2AJ1, OR2AK2, OR2AP1, OR2AT4, OR2B11, OR2B2, OR2B3, OR2B6, OR2C1, OR2C3, OR2D2, OR2D3, OR2F1, OR2F2, OR2G2, OR2G3, OR2G6, OR2H1, OR2H2, OR2J1, OR2J2, OR2J3, OR2K2, OR2L13, OR2L2, OR2L3, OR2L5, OR2L8, OR2M2, OR2M3, OR2M4, OR2M5, OR2M7, OR2S2, OR2T1, OR2T10, OR2T11, OR2T12, OR2T2, OR2T27, OR2T29, OR2T3, OR2T33, OR2T34, OR2T35, OR2T4, OR2T5, OR2T6, OR2T7, OR2T8, OR2V1, OR2V2, OR2W1, OR2W3, OR2Y1, OR2Z1, OR3A1, OR3A2, OR3A3, OR4A15, OR4A16, OR4A47, OR4A5, OR4A8, OR4B1, OR4C11, OR4C12, OR4C13, OR4C15, OR4C16, OR4C3, OR4C45, OR4C46, OR4C5, OR4C6, OR4D1, OR4D10, OR4D11, OR4D2, OR4D5, OR4D6, OR4D9, OR4E1, OR4E2, OR4F15, OR4F16, OR4F17, OR4F21, OR4F29, OR4F3, OR4F4, OR4F5, OR4F6, OR4K1, OR4K13, OR4K14, OR4K15, OR4K17, OR4K2, OR4K3, OR4K5, OR4L1, OR4M1, OR4M2, OR4N2, OR4N4, OR4N5, OR4P4, OR4Q2, OR4Q3, OR4S1, OR4S2, OR4X1, OR4X2, OR51A2, OR51A4, OR51A7, OR51B2, OR51B4, OR51B5, OR51B6, OR51D1, OR51E1, OR51E2, OR51F1, OR51F2, OR51G1, OR51G2, OR51H1, OR51I1, OR51I2, OR51J1, OR51L1, OR51M1, OR51Q1, OR51S1, OR51T1, OR51V1, OR52A1, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR52Z1, OR56A1, OR56A3, OR56A4, OR56A5, OR56B1, OR56B4, OR5A1, OR5A2, OR5AC1, OR5AC2, OR5AK2, OR5AN1, OR5AP2, OR5AR1, OR5AS1, OR5AU1, OR5B12, OR5B17, OR5B2, OR5B21, OR5B3, OR5C1, OR5D13, OR5D14, OR5D16, OR5D18, OR5F1, OR5G3, OR5H1, OR5H14, OR5H15, OR5H2, OR5H6, OR5H8, OR5I1, OR5J2, OR5K1, OR5K2, OR5K3, OR5K4, OR5L1, OR5L2, OR5M1, OR5M10, OR5M11, OR5M3, OR5M8, OR5M9, OR5P2, OR5P3, OR5R1, OR5T1, OR5T2, OR5T3, OR5V1, OR5W2, OR6A2, OR6B1, OR6B2, OR6B3, OR6C1, OR6C2, OR6C3, OR6C4, OR6C6, OR6C65, OR6C68, OR6C70, OR6C74, OR6C75, OR6C76, OR6F1, OR6J1, OR6K2, OR6K3, OR6K6, OR6M1, OR6N1, OR6N2, OR6P1, OR6Q1, OR6S1, OR6T1, OR6V1, OR6X1, OR6Y1, OR7A10, OR7A17, OR7A5, OR7C1, OR7C2, OR7D2, OR7D4, OR7E24, OR7G1, OR7G2, OR7G3, OR8A1, OR8B12, OR8B2, OR8B3, OR8B4, OR8B8, OR8D1, OR8D2, OR8D4, OR8G1, OR8G5, OR8H1, OR8H2, OR8H3, OR8I2, OR8J1, OR8J2, OR8J3, OR8K1, OR8K3, OR8K5, OR8S1, OR8U1, OR8U8, OR9A2, OR9A4, OR9G1, OR9G4, OR9G9, OR9H1P, OR9I1, OR9K2, OR9Q1, OR9Q2, ORAI1, ORAI2, ORAI3, ORAOV1, ORC1, ORC2, ORC3, ORC4, ORC5, ORC6, ORM1, ORM2, ORMDL1, ORMDL2, ORMDL3, OS9, OSBP, OSBP2, OSBPL10, OSBPL11, OSBPL1A, OSBPL2, OSBPL3, OSBPL5, OSBPL6, OSBPL7, OSBPL8, OSBPL9, OSCAR, OSCP1, OSER1, OSGEP, OSGEPL1, OSGIN1, OSGIN2, OSM, OSMR, OSR1, OSR2, OST4, OSTC, OSTF1, OSTM1, OSTN, OTC, OTOA, OTOF, OTOG, OTOGL, OTOL1, OTOP1, OTOP2, OTOP3, OTOR, OTOS, OTP, OTUB1, OTUB2, OTUD1, OTUD3, OTUD4, OTUD5, OTUD6A, OTUD6B, OTUD7A, OTUD7B, OTULIN, OTX1, OTX2, OVCA2, OVCH1, OVCH2, OVGP1, OVOL1, OVOL2, OVOL3, OXA1L, OXCT1, OXCT2, OXER1, OXGR1, OXLD1, OXNAD1, OXR1, OXSM, OXSR1, OXT, OXTR, P2RX1, P2RX2, P2RX3, P2RX4, P2RX5, P2RX5-TAX1BP3, P2RX6, P2RX7, P2RY1, P2RY10, P2RY11, P2RY12, P2RY13, P2RY14, P2RY2, P2RY4, P2RY6, P2RY8, P3H1, P3H2, P3H3, P3H4, P4HA1, P4HA2, P4HA3, P4HB, P4HTM, PA2G4, PAAF1, PABPC1, PABPC1L, PABPC1L2A, PABPC1L2B, PABPC3, PABPC4, PABPC4L, PABPC5, PABPN1, PABPN1L, PACRG, PACRGL, PACS1, PACS2, PACSIN1, PACSIN2, PACSIN3, *PADI1, PADI2, PADI3, PADI4, PADI6*, PAEP, PAF1, PAFAH1B1, PAFAH1B2, PAFAH1B3, PAFAH2, PAG1, PAGE1, PAGE2, PAGE2B, PAGE3, PAGE4, PAGE5, PAGR1, PAH, PAICS, PAIP1, PAIP2, PAIP2B, PAK1, PAK1IP1, PAK2, PAK3, PAK4, PAK5, PAK6, PALB2, PALD1, PALLD, PALM, PALM2, PALM2-AKAP2, PALM3, PALMD, PAM, PAM16, PAMR1, PAN2, PAN3, PANK1, PANK2, PANK3, PANK4, PANO1, PANX1, PANX2, PANX3, PAOX, PAPD4, PAPD5, PAPD7, PAPLN, PAPOLA, PAPOLB, PAPOLG, PAPPA, PAPPA2, PAPSS1, PAPSS2, PAQR3, PAQR4, PAQR5, PAQR6, PAQR7, PAQR8, PAQR9, PARD3, PARD3B, PARD6A, PARD6B, PARD6G, PARG, PARK7, PARL, PARM1, PARN, PARP1, PARP10, PARP11, PARP12, PARP14, PARP15, PARP16, PARP2, PARP3, PARP4, PARP6, PARP8, PARP9, PARPBP, PARS2, PARVA, PARVB, PARVG, PASD1, PASK, PATE1, PATE2, PATE3, PATE4, PATJ, PATL1, PATL2, PATZ1, PAWR, PAX1, PAX2, PAX3, PAX4, PAX5, PAX6, PAX7, PAX8, PAX9, PAXBP1, PAXIP1, PAXX, PBDC1, PBK, PBLD, PBOV1, PBRM1, PBX1, PBX2, PBX3, PBX4, PBXIP1, PC, PCBD1, PCBD2, PCBP1, PCBP2, PCBP3, PCBP4, PCCA, PCCB, PCDH1, PCDH10, PCDH11X, PCDH11Y, PCDH12, PCDH15, PCDH17, PCDH18, PCDH19, PCDH20, PCDH7, PCDH8, PCDH9, PCDHA1, PCDHA10, PCDHA11, PCDHA12, PCDHA13, PCDHA2, PCDHA3, PCDHA4, PCDHA5, PCDHA6, PCDHA7, PCDHA8, PCDHA9, PCDHAC1, PCDHAC2, PCDHB1, PCDHB10, PCDHB11, PCDHB12, PCDHB13, PCDHB14, PCDHB15, PCDHB16, PCDHB2, PCDHB3, PCDHB4, PCDHB5, PCDHB6, PCDHB7, PCDHB8, PCDHB9, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PCDHGC3, PCDHGC4, PCDHGC5, PCED1A, PCED1B, PCF11, PCGF1, PCGF2, PCGF3, PCGF5, PCGF6, PCID2, PCIF1, PCK1, PCK2, PCLAF, PCLO, PCM1, PCMT1, PCMTD1, PCMTD2, PCNA, PCNP, PCNT, PCNX1, PCNX2, PCNX3, PCNX4, PCOLCE, PCOLCE2, PCOTH, PCP2, PCP4, PCP4L1, PCSK1, PCSK1N, PCSK2, PCSK4, PCSK5, PCSK6, PCSK7, PCSK9, PCTP, PCYOX1, PCYOX1L, PCYT1A, PCYT1B, PCYT2, PDAP1, PDC, PDCD1, PDCD10, PDCD11, PDCD1LG2, PDCD2, PDCD2L, PDCD4, PDCD5, PDCD6, PDCD6IP, PDCD7, PDCL, PDCL2, PDCL3, PDE10A, PDE11A, PDE12, PDE1A, PDE1B, PDE1C, PDE2A, PDE3A, PDE3B, PDE4A, PDE4B, PDE4C, PDE4D, PDE4DIP, PDE5A, PDE6A, PDE6B, PDE6C, PDE6D, PDE6G, PDE6H, PDE7A, PDE7B, PDE8A, PDE8B, PDE9A, PDF, PDGFA, PDGFB, PDGFC, PDGFD, PDGFRA, PDGFRB, PDGFRL, PDHA1, PDHA2, PDHB, PDHX, PDIA2, PDIA3, PDIA4, PDIA5, PDIA6, PDIK1L, PDILT, PDK1, PDK2, PDK3, PDK4, PDL1M1, PDL1M2, PDL1M3, PDL1M4, PDL1M5, PDL1M7, PDP1, PDP2, PDPK1, PDPN, PDPR, PDRG1, PDS5A, PDS5B, PDSS1, PDSS2, PDX1, PDXDC1, PDXK, PDXP, PDYN, PDZD11, PDZD2, PDZD3, PDZD4, PDZD7, PDZD8, PDZD9, PDZK1, PDZK1IP1, PDZRN3, PDZRN4, PEA15, PEAK1, PEAR1, PEBP1, PEBP4, PECAM1, PECR, PEF1, PEG10, PEG3, *PELI1, PELI2, PELI3*, PELO, PELP1, PEMT, PENK, PEPD, PER1, PER2, PER3, PERM1, PERP, PES1, PET100, PET117, PEX1, PEX10, PEX11A, PEX11B, PEX11G, PEX12, PEX13, PEX14, PEX16, PEX19, PEX2, PEX26, PEX3, PEX5, PEX5L, PEX6, PEX7, PF4, PF4V1, PFAS, PFDN1, PFDN2, PFDN4, PFDN5, PFDN6, PFKFB1, PFKFB2, PFKFB3, PFKFB4, PFKL, PFKM, PFKP, PFN1, PFN2, PFN3, PFN4, PGA3, PGA4, PGA5, PGAM1, PGAM2, PGAM4, PGAM5, PGAP1, PGAP2, PGAP3, PGBD1, PGBD2, PGBD4, PGBD5, PGC, PGD, PGF, PGGHG, PGGT1B, PGK1, PGK2, PGLS, PGLYRP1, PGLYRP2, PGLYRP3, PGLYRP4, PGM1, PGM2, PGM2L1, PGM3, PGM5, PGP, PGPEP1, PGPEP1L, PGR, PGRMC1, PGRMC2, PGS1, PHACTR1, PHACTR2, PHACTR3, PHACTR4, PHAX, PHB, PHB2, PHC1, PHC2, PHC3, PHEX, PHF1, PHF10, PHF11, PHF12, PHF13, PHF14, PHF19, PHF2, PHF20, PHF20L1, PHF21A, PHF21B, PHF23, PHF24, PHF3, PHF5A, PHF6, PHF7, PHF8, PHGDH, PHGR1, PHIP, PHKA1, PHKA2, PHKB, PHKG1, PHKG2, PHLDA1, PHLDA2, PHLDA3, PHLDB1, PHLDB2, PHLDB3, PHLPP1, PHLPP2, PHOSPHO1, PHOSPHO2, PHOX2A, PHOX2B, PHPT1, PHRF1, PHTF1, PHTF2, PHYH, PHYHD1, PHYHIP, PHYHIPL, PHYKPL, PI15, PI16, PI3, PI4K2A, PI4K2B, PI4KA, PI4KB, PIANP, PIAS1, PIAS2, PIAS3, PIAS4, PIBF1, PICALM, PICK1, PID1, PIDD1, PIEZO1, PIEZO2, PIF1, PIFO, PIGA, PIGB, PIGBOS1, PIGC, PIGF, PIGG, PIGH, PIGK, PIGL, PIGM, PIGN, PIGO, PIGP, PIGQ, PIGR, PIGS, PIGT, PIGU, PIGV, PIGW, PIGX, PIGY, PIGZ, PIH1D1, PIH1D2, PIH1D3, PIK3AP1, PIK3C2A, PIK3C2B, PIK3C2G, PIK3C3, PIK3CA, PIK3CB, PIK3CD, PIK3CG, PIK3IP1, PIK3R1, PIK3R2, PIK3R3, PIK3R4, PIK3R5, PIK3R6, PIKFYVE, PILRA, PILRB, PIM1, PIM2, PIM3, PIMREG, PIN1, PIN4, PINK1, PINLYP, PINX1, PIP, PIP4K2A, PIP4K2B, PIP4K2C, PIP5K1A, PIP5K1B, PIP5K1C, PIP5KL1, PIPOX, PIR, PIRT, PISD, PITHD1, PITPNA, PITPNB, PITPNC1, PITPNM1, PITPNM2, PITPNM3, PITRM1, PITX1, PITX2, PITX3, PIWIL1, PIWIL2, PIWIL3, PIWIL4, PJA1, PJA2, PKD1, PKD1L1, PKD1L2, PKD1L3, PKD2, PKD2L1, PKD2L2, PKDCC, PKDREJ, PKHD1, PKHDIL1, PKIA, PKIB, PKIG, PKLR, PKM, PKMYT1, PKN1, PKN2, PKN3, PKNOX1, PKNOX2, PKP1, PKP2, PKP3, PKP4, PLA1A, PLA2G10, PLA2G12A, PLA2G12B, PLA2G15, PLA2G16, PLA2G1B, PLA2G2A, PLA2G2C, PLA2G2D, PLA2G2E, PLA2G2F, PLA2G3, PLA2G4A, PLA2G4B, PLA2G4C, PLA2G4D, PLA2G4E, PLA2G4F, PLA2G5, PLA2G6, PLA2G7, PLA2R1, PLAA, PLAC1, PLAC4, PLAC8, PLAC8L1, PLAC9, PLAG1, PLAGL1, PLAGL2, PLAT, PLAU, PLAUR, PLB1, PLBD1, PLBD2, PLCB1, PLCB2, PLCB3, PLCB4, PLCD1, PLCD3, PLCD4, PLCE1, PLCG1, PLCG2, PLCH1, PLCH2, PLCL1, PLCL2, PLCXD1, PLCXD2, PLCXD3, PLCZ1, PLD1, PLD2, PLD3, PLD4, PLD5, PLD6, PLEC, PLEK, PLEK2, PLEKHA1, PLEKHA2, PLEKHA3, PLEKHA4, PLEKHA5, PLEKHA6, PLEKHA7, PLEKHA8, PLEKHB1, PLEKHB2, PLEKHD1, PLEKHF1, PLEKHF2, PLEKHG1, PLEKHG2, PLEKHG3, PLEKHG4, PLEKHG4B, PLEKHG5, PLEKHG6, PLEKHG7, PLEKHH1, PLEKHH2, PLEKHH3, PLEKHJ1, PLEKHM1, PLEKHM2, PLEKHM3, PLEKHN1, PLEKHO1, PLEKHO2, PLEKHS1, PLET1, PLG, PLGLB1, PLGLB2, PLGRKT, PLIN1, PLIN2, PLIN3, PLIN4, PLIN5, PLK1, PLK2, PLK3, PLK4, PLK5, PLLP, PLN, PLOD1, PLOD2, PLOD3, PLP1, PLP2, PLPBP, PLPP1, PLPP2, PLPP3, PLPP4, PLPP5, PLPP6, PLPP7, PLPPR1, PLPPR2, PLPPR3, PLPPR4, PLPPR5, PLRG1, PLS1, PLS3, PLSCR1, PLSCR2, PLSCR3, PLSCR4, PLSCR5, PLTP, PLVAP, PLXDC1, PLXDC2, PLXNA1, PLXNA2, PLXNA3, PLXNA4, PLXNB1, PLXNB2, PLXNB3, PLXNC1, PLXND1, PM20D1, PM20D2, PMAIP1, PMCH, PMEL, PMEPA1, PMF1, PMF1-BGLAP, PMFBP1, PML, PMM1, PMM2, PMP2, PMP22, PMPCA, PMPCB, PMS1, PMS2, PMVK, PNCK, PNISR, PNKD, PNKP, PNLDC1, PNLIP, PNLIPRP1, PNLIPRP2, PNLIPRP3, PNMA1, PNMA2, PNMA3, PNMA5, PNMA6A, PNMA6E, PNMA6F, PNMA8A, PNMA8B, PNMA8C, PNMT, PNN, PNO1, PNOC, PNP, PNPLA1, PNPLA2, PNPLA3, PNPLA4, PNPLA5, PNPLA6, PNPLA7, PNPLA8, PNPO, PNPT1, PNRC1, PNRC2, POC1A, POC1B, POC1B-GALNT4, POC5, PODN, PODNL1, PODXL, PODXL2, POF1B, POFUT1, POFUT2, POGK, POGLUT1, POGZ, POLA1, POLA2, POLB, POLD1, POLD2, POLD3, POLD4, POLDIP2, POLDIP3, POLE, POLE2, POLE3, POLE4, POLG, POLG2, POLH, POLI, POLK, POLL, POLM, POLN, POLQ, POLR1A, POLR1B, POLR1C, POLR1D, POLR1E, POLR2A, POLR2B, POLR2C, POLR2D, POLR2E, POLR2F, POLR2G, POLR2H, POLR2I, POLR2J, POLR2J2, POLR2J3, POLR2K, POLR2L, POLR2M, POLR3A, POLR3B, POLR3C, POLR3D, POLR3E, POLR3F, POLR3G, POLR3GL, POLR3H, POLR3K, POLRMT, POM121, POM121C, POM121L12, POM121L2, POMC, POMGNT1, POMGNT2, POMK, POMP, POMT1, POMT2, POMZP3, PON1, PON2, PON3, POP1, POP4, POP5, POP7, POPDC2, POPDC3, POR, PORCN, POSTN, POT1, POTEA, POTEB, POTEB2, POTEB3, POTEC, POTED, POTEE, POTEF, POTEG, POTEH, POTEI, POTEJ, POTEM, POU1F1, POU2AF1, POU2F1, POU2F2, POU2F3, POU3F1, POU3F2, POU3F3, POU3F4, POU4F1, POU4F2, POU4F3, POU5F1, POU5F1B, POU5F2, POU6F1, POU6F2, PP2D1, PPA1, PPA2, PPAN, PPAN-P2RY11, PPARA, PPARD, PPARG, PPARGC1A, PPARGC1B, PPAT, PPBP, PPCDC, PPCS, PPDPF, PPEF1, PPEF2, PPFIA1, PPFIA2, PPFIA3, PPFIA4, PPFIBP1, PPFIBP2, PPHLN1, PPIA, PPIAL4A, PPIAL4C, PPIAL4D, PPIAL4E, PPIAL4F, PPIAL4G, PPIB, PPIC, PPID, PPIE, PPIF, PPIG, PPIH, PPIL1, PPIL2, PPIL3, PPIL4, PPIL6, PPIP5K1, PPIP5K2, PPL, PPM1A, PPM1B, PPM1D, PPM1E, PPM1F, PPM1G, PPM1H, PPM1J, PPM1K, PPM1L, PPM1M, PPM1N, PPME1, PPOX, PPP1CA, PPP1CB, PPP1CC, PPP1R10, PPP1R11, PPP1R12A, PPP1R12B, PPP1R12C, PPP1R13B, PPP1R13L, PPP1R14A, PPP1R14B, PPP1R14C, PPP1R14D, PPP1R15A, PPP1R15B, PPP1R16A, PPP1R16B, PPP1R17, PPP1R18, PPP1R1A, PPP1R1B, PPP1R1C, PPP1R2, PPP1R21, PPP1R26, PPP1R27, PPP1R2P3, PPP1R2P9, PPP1R32, PPP1R35, PPP1R36, PPP1R37, PPP1R3A, PPP1R3B, PPP1R3C, PPP1R3D, PPP1R3E, PPP1R3F, PPP1R3G, PPP1R42, PPP1R7, PPP1R8, PPP1R9A, PPP1R9B, PPP2CA, PPP2CB, PPP2R1A, PPP2R1B, PPP2R2A, PPP2R2B, PPP2R2C, PPP2R2D, PPP2R3A, PPP2R3B, PPP2R3C, PPP2R5A, PPP2R5B, PPP2R5C, PPP2R5D, PPP2R5E, PPP3CA, PPP3CB, PPP3CC, PPP3R1, PPP3R2, PPP4C, PPP4R1, PPP4R2, PPP4R3A, PPP4R3B, PPP4R3CP, PPP4R4, PPP5C, PPP5D1, PPP6C, PPP6R1, PPP6R2, PPP6R3, PPRC1, PPT1, PPT2, PPT2-EGFL8, PPTC7, PPWD1, PPY, PQBP1, PQLC1, PQLC2, PQLC2L, PQLC3, PRAC1, PRAC2, PRADC1, PRAF2, PRAG1, PRAM1, PRAME, PRAMEF1, PRAMEF10, PRAMEF11, PRAMEF12, PRAMEF13, PRAMEF14, PRAMEF15, PRAMEF17, PRAMEF18, PRAMEF19, PRAMEF2, PRAMEF20, PRAMEF25, PRAMEF26, PRAMEF27, PRAMEF33, PRAMEF4, PRAMEF5, PRAMEF6, PRAMEF7, PRAMEF8, PRAMEF9, PRAPI, PRB1, PRB2, PRB3, PRB4, PRC1, PRCC, PRCD, PRCP, PRDM1, PRDM10, PRDM11, PRDM12, PRDM13, PRDM14, PRDM15, PRDM16, PRDM2, PRDM4, PRDM5, PRDM6, PRDM7, PRDM8, PRDM9, PRDX1, PRDX2, PRDX3, PRDX4, PRDX5, PRDX6, PREB, PRELID1, PRELID2, PRELID3A, PRELID3B, PRELP, PREP, PREPL, PREX1, PREX2, PRF1, PRG2, PRG3, PRG4, PRH1, PRH2, PRICKLE1, PRICKLE2, PRICKLE3, PRICKLE4, PRIMI, PRIM2, PRIMA1, PRIMPOL, PRKAA1, PRKAA2, PRKAB1, PRKAB2, PRKACA, PRKACB, PRKACG, PRKAG1, PRKAG2, PRKAG3, PRKAR1A, PRKAR1B, PRKAR2A, PRKAR2B, PRKCA, PRKCB, PRKCD, PRKCE, PRKCG, PRKCH, PRKCI, PRKCQ, PRKCSH, PRKCZ, PRKD1, PRKD2, PRKD3, PRKDC, PRKG1, PRKG2, PRKN, PRKRA, PRKRIP1, PRKX, PRL, PRLH, PRLHR, PRLR, PRM1, PRM2, PRM3, PRMT1, PRMT2, PRMT3, PRMT5, PRMT6, PRMT7, PRMT8, PRMT9, PRND, PRNP, PRNT, PROB1, PROC, PROCA1, PROCR, PRODH, PRODH2, PROK1, PROK2, PROKR1, PROKR2, PROM1, PROM2, PROP1, PRORY, PROS1, PROSER1, PROSER2, PROSER3, PROXI, PROX2, PROZ, PRPF18, PRPF19, PRPF3, PRPF31, PRPF38A, PRPF38B, PRPF39, PRPF4, PRPF40A, PRPF40B, PRPF4B, PRPF6, PRPF8, PRPH, PRPH2, PRPS1, PRPS1L1, PRPS2, PRPSAP1, PRPSAP2, PRR11, PRR12, PRR13, PRR14, PRR14L, PRR15, PRR15L, PRR16, PRR18, PRR19, PRR20A, PRR20B, PRR20C, PRR20D, PRR20E, PRR21, PRR22, PRR23A, PRR23B, PRR23C, PRR23D1, PRR23D2, PRR25, PRR26, PRR27, PRR29, PRR3, PRR30, PRR32, PRR34, PRR35, PRR36, PRR4, PRR5, PRR5-ARHGAP8, PRR5L, PRR7, PRR9, PRRC1, PRRC2A, PRRC2B, PRRC2C, PRRG1, PRRG2, PRRG3, PRRG4, PRRT1, PRRT2, PRRT3, PRRT4, PRRX1, PRRX2, PRSS1, PRSS12, PRSS16, PRSS2, PRSS21, PRSS22, PRSS23, PRSS27, PRSS3, PRSS33, PRSS35, PRSS36, PRSS37, PRSS38, PRSS41, PRSS42, PRSS45, PRSS46, PRSS48, PRSS50, PRSS51, PRSS53, PRSS54, PRSS55, PRSS56, PRSS57, PRSS58, PRSS8, PRTFDC1, PRTG, PRTN3, PRUNE1, PRUNE2, PRX, PRY, PRY2, PSAP, PSAPLI, PSATI, PSCA, PSD, PSD2, PSD3, PSD4, PSENI, PSEN2, PSENEN, PSG1, PSG11, PSG2, PSG3, PSG4, PSG5, PSG6, PSG7, PSG8, PSG9, PSIP1, PSKH1, PSKH2, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC3IP, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSMEl, PSME2, PSME3, PSME4, PSMF1, PSMG1, PSMG2, PSMG3, PSMG4, PSORSICI, PSORS1C2, PSPC1, PSPH, PSPN, PSRC1, PSTK, PSTPIP1, PSTPIP2, PTAFR, PTAR1, PTBP1, PTBP2, PTBP3, PTCD1, PTCD2, PTCD3, PTCH1, PTCH2, PTCHD1, PTCHD3, PTCHD4, PTCRA, PTDSS1, PTDSS2, PTEN, PTER, PTF1A, PTGDR, PTGDR2, PTGDS, PTGER1, PTGER2, PTGER3, PTGER4, PTGES, PTGES2, PTGES3, PTGES3L, PTGES3L-AARSD1, PTGFR, PTGFRN, PTGIR, PTGIS, PTGR1, PTGR2, PTGS1, PTGS2, PTH, PTH1R, PTH2, PTH2R, PTHLH, PTK2, PTK2B, PTK6, PTK7, PTMA, PTMS, PTN, PTOV1, PTP4A1, PTP4A2, PTP4A3, PTPA, PTPDC1, PTPMT1, PTPN1, PTPN11, PTPN12, PTPN13, PTPN14, PTPN18, PTPN2, PTPN20, PTPN21, PTPN22, PTPN23, PTPN3, PTPN4, PTPN5, PTPN6, PTPN7, PTPN9, PTPRA, PTPRB, PTPRC, PTPRCAP, PTPRD, PTPRE, PTPRF, PTPRG, PTPRH, PTPRJ, PTPRK, PTPRM, PTPRN, PTPRN2, PTPRO, PTPRQ, PTPRR, PTPRS, PTPRT, PTPRU, PTPRZ1, PTRH1, PTRH2, PTRHD1, PTS, PTTG1, PTTG1IP, PTTG2, PTX3, PTX4, PUDP, PUF60, PUMI, PUM2, PUM3, PURA, PURB, PURG, PUSI, PUS10, PUS3, PUS7, PUS7L, PUSL1, PVALB, PVR, PVRIG, PWP1, PWP2, PWWP2A, PWWP2B, PXDC1, PXDN, PXDNL, PXK, PXMP2, PXMP4, PXN, PXT1, PXYLP1, PYCARD, PYCR1, PYCR2, PYCR3, PYDC1, PYDC2, PYGB, PYGL, PYGM, PYGO1, PYGO2, PYHIN1, PYM1, PYROXD1, PYROXD2, PYURF, PYY, PZP, QARS, QDPR, QKI, QPCT, QPCTL, QPRT, QRFP, QRFPR, QRICH1, QRICH2, QRSL1, QSER1, QSOX1, QSOX2, QTRT1, QTRT2, R3HCC1, R3HCC1L, R3HDM1, R3HDM2, R3HDM4, R3HDML, RAB10, RAB11A, RAB11B, RAB11FIP1, RAB11FIP2, RAB11FIP3, RAB11FIP4, RAB11FIP5, RAB12, RAB13, RAB14, RAB15, RAB17, RAB18, RAB19, RAB1A, RAB1B, RAB20, RAB21, RAB22A, RAB23, RAB24, RAB25, RAB26, RAB27A, RAB27B, RAB28, RAB29, RAB2A, RAB2B, RAB30, RAB31, RAB32, RAB33A, RAB33B, RAB34, RAB35, RAB36, RAB37, RAB38, RAB39A, RAB39B, RAB3A, RAB3B, RAB3C, RAB3D, RAB3GAP1, RAB3GAP2, RAB3IL1, RAB3IP, RAB40A, RAB40AL, RAB40B, RAB40C, RAB41, RAB42, RAB43, RAB44, RAB4A, RAB4B, RAB4B-EGLN2, RAB5A, RAB5B, RAB5C, RAB6A, RAB6B, RAB6C, RAB7A, RAB7B, RAB8A, RAB8B, RAB9A, RAB9B, RABACI, RABEPI, RABEP2, RABEPK, RABGAP1, RABGAP1L, RABGEF1, RABGGTA, RABGGTB, RABIF, RABL2A, RABL2B, RABL3, RABL6, RAC1, RAC2, RAC3, RACGAP1, RACK1, RAD1, RAD17, RAD18, RAD21, RAD21L1, RAD23A, RAD23B, RAD50, RAD51, RAD51AP1, RAD51AP2, RAD51B, RAD51C, RAD51D, RAD52, RAD54B, RAD54L, RAD54L2, RAD9A, RAD9B, RADIL, RAEl, RAETIE, RAETIG, RAETIL, RAF1, RAG1, RAG2, RAIl, RAI14, RAI2, RALA, RALB, RALBP1, RALGAPA1, RALGAPA2, RALGAPB, RALGDS, RALGPS1, RALGPS2, RALY, RALYL, RAMP1, RAMP2, RAMP3, RAN, RANBP1, RANBP10, RANBP17, RANBP2, RANBP3, RANBP3L, RANBP6, RANBP9, RANGAP1, RANGRF, RAP1A, RAP1B, RAP1GAP, RAP1GAP2, RAP1GDS1, RAP2A, RAP2B, RAP2C, RAPGEF1, RAPGEF2, RAPGEF3, RAPGEF4, RAPGEF5, RAPGEF6, RAPGEFL1, RAPH1, RAPSN, RARA, RARB, RARG, RARRESI, RARRES2, RARRES3, RARS, RARS2, RASA1, RASA2, RASA3, RASA4, RASA4B, RASAL1, RASAL2, RASAL3, RASD1, RASD2, RASEF, RASGEF1A, RASGEFIB, RASGEFIC, RASGRF1, RASGRF2, RASGRP1, RASGRP2, RASGRP3, RASGRP4, RASIP1, RASL10A, RASL10B, RASL11A, RASL11B, RASL12, RASSF1, RASSF10, RASSF2, RASSF3, RASSF4, RASSF5, RASSF6, RASSF7, RASSF8, RASSF9, RAVERI, RAVER2, RAX, RAX2, RB1, RB1CC1, RBAK, RBAK-RBAKDN, RBBP4, RBBP5, RBBP6, RBBP7, RBBP8, RBBP8NL, RBBP9, RBCK1, RBFA, RBFOX1, RBFOX2, RBFOX3, RBKS, RBL1, RBL2, RBM10, RBM11, RBM12, RBM12B, RBM14, RBM14-RBM4, RBM15, RBM15B, RBM17, RBM18, RBM19, RBM20, RBM22, RBM23, RBM24, RBM25, RBM26, RBM27, RBM28, RBM3, RBM33, RBM34, RBM38, RBM39, RBM4, RBM41, RBM42, RBM43, RBM44, RBM45, RBM46, RBM47, RBM48, RBM4B, RBM5, RBM6, RBM7, RBM8A, RBMS1, RBMS2, RBMS3, RBMX, RBMX2, RBMXL1, RBMXL2, RBMXL3, RBMYIA1, RBMY1B, RBMY1D, RBMY1E, RBMY1F, RBMY1J, RBP1, RBP2, RBP3, RBP4, RBP5, RBP7, RBPJ, RBPJL, RBPMS, RBPMS2, RBSN, RBX1, RC3H1, RC3H2, RCAN1, RCAN2, RCAN3, RCBTB1, RCBTB2, RCC1, RCC1L, RCC2, RCCD1, RCE1, RCHY1, RCL1, RCN1, RCN2, RCN3, RCOR1, RCOR2, RCOR3, RCSD1, RCVRN, RD3, RD3L, RDH10, RDH11, RDH12, RDH13, RDH14, RDH16, RDH5, RDH8, RDM1, RDX, REC114, REC8, RECK, RECQL, RECQL4, RECQL5, REEP1, REEP2, REEP3, REEP4, REEP5, REEP6, REGIA, REG1B, REG3A, REG3G, REG4, REL, RELA, RELB, RELL1, RELL2, RELN, RELT, REM1, REM2, REN, RENBP, REP15, REPIN 1, REPS1, REPS2, RER1, RERE, RERG, RERGL, RESP18, REST, RET, RETN, RETNLB, RETREGI, RETREG2, RETREG3, RETSAT, REV1, REV3L, REXO1, REXO2, REXO4, REXO5, RFC1, RFC2, RFC3, RFC4, RFC5, RFESD, RFFL, RFK, RFLNA, RFLNB, RFNG, RFPL1, RFPL2, RFPL3, RFPL3S, RFPL4A, RFPL4AL1, RFPL4B, RFT1, RFTN1, RFTN2, RFWD2, RFWD3, RFX1, RFX2, RFX3, RFX4, RFX5, RFX6, RFX7, RFX8, RFXANK, RFXAP, RGCC, RGL1, RGL2, RGL3, RGL4, RGMA, RGMB, RGN, RGP1, RGPD1, RGPD2, RGPD3, RGPD4, RGPD5, RGPD6, RGPD8, RGR, RGS1, RGS10, RGS11, RGS12, RGS13, RGS14, RGS16, RGS17, RGS18, RGS19, RGS2, RGS20, RGS21, RGS22, RGS3, RGS4, RGS5, RGS6, RGS7, RGS7BP, RGS8, RGS9, RGS9BP, RGSL1, RHAG, RHBDD1, RHBDD2, RHBDD3, RHBDF1, RHBDF2, RHBDL1, RHBDL2, RHBDL3, RHBG, RHCE, RHCG, RHD, RHEB, RHEBL1, RHNO1, RHO, RHOA, RHOB, RHOBTB1, RHOBTB2, RHOBTB3, RHOC, RHOD, RHOF, RHOG, RHOH, RHOJ, RHOQ, RHOT1, RHOT2, RHOU, RHOV, RHOXF1, RHOXF2, RHOXF2B, RHPN1, RHPN2, RIBC1, RIBC2, RIC1, RIC3, RIC8A, RIC8B, RICTOR, RIDA, RIF1, RIIAD1, RILP, RILPL1, RILPL2, RIMBP2, RIMBP3, RIMBP3B, RIMBP3C, RIMKLA, RIMKLB, RIMS1, RIMS2, RIMS3, RIMS4, RIN1, RIN2, RIN3, RING1, RINL, RINT1, RIOK1, RIOK2, RIOK3, RIOX1, RIOX2, RIPK1, RIPK2, RIPK3, RIPK4, RIPOR1, RIPOR2, RIPOR3, RIPPLY1, RIPPLY2, RIPPLY3, RIT1, RIT2, RITA1, RLBP1, RLF, RLIM, RLN1, RLN2, RLN3, RMDN1, RMDN2, RMDN3, RMI1, RMI2, RMND1, RMND5A, RMND5B, RNASE1, RNASE10, RNASE11, RNASE12, RNASE13, RNASE2, RNASE3, RNASE4, RNASE6, RNASE7, RNASE8, RNASE9, RNASEH1, RNASEH2A, RNASEH2B, RNASEH2C, RNASEK, RNASEK-C17orf49, RNASEL, RNASET2, RND1, RND2, RND3, RNF10, RNF103, RNF103-CHMP3, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RNGTT, RNH1, RNLS, RNMT, RNPC3, RNPEP, RNPEPL1, RNPS1, ROBO1, ROBO2, ROBO3, ROBO4, ROCK1, ROCK2, ROGDI, ROM1, ROMO1, ROPN1, ROPN1B, ROPN1L, ROR1, ROR2, RORA, RORB, RORC, ROS1, RP1, RP1L1, RP2, RP9, RPA1, RPA2, RPA3, RPA4, RPAIN, RPAP1, RPAP2, RPAP3, RPE, RPE65, RPEL1, RPF1, RPF2, RPGR, RPGRIP1, RPGRIP1L, RPH3A, RPH3AL, RPIA, RPL10, RPL10A, RPL10L, RPL11, RPL12, RPL13, RPL13A, RPL14, RPL15, RPL17, RPL17-C18orf32, RPL18, RPL18A, RPL19, RPL21, RPL22, RPL22L1, RPL23, RPL23A, RPL24, RPL26, RPL26L1, RPL27, RPL27A, RPL28, RPL29, RPL3, RPL30, RPL31, RPL32, RPL34, RPL35, RPL35A, RPL36, RPL36A, RPL36A-HNRNPH2, RPL36AL, RPL37, RPL37A, RPL38, RPL39, RPL39L, RPL3L, RPL4, RPL41, RPL5, RPL6, RPL7, RPL7A, RPL7L1, RPL8, RPL9, RPLPO, RPLP1, RPLP2, RPN1, RPN2, RPP14, RPP21, RPP25, RPP25L, RPP30, RPP38, RPP40, RPRD1A, RPRD1B, RPRD2, RPRM, RPRML, RPS10, RPS10-NUDT3, RPS11, RPS12, RPS13, RPS14, RPS15, RPS15A, RPS16, RPS17, RPS18, RPS19, RPS19BP1, RPS2, RPS20, RPS21, RPS23, RPS24, RPS25, RPS26, RPS27, RPS27A, RPS27L, RPS28, RPS29, RPS3, RPS3A, RPS4X, RPS4Y1, RPS4Y2, RPS5, RPS6, RPS6KA1, RPS6KA2, RPS6KA3, RPS6KA4, RPS6KA5, RPS6KA6, RPS6KB1, RPS6KB2, RPS6KC1, RPS6KL1, RPS7, RPS8, RPS9, RPSA, RPTN, RPTOR, RPUSD1, RPUSD2, RPUSD3, RPUSD4, RRAD, RRAGA, RRAGB, RRAGC, RRAGD, RRAS, RRAS2, RRBP1, RREB1, RRH, RRM1, RRM2, RRM2B, RRN3, RRNAD1, RRP1, RRP12, RRP15, RRP1B, RRP36, RRP7A, RRP8, RRP9, RRS1, RS1, RSAD1, RSAD2, RSBN1, RSBN1L, RSC1A1, RSF1, RSG1, RSL1D1, RSL24D1, RSPH1, RSPH10B, RSPH10B2, RSPH14, RSPH3, RSPH4A, RSPH6A, RSPH9, RSPO1, RSPO2, RSPO3, RSPO4, RSPRY1, RSRC1, RSRC2, RSRP1, RSU1, RTBDN, RTCA, RTCB, RTEL1, RTEL1-TNFRSF6B, RTF1, RTFDC1, RTKN, RTKN2, RTL1, RTL10, RTL3, RTL4, RTL5, RTL6, RTL8A, RTL8B, RTL8C, RTL9, RTN1, RTN2, RTN3, RTN4, RTN4IP1, RTN4R, RTN4RL1, RTN4RL2, RTP1, RTP2, RTP3, RTP4, RTP5, RTTN, RUBCN, RUBCNL, RUFY1, RUFY2, RUFY3, RUFY4, RUNDC1, RUNDC3A, RUNDC3B, RUNX1, RUNX1T1, RUNX2, RUNX3, RUSC1, RUSC2, RUVBL1, RUVBL2, RWDD1, RWDD2A, RWDD2B, RWDD3, RWDD4, RXFP1, RXFP2, RXFP3, RXFP4, RXRA, RXRB, RXRG, RYBP, RYK, RYR1, RYR2, RYR3, S100A1, S100A10, S100A11, S100A12, S100A13, S100A14, S100A16, S100A2, S100A3, S100A4, S100A5, S100A6, S100A7, S100A7A, S100A7L2, S100A8, S100A9, S100B, S100G, S100P, S100PBP, S100Z, S1PR1, S1PR2, S1PR3, S1PR4, S1PR5, SAA1, SAA2, SAA2-SAA4, SAA4, SAAL1, SAC3D1, SACM1L, SACS, SAE1, SAFB, SAFB2, SAG, SAGE1, SALL1, SALL2, SALL3, SALL4, SAMD1, SAMD10, SAMD11, SAMD12, SAMD13, SAMD14, SAMD15, SAMD3, SAMD4A, SAMD4B, SAMD5, SAMD7, SAMD8, SAMD9, SAMD9L, SAMHD1, SAMM50, SAMSN1, SAP130, SAP18, SAP25, SAP30, SAP30BP, SAP30L, SAPCD1, SAPCD2, SAR1A, SAR1B, SARAF, SARDH, SARM1, SARNP, SARS, SARS2, SART1, SART3, SASH1, SASH3, SASS6, SAT1, SAT2, SATB1, SATB2, SATL1, SAV1, SAXO1, SAXO2, SAYSD1, SBDS, SBF1, SBF2, SBK1, SBK2, SBK3, SBNO1, SBNO2, SBSN, SBSPON, SC5D, SCAF1, SCAF11, SCAF4, SCAF8, SCAI, SCAMP1, SCAMP2, SCAMP3, SCAMP4, SCAMP5, SCAND1, SCAP, SCAPER, SCARA3, SCARA5, SCARB1, SCARB2, SCARF1, SCARF2, SCART1, SCCPDH, SCD, SCD5, SCEL, SCFD1, SCFD2, SCG2, SCG3, SCG5, SCGB1A1, SCGB1C1, SCGB1C2, SCGB1D1, SCGB1D2, SCGB1D4, SCGB2A1, SCGB2A2, SCGB2B2, SCGB3A1, SCGB3A2, SCGN, SCHIP1, SCIMP, SCIN, SCLT1, SCLY, SCMH1, SCML1, SCML2, SCML4, SCN10A, SCN11A, SCN1A, SCN1B, SCN2A, SCN2B, SCN3A, SCN3B, SCN4A, SCN4B, SCN5A, SCN7A, SCN8A, SCN9A, SCNM1, SCNN1A, SCNN1B, SCNN1D, SCNN1G, SCO1, SCO2, SCOC, SCP2, SCP2D1, SCPEP1, SCRG1, SCRIB, SCRN1, SCRN2, SCRN3, SCRT1, SCRT2, SCT, SCTR, SCUBE1, SCUBE2, SCUBE3, SCX, SCYL1, SCYL2, SCYL3, SDAD1, SDC1, SDC2, SDC3, SDC4, SDCBP, SDCBP2, SDCCAG3, SDCCAG8, SDE2, SDF2, SDF2L1, SDF4, SDHA, SDHAF1, SDHAF2, SDHAF3, SDHAF4, SDHB, SDHC, SDHD, SDK1, SDK2, SDR16C5, SDR39U1, SDR42E1, SDR42E2, SDR9C7, SDS, SDSL, SEBOX, SEC11A, SEC11C, SEC13, SEC14L1, SEC14L2, SEC14L3, SEC14L4, SEC14L5, SEC14L6, SEC16A, SEC16B, SEC22A, SEC22B, SEC22C, SEC23A, SEC23B, SEC23IP, SEC24A, SEC24B, SEC24C, SEC24D, SEC31A, SEC31B, SEC61A1, SEC61A2, SEC61B, SEC61G, SEC62, SEC63, SECISBP2, SECISBP2L, SECTM1, SEH1L, SEL1L, SEL1L2, SEL1L3, SELE, SELENBP1, SELENOF, SELENOH, SELENOI, SELENOK, SELENOM, SELENON, SELENOO, SELENOP, SELENOS, SELENOT, SELENOV, SELENOW, SELL, SELP, SELPLG, SEMi, SEMA3A, SEMA3B, SEMA3C, SEMA3D, SEMA3E, SEMA3F, SEMA3G, SEMA4A, SEMA4B, SEMA4C, SEMA4D, SEMA4F, SEMA4G, SEMA5A, SEMA5B, SEMA6A, SEMA6B, SEMA6C, SEMA6D, SEMA7A, SEMG1, SEMG2, SENP1, SENP2, SENP3, SENP3-EIF4A1, SENP5, SENP6, SENP7, SENP8, SEPHS1, SEPHS2, SEPSECS, SEPT1, SEPT10, SEPT11, SEPT12, SEPT14, SEPT2, SEPT3, SEPT4, SEPT5, SEPT6, SEPT7, SEPT8, SEPT9, SERAC1, SERBP1, SERF1A, SERF1B, SERF2, SERGEF, SERHL2, SERINC1, SERINC2, SERINC3, SERINC4, SERINC5, SERP1, SERP2, SERPINA1, SERPINA10, SERPINA11, SERPINA12, SERPINA2, SERPINA3, SERPINA4, SERPINA5, SERPINA6, SERPINA7, SERPINA9, SERPINB1, SERPINB10, SERPINB11, SERPINB12, SERPINB13, SERPINB2, SERPINB3, SERPINB4, SERPINB5, SERPINB6, SERPINB7, SERPINB8, SERPINB9, SERPINC1, SERPIND1, SERPINE1, SERPINE2, SERPINE3, SERPINF1, SERPINF2, SERPINGI, SERPINHI, SERPINII, SERPINI2, SERTAD1, SERTAD2, SERTAD3, SERTAD4, SERTM1, SESN1, SESN2, SESN3, SESTD1, SET, SETBP1, SETD1A, SETD1B, SETD2, SETD3, SETD4, SETD5, SETD6, SETD7, SETD9, SETDB1, SETDB2, SETMAR, SETSIP, SETX, SEZ6, SEZ6L, SEZ6L2, SF1, SF3A1, SF3A2, SF3A3, SF3B1, SF3B2, SF3B3, SF3B4, SF3B5, SF3B6, SFI1, SFMBT1, SFMBT2, SFN, SFPQ, SFR1, SFRP1, SFRP2, SFRP4, SFRP5, SFSWAP, SFT2D1, SFT2D2, SFT2D3, SFTA2, SFTA3, SFTPA1, SFTPA2, SFTPB, SFTPC, SFTPD, SFXN1, SFXN2, SFXN3, SFXN4, SFXN5, SGCA, SGCB, SGCD, SGCE, SGCG, SGCZ, SGF29, SGIP1, SGK1, SGK2, SGK3, SGK494, SGMS1, SGMS2, SGO1, SG02, SGPL1, SGPP1, SGPP2, SGSH, SGSM1, SGSM2, SGSM3, SGTA, SGTB, SH2B1, SH2B2, SH2B3, SH2D1A, SH2D1B, SH2D2A, SH2D3A, SH2D3C, SH2D4A, SH2D4B, SH2D5, SH2D6, SH2D7, SH3BGR, SH3BGRL, SH3BGRL2, SH3BGRL3, SH3BP1, SH3BP2, SH3BP4, SH3BP5, SH3BP5L, SH3D19, SH3D21, SH3GL1, SH3GL2, SH3GL3, SH3GLB1, SH3GLB2, SH3KBP1, SH3PXD2A, SH3PXD2B, SH3RF1, SH3RF2, SH3RF3, SH3TC1, SH3TC2, SH3YL1, SHANKI, SHANK2, SHANK3, SHARPIN, SHB, SHBG, SHC1, SHC2, SHC3, SHC4, SHCBP1, SHCBP1L, SHD, SHE, SHF, SHH, SHISA2, SHISA3, SHISA4, SHISA5, SHISA6, SHISA7, SHISA8, SHISA9, SHKBP1, SHMT1, SHMT2, SHOC2, SHOX, SHOX2, SHPK, SHPRH, SHQ1, SHROOMI, SHROOM2, SHROOM3, SHROOM4, SHTN1, SI, SIAE, SIAH1, SIAH2, SIAH3, SIDT1, SIDT2, SIGIRR, SIGLECI, SIGLEC10, SIGLEC11, SIGLEC12, SIGLEC14, SIGLEC15, SIGLEC5, SIGLEC6, SIGLEC7, SIGLEC8, SIGLEC9, SIGLECLI, SIGMARI, SIK1, SIK2, SIK3, SIKE1, SIL1, SIM1, SIM2, SIMC1, SIN3A, SIN3B, SIPA1, SIPA1L1, SIPA1L2, SIPA1L3, SIRPA, SIRPB1, SIRPB2, SIRPD, SIRPG, SIRT1, SIRT2, SIRT3, SIRT4, SIRT5, SIRT6, SIRT7, SIT1, SIVA1, SIX1, SIX2, SIX3, SIX4, SIX5, SIX6, SKAl, SKA2, SKA3, SKAP1, SKAP2, SKI, SKIDA1, SKIL, SKIV2L, SKIV2L2, SKOR1, SKOR2, SKP1, SKP2, SLA, SLA2, SLAINI, SLAIN2, SLAMFI, SLAMF6, SLAMF7, SLAMF8, SLAMF9, SLBP, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC15A5, SLC16A1, SLC16A10, SLC16A11, SLC16A12, SLC16A13, SLC16A14, SLC16A2, SLC16A3, SLC16A4, SLC16A5, SLC16A6, SLC16A7, SLC16A8, SLC16A9, SLC17A1, SLC17A2, SLC17A3, SLC17A4, SLC17A5, SLC17A6, SLC17A7, SLC17A8, SLC17A9, SLC18A1, SLC18A2, SLC18A3, SLC18B1, SLC19A1, SLC19A2, SLC19A3, SLC1A1, SLC1A2, SLC1A3, SLC1A4, SLC1A5, SLC1A6, SLC1A7, SLC20A1, SLC20A2, SLC22A1, SLC22A10, SLC22A11, SLC22A12, SLC22A13, SLC22A14, SLC22A15, SLC22A16, SLC22A17, SLC22A18, SLC22A18AS, SLC22A2, SLC22A23, SLC22A24, SLC22A25, SLC22A3, SLC22A31, SLC22A4, SLC22A5, SLC22A6, SLC22A7, SLC22A8, SLC22A9, SLC23A1, SLC23A2, SLC23A3, SLC24A1, SLC24A2, SLC24A3, SLC24A4, SLC24A5, SLC25A1, SLC25A10, SLC25A11, SLC25A12, SLC25A13, SLC25A14, SLC25A15, SLC25A16, SLC25A17, SLC25A18, SLC25A19, SLC25A2, SLC25A20, SLC25A21, SLC25A22, SLC25A23, SLC25A24, SLC25A25, SLC25A26, SLC25A27, SLC25A28, SLC25A29, SLC25A3, SLC25A30, SLC25A31, SLC25A32, SLC25A33, SLC25A34, SLC25A35, SLC25A36, SLC25A37, SLC25A38, SLC25A39, SLC25A4, SLC25A40, SLC25A41, SLC25A42, SLC25A43, SLC25A44, SLC25A45, SLC25A46, SLC25A47, SLC25A48, SLC25A5, SLC25A51, SLC25A52, SLC25A53, SLC25A6, SLC26A1, SLC26A10, SLC26A11, SLC26A2, SLC26A3, SLC26A4, SLC26A5, SLC26A6, SLC26A7, SLC26A8, SLC26A9, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC2A1, SLC2A10, SLC2A11, SLC2A12, SLC2A13, SLC2A14, SLC2A2, SLC2A3, SLC2A4, SLC2A4RG, SLC2A5, SLC2A6, SLC2A7, SLC2A8, SLC2A9, SLC30A1, SLC30A10, SLC30A2, SLC30A3, SLC30A4, SLC30A5, SLC30A6, SLC30A7, SLC30A8, SLC30A9, SLC31A1, SLC31A2, SLC32A1, SLC33A1, SLC34A1, SLC34A2, SLC34A3, SLC35A1, SLC35A2, SLC35A3, SLC35A4, SLC35A5, SLC35B1, SLC35B2, SLC35B3, SLC35B4, SLC35C1, SLC35C2, SLC35D1, SLC35D2, SLC35D3, SLC35E1, SLC35E2, SLC35E2B, SLC35E3, SLC35E4, SLC35F1, SLC35F2, SLC35F3, SLC35F4, SLC35F5, SLC35F6, SLC35G1, SLC35G2, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A10, SLC38A11, SLC38A2, SLC38A3, SLC38A4, SLC38A5, SLC38A6, SLC38A7, SLC38A8, SLC38A9, SLC39A1, SLC39A10, SLC39A11, SLC39A12, SLC39A13, SLC39A14, SLC39A2, SLC39A3, SLC39A4, SLC39A5, SLC39A6, SLC39A7, SLC39A8, SLC39A9, SLC3A1, SLC3A2, SLC40A1, SLC41A1, SLC41A2, SLC41A3, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, SLC48A1, SLC4A1, SLC4A10, SLC4A11, SLC4A1AP, SLC4A2, SLC4A3, SLC4A4, SLC4A5, SLC4A7, SLC4A8, SLC4A9, SLC50A1, SLC51A, SLC51B, SLC52A1, SLC52A2, SLC52A3, SLC5A1, SLC5A10, SLC5A11, SLC5A12, SLC5A2, SLC5A3, SLC5A4, SLC5A5, SLC5A6, SLC5A7, SLC5A8, SLC5A9, SLC6A1, SLC6A11, SLC6A12, SLC6A13, SLC6A14, SLC6A15, SLC6A16, SLC6A17, SLC6A18, SLC6A19, SLC6A2, SLC6A20, SLC6A3, SLC6A4, SLC6A5, SLC6A6, SLC6A7, SLC6A8, SLC6A9, SLC7A1, SLC7A10, SLC7A11, SLC7A13, SLC7A14, SLC7A2, SLC7A3, SLC7A4, SLC7A5, SLC7A6, SLC7A6OS, SLC7A7, SLC7A8, SLC7A9, SLC8A1, SLC8A2, SLC8A3, SLC8B1, SLC9A1, SLC9A2, SLC9A3, SLC9A3R1, SLC9A3R2, SLC9A4, SLC9A5, SLC9A6, SLC9A7, SLC9A8, SLC9A9, SLC9B1, SLC9B2, SLC9C1, SLC9C2, SLCO1A2, SLCO1B1, SLCO1B3, SLCO1B7, SLCO1C1, SLCO2A1, SLCO2B1, SLCO3A1, SLCO4A1, SLCO4C1, SLCO5A1, SLCO6A1, SLF1, SLF2, SLFN11, SLFN12, SLFN12L, SLFN13, SLFN14, SLFN5, SLFNL1, SLIRP, SLIT1, SLIT2, SLIT3, SLITRK1, SLITRK2, SLITRK3, SLITRK4, SLITRK5, SLITRK6, SLK, SLMAP, SLN, SLPI, SL™, SLU7, SLURP1, SLURP2, SLX1A, SLX1B, SLX4, SLX4IP, SMAD1, SMAD2, SMAD3, SMAD4, SMAD5, SMAD6, SMAD7, SMAD9, SMAGP, SMAP1, SMAP2, SMARCA1, SMARCA2, SMARCA4, SMARCA5, SMARCAD1, SMARCAL1, SMARCB1, SMARCC1, SMARCC2, SMARCD1, SMARCD2, SMARCD3, SMARCE1, SMC1A, SMC1B, SMC2, SMC3, SMC4, SMC5, SMC6, SMCHD1, SMCO1, SMCO2, SMCO3, SMCO4, SMCP, SMCR8, SMDT1, SMG1, SMG5, SMG6, SMG7, SMG8, SMG9, SMIM1, SMIM10, SMIM10L1, SMIM10L2A, SMIM10L2B, SMIM11A, SMIM11B, SMIM12, SMIM13, SMIM14, SMIM15, SMIM17, SMIM18, SMIM19, SMIM2, SMIM20, SMIM21, SMIM22, SMIM23, SMIM24, SMIM26, SMIM27, SMIM28, SMIM29, SMIM3, SMIM30, SMIM31, SMIM4, SMIM5, SMIM6, SMIM7, SMIM8, SMIM9, SMKR1, SMLR1, SMN1, SMN2, SMNDC1, SMO, SMOC1, SMOC2, SMOX, SMPD1, SMPD2, SMPD3, SMPD4, SMPDL3A, SMPDL3B, SMPX, SMR3A, SMR3B, SMS, SMTN, SMTNL1, SMTNL2, SMU1, SMUG1, SMURF1, SMURF2, SMYD1, SMYD2, SMYD3, SMYD4, SMYD5, SNAI1, SNAI2, SNAI3, SNAP23, SNAP25, SNAP29, SNAP47, SNAP91, SNAPC1, SNAPC2, SNAPC3, SNAPC4, SNAPC5, SNAPIN, SNCA, SNCAIP, SNCB, SNCG, SND1, SNED1, SNF8, SNHG28, SNIP1, SNN, SNPH, SNRK, SNRNP200, SNRNP25, SNRNP27, SNRNP35, SNRNP40, SNRNP48, SNRNP70, SNRPA, SNRPA1, SNRPB, SNRPB2, SNRPC, SNRPD1, SNRPD2, SNRPD3, SNRPE, SNRPF, SNRPG, SNRPN, SNTA1, SNTB1, SNTB2, SNTG1, SNTG2, SNTN, SNU13, SNUPN, SNURF, SNW1, SNX1, SNX10, SNX11, SNX12, SNX13, SNX14, SNX15, SNX16, SNX17, SNX18, SNX19, SNX2, SNX20, SNX21, SNX22, SNX24, SNX25, SNX27, SNX29, SNX3, SNX30, SNX31, SNX32, SNX33, SNX4, SNX5, SNX6, SNX7, SNX8, SNX9, SOAT1, SOAT2, SOBP, SOCS1, SOCS2, SOCS3, SOCS4, SOCS5, SOCS6, SOCS7, SOD1, SOD2, SOD3, SOGA1, SOGA3, SOHLH1, SOHLH2, SON, SORBS1, SORBS2, SORBS3, SORCS1, SORCS2, SORCS3, SORD, SORL1, SORT1, SOS1, SOS2, SOST, SOSTDC1, SOWAHA, SOWAHB, SOWAHC, SOWAHD, SOX1, SOX10, SOX11, SOX12, SOX13, SOX14, SOX15, SOX17, SOX18, SOX2, SOX21, SOX3, SOX30, SOX4, SOX5, SOX6, SOX7, SOX8, SOX9, SP1, SP100, SP110, SP140, SP140L, SP2, SP3, SP4, SP5, SP6, SP7, SP8, SP9, SPA17, SPAAR, SPACA1, SPACA3, SPACA4, SPACA5, SPACA5B, SPACA6, SPACA7, SPACA9, SPAG1, SPAG11A, SPAG11B, SPAG16, SPAG17, SPAG4, SPAG5, SPAG6, SPAG7, SPAG8, SPAG9, SPAM1, SPANXA1, SPANXA2, SPANXB1, SPANXC, SPANXD, SPANXN1, SPANXN2, SPANXN3, SPANXN4, SPANXN5, SPARC, SPARCL1, SPART, SPAST, SPATA1, SPATA12, SPATA13, SPATA16, SPATA17, SPATA18, SPATA19, SPATA2, SPATA20, SPATA21, SPATA22, SPATA24, SPATA25, SPATA2L, SPATA3, SPATA31A1, SPATA31A3, SPATA31A5, SPATA31A6, SPATA31A7, SPATA31D1, SPATA31D3, SPATA31D4, SPATA31E1, SPATA32, SPATA33, SPATA4, SPATA45, SPATA46, SPATA5, SPATA5L1, SPATA6, SPATA6L, SPATA7, SPATA8, SPATA9, SPATC1, SPATC1L, SPATS1, SPATS2, SPATS2L, SPC24, SPC25, SPCS1, SPCS2, SPCS3, SPDEF, SPDL1, SPDYA, SPDYC, SPDYE1, SPDYE16, SPDYE2, SPDYE2B, SPDYE3, SPDYE4, SPDYE5, SPDYE6, SPECC1, SPECC1L, SPECC1L-ADORA2A, SPEF1, SPEF2, SPEG, SPEM1, SPEN, SPERT, SPESP1, SPG11, SPG21, SPG7, SPHAR, SPHK1, SPHK2, SPHKAP, SPI1, SPIB, SPIC, SPICE1, SPIDR, SPIN1, SPIN2A, SPIN2B, SPIN3, SPIN4, SPINK1, SPINK13, SPINK14, SPINK2, SPINK4, SPINK5, SPINK6, SPINK7, SPINK8, SPINK9, SPINT1, SPINT2, SPINT3, SPINT4, SPIRE1, SPIRE2, SPN, SPNS1, SPNS2, SPNS3, SPO11, SPOCD1, SPOCK1, SPOCK2, SPOCK3, SPON1, SPON2, SPOP, SPOPL, SPOUT1, SPP1, SPP2, SPPL2A, SPPL2B, SPPL2C, SPPL3, SPR, SPRED1, SPRED2, SPRED3, SPRN, SPRR1A, SPRR1B, SPRR2A, SPRR2B, SPRR2D, SPRR2E, SPRR2F, SPRR2G, SPRR3, SPRR4, SPRR5, SPRTN, SPRY1, SPRY2, SPRY3, SPRY4, SPRYD3, SPRYD4, SPRYD7, SPSB1, SPSB2, SPSB3, SPSB4, SPTA1, SPTAN1, SPTB, SPTBN1, SPTBN2, SPTBN4, SPTBN5, SPTLC1, SPTLC2, SPTLC3, SPTSSA, SPTSSB, SPTY2D1, SPTY2D1-AS1, SPX, SPZ1, SQLE, SQOR, SQSTM1, SRA1, SRBD1, SRC, SRCAP, SRCIN1, SRD5A1, SRD5A2, SRD5A3, SREBF1, SREBF2, SREK1, SREK1IP1, SRF, SRFBP1, SRGAP1, SRGAP2, SRGAP2B, SRGAP2C, SRGAP3, SRGN, SRI, SRL, SRM, SRMS, SRP14, SRP19, SRP54, SRP68, SRP72, SRP9, SRPK1, SRPK2, SRPK3, SRPRA, SRPRB, SRPX, SRPX2, SRR, SRRD, SRRM1, SRRM2, SRRM3, SRRM4, SRRM5, SRRT, SRSF1, SRSF10, SRSF11, SRSF12, SRSF2, SRSF3, SRSF4, SRSF5, SRSF6, SRSF7, SRSF8, SRSF9, SRXN1, SRY, SS18, SS18L1, SS18L2, SSB, SSBP1, SSBP2, SSBP3, SSBP4, SSC4D, SSC5D, SSFA2, SSH1, SSH2, SSH3, SSMEM1, SSNA1, SSPN, SSPO, SSR1, SSR2, SSR3, SSR4, SSRP1, SSSCA1, SST, SSTR1, SSTR2, SSTR3, SSTR4, SSTR5, SSU72, SSU72P8, SSUH2, SSX1, SSX2, SSX2B, SSX2IP, SSX3, SSX4, SSX4B, SSX5, SSX7, ST13, ST14, ST18, ST20, ST20-MTHFS, ST3GAL1, ST3GAL2, ST3GAL3, ST3GAL4, ST3GAL5, ST3GAL6, ST5, ST6GAL1, ST6GAL2, ST6GALNAC1, ST6GALNAC2, ST6GALNAC3, ST6GALNAC4, ST6GALNAC5, ST6GALNAC6, ST7, ST7L, ST8SIA1, ST8SIA2, ST8SIA3, ST8SIA4, ST8SIA5, ST8SIA6, STAB1, STAB2, STAC, STAC2, STAC3, STAG1, STAG2, STAG3, STAM, STAM2, STAMBP, STAMBPL1, STAP1, STAP2, STAR, STARD10, STARD13, STARD3, STARD3NL, STARD4, STARD5, STARD6, STARD7, STARD8, STARD9, STAT1, STAT2, STAT3, STAT4, STAT5A, STAT5B, STAT6, STATH, STAU1, STAU2, STBD1, STC1, STC2, STEAP1, STEAP1B, STEAP2, STEAP3, STEAP4, STH, STIL, STIM1, STIM2, STIP1, STK10, STK11, STK11IP, STK16, STK17A, STK17B, STK19, STK24, STK25, STK26, STK3, STK31, STK32A, STK32B, STK32C, STK33, STK35, STK36, STK38, STK38L, STK39, STK4, STK40, STKLD1, STMN1, STMN2, STMN3, STMN4, STMND1, STN1, STOM, STOML1, STOML2, STOML3, STON1, STON1-GTF2A1L, STON2, STOX1, STOX2, STPG1, STPG2, STPG3, STPG4, STRA6, STRA8, STRADA, STRADB, STRAP, STRBP, STRC, STRIP1, STRIP2, STRN, STRN3, STRN4, STS, STT3A, STT3B, STUB1, STUM, STX10, STX11, STX12, STX16, STX16-NPEPL1, STX17, STX18, STX19, STX1A, STX1B, STX2, STX3, STX4, STX5, STX6, STX7, STX8, STXBP1, STXBP2, STXBP3, STXBP4, STXBP5, STXBP5L, STXBP6, STYK1, STYX, STYXL1, SUB1, SUCLA2, SUCLG1, SUCLG2, SUCNR1, SUCO, SUDS3, SUFU, SUGCT, SUGP1, SUGP2, SUGT1, SULF1, SULF2, SULT1A1, SULT1A2, SULT1A3, SULT1A4, SULT1B1, SULT1C2, SULT1C3, SULT1C4, SULT1E1, SULT2A1, SULT2B1, SULT4A1, SULT6B1, SUMF1, SUMF2, SUMO1, SUMO2, SUMO3, SUMO4, SUN1, SUN2, SUN3, SUN5, SUOX, SUPT16H, SUPT20H, SUPT3H, SUPT4H1, SUPT5H, SUPT6H, SUPT7L, SUPV3L1, SURF1, SURF2, SURF4, SURF6, SUSD1, SUSD2, SUSD3, SUSD4, SUSD5, SUSD6, SUV39H1, SUV39H2, SUZ12, SV2A, SV2B, SV2C, SVBP, SVEP1, SVIL, SVIP, SVOP, SVOPL, SWAP70, SWI5, SWSAP1, SWT1, SYAP1, SYBU, SYCE1, SYCE1L, SYCE2, SYCE3, SYCN, SYCP1, SYCP2, SYCP2L, SYCP3, SYDE1, SYDE2, SYF2, SYK, SYMPK, SYN1, SYN2, SYN3, SYNC, SYNCRIP, SYNDIG1, SYNDIG1L, SYNE1, SYNE2, SYNE3, SYNE4, SYNGAP1, SYNGR1, SYNGR2, SYNGR3, SYNGR4, SYNJ1, SYNJ2, SYNJ2BP, SYNJ2BP-COX16, SYNM, SYNPO, SYNPO2, SYNPO2L, SYNPR, SYNRG, SYP, SYPL1, SYPL2, SYS1, SYS1-DBNDD2, SYT1, SYT10, SYT11, SYT12, SYT13, SYT14, SYT15, SYT16, SYT17, SYT2, SYT3, SYT4, SYT5, SYT6, SYT7, SYT8, SYT9, SYTL1, SYTL2, SYTL3, SYTL4, SYTL5, SYVN1, SZRD1, SZT2, T, TAAR1, TAAR2, TAAR5, TAAR6, TAAR8, TAAR9, TAB1, TAB2, TAB3, TAC1, TAC3, TAC4, TACC1, TACC2, TACC3, TACO1, TACR1, TACR2, TACR3, TACSTD2, TADA1, TADA2A, TADA2B, TADA3, TAF1, TAF10, TAF11, TAF12, TAF13, TAF15, TAF1A, TAF1B, TAF1C, TAF1D, TAF1L, TAF2, TAF3, TAF4, TAF4B, TAF5, TAF5L, TAF6, TAF6L, TAF7, TAF7L, TAF8, TAF9, TAF9B, TAGAP, TAGLN, TAGLN2, TAGLN3, TAL1, TAL2, TALDO1, TAMM41, TANC1, TANC2, TANGO2, TANGO6, TANK, TAOK1, TAOK2, TAOK3, TAP1, TAP2, TAPBP, TAPBPL, TAPT1, TARBP1, TARBP2, TARDBP, TARM1, TARS, TARS2, TARSL2, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R46, TAS2R5, TAS2R50, TAS2R60, TAS2R7, TAS2R8, TAS2R9, TASP1, TAT, TATDN1, TATDN2, TATDN3, TAX1BP1, TAX1BP3, TAZ, TBATA, TBC1D1, TBC1D10A, TBC1D10B, TBC1D10C, TBC1D12, TBC1D13, TBC1D14, TBC1D15, TBC1D16, TBC1D17, TBC1D19, TBC1D2, TBC1D20, TBC1D21, TBC1D22A, TBC1D22B, TBC1D23, TBC1D24, TBC1D25, TBC1D26, TBC1D28, TBC1D29, TBC1D2B, TBC1D3, TBC1D30, TBC1D31, TBC1D32, TBC1D3B, TBC1D3C, TBC1D3D, TBC1D3E, TBC1D3F, TBC1D3G, TBC1D3H, TBC1D3I, TBC1D3K, TBC1D3L, TBC1D4, TBC1D5, TBC1D7, TBC1D8, TBC1D8B, TBC1D9, TBC1D9B, TBCA, TBCB, TBCC, TBCCD1, TBCD, TBCE, TBCEL, TBCK, TBK1, TBKBP1, TBL1X, TBL1XR1, TBL1Y, TBL2, TBL3, TBP, TBPL1, TBPL2, TBR1, TBRG1, TBRG4, TBX1, TBX10, TBX15, TBX18, TBX19, TBX2, TBX20, TBX21, TBX22, TBX3, TBX4, TBX5, TBX6, TBXA2R, TBXAS1, TC2N, TCAF1, TCAF2, TCAIM, TCAP, TCEA1, TCEA2, TCEA3, TCEAL1, TCEAL2, TCEAL3, TCEAL4, TCEAL5, TCEAL6, TCEAL7, TCEAL8, TCEAL9, TCEANC, TCEANC2, TCERG1, TCERG1L, TCF12, TCF15, TCF19, TCF20, TCF21, TCF23, TCF24, TCF25, TCF3, TCF4, TCF7, TCF7L1, TCF7L2, TCFL5, TCHH, TCHHL1, TCHP, TCIRG1, TCL1A, TCL1B, TCN1, TCN2, TCOF1, TCP1, TCP10, TCP10L, TCP10L2, TCP11, TCP11L1, TCP11L2, TCP11X2, TCTA, TCTE1, TCTE3, TCTEX1D1, TCTEX1D2, TCTEX1D4, TCTN1, TCTN2, TCTN3, TDG, TDGF1, TDO2, TDP1, TDP2, TDRD1, TDRD10, TDRD12, TDRD15, TDRD3, TDRD5, TDRD6, TDRD7, TDRD9, TDRKH, TDRP, TEAD1, TEAD2, TEAD3, TEAD4, TEC, TECPR1, TECPR2, TECR, TECRL, TECTA, TECTB, TEDDM1, TEF, TEFM, TEK, TEKT1, TEKT2, TEKT3, TEKT4, TEKT5, TELO2, TEN1, TEN1-CDK3, TENM1, TENM2, TENM3, TENM4, TEP1, TEPP, TEPSIN, TERB1, TERB2, TERF1, TERF2, TERF2IP, TERT, TES, TESC, TESK1, TESK2, TESMIN, TESPA1, TET1, TET2, TET3, TEX10, TEX101, TEX11, TEX12, TEX13A, TEX13B, TEX13C, TEX13D, TEX14, TEX15, TEX19, TEX2, TEX22, TEX26, TEX261, TEX264, TEX28, TEX29, TEX30, TEX33, TEX35, TEX36, TEX37, TEX38, TEX43, TEX44, TEX45, TEX46, TEX47, TEX48, TEX49, TEX50, TEX51, TEX9, TF, TFAM, TFAP2A, TFAP2B, TFAP2C, TFAP2D, TFAP2E, TFAP4, TFB1M, TFB2M, TFCP2, TFCP2L1, TFDP1, TFDP2, TFDP3, TFE3, TFEB, TFEC, TFF1, TFF2, TFF3, TFG, TFIP11, TFPI, TFPI2, TFPT, TFR2, TFRC, TG, TGDS, TGFA, TGFB1, TGFB1I1, TGFB2, TGFB3, TGFBI, TGFBR1, TGFBR2, TGFBR3, TGFBR3L, TGFBRAP1, TGIF1, TGIF2, TGIF2-C20orf24, TGIF2LX, TGIF2LY, TGM1, TGM2, TGM3, TGM4, TGM5, TGM6, TGM7, TGOLN2, TGS1, TH, THADA, THAP1, THAP10, THAPi11, THAP12, THAP2, THAP3, THAP4, THAP5, THAP6, THAP7, THAP8, THAP9, THBD, THBS1, THBS2, THBS3, THBS4, THEG, THEGL, THEM4, THEM5, THEM6, THEMIS, THEMIS2, THG1L, THNSL1, THNSL2, THOC1, THOC2, THOC3, THOC5, THOC6, THOC7, THOP1, THPO, THRA, THRAP3, THRB, THRSP, THSD1, THSD4, THSD7A, THSD7B, THTPA, THUMPD1, THUMPD2, THUMPD3, THY1, THYN1, TIA1, TIAF1, TIAL1, TIAM1, TIAM2, TICAM1, TICAM2, TICRR, TIE1, TIFA, TIFAB, TIGAR, TIGD1, TIGD2, TIGD3, TIGD4, TIGD5, TIGD6, TIGD7, TIGIT, TIMD4, TIMELESS, TIMM10, TIMM10B, TIMM13, TIMM17A, TIMM17B, TIMM21, TIMM22, TIMM23, TIMM23B, TIMM29, TIMM44, TIMM50, TIMM8A, TIMM8B, TIMM9, TIMMDC1, TIMP1, TIMP2, TIMP3, TIMP4, TINAG, TINAGL1, TINCR, TINF2, TIPARP, TIPIN, TIPRL, TIRAP, TISP43, TJAP1, TJP1, TJP2, TJP3, TK1, TK2, TKFC, TKT, TKTL1, TKTL2, TLCD1, TLCD2, TLDC1, TLDC2, TLE1, TLE2, TLE3, TLE4, TLE6, TLK1, TLK2, TLL1, TLL2, TLN1, TLN2, TLNRD1, TLR1, TLR10, TLR2, TLR3, TLR4, TLR5, TLR6, TLR7, TLR8, TLR9, TLX1, TLX2, TLX3, TM2D1, TM2D2, TM2D3, TM4SF1, TM4SF18, TM4SF19, TM4SF19-TCTEX1D2, TM4SF20, TM4SF4, TM4SF5, TM6SF1, TM6SF2, TM7SF2, TM7SF3, TM9SF1, TM9SF2, TM9SF3, TM9SF4, TMA16, TMA7, TMBIM1, TMBIM4, TMBIM6, TMC1, TMC2, TMC3, TMC4, TMC5, TMC6, TMC7, TMC8, TMCC1, TMCC2, TMCC3, TMCO1, TMCO2, TMCO3, TMCO4, TMCO5A, TMCO6, TMED1, TMED10, TMED2, TMED3, TMED4, TMED5, TMED6, TMED7, TMED7-TICAM2, TMED8, TMED9, TMEFF1, TMEFF2, TMEM100, TMEM101, TMEM102, TMEM104, TMEM105, TMEM106A, TMEM106B, TMEM106C, TMEM107, TMEM108, TMEM109, TMEM11, TMEM110, TMEM110-MUSTN1, TMEM114, TMEM115, TMEM116, TMEM117, TMEM119, TMEM120A, TMEM120B, TMEM121, TMEM121B, TMEM123, TMEM125, TMEM126A, TMEM126B, TMEM127, TMEM128, TMEM129, TMEM130, TMEM131, TMEM131L, TMEM132A, TMEM132B, TMEM132C, TMEM132D, TMEM132E, TMEM133, TMEM134, TMEM135, TMEM136, TMEM138, TMEM139, TMEM140, TMEM141, TMEM143, TMEM144, TMEM145, TMEM147, TMEM14A, TMEM14B, TMEM14C, TMEM150A, TMEM150B, TMEM150C, TMEM151A, TMEM151B, TMEM154, TMEM155, TMEM156, TMEM158, TMEM159, TMEM160, TMEM161A, TMEM161B, TMEM163, TMEM164, TMEM165, TMEM167A, TMEM167B, TMEM168, TMEM169, TMEM17, TMEM170A, TMEM170B, TMEM171, TMEM173, TMEM174, TMEM175, TMEM176A, TMEM176B, TMEM177, TMEM178A, TMEM178B, TMEM179, TMEM179B, TMEM18, TMEM181, TMEM182, TMEM183A, TMEM184A, TMEM184B, TMEM184C, TMEM185A, TMEM185B, TMEM186, TMEM187, TMEM189, TMEM189-UBE2V1, TMEM19, TMEM190, TMEM191B, TMEM191C, TMEM192, TMEM196, TMEM198, TMEM199, TMEM2, TMEM200A, TMEM200B, TMEM200C, TMEM201, TMEM202, TMEM203, TMEM204, TMEM205, TMEM206, TMEM207, TMEM208, TMEM209, TMEM210, TMEM211, TMEM212, TMEM213, TMEM214, TMEM215, TMEM216, TMEM217, TMEM218, TMEM219, TMEM220, TMEM221, TMEM222, TMEM223, TMEM225, TMEM225B, TMEM229A, TMEM229B, TMEM230, TMEM231, TMEM232, TMEM233, TMEM234, TMEM235, TMEM236, TMEM237, TMEM238, TMEM239, TMEM240, TMEM241, TMEM242, TMEM243, TMEM244, TMEM245, TMEM246, TMEM247, TMEM248, TMEM249, TMEM25, TMEM250, TMEM251, TMEM252, TMEM253, TMEM254, TMEM255A, TMEM255B, TMEM256, TMEM256-PLSCR3, TMEM257, TMEM258, TMEM259, TMEM26, TMEM260, TMEM262, TMEM263, TMEM265, TMEM266, TMEM267, TMEM268, TMEM269, TMEM27, TMEM270, TMEM30A, TMEM30B, TMEM31, TMEM33, TMEM35A, TMEM35B, TMEM37, TMEM38A, TMEM38B, TMEM39A, TMEM39B, TMEM40, TMEM41A, TMEM41B, TMEM42, TMEM43, TMEM44, TMEM45A, TMEM45B, TMEM47, TMEM5, TMEM50A, TMEM50B, TMEM51, TMEM52, TMEM52B, TMEM53, TMEM54, TMEM55A, TMEM55B, TMEM56, TMEM56-RWDD3, TMEM57, TMEM59, TMEM59L, TMEM60, TMEM61, TMEM62, TMEM63A, TMEM63B, TMEM63C, TMEM64, TMEM65, TMEM67, TMEM68, TMEM69, TMEM70, TMEM71, TMEM72, TMEM74, TMEM74B, TMEM78, TMEM79, TMEM80, TMEM81, TMEM82, TMEM86A, TMEM86B, TMEM87A, TMEM87B, TMEM88, TMEM88B, TMEM89, TMEM8A, TMEM8B, TMEM9, TMEM91, TMEM92, TMEM94, TMEM95, TMEM97, TMEM98, TMEM99, TMEM9B, TMF1, TMIE, TMIGD1, TMIGD2, TMIGD3, TMLHE, TMOD1, TMOD2, TMOD3, TMOD4, TMPO, TMPPE, TMPRSS11A, TMPRSS11B, TMPRSS11D, TMPRSS11E, TMPRSS11F, TMPRSS12, TMPRSS13, TMPRSS15, TMPRSS2, TMPRSS3, TMPRSS4, TMPRSS4-AS1, TMPRSS5, TMPRSS6, TMPRSS7, TMPRSS9, TMSB10, TMSB15A, TMSB15B, TMSB4X, TMSB4Y, TMTC1, TMTC2, TMTC3, TMTC4, TMUB1, TMUB2, TMX1, TMX2, TMX2-CTNND1, TMX3, TMX4, TNC, TNF, TNFAIP1, TNFAIP2, TNFAIP3, TNFAIP6, TNFAIP8, TNFAIP8L1, TNFAIP8L2, TNFAIP8L3, TNFRSF10A, TNFRSF10B, TNFRSF10C, TNFRSF10D, TNFRSF11A, TNFRSF11B, TNFRSF12A, TNFRSF13B, TNFRSF13C, TNFRSF14, TNFRSF17, TNFRSF18, TNFRSF19, TNFRSF1A, TNFRSF1B, TNFRSF21, TNFRSF25, TNFRSF4, TNFRSF6B, TNFRSF8, TNFRSF9, TNFSF10, TNFSF11, TNFSF12, TNFSF12-TNFSF13, TNFSF13, TNFSF13B, TNFSF14, TNFSF15, TNFSF18, TNFSF4, TNFSF8, TNFSF9, TNIK, TNIP1, TNIP2, TNIP3, TNK1, TNK2, TNKS, TNKS1BP1, TNKS2, TNMD, TNN, TNNC1, TNNC2, TNNI1, TNNI2, TNNI3, TNNI3K, TNNT1, TNNT2, TNNT3, TNP1, TNP2, TNPO1, TNPO2, TNPO3, TNR, TNRC18, TNRC6A, TNRC6B, TNRC6C, TNS1, TNS2, TNS3, TNS4, TNXB, TOB1, TOB2, TOE1, TOGARAMI, TOGARAM2, TOLLIP, TOM1, TOM1L1, TOM1L2, TOMM20, TOMM20L, TOMM22, TOMM34, TOMM40, TOMM40L, TOMM5, TOMM6, TOMM7, TOMM70, TONSL, TOPI, TOP1MT, TOP2A, TOP2B, TOP3A, TOP3B, TOPAZ1, TOPBP1, TOPORS, TOR1A, TOR1AIP1, TOR1AIP2, TOR1B, TOR2A, TOR3A, TOR4A, TOX, TOX2, TOX3, TOX4, TP53, TP53AIP1, TP53BP1, TP53BP2, TP53I11, TP53I13, TP53I3, TP53INP1, TP53INP2, TP53RK, TP53TG3, TP53TG3B, TP53TG3C, TP53TG3D, TP53TG3E, TP53TG3F, TP53TG5, TP63, TP73, TPBG, TPBGL, TPCN1, TPCN2, TPD52, TPD52L1, TPD52L2, TPD52L3, TPGS1, TPGS2, TPH1, TPH2, TPI1, TPK1, TPM1, TPM2, TPM3, TPM4, TPMT, TPO, TPP1, TPP2, TPPP, TPPP2, TPPP3, TPR, TPRA1, TPRG1, TPRG1L, TPRKB, TPRN, TPRX1, TPSAB1, TPSB2, TPSD1, TPSG1, TPST1, TPST2, TPT1, TPTE, TPTE2, TPX2, TRA2A, TRA2B, TRABD, TRABD2A, TRABD2B, TRAC, TRADD, TRAF1, TRAF2, TRAF3, TRAF3IP1, TRAF3IP2, TRAF3IP3, TRAF4, TRAF5, TRAF6, TRAF7, TRAFD1, TRAIP, TRAJ1, TRAJ10, TRAJ11, TRAJ12, TRAJ13, TRAJ14, TRAJ16, TRAJ17, TRAJ18, TRAJ19, TRAJ2, TRAJ20, TRAJ21, TRAJ22, TRAJ23, TRAJ24, TRAJ25, TRAJ26, TRAJ27, TRAJ28, TRAJ29, TRAJ3, TRAJ30, TRAJ31, TRAJ32, TRAJ33, TRAJ34, TRAJ35, TRAJ36, TRAJ37, TRAJ38, TRAJ39, TRAJ4, TRAJ40, TRAJ41, TRAJ42, TRAJ43, TRAJ44, TRAJ45, TRAJ46, TRAJ47, TRAJ48, TRAJ49, TRAJ5, TRAJ50, TRAJ52, TRAJ53, TRAJ54, TRAJ56, TRAJ57, TRAJ58, TRAJ59, TRAJ6, TRAJ61, TRAJ7, TRAJ9, TRAK1, TRAK2, TRAM1, TRAM1L1, TRAM2, TRANK1, TRAP1, TRAPPC1, TRAPPC10, TRAPPC11, TRAPPC12, TRAPPC13, TRAPPC2, TRAPPC2L, TRAPPC3, TRAPPC3L, TRAPPC4, TRAPPC5, TRAPPC6A, TRAPPC6B, TRAPPC8, TRAPPC9, TRAT1, TRAV10, TRAV1-1, TRAV1-2, TRAV12-1, TRAV12-2, TRAV12-3, TRAV13-1, TRAV13-2, TRAV14DV4, TRAV16, TRAV17, TRAV18, TRAV19, TRAV2, TRAV20, TRAV21, TRAV22, TRAV23DV6, TRAV24, TRAV25, TRAV26-1, TRAV26-2, TRAV27, TRAV29DV5, TRAV3, TRAV30, TRAV34, TRAV36DV7, TRAV38-1, TRAV38-2DV8, TRAV39, TRAV4, TRAV40, TRAV41, TRAV5, TRAV6, TRAV7, TRAV8-1, TRAV8-2, TRAV8-3, TRAV8-4, TRAV8-6, TRAV8-7, TRAV9-1, TRAV9-2, TRBC2, TRBJ2-1, TRBJ2-2, TRBJ2-2P, TRBJ2-3, TRBJ2-4, TRBJ2-5, TRBJ2-6, TRBJ2-7, TRBV10-1, TRBV10-2, TRBV10-3, TRBV11-1, TRBV19, TRBV2, TRBV20-1, TRBV20OR9-2, TRBV21OR9-2, TRBV23-1, TRBV23OR9-2, TRBV24-1, TRBV25-1, TRBV27, TRBV28, TRBV29-1, TRBV30, TRBV3-1, TRBV4-1, TRBV4-2, TRBV5-1, TRBV5-3, TRBV5-4, TRBV5-5, TRBV5-6, TRBV5-7, TRBV6-1, TRBV6-4, TRBV6-5, TRBV6-6, TRBV6-7, TRBV6-8, TRBV7-1, TRBV7-3, TRBV7-4, TRBV7-6, TRBV7-7, TRBV7-9, TRBV9, TRDC, TRDD1, TRDD2, TRDD3, TRDJ1, TRDJ2, TRDJ3, TRDJ4, TRDMT1, TRDN, TRDV1, TRDV2, TRDV3, TREH, TREM1, TREM2, TREML1, TREML2, TREML4, TRERF1, TREX1, TREX2, TRGC1, TRGC2, TRGJ1, TRGJ2, TRGJP, TRGJP1, TRGJP2, TRGV1, TRGV10, TRGV11, TRGV2, TRGV3, TRGV4, TRGV5, TRGV8, TRGV9, TRH, TRHDE, TRHR, TRIAP1, TRIB1, TRIB2, TRIB3, TRIL, TRIM10, TRIM11, TRIM13, TRIM14, TRIM15, TRIM16, TRIM16L, TRIM17, TRIM2, TRIM21, TRIM22, TRIM23, TRIM24, TRIM25, TRIM26, TRIM27, TRIM28, TRIM29, TRIM3, TRIM31, TRIM32, TRIM33, TRIM34, TRIM35, TRIM36, TRIM37, TRIM38, TRIM39, TRIM39-RPP21, TRIM4, TRIM40, TRIM41, TRIM42, TRIM43, TRIM43B, TRIM44, TRIM45, TRIM46, TRIM47, TRIM48, TRIM49, TRIM49B, TRIM49C, TRIM49D1, TRIM49D2, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM66, TRIM67, TRIM68, TRIM69, TRIM6-TRIM34, TRIM7, TRIM71, TRIM72, TRIM73, TRIM74, TRIM75P, TRIM77, TRIM8, TRIM9, TRIML1, TRIML2, TRIO, TRIOBP, TRIP10, TRIP11, TRIP12, TRIP13, TRIP4, TRIP6, TRIQK, TRIR, TRIT1, TRMO, TRMT1, TRMT10A, TRMT10B, TRMT10C, TRMT11, TRMT112, TRMT12, TRMT13, TRMT1L, TRMT2A, TRMT2B, TRMT44, TRMT5, TRMT6, TRMT61A, TRMT61B, TRMU, TRNAU1AP, TRNP1, TRNT1, TRO, TROAP, TROVE2, TRPA1, TRPC1, TRPC3, TRPC4, TRPC4AP, TRPC5, TRPC50S, TRPC6, TRPC7, TRPM1, TRPM2, TRPM3, TRPM4, TRPM5, TRPM6, TRPM7, TRPM8, TRPS1, TRPT1, TRPV1, TRPV2, TRPV3, TRPV4, TRPV5, TRPV6, TRRAP, TRUB1, TRUB2, TSACC, TSC1, TSC2, TSC22D1, TSC22D2, TSC22D3, TSC22D4, TSEN15, TSEN2, TSEN34, TSEN54, TSFM, TSG101, TSGA10, TSGA10IP, TSGA13, TSHB, TSHR, TSHZ1, TSHZ2, TSHZ3, TSKS, TSKU, TSLP, TSN, TSNAREl, TSNAX, TSNAX-DISC1, TSNAXIP1, TSPAN1, TSPAN10, TSPAN11, TSPAN12, TSPAN13, TSPAN14, TSPAN15, TSPAN16, TSPAN17, TSPAN18, TSPAN19, TSPAN2, TSPAN3, TSPAN31, TSPAN32, TSPAN33, TSPAN4, TSPAN5, TSPAN6, TSPAN7, TSPAN8, TSPAN9, TSPEAR, TSPO, TSPO2, TSPOAP1, TSPY1, TSPY10, TSPY2, TSPY3, TSPY4, TSPY8, TSPYL1, TSPYL2, TSPYL4, TSPYL5, TSPYL6, TSR1, TSR2, TSR3, TSSC4, TSSKlB, TSSK2, TSSK3, TSSK4, TSSK6, TST, TSTA3, TSTD1, TSTD2, TSTD3, TTBK1, TTBK2, TTC1, TTC12, TTC13, TTC14, TTC16, TTC17, TTC19, TTC21A, TTC21B, TTC22, TTC23, TTC23L, TTC24, TTC25, TTC26, TTC27, TTC28, TTC29, TTC3, TTC30A, TTC30B, TTC31, TTC32, TTC33, TTC34, TTC36, TTC37, TTC38, TTC39A, TTC39B, TTC39C, TTC4, TTC5, TTC6, TTC7A, TTC7B, TTC8, TTC9, TTC9B, TTC9C, TTF1, TTF2, TTI1, TTI2, TTK, TTL, TTLL1, TTLL10, TTLL11, TTLL12, TTLL13P, TTLL2, TTLL3, TTLL4, TTLL5, TTLL6, TTLL7, TTLL8, TTLL9, TTN, TTPA, TTPAL, TTR, TTYH1, TTYH2, TTYH3, TUB, TUBA1A, TUBAIB, TUBAIC, TUBA3C, TUBA3D, TUBA3E, TUBA4A, TUBA4B, TUBA8, TUBAL3, TUBB, TUBB1, TUBB2A, TUBB2B, TUBB3, TUBB4A, TUBB4B, TUBB6, TUBB8, TUBD1, TUBE1, TUBG1, TUBG2, TUBGCP2, TUBGCP3, TUBGCP4, TUBGCP5, TUBGCP6, TUFM, TUFT1, TULP1, TULP2, TULP3, TULP4, TUNAR, TUSC1, TUSC2, TUSC3, TUSC5, TUT1, TVP23A, TVP23B, TVP23C, TVP23C-CDRT4, TWF1, TWF2, TWISTI, TWIST2, TWISTNB, TWNK, TWSG1, TXK, TXLNA, TXLNB, TXLNG, TXN, TXN2, TXNDC11, TXNDC12, TXNDC15, TXNDC16, TXNDC17, TXNDC2, TXNDC5, TXNDC8, TXNDC9, TXNIP, TXNL1, TXNL4A, TXNL4B, TXNRD1, TXNRD2, TXNRD3, TXNRD3NB, TYK2, TYMP, TYMS, TYR, TYRO3, TYROBP, TYRP1, TYSND1, TYW1, TYW1B, TYW3, TYW5, U2AF1, U2AF1L4, U2AF1L5, U2AF2, U2SURP, UACA, UAP1, UAP1L1, UBA1, UBA2, UBA3, UBA5, UBA52, UBA6, UBA7, UBAC1, UBAC2, UBALDI, UBALD2, UBAP1, UBAPIL, UBAP2, UBAP2L, UBASH3A, UBASH3B, UBB, UBC, UBD, UBE2A, UBE2B, UBE2C, UBE2D1, UBE2D2, UBE2D3, UBE2D4, UBE2E1, UBE2E2, UBE2E3, UBE2F, UBE2F-SCLY, UBE2G1, UBE2G2, UBE2H, UBE2I, UBE2J1, UBE2J2, UBE2K, UBE2L3, UBE2L5P, UBE2L6, UBE2M, UBE2N, UBE2NL, UBE20, UBE2Q1, UBE2Q2, UBE2Q2L, UBE2QL1, UBE2R2, UBE2S, UBE2T, UBE2U, UBE2V1, UBE2V2, UBE2W, UBE2Z, UBE3A, UBE3B, UBE3C, UBE3D, UBE4A, UBE4B, UBFD1, UBIAD1, UBL3, UBL4A, UBL4B, UBL5, UBL7, UBLCP1, UBN1, UBN2, UBOX5, UBP1, UBQLN1, UBQLN2, UBQLN3, UBQLN4, UBQLNL, UBR1, UBR2, UBR3, UBR4, UBR5, UBR7, UBTD1, UBTD2, UBTF, UBTFL1, UBXN1, UBXN10, UBXN11, UBXN2A, UBXN2B, UBXN4, UBXN6, UBXN7, UBXN8, UCHL1, UCHL3, UCHL5, UCK1, UCK2, UCKL1, UCMA, UCN, UCN2, UCN3, UCP1, UCP2, UCP3, UEVLD, UFC1, UFD1, UFL1, UFM1, UFSP1, UFSP2, UGCG, UGDH, UGGT1, UGGT2, UGP2, UGT1A1, UGT1A10, UGT1A3, UGT1A4, UGT1A5, UGT1A6, UGT1A7, UGT1A8, UGT1A9, UGT2A1, UGT2A2, UGT2A3, UGT2B10, UGT2B111, UGT2B15, UGT2B17, UGT2B28, UGT2B4, UGT2B7, UGT3A1, UGT3A2, UGT8, UHMK1, UHRF1, UHRF1BP1, UHRF1BP1L, UHRF2, UIMC1, ULBP1, ULBP2, ULBP3, ULK1, ULK2, ULK3, ULK4, UMAD1, UMOD, UMODL1, UMPS, UNC119, UNC119B, UNC13A, UNC13B, UNC13C, UNC13D, UNC45A, UNC45B, UNC50, UNC5A, UNC5B, UNC5C, UNC5CL, UNC5D, UNC79, UNC80, UNC93A, UNC93B1, UNCX, UNG, UNK, UNKL, UPB1, UPF1, UPF2, UPF3A, UPF3B, UPK1A, UPK1B, UPK2, UPK3A, UPK3B, UPK3BL1, UPP1, UPP2, UPRT, UQCC1, UQCC2, UQCC3, UQCR10, UQCR11, UQCRB, UQCRC1, UQCRC2, UQCRF S1, UQCRH, UQCRHL, UQCRQ, URAD, URB1, URB2, URGCP, URGCP-MRPS24, URIl, URM1, UROC1, UROD, UROS, USB1, USEl, USF1, USF2, USF3, USH1C, USH1G, USH2A, USHBP1, USMG5, USO1, USP1, USP10, USP11, USP12, USP13, USP14, USP15, USP16, USP17L1, USP17L10, USP17L11, USP17L12, USP17L13, USP17L15, USP17L17, USP17L18, USP17L19, USP17L2, USP17L20, USP17L21, USP17L22, USP17L23, USP17L24, USP17L25, USP17L26, USP17L27, USP17L28, USP17L29, USP17L3, USP17L30, USP17L4, USP17L5, USP17L7, USP17L8, USP18, USP19, USP2, USP20, USP21, USP22, USP24, USP25, USP26, USP27X, USP28, USP29, USP3, USP30, USP31, USP32, USP33, USP34, USP35, USP36, USP37, USP38, USP39, USP4, USP40, USP41, USP42, USP43, USP44, USP45, USP46, USP47, USP48, USP49, USP5, USP50, USP51, USP53, USP54, USP6, USP6NL, USP7, USP8, USP9X, USP9Y, USPL1, UST, UTF1, UTP11, UTP14A, UTP14C, UTP15, UTP18, UTP20, UTP23, UTP3, UTP4, UTP6, UTRN, UTS2, UTS2B, UTS2R, UTY, UVRAG, UVSSA, UXS1, UXT, VAC14, VAMP1, VAMP2, VAMP3, VAMP4, VAMP5, VAMP7, VAMP8, VANGLI, VANGL2, VAPA, VAPB, VARS, VARS2, VASH1, VASH2, VASN, VASP, VAT1, VAT1L, VAV1, VAV2, VAV3, VAX1, VAX2, VBP1, VCAM1, VCAN, VCL, VCP, VCPIP1, VCPKMT, VCX, VCX2, VCX3A, VCX3B, VCY, VCY1B, VDAC1, VDAC2, VDAC3, VDR, VEGFA, VEGFB, VEGFC, VEGFD, VENTX, VEPH1, VEZF1, VEZT, VGF, VGLL1, VGLL2, VGLL3, VGLL4, VHL, VHLL, VIL1, VILL, VIM, VIP, VIPAS39, VIPR1, VIPR2, VIRMA, VIT, VKORC1, VKORC1L1, VLDLR, VMA21, VMAC, VMO1, VMP1, VN1R1, VN1R2, VN1R4, VN1R5, VNN1, VNN2, VNN3, VOPP1, VPREB1, VPREB3, VPS11, VPS13A, VPS13B, VPS13C, VPS13D, VPS16, VPS18, VPS25, VPS26A, VPS26B, VPS28, VPS29, VPS33A, VPS33B, VPS35, VPS36, VPS37A, VPS37B, VPS37C, VPS37D, VPS39, VPS41, VPS45, VPS4A, VPS4B, VPS50, VPS51, VPS52, VPS53, VPS54, VPS72, VPS8, VPS9D1, VRK1, VRK2, VRK3, VRTN, VSIG1, VSIG10, VSIG10L, VSIG10L2, VSIG2, VSIG4, VSIG8, VSIR, VSNL1, VSTM1, VSTM2A, VSTM2B, VSTM2L, VSTM4, VSTM5, VSX1, VSX2, VTA1, VTCN1, VTI1A, VTI1B, VTN, VWA1, VWA2, VWA3A, VWA3B, VWA5A, VWA5B1, VWA5B2, VWA7, VWA8, VWC2, VWC2L, VWCE, VWDE, VWF, WAC, WAPL, WARS, WARS2, WAS, WASF1, WASF2, WASF3, WASHC1, WASHC2A, WASHC2C, WASHC3, WASHC4, WASHC5, WASL, WBP1, WBP11, WBP1L, WBP2, WBP2NL, WBP4, WDCP, WDFY1, WDFY2, WDFY3, WDFY4, WDHD1, WDPCP, WDR1, WDR11, WDR12, WDR13, WDR17, WDR18, WDR19, WDR20, WDR24, WDR25, WDR26, WDR27, WDR3, WDR31, WDR33, WDR34, WDR35, WDR36, WDR37, WDR38, WDR4, WDR41, WDR43, WDR44, WDR45, WDR45B, WDR46, WDR47, WDR48, WDR49, WDR5, WDR53, WDR54, WDR55, WDR59, WDR5B, WDR6, WDR60, WDR61, WDR62, WDR63, WDR64, WDR66, WDR7, WDR70, WDR72, WDR73, WDR74, WDR75, WDR76, WDR77, WDR78, WDR81, WDR82, WDR83, WDR83OS, WDR86, WDR87, WDR88, WDR89, WDR90, WDR91, WDR92, WDR93, WDR97, WDSUB1, WDTC1, WDYHV1, WEE1, WEE2, WFDC1, WFDC10A, WFDC10B, WFDC11, WFDC12, WFDC13, WFDC2, WFDC3, WFDC5, WFDC6, WFDC8, WFDC9, WFIKKN1, WFIKKN2, WFS1, WHAMM, WHRN, WIF1, WIPF1, WIPF2, WIPF3, WIPI1, WIPI2, WISP1, WISP2, WISP3, WIZ, WLS, WNK1, WNK2, WNK3, WNK4, WNT1, WNT10A, WNT10B, WNT11, WNT16, WNT2, WNT2B, WNT3, WNT3A, WNT4, WNT5A, WNT5B, WNT6, WNT7A, WNT7B, WNT8A, WNT8B, WNT9A, WNT9B, WRAP53, WRAP73, WRB, WRN, WRNIP1, WSB1, WSB2, WSCD1, WSCD2, WT1, WTAP, WTH3DI, WTIP, WWC1, WWC2, WWC3, WWOX, WWP1, WWP2, WWTR1, XAB2, XAF1, XAGE1A, XAGE1B, XAGE2, XAGE3, XAGE5, XBP1, XCL1, XCL2, XCR1, XDH, XG, XIAP, XIRP1, XIRP2, XK, XKR3, XKR4, XKR5, XKR6, XKR7, XKR8, XKR9, XKRX, XPA, XPC, XPNPEP1, XPNPEP2, XPNPEP3, XPO1, XPO4, XPO5, XPO6, XPO7, XPOT, XPR1, XRCC1, XRCC2, XRCC3, XRCC4, XRCC5, XRCC6, XRN1, XRN2, XRRA1, XXYLT1, XYLB, XYLT1, XYLT2, YAE1D1, YAF2, YAP1, YARS, YARS2, YBEY, YBX1, YBX2, YBX3, YDJC, YEATS2, YEATS4, YES1, YIF1A, YIF1B, YIPF1, YIPF2, YIPF3, YIPF4, YIPF5, YIPF6, YIPF7, YJEFN3, YKT6, YLPM1, YME1L1, YOD1, YPEL1, YPEL2, YPEL3, YPEL4, YPEL5, YRDC, YTHDC1, YTHDC2, YTHDF1, YTHDF2, YTHDF3, YWHAB, YWHAE, YWHAG, YWHAH, YWHAQ, YWHAZ, YY1, YY1AP1, YY2, Z82206.1, Z83844.1, Z84492.1, Z98749.3, Z98752.3, ZACN, ZADH2, ZAN, ZAP70, ZAR1, ZAR1L, ZBBX, ZBED1, ZBED2, ZBED3, ZBED4, ZBED5, ZBED6, ZBED6CL, ZBED8, ZBED9, ZBP1, ZBTB1, ZBTB10, ZBTB11, ZBTB12, ZBTB14, ZBTB16, ZBTB17, ZBTB18, ZBTB2, ZBTB20, ZBTB21, ZBTB22, ZBTB24, ZBTB25, ZBTB26, ZBTB3, ZBTB32, ZBTB33, ZBTB34, ZBTB37, ZBTB38, ZBTB39, ZBTB4, ZBTB40, ZBTB41, ZBTB42, ZBTB43, ZBTB44, ZBTB45, ZBTB46, ZBTB47, ZBTB48, ZBTB49, ZBTB5, ZBTB6, ZBTB7A, ZBTB7B, ZBTB7C, ZBTB8A, ZBTB8B, ZBTB8OS, ZBTB9, ZC2HC1A, ZC2HC1B, ZC2HC1C, ZC3H10, ZC3H11A, ZC3H11B, ZC3H12A, ZC3H12B, ZC3H12C, ZC3H12D, ZC3H13, ZC3H14, ZC3H15, ZC3H18, ZC3H3, ZC3H4, ZC3H6, ZC3H7A, ZC3H7B, ZC3H8, ZC3HAV1, ZC3HAV1L, ZC3HC1, ZC4H2, ZCCHC10, ZCCHC11, ZCCHC12, ZCCHC13, ZCCHC14, ZCCHC17, ZCCHC18, ZCCHC2, ZCCHC24, ZCCHC3, ZCCHC4, ZCCHC6, ZCCHC7, ZCCHC8, ZCCHC9, ZCRB1, ZCWPW1, ZCWPW2, ZDBF2, ZDHHC1, ZDHHC11, ZDHHC11B, ZDHHC12, ZDHHC13, ZDHHC14, ZDHHC15, ZDHHC16, ZDHHC17, ZDHHC18, ZDHHC19, ZDHHC2, ZDHHC20, ZDHHC21, ZDHHC22, ZDHHC23, ZDHHC24, ZDHHC3, ZDHHC4, ZDHHC5, ZDHHC6, ZDHHC7, ZDHHC8, ZDHHC9, ZEB1, ZEB2, ZER1, ZFAND1, ZFAND2A, ZFAND2B, ZFAND3, ZFAND4, ZFAND5, ZFAND6, ZFAT, ZFC3H1, ZFHX2, ZFHX3, ZFHX4, ZFP1, ZFP14, ZFP2, ZFP28, ZFP3, ZFP30, ZFP36, ZFP36L1, ZFP36L2, ZFP37, ZFP41, ZFP42, ZFP57, ZFP62, ZFP64, ZFP69, ZFP69B, ZFP82, ZFP90, ZFP91, ZFP91-CNTF, ZFP92, ZFPL1, ZFPM1, ZFPM2, ZFR, ZFR2, ZFX, ZFY, ZFYVE1, ZFYVE16, ZFYVE19, ZFYVE21, ZFYVE26, ZFYVE27, ZFYVE28, ZFYVE9, ZG16, ZG16B, ZGLP1, ZGPAT, ZGRF1, ZHX1, ZHX1-C8orf76, ZHX2, ZHX3, ZIC1, ZIC2, ZIC3, ZIC4, ZIC5, ZIK1, ZIM2, ZIM3, ZKSCAN1, ZKSCAN2, ZKSCAN3, ZKSCAN4, ZKSCAN5, ZKSCAN7, ZKSCAN8, ZMAT1, ZMAT2, ZMAT3, ZMAT4, ZMAT5, ZMIZ1, ZMIZ2, ZMPSTE24, ZMYM1, ZMYM2, ZMYM3, ZMYM4, ZMYM5, ZMYM6, ZMYND10, ZMYND11, ZMYND12, ZMYND15, ZMYND19, ZMYND8, ZNF10, ZNF100, ZNF101, ZNF106, ZNF107, ZNF112, ZNF114, ZNF117, ZNF12, ZNF121, ZNF124, ZNF131, ZNF132, ZNF133, ZNF134, ZNF135, ZNF136, ZNF138, ZNF14, ZNF140, ZNF141, ZNF142, ZNF143, ZNF146, ZNF148, ZNF154, ZNF155, ZNF157, ZNF16, ZNF160, ZNF165, ZNF169, ZNF17, ZNF174, ZNF175, ZNF177, ZNF18, ZNF180, ZNF181, ZNF182, ZNF184, ZNF185, ZNF189, ZNF19, ZNF195, ZNF197, ZNF2, ZNF20, ZNF200, ZNF202, ZNF205, ZNF207, ZNF208, ZNF211, ZNF212, ZNF213, ZNF214, ZNF215, ZNF217, ZNF219, ZNF22, ZNF221, ZNF222, ZNF223, ZNF224, ZNF225, ZNF226, ZNF227, ZNF229, ZNF23, ZNF230, ZNF232, ZNF233, ZNF234, ZNF235, ZNF236, ZNF239, ZNF24, ZNF248, ZNF25, ZNF250, ZNF251, ZNF253, ZNF254, ZNF256, ZNF257, ZNF26, ZNF260, ZNF263, ZNF264, ZNF266, ZNF267, ZNF268, ZNF273, ZNF274, ZNF275, ZNF276, ZNF277, ZNF28, ZNF280A, ZNF280B, ZNF280C, ZNF280D, ZNF281, ZNF282, ZNF283, ZNF284, ZNF285, ZNF286A, ZNF286B, ZNF287, ZNF292, ZNF296, ZNF3, ZNF30, ZNF300, ZNF302, ZNF304, ZNF311, ZNF316, ZNF317, ZNF318, ZNF319, ZNF32, ZNF320, ZNF322, ZNF324, ZNF324B, ZNF326, ZNF329, ZNF330, ZNF331, ZNF333, ZNF334, ZNF335, ZNF337, ZNF33A, ZNF33B, ZNF34, ZNF341, ZNF343, ZNF345, ZNF346, ZNF347, ZNF35, ZNF350, ZNF354A, ZNF354B, ZNF354C, ZNF358, ZNF362, ZNF365, ZNF366, ZNF367, ZNF37A, ZNF382, ZNF383, ZNF384, ZNF385A, ZNF385B, ZNF385C, ZNF385D, ZNF391, ZNF394, ZNF395, ZNF396, ZNF397, ZNF398, ZNF404, ZNF407, ZNF408, ZNF41, ZNF410, ZNF414, ZNF415, ZNF416, ZNF417, ZNF418, ZNF419, ZNF420, ZNF423, ZNF425, ZNF426, ZNF428, ZNF429, ZNF43, ZNF430, ZNF431, ZNF432, ZNF433, ZNF436, ZNF438, ZNF439, ZNF44, ZNF440, ZNF441, ZNF442, ZNF443, ZNF444, ZNF445, ZNF446, ZNF449, ZNF45, ZNF451, ZNF454, ZNF460, ZNF461, ZNF462, ZNF467, ZNF468, ZNF469, ZNF470, ZNF471, ZNF473, ZNF474, ZNF479, ZNF48, ZNF480, ZNF483, ZNF484, ZNF485, ZNF486, ZNF487, ZNF488, ZNF490, ZNF491, ZNF492, ZNF493, ZNF496, ZNF497, ZNF500, ZNF501, ZNF502, ZNF503, ZNF506, ZNF507, ZNF510, ZNF511, ZNF512, ZNF512B, ZNF513, ZNF514, ZNF516, ZNF517, ZNF518A, ZNF518B, ZNF519, ZNF521, ZNF524, ZNF525, ZNF526, ZNF527, ZNF528, ZNF529, ZNF530, ZNF532, ZNF534, ZNF536, ZNF540, ZNF541, ZNF543, ZNF544, ZNF546, ZNF547, ZNF548, ZNF549, ZNF550, ZNF551, ZNF552, ZNF554, ZNF555, ZNF556, ZNF557, ZNF558, ZNF559, ZNF559-ZNF177, ZNF560, ZNF561, ZNF562, ZNF563, ZNF564, ZNF565, ZNF566, ZNF567, ZNF568, ZNF569, ZNF57, ZNF570, ZNF571, ZNF572, ZNF573, ZNF574, ZNF575, ZNF576, ZNF577, ZNF578, ZNF579, ZNF580, ZNF581, ZNF582, ZNF583, ZNF584, ZNF585A, ZNF585B, ZNF586, ZNF587, ZNF587B, ZNF589, ZNF592, ZNF593, ZNF594, ZNF595, ZNF596, ZNF597, ZNF598, ZNF599, ZNF600, ZNF605, ZNF606, ZNF607, ZNF608, ZNF609, ZNF610, ZNF611, ZNF613, ZNF614, ZNF615, ZNF616, ZNF618, ZNF619, ZNF620, ZNF621, ZNF622, ZNF623, ZNF624, ZNF625, ZNF625-ZNF20, ZNF626, ZNF627, ZNF628, ZNF629, ZNF630, ZNF638, ZNF639, ZNF641, ZNF644, ZNF645, ZNF646, ZNF648, ZNF649, ZNF652, ZNF653, ZNF654, ZNF655, ZNF658, ZNF66, ZNF660, ZNF662, ZNF664, ZNF665, ZNF667, ZNF668, ZNF669, ZNF670, ZNF670-ZNF695, ZNF671, ZNF672, ZNF674, ZNF675, ZNF676, ZNF677, ZNF678, ZNF679, ZNF680, ZNF681, ZNF682, ZNF683, ZNF684, ZNF687, ZNF688, ZNF689, ZNF69, ZNF691, ZNF692, ZNF695, ZNF696, ZNF697, ZNF699, ZNF7, ZNF70, ZNF700, ZNF701, ZNF703, ZNF704, ZNF705A, ZNF705B, ZNF705D, ZNF705E, ZNF705G, ZNF706, ZNF707, ZNF708, ZNF709, ZNF71, ZNF710, ZNF711, ZNF713, ZNF714, ZNF716, ZNF717, ZNF718, ZNF720, ZNF721, ZNF724, ZNF726, ZNF727, ZNF728, ZNF729, ZNF730, ZNF732, ZNF735, ZNF736, ZNF737, ZNF738, ZNF74, ZNF740, ZNF746, ZNF747, ZNF749, ZNF750, ZNF75A, ZNF75D, ZNF76, ZNF761, ZNF763, ZNF764, ZNF765, ZNF766, ZNF768, ZNF77, ZNF770, ZNF771, ZNF772, ZNF773, ZNF774, ZNF775, ZNF776, ZNF777, ZNF778, ZNF780A, ZNF780B, ZNF781, ZNF782, ZNF783, ZNF784, ZNF785, ZNF786, ZNF787, ZNF788, ZNF789, ZNF79, ZNF790, ZNF791, ZNF792, ZNF793, ZNF799, ZNF8, ZNF80, ZNF800, ZNF804A, ZNF804B, ZNF805, ZNF808, ZNF81, ZNF813, ZNF814, ZNF816, ZNF816-ZNF321P, ZNF821, ZNF823, ZNF827, ZNF829, ZNF83, ZNF830, ZNF831, ZNF835, ZNF836, ZNF837, ZNF839, ZNF84, ZNF841, ZNF843, ZNF844, ZNF845, ZNF846, ZNF85, ZNF850, ZNF852, ZNF853, ZNF860, ZNF862, ZNF865, ZNF878, ZNF879, ZNF880, ZNF883, ZNF888, ZNF891, ZNF90, ZNF91, ZNF92, ZNF93, ZNF98, ZNF99, ZNFX1, ZNHIT1, ZNHIT2, ZNHIT3, ZNHIT6, ZNRD1, ZNRF1, ZNRF2, ZNRF3, ZNRF4, ZP1, ZP2, ZP3, ZP4, ZPBP, ZPBP2, ZPLD1, ZPR1, ZRANB1, ZRANB2, ZRANB3, ZRSR1, ZRSR2, ZSCAN1, ZSCAN10, ZSCAN12, ZSCAN16, ZSCAN18, ZSCAN2, ZSCAN20, ZSCAN21, ZSCAN22, ZSCAN23, ZSCAN25, ZSCAN26, ZSCAN29, ZSCAN30, ZSCAN31, ZSCAN32, ZSCAN4, ZSCAN5A, ZSCAN5B, ZSCAN5C, ZSCAN9, ZSWIM1, ZSWIM2, ZSWIM3, ZSWIM4, ZSWIM5, ZSWIM6, ZSWIM7, ZSWIM8, ZUFSP, ZW10, ZWTLCH, ZWINT, ZXDA, ZXDB, ZXDC, ZYG11A, ZYG11B, ZYX, ZZEF1, and ZZZ3.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex© and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a provided compound and one or more additional therapeutic agents. The therapeutic agent may be administered together with a provided compound, or may be administered prior to or following administration of a provided compound. Suitable therapeutic agents are described in further detail below. In certain embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disesase, ulcerative colitis, or inflammatory bowel disease comprising administering to a patient in need thereof a provided compound and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a provided compound and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®.

In another embodiment, the present invention provides a method of treating a hematological malignancy comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a provided compound and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a provided compound and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereofa provided compound and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a provided compound and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocitic leukemia, diffuse large B-cell lymphoma, Hodgkin's disease, small-cell lung cancer, non-small-cell lung cancer, myelodysplastic syndrome, lymphoma, a hematological neoplasm, or solid tumor.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of modulating CRBN activity in a biological sample comprising the step of contacting said biological sample with a compound of this invention, or a composition comprising said compound.

According to another embodiment, the invention relates to a method of binding CRBN, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Binding CRBN (or a mutant thereof) activity in a biological sample is useful for a variety of purposes that are known to one of skill in the art. Examples of such purposes include, but are not limited to, biological specimen storage and biological assays.

Another embodiment of the present invention relates to a method of modulating CRBN activity in a patient comprising the step of administering to said patient a compound of the present invention, or a composition comprising said compound.

According to another embodiment, the invention relates to a method of modulating the activity of CRBN, or a mutant thereof, in a patient comprising the step of administering to said patient a compound of the present invention, or a composition comprising said compound. According to certain embodiments, the invention relates to a method of reversibly or irreversibly modulating one or more of CRBN, or a mutant thereof, activity in a patient comprising the step of administering to said patient a compound of the present invention, or a composition comprising said compound. In other embodiments, the present invention provides a method for treating a disorder mediated by CRBN, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR1 ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3K$\alpha$, PI3K$\gamma$, PI3K$\delta$, PI3K$\beta$, PI3K-C2$\alpha$, PI3K-C2$\beta$, PI3K-C2$\gamma$, Vps34, p110-$\alpha$, p110-$\beta$, p110-$\gamma$, p110-$\delta$, p85-$\alpha$, p85-$\beta$, p55-$\gamma$, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218, U.S. Pat. No. 7,514,444, WO2011090760, and U.S. Pat. No. 8,338,439, the entirety of each of which is herein incorporated by reference.

Further examples of SYK inhibitory compounds, and conditions treatable by such compounds in combination with compounds of this invention can be found in WO2003063794, U.S. Pat. No. 7,557,210, WO2005007623, U.S. Pat. No. 7,173,015, WO2006078846, and U.S. Pat. No. 7,449,458, the entirety of each of which is herein incorporated by reference.

Further examples of PI3K inhibitory compounds, and conditions treatable by such compounds in combination with compounds of this invention can be found in WO2004019973, U.S. Pat. No. 7,713,943, WO2004089925, U.S. Pat. No. 6,949,537, WO2007016176, U.S. Pat. Nos. 7,402,325, 8,138,347, WO2002088112, U.S. Pat. No. 7,071,189, WO2007084786, U.S. Pat. No. 8,217,035, WO2007129161, U.S. Pat. No. 7,781,433, WO2006122806, U.S. Pat. No. 7,667,039, WO2005113554, U.S. Pat. No. 7,932,260, WO2007044729, and U.S. Pat. No. 7,989,622, the entirety of each of which is herein incorporated by reference.

Further examples of JAK inhibitory compounds, and conditions treatable by such compounds in combination with compounds of this invention can be found in WO2009114512, U.S. Pat. No. 8,185,616, WO2008109943, U.S. Pat. No. 8,486,941, WO2007053452, U.S. Pat. No. 7,528,143, WO200142246, U.S. Pat. No. 6,627,754, WO2007070514, and U.S. Pat. No. 7,598,257, the entirety of each of which is herein incorporated by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MM1270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, 5-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/

Fni4, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTOR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/070024, US 2011/0165156, WO 2011/0107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgGI, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MED14736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/0053941, WO 2009/132238, US 2011/0136796, WO 2011/056652, US 2012/0277217, WO 2012/142237, US 2014/0066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo*, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAdl), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-lh68/GLV-lh153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TGO1 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCTO2124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by refenrece in its entirety. In some embodimetne, an immuno-oncology agent is selected from the examples described in Table 1 of Jerry L. Adams ET. AL. In some embodiments, an immuno-oncology agent is a small molecule targeting an immuno-oncoloby target selected from those listed in Table 2 of Jerry L. Adams ET. AL. In some embodiments, an immuno-oncology agent is a small molecule agent selectd from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by refenrece in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the conten of which is incorporated herein by reference in its entirety. In some embodiments, an immuno-oncology agent is a bispecific T cell engager (BiTE®) antibody construct. In some embodimens, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodimens, a bispecific T cell engager (BiTE®) antibody construct activates T cells. In some embodimens, a bispecific T cell engager (BiTE®) antibody construct activates T cells, which release cytokines inducing upregulation of intercellular adhesion molecule 1 (ICAM-1) and FAS on bystander cells. In some embodimens, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-acticvated T cells. In some embodiment, the bystander cells comprises tumor-associated antigen (TAA) negatgive cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgGI anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgGI Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KTR) inhibitors. KTR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgGI, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

General Synthetic Methods

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

TABLE 2

Analytical instruments

| | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give MH+] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase were used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give MH+] and equipped with Xbridge C18, 2.1X50 mm columns packed with 5 mm C18-coated silica or Kinetex EVO C18 2.1X30 mm columns packed with 5 mm C18-coated silica, eluting with 0.05 vol % NH$_3$H$_2$O in water (solvent A) and acetonitrile (solvent B).

HPLC Analytical Method: HPLC was carried out on X Bridge C18 150*4.6 mm, 5 micron. Column flow was 1.0 ml/min and mobile phase were used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19) mm, 5μ. Column flow was 16.0 ml/min. Mobile phase were used (A) 0.1% Formic Acid in Water and (B) Acetonitrile Basic method used (A) 5 mM ammonium bicarbonate and 0.1% NH3 in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

INTERMEDIATES

6-Bromo-9H-pyrido[2,3-b]indole (Intermediate A)

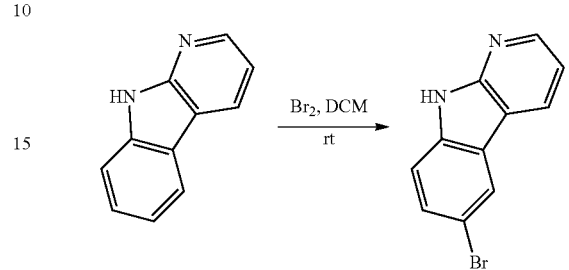

To a stirred solution of 9H-pyrido[2,3-b]indole (3 g, 17.9 mmol) in DCM (50 mL) was added dropwise of Br$_2$ (3.4 g, 21.4 mmol) at 0° C. To the mixture was added aq. NaHCO$_3$ (100 mL), extracted with EA (200 mL). The organic layer was washed with brine (50 mL), dried over Na$_2$SO$_4$, filtered, concentrated to give product 6-bromo-9H-pyrido[2,3-b]indole (2.7 g, 61% yield) as yellow solid. $^1$H NMR (400 MHz, DMSO-d$_6$) δ 12.02 (s, 1H), 8.60 (dd, J=1.2 Hz, J=7.6 Hz, 1H), 8.48-8.44 (m, 2H), 7.60-7.58 (m, 1H), 7.48 (d, J=8.4 Hz, 1H), 7.26 (dd, J=4.8 Hz, J=7.6 Hz, 1H). LC/MS (ESI, m/z): [M+1]$^+$=247.8.

tert-Butyl methyl(3-(prop-2-yn-1-yloxy)propyl)carbamate (Intermediate B)

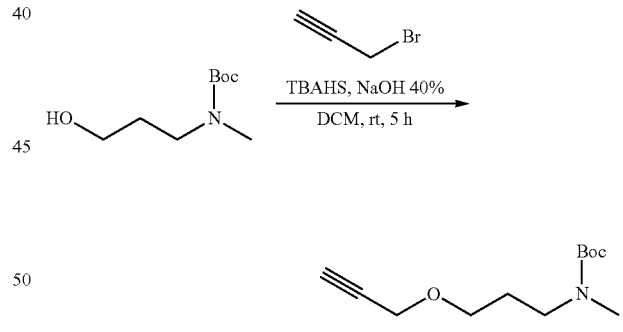

To a solution of tert-butyl (3-hydroxypropyl)(methyl) carbamate (2 g, 10.6 mmol) in DCM (30 mL) was added aq. NaOH (40%, 20 mL), 3-bromoprop-1-yne (1.9 g, 15.9 mmol) and TBAHS (180 mg, 0.530 mmol) at rt. The mixture was stirred for 3 h at rt. To the mixture was added H$_2$O (100 mL), extracted with DCM (100 mL). The organic layer was washed with brine (50 mL), dried over Na$_2$SO$_4$, filtered, concentrated and purified by column (PE/EA=20/1 to 10/1 to 4/1) to give product tert-butyl methyl(3-(prop-2-yn-1-yloxy)propyl)carbamate (1.4 g, 58% yield) as a yellow oil. $^1$H NMR (400 MHz, CDCl$_3$) δ 4.14 (d, J=6.4 Hz, 2H), 3.53 (t, J=6.4 Hz, 2H), 3.29 (t, J=6.8 Hz, 2H), 2.86 (s, 3H), 2.42 (t, J=2.4 Hz, 1H), 1.85-1.78 (m, 2H), 1.46 (s, 9H). LC/MS (ESI, m/z): [M+1]$^+$=227.9 tert-Butyl (2-(2-(prop-2-yn-1-yloxy)ethoxy)ethyl) carbamate (Intermediate C)

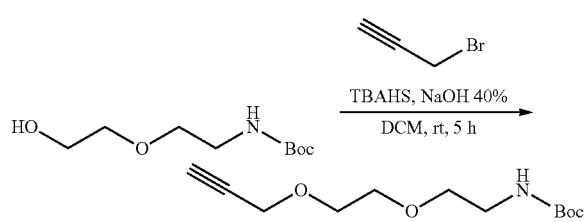

To a solution of tert-butyl (2-(2-hydroxyethoxy)ethyl) carbamate (2 g, 9.74 mmol) in DCM (30 mL) was added aq. NaOH (40%, 20 mL), 3-bromoprop-1-yne (1.7 g, 14.6 mmol) and TBAHS (0.17 g, 0.487 mmol) at rt. The mixture was stirred at room temperature for 3 h. To the mixture was added H$_2$O (100 mL), extracted with DCM (100 mL). The organic layer was washed with brine (50 mL), dried over Na$_2$SO$_4$, filtered, concentrated and purified by column (PE/EA=20/1 to 10/1 to 4/1) to give product tert-butyl (2-(2-(prop-2-yn-1-yloxy)ethyl)carbamate (1.6 g, 68% yield) as a yellow oil. $^1$H NMR (400 MHz, CDCl$_3$) δ 4.98 (br s, 1H), 4.21 (d, J=2.0 Hz, 2H), 3.71-3.69 (m, 2H), 3.66-3.63 (m, 2H), 3.55 (t, J=5.2 Hz, 2H), 3.34-3.30 (m, 2H), 2.45 (t, J=2.4 Hz, 1H), 1.45 (s, 9H); LC/MS (ESI, m/z): [M+1]$^+$=243.9.

2-(2-(2-(benzyloxy)ethoxy)ethoxy)ethanol (Intermediate D)

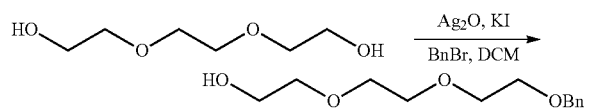

To a mixture of Ag$_2$O (12.4 g, 100 mmol) and KI (4.42 g, 26.64 mmol) in DCM (200 mL) was added 2,2'-(ethane-1,2-diylbis(oxy))diethanol (10 g, 66.6 mmol) dropwise at room temperature. Then BnBr (12.5 g, 73.26 mmol) was added dropwise into the mixture over 10 min. After addition, the mixture was stirred at room temperature for 2 h. The reaction mixture was filtered. The combined filtrate was concentrated under reduced pressure. The residue was purified by silica gel column chromatography to give 2-(2-(2-(benzyloxy)ethoxy)ethoxy)ethanol (7 g, 43.8%) as a colorless oil. LC/MS (ESI, m/z): [M+1]$^+$=241.0.

9H-Pyrido[2,3-b]indole-6-carbonitrile (Intermediate E)

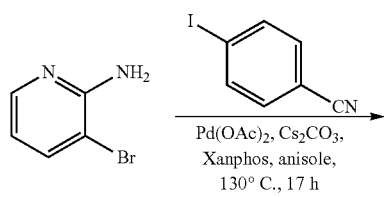

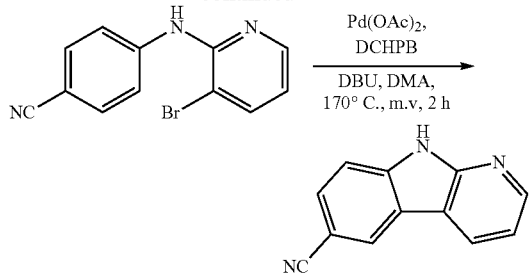

Step 1: 4-((3-bromopyridin-2-yl)amino)benzonitrile

A mixture of 3-bromopyridin-2-amine (10 g, 57.8 mmol), 4-iodobenzonitrile (13.2 g, 57.8 mmol), palladium acetate (0.65 g, 2.89 mmol), xantphos (1.67 g, 2.89 mmol) and caesium carbonate (28.2 g, 86.7 mmol) in anisole was degassed with nitrogen, heated to 130° C. and stirred for 17 hours under nitrogen atmosphere. The reaction was cooled to r.t and filtered. The filtrate was concentrated in vacuum. The residue was purified by column chromatography (Petroleum ether/EtOAc=6:1) to give 4-((3-bromopyridin-2-yl)amino)benzonitrile (9.7 g, 61.3% yield) as a yellow solid. LC/MS (ESI, m/z): [M+1]$^+$=275.1.

Step 2: 9H-pyrido[2,3-b]indole-6-carbonitrile

A mixture of 4-((3-bromopyridin-2-yl)amino)benzonitrile (2 g, 7.30 mmol), palladium acetate (0.16 g, 0.73 mmol), DUB (2.2 g, 14.6 mmol) and DCHPB (0.51 g, 1.46 mmol) in DMA (10 mL) was degassed with nitrogen, heated to 170° C. and stirred for 2 hours under microwave condition. The reaction was cooled to r.t and filtered. The filtrate was purified via reverse phase column chromatography (CH$_3$CN/H$_2$O=5%-80%) to give 9H-pyrido[2,3-b]indole-6-carbonitrile (0.75 g, 53.5% yield) as a white solid. LC/MS (ESI, m/z): [M+1]$^+$=194.3.

4-Bromo-9H-pyrido[2,3-b]indole (Intermediate F)

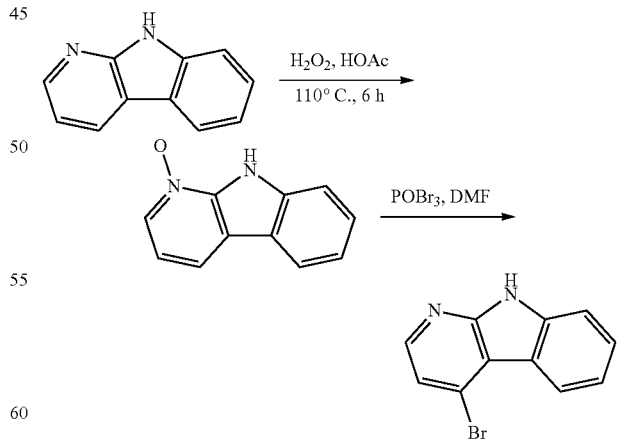

Step 1: 9H-pyrido[2,3-b]indole 1-oxide

To a stirred solution of 9H-pyrido[2,3-b]indole (100 mg, 0.595 mmol) in HOAc (2 mL) was added H$_2$O$_2$ (30%, 472 mg, 4.17 mmol) dropwise. The mixture was heated to 110° C. and refluxed for 4 h. The mixture was concentrated under reduced pressure to remove the solvent. The residue was adjust to pH=8 with aq. K₂CO₃. The result solution was stirred for overnight at rt. To the mixture was added H₂O (20 mL), extracted with EA (50 mL). The organic layer was washed with brine (30 mL), dried over Na₂SO₄, filtered, concentrated to give product 9H-pyrido[2,3-b]indole 1-oxide (80 mg, 73% yield) as a white solid. ¹H NMR (400 MHz, CDCl₃) δ 12.58 (br s, 1H), 8.35 (dd, J=0.8 Hz, J=6.4 Hz, 1H), 8.22-8.17 (m, 2H), 7.58-7.51 (m, 2H), 7.32-7.28 (m, 1H), 7.23 (dd, J=6.4 Hz, J=7.6 Hz, 1H).

Step 2: 4-bromo-9H-pyrido[2,3-b]indole

To a stirred solution of 9H-pyrido[2,3-b]indole 1-oxide (1 g, 5.43 mmol) in DMF (30 mL) was added POBr₃ (4.68 g, 16.3 mmol) at 0° C. under N₂. The mixture was stirred at room temperature overnight. To the mixture was added H₂O (100 mL), extracted with EA (200 mL). The organic layer was washed with brine (100 mL), dried over Na₂SO₄, filtered, concentrated to give product 4-bromo-9H-pyrido[2,3-b]indole (700 mg, 54% yield) as a yellow solid. ¹H NMR (400 MHz, CDCl₃) δ. 9.28 (br s, 1H), 8.61 (d, J=8.0 Hz, 1H), 8.25 (d, J=5.4 Hz, 1H), 7.59-7.52 (m, 2H), 7.40 (d, J=5.4 Hz, 1H), 7.39-7.35 (m, 1H).

5-Bromo-9H-pyrido[2,3-b]indole (Intermediate G)

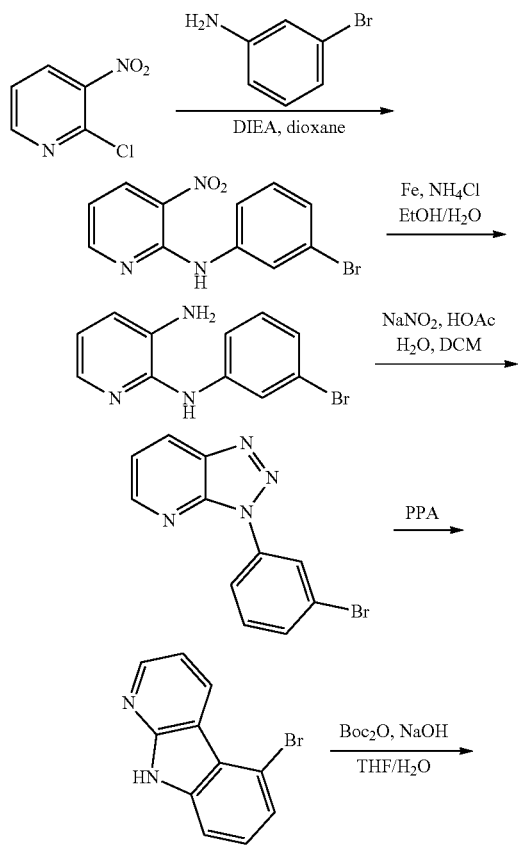

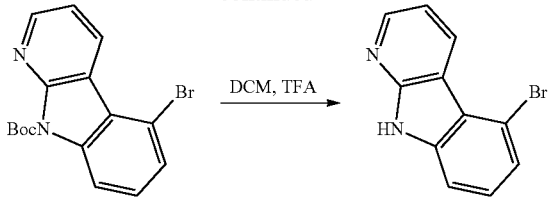

Step 1: N-(3-bromophenyl)-3-nitropyridin-2-amine

To a solution of 2-chloro-3-nitro-pyridine (5.00 g, 315 mmol) and 3-bromoaniline (5.97 g, 34.7 mmol) in dioxane (40 mL) was added DIEA (12.2 g, 94.6 mmol). The reaction mixture was stirred at 115° C. for 2 days. On completion, the mixture was concentrated in vacuo. The residue was purified by silica gel chromatography to give N-(3-bromophenyl)-3-nitropyridin-2-amine (8.00 g, 86% yield) as a red solid. LC/MS (ESI, m/z): [M+1]⁺=295.1.

Step 2: N²-(3-bromophenyl)pyridine-2,3-diamine

To a solution of N-(3-bromophenyl)-3-nitropyridin-2-amine (5.00 g, 17.0 mmol) and NH₄Cl (9.09 g, 170 mmol) in a mixed solvent of H₂O (80 mL) and EtOH (80 mL) was added Fe (9.49 g, 170 mmol). The reaction mixture was stirred at 80° C. for 1 hr. On completion, the mixture was diluted with water (80 mL) and extracted with EA (2×80 mL). The organic layers were washed with brine (2×100 mL), dried over anhydrous Na₂SO₄, filtered and concentrated in vacuo to give N²-(3-bromophenyl)pyridine-2,3-diamine (4.00 g, 89% yield) as a brown solid. The crude was used for the next step directly without further purification. LC/MS (ESI, m/z): [M+1]⁺=265.1.

Step 3: 3-(3-bromophenyl)-3H-[1,2,3]triazolo[4,5-b]pyridine

To a solution of N2-(3-bromophenyl)pyridine-2,3-diamine (4.00 g, 15.1 mmol) in a mixed solvent of HOAc (25 mL) and DCM (25 mL) was added a solution of NaNO₂ (1.36 g, 19.7 mmol) in H₂O (15 mL) dropwise at 0° C. The reaction mixture was stirred at 25° C. for 30 minutes. On completion, the mixture was diluted with water (50 mL), extracted with DCM (2×50 mL). The organic layer was washed with brine (2×50 mL), dried over anhydrous Na₂SO₄, filtered and concentrated in vacuo to give 3-(3-bromophenyl)-3H-[1,2,3]triazolo[4,5-b]pyridine (4.10 g, 98% yield) as a brown solid. The crude was used for the next step directly without further purification. LC/MS (ESI, m/z): [M+1]⁺=276.1.

Step 4: 5-bromo-9H-pyrido[2,3-b]indole

A mixture of 3-(3-bromophenyl)-3H-[1,2,3]triazolo[4,5-b]pyridine (3.60 g, 13.1 mmol) in PPA (20 mL) was heated at 170° C. for 3 hr. On completion, the mixture was poured into the ice water (200 mL), stirred for 1 hrs, filtered. The solid cake was washed with ice-water and dried to give 5-bromo-9H-pyrido[2,3-b]indole (3.2 g, quant.). The crude was used next step without further purification.

Step 5: tert-butyl 5-bromo-9H-pyrido[2,3-b]indole-9-carboxylate

A mixture of 5-bromo-9H-pyrido[2,3-b]indole (10.0 g, 40.0 mmol) in THF/H₂O (100 mL/100 mL) was added Boc₂O (17.4 g, 80.0 mmol) and NaOH (4.8 g, 120.0 mmol). The mixture was stirred at r.t for 3 hr. On completion, the mixture was poured into the water (200 mL), extracted with EA (2×100 mL). The organic layer was washed with brine (2×100 mL), dried over anhydrous Na₂SO₄, filtered and concentrated in vacuo. The residue was purified by column chromatography to give tert-butyl 5-bromo-9H-pyrido[2,3-b]indole-9-carboxylate (4.10 g, 7% yield for two steps) as a brown solid. LC/MS (ESI, m/z): [M+1]+=348.1.

Step 6: 5-bromo-9H-pyrido[2,3-b]indole

A mixture of tert-butyl 5-bromo-9H-pyrido[2,3-b]indole-9-carboxylate (9.0 g, 25.9 mmol) in DCM (20 mL) was added TFA (15 mL). The mixture was stirred at r.t for 16 h. On completion, the mixture was concentrated to give 5-bromo-9H-pyrido[2,3-b]indole (6.0 g, 94% yield) as a brown solid. LC/MS (ESI, m/z): [M+1]+=248.1.

2-Chloro-9H-pyrido[2,3-b]indole (Intermediate H)

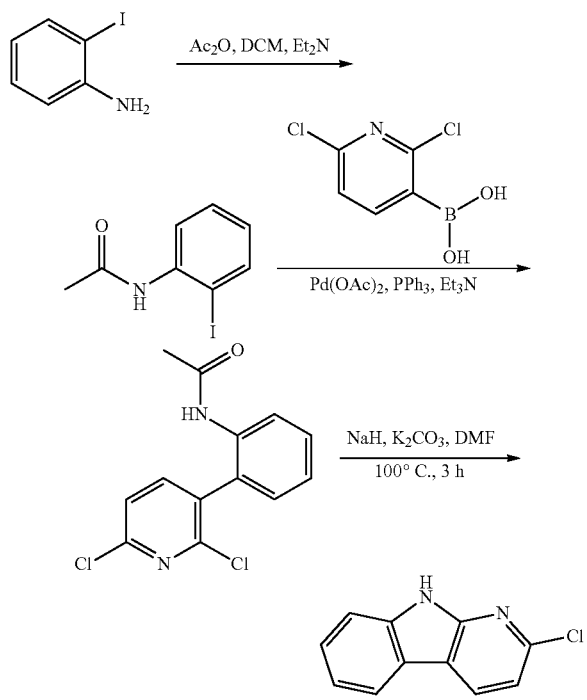

Step 1: N-(2-iodophenyl)acetamide

A mixture of 2-iodoaniline (2.2 g, 10.0 mmol), Ac₂O (1.2 g, 12.0 mmol) and Et₃N (2.2 g, 22 mmol) in DCM was degassed with nitrogen, the mixture was stirred for 16 hours at r.t. The reaction was concentrated in vacuo. The residue was purified by column chromatography to give N-(2-iodophenyl)acetamide (1.6 g, 58% yield) as a white solid. LC/MS (ESI, m/z): [M+1]+=262.1.

Step 2: N-(2-(2,6-dichloropyridin-3-yl)phenyl)acetamide

A mixture of N-(2-iodophenyl)acetamide (261 mg, 1.0 mmol), (2,6-dichloropyridin-3-yl)boronic acid (230 mg, 1.2 mmol), palladium acetate (11 mg, 0.05 mmol), PPh₃ (26 mg, 0.1 mmol) and Et₃N (303 mg, 3.0 mmol) in DMF was degassed with nitrogen, heated to 100° C. and stirred for 16 hours. The mixture was cooled to r.t, diluted with water and extracted with EA. The combined organic layer was washed with brine, dried over anhydrous sodium sulfate, filtered and concentrated in vacuo. The residue was purified by column chromatography to give N-(2-(2,6-dichloropyridin-3-yl)phenyl)acetamide (180 mg, 69% yield) as a white solid. LC/MS (ESI, m/z): [M+1]+=282.1

Step 3: 2-chloro-9H-pyrido[2,3-b]indole

A mixture of N-(2-(2,6-dichloropyridin-3-yl)phenyl)acetamide (180 mg, 0.64 mmol), K₂CO₃ (265 mg, 1.92 mmol) and 60% NaH (52 mg, 1.28 mmol) in DMF was degassed with nitrogen, heated to 100° C. and stirred for 4 hours. The reaction was cooled to r.t, diluted with water and extracted with EA. The combined organic layer was washed with brine, dried over anhydrous sodium sulfate, filtered and concentrated in vacuo. The residue was purified by column chromatography to give 2-chloro-9H-pyrido[2,3-b]indole (50 mg, 43% yield) as a white solid. ¹H NMR (400 MHz, DMSO-d₆) δ 12.04 (s, 1H), 8.56 (d, J=8.0 Hz, 1H), 8.18 (d, J=8.0, 1H), 7.56-7.44 (m, 2H), 7.31-7.22 (m, 2H). LC/MS (ESI, m/z): [M+1]+=203.8.

2-Fluoro-9H-pyrido[2,3-b]indole (Intermediate I) and N-(4-methoxybenzyl)-9H-pyrido[2,3-b]indol-2-amine (Intermediate J)

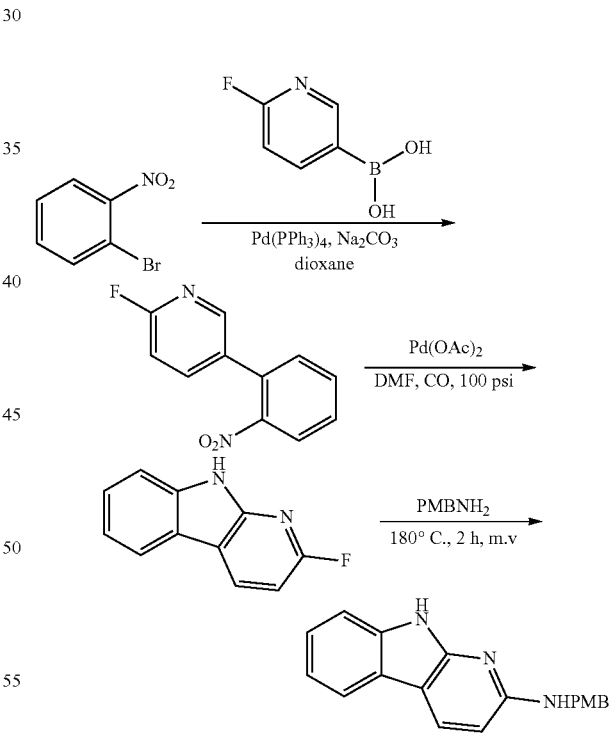

Step 1: 2-fluoro-5-(2-nitrophenyl)pyridine

A mixture of 1-bromo-2-nitrobenzene (3 g, 14.85 mmol), (6-fluoropyridin-3-yl)boronic acid (2.511 g, 17.82 mmol), Pd(PPh₃)₄ (857 mg, 0.7425 mmol) and Na₂CO₃ (3.94 g, 37.125 mmol) in dioxane (30 mL) and H₂O (5 mL) was heated to 110° C. and stirred overnight under nitrogen atmosphere. The reaction mixture was cooled to r.t and concentrated in vacuum. The residue was diluted with water and extract with EtOAc. The combined organic layers was washed with brine, dried over Na$_2$SO$_4$, filtered and concentrated in vacuum. The residue was purified by silica gel column chromatography (PE/EA=4:1) to give 2-fluoro-5-(2-nitrophenyl)pyridine (2.2 g, 68.2%) as a yellow solid. LC/MS (ESI, m/z): [M+1]$^+$=219.2

Step 2: 2-fluoro-9H-pyrido[2,3-b]indole

To a mixture of 2-fluoro-5-(2-nitrophenyl)pyridine (2.2 g, 10.0 mmol) and 1,10-phenanthroline (63 mg, 0.35 mmol) in DMF (10 mL) was added Pd(OAc)$_2$ (11.2 mg, 0.05 mmol). The reactor system was sealed and purged three times with nitrogen followed by carbon monoxide. The system was pressurized with carbon monoxide (100 psi) and heated at 140° C. for 18 h. The mixture was cooled to r.t, diluted with water and extracted with EA. The combined organic layer was washed with brine, dried over anhydrous sodium sulfate, filtered and concentrated in vacuo. The residue was purified by column chromatography (PE/EA=1:1) to give 2-fluoro-9H-pyrido[2,3-b]indole (1.2 g, 64.5%) as a yellow solid. $^1$H NMR (400 MHz, DMSO-d$_6$) δ 12.01 (br. s., 1H), 8.66 (t, J=8.1 Hz, 1H), 8.15 (d, J=7.7 Hz, 1H), 7.52 (d, J=8.13 Hz, 1H), 7.45 (t, J=7.7 Hz, 1H), 7.26 (t, J=7.7 Hz, 1H), 6.94 (d, J=8.1 Hz, 1H). LC/MS (ESI, m/z): [M+1]$^+$=186.9.

Step 3: N-(4-methoxybenzyl)-9H-pyrido[2,3-b]indol-2-amine

A mixture of 2-fluoro-9H-pyrido[2,3-b]indole (800 mg, 4.3 mmol) and PMB-NH$_2$ (5 mL) was heated to 180° C. under nitrogen atmosphere in microwave irradiation for 2 h. The reaction mixture was cooled to room temperature and purified by silica gel column chromatography (PE/EA=4:1) to give N-(4-methoxybenzyl)-9H-pyrido[2,3-b]indol-2-amine (1.0 g, 76.7%) as a white solid. LC/MS (ESI, m/z): [M+1]$^+$=304.1.

2-Methoxy-9H-pyrido[2,3-b]indole (Intermediate K)

Step 1: 2-methoxy-5-(2-nitrophenyl)pyridine

A mixture of 1-bromo-2-nitrobenzene (3.0 g, 14.8 mmol), (6-methoxypyridin-3-yl)boronic acid (2.7 g, 17.8 mmol) N$_2$CO$_3$ (4.7 g, 44.5 mmol) and Tetrakis(triphenylphosphine)palladium(1.4 g, 1.2 mmol) in 1,4-dioxane was degassed with nitrogen, heated to 110° C. and stirred for 1.5 hours under nitrogen atmosphere and microwave. The reaction was cooled to r.t, filtered and concentrated in vacuo. The residue was diluted with water, extracted with EA. The combined organic layer was washed with brine, dried over anhydrous sodium sulfate, filtered and concentrated in vacuo. The residue was purified by column chromatography to give 2-methoxy-5-(2-nitrophenyl)pyridine (590 mg, 17% yield) as a yellow solid. LC/MS (ESI, m/z): [M+1]$^+$=231.2.

Step 2: 2-methoxy-9H-pyrido[2,3-b]indole

A solution of 2-methoxy-5-(2-nitrophenyl)pyridine (590 mg, 2.5 mmol) in anhydrous tetrahydrofuran (10 mL) was sealed and purged three times with nitrogen. Phenyl magnesium bromide (10 ml, 10 mmol) was slowly added to the above solution in 10 mins at 0° C. During this period, the internal temperature was closely monitored and kept under 3° C. After addition, the reaction mixture was stirred at 0° C. for 30 minutes. The reaction was quenched by sat. aq. ammonium chloride, extracted with EA. The combined organic layer was washed with brine, dried over anhydrous sodium sulfate, filtered and concentrated in vacuo. The residue was purified by column chromatography to give 2-methoxy-9H-pyrido[2,3-b]indole (100 mg, 20% yield) as a white solid. LC/MS (ESI, m/z): [M+1]$^+$=199.2

2-(Trifluoromethyl)-9H-pyrido[2,3-b]indole (Intermediate L)

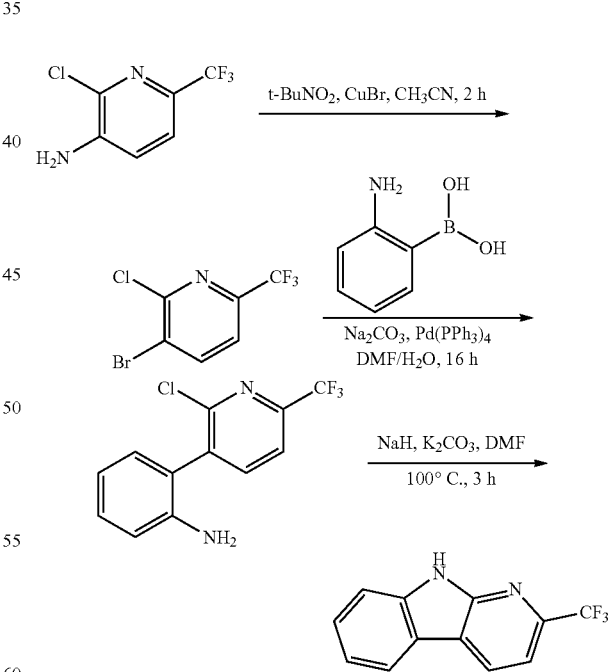

Step 1: 3-bromo-2-chloro-6-(trifluoromethyl)pyridine

A mixture of 2-chloro-6-(trifluoromethyl)pyridin-3-amine (196 mg, 1.0 mmol), CuBr (446 mg, 2.0 mmol) and

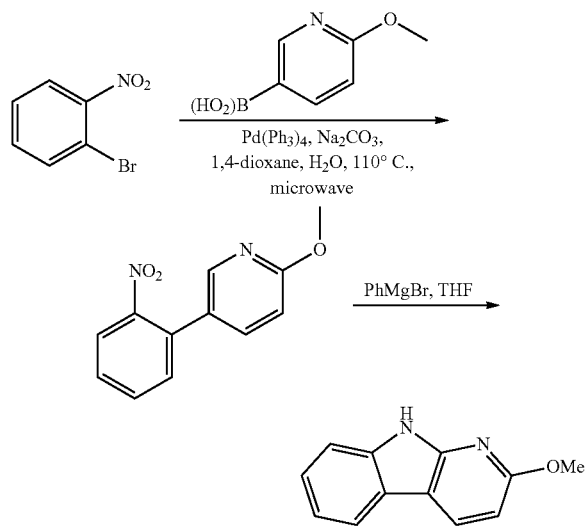

t-BuNO$_2$ (206 mg, 2.0 mmol) in CH$_3$CN was degassed with nitrogen, the mixture was stirred at r.t for 2 hours. The mixture was diluted with water extracted with EA. The combined organic layer was washed with brine, dried over anhydrous sodium sulfate, filtered and concentrated in vacuo. The residue was purified by column chromatography to give 3-bromo-2-chloro-6-(trifluoromethyl)pyridine (182 mg, 70% yield) as a yellow solid. LC/MS (ESI, m/z): [M+1]$^+$=261.1.

Step 2: 2-(2-chloro-6-(trifluoromethyl)pyridin-3-yl) aniline

A mixture of 3-bromo-2-chloro-6-(trifluoromethyl)pyridine (258 mg, 1.0 mmol), (2-aminophenyl)boronic acid (163 mg, 1.2 mmol), Pd(PPh$_3$)$_4$ (58 mg, 0.05 mmol) and Na$_2$CO$_3$ (212 mg, 2.0 mmol) in DMF/H$_2$O (5 mL/0.5 mL) was degassed with nitrogen, heated to 100° C. and stirred for 16 hours. The mixture was cooled to r.t, diluted with water and extracted with EA. The combined organic layer was washed with brine, dried over anhydrous sodium sulfate, filtered and concentrated in vacuo. The residue was purified by column chromatography to give 2-(2-chloro-6-(trifluoromethyl) pyridin-3-yl)aniline (180 mg, 66% yield) as a white solid. LC/MS (ESI, m/z): [M+1]$^+$=273.1.

Step 3: 2-(trifluoromethyl)-9H-pyrido[2,3-b]indole

A mixture of 2-(2-chloro-6-(trifluoromethyl)pyridin-3-yl) aniline (120 mg, 0.44 mmol), K$_2$CO$_3$ (18 mg, 1.32 mmol) and 60% NaH (40 mg, 1.32 mmol) in DMF was degassed with nitrogen, heated to 100° C. and stirred for 4 hours. The reaction was cooled to r.t, diluted with water and extracted with EA. The combined organic layer was washed with brine, dried over anhydrous sodium sulfate, filtered and concentrated in vacuo. The residue was purified by column chromatography to give 2-(trifluoromethyl)-9H-pyrido[2,3-b]indole (42 mg, 40% yield) as a yellow solid. $^1$H NMR (400 MHz, DMSO-d$_6$) δ 12.26 (s, 1H), 8.78 (d, J=7.9 Hz, 1H), 8.30 (d, J=7.9 Hz, 1H), 7.69 (d, J=7.9 Hz, 1H), 7.58-7.56 (m, 2H), 7.38-7.14 (m, 1H). LC/MS (ESI, m/z): [M+1]$^+$=237.1.

3-(7-Bromo-9H-pyrido[2,3-b]indol-9-yl)piperidine-2,6-dione (Intermediate M)

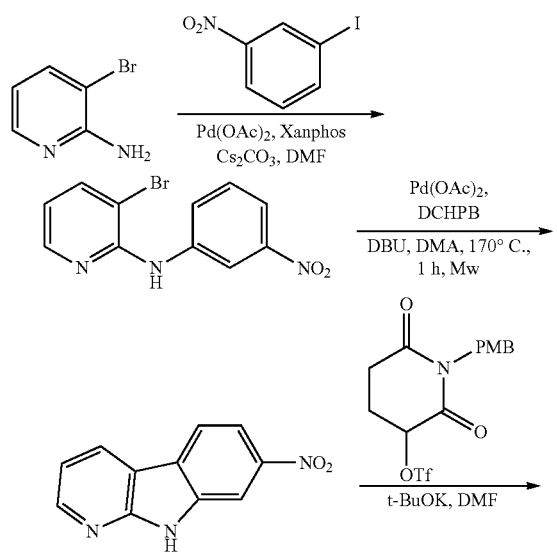

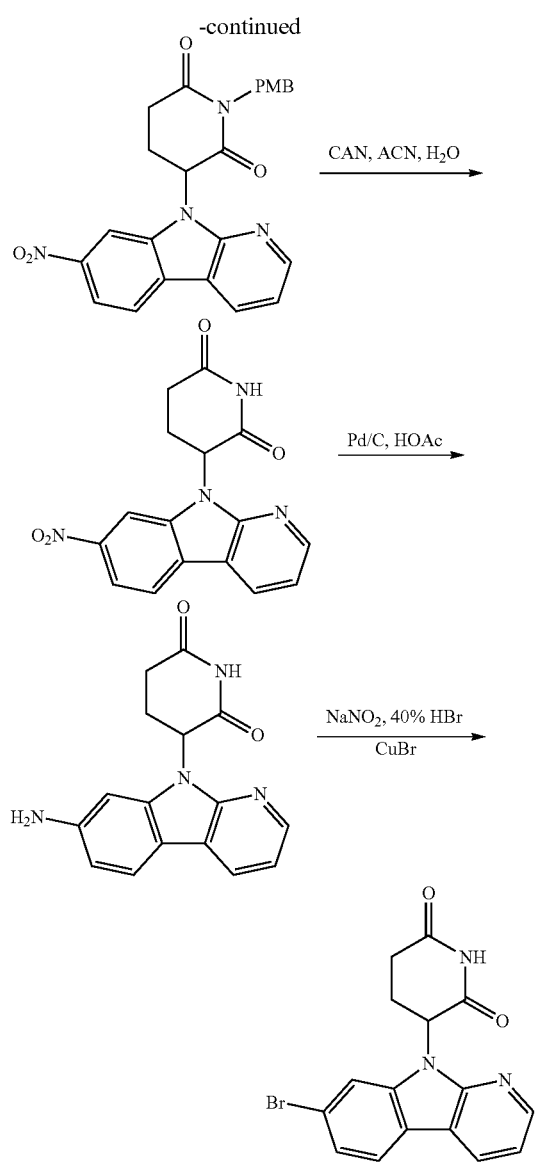

Step 1: 3-bromo-N-(3-nitrophenyl)pyridin-2-amine

To a mixture of 3-bromopyridin-2-amine (5 g, 28.9 mmol), 1-iodo-3-nitrobenzene (7.2 g, 28.9 mmol), xanphos (1.07 g, 2.89 mmol), Cs$_2$CO$_3$ (18.9 g, 57.8 mmol) in DMF (50 mL) was added Pd(OAc)$_2$ (323.7 mg, 1.44 mmol). The mixture was degrassed with N$_2$ and stirred at 130° C. overnight. The reaction mixture was cooled to room temperature, poured into water, and extracted with EtOAc(3× 200 mL). The combined organic layer was washed with water and brine, dried over anhydrous sodium sulfate, filtered and concentrated in vacuo. The residue was purified by flash chromatography eluting with EA/PE=20% to give 3-bromo-N-(3-nitrophenyl)pyridin-2-amine (5.6 g, 65.7%) as a light yellow solid. LC/MS (ESI, m/z): [M+1]$^+$=294.0, 296.0.

Step 2: 7-nitro-9H-pyrido[2,3-b]indole

To a mixture of 3-bromo-N-(3-nitrophenyl)pyridin-2-amine (4 g, 6.78 mmol), DCPHB (474 mg, 1.356 mmol), DBU (4.12 g, 27.12 mmol) in DMA (12 mL) was added Pd(OAc)₂ (152 mg, 0.678 mmol). The mixture was degrassed with N₂ and stirred at 170° C. for 1h. The reaction mixture was cooled to room temperature, poured into water and extracted with EtOAc(3×50 mL). The combined organic layer was washed with water and brine, dried over anhydrous sodium sulfate, filtered and concentrated in vacuo. The residue was purified by flash chromatography eluting with EA/PE=1:1 to give 7-nitro-9H-pyrido[2,3-b]indole (1 g, 34.4%) as a light yellow solid. $^1$H NMR (400 MHz, DMSO-d₆) δ 12.40 (s, 1H), 8.72 (dd, J=7.75, 1.25 Hz, 1H), 8.59 (dd, J=4.75, 1.50 Hz, 1H), 8.44 (d, J=8.63 Hz, 1H), 8.33 (d, J=2.00 Hz, 1H), 8.12 (dd, J=8.63, 2.13 Hz, 1H), 7.35 (dd, J=7.75, 4.75 Hz, 1H); LC/MS (ESI, m/z): [M+1]⁺=214.1.

Step 3: 1-(4-methoxybenzyl)-3-(7-nitro-9H-pyrido [2,3-b]indol-9-yl)piperidine-2,6-dione To a solution of 7-nitro-9H-pyrido[2,3-b]indole (910 mg, 4.272 mmol) in THF (10 mL) and DMF (2 mL) was added t-BuOK (718 mg, 6.41 mmol) at 0° C. under nitrogen atmosphere. After addition, the mixture was stirred at 0° C.-5° C. for 1 h. Then the 1-(4-methoxybenzyl)-2,6-dioxopiperidin-3-yl trifluoromethanesulfonate (2.44 g, 6.41 mmol) in THF (10 mL) was added dropwise at 0° C.-5° C. over 20 min. After addition, the mixture was stirred at 0° C.-5° C. for additional 1 h. The reaction mixture was quenched by water and extract with EtOAc (3×20 mL). The combined organic layer were washed with water and brine, dried over anhydrous sodium sulfate, filtered and concentrated under reduced. The residue was triturated with EtOAc and filtered to give 1-(4-methoxybenzyl)-3-(7-nitro-9H-pyrido[2,3-b]indol-9-yl)piperidine-2,6-dione (1.3 g, 68.6%) as a yellow solid. The crude was used directly in the next step without further purification. LC/MS (ESI, m/z): [M+1]⁺=445.2.

Step 4: 3-(7-nitro-9H-pyrido[2,3-b]indol-9-yl)piperidine-2,6-dione

To a solution of 1-(4-methoxybenzyl)-3-(7-nitro-9H-pyrido[2,3-b]indol-9-yl)piperidine-2,6-dione (1.7 g, 3.83 mmol) in CH₃CN (20 mL) was added CAN (10.5 g, 19.15 mmol) in water (5 mL) at 0° C. dropwise. After addition, the mixture was stirred at room temperature overnight. The mixture was poured into water (50 mL) and extract with EtOAc (3×50 mL). The combined organic layers was washed with brine, dried over anhydrous sodium sulfate, filtered and concentrated in vacuo. The residue was triturated with EtOAc and filtered to give 3-(7-nitro-9H-pyrido [2,3-b]indol-9-yl)piperidine-2,6-dione (850 mg, 68.5%) as a light yellow solid. LC/MS (ESI, m/z): [M+1]⁺=325.2.

Step 5: 3-(7-amino-9H-pyrido[2,3-b]indol-9-yl)piperidine-2,6-dione

To a solution of 3-(7-nitro-9H-pyrido[2,3-b]indol-9-yl) piperidine-2,6-dione (850 mg, 2.62 mmol) in EtOAc (5 mL) was added 10% palladium on activated carbon (270 mg, 0.262 mmol). The mixture was hydrogened at room temperature overnight. The reaction mixture was filtered and the filtrate was concentrated under reduced pressure. The residue was dried to give 3-(7-amino-9H-pyrido[2,3-b]indol-9-yl)piperidine-2,6-dione (764 mg, 99%) as a white solid, which was used directly in the next step without further purification. LC/MS (ESI, m/z): [M+1]⁺=295.2.

Step 6: 3-(7-bromo-9H-pyrido[2,3-b]indol-9-yl) piperidine-2,6-dione

To a solution of 3-(7-amino-9H-pyrido[2,3-b]indol-9-yl) piperidine-2,6-dione (661 mg, 2.26 mmol) in 40% HBr solution (5 mL) was added NaNO₂ (156 mg, 2.26 mmol) at 0° C. After addition, the mixture was stirred at 0° C. for 30 min. Then the above solution was added dropwise into a solution of CuBr (972 mg, 6.78 mmol) in 40% HBr solution (5 mL). The mixture was stirred at room temperature for 2 h. Then the mixture was poured into water (50 mL). The mixture was basified to pH 8 by sat. aq. NaHCO₃ and extracted with EtOAc (3×50 mL). The combined organic layers were washed with brine, dried over anhydrous sodium sulfate, filtered and concentrated in vacuo. The residue was purified by prep-HPLC to give 3-(7-bromo-9H-pyrido[2,3-b]indol-9-yl)piperidine-2,6-dione (382 mg, 47.1%) as a yellow solid. LC/MS (ESI, m/z): [M+1]⁺=358.1, 360.1.

1-Methoxy-9H-pyrido[3,4-b]indole (Intermediate N)

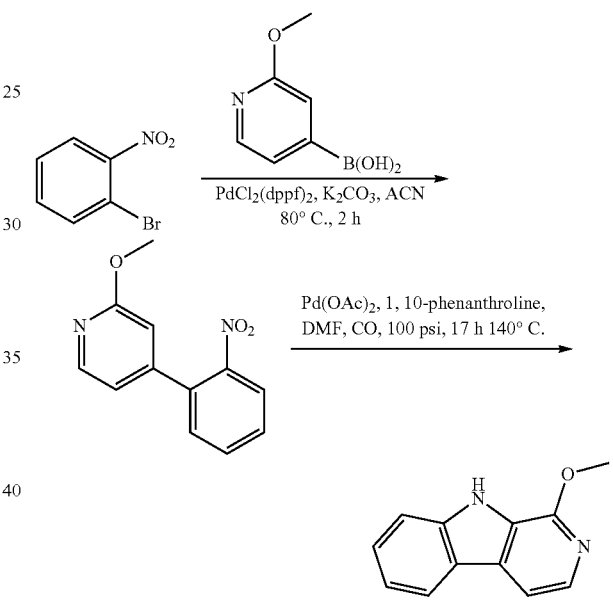

Step 1: 2-methoxy-4-(2-nitrophenyl)pyridine

A mixture of 1-bromo-2-nitrobenzene (1.1 g, 5.45 mmol), (2-methoxypyridin-4-yl)boronic acid (1.0 g, 6.54 mmol), 1,1'-Bis(diphenylphosphino)ferrocene-palladium(II)dichloride dichloromethane complex (0.44 g, 0.54 mmol) and potassium carbonate (1.5 g, 10.9 mmol) in acetonitrile (20 mL) and water (5 mL) was degassed with nitrogen, heated to 80° C. and stirred for 2 hours under nitrogen atmosphere. The reaction was cooled to r.t and filtered. The filtrate was diluted with water, extracted with EA. The combined organic layer was washed with brine, dried over anhydrous sodium sulfate, filtered and concentrated in vacuo. The residue was purified by column chromatography (Petroleum ether/EtOAc=1:1) to give 2-methoxy-4-(2-nitrophenyl)pyridine (1.1 g, 88.0% yield) as a yellow solid. LC/MS (ESI, m/z): [M+1]⁺=231.1.

Step 2: 1-methoxy-9H-pyrido[3,4-b]indole

A solution of 2-methoxy-4-(2-nitrophenyl)pyridine (1.1 g, 4.78 mmol) in DMF (15 mL) was added Pd(OAc)₂ (5.4 mg, 0.02 mmol) and 1,10-phenanthroline (30.1 mg, 0.17 mmol). The reactor system was sealed and purged three times with nitrogen followed by carbon monoxide. The system was pressurized with carbon monoxide (100 psi) and heated at 140° C. for 17 h. The mixture was cooled to rt, diluted with water and extracted with EA. The combined organic layer was washed with brine, dried over anhydrous sodium sulfate, filtered and concentrated in vacuo. The residue was purified by column chromatography (Petroleum ether/EtOAc=1:1) to give 1-methoxy-9H-pyrido[3,4-b]indole (0.75 g, 78.9% yield) as a yellow solid. LC/MS (ESI, m/z): [M+1]$^+$=199.1.

9H-Pyrido[3,4-b]indole (Intermediate O)

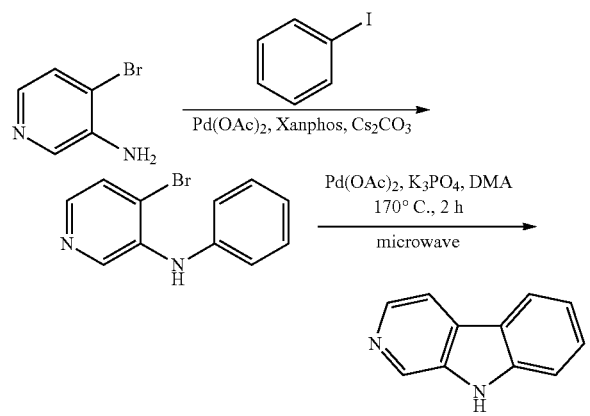

Step 1: 4-bromo-N-phenylpyridin-3-amine

A mixture of 4-bromopyridin-3-amine (865 mg, 5.0 mmol), iodobenzene (1.02 mg, 5.0 mmol), xantphos (288 mg, 0.5 mmol) and Cs$_2$CO$_3$ (2.46 g, 7.5 mmol) in DMF was degassed with nitrogen, heated to 130° C. and stirred for 16 hours under microwave condition. The reaction was cooled to r.t and filtered. The filtrate was diluted with water, extracted with EA. The combined organic layer was washed with brine, dried over anhydrous sodium sulfate, filtered and concentrated in vacuo. The residue was purified by column chromatography to give 4-bromo-N-phenylpyridin-3-amine (311 mg, 25% yield) as a yellow solid. LC/MS (ESI, m/z): [M+1]$^+$=250.1.

Step 2: 9H-pyrido[3,4-b]indole

A mixture of 4-bromo-N-phenylpyridin-3-amine (500 mg, 2.0 mmol), palladium acetate (89 mg, 0.4 mmol) and K$_3$PO$_4$ (1.27 g, 6.0 mmol) in DMA (10 mL) was degassed with nitrogen, heated to 170° C. and stirred for 2 hours under microwave condition. The reaction was cooled to r.t and filtered. The filtrate was purified via reverse phase column chromatography (CH$_3$CN/H$_2$O=5%-80%) to give 9H-pyrido[3,4-b]indole (120 mg, 28% yield) as white solid. $^1$H NMR (400 MHz, DMSO-d$_6$) δ 12.57 (s, 1H), 9.27 (s, 1H), 8.74 (d, J=6.1 Hz, 1H), 8.58 (d, J=6.1 Hz, 1H), 8.51 (d, J=8.0 Hz, 1H), 7.82-7.76 (m, 2H), 7.55-7.27 (m, 1H). LC/MS (ESI, m/z): [M+1]$^+$=169.2.

5H-Pyrido[4,3-b]indole (Intermediate P)

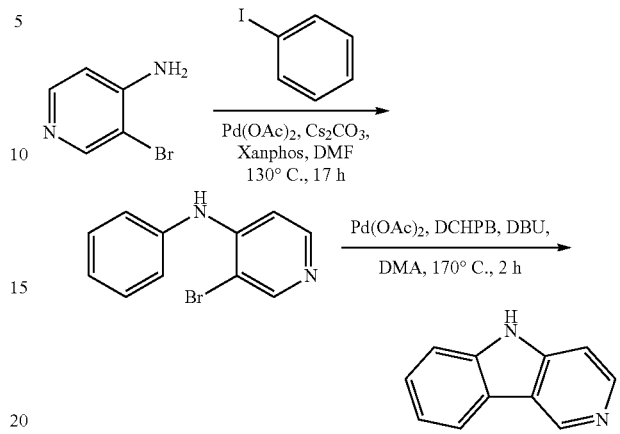

Step 1: 3-bromo-N-phenylpyridin-4-amine

A mixture of 3-bromopyridin-4-amine (1.1 g, 6.36 mmol), iodobenzene (1.3 g, 6.36 mmol), palladium acetate (0.14 g, 0.64 mmol), xantphos (0.37 g, 0.64 mmol) and caesium carbonate (4.1 g, 12.7 mmol) in DMF was degassed with nitrogen, heated to 130° C. and stirred for 17 hours under nitrogen atmosphere. The reaction was cooled to r.t and filtered. The filtrate was diluted with water and extracted with EA. The combined organic layer was washed with brine, dried over anhydrous sodium sulfate, filtered and concentrated in vacuo. The residue was purified by column chromatography (Petroleum ether/EtOAc=6:1) to give 3-bromo-N-phenylpyridin-4-amine (0.87 g, 55.0% yield) as a yellow solid. LC/MS (ESI, m/z): [M+1]$^+$=250.1.

Step 2: 5H-pyrido[4,3-b]indole

A mixture of 3-bromo-N-phenylpyridin-4-amine (0.87 g, 3.49 mmol), palladium acetate (78.4 mg, 0.35 mmol), DUB (1.1 g, 6.99 mmol) and DCHPB (0.24 g, 0.70 mmol) in DMA (10 mL) was degassed with nitrogen, heated to 170° C. and stirred for 2 hours under microwave condition. The reaction was cooled to r.t and filtered. The filtrate was purified via reverse phase column chromatography (CH$_3$CN/H$_2$O=5%-80%) to give 5H-pyrido[4,3-b]indole (0.30 g, 51.1% yield) as a yellow solid. LC/MS (ESI, m/z): [M+1]$^+$=169.3.

3,5-Dibromopyridin-2-amine (Intermediate Q)

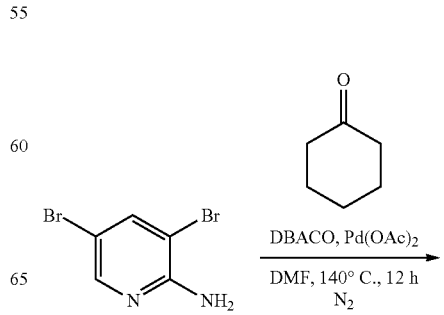

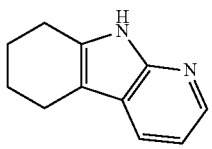

A mixture of 3,5-dibromopyridin-2-amine (5.0 g, 19.8 mmol), cyclohexanone (3.9 g, 39.7 mmol), DABCO (6.6 g, 59.5 mmol) and Pd(OAc)$_2$ (440 mg, 2.0 mmol) in DMF was degassed with nitrogen, heated to 140° C. and stirred for 16 hours under nitrogen atmosphere. The reaction was cooled to r.t, filtered and concentrated in vacuo. The residue was diluted with water, extracted with EA. The combined organic layer was washed with brine, dried over anhydrous sodium sulfate, filtered and concentrated in vacuo. The residue was purified via reverse phase column chromatography (CH$_3$CN/H$_2$O=5%-80%) to give 6,7,8,9-tetrahydro-5H-pyrido[2,3-b]indole (210 mg, 14% yield) as a white solid. LC/MS (ESI, m/z): [M+1]$^+$=173.2.

6-Benzyl-6,7,8,9-tetrahydro-5H-pyrrolo[2,3-b:4,5-c'] dipyridine (Intermediate R)

9H-Pyrimido[4,5-b]indole (Intermediate S)

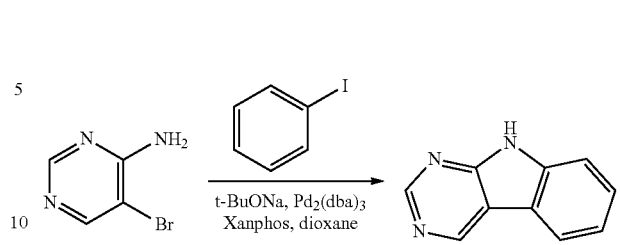

A mixture of 5-bromopyrimidin-4-amine (1 g, 5.78 mmol), iodobenzene (1.18 g, 5.78 mmol), xantphos (334 mg, 0.578 mmol), sodium tert-butoxide (1.66 g, 17.34 mmol) and tris(dibenzylideneacetone)dipalladium (0) (0.52 g, 0.58 mmol) in dioxane was degassed with nitrogen, heated to 110° C. and stirred for 24 hours. The reaction was cooled to r.t, poured into water and extracted with EtOAc (3×100 mL). The combined organic layer was washed with brine, dried over anhydrous sodium sulfate, filtered and concentrated in vacuum. The residue was purified by flash chromatography (EtOAc/DCM=80%) to give 9H-pyrimido [4,5-b]indole (370 mg, 37.9% yield) as a yellow solid. LC/MS (ESI, m/z): [M+1]$^+$=170.0.

8H-Thieno[2,3-b]indole (Intermediate T)

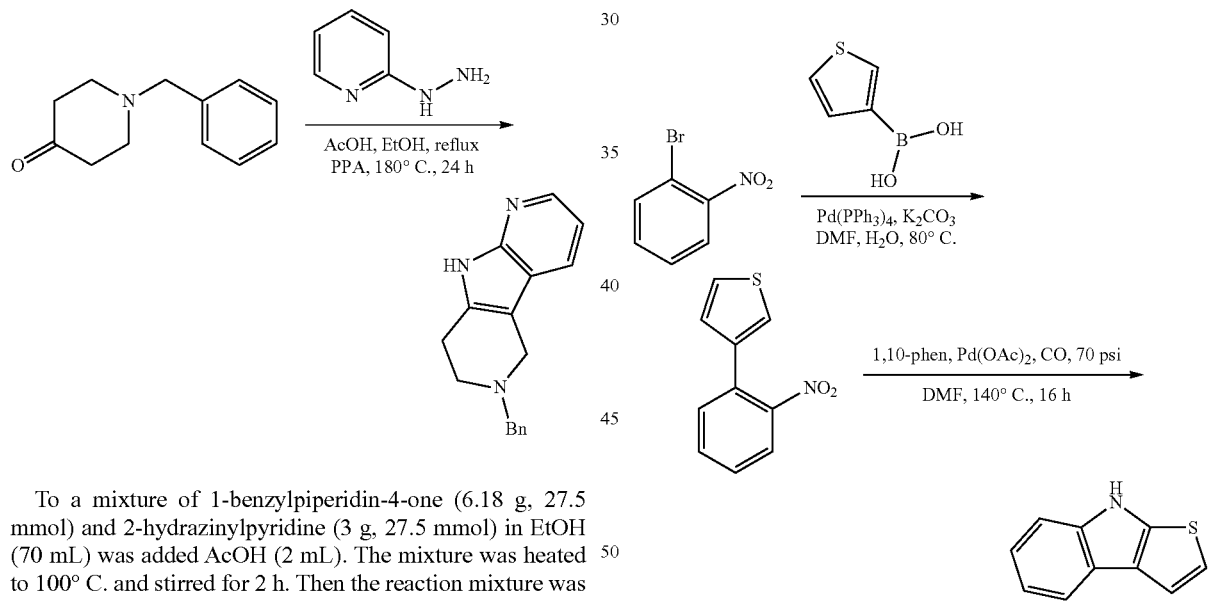

To a mixture of 1-benzylpiperidin-4-one (6.18 g, 27.5 mmol) and 2-hydrazinylpyridine (3 g, 27.5 mmol) in EtOH (70 mL) was added AcOH (2 mL). The mixture was heated to 100° C. and stirred for 2 h. Then the reaction mixture was cooled to room temperature and concentrated under reduced pressure. The residue was diluted with 2M NaOH (aq) and extracted with DCM. The combined organic layers were concentrated under reduced pressure. The residue was purified by flash chromatography eluting with MeOH/DCM=5%-10% to get the crude intermediate (7 g) which was mixed with PPA (60 g), heated to 180° C. and stirred for 24 h. Then the mixture was cooled to 60° C., ice (100 g) was added carefully to break the gum. The mixture was treated with 2M NaOH to pH=8 and extracted with EtOAc (3×200 mL). The combined organic layers were concentrated under reduced pressure. The residue was triturated with EA to give 6-benzyl-6,7,8,9-tetrahydro-5H-pyrrolo[2,3-b:4,5-c']dipyridine (2.2 g, 30.2%) as a yellow solid. LC/MS (ESI, m/z): [M+1]$^+$=264.0.

Step 1. 3-(2-nitrophenyl)thiophene

A solution of thiophen-3-ylboronic acid (1.9 g, 14.9 mmol), 1-bromo-2-nitrobenzene (2 g, 9.90 mmol), Pd(PPh$_3$)$_4$ (572 mg, 0.495 mmol), K$_2$CO$_3$ (2.7 g, 19.8 mmol) in H$_2$O/DMF (10 mL/30 mL) was heated to 80° C. and stirred under N$_2$ overnight. To the mixture was added H$_2$O (50 mL), extracted with EA (100 mL). The organic layer was washed with brine (30 mL), dried over Na$_2$SO$_4$, filtered, concentrated and purified by column (PE/EA=100/1 to 50/1 to 20/1) to give the product 3-(2-nitrophenyl)thiophene (1.6 g, 50% yield) as a white solid. $^1$H NMR (400 MHz, CDCl$_3$) δ 7.79 (dd, J=1.2 Hz, J=8.0 Hz, 1H), 7.60-7.56 (m, 1H), 7.50-7.43 (m, 2H), 7.39-7.37 (m, 1H), 7.33-7.32 (m, 1H), 7.08 (dd, J=1.2 Hz, J=5.2 Hz, 1H).

Step 2: 8H-thieno[2,3-b]indole

A mixture of 3-(2-nitrophenyl)thiophene (800 mg, 3.88 mmol), Pd(OAc)$_2$ (17 mg, 0.078 mmol), 1,10-phenanthroline (28 mg, 0.155 mmol) and DMF (15 mL) was heated to 140° C. and stirred for 16 h under CO (70 psi). To the cooled mixture was added H$_2$O (50 mL), extracted with EA (100 mL). the organic layer was washed with brine (50 mL), dried over Na$_2$SO$_4$, filtered, concentrated and purified by column (PE/EA=100/1 to 50/1 to 20/1) to give product 8H-thieno[2,3-b]indole (500 mg, 74% yield) as a white solid. $^1$H NMR (400 MHz, CDCl$_3$) δ 8.25 (br s, 1H), 7.81-7.79 (m, 1H), 7.43-7.41 (m, 1H), 7.35 (d, J=5.2 Hz, 1H), 7.27-7.17 (m, 2H), 6.89 (d, J=5.2 Hz, 1H).

5-Bromo-8H-thieno[2,3-b]indole (Intermediate U)

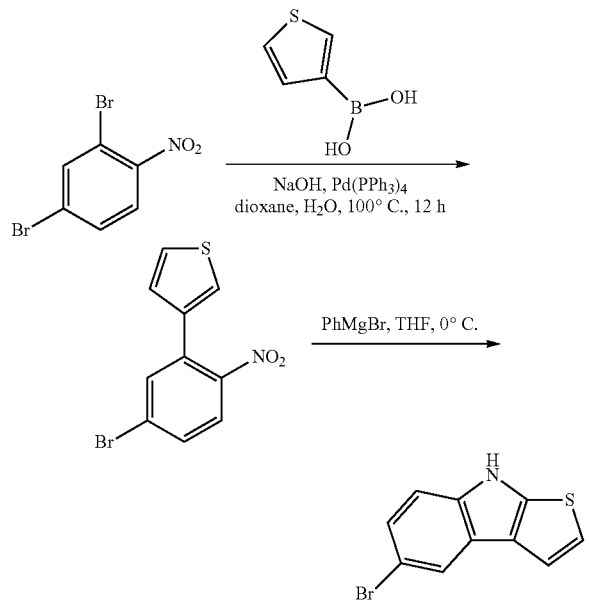

Step 1: 3-(5-bromo-2-nitrophenyl)thiophene

A solution of thiophen-3-ylboronic acid (0.9 g, 7.12 mmol), 2,4-dibromo-1-nitrobenzene (2 g, 7.12 mmol), Pd(PPh$_3$)$_4$ (247 mg, 0.214 mmol) and NaOH (854 mg, 21.4 mmol) in dioxane/H$_2$O (50 mL/10 mL) was heated to 100° C. and stirred under N$_2$ overnight. To the mixture was added H$_2$O (50 mL), extracted with EA (100 mL). The organic layer was washed with brine (50 mL), dried over Na$_2$SO$_4$, filtered, concentrated and purified by column and prep-HPLC to give product 3-(5-bromo-2-nitrophenyl)thiophene (300 mg, 33% yield) as a white solid. $^1$H NMR (400 MHz, CDCl$_3$) δ 7.70 (d, J=8.4 Hz, 1H), 7.66 (d, J=2.0 Hz, 1H), 7.59 (dd, J=2.0 Hz, J=8.8 Hz, 1H), 7.41-7.39 (m, 1H), 7.36-7.35 (m, 1H), 7.06 (dd, J=1.2 Hz, J=5.2 Hz, 1H).

Step 2: 5-bromo-8H-thieno[2,3-b]indole

To a solution of 3-(5-bromo-2-nitrophenyl)thiophene (250 mg, 0.880 mmol) in THF (10 mL) was added PhMgBr (1 N in THF) at 0° C. and stirred for 2 h at 0° C. under N$_2$. To the mixture was added aq. NH$_4$Cl (20 mL), extracted with EA (50 mL). The organic layer was washed with brine (30 mL), dried over Na$_2$SO$_4$, filtered, concentrated and purified by column (PE/EA=20/1 to 10/1 to 4/1) to give product 5-bromo-8H-thieno[2,3-b]indole (100 mg, 45% yield) as a white solid.

4H-Thiazolo[4,5-b]indole (Intermediate V)

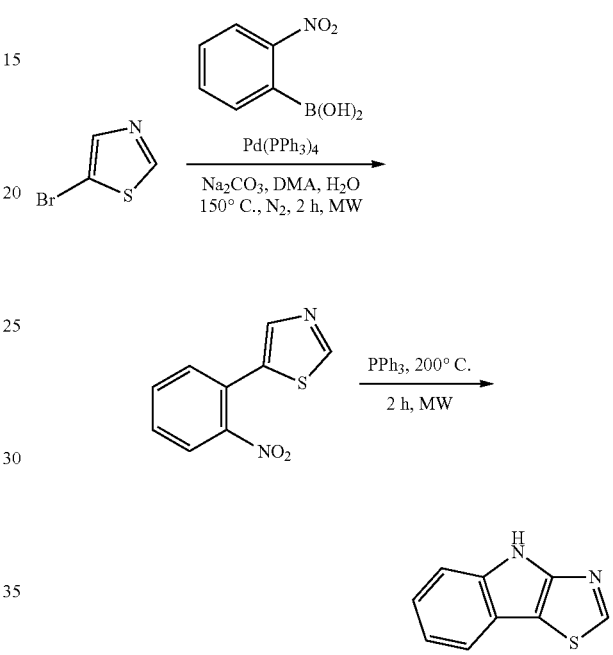

Step 1: 5-(2-nitrophenyl)thiazole

A mixture of 5-bromothiazole (200 mg, 1.2 mmol), (2-nitrophenyl)boronic acid (306 mg, 1.8 mmol), Na$_2$CO$_3$ (259 mg, 2.4 mmol) and Pd(PPh$_3$)$_4$ (141 mg, 0.1 mmol) in DMA (5 mL) was degassed with nitrogen, heated to 150° C. and stirred for 2 hours under nitrogen atmosphere and microwave. The reaction was cooled to r.t, filtered and concentrated in vacuo. The residue was diluted with water, extracted with EA. The combined organic layer was washed with brine, dried over anhydrous sodium sulfate, filtered and concentrated in vacuo. The residue was purified by column chromatography to give 5-(2-nitrophenyl)thiazole (130 mg, 52% yield) as a yellow solid. LC/MS (ESI, m/z): [M+1]$^+$=207.2

Step 2: 4H-thiazolo[4,5-b]indole

A mixture of 5-(2-nitrophenyl)thiazole (100 mg, 0.5 mmol) and PPh$_3$ (382 mg, 1.5 mmol) in DCB (3 mL) was heated at 200° C. for 2 hrs under microwave condition. The reaction mixture was cooled to r.t, filtered and concentrated under reduced pressure. The residue was purified by column chromatography to give 4H-thiazolo[4,5-b]indole (60 mg, 72% yield) as a yellow oil. LC/MS (ESI, m/z): [M+1]$^+$=175.2.

4H-Thiazolo[5,4-b]indole (Intermediate W)

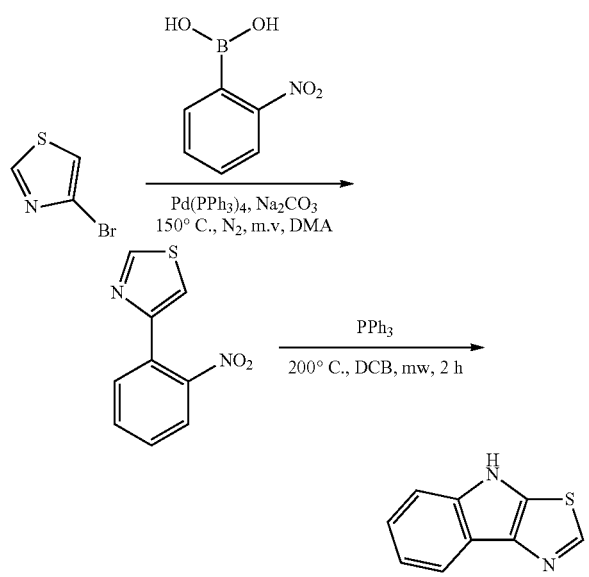

Step 1: 4-(2-nitrophenyl)thiazole

A mixture of 4-bromothiazole (3.0 g, 18.3 mmol), (2-nitrophenyl)boronic acid (4.6 g, 27.4 mmol), tetrakis(triphenylphosphine)palladium(0) (1.0 g, 0.91 mmol) and sodium carbonate (3.9 g, 36.6 mmol) in DMA (15 mL) and water (0.5 mL) was degassed with nitrogen, heated to 150° C. and stirred for 2 hours under microwave condition. The reaction was cooled to r.t and filtered. The filtrate was diluted with water, extracted with EA. The combined organic layer was washed with brine, dried over anhydrous sodium sulfate, filtered and concentrated in vacuo. The residue was purified by column chromatography (Petroleum ether/EtOAc=4:1) to give 4-(2-nitrophenyl)thiazole (2.35 g, 62.3% yield) as a yellow solid. LC/MS (ESI, m/z): [M+1]$^+$=207.1.

Step 2: 4H-thiazolo[5,4-b]indole

A mixture of 4-(2-nitrophenyl)thiazole (2.1 g, 10.2 mmol) and PPh$_3$ (8.0 g, 30.6 mmol) in DCB (15 mL) was heated at 200° C. for 2 h under microwave condition. The reaction mixture was cooled to r.t, filtered and concentrated under reduced pressure. The residue was purified by column chromatography (Petroleum ether/Ethyl acetate=2 to 1) to give 4H-thiazolo[5,4-b]indole (0.7 g, 39.5% yield) as a yellow solid. LC/MS (ESI, m/z): [M+1]$^+$=175.1.

5-Phenyl-1,3-dihydro-2H-benzo[e][1,4]diazepin-2-one (Intermediate X)

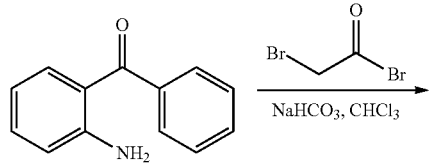

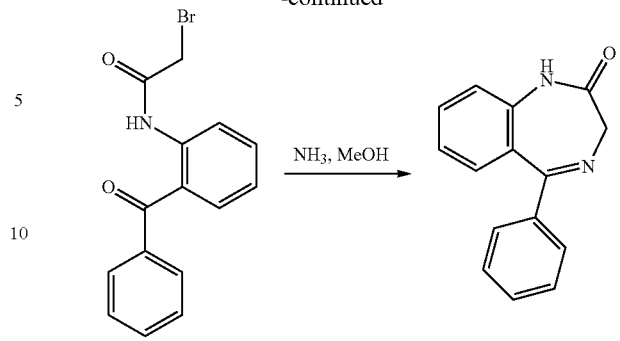

Step 1: N-(2-benzoylphenyl)-2-bromoacetamide

A mixture of (2-aminophenyl)(phenyl)methanone (394 mg, 2.0 mmol), NaHCO$_3$ (336 mg, 4.0 mmol) and 2-bromoacetyl bromide (482 mg, 2.4 mmol) in CHCl$_3$ was degassed with nitrogen, the mixture was stirred at r.t for 16 hours under nitrogen atmosphere. The residue was diluted with water, extracted with DCM. The combined organic layer was washed with brine, dried over anhydrous sodium sulfate, concentrated in vacuo to give N-(2-benzoylphenyl)-2-bromoacetamide (600 mg) which was used for next step without further purification. LC/MS (ESI, m/z): [M+1]$^+$=319.1.

Step 2: 5-phenyl-1,3-dihydro-2H-benzo[e][1,4]diazepin-2-one

A solution of N-(2-benzoylphenyl)-2-bromoacetamide (600 mg, 2.0 mmol) was dissolved in NH$_3$/MeOH at 0° C., then heated to 70° C. and stirred for 16 hours under nitrogen atmosphere. The reaction was cooled to r.t and stirred at r.t for 16 hours under nitrogen atmosphere. The mixture was concentrated in vacuo. The residue was purified by column chromatography to give 5-phenyl-1,3-dihydro-2H-benzo[e][1,4]diazepin-2-one (150 mg, two steps 32% yield) as a yellow solid. LC/MS (ESI, m/z): [M+1]$^+$=237.2.

9H-Benzo[d]imidazo[1,2-a]imidazole (Intermediate Y)

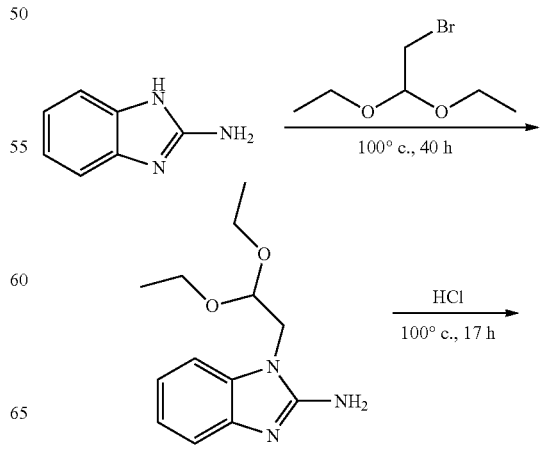

-continued

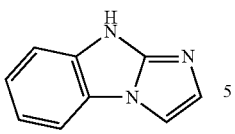

Step 1: 1-(2,2-diethoxyethyl)-1H-benzo[d]imidazol-2-amine

To a solution of 1H-benzo[d]imidazol-2-amine (665 mg, 5.0 mmol) in DMF (10 mL) was added KOH (0.56 g, 10.0 mmol). The reaction mixture was stirred for 40 h at 100° C. The reaction mixture was cooled to room temperature, diluted with water and extracted with EtOAc. The combined organic layer was dried over Na$_2$SO$_4$, filtered and concentrated in vacuo. The residue was purified by silica gel column chromatography to give 1-(2,2-diethoxyethyl)-1H-benzo[d]imidazol-2-amine (410 mg, 32.8% yield) as a yellow solid. LC/MS (ESI, m/z): [M+1]$^+$=250.3.

Step 2: 9H-benzo[d]imidazo[1,2-a]imidazole

To a solution of 1-(2,2-diethoxyethyl)-1H-benzo[d]imidazol-2-amine (330 mg, 1.33 mmol) in conc. HCl (10 mL) was heated to 100° C. and stirred for 17 h. The reaction mixture was cooled to room temperature, poured into ice-water. The mixture was filtered and the solid was purified by silica gel column chromatography to give 9H-benzo[d]imidazo[1,2-a]imidazole (70 mg, 35.0% yield) as a yellow solid. LC/MS (ESI, m/z): [M+1]$^+$=158.1.

EXAMPLES

Example 1. 3-(9H-Carbazol-9-yl)piperidine-2,6-dione (I-1)

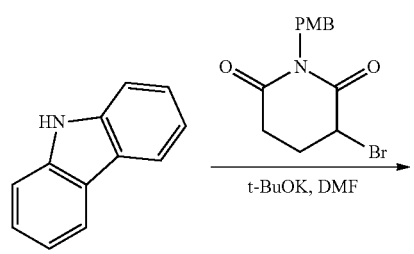

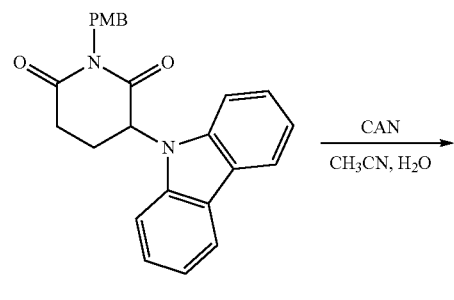

-continued

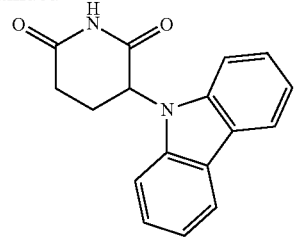

I-1

Step 1. 3-(9H-Carbazol-9-yl)-1-(4-methoxybenzyl)piperidine-2,6-dione

To a solution of 9H-carbazole (2.0 g, 12.0 mmol) in DMF (20 mL) was added t-BuOK (1.61 g, 14.4 mmol) at 0° C. The mixture was stirred at 0-10° C. for 1 hour under N$_2$. Then 3-bromo-1-(4-methoxybenzyl)piperidine-2,6-dione (5.59 g, 18.0 mmol) in DMF (30 mL) was added to the reaction mixture at 0-10° C. during 20 minutes. After addition, the mixture was stirred at room temperature for 17 hours under N$_2$. On completion, the reaction was quenched by water and extracted with EA. The combined organic layer was washed with water and brine, dried over anhydrous Na$_2$SO$_4$, filtered and concentrated in vacuo. The residue was purified by column chromatography to give the titled compound (0.35 g, 7.4% yield) as a yellow solid. LC-MS (ESI$^+$): m/z 399.3 (M+H)$^+$.

Step 2. 3-(9H-Carbazol-9-yl)piperidine-2,6-dione

To a solution of 3-(9H-carbazol-9-yl)-1-(4-methoxybenzyl)piperidine-2,6-dione (0.1 g, 0.25 mmol) in CH$_3$CN (4 mL) was added Diammonium cerium(IV) nitrate (0.41 g, 0.75 mmol) in water (1 mL) at 0° C. The reaction mixture was stirred at this temperature for 1 hour, then diluted with water. The mixture was purified via reverse phase column chromatography (CH$_3$CN/H$_2$O=5%-80%) to give the titled compound (7.5 mg, 10.7%) as a white solid. $^1$H NMR (400 MHz, DMSO-d$_6$) δ 8.49 (dd, J=7.5, 1.3 Hz, 1H), 8.25 (d, J=7.5 Hz, 1H), 8.11-8.01 (m, 1H), 7.88 (s, 1H), 7.57-7.40 (m, 3H), 7.34-7.29 (m, 2H), 5.51 (m, 1H), 3.08-2.94 (m, 2H), 2.74-2.53 (m, 2H). LC-MS (ESI$^+$): m/z 279.2 (M+H)$^+$.

Example 2. 3-(9H-pyrido[2,3-b]indol-9-yl)piperidine-2,6-dione (I-2)

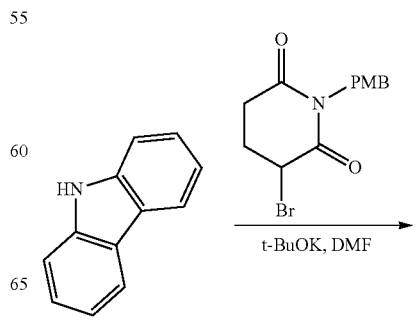

-continued

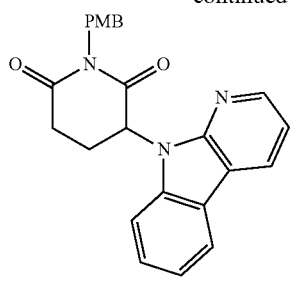

I-2

Step 1. 1-(4-Methoxybenzyl)-3-(9H-pyrido[2,3-b]indol-9-yl)piperidine-2,6-dione To a solution of 9H-pyrido[2,3-b]indole (2 g, 12 mmol) in DMF (30 mL) was added t-BuOK (1.34 g, 12 mmol) at 0° C. The mixture was stirred at 0-10° C. for 2 hour under $N_2$. Then a solution of 3-bromo-1-(4-methoxybenzyl)piperidine-2,6-dione (5.6 g, 18 mmol) in DMF (20 mL) was added to the reaction mixture at 0-10° C. during 30 minutes. The mixture was warmed to room temperature and stirred for 30 minutes under $N_2$. The reaction was quenched water (50 mL) and extracted with EA (3×50 mL). The combined organic layer was concentrated in vacuo. The residue was purified by column chromatography (PE/EA) to give the crude compound mix with the 9H-pyrido[2,3-b]indole. Then the mixture was purified with prep HPLC eluting with ACN/$H_2O$ (0.1% HCOOH) to get the title compound (538 mg) as a white solid (yield: 11.2%). LC-MS (ESI$^+$): m/z 400.1 (M+H)$^+$.

Step 2. 3-(9H-Pyrido[2,3-b]indol-9-yl)piperidine-2,6-dione

To a solution of 1-(4-methoxybenzyl)-3-(9H-pyrido[2,3-b]indol-9-yl)piperidine-2,6-dione (400 mg, 1 mmol) in toluene (10 ml) was added MsOH (1.8 g, 20 mmol). The mixture was warmed to 100° C. and stirred for 2 h. The reaction mixture was cooled to room temperature and concentrated in vacuo. The residue was poured into ice/water (50 mL), extracted with EA (3×50 mL). The combined organic layer was washed with brine (50 mL), dried over $Na_2SO_4$, filtered and concentrated in vacuo. The residue was purified with prep HPLC eluting with ACN/$H_2O$ (0.1% HCOOH) to get the titled compound (120 mg, 43% yield) as a white solid. 1H NMR (400 MHz, DMSO-d6) δ: 11.15 (s, 1H), 8.53-8.62 (m, 1H), 8.43 (dd, J=4.88, 1.50 Hz, 1H), 8.24 (d, J=7.63 Hz, 1H), 7.62 (d, J=7.88 Hz, 1H), 7.46-7.56 (m, 1H), 7.24-7.37 (m, 2H), 6.05 (br. s., 1H), 2.93-3.21 (m, 2H), 2.63-2.77 (m, 1H), 2.07-2.18 (m, 1H). LC-MS (ESI$^+$): m/z 280.0 (M+H)$^+$.

Example 3. 3-(6-Amino-9H-pyrido[2,3-b]indol-9-yl)piperidine-2,6-dione (I-5)

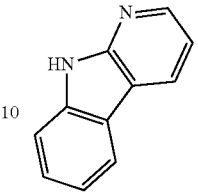

conc. HNO$_3$
conc. H$_2$SO$_4$

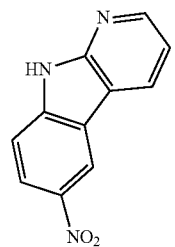

Boc$_2$O, DMAP
ACN

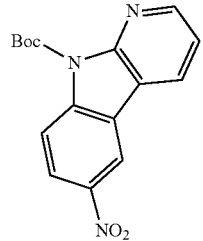

TFA, DCM

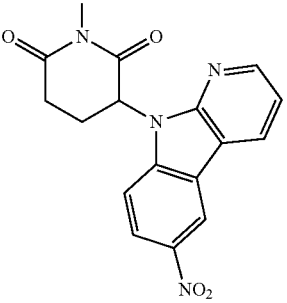

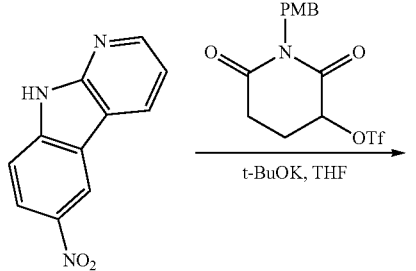

t-BuOK, THF

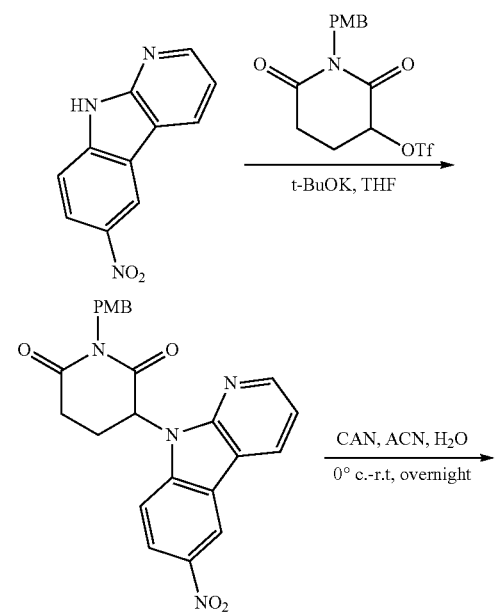

CAN, ACN, H$_2$O
0° c.-r.t, overnight

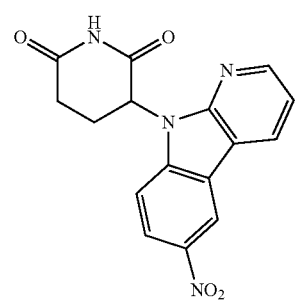

Pd/C, EA, THF
r.t, overnight

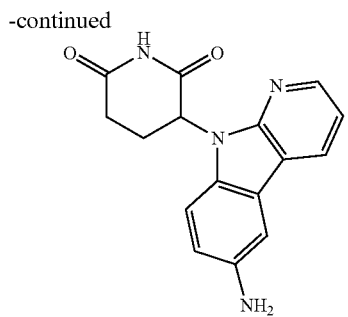

I-5

Step 1. 6-Nitro-9H-pyrido[2,3-b]indole

To a solution of 9H-pyrido[2,3-b]indole (504 mg, 3 mmol) in conc. $H_2SO_4$ (5 ml) was added dropwise a solution of nitric acid (68%-70% solution in water)(297 mg, 3.3 mol) in con.$H_2SO_4$ (5 ml) at −5° C.-0° C. over 20 mins. After addition, the mixture was added into ice water, then basified by addition of saturated NaOH solution to PH>8. The mixture was extracted with EtOAc (3*200 ml), the combined organic layers were evaporated to give the title compound as a yellow solid (500 mg, 78.2% yield) that was used directly in the next step without further purification. LC-MS (ESI+): m/z 214.2 (M+H)+.

Step 2. tert-Butyl 6-nitro-9H-pyrido[2,3-b]indole-9-carboxylate

To a solution of 6-nitro-9H-pyrido[2,3-b]indole (500 mg, 2.35 mmol) in DCM (10 ml) was added $Boc_2O$ (767 mg, 3.52 mmol) and DMAP (57.2 mg, 0.468 mmol). The mixture was stirred at room temperature overnight. The reaction mixture was evaporated. The residue was purified by silica gel chromatography (PE:EA=3:1) to give the title compound as a white solid (385 mg, 52.1% yield). 1H NMR (400 MHz, $CDCl_3$) δ: 8.90 (d, J=2.13 Hz, 1H), 8.75 (dd, J=4.82, 1.56 Hz, 1H), 8.35-8.47 (m, 3H), 7.44 (dd, J=7.75, 4.88 Hz, 1H), 1.80 (s, 9H).

Step 3. 6-Nitro-9H-pyrido[2,3-b]indole

To a solution of tert-butyl 6-nitro-9H-pyrido[2,3-b]indole-9-carboxylate (300 mg, 0.96 mmol) in DCM (6 ml) was added TFA (2 ml). The mixture was stirred at room temperature overnight. The reaction mixture was concentrated. The residue was resolved in DCM (20 ml), washed with saturated $NaHCO_3$ solution (2*20 ml), the organic phase was washed with brine, dried over $Na_2SO_4$, filtered and concentrated in vacuo to give the crude titled compound (200 mg, 95.4% yield) as a yellow solid. LC-MS (ESI+): m/z 214.2 (M+H)+

Step 4. 1-(4-Methoxybenzyl)-3-(6-nitro-9H-pyrido[2,3-b]indol-9-yl)piperidine-2,6-dione To a solution of 6-nitro-9H-pyrido[2,3-b]indole (210 mg, 1 mmol) in THF (10 mL) was added t-BuOK (168 mg, 1.5 mmol) at 0° C. The mixture was stirred at 0-10° C. for 1 hour under $N_2$. Then a solution of [1-[(4-methoxyphenyl) methyl]-2, 6-dioxo-3-piperidyl]trifluoromethanesulfonate (457 mg, 1.2 mmol) in THF (10 mL) was added to the reaction mixture at 0-10° C. during 20 minutes. The mixture was stirred at 0-10° C. for 30 minutes under N2. Additional solution of [1-[(4-methoxyphenyl) methyl]-2, 6-dioxo-3-piperidyl]trifluoromethanesulfonate (114 mg, 0.3 mmol) in THF (5 mL) was added to the reaction mixture at 0-10° C. dropwise. The mixture was stirred at 0-10° C. for another 30 minutes under N2. On completion, the reaction was quenched water (40 mL) and extracted with EA (3×50 mL). The combined organic layer was concentrated in vacuo. The residue was purified by column chromatography to give the titled compound (400 mg) as a yellow solid. LC-MS (ESI+): m/z 445 (M+H)+.

Step 5. 3-(6-Nitro-9H-pyrido[2,3-b]indol-9-yl)piperidine-2,6-dione

To a solution of 1-(4-methoxybenzyl)-3-(6-nitro-9H-pyrido[2,3-b]indol-9-yl)piperidine-2,6-dione (400 mg, 0.90 mmol) in $CH_3CN$ (10 ml) was added a solution of CAN (2.46 g, 0.45 mmol) in water (3 ml) at 0° C. After addition, the mixture was warmed to room temperature and stirred overnight. The reaction mixture was poured into water (50 ml), extract with EtOAc (3*50 ml), the combined organic layers were concentrated in vacuo. The residue was triturated with DMF/EA and filtrated to give the titled compound (130 mg, 44.4% yield) as a grey solid. LC-MS (ESI+): m/z 325.0 (M+H)+.

Step 6. 3-(6-Amino-9H-pyrido[2,3-b]indol-9-yl)piperidine-2,6-dione (I-5)

To a solution of 3-(6-nitro-9H-pyrido[2,3-b]indol-9-yl)piperidine-2,6-dione (130 mg, 0.401 mmol) in THF (5 ml) and EA (5 ml) was added palladium on activated carbon 10% Pd (50 mg) The mixture was stirred at room temperature under hydrogen overnight. The reaction mixture was filtered, the filtrate was concentrated under reduce pressure, the residue was triturated with DMF/EA and filtrated to give the title compound (55 mg, 46.4% yield) as a grey solid. LC-MS (ESI+): m/z 295.0 (M+H)+. 1H NMR (400 MHz, DMSO-d6) δ: 11.08 (s, 1H), 8.26-8.39 (m, 2H), 7.24-7.36 (m, 2H), 7.14 (dd, J=7.63, 4.88 Hz, 1H), 6.85 (dd, J=8.63, 2.13 Hz, 1H), 5.90 (br. s., 1H), 4.87 (br. s., 2H), 2.93-3.08 (m, 2H), 2.68 (d, J=12.26 Hz, 1H), 2.01-2.11 (m, 1H).

Example 4. N-(9-(2,6-Dioxopiperidin-3-yl)-9H-pyrido[2,3-b]indol-6-yl)acetamide (I-8)

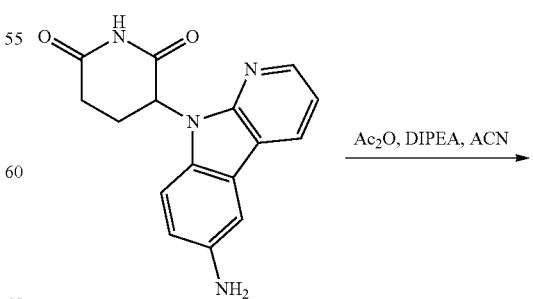

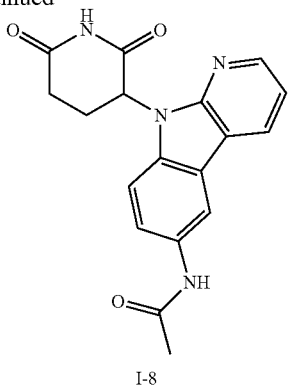

I-8

To a solution of 3-(6-amino-9H-pyrido[2,3-b]indol-9-yl)piperidine-2,6-dione (40 mg crude, 0.136 mmol) in ACN (5 ml) was added acetic anhydride (5 drops) and DIPEA (10 drops). The mixture was stirred at room temperature for 2 h. The mixture was filtered, the filtrate cake was dissolved in DCM, washed with 1M HCl (2*10 ml), the organic phase was concentrated and dried to give the titled compound (8 mg, 17.4% yield) as a white solid. $^1$H NMR (400 MHz, DMSO-$d_6$) δ: 11.14 (s, 1H), 10.02 (s, 1H), 8.45-8.55 (m, 2H), 8.35-8.45 (m, 1H), 7.46-7.61 (m, 2H), 7.25 (dd, J=7.69, 4.82 Hz, 1H), 6.02 (br. s., 1H), 2.93-3.17 (m, 2H), 2.63-2.76 (m, 1H), 2.06-2.14 (m, 4H). LC-MS (ESI$^+$): m/z 337.0 (M+H)$^+$.

Example 5. 1-(9-(2,6-Dioxopiperidin-3-yl)-9H-pyrido[2,3-b]indol-6-yl)-3-ethylurea (I-9)

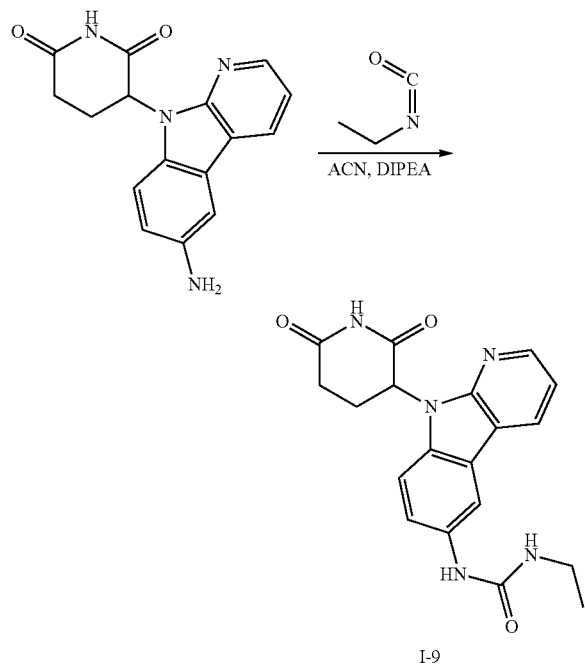

I-9

To a solution of 3-(6-amino-9H-pyrido[2,3-b]indol-9-yl)piperidine-2,6-dione (25 mg, 0.085 mmol) in ACN (5 ml) was added ethyl isocyanate (3 drops) and DIPEA (6 drops). The mixture was stirred at room temperature for 4 h. The mixture was concentrated in vacuo and the residue was purified by prep HPLC to give the title compound (8 mg, 25.7% yield) as a white solid. $^1$H NMR (400 MHz, DMSO-$d_6$) δ: 11.13 (s, 1H), 8.43-8.54 (m, 2H), 8.39 (dd, J=4.82, 1.44 Hz, 1H), 8.27 (d, J=1.88 Hz, 1H), 7.37-7.52 (m, 2H), 7.22 (dd, J=7.63, 4.88 Hz, 1H), 6.12 (t, J=5.50 Hz, 1H), 5.99 (br. s., 1H), 3.10-3.20 (m, 2H), 2.90-3.07 (m, 2H), 2.65-2.75 (m, 1H), 2.06-2.16 (m, 1H), 1.03-1.13 (m, 3H). LC-MS (ESI$^+$): m/z 366.3 (M+H)$^+$.

Example 6. Time-Resolved Fluorescence Resonance Energy Transfer (TR-FRET) Assay

Equal volumes of His-tagged CRBN-DDB1 complex (56 nM) was mixed with Eu-cryptate labeled Anti-6HIS-monoclonal antibody (50× dilution from the commercial stock solution, Vender: Cisbio, Cat. #61HI2KLA) in a final buffer containing 20 mM HEPES pH 7.0, 150 mM NaCl, 0.005% Tween-20. The solution was then mixed with Cy5-labeled thalidomide (final 8 nM) and various concentrations of compounds (a serial 3-fold dilution with the top concentration 200 uM). The mixture were incubated at room temperature for 1 hour. FRET signals were measured on an EnVision plate reader (Perkin Elmer) by exciting at 340 nm and recording emission at both 615 nm as no FRET control and 665 nm as the FRET signals with a 60 microsecond delay. FRET efficiency was calculated as the ratio of fluorescent signals at 665 nM/615 nM. Quantitative loss of FRET efficiency as a function of compound concentrations was fitted by a four-parameter Logistic Function using GraphPad Prism 7.0 and the IC$_{50}$ values were reported for each compound.

Table 3 shows the results for selected compounds in the time-resolved fluorescence resonance energy transfer (TR-FRET) assay. The compound numbers correspond to the compound numbers in Table 1. Compounds having an activity designated as "A" provided an IC$_{50}$ of <10 µM; compounds having an activity designated as "B" provided an IC$_{50}$ of 10-30 µM; compounds having an activity designated as "C" provided an IC$_{50}$ of 30-100 µM; and compounds having an activity designated as "D" provided an IC$_{50}$ of >100 µM. For reference, the known CRBN binders provided the following IC$_{50}$ values in the TR-FRET assay: thalidomide (IC$_{50}$=2.9 µM), lenalidomide (IC$_{50}$=1.17 µM) and pomalidomide (IC$_{50}$=1.28 µM).

TABLE 3

| TR-FRET Assay Results | |
| --- | --- |
| CMPD # | CRBN HTRF IC$_{50}$ (µM) |
| I-1 | B |
| I-2 | A |
| I-3 | C |
| I-5 | A |
| I-8 | A |
| I-9 | A |
| I-26 | A |
| I-27 | A |
| I-28 | A |
| I-29 | B |
| I-30 | A |
| I-31 | A |
| I-32 | B |
| I-33 | A |
| I-34 | A |
| I-35 | A |
| I-36 | A |
| I-37 | B |
| I-38 | A |

TABLE 3-continued

TR-FRET Assay Results

| CMPD # | CRBN HTRF IC$_{50}$ (µM) |
| --- | --- |
| I-39 | A |
| I-40 | B |
| I-41 | C |
| I-42 | D |
| I-43 | C |
| I-44 | A |
| I-45 | B |
| I-46 | A |
| I-47 | A |
| I-48 | A |
| I-49 | A |
| I-50 | A |
| I-51 | A |
| I-52 | A |
| I-53 | B |
| I-54 | B |
| I-55 | C |
| I-56 | B |
| I-57 | A |
| I-58 | B |
| I-59 | A |
| I-60 | A |
| I-61 | A |
| I-62 | A |
| I-63 | A |
| I-64 | A |
| I-65 | C |
| I-66 | B |
| I-67 | B |
| I-68 | C |
| I-69 | D |
| I-70 | B |
| I-71 | A |
| I-72 | A |
| I-73 | B |
| I-74 | B |
| I-75 | A |
| I-76 | A |
| I-77 | A |
| I-78 | A |
| I-79 | A |
| I-80 | B |
| I-81 | B |
| I-82 | B |
| I-83 | A |
| I-84 | A |
| I-85 | B |
| I-86 | A |
| I-87 | A |
| I-88 | A |
| I-89 | A |
| I-90 | B |
| I-91 | C |
| I-92 | A |
| I-93 | A |
| I-94 | C |
| I-99 | C |
| I-100 | A |
| I-101 | A |
| I-102 | B |
| I-103 | A |
| I-105 | B |
| I-106 | B |

Example 7. General Method A. 3-(6-Bromo-9H-pyrido[2,3-b]indol-9-yl)piperidine-2,6-dione (I-26), tert-Butyl (2-((3-(9-(2,6-dioxopiperidin-3-yl)-9H-pyrido[2,3-b]indol-6-yl)prop-2-yn-1-yl)oxy)ethyl) carbamate (I-33), and tert-butyl (2-(3-(9-(2,6-dioxopiperidin-3-yl)-9H-pyrido[2,3-b]indol-6-yl) propoxy)ethyl)carbamate (I-34)

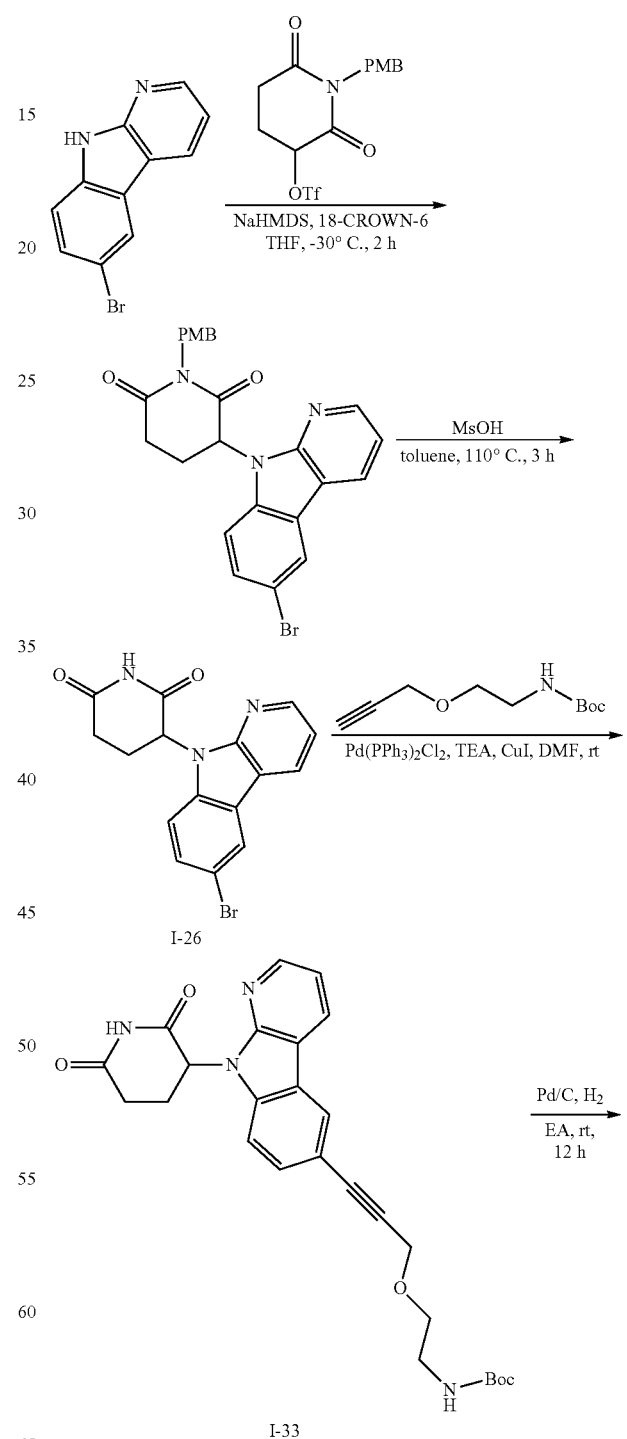

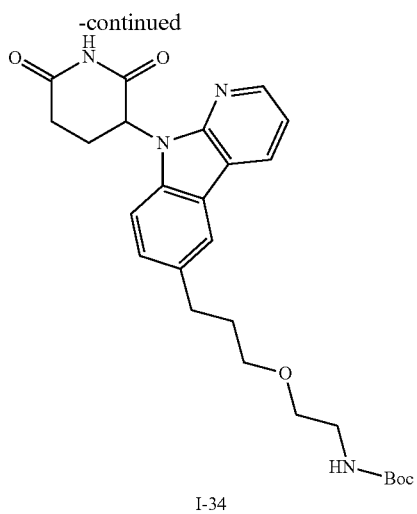

I-34

Step 1: 3-(6-bromo-9H-pyrido[2,3-b]indol-9-yl)-1-(4-methoxybenzyl)piperidine-2,6-dione To a stirred solution of Intermediate A (200 mg, 0.810 mmol) and 18-crown-6 (43 mg, 0.162 mmol) in dry THF (10 mL) was added dropwise NaHMDS (0.6 mL, 2 M in THF) at −30° C. under $N_2$. The mixture was stirred for 1 h at −30° C. under $N_2$. Then to the mixture was added a solution of 1-(4-methoxybenzyl)-2,6-dioxopiperidin-3-yl trifluoromethanesulfonate (463 mg, 1.21 mmol) in THF (5 mL) dropwise at −30° C. under $N_2$. The mixture was stirred at −30° C. for 2 h. The mixture was added to aq. $NH_4Cl$ (20 mL), extracted with EA (50 mL). The organic layer was washed with brine (30 mL), dried over $Na_2SO_4$, filtered, concentrated and purified by column (PE/EA/DCM=10/1/1 to 3/1/1) to give product 3-(6-bromo-9H-pyrido[2,3-b]indol-9-yl)-1-(4-methoxybenzyl)piperidine-2,6-dione (220 mg, 57% yield) as a yellow oil. $^1$H NMR (400 MHz, $CDCl_3$) δ 8.41 (dd, J=1.6 Hz, J=4.8 Hz, 1H), 8.29 (dd, J=1.2 Hz, J=7.6 Hz, 1H), 8.20 (J=1.6 Hz, 1H), 7.45 (dd, J=2.0 Hz, J=8.6 Hz, 1H), 7.40 (d, J=8.8 Hz, 2H), 7.24-7.21 (m, 1H), 6.84 (d, J=8.8 Hz, 3H), 5.90-5.87 (m, 1H), 5.01 (dd, J=13.6 Hz, J=20.4 Hz, 2H), 3.81 (s, 3H), 3.09-2.84 (m, 4H); LC/MS (ESI, m/z): [M+1]$^+$=479.1.

Step 2: 3-(6-bromo-9H-pyrido[2,3-b]indol-9-yl)piperidine-2,6-dione (I-26)

A mixture of 3-(6-bromo-9H-pyrido[2,3-b]indol-9-yl)-1-(4-methoxybenzyl)piperidine-2,6-dione (1.3 g, 2.72 mmol), MsOH (10 mL) and toluene (20 mL) was heated to 110° C. and stirred for 3 h under $N_2$. The mixture was concentrated to remove toluene. Then to the mixture was added EA (50 mL), washed with brine (50 mL) to remove MsOH. The organic layer was dried over $Na_2SO_4$, concentrated with silica gel and purified by column (PE/EA=1/1) to give product I-26 (500 mg, 51% yield) as a white solid. $^1$H NMR (400 MHz, DMSO-$d_6$) δ 11.13 (br s, 1H), 8.64 (dd, J=1.6 Hz, J=7.6 Hz, 1H), 8.52 (d, J=2.0 Hz, 1H), 8.47 (dd, J=1.6 Hz, J=4.8 Hz, 1H), 7.68-7.62 (m, 2H), 7.31 (dd, J=4.8 Hz, J=7.6 Hz, 1H), 6.06 (s, 1H), 3.16-2.96 (m, 2H), 2.73-2.67 (m, 1H), 2.16-2.13 (m, 1H). LC/MS (ESI, m/z): [M+1]$^+$=358.0/360.0.

Step 3: tert-butyl (2-((3-(9-(2,6-dioxopiperidin-3-yl)-9H-pyrido[2,3-b]indol-6-yl)prop-2-yn-1-yl)oxy)ethyl)carbamate (I-33)

A mixture of I-26 (100 mg, 0.279 mmol), tert-butyl (2-(prop-2-yn-1-yloxy)ethyl)carbamate (166 mg, 0.840 mmol), Pd(PPh$_3$)$_2$Cl$_2$ (30 mg, 0.042 mmol), CuI (4 mg, 0.022 mmol), TEA (283 mg, 2.80 mmol), and DMF (5 mL) was heated to 80° C. under microwave for 1.5 h under $N_2$. The mixture was poured into 1N HCl (20 mL), extracted with EA (50 mL). The organic layer was washed with brine (20 mL), dried over $Na_2SO_4$, filtered, concentrated and purified by column (PE/EA=10/1 to 5/1 to 2/1) to give product I-33 (30 mg, 23% yield) as a white solid. $^1$H NMR (400 MHz, DMSO-$d_6$) δ 11.17 (s, 1H), 8.62 (dd, J=1.2 Hz, J=7.6 Hz, 1H), 8.46 (dd, J=1.6 Hz, J=4.8 Hz, 1H), 8.43 (s, 1H), 7.66-7.58 (m, 2H), 7.33-7.30 (m, 1H), 8.87 (s, 1H), 6.07 (br s, 1H), 4.42 (s, 2H), 3.54 (t, J=6.0 Hz, 2H), 3.17-3.01 (m, 4H), 2.69-2.66 (m, 1H), 2.16-2.13 (m, 1H), 1.38 (s, 9H). LC/MS (ESI, m/z): [M+1]$^+$=477.2.

Step 4: tert-butyl (2-(3-(9-(2,6-dioxopiperidin-3-yl)-9H-pyrido[2,3-b]indol-6-yl)propoxy)ethyl)carbamate (I-34)

A mixture of tert-butyl I-33 (10 mg, 0.021 mmol), Pd/C (2 mg) and EA (2 mL) was stirred for 12 h under $H_2$ at rt. The mixture was filtered, added $H_2O$ (10 mL), extracted with EA (20 mL). The organic layer was concentrated and purified by Prep-HPLC to give product I-34 (3 mg, 30% yield) as a white solid. $^1$H NMR (400 MHz, DMSO-$d_6$) δ 11.13 (s, 1H), 8.53 (d, J=7.6 Hz, 1H), 8.40 (d, J=4.4 Hz, 1H), 8.05 (s, 1H), 7.52 (d, J=8.0 Hz, 1H), 7.36 (d, J=8.4 Hz, 1H), 7.26-7.23 (m, 1H), 6.81 (t, J=5.2 Hz, 1H), 6.01 (br s, 1H), 3.43-3.39 (m, 3H), 3.19-2.97 (m, 4H), 2.79 (t, J=7.2 Hz, 2H), 2.72-2.68 (m, 1H), 2.12-2.10 (m, 1H), 2.03-1.96 (m, 1H), 1.91-1.85 (m, 2H), 1.37 (m, 9H); LC/MS (ESI, m/z): [M−55]$^+$=425.2.

Characterization data for further compounds prepared by Method A are presented in Table 4 below. Compounds in Table 4 were prepared by methods substantially similar to the steps described to prepare I-26, I-33, and I-34.

TABLE 4

Compounds prepared according to Method A.

| I-# | Intermediates | LC/MS (ESI, m/z) | $^1$H NMR (400 MHz) |
|---|---|---|---|
| I-33 | I-26 + B | [M + 1]$^+$ = 505.2 | (CDCl$_3$) δ 8.45 (dd, J = 1.2 Hz, J = 5.0 Hz, 1 H), 8.33 (dd, J = 1.6 Hz, J = 7.6 Hz, 1 H), 8.20 (d, J = 1.2 Hz, 1 H), 8.10 (s, 1 H), 7.58 (dd, J = 1.6 Hz, J = 8.4 Hz, 1 H), 7.25-7.20 (m, 2 H), 5.91-5.88 (m, 1 H), 4.41 (s, 2 H), 3.64 (t, J = 6.8 Hz, 2 H), 3.34 (t, J = 7.2 Hz, 2 H), 310-2.91 (m, 3 H), 2.89 (s, 3 H), 2.36-2.30 (m, 1 H), 1.91-1.84 (m, 2 H), 1.46 (s, 9 H) |

TABLE 4-continued

Compounds prepared according to Method A.

| I-# | Intermediates | LC/MS (ESI, m/z) | $^1$H NMR (400 MHz) |
|---|---|---|---|
| I-34 | I-33 | [M − 55]$^+$ = 453.2 | (CDCl$_3$) δ 8.41 (dd, J = 1.6 Hz, J = 4.8 Hz, 1 H), 8.32 (d, J = 7.6 Hz, 1 H), 8.15 (s, 1 H), 7.91 (d, J = 0.8 Hz, 1 H), 7.33 (dd, J = 1.6 Hz, J = 8.4 Hz, 1 H), 7.21 (d, J = 5.2 Hz, J = 7.6 Hz, 1 H), 7.17 (d, J = 8.4 Hz, 1 H), 5.94 (br s, 1 H), 3.47-3.42 (m, 4 H), 3.31 (t, J = 6.8 Hz, 2 H), 3.07-2.95 (m, 3 H), 2.88-2.84 (m, 5 H), 2.33-2.29 (m, 1 H), 2.01-1.93 (m, 2 H), 1.85-1.78 (m, 2 H), 1.46 (s, 9 H); |
| I-47 | I-26 + ((2-(2-(prop-2-yn-1-yloxy)eth-oxy)eth-oxy)methyl)benzene | [M + 1]$^+$ = 512.2 | (CDCl$_3$) δ 8.44 (dd, J = 1.2 Hz, J = 4.8 Hz, 1 H), 8.30 (dd, J = 1.2 Hz, J = 7.6 Hz, 1 H), 8.20 (d, J = 0.8 Hz, 1 H), 8.17 (br s, 1 H), 7.57 (dd, J = 1.4 Hz, J = 8.4 Hz, 1 H), 7.37-7.31 (m, 4 H), 7.29-7.18 (m, 3 H), 5.87-5.84 (m, 1 H), 4.58 (s, 2 H), 4.48 (s, 2 H), 3.83-3.80 (m, 2 H), 3.77-3.71 (m, 4 H), 3.69-3.64 (m, 2 H), 3.09-2.92 (m, 3 H), 2.32-2.28 (m, 1 H). |
| I-46 | I-47 | [M + 1]$^+$ = 426.1 | (CDCl$_3$) δ 8.41 (dd, J = 1.2 Hz, J = 4.8 Hz, 1 H), 8.31 (dd, J = 1.4 Hz, J= 7.6 Hz, 1 H), 8.28 (s, 1 H), 7.92 (d, J = 0.4 Hz, 1 H), 7.33 (dd, J = 1.2 Hz, J = 8.4 Hz, 1 H), 7.21-7.16 (m, 2 H), 5.90 (dd, J = 4.8 Hz, J = 8.0 Hz, 1 H), 3.76-3.74 (m, 2 H), 3.71-3.69 (m, 2 H), 3.65-3.60 (m, 4 H), 3.52 (t, J = 6.4 Hz, 2 H), 3.08-2.85 (m, 5 H), 2.59 (br s, 1 H), 2.32-2.26 (m, 1 H), 2.04-1.97 (m, 2 H). |
| I-63 | I-26 + C | [M − Boc + 1]$^+$ = 421.3 | (CDCl$_3$) δ 8.45 (dd, J = 1.2 Hz, J = 4.8 Hz, 1vH), 8.34 (dd, J = 0.8 Hz, J = 7.6 Hz, 1 H), 8.21 (d, J = 0.8 Hz, 1 H), 8.15 (s, 1 H), 7.59 (dd, J = 1.2 Hz, J = 8.4 Hz, 1 H), 7.26-7.18 (m, 2 H), 5.95-5.89 (m, 1 H), 5.01 (br s, 1 H), 4.48 (s, 2 H), 3.81-3.79 (m, 2 H), 3.71-3.69 (m, 2 H), 3.58 (t, J = 5.2 Hz, 2 H), 3.35 (dd, J = 4.8 Hz, J = 9.2 Hz, 2 H), 3.09-2.88 (m, 3 H), 2.35-2.31 (m, 1 H), 1.44 (s, 9 H) |
| I-62 | I-63 | [M − Boc + 1]$^+$ = 425.2 | (CDCl$_3$) δ 8.41 (dd, J = 1.2 Hz, J = 4.8 Hz, 1 H), 8.31 (dd, J = 1.6 Hz, J = 7.6 Hz, 1 H), 8.22 (br s, 1 H), 7.92 (d, J = 0.8 Hz, 1 H), 7.33 (dd, J = 1.6 Hz, J = 8.4 Hz, 1 H), 7.21-7.16 (m, 2 H), 5.90 (dd, J = 4.8 Hz, J = 12 Hz, 1 H), 5.04 (br s, 1 H), 3.64-3.50 (m, 8 H), 3.35-3.32 (m, 2 H), 3.12-2.85 (m, 5 H), 2.32-2.28 (m, 1 H), 2.04-1.97 (m, 2 H), 1.43 (s, 9 H); |
| I-32 | E | [M + 1]$^+$ = 305.3 | (DMSO-d$_6$) δ 11.22 (s, 1 H), 8.85 (d, J = 1.3 Hz, 1 H), 8.72-8.69 (m, 1 H), 8.55-8.53 (m, 1 H), 7.95-7.83 (m, 2 H), 7.40 (dd, J = 7.7, 4.9 Hz, 1 H), 6.13 (s, 1 H), 3.18-2.98 (m, 2 H), 2.80-2.63 (m, 1 H), 2.24-2.09 (m, 1 H) |
| I-31 | F | [M + 1]$^+$ = 358.0, 360.0 | (DMSO-d$_6$) δ. 11.19 (s, 1 H), 8.57 (d, J = 8.0 Hz, 1 H), 8.31 (d, J = 5.2 Hz, 1 H), 7.72 (s, 1 H), 7.63 (t, J = 7.6 Hz, 1 H), 7.56 (d, J = 5.2 Hz, 1 H), 7.41 (t, J = 7.4 Hz, 1 H), 6.10 (s, 1 H), 3.13-2.99 (m, 2 H), 2.74-2.67 (m, 1 H), 2.17-2.15 (m, 1 H) |
| I-49 | I-31 + ((2-(2-(prop-2-yn-1-yloxy)ethoxy)eth-oxy)methyl)benzene | [M + 1]$^+$ = 512.3 | (CDCl$_3$) δ 8.54 (d, J = 7.8 Hz, 1 H), 8.35 (d, J = 5.1 Hz, 1 H), 8.26 (s, 1 H), 7.56-7.45 (m, 1 H), 7.36-7.29 (m, 6 H), 7.27-7.25 (m, 1 H), 7.22 (d, J = 5.1 Hz, 1 H), 5.90-5.86 (m, 1 H), 4.66 (s, 2 H), 4.57 (s, 2 H), 3.91-3.88 (m, 2 H), 3.79-3.76 (m, 2 H), 3.76-3.71 (m, 2 H), 3.69-3.63 (m, 2 H), 3.12-2.86 (m, 3 H), 2.32-2.25 (m, 1 H) |
| I-48 | I-49 | [M + 1]$^+$ = 426.3 | (CDCl$_3$) δ 8.43-8.26 (m, 2 H), 8.18 (d, J = 7.8 Hz, 1 H), 7.50-7.45 (m, 1 H), 7.36-7.24 (m, 2 H), 7.03 (d, J = 5.0 Hz, 1 H), 5.95-5.92 (m, 1 H), 3.76-3.59 (m, 10 H), 3.36-3.23 (m, 2 H), 3.14-2.84 (m, 3 H), 2.33-2.22 (m, 1 H), 2.21-2.08 (m, 2 H) |
| I-57 | I-31 + C | [M + 1]$^+$ = 525.4 | (CDCl$_3$) δ 8.32 (d, J = 5.1 Hz, 1 H), 8.20 (d, J = 7.9 Hz, 1 H), 8.12 (s, 1 H), 7.52-7.47 (m, 1 H), 7.37-7.26 (m, 2 H), 7.07-7.05 (m, 1 H), 5.96 (s, 1 H), 5.00 (s, 1 H), 3.66-3.56 (m, 8 H), 3.41-3.24 (m, 4 H), 3.07-2.99 (m, 3 H), 2.34-2.29 (m, 1 H), 2.18-2.11 (m, 2 H), 1.43 (s, 9 H) |
| I-30 | G | [M + 1]$^+$ = 358.1, 360.1 | (DMSO-d$_6$) δ 11.19 (s, 1 H), 8.91 (dd, J = 1.2, 7.6 Hz, 1 H), 8.53 (d, J = 4.0 Hz, 1 H), 7.72 (s, 1 H), 7.56-7.51 (m, 1 H), 7.49-7.45 (m, 1 H), 7.40-7.37 (m, 1 H), 6.19-6.00 (m, 1 H), 3.12-2.99 (m, 2 H), 2.74-2.67 (m, 1 H), 2.17-2.14 (m, 1 H) |
| I-52 | I-30 + ((2-(2-(prop-2-yn-1-yloxy)ethoxy)eth-oxy)methyl)benzene | [M + 1]$^+$ = 512.3 | (DMSO-d$_6$) δ 11.17 (s, 1 H), 8.82 (dd, J = 7.8, 1.6 Hz, 1 H), 8.48 (dd, J = 4.8, 1.6 Hz, 1 H), 7.74-7.69 (m, 1 H), 7.53 (t, J = 8.0 Hz, 1 H), 7.44-7.19 (m, 7 H), 6.09 (s, 1 H), 4.66 (s, 2 H), 4.48 (s, 2 H), 3.84-3.73 (m, 2 H), 3.71-3.52 (m, 6 H), 3.17-2.93 (m, 2 H), 2.81-2.64 (m, 1 H), 2.25-2.04 (m, 1 H) |
| I-51 | I-52 | [M + 1]$^+$ = 426.3 | (DMSO-d$_6$) δ 11.15 (s, 1 H), 8.55 (dd, J = 7.6, 1.6 Hz, 1 H), 8.42 (d, J = 3.7 Hz, 1 H), 7.48-7.42 (m, 2 H), 7.31-7.27 (m, 1 H), 7.19-7.04 (m, 1 H), 6.03 (s, 1 H), 4.59 (s, 1 H), 3.66-3.42 (m, 10 H), 3.27-3.17 (m, 2 H), 3.05-2.97 (m, 2 H), 2.76-2.64 (m, 1 H), 2.16-2.05 (m, 1 H), 1.99-1.92 (m, 2 H) |

TABLE 4-continued

Compounds prepared according to Method A.

| I-# | Intermediates | LC/MS (ESI, m/z) | $^1$H NMR (400 MHz) |
|---|---|---|---|
| I-61 | I-30 + C | [M + 1]$^+$ = 360.28 | (DMSO-d$_6$) δ 11.18 (s, 1 H), 8.81 (dd, J = 7.8, 1.6 Hz, 1 H), 8.50 (dd, J = 4.8, 1.7 Hz, 1 H), 7.73-7.68 (m, 1 H), 7.54 (t, J = 7.9 Hz, 1 H), 7.45-7.28 (m, 2 H), 6.80-6.76 (m, 1 H), 6.08 (s, 1 H), 4.65 (s, 2 H), 3.81-3.70 (m, 2 H), 3.62 (dd, J = 5.7, 3.6 Hz, 2 H), 3.43 (t, J = 6.1 Hz, 2 H), 3.17-2.96 (m, 3 H), 2.76-2.64 (m, 1 H), 2.50-2.45 (m, 1 H), 2.17-2.13 (m, 1 H), 1.35 (s, 9 H) |
| I-60 | I-61 | [M + 1]$^+$ = 525.1 | (DMSO-d$_6$) δ 11.15 (s, 1 H), 8.54 (dd, J = 7.9, 1.5 Hz, 1 H), 8.42 (dd, J = 4.9, 1.5 Hz, 1 H), 7.52-7.40 (m, 2 H), 7.28 (dd, J = 7.8, 4.9 Hz, 1 H), 7.11 (d, J = 7.4 Hz, 1 H), 6.77-6.74 (m, 1 H), 6.10-6.00 (m, 1 H), 3.61-3.50 (m, 6 H), 3.43 (t, J = 6.1 Hz, 2 H), 3.23-3.20 (m, 2 H), 3.12-2.96 (m, 4 H), 2.72-2.65 (m, 1 H), 2.12-2.06 (m, 1 H), 1.99-1.89 (m, 2 H), 1.34 (s, 9 H) |
| I-75 | H | [M + 1]$^+$ = 314.1 | DMSO-d$_6$ δ 11.21 (s, 1 H), 8.63 (d, J = 8.0 Hz, 1 H), 8.26 (d, J = 8.0, 1 H), 7.64-7.62 (m, 1 H), 7.58-7.49 (m, 1 H), 7.40-7.29 (m, 2 H), 6.06-6.00 (m, 1 H), 3.12-2.96 (m, 2 H), 2.74-2.66 (m, 1 H), 2.22-2.11 (m, 1 H) |
| I-74 | I-75 + C | [M + 1]$^+$ = 520.8 | (DMSO-d$_6$) δ 11.17 (s, 1 H), 8.58 (d, J = 7.6 Hz, 1 H), 8.25 (d, J = 8.0 Hz, 1 H), 7.68-7.38 (m, 3 H), 7.32 (t, J = 7.6 Hz, 1 H), 6.79 (s, 1 H), 6.05 (s, 1 H), 4.47 (s, 2 H), 3.67-3.65 (m, 2 H), 3.58-3.56 (m, 2 H), 3.40-3.34 (m, 2 H), 3.10-3.05 (m, 4 H), 2.78-2.64 (m, 1 H), 2.20-2.09 (m, 1 H), 1.37 (s, 9 H) |
| I-73 | I-74 | [M + 1]$^+$ = 525.2 | (DMSO-d$_6$) δ 11.14 (s, 1 H), 8.43 (d, J = 7.6 Hz, 1 H), 8.16 (d, J = 8.0 Hz, 1 H), 7.58-7.56 (m, 1 H), 7.48-7.44 (m, 1 H), 7.30-7.17 (m, 1 H), 7.14 (d, J = 8.0 Hz, 1 H), 6.76-6.73 (m, 1 H), 5.99 (s, 1 H), 3.54-3.41 (m, 6 H), 3.40-3.36 (m, 2 H), 3.08-3.01 (m, 4 H), 2.88 (t, J = 7.6 Hz, 2 H), 2.72-2.65 (m, 1 H), 2.19-2.09 (m, 1 H), 2.01-1.90 (m, 2 H), 1.36 (s, 9 H) |
| I-84 | I | [M + 1]$^+$ = 298.1 | (CDCl$_3$) δ 8.38 (t, J = 7.9 Hz, 1 H). 8.12 (br. s., 1 H), 8.05 (d, J = 7.8 Hz, 1 H), 7.51-7.43 (m, 1 H), 7.37-7.30 (m, 1 H), 7.26-7.24 (m, 1H), 6.84-6.82 (m, 1 H), 5.81-5.76 (m, 1 H), 3.15-2.88 (m, 3 H), 2.34-2.28 (m, 1 H) |
| I-78 | J | [M + 1]$^+$ = 295.2 | DMSO-d$_6$ δ 11.10 (s, 1 H), 8.07 (d, J = 8.3 Hz, 1 H), 7.86 (d, J = 7.5 Hz, 1 H), 7.40-7.38 (m, 1 H), 7.25-7.11 (m, 2 H), 6.36 (d, J = 8.3 Hz, 1 H), 6.14 (s, 2 H), 5.82-5.78 (m, 1 H), 3.15-2.92 (m, 2 H), 2.72-2.67 (m, 1 H), 2.00-2.11 (m, 1 H) |
| I-82 | K | [M + 1]+ = 309.3 | (DMSO-d$_6$) δ 11.18 (s, 1 H), 8.43 (d, J = 8.3 Hz, 1 H), 8.08 (dd, J = 8.0, 1.2 Hz, 1 H), 7.59 (d, J = 8.2 Hz, 1 H), 7.44-7.35 (m, 1 H), 7.27-7.21 (m, 1 H), 6.68 (d, J = 8.3 Hz, 1 H), 5.97-5.83 (m, 1 H), 3.90 (s, 3 H), 3.14-2.92 (m, 2 H), 2.79-2.65 (m, 1 H), 2.23-2.11 (m, 1 H) |
| I-83 | I-82 | [M + 1]$^+$ = 295.3 | (DMSO-d$_6$) δ 11.14 (s, 1 H), 10.81 (s, 1 H), 8.34 (d, J = 8.3 Hz, 1 H), 8.01 (d, J = 7.7 Hz, 1 H), 7.51 (d, J = 8.3 Hz, 1 H), 7.39-7.29 (m, 1 H), 7.21 (t, J = 7.4 Hz, 1 H), 6.52 (d, J = 8.3 Hz, 1 H), 5.85 (dd, J = 12.8, 5.2 Hz, 1 H), 3.16 (s, 1 H), 3.04-2.91 (m, 1 H), 2.77-2.64 (m, 1 H), 2.14-2.04 (m, 1 H) |
| I-85 | L | [M + 1]$^+$ = 348.2 | (DMSO-d$_6$) δ 11.24 (s, 1 H), 8.86 (d, J = 8.0, 1 H), 8.38 (d, J = 8.0, 1 H), 7.78 (d, J = 8.0 Hz, 1 H), 7.73-7.71 (m, 1 H), 7.65-7.61 (m, 1 H), 7.39 (t, J = 8.0 Hz, 1 H), 6.25-5.97 (m, 1 H), 3.21-2.93 (m, 2 H), 2.83-2.69 (m, 1 H), 2.28-2.15 (m, 1 H) |
| I-58 | M + C | [M + 1]$^+$ = 525.3 | (DMSO-d$_6$) δ 11.13 (s, 1 H), 8.49 (dd, J = 7.63, 1.50 Hz, 1 H), 8.38 (dd, J = 4.75, 1.38 Hz, 1 H), 8.11 (d, J = 7.88 Hz, 1 H), 7.47 (br. s., 1 H), 7.24 (dd, J = 7.63, 4.88 Hz, 1 H), 7.18-7.12 (m, 1 H), 6.77-6.74 (m, 1 H), 6.01 (br. s., 1 H), 3.55-3.47 (m, 4 H), 3.45-3.37 (m, 4 H), 3.11-3.01 (m, 4 H), 2.82-2.78 (m, 2 H), 2.73-2.68 (m, 1 H), 2.15-2.05 (m, 1 H), 1.96-1.83 (m, 2 H), 1.36 (s, 9 H) |
| I-53 | M + ((2-(2-(prop-2-yn-1-yloxy)ethoxy)ethoxy)methyl)benzene | [M + 1]$^+$ = 426.2 | (CDCl$_3$) δ 8.77 (br. s., 1 H), 8.32 (dd, J = 4.9, 1.4 Hz, 1 H), 8.21 (dd, J = 7.6, 1.4 Hz, 1 H), 7.92 (d, J = 8.0 Hz, 1 H), 7.12-7.02 (m, 3 H), 5.90-5.85 (m, 1 H), 3.48-3.73 (m, 8 H), 3.33-3.44 (m, 2 H), 2.73-3.03 (m, 5 H), 2.15-2.26 (m, 1 H), 1.81-1.99 (m, 2 H) |

TABLE 4-continued

Compounds prepared according to Method A.

| I-# | Intermediates | LC/MS (ESI, m/z) | $^1$H NMR (400 MHz) |
|---|---|---|---|
| I-65 | N | [M + 1]$^+$ = 310.0 | DMSO-d$_6$) δ 11.14 (s, 1 H), 8.23 (d, J = 7.8 Hz, 1 H), 7.92 (d, J = 5.4 Hz, 1 H), 7.86-7.77 (m, 2 H), 7.64-7.56 (m, 1 H), 7.33-7.29 (m, 1 H), 5.94-5.89 (m, 1 H), 3.93 (s, 3 H), 3.10-2.97 (m, 1 H), 2.75-2.59 (m, 2 H), 2.25-2.13 (m, 1 H) |
| I-42 | O | [M + 1]$^+$ = 280.1 | (DMSO-d$_6$) δ 12.98 (s, 1 H), 11.53 (s, 1 H), 9.47 (s, 1 H), 8.92 (d, J = 6.8 Hz, 1 H), 8.75 (dd, J = 6.8, 1.2 Hz, 1 H), 8.55 (d, J = 7.9 Hz, 1 H), 7.95-7.78 (m, 2 H), 7.52-7.48 (m, 1 H), 6.24-6.03 (m, 1 H), 3.06-2.94 (m, 1 H), 2.92-2.82 (m, 2 H), 2.61-2.52 (m, 1 H) |
| I-43 | P | [M + 1]$^+$ = 280.1 | (DMSO-d$_6$) δ 11.53 (s, 1 H), 9.92 (s, 1 H), 8.73 (d, J = 7.1 Hz, 1 H), 8.36 (d, J = 7.8 Hz, 1 H), 8.11 (d, J = 7.1 Hz, 1 H), 7.85-7.73 (m, 2 H), 7.55 (t, J = 7.5 Hz, 1 H), 6.00-5.95 (m, 1 H), 2.98-2.79 (m, 3 H), 2.03-1.95 (m, 1 H) |
| I-70 | Q | [M + 1]$^+$ = 284.4 | (DMSO-d$_6$) δ 11.04 (s, 1 H), 8.08 (dd, J = 4.8, 1.6 Hz, 1 H), 7.78 (dd, J = 7.6, 1.6 Hz, 1 H), 7.02 (dd, J = 7.6, 4.8 Hz, 1 H), 5.32 (t, J = 4.9 Hz, 1 H), 2.93 (d, J = 12.1 Hz, 2 H), 2.68-2.61 (m, 5 H), 2.10-1.94 (m, 1 H), 1.85 (d, J = 25.2 Hz, 4 H) |
| I-55 | R | [M + 1]$^+$ = 375.2 | (DMSO-d$_6$) δ 11.06 (s, 1 H), 8.09 (d, J = 3.6 Hz, 1 H), 7.79-7.73 (m, 1 H), 7.42-7.38 (m, 2 H), 7.38-7.33 (m, 2 H), 7.30-7.25 (m, 1 H), 7.01 (dd, J = 7.8, 4.8 Hz, 1 H), 5.52 (br. s., 1 H), 3.76 (s, 2 H), 3.65-3.55 (m, 2 H), 2.97-2.74 (m, 6 H), 2.66-2.60 (m, 1 H), 2.14-2.06 (m, 1 H) |
| I-67$^a$ | S | [M + 1]$^+$ = 281.2 | (DMSO-d$_6$) δ 11.24 (br. s., 1 H), 9.51 (s, 1 H), 8.97 (s, 1 H), 8.33 (d, J = 7.7 Hz, 1 H), 7.74-7.59 (m, 2 H), 7.42 (t, J = 7.5 Hz, 1 H), 6.08-6.05 (m, 1 H), 3.11-2.98 (m, 2 H), 2.80-2.66 (m, 1 H), 2.24-2.12 (m, 1 H) |
| I-72 | T | [M + 1]$^+$ = 285.0 | (DMSO-d$_6$) δ 11.22 (s, 1 H), 7.83 (d, J = 7.6 Hz, 1 H), 7.58 (d, J = 8.0 Hz, 1 H), 7.48 (d, J = 5.2 Hz, 1 H), 7.27-7.23 (m, 1 H), 7.18-7.13 (m, 2 H), 5.90 (dd, J = 4.8 Hz, J = 12.8 Hz, 1 H), 3.03-2.95 (m, 1 H), 2.78-2.65 (m, 2 H), 2.27-2.21 (m, 1 H) |
| I-88 | U | [M + 1]$^+$ = 363.0, 365.0 | DMSO-d$_6$) δ 11.23 (s, 1 H), 8.08 (s, J = 2.0 Hz, 1 H), 7.56 (d, J = 9.2 Hz, 1 H), 7.50 (d, J = 5.2 Hz, 1 H), 7.39 (dd, J = 2.0 Hz, J = 8.4 Hz, 1 H), 7.18 (d, J = 5.2 Hz, 1 H), 5.91 (dd, J = 4.8 Hz, J = 13.2 Hz, 1 H), 3.01-2.92 (m, 1 H), 2.77-2.64 (m, 2 H), 2.29-2.22 (m, 1 H) |
| I-66 | V | [M + 1]$^+$ = 286.0 | CDl$_3$) δ 8.73 (s, 1 H), 8.11 (s, 1 H), 7.79 (d, J = 7.9 Hz, 1 H), 7.41-7.32 (m, 2 H), 7.30-7.26 (m, 1 H), 5.55-5.50 (m, 1 H), 3.26-3.08 (m, 1 H), 3.06-2.83 (m, 2 H), 2.44-2.37 (m, 1 H) |
| I-87 | W | [M + 1]$^+$ = 285.8 | DMSO-d$_6$) δ 11.24 (s, 1 H), 8.81 (s, 1 H), 7.92 (d, J = 7.5 Hz, 1 H), 7.68 (d, J = 8.4 Hz, 1 H), 7.40-7.16 (m, 2 H), 6.01-5.96 (m, 1 H), 3.06-2.89 (m, 1 H), 2.82-2.58 (m, 2 H), 2.33-2.16 (m, 1 H) |
| I-41$^a$ | X | [M + 1]$^+$ = 348.0 | DMSO-d$_6$) δ 10.98-10.94 (m, 1 H), 7.70-7.63 (m, 1 H), 7.61-7.55 (m, 1 H), 7.56-7.38 (m, 5 H), 7.36-7.28 (m, 1 H), 7.26-7.23 (m, 1 H), 5.10-4.82 (m, 1 H), 4.56-4.47 (m, 1 H), 3.80-3.70 (m, 1 H), 2.90-2.54 (m, 2 H), 2.46-2.32 (m, 1 H), 2.10-1.73 (m, 1 H) |
| I-94$^b$ | Y | [M + 1]$^+$ = 269.0 | DMSO-d$_6$) δ 11.46 (s, 1 H), 8.30 (d, J = 2.4 Hz, 1 H), 8.14-8.08 (m, 1 H), 7.78 (d, J = 8.0 Hz, 1 H), 7.73 (d, J = 2.4 Hz, 1 H), 7.59-7.48 (m, 2 H), 5.64 (dd, J = 13.2, 5.2 Hz, 1 H), 2.96-2.87 (m, 1 H), 2.81-2.67 (m, 2 H), 2.41-2.39 (m, 1 H) |
| I-99$^b$ | Y | [M + 1]$^+$ = 269.0 | DMSO-d$_6$) δ 11.17 (s, 1 H), 8.20 (s, 1 H), 7.81 (d, J = 7.4 Hz, 1 H), 7.73 (d, J = 1.5 Hz, 1 H), 7.53 (d, J = 8.1 Hz, 1 H), 7.36-7.27 (m, 1 H), 7.28-7.18 (m, 1 H), 7.01 (d, J = 1.5 Hz, 1 H), 5.70-5.66 (m, 1 H), 3.10-3.07 (m, 1 H), 2.94-2.92 (m, 1 H), 2.81-2.75 (m, 1 H), 2.41-2.34 (m, 1 H) |

$^a$5 equiv. of CAN in CH$_3$CN/H$_2$O at 0° C. was used for removal of the PMB group.
$^b$Mixtures of I-94 and I-99 were obtained during removal of the PMB group and characterized by NOE after separation.

Example 8. Syntheses of 3-(6-(methylamino)-9H-pyrido[2,3-b]indol-9-yl)piperidine-2,6-dione (I-27)

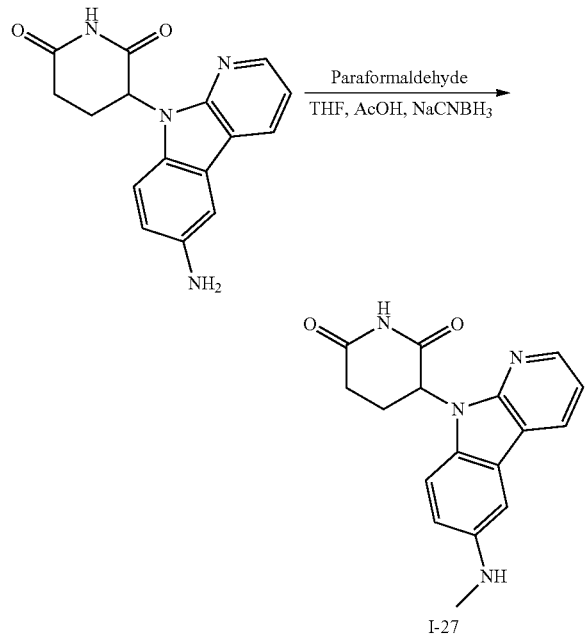

To a mixture of 3-(6-amino-9H-pyrido[2,3-b]indol-9-yl)piperidine-2,6-dione (100 mg, 0.34 mmol, I-5) and paraformaldehyde (51 mg, 1.7 mmol) in THF (5 mL) was added AcOH (2 drops). The mixture was stirred at room temperature for 1 h. Then NaCNBH$_3$ (42.7 mg, 0.68 mmol) was added in one portion. The reaction mixture was stirred at room temperature overnight. The reaction mixture was poured into water, extract with EtOAc (3×20 mL). The combined organic layers were concentrated under reduced pressure. The residue was purified via reverse phase column chromatography (CH$_3$CN/H$_2$O=5%-80%) to give I-27 (4.2 mg, 4.0%) as a white solid. $^1$H NMR (400 MHz, DMSO-d$_6$) δ 11.09 (s, 1H), 8.45-8.43 (m, 1H), 8.33 (dd, J=4.9, 1.5 Hz, 1H), 7.35-7.32 (m, 1H), 7.29-7.26 (m, 1H), 7.17-7.13 (m, 1H), 6.86 (dd, J=8.7, 2.2 Hz, 1H), 5.91 (br. s., 1H), 5.43 (br. s., 1H), 3.07-2.96 (m, 2H), 2.78 (s, 3H), 2.71-2.64 (m, 1H), 2.11-2.03 (m, 1H); LC/MS (ESI, m/z): [M+1]$^+$=309.34.

Example 9. Synthesis of 3-(6-(Dimethylamino)-9H-pyrido[2,3-b]indol-9-yl)piperidine-2,6-dione (I-28)

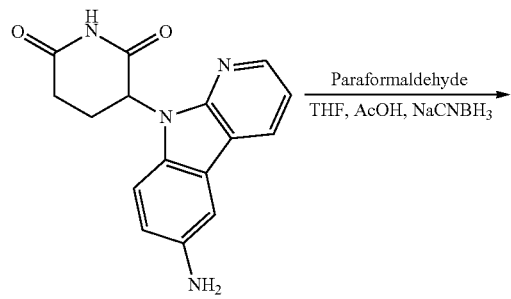

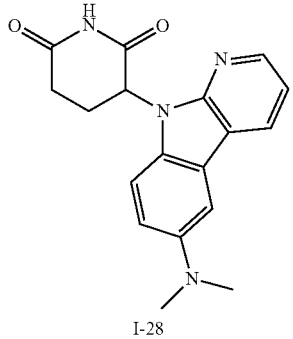

To a mixture of I-5 (50 mg, 0.17 mmol) and paraformaldehyde (25.5 mg, 0.85 mmol) in THF (5 mL) was added AcOH (2 drops). The mixture was stirred at room temperature for 1 h. Then NaCNBH$_3$ (21.3 mg, 0.34 mmol) was added in one portion. The reaction mixture was warmed to 40° C. and stirred overnight. The reaction mixture was poured into water and extract with EtOAc (3×20 mL). The combined organic layers were concentrated under reduced pressure. The residue was purified via reverse phase column chromatography (CH$_3$CN/H$_2$O=5%-80%) to give I-28 (5.6 mg, 10.2%) as a white solid. $^1$H NMR (400 MHz, CDCl$_3$) δ 8.32 (dd, J=4.9, 1.5 Hz, 1H), 8.22 (dd, J=7.7, 1.5 Hz, 1H), 8.17 (br. s., 1H), 7.40-7.38 (m, 1H), 7.10-7.01 (m, 3H), 5.83-5.78 (m, 1H), 3.00-2.78 (m, 9H), 2.26-2.13 (m, 1H); LC/MS (ESI, m/z): [M+1]$^+$=323.0.

Example 10. Synthesis of ethyl (9-(2,6-dioxopiperidin-3-yl)-9H-pyrido[2,3-b]indol-6-yl)carbamate (I-29)

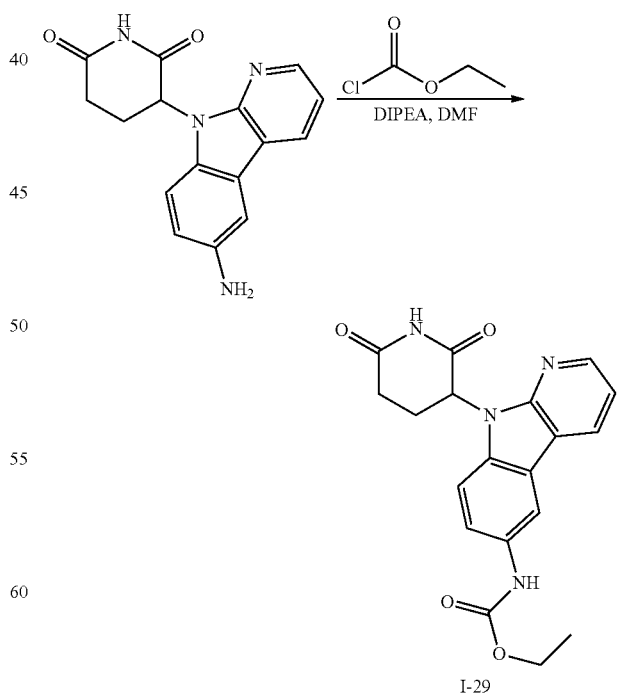

To a stirred solution of I-5 (51 mg, 0.175 mmol) in MeCN (4 mL) was added ethyl carbonochloridate (56 mg, 0.52 mmol) and DIPEA (111 mg, 0.865 mmol). The reaction mixture was stirred at r.t for 2 hours. The reaction mixture was concentrated under reduced pressure and purified via reverse phase column chromatography (CH$_3$CN/H$_2$O=5%-80%) to give I-29 (7.2 mg, 19.3%) as a white solid. $^1$H NMR (400 MHz, DMSO-d$_6$) δ 11.13 (s, 1H), 9.62 (br. s., 1H), 8.49 (dd, J=7.7, 1.6 Hz, 1H), 8.41 (dd, J=4.9, 1.5 Hz, 1H), 8.32 (br. s., 1H), 7.58-7.42 (m, 2H), 7.33-7.10 (m, 1H), 6.01 (br. s., 1H), 4.16 (q, J=7.1 Hz, 2H), 3.07-2.94 (m, 2H), 2.74-2.64 (m, 1H), 2.16-2.02 (m, 1H), 1.27 (t, J=7.1 Hz, 3H); LC/MS (ESI, m/z): [M+1]$^+$=367.32.

Example 11. Method B. Synthesis of tert-butyl (2-(2-(2-((9-(2,6-dioxopiperidin-3-yl)-9H-pyrido[2,3-b]indol-6-yl)amino)ethoxy)ethoxy)ethyl)carbamate (I-35)

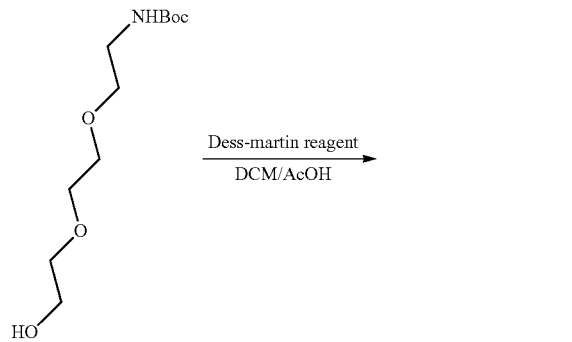

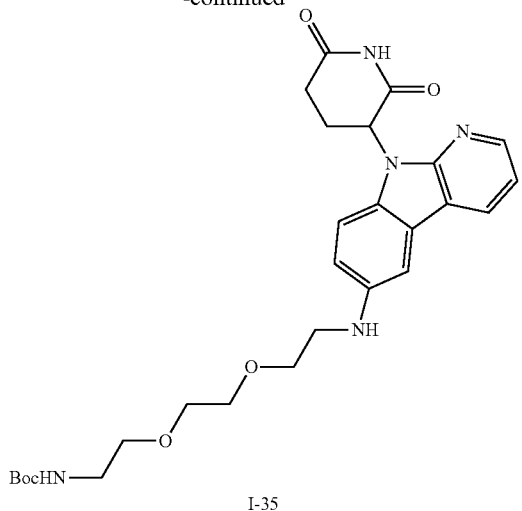

Step 1: tert-butyl (2-(2-(2-oxoethoxy)ethoxy)ethyl)carbamate

To a mixture of tert-butyl (2-(2-(2-hydroxyethoxy)ethoxy)ethyl)carbamate (2 g, 8.03 mmol) and dess-martin periodinane in dichloromethane (20 mL) was added AcOH (1 mL). The mixture was stirred at room temperature overnight. The reaction mixture was concentrated under reduced pressure and purified by flash chromatography to give tert-butyl (2-(2-(2-oxoethoxy)ethoxy)ethyl)carbamate (300 mg, 15.2%) as a colorless oil. LC/MS (ESI, m/z): [M+1]$^+$=248.1.

Step 2: tert-butyl (2-(2-(2-((9-(2,6-dioxopiperidin-3-yl)-9H-pyrido[2,3-b]indol-6-yl)amino)ethoxy)ethoxy)ethyl)carbamate (I-35)

To a mixture of I-5 (200 mg, 0.68 mmol) and (2-(2-(2-oxoethoxy)ethoxy)ethyl)carbamate (176 mg, 0.714 mmol) in THF (5 mL) was added AcOH (5 drops). The mixture was stirred at room temperature for 2 h. Then NaCNBH$_3$ (21.3 mg, 0.34 mmol) was added in portions. The reaction mixture was warmed to 40° C. and stirred for 2 h. The reaction mixture was poured into water and extract with EtOAc (3×20 mL). The combined organic layers were concentrated under reduced pressure. The residue was purified via reverse phase column chromatography (CH$_3$CN/H$_2$O=5%-80%) to give I-35 (70 mg, 19.6%) as a yellow solid. $^1$H NMR (400 MHz, DMSO-d$_6$) δ 11.09 (br. s., 1H), 8.42 (dd, J=7.6, 1.5 Hz, 1H), 8.33 (dd, J=4.8, 1.5 Hz, 1H), 7.36-7.32 (m, 2H), 7.17-7.13 (m, 1H), 6.92 (dd, J=8.8, 2.2 Hz, 1H), 6.79-6.76 (m, 1H), 5.91 (br. s., 1H), 5.30 (br. s., 1H), 3.66-3.62 (m, 2H), 3.60-3.50 (m, 4H), 3.41-3.29 (m, 4H), 3.12-2.95 (m, 4H), 2.71-2.65 (m, 1H), 2.12-2.01 (m, 1H), 1.37 (s, 9H); LC/MS (ESI, m z): [M+1]$^+$=526.55

Characterization data for further compounds prepared by Method B are presented in Table 5 below. Compounds in Table 5 were prepared by methods substantially similar to those described to prepare I-35.

TABLE 5

Compounds prepared according to Method B.

| I-# | Intermediates | LC/MS (ESI, m/z) | ¹H NMR (400 MHz) |
|---|---|---|---|
| I-50 | I-5 + D | [M + 1]⁺ = 517.3 | (DMSO-d₆) δ 11.09 (br. s., 1 H), 8.40 (dd, J = 1.6, 1.4 Hz, 1 H), 8.32 (dd, J = 4.8, 1.3 Hz, 1 H), 7.43-7.21(m, 7 H), 7.16-7.13 (m, 1 H), 6.92-6.89(m, 1 H), 5.91 (br. s., 1 H), 5.39-5.15 (m, 1 H), 4.48 (s, 2 H), 3.66-3.63 (m, 2 H), 3.59-3.56 (m, 8 H), 3.31-3.26 (m, 2 H), 3.07-2.93 (m, 2 H), 2.72-2.64 (m, 1 H), 2.10-2.02 (m, 1 H) |

Example 12. Synthesis of tert-butyl (2-(2-(2-(((9-(2,6-dioxopiperidin-3-yl)-9H-pyrido[2,3-b]indol-6-yl)methyl)amino)-2-oxoethoxy)ethoxy)ethyl)carbamate (I-36)

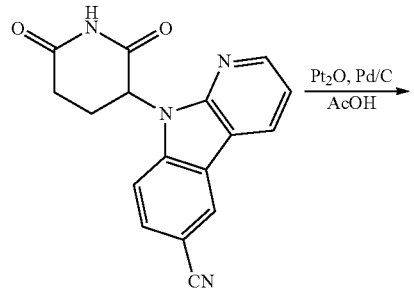

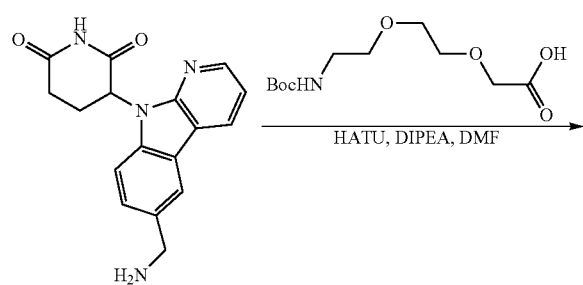

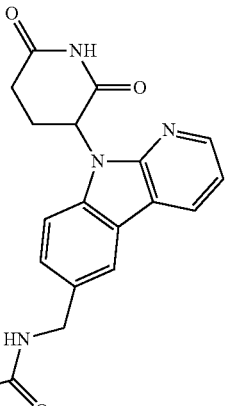

I-36

Step 1: 3-(6-(aminomethyl)-9H-pyrido[2,3-b]indol-9-yl)piperidine-2,6-dione

A solution of I-32 (1.2 g, 3.95 mmol) in AcOH (10 mL) was added Palladium 10% on Carbon (0.24 g) and platinum (IV) oxide (0.12 g). The reactor system was sealed and purged three times with nitrogen followed by hydrogen. The system was pressurized with hydrogen (80 psi) and heated at 60° C. for 2 h. The mixture was cooled to r.t and filtered. The filtrate was diluted with water and freeze-dried to give 3-(6-(aminomethyl)-9H-pyrido[2,3-b]indol-9-yl)piperidine-2,6-dione (0.4 g, 33.1% yield) as a white solid. LC/MS (ESI, m/z): [M+1]⁺=309.3

Step 2: tert-butyl (2-(2-(2-(((9-(2,6-dioxopiperidin-3-yl)-9H-pyrido[2,3-b]indol-6-yl)methyl)amino)-2-oxoethoxy)ethoxy)ethyl)carbamate (I-36)

To a solution of 3-(6-(aminomethyl)-9H-pyrido[2,3-b]indol-9-yl)piperidine-2,6-dione (30 mg, 0.097 mmol) in DMF (2 mL) was added HATU (55.5 mg, 0.15 mmol), 2,2-dimethyl-4-oxo-3,8,11-trioxa-5-azatridecan-13-oic acid (38.4 mg, 0.15 mmol) and DIPEA (37.8 mg, 0.29 mmol) at r.t. under nitrogen. The reaction was stirred at r.t for 2 h. The reaction mixture was directly purified via reverse phase column chromatography (CH₃CN/H₂O=5%-80%) to give I-36 (3.0 mg, 5.6%) as a white solid. ¹H NMR (400 MHz, CDCl₃) δ 8.52-8.32 (m, 3H), 8.06 (s, 1H), 7.47-7.44 (m, 1H), 7.35 (br s, 1H), 7.25-7.22 (m, 2H), 5.97-5.93 (m, 1H), 4.81 (br s, 1H), 4.71-4.59 (m, 2H), 4.07 (s, 2H), 3.72-3.49 (m, 4H), 3.37-3.35 (m, 2H), 3.20-2.88 (m, 5H), 2.35-2.30 (m, 1H), 1.42 (s, 9H); LC/MS (ESI, m/z): [M−Boc+1]⁺=454.3.

Example 13. Synthesis of tert-butyl (2-(2-(3-((9-(2, 6-dioxopiperidin-3-yl)-9H-pyrido[2,3-b]indol-6-yl) methyl)ureido)ethoxy)ethyl)carbamate (I-37)

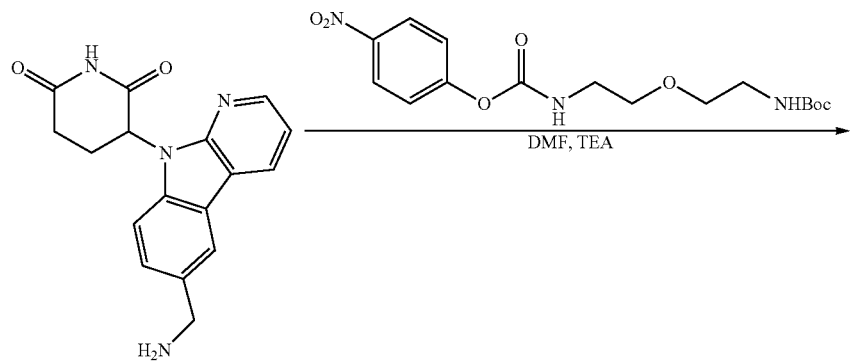

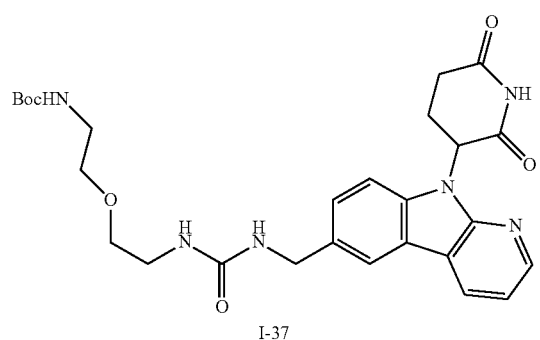

I-37

To a solution of 3-(6-(aminomethyl)-9H-pyrido[2,3-b]indol-9-yl)piperidine-2,6-dione (45 mg, 0.15 mmol) in DMF (2 mL) was added 4-nitrophenyl (2-(2-(((tert-butoxycarbonyl)amino)ethoxy)ethyl)carbamate (54.0 mg, 0.15 mmol) and triethylamine (22 mg, 0.22 mmol) at r.t. under nitrogen. The reaction was stirred at r.t for 2 h. The reaction mixture was directly purified via reverse phase column chromatography (CH$_3$CN/H$_2$O=5%-80%) to give I-37 (21 mg, 26.7%) as a colorless soil. $^1$H NMR (400 MHz, DMSO-d$_6$) δ 11.14 (s, 1H), 8.53 (dd, J=7.8, 1.5 Hz, 1H), 8.41 (dd, J=4.8, 1.5 Hz, 1H), 8.08 (s, 1H), 7.55 (br s, 1H), 7.43-7.41 (m, 1H), 7.28-7.24 (m, 1H), 6.78-6.75 (m, 2H), 6.49-6.45 (m, 1H), 6.02-5.96 (m, 1H), 4.36 (d, J=5.8 Hz, 2H), 4.13-4.00 (m, 4H), 3.62-3.58 (m, 2H), 3.21-3.00 (m, 4H), 2.76-2.64 (m, 2H), 1.36 (s, 9H); LC/MS (ESI, m/z): [M-Boc+1]=439.0.

Example 14. Synthesis of 2-(2-((tert-butoxycarbonyl)amino)ethoxy)ethyl ((9-(2,6-dioxopiperidin-3-yl)-9H-pyrido[2,3-b]indol-6-yl)methyl)carbamate (I-38)

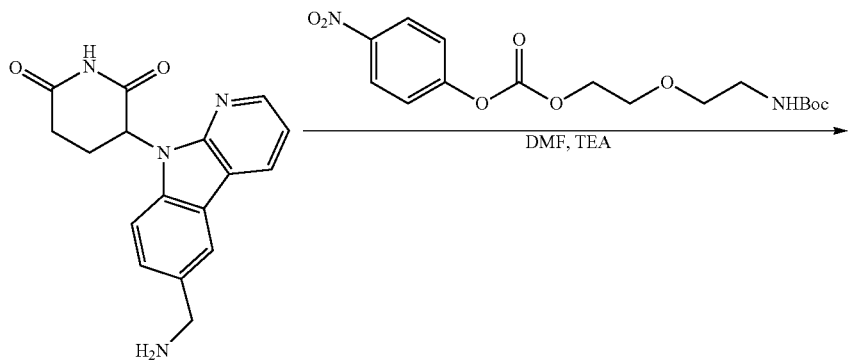

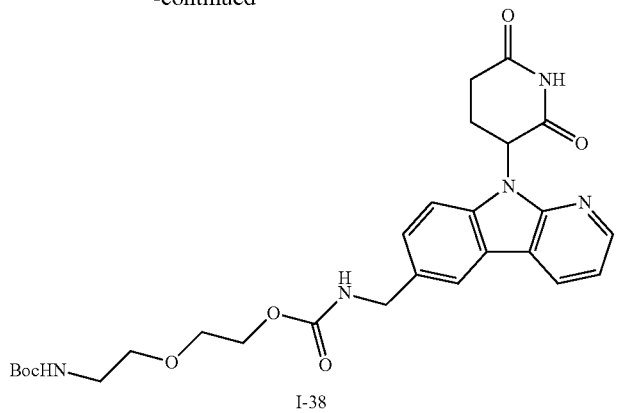

I-38

I-38 was synthesized via the same method as I-37.

¹H NMR (400 MHz, DMS O-d₆) δ 11.14 (s, 1H), 8.54 (dd, J=7.7, 1.5 Hz, 1H), 8.42 (dd, J=4.8, 1.5 Hz, 1H), 8.09 (s, 1H), 7.84-7.81 (m, 1H), 7.58-7.55 (m, 1H), 7.44-7.41 (m, 1H), 7.28-7.24 (m, 1H), 6.77 (br s, 1H), 6.01 (br s, 1H), 4.34 (d, J=6.0 Hz, 2H), 4.13-3.97 (m, 5H), 3.62-3.52 (m, 3H), 3.10-3.01 (m, 3H), 2.72-2.67 (m, 1H), 1.36 (s, 9H); LC/MS (ESI, m/z): [M−Boc+1]⁺=440.0.

Example 15. Synthesis of 9-(2,6-dioxopiperidin-3-yl)-9H-pyrido[2,3-b]indole-2-carbonitrile (I-81) and 3-(2-(aminomethyl)-9H-pyrido[2,3-b]indol-9-yl)piperidine-2,6-dione (I-91)

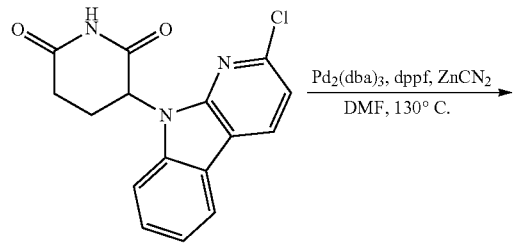

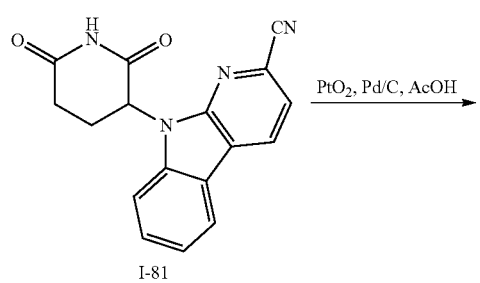

I-81

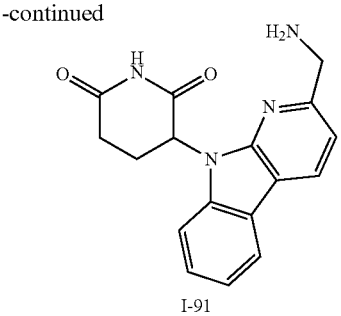

I-91

Step 1: 9-(2,6-dioxopiperidin-3-yl)-9H-pyrido[2,3-b]indole-2-carbonitrile (I-81)

A mixture of I-75 (120 mg, 0.4 mmol), dppf (44 mg, 0.08 mmol), Pd₂(dba)₃ (36 mg, 0.04 mmol) and ZnCN₂ (94 mg, 0.8 mmol) in DMF was degassed with nitrogen, heated to 130° C. and stirred for 16 hours in sealed tube. The reaction was cooled to r.t, diluted with water and extracted with EA. The combined organic layer was washed with brine, dried over anhydrous sodium sulfate, filtered and concentrated in vacuo. The residue was purified by via reverse phase column chromatography (CH₃CN/H₂O=5%-80%) to give I-81 (40 mg, 33% yield) as a white solid. ¹H NMR (400 MHz, DMSO-d₆) δ 11.23 (s, 1H), 8.83 (d, J=8.4 Hz, 1H), 8.38 (d, J=7.8 Hz, 1H), 7.91 (d, J=7.8 Hz, 1H), 7.76-7.56 (m, 2H), 7.44-7.29 (m, 1H), 6.11 (s, 1H), 3.13-2.99 (m, 2H), 2.80-2.68 (m, 1H), 2.22-2.16 (m, 1H). LC/MS (ESI, m/z): [M+1]⁺=304.9.

Step 2: 3-(2-(aminomethyl)-9H-pyrido[2,3-b]indol-9-yl)piperidine-2,6-dione (I-91)

A mixture of I-81 (30 mg, 0.1 mmol), PtO₂ (10 mg) and Palladium 10% on Carbon (30 mg) in AcOH (5 mL). The reactor system was sealed and purged three times with nitrogen followed by hydrogen. The system was pressurized with hydrogen (80 psi) and heated at r.t for 2 h. The mixture was filtered and concentrated in vacuo. The residue was purified by by via reverse phase column chromatography (CH₃CN/H₂O=5%-80%) to give I-91 (10 mg, 33% yield) as a white solid. ¹H NMR (400 MHz, DMSO-d₆) δ 8.55 (d, J=7.6 Hz, 1H), 8.31 (s, 1H), 8.20 (d, J=7.6 Hz, 1H), 7.61-7.58 (m, 1H), 7.49 (t, J=7.6 Hz, 1H), 7.39-7.19 (m, 2H), 6.11 (s, 1H), 4.09 (s, 2H), 3.50-3.20 (m, 3H), 3.05-2.96 (m, 1H), 2.77-2.61 (m, 1H), 2.14-2.02 (m, 1H). LC/MS (ESI, m/z): [M+1]⁺=308.6.

Example 16. Synthesis of 9-(2,6-dioxopiperidin-3-yl)-9H-pyrido[2,3-b]indole-4-carbonitrile (I-76)

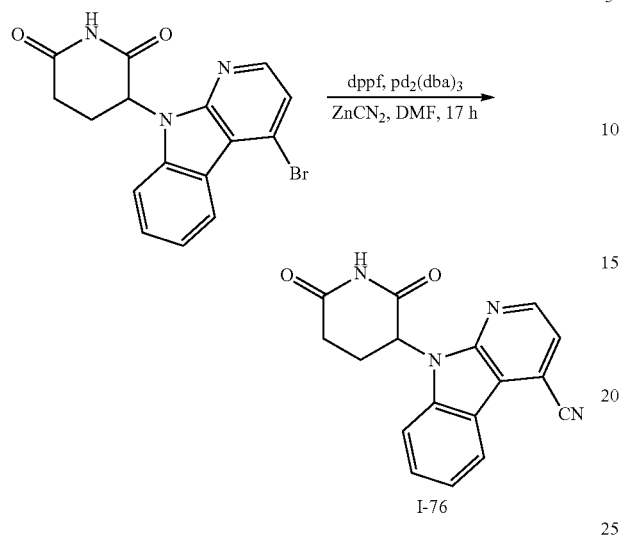

I-76 was synthesized via the same method as I-81. $^1$H NMR (400 MHz, DMSO-d$_6$) δ 11.23 (s, 1H), 8.66 (d, J=5.0 Hz, 1H), 8.39 (d, J=7.9 Hz, 1H), 7.88-7.61 (m, 3H), 7.50-7.45 (m, 1H), 6.16 (s, 1H), 3.18-2.93 (m, 2H), 2.80-2.63 (m, 1H), 2.26-2.11 (m, 1H); LC/MS (ESI, m/z): [M+1]$^+$=305.1.

Example 17. Synthesis of 3-(2-methyl-9H-pyrido[2,3-b]indol-9-yl)piperidine-2,6-dione (I-86)

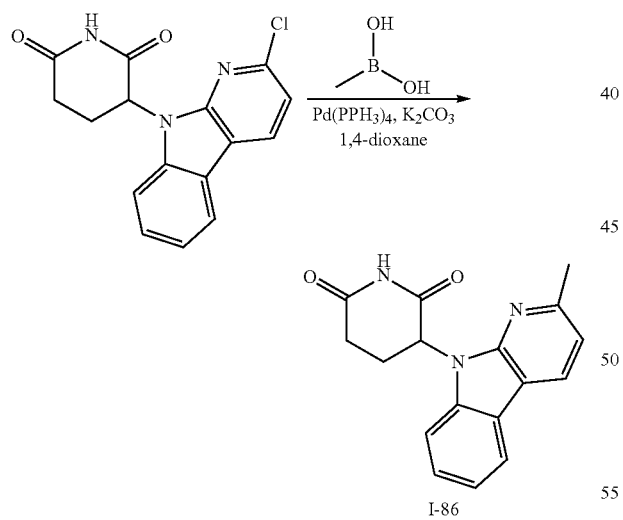

A mixture of I-75 (31 mg, 0.1 mmol), methylboronic acid (18 mg, 0.3 mmol), Pd (PPh$_3$)$_4$ (36 mg, 0.04 mmol) and K$_2$CO$_3$ (40 mg, 0.3 mmol) in 1,4-dioxane was degassed with nitrogen, heated to 100° C. and stirred for 16 hours in sealed tube. The reaction was cooled to r.t, diluted with water and extracted with EA. The combined organic layer was washed with brine, dried over anhydrous sodium sulfate, filtered and concentrated in vacuo. The residue was purified by via reverse phase column chromatography (CH$_3$CN/H$_2$O=5%-80%) to give I-86 (6 mg, 20% yield) as a white solid. $^1$H NMR (400 MHz, DMSO-d$_6$) δ 11.09 (s, 1H), 8.38 (d, J=7.6 Hz, 1H), 8.11 (d, J=7.6 Hz, 1H), 7.53-7.36 (m, 2H), 7.22-7.20 (m, 1H), 7.11-7.08 (m, 1H), 5.98 (s, 1H), 3.14-2.89 (m, 2H), 2.67-2.63 (m, 1H), 2.54 (s, 3H), 2.08-2.04 (m, 1H); LC/MS (ESI, m/z): [M+1]$^+$=294.6.

Example 18. Synthesis of 3-(4-methyl-9H-pyrido[2,3-b]indol-9-yl)piperidine-2,6-dione (I-86)

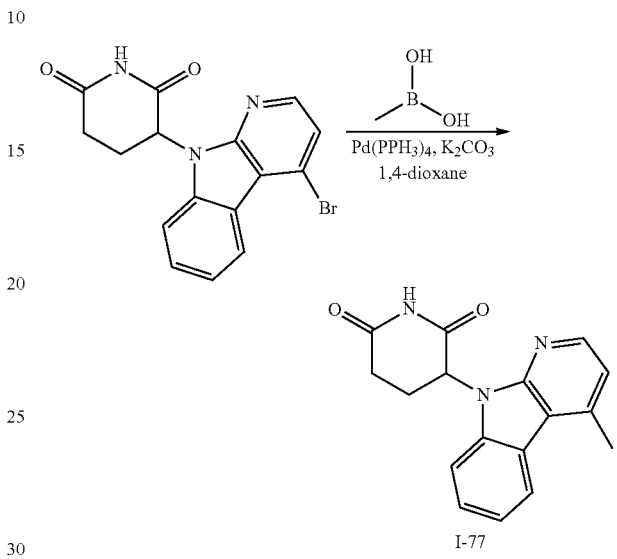

I-77 was synthesized via the same method as I-86. $^1$H NMR (400 MHz, DMSO-d$_6$) δ 11.14 (s, 1H), 8.29 (d, J=4.9 Hz, 1H), 8.19 (d, J=7.8 Hz, 1H), 7.65-7.60 (m, 1H), 7.52 (t, J=7.7 Hz, 1H), 7.31 (t, J=7.5 Hz, 1H), 7.10 (d, J=5.0 Hz, 1H), 6.05 (s, 1H), 3.15-2.96 (m, 2H), 2.84 (s, 3H), 2.72-2.67 (m, 1H), 2.14-2.07 (m, 1H); LC/MS (ESI, m/z): [M+1]$^+$=293.6

Example 19. Synthesis of 3-(6-bromo-2-fluoro-9H-pyrido[2,3-b]indol-9-yl)piperidine-2,6-dione (I-92)

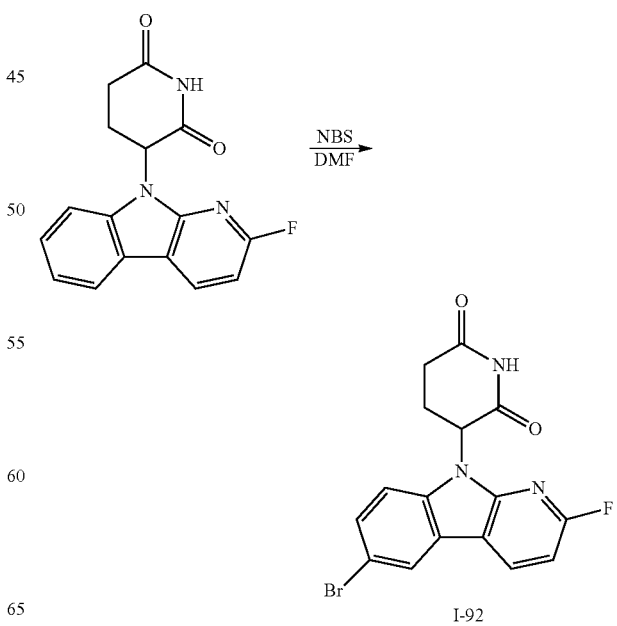

To a stirred solution of I-84 (10 mg, 0.036 mmol) in DMF (1 mL) was added NBS (6 mg, 0.036 mmol) at rt. The mixture was stirred at room temperature overnight. The mixture was purified by Prep-HPLC to give product I-92 (3 mg, 24% yield) as a white solid. $^1$H NMR (400 MHz, DMSO-$d_6$) δ 11.22 (s, 1H), 8.80 (t, J=8.4 Hz, 1H), 8.52 (s, 1H), 7.65 (s, 2H), 7.07 (d, J=8.0 Hz, 1H), 5.99 (d, J=6.4 Hz, 1H), 3.03-2.99 (m, 2H), 2.73-2.67 (m, 1H), 2.19-2.15 (m, 1H). LC/MS (ESI, m/z): [M+1]$^+$=376.0/378.0.

Example 20. Synthesis of 3-(2-(methylamino)-9H-pyrido[2,3-b]indol-9-yl)piperidine-2,6-dione (I-79) and 3-(2-(dimethylamino)-9H-pyrido[2,3-b]indol-9-yl)piperidine-2,6-dione (I-80)

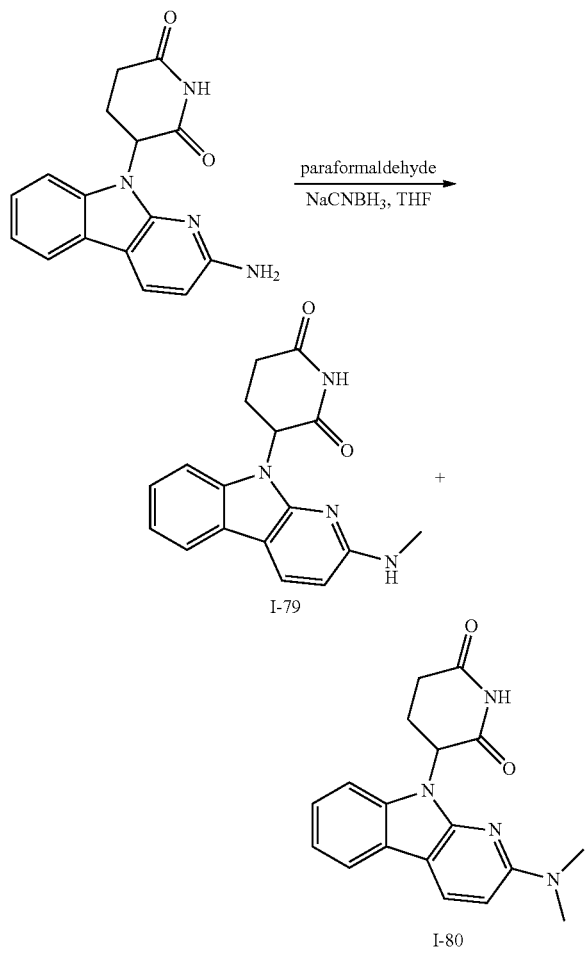

To a mixture of I-78 (50 mg, 0.17 mmol) and paraformaldehyde (10.2 mg, 0.34 mmol) in THF (5 mL) was added AcOH (2 drops). The mixture was stirred at room temperature for 2 h. Then NaCNBH$_3$ (21.4 mg, 0.34 mmol) was added. The reaction mixture was heated to 40° C. and stirred overnight. The reaction mixture was poured into water and extract with EtOAc. The combined organic layers was concentrated in vacuo. The residue was purified by Prep-HPLC to give I-79 (3.2 mg, 6.1%) and I-80 (7.1 mg, 13% yield) as white solids. $^1$H NMR (400 MHz, CDCl$_3$) δ 8.11 (br. s., 1H), 8.02 (d, J=8.4 Hz, 1H), 7.86 (d, J=7.6 Hz, 1H), 7.27-7.34 (m, 1H), 7.24-7.16 (m, 2H), 6.30 (d, J=8.4 Hz, 1H), 5.66-5.61 (m, 1H), 4.59 (br. s., 1H), 3.09-2.83 (m, 6H), 2.30-2.21 (m, 1H); LC/MS (ESI, m/z): [M+1]$^+$=309.1; and $^1$H NMR (400 MHz, CDCl$_3$) δ 8.14 (br. s., 1H), 8.05 (d, J=8.6 Hz, 1H), 7.86 (d, J=7.6 Hz, 1H), 7.27-7.34 (m, 1H), 7.15-7.24 (m, 2H), 6.43 (d, J=8.6 Hz, 1H), 5.57-5.52 (m, 1H), 3.17-2.92 (m, 8H), 2.91-2.77 (m, 1H), 2.31-2.21 (m, 1H); LC/MS (ESI, m/z): [M+1]$^+$=323.0.

Example 21. Synthesis of N-(9-(2,6-dioxopiperidin-3-yl)-9H-pyrido[2,3-b]indol-2-yl)acetamide (I-90)

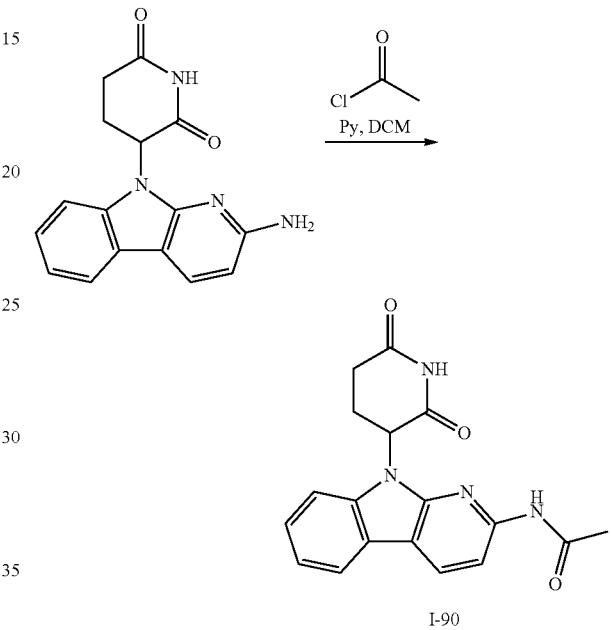

To a stirred solution of I-78 (30 mg, 0.102 mmol) in DCM (3 mL) was added acetyl chloride (3 drops) and pyridine (6 drops). The reaction mixture was stirred at r.t overnight. The reaction mixture was concentrated in vacuo and purified via reverse phase column chromatography (CH$_3$CN/H$_2$O=5%-80%) to give I-90 (12 mg, 35.0%) as a white solid. $^1$H NMR (400 MHz, DMSO-$d_6$) δ 11.14 (s, 1H), 10.39 (s, 1H), 8.48 (d, J=8.4 Hz, 1H), 8.10 (d, J=7.6 Hz, 1H), 8.01 (br. s., 1H), 7.60-7.58 (m, 1H), 7.44 (t, J=7.5 Hz, 1H), 7.26 (t, J=7.5 Hz, 1H), 5.91-5.86 (m, 1H), 3.06-2.90 (m, 1H), 2.80-2.63 (m, 1H), 2.14-2.20 (m, 5H); LC/MS (ESI, m/z): [M+1]$^+$=337.1.

Example 22. Synthesis of 3-(2-hydroxy-9H-pyrido[2,3-b]indol-9-yl)piperidine-2,6-dione (I-83)

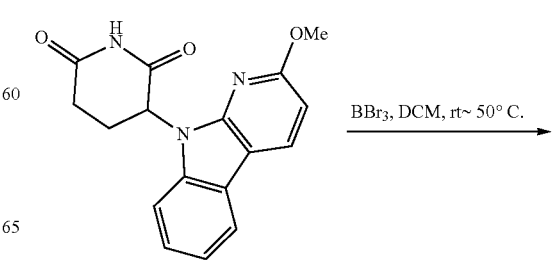

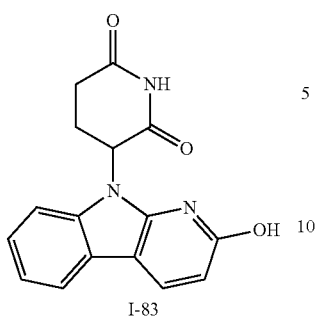

I-83

I-82 (36 mg, 0.1 mmol) was added to boron tribromide 17% in methylene chloride (10 mL). The reaction mixture was heated to 50° C. and stirred for 16 h under nitrogen atmosphere. The reaction was cooled to r.t and concentrated under reduced pressure. The residue was purified via reverse phase column chromatography (CH$_3$CN/H$_2$O=5%-80%) to give I-83 (5.1 mg, 15% yield) as a white solid. $^1$H NMR (400 MHz, DMSO-d$_6$) δ 11.14 (s, 1H), 10.81 (s, 1H), 8.34 (d, J=8.3 Hz, 1H), 8.01 (d, J=7.7 Hz, 1H), 7.51 (d, J=8.3 Hz, 1H), 7.39-7.29 (m, 1H), 7.21 (t, J=7.4 Hz, 1H), 6.52 (d, J=8.3 Hz, 1H), 5.85 (dd, J=12.8, 5.2 Hz, 1H), 3.16 (s, 1H), 3.04-2.91 (m, 1H), 2.77-2.64 (m, 1H), 2.14-2.04 (m, 1H). LC/MS (ESI, m/z): [M+1]$^+$=295.3.

Example 23. Synthesis of 3-(3-(3-(2-(2-aminoethoxy)ethoxy)propyl)-9H-pyrido[2,3-b]indol-9-yl)piperidine-2,6-dione (I-59)

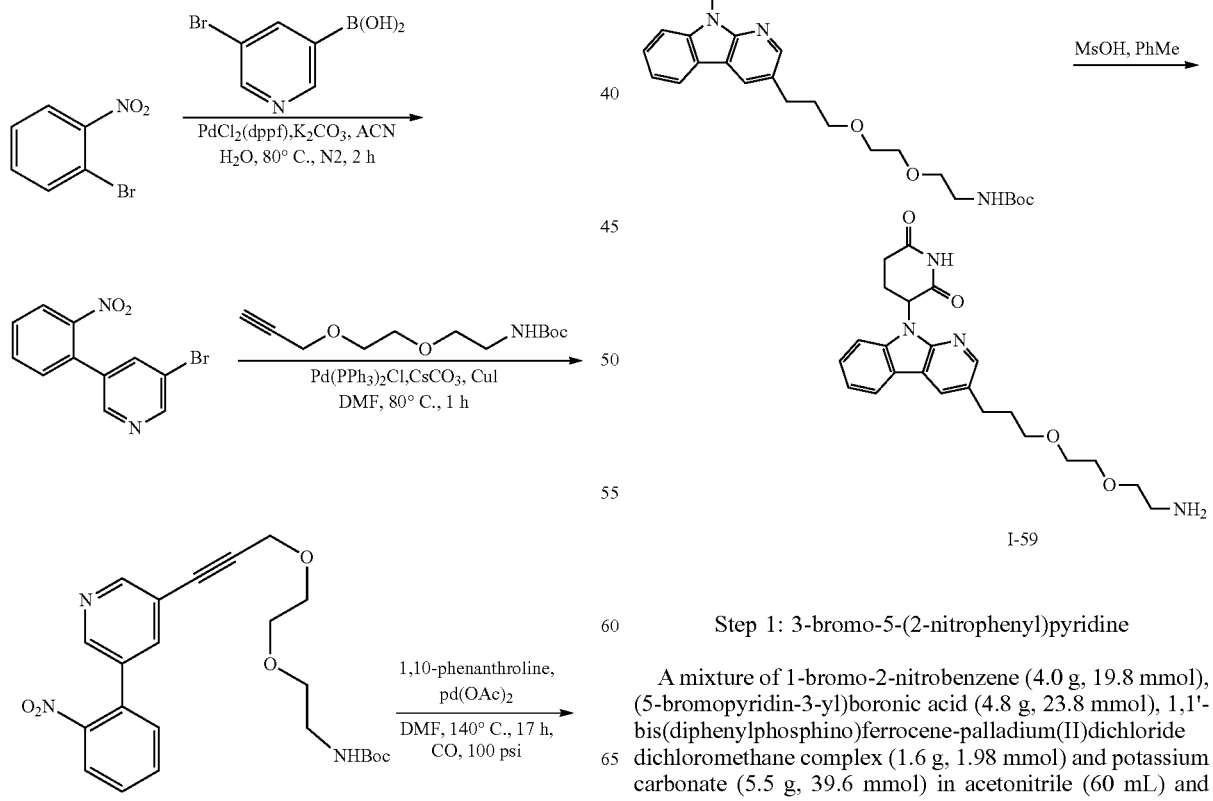

Step 1: 3-bromo-5-(2-nitrophenyl)pyridine

A mixture of 1-bromo-2-nitrobenzene (4.0 g, 19.8 mmol), (5-bromopyridin-3-yl)boronic acid (4.8 g, 23.8 mmol), 1,1'-bis(diphenylphosphino)ferrocene-palladium(II)dichloride dichloromethane complex (1.6 g, 1.98 mmol) and potassium carbonate (5.5 g, 39.6 mmol) in acetonitrile (60 mL) and water (15 mL) was degassed with nitrogen, heated to 80° C.

and stirred for 2 hours under nitrogen atmosphere. The reaction was cooled to r.t and filtered. The filtrate was concentrated in vacuo. The residue was diluted with water, extracted with EA. The combined organic layer was washed with brine, dried over anhydrous sodium sulfate, filtered and concentrated in vacuo. The residue was purified by column chromatography (Petroleum ether/EtOAc=2:1) to give 3-bromo-5-(2-nitrophenyl)pyridine (3.2 g, 58.2% yield) as a yellow solid. LC/MS (ESI, m/z): [M+1]$^+$=280.1.

Step 2: tert-butyl (2-(2-((3-(5-(2-nitrophenyl)pyridin-3-yl)prop-2-yn-1-yl)oxy)ethoxy)ethyl)carbamate A mixture of 3-bromo-5-(2-nitrophenyl)pyridine (1.4 g, 5.0 mmol), tert-butyl (2-(2-(prop-2-yn-1-yloxy)ethoxy)ethyl)carbamate (2.4 g, 10.0 mmol), CuI (77 mg, 0.4 mmol), caesium carbonate (4.9 g, 15.1 mmol) and palladium(II)bis(triphenylphosphine) dichloride (0.35 g, 0.5 mmol) in DMF (20 mL) was degassed with nitrogen, heated to 80° C. and stirred for 1 hour under microwave condition. The reaction was cooled to r.t and filtered. The filtrate was diluted with water, extracted with EA. The combined organic layer was washed with brine, dried over anhydrous sodium sulfate, filtered and concentrated in vacuo. The residue was purified by column chromatography (Petroleum ether/EtOAc=4:1) to give tert-butyl (2-(2-((3-(5-(2-nitrophenyl)pyridin-3-yl)prop-2-yn-1-yl)oxy)ethoxy)ethyl)carbamate (1.4 g, 63.3% yield) as a yellow oil. LC/MS (ESI, m/z): [M+1]$^+$=442.1.

Step 3: tert-butyl (2-(2-((3-(9H-pyrido[2,3-b]indol-3-yl)prop-2-yn-1-yl)oxy)ethoxy)ethyl)carbamate A solution of tert-butyl (2-(2-((3-(5-(2-nitrophenyl)pyridin-3-yl)prop-2-yn-1-yl)oxy)ethoxy)ethyl)carbamate (1.4 g, 3.17 mmol) in DMF (30 mL) was added Pd(OAc)$_2$ (3.6 mg, 0.016 mmol) and 1,10-phenanthroline (20.0 mg, 0.11 mmol). The reactor system was sealed and purged three times with nitrogen followed by carbon monoxide. The system was pressurized with carbon monoxide (100 psi) and heated at 140° C. for 17 h. The mixture was cooled to rt, diluted with water and extracted with EA. The combined organic layer was washed with brine, dried over anhydrous sodium sulfate, filtered and concentrated in vacuo. The residue was purified by column chromatography (Petroleum ether/EtOAc=2:1) to give tert-butyl (2-(2-((3-(9H-pyrido[2,3-b]indol-3-yl)prop-2-yn-1-yl)oxy)ethoxy)ethyl)carbamate (0.85 g, 65.4% yield) as a yellow oil. LC/MS (ESI, m/z): [M+1]$^+$=410.1.

Step 4: tert-butyl (2-(2-((3-(9-(1-(4-methoxybenzyl)-2,6-dioxopiperidin-3-yl)-9H-pyrido[2,3-b]indol-3-yl)prop-2-yn-1-yl)oxy)ethoxy)ethyl)carbamate To a stirred solution of tert-butyl (2-(2-((3-(9H-pyrido[2,3-b]indol-3-yl)prop-2-yn-1-yl)oxy)ethoxy)ethyl)carbamate (0.2 g, 0.49 mmol) and 18-crown-6 (26 mg, 0.098 mmol) in THF (4 mL) was added NaHMDS (0.37 mL, 2 M in THF, 0.73 mmol) dropwise at −30° C. under nitrogen atmosphere. The mixture was stirred for 1 h at −30° C. under nitrogen atmosphere. Then a solution of 1-(4-methoxybenzyl)-2,6-dioxopiperidin-3-yl trifluoromethanesulfonate (0.28 g, 0.73 mmol) in THF (2 mL) was added to the reaction dropwise at −30° C. under nitrogen atmosphere. After addition, the mixture was stirred for 2 h at −30° C. The reaction mixture was quenched by sat.aq. ammonium chloride and extracted with EA. The combined organic layer was washed with brine, dried over anhydrous sodium sulfate, filtered and concentrated in vacuo. The residue was purified by column chromatography (Petroleum ether/EtOAc=2:1) to give tert-butyl (2-(2-((3-(9-(1-(4-methoxybenzyl)-2,6-dioxopiperidin-3-yl)-9H-pyrido[2,3-b]indol-3-yl)prop-2-yn-1-yl)oxy)ethoxy)ethyl)carbamate (0.15 g, 48.4% yield) as a yellow solid. LC/MS (ESI, m/z): [M+1]$^+$=641.8.

Step 5: tert-butyl (2-(2-(3-(9-(1-(4-methoxybenzyl)-2,6-dioxopiperidin-3-yl)-9H-pyrido[2,3-b]indol-3-yl)propoxy)ethoxy)ethyl)carbamate A solution of tert-butyl (2-(2-((3-(9-(1-(4-methoxybenzyl)-2,6-dioxopiperidin-3-yl)-9H-pyrido[2,3-b]indol-3-yl)prop-2-yn-1-yl)oxy)ethoxy)ethyl)carbamate (150 mg, 0.23 mmol) in EA (10 mL) was added Palladium 10% on Carbon (30 mg) and acetic acid (2 drops). The reactor system was sealed and purged three times with nitrogen followed by hydrogen. The system was pressurized with hydrogen and stirred for 17 h. The mixture was filtered and concentrated in vacuo to give tert-butyl (2-(2-(3-(9-(1-(4-methoxybenzyl)-2,6-dioxopiperidin-3-yl)-9H-pyrido[2,3-b]indol-3-yl)propoxy)ethoxy)ethyl)carbamate (150 mg, quant.) as a yellow oil. LC/MS (ESI, m/z): [M+1]$^+$=645.8

Step 6: 3-(3-(3-(2-(2-aminoethoxy)ethoxy)propyl)-9H-pyrido[2,3-b]indol-9-yl)piperidine-2,6-dione (I-59)

To a stirred solution of tert-butyl (2-(2-(3-(9-(1-(4-methoxybenzyl)-2,6-dioxopiperidin-3-yl)-9H-pyrido[2,3-b]indol-3-yl)propoxy)ethoxy)ethyl)carbamate (0.14 g, 0.22 mmol) in toluene (2 mL) was added methanesulfonic acid (1 mL). The reaction mixture was heated to 110° C. and stirred for 2 h under nitrogen atmosphere. The reaction was cooled to r.t and concentrated under reduced pressure to remove toluene. The residue was purified via reverse phase column chromatography (CH$_3$CN/H$_2$O=5%-80%) to give 3-(3-(3-(2-(2-aminoethoxy)ethoxy)propyl)-9H-pyrido[2,3-b]indol-9-yl)piperidine-2,6-dione (3 mg, 3.3% yield) as a white solid. $^1$H NMR (400 MHz, DMSO-d$_6$) δ 8.43-8.39 (m, 2H), 8.29 (d, J=1.9 Hz, 1H), 8.20 (d, J=7.7 Hz, 1H), 7.60-7.58 (m, 1H), 7.49 (t, J=7.4 Hz, 1H), 7.27 (t, J=7.4 Hz, 1H), 6.01 (s, 1H), 3.59-3.51 (m, 8H), 3.47-3.43 (m, 4H), 2.90-2.78 (m, 4H), 2.75-2.65 (m, 1H), 2.16-2.06 (m, 1H), 1.96-1.85 (m, 2H). LC/MS (ESI, m/z): [M+1]$^+$=425.2

Example 24. Synthesis of 3-(3-(3-(2-(2-hydroxyethoxy)ethoxy)propyl)-9H-pyrido[2,3-b]indol-9-yl)piperidine-2,6-dione (I-54)

I-54 was synthesized via the same method as I-59 substituting Intermediate C with ((2-(2-(prop-2-yn-1-yloxy)ethoxy)ethoxy)methyl)benzene in Step 2. $^1$H NMR (400 MHz, CDCl$_3$) δ 8.34-8.24 (m, 2H), 8.11-8.05 (m, 2H), 7.55-7.44 (m, 1H), 7.35-7.28 (m, 2H), 5.37-5.32 (m, 1H), 3.81-3.58 (m, 9H), 3.52-3.48 (m, 2H), 3.05-2.90 (m, 5H), 2.27-2.18 (m, 1H), 2.04-1.99 (m, 2H); LC/MS (ESI, m/z): [M+1]$^+$=426.0

Example 25. Synthesis of 3-(9H-pyrrolo[2,3-b:5,4-c']dipyridin-9-yl)piperidine-2,6-dione (I-69)

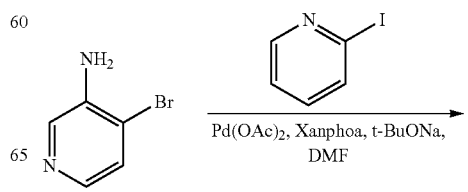

301

-continued

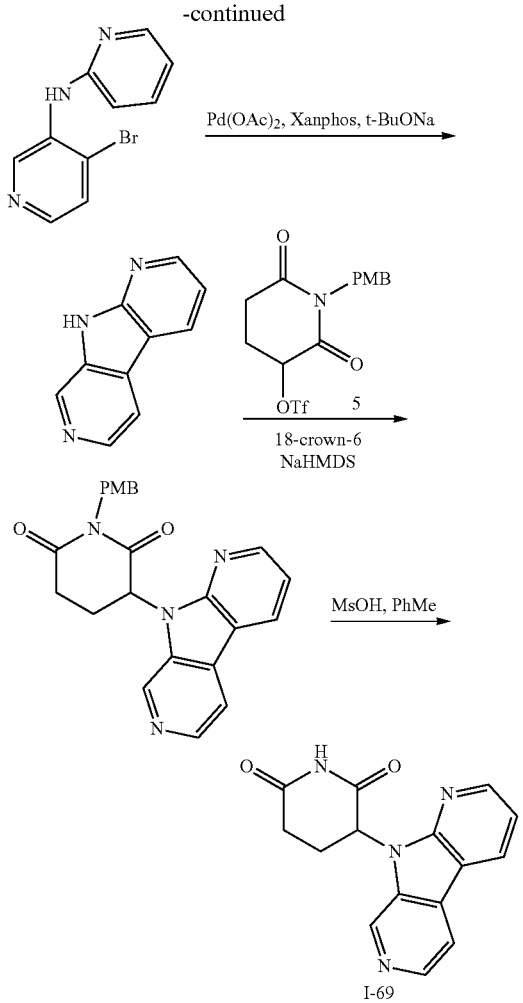

Step 1: N-(4-bromopyridin-3-yl)pyridin-2-amine

A mixture of 4-bromopyridin-3-amine (1 g, 5.78 mmol), 2-iodopyridine (1.4 g, 6.94 mmol), palladium acetate (0.13 g, 0.58 mmol), xantphos (0.34 g, 0.58 mmol) and sodium tert-butoxide (0.83 g, 8.67 mmol) in toluene (20 mL) was degassed with nitrogen, heated to 130° C. and stirred for 17 hours under nitrogen atmosphere. The reaction was cooled to r.t and filtered. The filtrate was concentrated in vacuum. The residue was purified by column chromatography (Petroleum ether/EtOAc=2:1) to give N-(4-bromopyridin-3-yl)pyridin-2-amine (1.0 g, 69.4% yield) as a yellow solid. LC/MS (ESI, m/z): [M+1]$^+$=251.1.

Step 2: 9H-pyrrolo[2,3-b:5,4-c']dipyridine

A mixture of N-(4-bromopyridin-3-yl)pyridin-2-amine (1.0 g, 4.0 mmol), palladium acetate (90 mg, 0.40 mmol), potassium carbonate (0.83 g, 6.0 mmol) and tricyclohexylphosphine tetrafluroborate (0.29 g, 0.80 mmol) in DMA (10 mL) was degassed with nitrogen, heated to 170° C. and stirred for 2 hours under microwave conditions. The reaction was cooled to r.t and filtered. The filtrate was purified via reverse phase column chromatography (CH$_3$CN/H$_2$O=5%-80%) to give 9H-pyrrolo[2,3-b:5,4-c']dipyridine (0.35 g, 52.2% yield) as a yellow solid. LC/MS (ESI, m/z): [M+1]$^+$=170.1.

302

Step 3: 1-(4-methoxybenzyl)-3-(9H-pyrrolo[2,3-b:5,4-c']dipyridin-9-yl)piperidine-2,6-dione To a stirred solution of 9H-pyrrolo[2,3-b:5,4-c']dipyridine (0.5 g, 2.96 mmol) and 18-crown-6 (0.16 g, 0.59 mmol) in THF (10 mL) was added NaHMDS (2.2 mL, 2 M in THF, 4.44 mmol) dropwise at −30° C. under nitrogen atmosphere. The mixture was stirred for 1 h at −30° C. under nitrogen atmosphere. Then a solution of 1-(4-methoxybenzyl)-2,6-dioxopiperidin-3-yl trifluoromethanesulfonate (1.7 g, 4.44 mmol) in THF (10 mL) was added to the reaction dropwise at −30° C. under nitrogen atmosphere. After addition, the mixture was stirred for 2 h at −30° C. and quenched by sat.aq. ammonium chloride. The residue was purified via reverse phase column chromatography (CH$_3$CN/H$_2$O=5%-80%) to give 1-(4-methoxybenzyl)-3-(9H-pyrrolo[2,3-b:5,4-c']dipyridin-9-yl)piperidine-2,6-dione (140 mg, 11.9% yield) as a white solid. LC/MS (ESI, m/z): [M+1]$^+$=401.8.

Step 4: 3-(9H-pyrrolo[2,3-b:5,4-c']dipyridin-9-yl)piperidine-2,6-dione (I-69)

To a stirred solution of 1-(4-methoxybenzyl)-3-(9H-pyrrolo[2,3-b:5,4-c']dipyridin-9-yl)piperidine-2,6-dione (0.14 g, 0.35 mmol) in toluene (2 mL) was added methanesulfonic acid (2 mL). The reaction mixture was heated to 110° C. and stirred for 2 h under nitrogen atmosphere. The reaction was cooled to r.t and concentrated under reduced pressure to remove toluene. The residue was purified via reverse phase column chromatography (CH$_3$CN/H$_2$O=5%-80%) to give 3-(9H-pyrrolo[2,3-b:5,4-c']dipyridin-9-yl)piperidine-2,6-dione (2.4 mg, 2.4% yield) as a white solid. $^1$H NMR (400 MHz, DMSO-d$_6$) δ 11.57 (s, 1H), 9.95 (s, 1H), 9.32 (d, J=7.0 Hz, 1H), 9.10 (d, J=6.8 Hz, 1H), 8.96 (d, J=6.9 Hz, 1H), 8.04-7.87 (m, 1H), 7.40-7.37 (m, 1H), 6.19-6.14 (m, 1H), 3.05-2.80 (m, 3H), 2.07-1.91 (m, 1H). LC/MS (ESI, m/z): [M+1]$^+$=280.9.

Example 26. Synthesis of 3-(3-amino-9H-pyrido[2,3-b]indol-9-yl)piperidine-2,6-dione (I-39)

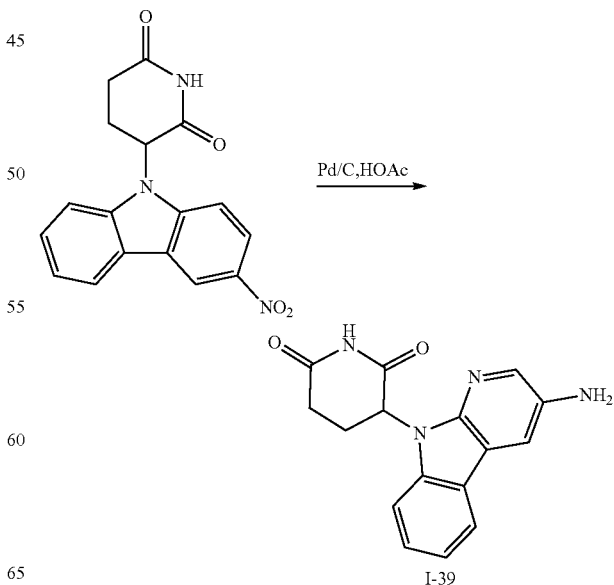

3-(3-Nitro-9H-pyrido[2,3-b]indol-9-yl)piperidine-2,6-dione was synthesized via the same method as I-69.

3-(3-Amino-9H-pyrido[2,3-b]indol-9-yl)piperidine-2,6-dione (I-39)

A solution of 3-(3-nitro-9H-pyrido[2,3-b]indol-9-yl)piperidine-2,6-dione (40 mg, 0.12 mmol) in EA (10 mL) was added palladium 10% on Carbon (12 mg) and acetic acid (1 drops). The reactor system was sealed and purged three times with nitrogen followed by hydrogen. The system was pressurized with hydrogen and stirred for 17 h. The mixture was filtered and concentrated in vacuo. The residue was purified via reverse phase column chromatography (CH$_3$CN/H$_2$O=5%-80%) to give 3-(3-amino-9H-pyrido[2,3-b]indol-9-yl)piperidine-2,6-dione (6 mg, 16.5% yield) as a white solid. $^1$H NMR (400 MHz, DMSO-d$_6$) δ 11.08 (s, 1H), 8.05-8.03 (m, 1H), 7.89 (d, J=2.5 Hz, 1H), 7.69 (d, J=2.5 Hz, 1H), 7.53-7.32 (m, 2H), 7.18-7.14 (m, 1H), 5.89-5.86 (m, 1H), 4.96 (s, 2H), 3.12-2.89 (m, 2H), 2.75-2.60 (m, 1H), 2.13-1.98 (m, 1H); LC/MS (ESI, m/z): [M+1]$^+$=295.4.

Example 27. Synthesis of tert-butyl 9-(2,6-dioxopiperidin-3-yl)-7,8-dihydro-5H-pyrrolo[2,3-b:4,5-c']dipyridine-6(9H)-carboxylate (I-40)

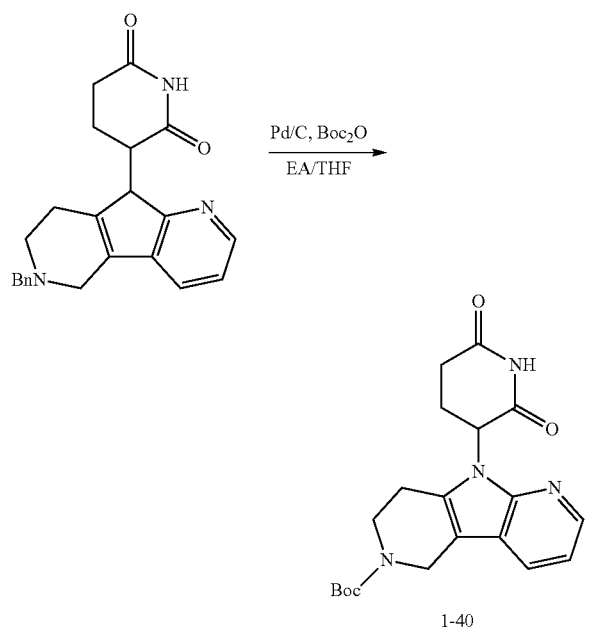

To a mixture of I-55 (42 mg, 0.112 mmol) and Boc$_2$O (36.6 mg, 0.168 mmol) in THF (1 mL) and EA (3 mL) was added palladium on activated carbon 10% Pd (12 mg). The mixture was stirred at room temperature under hydrogen atmosphere overnight. The reaction mixture was filtered. The filtrate was concentrated under reduce pressure. The residue was purified by flash chromatography to give tert-butyl 9-(2,6-dioxopiperidin-3-yl)-7,8-dihydro-5H-pyrrolo[2,3-b:4,5-c']dipyridine-6(9H)-carboxylate (25 mg, 58.4%) as a white solid. $^1$H NMR (400 MHz, DMSO-d$_6$) δ 11.08 (s, 1H), 8.14 (d, J=3.9 Hz, 1H), 7.90 (d, J=7.0 Hz, 1H), 7.07 (dd, J=7.8, 4.8 Hz, 1H), 5.54 (br. s., 1H), 4.41-4.58 (m, 2H), 3.76-3.71 (m, 2H), 2.99-2.84 (m, 2H), 2.81-2.73 (m, 2H), 2.70-2.58 (m, 1H), 2.15-2.06 (m, 1H), 1.44 (s, 9H); LC/MS (ESI, m/z): [M+1]$^+$=385.2.

Example 28. Synthesis of 3-(9H-pyrrolo[2,3-b:4,5-c']dipyridin-9-yl)piperidine-2,6-dione (I-56)

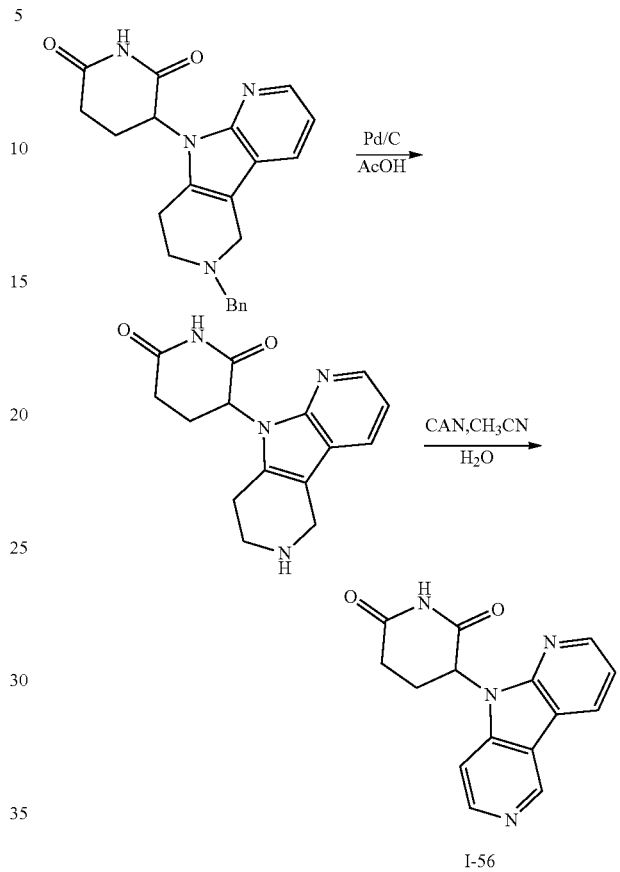

Step 1: 3-(7,8-dihydro-5H-pyrrolo[2,3-b:4,5-c']dipyridin-9(6H)-yl)piperidine-2,6-dione To a solution of 3-(6-benzyl-7,8-dihydro-5H-pyrrolo[2,3-b:4,5-c']dipyridin-9(6H)-yl)piperidine-2,6-dione (250 mg, 0.668 mmol) in AcOH (5 mL) was added palladium on activated carbon 10% Pd (71 mg). The mixture was stirred at room temperature overnight under hydrogen atmosphere. The reaction mixture was filtered. The filtrate was concentrated under reduce pressure. The residue was purified by prep HPLC to give 3-(7,8-dihydro-5H-pyrrolo[2,3-b:4,5-c']dipyridin-9(6H)-yl)piperidine-2,6-dione (120 mg, 63.3%) as a white solid. LC/MS (ESI, m/z): [M+1]$^+$=285.2.

Step 2: 3-(9H-pyrrolo[2,3-b:4,5-c']dipyridin-9-yl)piperidine-2,6-dione (I-56)

To a solution of 3-(7,8-dihydro-5H-pyrrolo[2,3-b:4,5-c']dipyridin-9(6H)-yl)piperidine-2,6-dione (100 mg, 0.352 mmol) in CH$_3$CN (5 mL) and H$_2$O (1 mL) was added CAN (964 mg, 1.76 mmol). The mixture was stirred at room temperature for 3h. The reaction mixture was poured into water, treated with sat. aq NaHCO$_3$ to pH 7 and extract with EtOAc (3×20 mL). The combined organic layers were concentrated under reduce pressure. The residue was purified by prep HPLC to give 3-(9H-pyrrolo[2,3-b:4,5-c']dipyridin-9-yl)piperidine-2,6-dione (5.5 mg, 5.6%) as a white solid. $^1$H NMR (400 MHz, DMSO-d$_6$) δ 11.36 (s, 1H), 9.88 (s, 1H), 9.00-8.84 (m, 2H), 8.75 (d, J=3.9 Hz, 1H), 8.30 (d, J=6.6 Hz, 1H), 7.67-7.63 (m, 1H), 6.31 (br. s., 1H), 3.09-2.94 (m, 2H), 2.81-2.76 (m, 1H), 2.34-2.23 (m, 1H); LC/MS (ESI, m/z): [M+1]$^+$=281.1.

Example 29. Synthesis of 3-(6-(9-hydroxynonanoyl)-5,6,7,8-tetrahydro-9H-pyrrolo[2,3-b:4,5-c']dipyridin-9-yl)piperidine-2,6-dione (I-68)

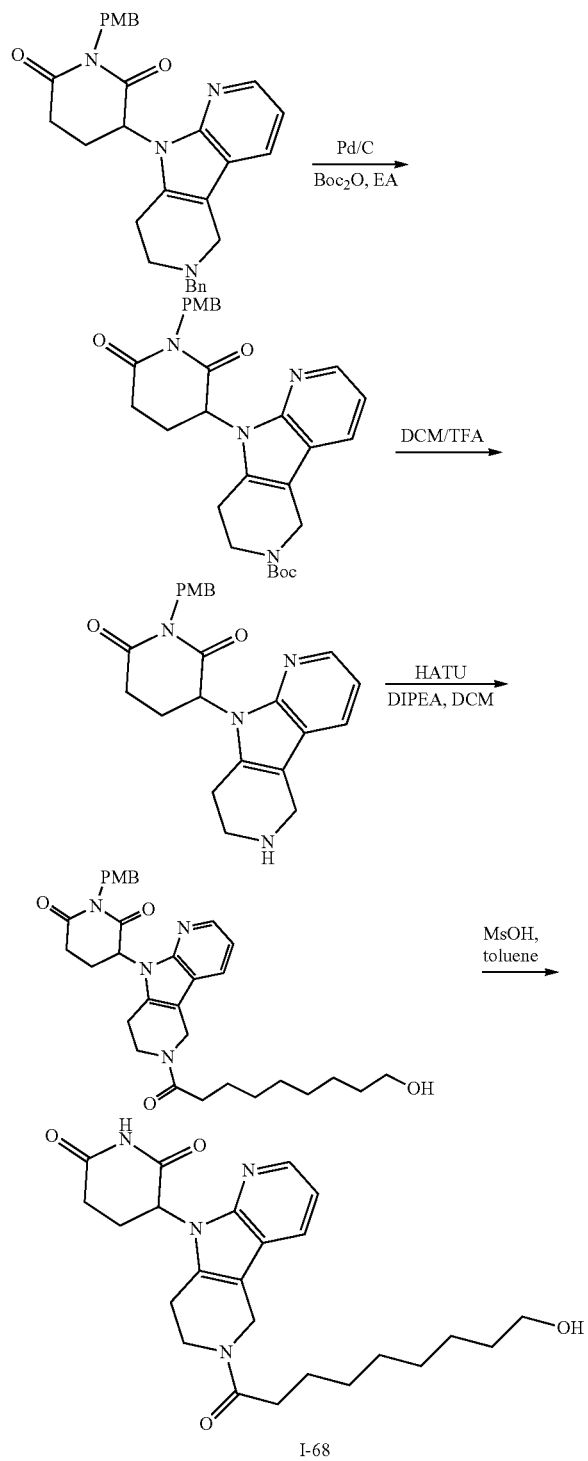

3-(6-Benzyl-5,6,7,8-tetrahydro-9H-pyrrolo[2,3-b:4,5-c'] dipyridin-9-yl)-1-(4-methoxybenzyl)piperidine-2,6-dione was synthesized en route to I-55.

Step 1: tert-butyl 9-(1-(4-methoxybenzyl)-2,6-dioxopiperidin-3-yl)-5,7,8,9-tetrahydro-6H-pyrrolo[2,3-b:4,5-c']dipyridine-6-carboxylate To a mixture of 3-(6-benzyl-5,6,7,8-tetrahydro-9H-pyrrolo[2,3-b:4,5-c']dipyridin-9-yl)-1-(4-methoxybenzyl)piperidine-2,6-dione (42 mg, 0.112 mmol) and Boc$_2$O (398 mg, 1.824 mmol) in EA (5 mL) was added palladium on activated carbon 10% Pd (161 mg, 0.152 mmol). The mixture was stirred at room temperature under hydrogen atmosphere overnight. The reaction mixture was filtered and the filtrate was concentrated under reduce pressure. The residue was purified by flash chromatography eluting with EA/PE=54% to give tert-butyl 9-(1-(4-methoxybenzyl)-2,6-dioxopiperidin-3-yl)-5,7,8,9-tetrahydro-6H-pyrrolo[2,3-b:4,5-c']dipyridine-6-carboxylate (212 mg, 27.7%) as a white solid. LC/MS (ESI, m/z): [M+1]$^+$=505.2.

Step 2: 1-(4-methoxybenzyl)-3-(5,6,7,8-tetrahydro-9H-pyrrolo[2,3-b:4,5-c']dipyridin-9-yl)piperidine-2,6-dione To a solution of tert-butyl 9-(1-(4-methoxybenzyl)-2,6-dioxopiperidin-3-yl)-5,7,8,9-tetrahydro-6H-pyrrolo[2,3-b:4,5-c']dipyridine-6-carboxylate (212 mg, 0.421 mmol) in DCM (5 mL) was added TFA (2 mL). The mixture was stirred at room temperature for 2 h. The mixture was concentrated under reduce pressure and the residue was used directly in the next step without further purification (160 mg, 94.2%) as a salt with TFA. LC/MS (ESI, m/z): [M+1]$^+$=405.0.

Step 3: 3-(6-(9-hydroxynonanoyl)-5,6,7,8-tetrahydro-9H-pyrrolo[2,3-b:4,5-c']dipyridin-9-yl)-1-(4-methoxybenzyl)piperidine-2,6-dione To a mixture of 1-(4-methoxybenzyl)-3-(5,6,7,8-tetrahydro-9H-pyrrolo[2,3-b:4,5-c']dipyridin-9-yl)piperidine-2,6-dione (212 mg, 0.421 mmol) and 9-hydroxynonanoic acid (237 mg, 1.364 mmol), HATU (518 mg, 1.364 mmol) in DCM (5 mL) was added DIPEA (480 mg, 3.72 mmol). The mixture was stirred at room temperature for 2 h. The mixture was diluted with DCM (20 mL) and washed with water. The organic layer was concentrated under reduce pressure and the residue was purified via reverse phase column chromatography (CH$_3$CN/H$_2$O=5%-80%) to give 3-(6-(9-hydroxynonanoyl)-5,6,7,8-tetrahydro-9H-pyrrolo[2,3-b:4,5-c']dipyridin-9-yl)-1-(4-methoxybenzyl)piperidine-2,6-dione (355 mg, 51.1%) as a white solid. LC/MS (ESI, m/z): [M+1]$^+$=561.2.

Step 4: 3-(6-(9-hydroxynonanoyl)-5,6,7,8-tetrahydro-9H-pyrrolo[2,3-b:4,5-c']dipyridin-9-yl)piperidine-2,6-dione (I-68)

To a solution of 3-(6-(9-hydroxynonanoyl)-5,6,7,8-tetrahydro-9H-pyrrolo[2,3-b:4,5-c']dipyridin-9-yl)-1-(4-methoxybenzyl)piperidine-2,6-dione (250 mg, 0.446 mmol) in toluene (5 mL) was added MsOH (430 mg, 4.46 mmol). The mixture was warmed to 105° C. and stirred for 2 h. The reaction mixture was cooled to room temperature and concentrated in vacuum. The residue was purified via reverse phase column chromatography (CH$_3$CN/H$_2$O=5%-80%) to give 3-(6-(9-hydroxynonanoyl)-5,6,7,8-tetrahydro-9H-pyr-rolo[2,3-b:4,5-c']dipyridin-9-yl)piperidine-2,6-dione (5.7 mg, 2.9%) as a white solid. ¹H NMR (400 MHz, DMSO-d₆) δ 11.08 (br. s., 1H), 8.17-8.11 (m, 1H), 7.92 (d, J=7.6 Hz, 1H), 7.12-7.01 (m, 1H), 5.51 (br. s., 1H), 4.76-4.59 (m, 2H), 4.33 (br. s., 1H), 3.98-3.76 (m, 2H), 2.98-2.62 (m, 6H), 2.46-2.43 (m, 2H), 2.16-2.04 (m, 1H), 1.54-1.52 (m, 2H), 1.42-1.37 (m, 2H), 1.32-1.17 (m, 9H); LC/MS (ESI, m/z): [M+1]⁺=441.2.

Example 30. Synthesis of tert-butyl 4-(2-(9-(2,6-dioxopiperidin-3-yl)-9H-pyrido[2,3-b]indol-6-yl)ethyl)piperazine-1-carboxylate (I-64)

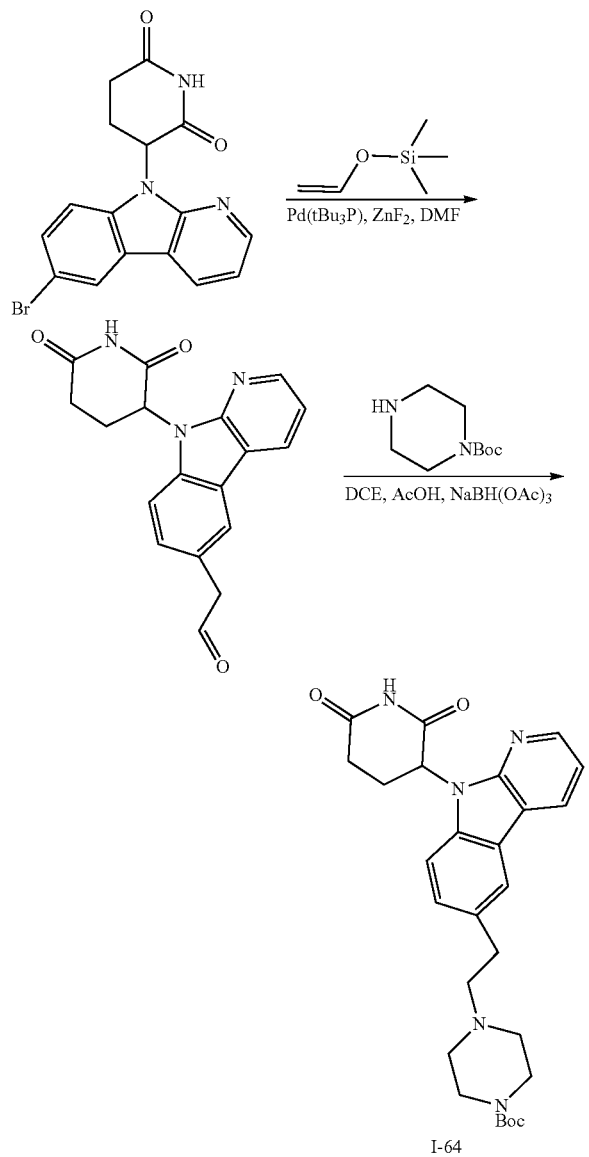

Step 1: 2-(9-(2,6-dioxopiperidin-3-yl)-9H-pyrido[2,3-b]indol-6-yl)acetaldehyde

To a three neck flask was added Pd(tBu₃P)₂ (357.7 mg, 0.7 mmol) and ZnF₂ (721 mg, 7 mmol). The mixture was degrassed with nitrogen, DMF (5 mL) was added. The mixture was stirred at room temperature for 10 min. Then the 3-(6-bromo-9H-pyrido[2,3-b]indol-9-yl)piperidine-2,6-dione (500 mg, 1.4 mmol) in DMF was added followed by trimethyl(vinyloxy)silane (1.624 g, 14 mmol). The reaction mixture was heated to 80° C. and stirred for 1h. Then the reaction mixture was cooled to r.t, quenched by brine and extract with EtOAc (3×50 mL). The combined organic layers were washed with brine, dried over anhydrous sodium sulfate, filtered and concentrated in vacuo. The residue was purified by flash chromatography (eluting with PE/EA=1:2) to give 2-(9-(2,6-dioxopiperidin-3-yl)-9H-pyrido[2,3-b]indol-6-yl)acetaldehyde (240 mg, 53.4%) as a yellow solid. LC/MS (ESI, m/z): [M+1]⁺=322.0.

Step 2: tert-butyl 4-(2-(9-(2,6-dioxopiperidin-3-yl)-9H-pyrido[2,3-b]indol-6-yl)ethyl)piperazine-1-carboxylate (I-64)

To a mixture of 2-(9-(2,6-dioxopiperidin-3-yl)-9H-pyrido[2,3-b]indol-6-yl)acetaldehyde (100 mg, 0.312 mmol) and tert-butyl piperazine-1-carboxylate (75.3 mg, 0.405 mmol) in DCE (5 mL) was added AcOH (3 drops). The mixture was stirred at room temperature for 2 h. Then NaBH(OAc)₃ (132 mg, 0.624 mmol) was added in portions. The reaction mixture was heated to 40° C. and stirred overnight. The reaction mixture was poured into water and extract with DCM (3×20 mL). The combined organic layers were washed with brine, dried over anhydrous sodium sulfate, filtered and concentrated in vacuo. The residue was purified by Prep-HPLC to give tert-butyl 4-(2-(9-(2,6-dioxopiperidin-3-yl)-9H-pyrido[2,3-b]indol-6-yl)ethyl)piperazine-1-carboxylate (33 mg, 21.5%) as a white solid. ¹H NMR (400 MHz, DMSO-d₆) δ 11.14 (s, 1H), 8.52 (dd, J=7.7, 1.6 Hz, 1H), 8.40 (dd, J=4.8, 1.5 Hz, 1H), 8.08 (s, 1H), 7.52-7.50 (m, 1H), 7.39-7.37 (m, 1H), 7.26-7.23 (m, 1H), 6.02 (br. s., 1H), 3.37-3.31 (m, 4H), 3.08-2.95 (m, 2H), 2.94-2.86 (m, 2H), 2.72-2.59 (m, 4H), 2.44-2.41 (m, 3H), 2.12-2.09 (m, 1H), 1.40 (s, 9H); LC/MS (ESI, m/z): [M+1]⁺=492.2.

Example 31. Synthesis of tert-butyl (1-(2-(9-(2,6-dioxopiperidin-3-yl)-9H-pyrido[2,3-b]indol-6-yl)ethyl)piperidin-4-yl)carbamate (I-71)

I-71 was synthesized via the same method as I-64 substituting tert-butyl piperazine-1-carboxylate with tert-butyl piperidin-4-ylcarbamate. ¹H NMR (400 MHz, DMSO-d₆) δ 11.14 (s, 1H), 8.52 (d, J=7.6 Hz, 1H), 8.40 (d, J=4.5 Hz, 1H), 8.06 (s, 1H) 7.52-7.50 (m, 1H), 7.38-7.23 (m, 2H), 6.76 (d, J=7.4 Hz, 1H), 6.01 (br. s., 1H), 2.80-3.31 (m, 8H), 2.72-2.57 (m, 4H), 2.12-2.00 (m, 3H), 1.72-1.69 (m, 2H), 1.38 (s, 9H); LC/MS (ESI, m/z): [M+1]⁺=506.2.

Example 32. Synthesis of 3-(3-bromo-8H-thieno[2,3-b]indol-8-yl)piperidine-2,6-dione (I-89)

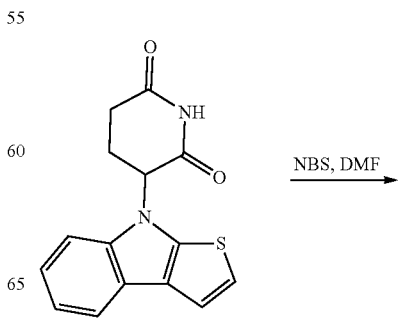

-continued

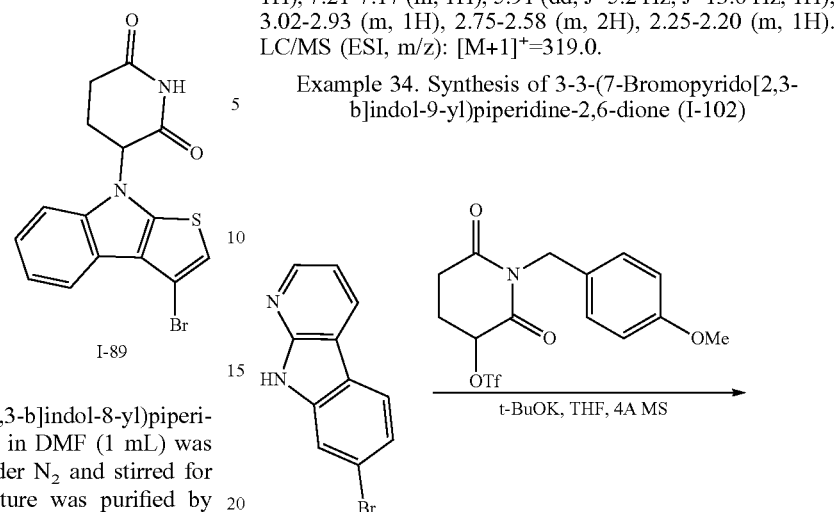

I-89

To a solution of 3-(8H-thieno[2,3-b]indol-8-yl)piperidine-2,6-dione (10 mg, 0.035 mmol) in DMF (1 mL) was added NBS (6 mg, 0.035 mmol) under $N_2$ and stirred for overnight at rt under $N_2$. The mixture was purified by prep-HPLC to give the product 3-(3-bromo-8H-thieno[2,3-b]indol-8-yl)piperidine-2,6-dione (3 mg, 16% yield) as a white solid. $^1$H NMR (400 MHz, DMSO-$d_6$) δ 11.24 (s, 1H), 7.82 (d, J=7.6 Hz, 1H), 7.73 (s, 1H), 7.60 (d, J=8.4 Hz, 1H), 7.30-7.26 (m, 1H), 7.21-7.17 (m, 1H), 5.91 (dd, J=5.2 Hz, J=13.6 Hz, 1H), 3.01-2.92 (m, 1H), 2.76-2.61 (m, 2H), 2.25-2.21 (m, 1H). LC/MS (ESI, m/z): [M+1]$^+$=363.0, 365.0.

Example 33. Synthesis of 3-(3-chloro-8H-thieno[2,3-b]indol-8-yl)piperidine-2,6-dione (I-93)

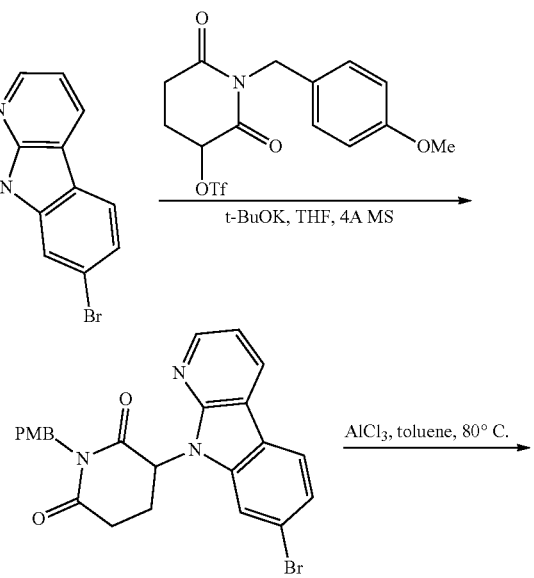

I-93

To a solution of 3-(8H-thieno[2,3-b]indol-8-yl)piperidine-2,6-dione (15 mg, 0.053 mmol) in DMF (1 mL) was added NCS (7 mg, 0.053 mmol) under $N_2$ at room temperature overnight. The mixture was purified by prep-HPLC to give the product 3-(3-chloro-8H-thieno[2,3-b]indol-8-yl)piperidine-2,6-dione (5 mg, 30% yield) as a white solid. $^1$H NMR (400 MHz, DMSO-$d_6$) δ 11.24 (s, 1H), 7.81 (d, J=7.6 Hz, 1H), 7.64 (s, 1H), 7.60 (d, J=8.4 Hz, 1H), 7.30-7.26 (m, 1H), 7.21-7.17 (m, 1H), 5.91 (dd, J=5.2 Hz, J=13.6 Hz, 1H), 3.02-2.93 (m, 1H), 2.75-2.58 (m, 2H), 2.25-2.20 (m, 1H). LC/MS (ESI, m/z): [M+1]$^+$=319.0.

Example 34. Synthesis of 3-3-(7-Bromopyrido[2,3-b]indol-9-yl)piperidine-2,6-dione (I-102)

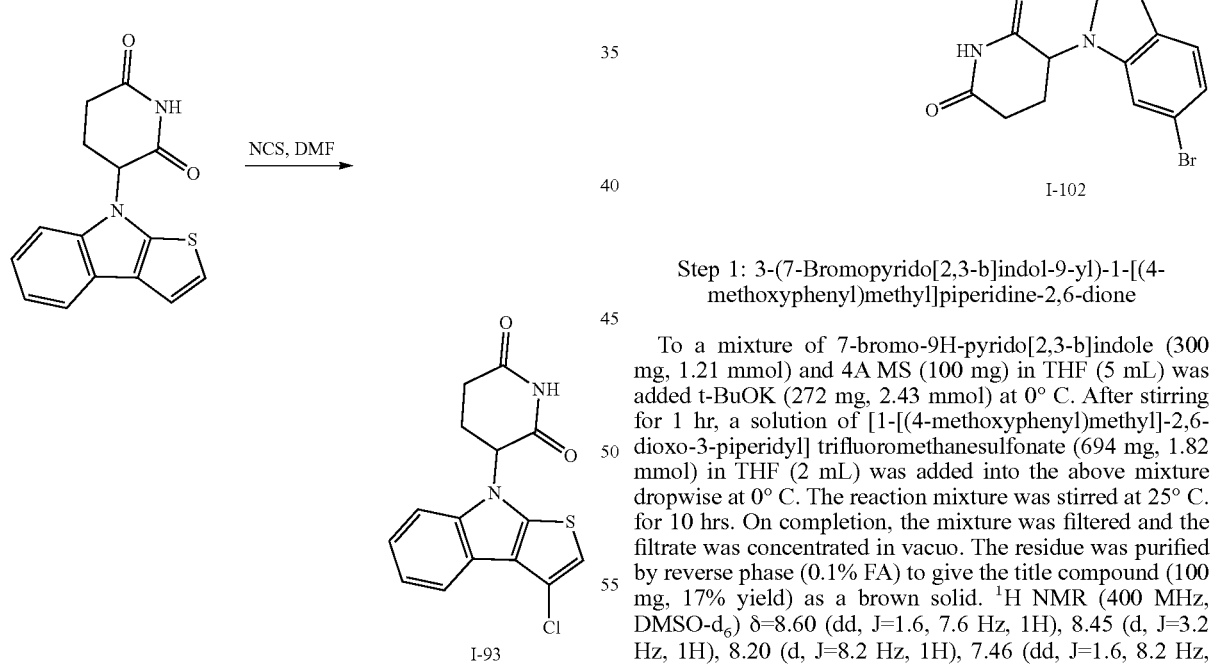

I-102

Step 1: 3-(7-Bromopyrido[2,3-b]indol-9-yl)-1-[(4-methoxyphenyl)methyl]piperidine-2,6-dione To a mixture of 7-bromo-9H-pyrido[2,3-b]indole (300 mg, 1.21 mmol) and 4A MS (100 mg) in THF (5 mL) was added t-BuOK (272 mg, 2.43 mmol) at 0° C. After stirring for 1 hr, a solution of [1-[(4-methoxyphenyl)methyl]-2,6-dioxo-3-piperidyl] trifluoromethanesulfonate (694 mg, 1.82 mmol) in THF (2 mL) was added into the above mixture dropwise at 0° C. The reaction mixture was stirred at 25° C. for 10 hrs. On completion, the mixture was filtered and the filtrate was concentrated in vacuo. The residue was purified by reverse phase (0.1% FA) to give the title compound (100 mg, 17% yield) as a brown solid. $^1$H NMR (400 MHz, DMSO-$d_6$) δ=8.60 (dd, J=1.6, 7.6 Hz, 1H), 8.45 (d, J=3.2 Hz, 1H), 8.20 (d, J=8.2 Hz, 1H), 7.46 (dd, J=1.6, 8.2 Hz, 1H), 7.31 (dd, J=4.8, 7.6 Hz, 1H), 7.26 (d, J=8.8 Hz, 2H), 7.18-7.13 (m, 1H), 6.88 (d, J=8.8 Hz, 2H), 6.22-6.11 (m, 1H), 4.88-4.79 (m, 2H), 3.73 (s, 3H), 3.19-3.11 (m, 2H), 2.94-2.88 (m, 1H), 2.23-2.16 (m, 1H).

Step 2: 3-3-(7-Bromopyrido[2,3-b]indol-9-yl)piperidine-2,6-dione (I-103)

To a solution of 3-(7-bromopyrido[2,3-b]indol-9-yl)-1-[(4-methoxyphenyl)methyl]piperidine-2,6-dione (60.0 mg, 125 umol) in toluene (2 mL) was added AlCl₃ (83.6 mg, 627 umol). The reaction mixture was stirred at 80° C. for 2 hrs. On completion, the mixture was quenched with water (20 mL), extracted with EA (2×20 mL). The organic layer was concentrated in vacuo. The residue was purified by prep-HPLC (column: Phenomenex Synergi C18 150*25*10 um; mobile phase: [water (0.225% FA)-ACN]; B %: 39%-66%, 9 min) to give the title compound (11.0 mg, 25% yield) as a white solid. ¹H NMR (400 MHz, DMSO-d₆) δ 11.16 (s, 1H), 8.60 (dd, J=1.6, 7.6 Hz, 1H), 8.46 (dd, J=1.2, 4.8 Hz, 1H), 8.20 (d, J=8.4 Hz, 1H), 7.97 (s, 1H), 7.46 (dd, J=1.6, 8.4 Hz, 1H), 7.31 (dd, J=4.8, 7.6 Hz, 1H), 6.10-5.95 (m, 1H), 3.22-3.08 (m, 1H), 3.05-2.92 (m, 1H), 2.78-2.65 (m, 1H), 2.20-2.10 (m, 1H); LC-MS (ESI⁺) m z 358.0, 360.0 (M+H, M+3)⁺.

Example 35. Synthesis of 3-(4-bromo-8H-thieno[2,3-b]indol-8-yl)piperidine-2,6-dione (I-103)

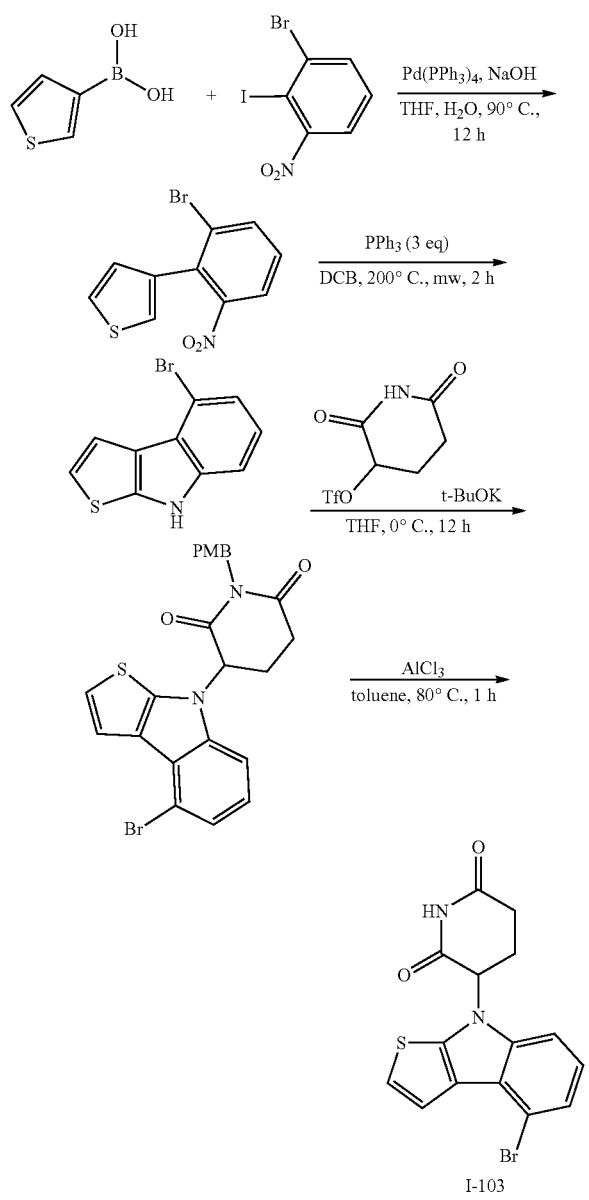

Step 1—3-(2-bromo-6-nitro-phenyl)thiophene

A mixture of 3-thienylboronic acid (10 g, 78 mmol), 1-bromo-2-iodo-3-nitro-benzene (26 g, 78 mmol), Pd(PPh₃)₄ (4.5 g, 3.91 mmol) and NaOH (9.4 g, 234 mmol) in THF (240 mL), H₂O (120 mL) was degassed and purged with N₂ for 3 times. And then the mixture was stirred at 90° C. for 12 hrs under N₂ atmosphere. The solution was diluted with water (200 mL) and extracted with ethyl acetate (200 mL*2). The combined organic layers were washed with brine (100 mL), dried over anhydrous Na₂SO₄, filtered and concentrated under reduced pressure. The residue was purified by column chromatography (SiO₂, Petroleum ether/Ethyl acetate=40/1 to 10/1) to give the title compound (20 g, 81% yield) as a yellow solid. 1H NMR (400 MHz, CDCl₃) δ=7.80 (dd, J=1.2, 8.4 Hz, 1H), 7.64 (m, 1H), 7.35 (m, 1H), 7.28 (t, J=8.0 Hz, 1H), 7.17 (dd, J=1.2, 2.8 Hz, 1H), 7.02 (m, 1H).

Step 2—8-bromo-4H-thieno[2,3-b]indole 3-(2-bromo-6-nitro-phenyl)thiophene (2 g, 7.04 mmol) and PPh₃ (5.54 g, 21 mmol) were taken up into a microwave tube in DCB (10 mL). The sealed tube was heated at 200° C. for 2 hrs under microwave. The reaction mixture was filtered and concentrated under reduced pressure. The residue was purified by column chromatography (SiO₂, Petroleum ether/Ethyl acetate=50:1 to 10/1) to get the title compound (0.5 g, 28% yield) as a yellow solid. LC-MS (ESI⁺) m/z 252.0 (M+H)⁺

Step 3—3-(8-bromothieno[2,3-b]indol-4-yl)-1-[(4-methoxyphenyl)methyl]piperidine-2,6-dione t-BuOK (445 mg, 3.97 mmol) was added to a solution of 8-bromo-4H-thieno[2,3-b]indole (500 mg, 1.98 mmol) in THF (10 mL) at 0° C. The resulting mixture was stirred at 0° C. for 30 min. Then a solution of [1-[(4-methoxyphenyl)methyl]-2,6-dioxo-3-piperidyl]trifluoromethanesulfonate (1.1 g, 2.97 mmol) in THF (10 mL) was added slowly at 0° C. After addition, the resulting solution was stirred at 0-25° C. for 11.5 hrs under N₂ atmosphere. The reaction mixture was quenched by water (10 mL) and extracted with ethyl acetate (3*20 mL). The combined organic phases were concentrated under reduced pressure to give a residue. The residue was purified by column chromatography (SiO₂, Petroleum ether/Ethyl acetate=10/1 to 3/1) to give the title compound (230 mg, 23% yield) as a yellow liquid. LC-MS (ESI⁺) m/z 485.0 (M+H)⁺.

Step 4—3-(8-bromothieno[2,3-b]indol-4-yl)piperidine-2,6-dione

To a solution of 3-(8-bromothieno[2,3-b]indol-4-yl)-1-[(4-methoxyphenyl)methyl]piperidine-2,6-dione (100 mg, 0.21 mmol) in toluene (1.0 mL) was added AlCl₃ (138 mg, 1.03 mmol). The mixture was stirred at 80° C. for 1 hr. The reaction mixture was concentrated under reduced pressure to give a residue. The residue was diluted with ethyl acetate (20 mL) and then quenched by addition HCl (2M, 20 mL) at 0° C. and extracted with ethyl acetate (15 mL*2). The combined organic layers were concentrated under reduced pressure. The residue was purified by column chromatography (SiO₂, Petroleum ether/Ethyl acetate=10/1 to 1/1) to give the title compound (40 mg, 37% yield) as a yellow solid. 1H NMR (400 MHz, DMSO-d6) δ=11.27 (s, 1H), 7.67-7.62 (m, 2H), 7.39 (d, J=7.6 Hz, 1H), 7.27-7.20 (m, 2H), 5.95 (m, 1H), 3.04-2.92 (m, 1H), 2.82-2.71 (m, 2H), 2.31-2.24 (m, 1H); LC-MS (ESI⁺) m/z 365.0 (M+H)⁺.

Example 36. Synthesis of 3-(6-bromo-2-chloro-9H-pyrido[2,3-b]indol-9-yl)piperidine-2,6-dione (I-104)

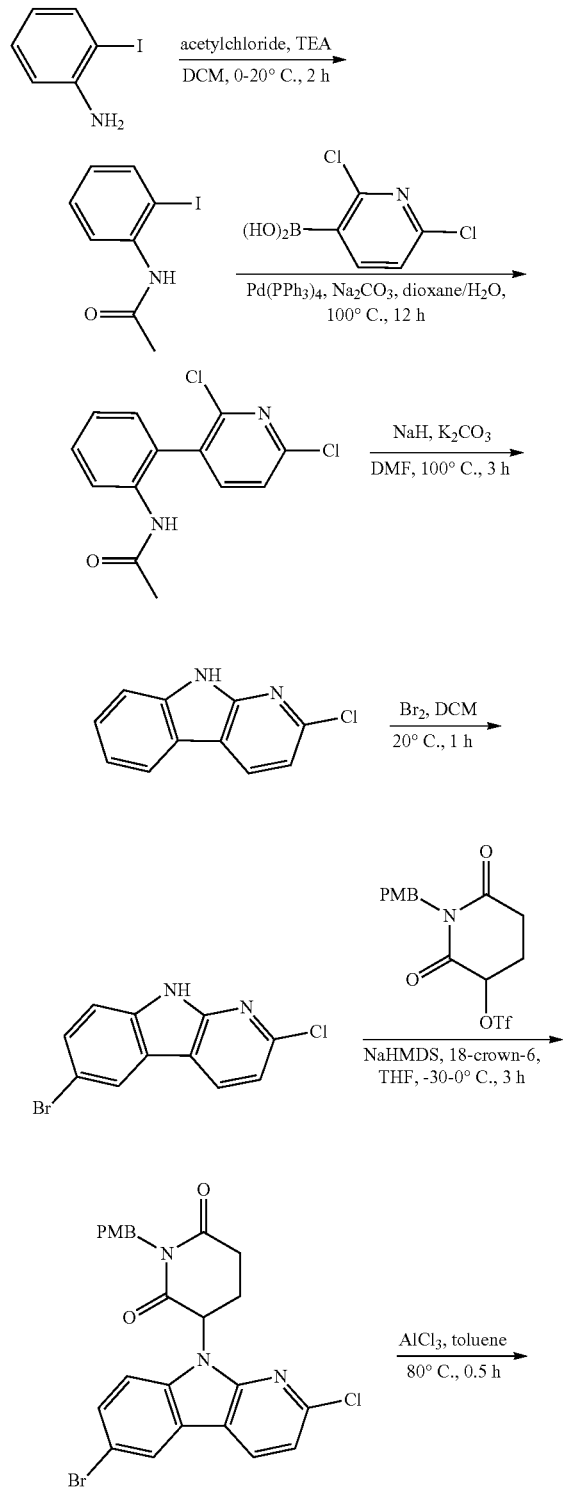

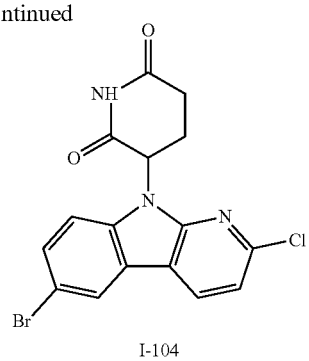

I-104

Step 1: N-(2-iodophenyl)acetamide

To a solution of 2-iodoaniline (23.6 g, 108 mmol) in DCM (250 mL) was added TEA (13.1 g, 129 mmol) and cooled to 0° C. Then acetylchloride (9.30 g, 119 mmol) was added to the reaction mixture at 0° C. by dropwise and stirred at 20° C. for 2 hours. On completion, the reaction mixture was quenched by water (200 mL) and extracted with dichloromethane (3×100 mL). The extracts was washed by brine (100 mL) and dried over anhydrous sodium sulfate, filtered and concentrated in vacuo to get the crude residue. The residue was purified by column chromatography (SiO₂, petroleum ether:dichloromethane:ethyl acetate=1:0:0 to 10:5:1) to give the title compound (25 g, 82% yield) as a white solid. ¹H NMR (400 MHz, CDCl₃) δ ppm 8.21 (d, J=7.6 Hz, 1H), 7.78 (d, J=8.0 Hz, 1H), 7.48 (s, 1H) 7.35 (td, J1=1.2 Hz, J2=8.4 Hz, 1H), 6.85 (t, J=7.2 Hz, 1H), 2.25 (s, 3H); LC-MS (ESI, m/z): [M+1]⁺=261.7.

Step 2: N-(2-(2,6-dichloropyridin-3-yl)phenyl)acetamide

To a solution of N-(2-iodophenyl)acetamide (5 g, 19.2 mmol) and (2,6-dichloro-3-pyridyl)boronic acid (3.67 g, 19.2 mmol) in dioxane (100 mL) and H₂O (20 mL). Then Na₂CO₃ (6.09 g, 57.5 mmol) and Pd(PPh₃)₄ (1.11 g, 958 umol) were added to the mixture under nitrogen protection. Then the reaction mixture was stirred at 100° C. for 12 hours. On completion, the reaction mixture was quenched by water (100 mL) and extracted with ethyl acetate (3×50 mL). The extracts was washed by brine (50 mL) and dried over anhydrous sodium sulfate, filtered and concentrated in vacuo to get the crude residue. The residue was purified by column chromatography (SiO2, petroleum ether:dichloromethane: petroleum ether=0:0:1 to 1:1:2) to give the title compound (2.3 g, 34% yield) as a yellow solid. LC-MS (ESI, m/z): [M+1]⁺=281.3.

Step 3: 2-chloro-9H-pyrido[2,3-b]indole

To a mixture of N-[2-(2,6-dichloro-3-pyridyl)phenyl]acetamide (1.7 g, 6.05 mmol) and K₂CO₃ (5.01 g, 36.3 mmol) in DMF (30 mL) was added NaH (483.70 mg, 12.09 mmol, 60% purity) under nitrogen protection. Then the mixture was stirred at 100° C. for 3 hours. On completion, the reaction mixture was poured into ice water (200 mL) and stirred for half an hour. Then the suspension was filtered to get the solid and dried in vacuo to give the title compound (1.2 g, 93% yield) as a yellow solid. LC-MS (ESI, m/z): [M+1]⁺=203.4.

Step 4: 6-bromo-2-chloro-9H-pyrido[2,3-b]indole

To a suspension of 2-chloro-9H-pyrido[2,3-b]indole (1 g, 4.93 mmol) in DCM (20 mL) was added Br$_2$ (946 mg, 5.92 mmol) in DCM (10 mL) and stirred at 20° C. for 1 hour. On completion, the reaction mixture was concentrated in vacuo and the residue poured into ice water (100 mL). Then suspension was quenched by saturated sodium sulfite aqueous solution (10 mL) and adjust PH=9 by saturated sodium bicarbonate aqueous solution. The solids was collected by filtration and triturated by ethyl acetate:petroleum ether=1:1(50 mL) to give the title compound (1.3 g, 84% yield) as a yellow solid. LC-MS (ESI, m/z): [M+1]$^+$=283.0.

Step 5: 3-(6-bromo-2-chloro-9H-pyrido[2,3-b]indol-9-yl)-1-(4-methoxybenzyl)piperidine-2,6-dione To a solution of 6-bromo-2-chloro-9H-pyrido[2,3-b]indole (1.1 g, 3.52 mmol) and 18-crown-6 (186 mg, 703 umol) in THF (20 mL) was added NaHMDS (1 M, 5.27 mL) at −30° C. by dropwise. After stirred at this temperature for 1 hour, [1-[(4-methoxyphenyl)methyl]-2,6-dioxo-3-piperidyl] trifluoromethanesulfonate (2.01 g, 5.27 mmol) in THF (20 mL) was added to the reaction mixture by dropwise and stirred at 0° C. for another 2 hours. On completion, the reaction mixture was diluted with ethyl acetate (100 mL) and quenched by saturated ammonia chloride aqueous solution (50 mL). The organic layers was washed by water (30 mL) and brine (30 mL) and dried over anhydrous sodium sulfate, filtered and concentrated in vacuo to get the crude residue. The residue was purified by column chromatography (SiO2, Petroleum ether/Ethyl acetate=1:0 to 5:1) to give the title compound (1.8 g, 99% yield) as a white solid. LC-MS (ESI, m/z): [M+1]$^+$=514.1.

Step 6: 3-(6-bromo-2-chloro-9H-pyrido[2,3-b]indol-9-yl)piperidine-2,6-dione

To a mixture of 3-(6-bromo-2-chloro-9H-pyrido[2,3-b]indol-9-yl)-1-(4-methoxybenz yl)piperidine-2,6-dione (1.70 g, 3.32 mmol) in toluene (40 mL) was added AlCl$_3$ (1.77 g, 13.3 mmol) and stirred at 80° C. for 0.5 hour. On completion, the reaction mixture was concentrated in vacuo and the residue was diluted with ethyl acetate (50 mL). Then the solution was quenched by 1N hydrochloric acid aqueous solution (20 mL) and water (20 mL). The mixture was extracted with ethyl acetate (3×30 mL) and washed by brine (30 mL), the extracts was dried over anhydrous sodium sulfate, filtered and concentrated in vacuo to get the crude residue. The crude residue was purified by silica gel chromatography (petroleum ether:ethyl acetate:dichloromethane=10:1:1 to 1:1:1) to give the title compound (0.8 g, 90% purity, 61.46% yield) as a gray solid. The product (50 mg, 90% purity) was purified by prep-HPLC (column: Phenomenex Synergi C18 150*25*10 um; mobile phase: [water (0.05% HCl)-ACN]; B %: 56%-76%, 9 min) to give the title compound (27.1 mg, 49.1% yield, 99.2% purity) as a white solid. $^1$H NMR (400 MHz, DMSO-d$_6$) δ=11.22 (s, 1H), 8.69 (d, J=8.0 Hz, 1H), 8.55 (d, J=2.0 Hz, 1H), 7.70-7.63 (m, 2H), 7.41 (d, J=8.0 Hz, 1H), 6.03 (s, 1H), 3.05-3.01 (m, 2H), 2.74-2.71 (m, 1H), 2.18 (m, 1H); LC-MS (ESI, m/z): [M+1]$^+$=394.1.

Example 37. Synthesis of 3-(9H-pyrrolo[2,3-b:5,4-b']dipyridin-9-yl)piperidine-2,6-dione (I-3)

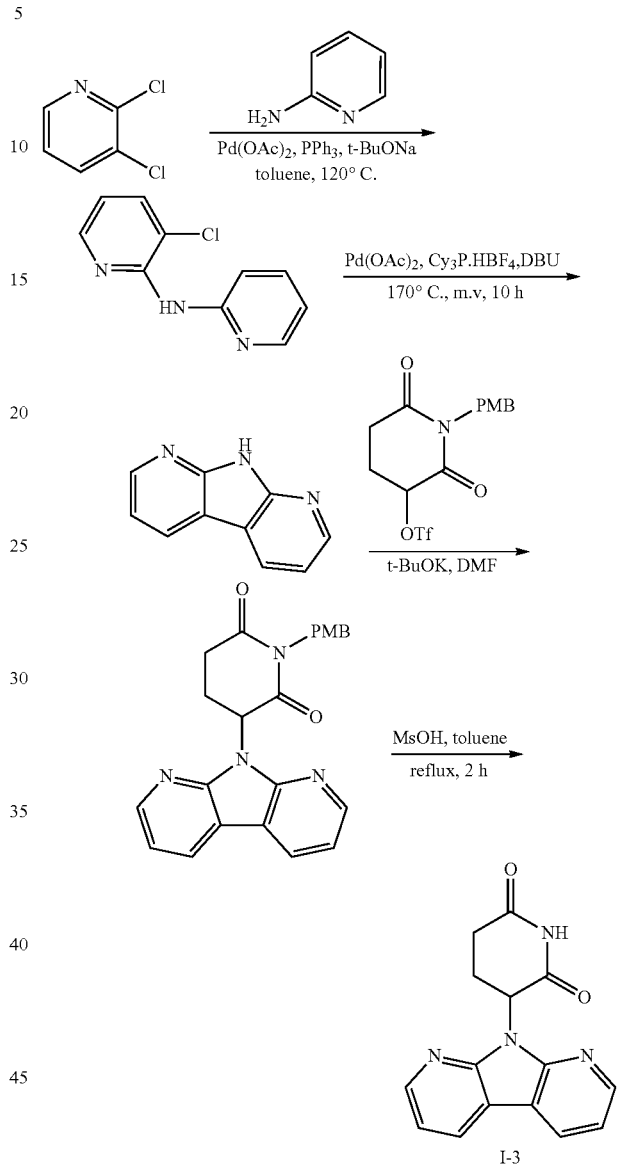

Step 1: 3-chloro-N-(pyridin-2-yl)pyridin-2-amine

A mixture of 2,3-dichloropyridine (5.0 g, 34.0 mmol), pyridin-2-amine (3.5 g, 37.4 mmol), Pd(OAc)$_2$ (0.38 g, 1.70 mmol), PPh$_3$ (0.89 g, 3.40 mmol) and t-BuONa (3.9 g, 40.8 mmol) in toluene (80 mL) was sparged with argon for about 10 min, placed under an argon atmosphere, and heated to 120° C. for 17 hours. The reaction mixture was cooled to room temperature and concentrated in vacuo. The residue was diluted with water (50 mL), extracted with EA (80 mL×2). The combined organic layer was washed with brine (50 mL×2), dried over anhydrous Na$_2$SO$_4$, filtered and concentrated in vacuum. The residue was purified by silica gel column chromatography (PE:EA=4/1) to give the product (4.3 g, 61.7%) as a yellow solid. LC-MS (ESI$^+$): m/z 206.2 (M+H)$^+$.

Step 2: 9H-pyrrolo[2,3-b:5,4-b']dipyridine

A mixture of 3-chloro-N-(pyridin-2-yl)pyridin-2-amine (0.5 g, 2.44 mmol), Pd(OAc)₂ (55.7 mg, 0.24 mmol), Tricyclohexylphosphonium tetrafluoroborate (0.18 g, 0.49 mmol) and DBU (0.74 g, 4.88 mmol) in DMA (10 mL) was added to the sealed tube. The mixture was sparged with argon for about 10 min, placed under an argon atmosphere, and heated to 170° C. for 10 hours in microwave condition. The reaction mixture was cooled to room temperature and diluted with water (30 mL), extracted with EA (40 mL×2). The combined organic layer was washed with water (40 mL×2) and brine (40 mL×2), dried over anhydrous Na₂SO₄, filtered and concentrated in vacuum. The residue was purified by silica gel column chromatography (PE:EA=2/1) to give the product (0.32 g, 78%) as a yellow solid. ¹H NMR (400 MHz, CDCl₃) δ 8.71-8.59 (m, 2H), 8.39-8.30 (m, 2H), 7.29-7.25 (m, 2H). LC-MS (ESI⁺): m/z 170.2 (M+H)⁺.

Step 3: 1-(4-methoxybenzyl)-3-(9H-pyrrolo[2,3-b:5,4-b']dipyridin-9-yl)piperidine-2,6-dione To a stirred solution of 9H-pyrrolo[2,3-b:5,4-b']dipyridine (320 mg, 1.89 mmol)
in DMF (10 mL) was added t-BuOK (254 mg, 2.27 mmol) at 0° C. under nitrogen atmosphere. The mixture was stirred at 0-10° C. for 1 hour. Then 1-(4-methoxybenzyl)-2,6-dioxopiperidin-3-yl trifluoromethanesulfonate (1.082 g, 2.84 mmol) in DMF (2 mL) was added to the reaction mixture at 0-10° C. during 10 minutes. After addition, the mixture was stirred at room temperature for 2 hours. On completion, the reaction was quenched by water and extracted with EA. The combined organic layer was washed with water and brine, dried over anhydrous sodium sulfate, filtered and concentrated in vacuo. The residue was purified by column chromatography (CH2Cl2/MeOH=20:1 to 10:1) to give 1-(4-methoxybenzyl)-3-(9H-pyrrolo[2,3-b:5,4-b']dipyridin-9-yl)piperidine-2,6-dione (200 mg, 27% yield) as a yellow solid. LC/MS (ESI, m/z): [M+1]⁺=401.5.

Step 4: 3-(9H-pyrrolo[2,3-b:5,4-b']dipyridin-9-yl)piperidine-2,6-dione (I-3)

To a stirred solution of 1-(4-methoxybenzyl)-3-(9H-pyrrolo[2,3-b:5,4-b']dipyridin-9-yl)piperidine-2,6-dione (200 mg, 0.5 mmol) in toluene (5 mL) was added methanesulfonic acid (1 mL). The reaction mixture was heated to 110° C. and stirred for 2 h under nitrogen atmosphere. The reaction was cooled to r.t and concentrated under reduced pressure to remove toluene. The residue was purified via reverse phase column chromatography (CH₃CN/H₂O=5%-80%) to give 3-(9H-pyrrolo[2,3-b:5,4-b']dipyridin-9-yl)piperidine-2,6-dione (16 mg, 11% yield) as a white solid. ¹H NMR (400 MHz, CDCl₃) δ 8.50 (d, J=1.6 Hz, 1H), 8.49 (d, J=1.6 Hz, 1H), 8.34 (d, J=1.6 Hz, 1H), 8.33 (d, J=1.6 Hz, 1H), 8.12 (br s, 1H), 7.28-7.25 (m, 2H), 6.07 (dd, J=12.6, 5.4 Hz, 1H), 3.47 (ddd, J=30.2, 13.2, 5.0 Hz, 1H), 3.04-2.87 (m, 2H), 2.35-2.28 (m, 1H); LC/MS (ESI, m/z): [M+1]⁺=281.1.

Example 38. Synthesis of 3-(7-chloro-9H-pyrido[2,3-b]indol-9-yl)piperidine-2,6-dione (I-106)

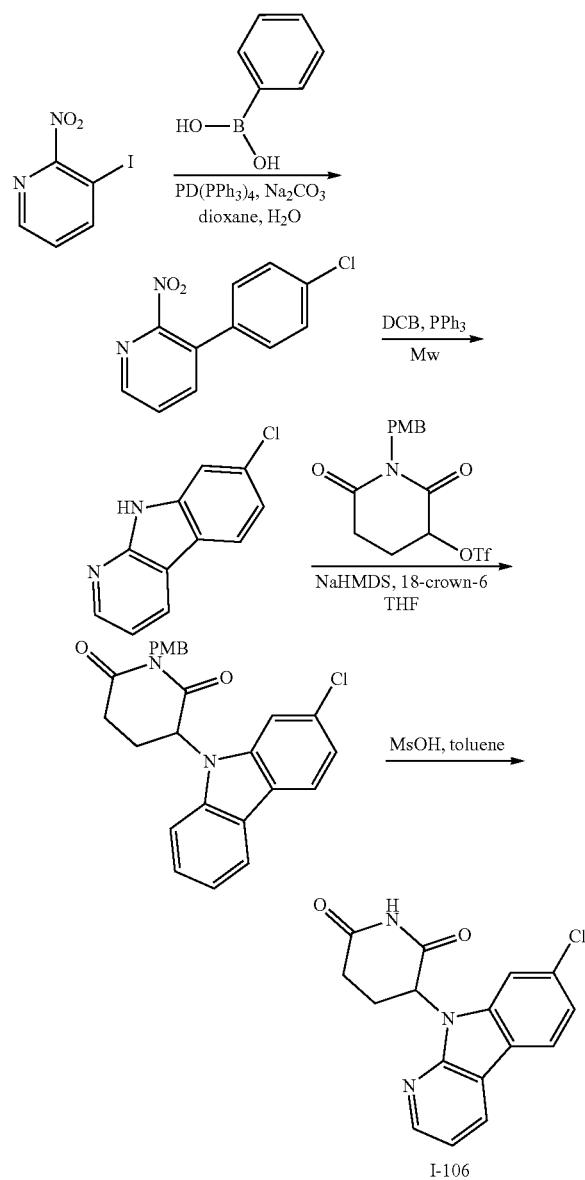

Step 1: 3-(4-chlorophenyl)-2-nitropyridine

A mixture of 3-iodo-2-nitropyridine (2 g, 8 mmol), (4-chlorophenyl)boronic acid (1.5 g, 9.6 mmol), Na₂CO₃ (1.7 g, 16 mmol) and Pd(PPh₃)₄ (277 mg, 0.24 mmol) in dioxane (20 mL) and water (10 mL) was degassed with nitrogen, heated to 110° C. and stirred for 18 hours under nitrogen atmosphere. The reaction was cooled to r.t, filtered and concentrated in vacuo. The residue was diluted with water, extracted with EA. The combined organic layer was washed with brine, dried over anhydrous sodium sulfate, filtered and concentrated in vacuo. The residue was purified by column chromatography (Petroleum ether/EtOAc=3:1) to give 3-(4-chlorophenyl)-2-nitropyridine (1.4 g, 75% yield) as a yellow solid. LC/MS (ESI, m/z): [M+1]⁺=234.6.

Step 2: 7-chloro-9H-pyrido[2,3-b]indole

A mixture of 3-(4-chlorophenyl)-2-nitropyridine (1 g, 4.27 mmol) and PPh$_3$ (3.36 g, 12.82 mmol) in DCB (5 mL) was heated at 200° C. for 2 hrs under microwave condition. The reaction mixture was cooled to r.t, filtered and concentrated under reduced pressure. The residue was purified by column chromatography (Petroleum ether/Ethyl acetate=1:1 to give 7-chloro-9H-pyrido[2,3-b]indole (112 mg, 13% yield) as a black solid. LC/MS (ESI, m/z): [M+1]$^+$=202.9.

Step 3: 3-(7-chloro-9H-pyrido[2,3-b]indol-9-yl)-1-(4-methoxybenzyl)piperidine-2,6-dione To a stirred solution of 7-chloro-9H-pyrido[2,3-b]indole (112 mg, 0.554 mmol) and 18-crown-6 (44 mg, 0.166 mmol) in THF (10 mL) was added NaHMDS (0.42 mL, 2 M in THF) dropwise at −30° C. under nitrogen atmosphere. The mixture was stirred for 1 h at −30° C. under nitrogen atmosphere. Then a solution of 1-(4-methoxybenzyl)-2,6-dioxopiperidin-3-yl trifluoromethanesulfonate (316.6 mg, 0.831 mmol) in THE (10 mL) was added to the reaction dropwise at −30° C. under nitrogen atmosphere. After addition, the mixture was stirred for 2 h at −30° C. and quenched by sat.aq. ammonium chloride, extracted with EA. The combined organic layers were washed with brine, dried over anhydrous sodium sulfate, filtered and concentrated in vacuo. The residue was purified by column chromatography (Petroleum ether/EtOAc=1:1) to give 3-(7-chloro-9H-pyrido[2,3-b]indol-9-yl)-1-(4-methoxybenzyl)piperidine-2, 6-dione (94 mg, 84.4% yield) as a pale yellow solid.

Step 4: 3-(7-chloro-9H-pyrido[2,3-b]indol-9-yl)piperidine-2,6-dione (I-106)

To a stirred solution of 3-(7-chloro-9H-pyrido[2,3-b]indol-9-yl)-1-(4-methoxybenzyl)piperidine-2,6-dione (94 mg, 0.22 mmol) in toluene (5 mL) was added methanesulfonic acid (1 mL). The reaction mixture was heated to 110° C. and stirred for 2 h under nitrogen atmosphere. The reaction was cooled to r.t and concentrated under reduced pressure to remove toluene. The residue was purified via reverse phase column chromatography (CH$_3$CN/H$_2$O=5%-80%) to give 3-(7-chloro-9H-pyrido[2,3-b]indol-9-yl)piperidine-2,6-dione (11 mg, 16% yield) as a white solid. $^1$H NMR (400 MHz, CDCl$_3$) δ 8.43 (dd, J=1.3, 4.9 Hz, 1H), 8.30 (dd, J=1.3, 7.7 Hz, 1H), 8.16 (br. s., 1H), 8.00 (d, J=8.1 Hz, 1H), 7.29 (dd, J=1.5, 8.4 Hz, 1H), 7.25-7.20 (m, 1H), 5.83 (dd, J=4.8, 12.4 Hz, 1H), 3.18-2.88 (m, 3H), 2.37-2.22 (m, 1H). LC/MS (ESI, m/z): [M+1]$^+$=314.0.

All of the U.S. patents, U.S. patent application publications, U.S. patent applications, foreign patents, foreign patent applications, and non-patent publications referred to in this specification are incorporated herein by reference in their entireties, including U.S. provisional application nos. 62/694,924, filed Jul. 6, 2018, 62/820,634, filed Mar. 19, 2019, and 62/863,949, filed Jun. 19, 2019.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A method of treating a CRBN-mediated disorder, disease, or condition in a patient comprising administering to said patient a compound of formula I-d:

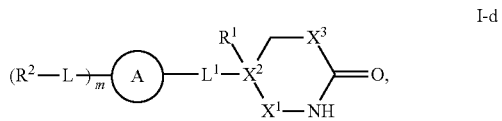

a pharmaceutically acceptable salt thereof, or a pharmaceutical composition thereof, wherein:
X$^1$ is —CH$_2$— or —C(O)—;
X$_2$ is a carbon atom;
X$_3$ is —CH$_2$—;
R$^1$ is hydrogen;
each R$^2$ is independently hydrogen, deuterium, R$^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;
each R$^3$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
each R is independently hydrogen, or an optionally substituted group selected from C1.6 aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each L is independently a covalent bond or a bivalent, saturated or unsaturated, straight or branched C$_{1-50}$ hydrocarbon chain, wherein 0-6 methylene units of L are independently replaced by —C(D)(H)-, —C(D)$_2$-, —Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

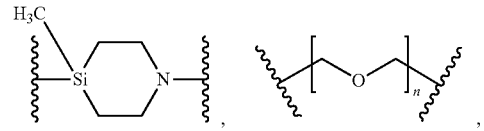

-continued

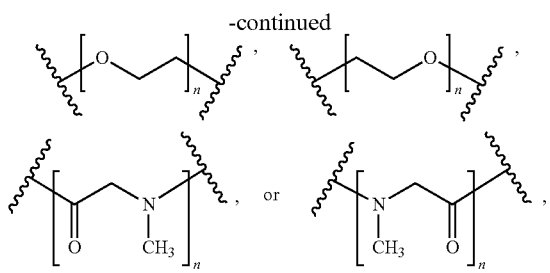

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, or sulfur;
Ring A is tricyclic ring

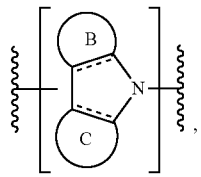

wherein
each of Ring B and Ring C is independently a fused ring selected from 6-membered aryl containing 0-2 nitrogens and a 5-membered heteroaryl with 1-2 heteroatoms independently selected from nitrogen, oxygen or sulfur;
--- is a single or double bond;
$L^1$ is a covalent bond;
each of n is independently 1, 2, 3, 4, 5, 6, 7, 8, 9, or 10; and
m is 0, 1, or 2.

2. The method of claim 1, wherein the disorder is a proliferative disorder.
3. The method of claim 2, wherein the proliferative disorder is a hematological cancer.
4. The method of claim 2, wherein the proliferative disorder is a leukemia.
5. The method of claim 4, wherein the leukemia is selected from the group consisting of acute leukemia, acute lymphoblastic leukemia (ALL), chronic lymphocytic leukemia (CLL), acute myelogenous leukemia, acute myeloid leukemia (AML), adult acute basophilic leukemia, adult acute eosinophilic leukemia, adult acute megakaryoblastic leukemia, adult acute minimally differentiated myeloid leukemia, adult acute monoblastic leukemia, adult acute monocytic leukemia, adult acute myeloblastic leukemia with maturation, adult acute myeloblastic leukemia without maturation, adult acute myeloid leukemia with abnormalities, adult acute myelomonocytic leukemia, adult erythroleukemia, adult pure erythroid leukemia, secondary acute myeloid leukemia, untreated adult acute myeloid leukemia, adult acute myeloid leukemia in remission, adult acute promyelocytic leukemia with PML-RARA, alkylating agent-related acute myeloid leukemia, prolymphocytic leukemia, and chronic myelomonocytic leukemia.
6. The method of claim 2, wherein the proliferative disorder is a lymphoma.
7. The method of claim 6, wherein the lymphoma is selected from the group consisting of adult grade III lymphomatoid granulomatosis, adult nasal type extranodal NK/T-cell lymphoma, anaplastic large cell lymphoma, angioimmunoblastic T-cell lymphoma, cutaneous B-Cell non-Hodgkin lymphoma, extranodal marginal zone lymphoma of mucosa-associated lymphoid tissue, hepatosplenic T-cell lymphoma, intraocular lymphoma, lymphomatous involvement of non-cutaneous extranodal site, mature T-cell and NK-cell non-Hodgkin lymphoma, nodal marginal zone lymphoma, post-transplant lymphoproliferative disorder, recurrent adult Burkitt lymphoma, recurrent adult diffuse large cell lymphoma, recurrent adult diffuse mixed cell lymphoma, recurrent adult diffuse small cleaved cell lymphoma, recurrent adult grade III lymphomatoid granulomatosis, recurrent adult immunoblastic lymphoma, recurrent adult lymphoblastic lymphoma, recurrent adult T-cell leukemia/lymphoma, recurrent cutaneous T-cell non-Hodgkin lymphoma, recurrent grade 1 follicular lymphoma, recurrent grade 2 follicular lymphoma, recurrent grade 3 follicular lymphoma, recurrent mantle cell lymphoma, recurrent marginal zone lymphoma, recurrent mycosis fungoides and Sezary syndrome, recurrent small lymphocytic lymphoma, refractory chronic lymphocytic leukemia, refractory hairy cell leukemia, Richter syndrome, small intestinal lymphoma, splenic marginal zone lymphoma, T-cell large granular lymphocyte leukemia, testicular lymphoma, Waldenstrom macroglobulinemia, adult T-cell leukemia-lymphoma, peripheral T-cell lymphoma, B-cell lymphoma, Hodgkin's disease, cutaneous T-cell lymphoma, diffuse large B-cell lymphoma, MALT lymphoma, mantle cell lymphoma, non-Hodgkins lymphoma, central nervous system lymphoma, refractory primary-cutaneous large B-cell lymphoma (Leg-type), relapsed or refractory chronic lymphocytic leukemia, refractory anemia, refractory anemia with excess blasts, refractory anemia with ringed sideroblasts, refractory cytopenia with multilineage dysplasia, and secondary myelodysplastic syndromes.
8. The method of claim 1, wherein the disorder is a neurological disorder.
9. The method of claim 8, wherein the neurological disorder is Alzheimer's disease.
10. The method of claim 1, wherein the disorder is a disorder associated with transplantation.
11. The method of claim 10, wherein the disorder associated with transplantation is graft-versus-host disease.
12. The method of claim 1, wherein $X^1$ is —C(O)—.

13. The method of claim 1, wherein each $R^2$ is independently hydrogen, $R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, or —C(O)N(R)$_2$.

14. The method of claim 1, wherein each L is independently a bivalent, saturated or unsaturated, straight or branched C$_{1-20}$ hydrocarbon chain, wherein 0-6 methylene units of L are independently replaced by —Cy-, —O—, —N(R)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, or —N(R)C(O)O—.

15. The method of claim 1, wherein each L is independently a bivalent, saturated or unsaturated, straight or branched C$_{1-20}$ hydrocarbon chain, wherein 0-6 methylene units of L are independently replaced by —Cy-, —O—, —N(R)—, —S—, or —C(O)—.

16. The method of claim 1, wherein each of Ring B and Ring C is independently a fused ring selected from 6-membered aryl containing 0-2 nitrogens.

17. The method of claim 1, wherein each L is independently a covalent bond.

18. The method of claim 1, wherein the compound is selected from:

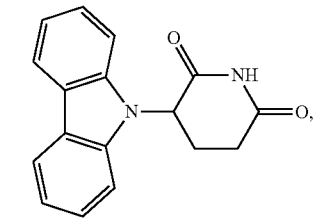
I-1

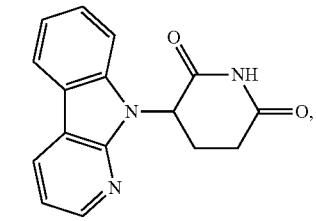
I-2

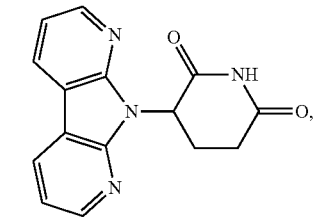
I-3

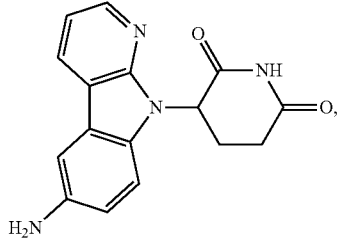
I-5

-continued

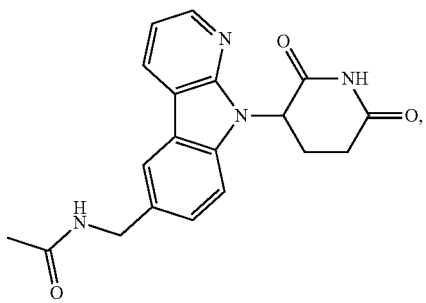
I-6

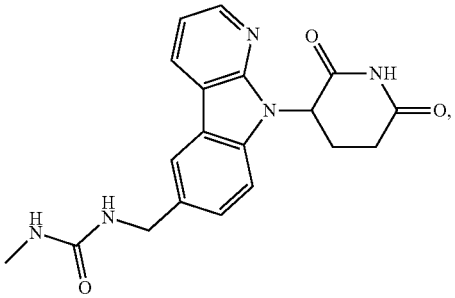
I-7

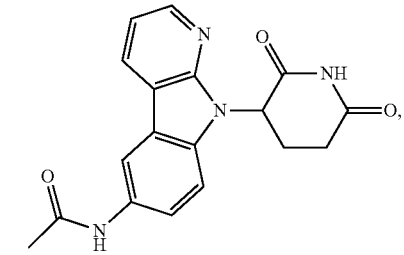
I-8

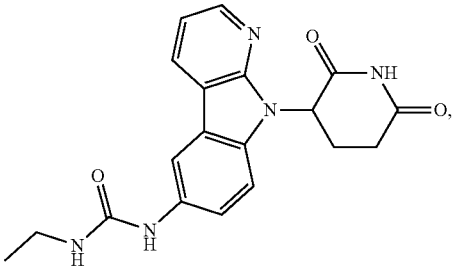
I-9

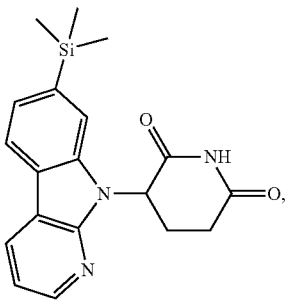
I-21

I-22
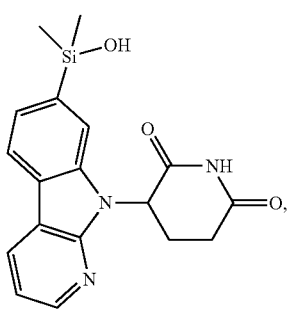
I-23
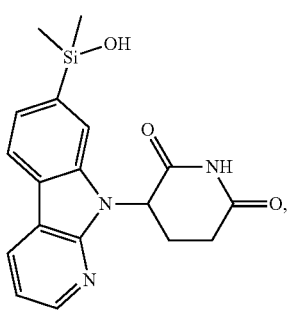
I-24
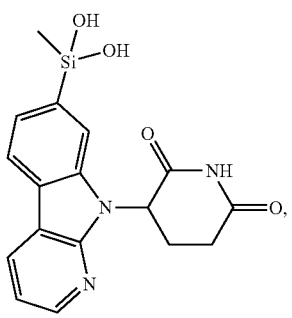
I-25
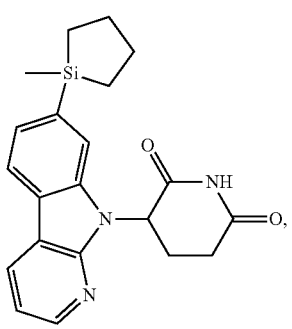
I-26
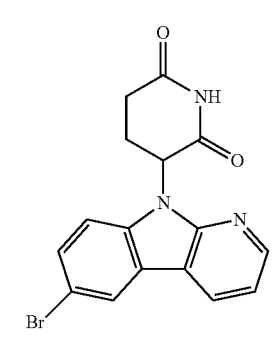
I-27
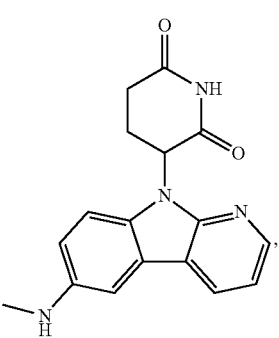
I-28
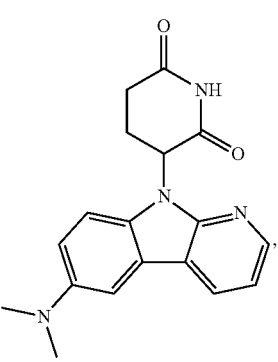
I-29
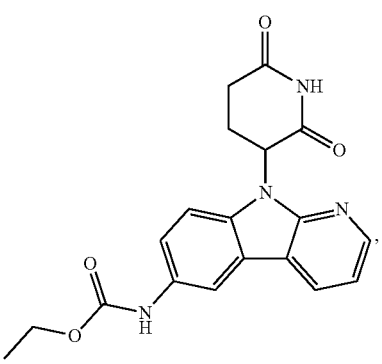
I-30
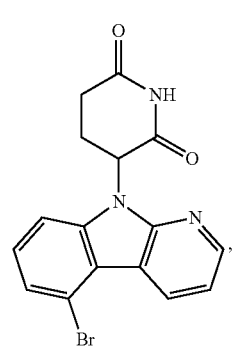

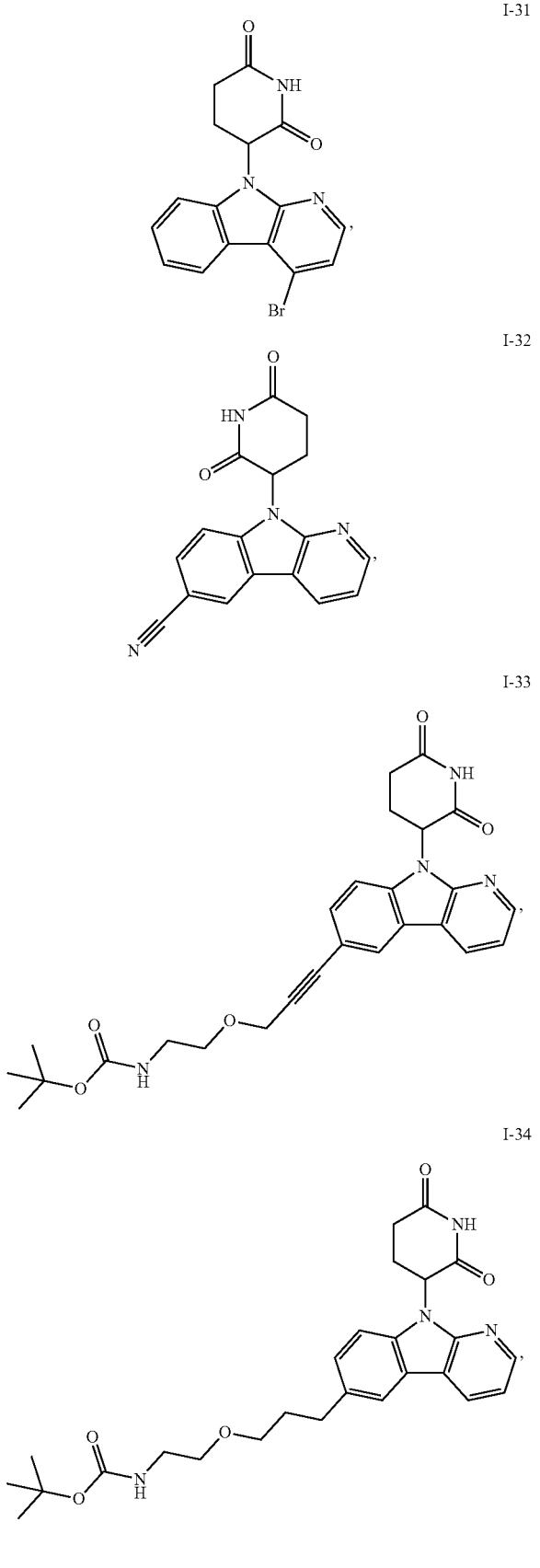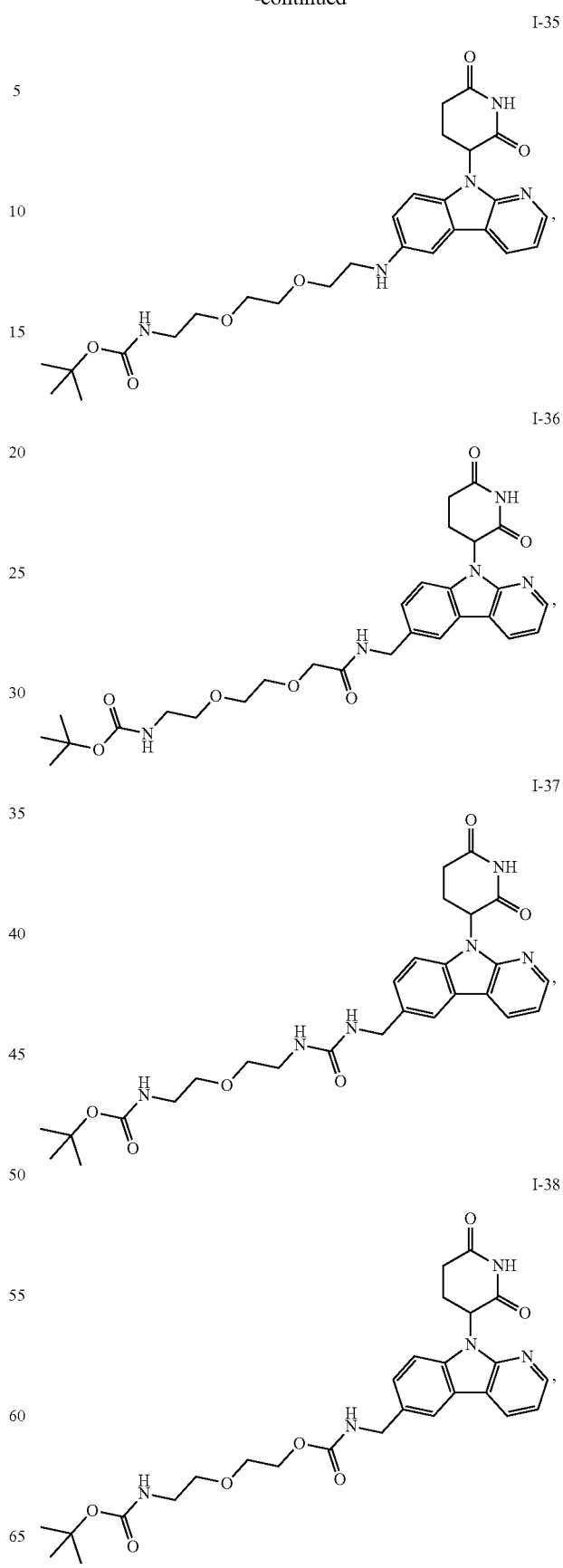

I-39

I-42

I-43

I-44

I-45

I-46

I-47

I-48
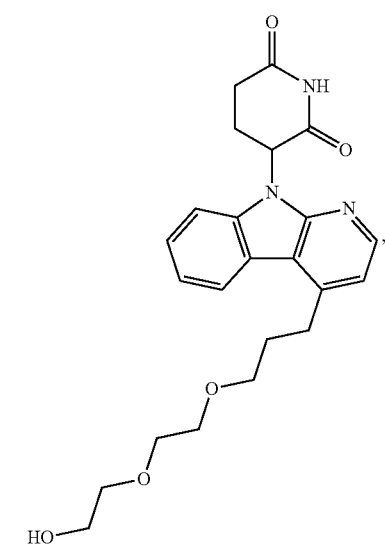
I-51
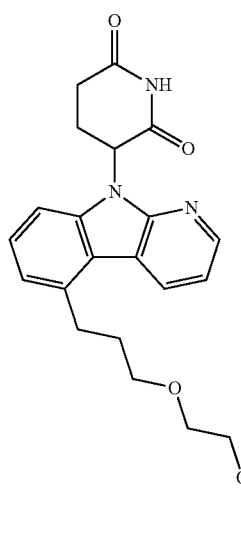
I-49
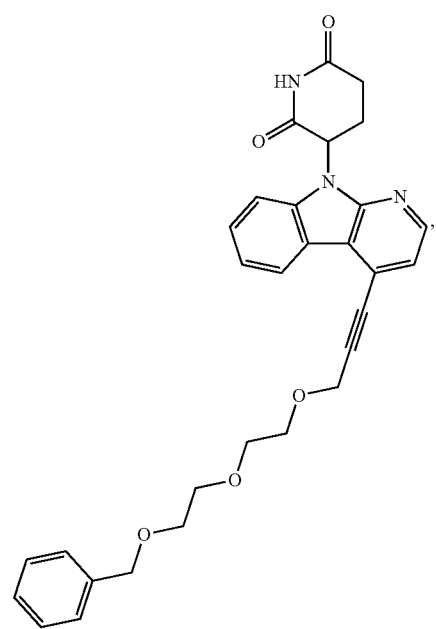
I-52
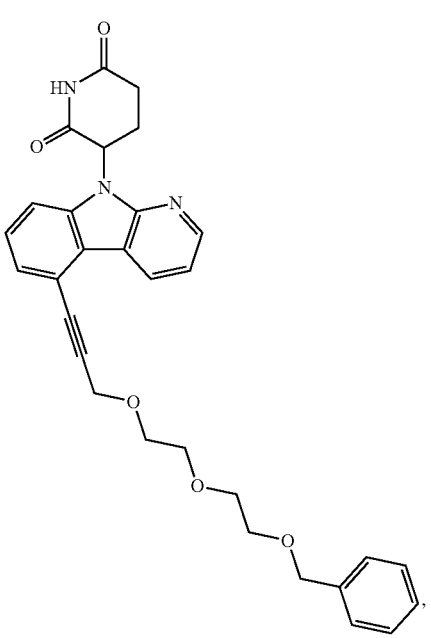
I-50
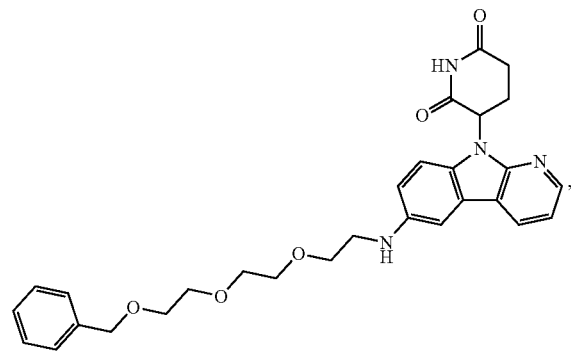
I-53
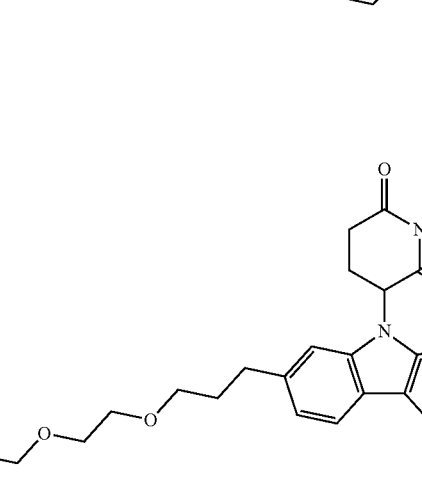

I-54
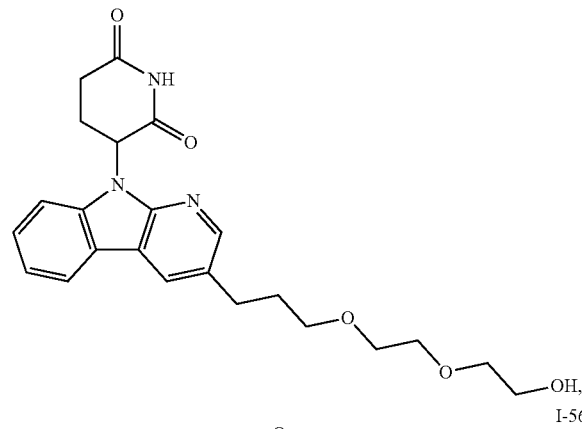
I-59
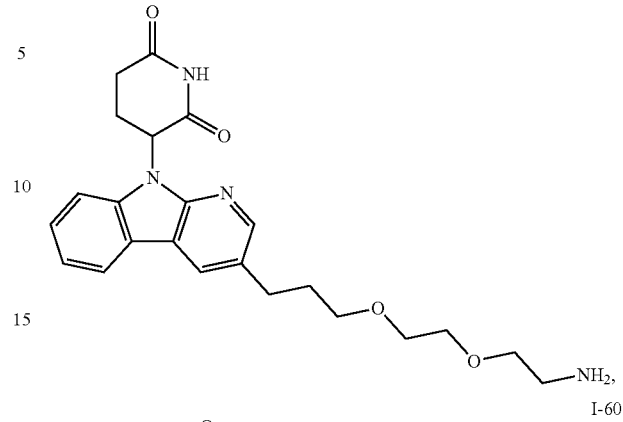
I-56
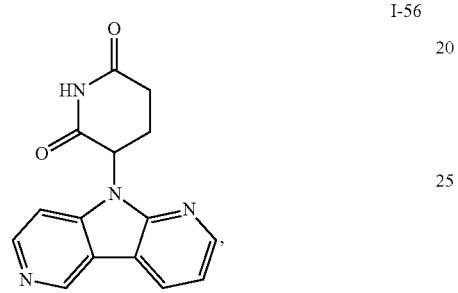
I-60
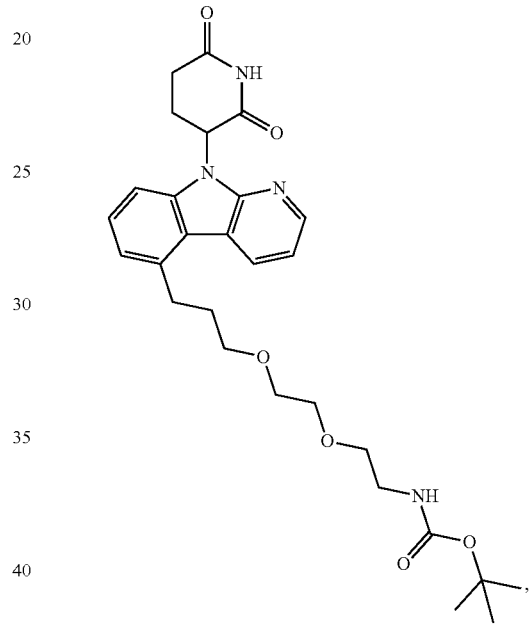
I-57
I-58
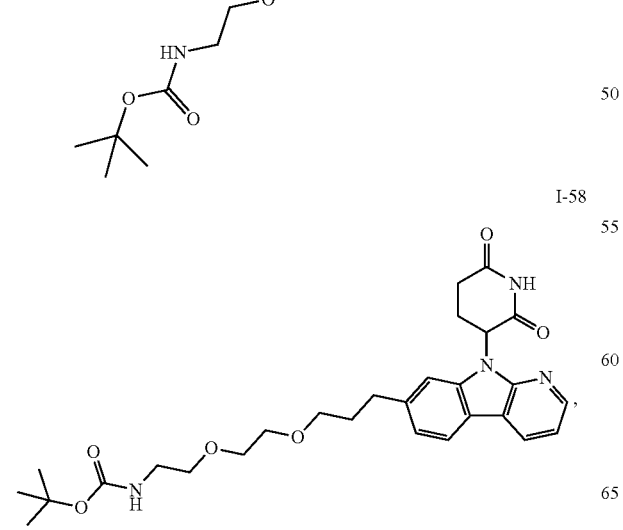
I-61
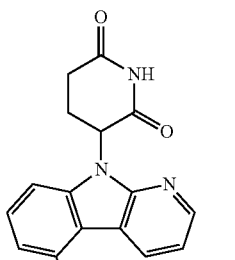

I-62
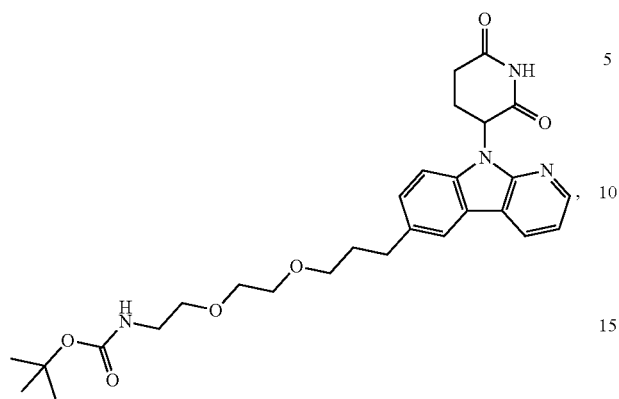
I-63
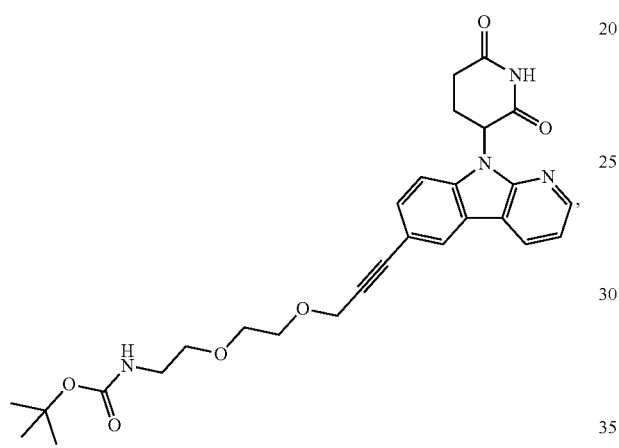
I-64
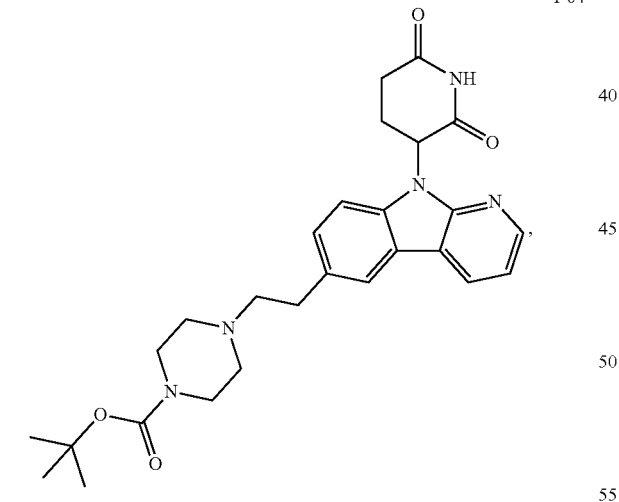
I-65
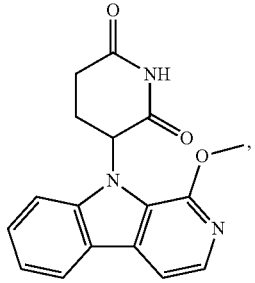
I-66
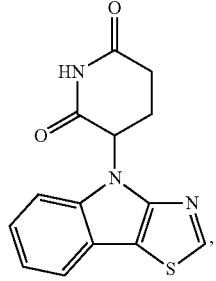
I-67
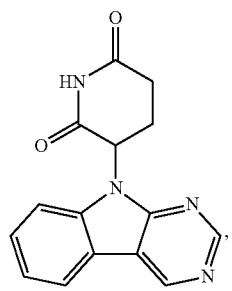
I-69
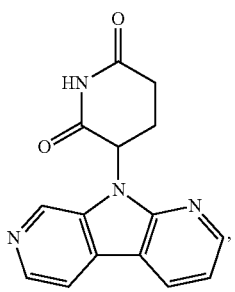
I-71
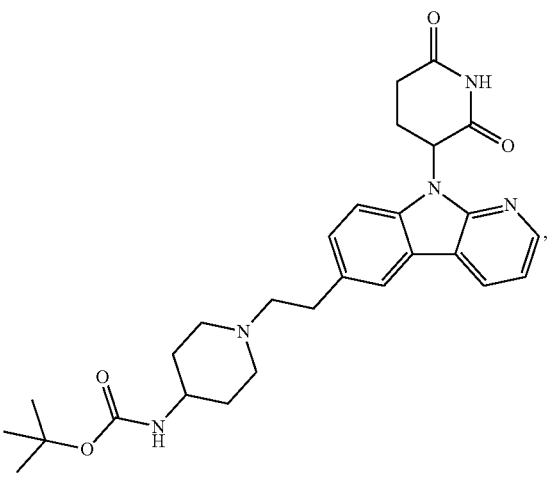

337
-continued
338
-continued
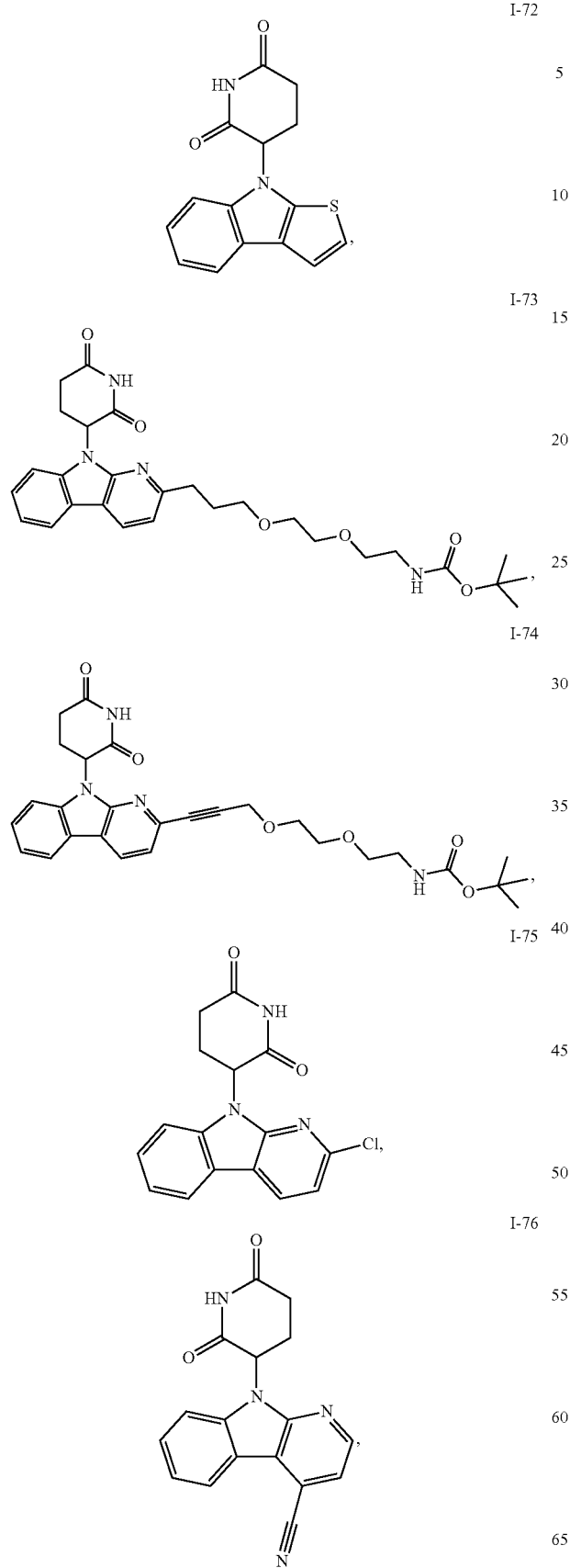
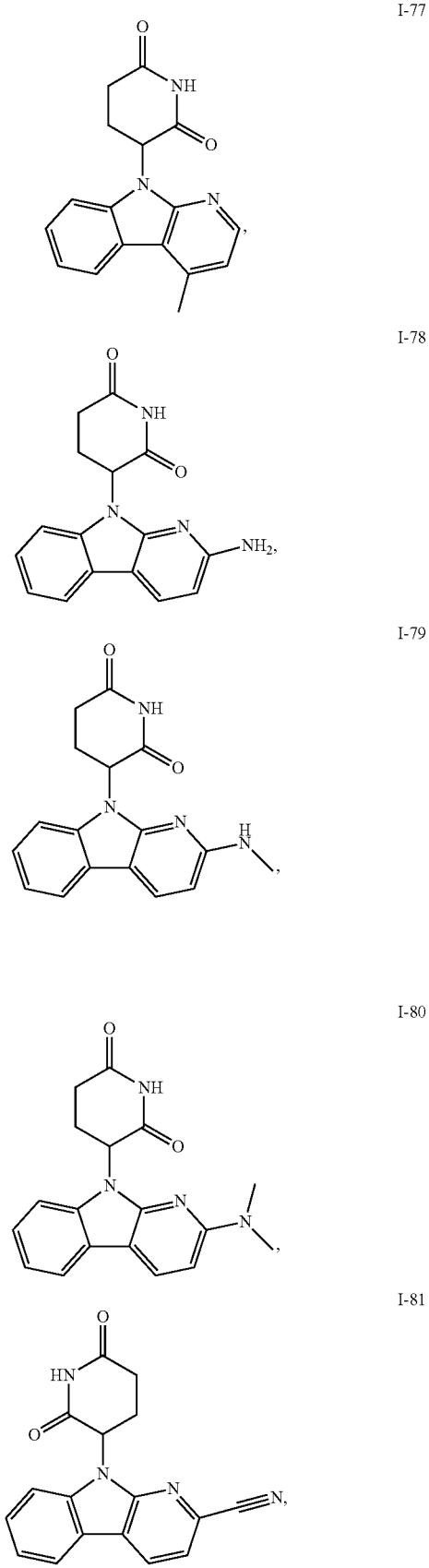

I-82
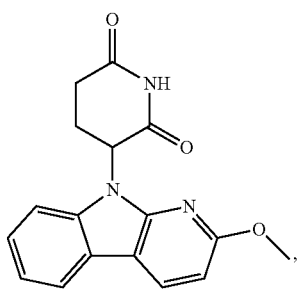
I-83
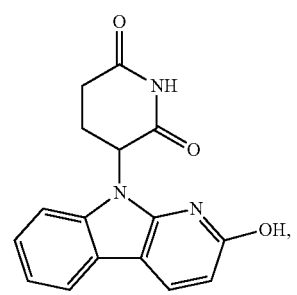
I-84
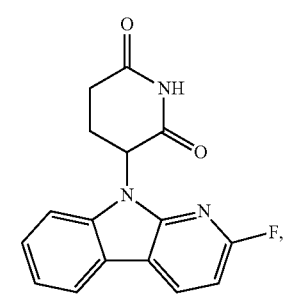
I-85
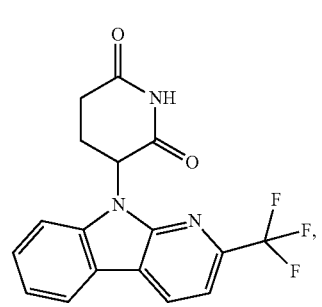
I-86
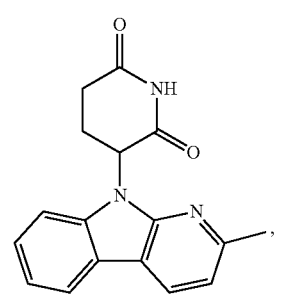
I-87
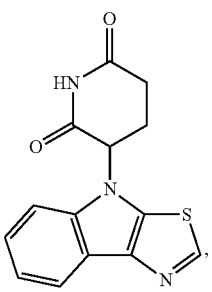
I-88
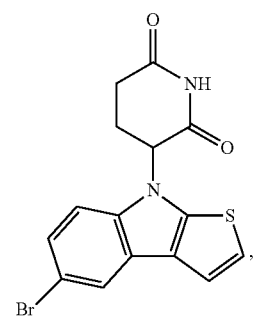
I-89
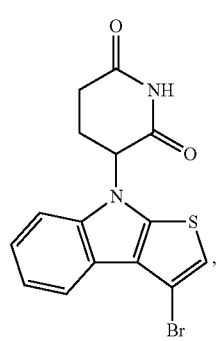
I-90
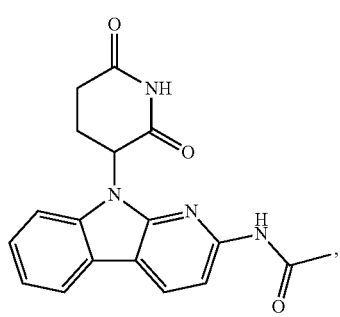
I-91
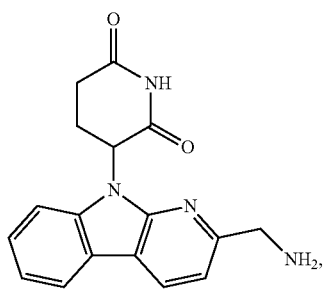

I-92 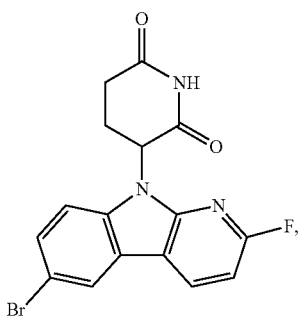
I-93 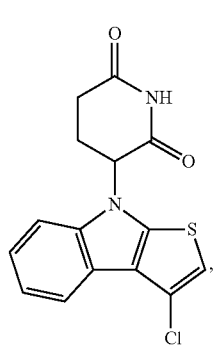
I-100 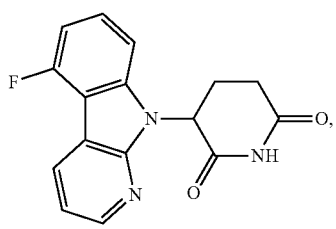
I-101 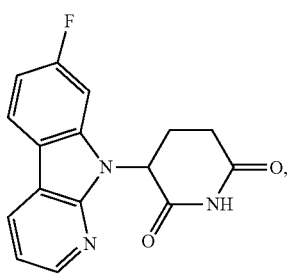
I-102 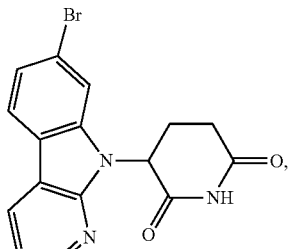
I-103 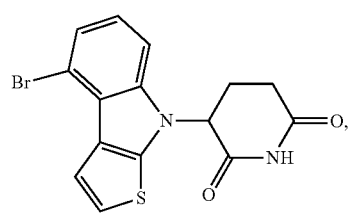
I-104 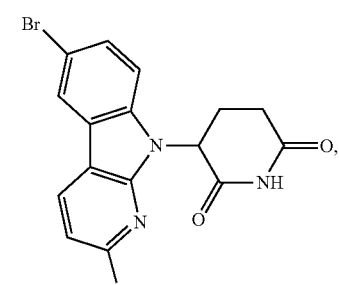
I-105 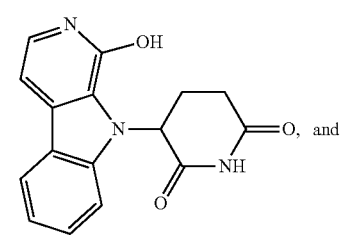
and
I-106 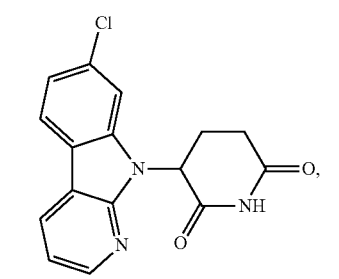
or a pharmaceutically acceptable salt thereof.
19. The method of claim 1, wherein the pharmaceutical composition comprises a pharmaceutically acceptable carrier, adjuvant, or vehicle.
* * * * *